United States Patent
Wang et al.

(10) Patent No.: US 11,111,233 B2
(45) Date of Patent: Sep. 7, 2021

(54) AMINO PYRIMIDINE COMPOUND FOR INHIBITING PROTEIN TYROSINE KINASE ACTIVITY

(71) Applicant: Shenzhen TargetRx, Inc., Guangdong (CN)

(72) Inventors: Yihan Wang, Guangdong (CN); Xingye Ren, Guangdong (CN); Jian Jin, Guangdong (CN); Huanyin Li, Guangdong (CN); Yixin Ai, Guangdong (CN)

(73) Assignee: Shenzhen TargetRx, Inc., Guangdong (CN)

( * ) Notice: Subject to any disclaimer, the term of this patent is extended or adjusted under 35 U.S.C. 154(b) by 0 days.

(21) Appl. No.: 16/256,203

(22) Filed: Jan. 24, 2019

(65) Prior Publication Data

US 2019/0152954 A1 May 23, 2019

Related U.S. Application Data

(63) Continuation-in-part of application No. PCT/CN2017/094102, filed on Jul. 24, 2017.

(30) Foreign Application Priority Data

Jul. 26, 2016 (CN) .......................... 201610594608.0

(51) Int. Cl.
| | |
|---|---|
| C07D 403/04 | (2006.01) |
| C07D 471/04 | (2006.01) |
| A61P 35/00 | (2006.01) |
| A61K 31/506 | (2006.01) |
| A61P 35/02 | (2006.01) |
| C07D 401/14 | (2006.01) |
| C07D 413/04 | (2006.01) |
| C07D 417/04 | (2006.01) |
| C07D 487/04 | (2006.01) |

(52) U.S. Cl.
CPC .......... *C07D 403/04* (2013.01); *A61K 31/506* (2013.01); *A61P 35/00* (2018.01); *A61P 35/02* (2018.01); *C07D 401/14* (2013.01); *C07D 413/04* (2013.01); *C07D 417/04* (2013.01); *C07D 471/04* (2013.01); *C07D 487/04* (2013.01)

(58) Field of Classification Search
CPC ... A61K 31/506; C07D 403/04; C07D 403/14
USPC .......................................... 514/275; 544/331
See application file for complete search history.

(56) References Cited

U.S. PATENT DOCUMENTS

| | | | |
|---|---|---|---|
| 9,908,884 B2 | 3/2018 | Gray et al. | |
| 2003/0087922 A1 | 5/2003 | Bethiel et al. | |
| 2017/0355696 A1 | 12/2017 | Jiang | |
| 2019/0047990 A1 | 2/2019 | Berdini et al. | |
| 2019/0152954 A1 | 5/2019 | Wang et al. | |

FOREIGN PATENT DOCUMENTS

| | | | |
|---|---|---|---|
| CN | 102482277 | A | 5/2012 |
| CN | 104803925 | A | 7/2015 |
| CN | 104892580 | A | 9/2015 |
| CN | 105085489 | A | 11/2015 |
| CN | 106749193 | A | 5/2017 |
| CN | 106749267 | A | 5/2017 |
| CN | 106831730 | A | 6/2017 |
| EP | 3405196 | B1 | 12/2019 |
| JP | 2004-529140 | A | 9/2004 |
| JP | 2018-532737 | A | 11/2018 |
| JP | 2019-504067 | A | 2/2019 |
| WO | WO 2002/079197 | A1 | 10/2002 |

(Continued)

OTHER PUBLICATIONS

Chawla et. al. Current Research & Information on Pharmaceutical Science, 2004, 5(1).*

(Continued)

*Primary Examiner* — Jeffrey H Murray

(74) *Attorney, Agent, or Firm* — Wolf, Greenfield & Sacks, P.C.

(57) ABSTRACT

An amino pyrimidine compound for inhibiting protein tyrosine kinase activity, a pharmaceutical composition thereof, preparation therefor, and an application thereof. Specifically, an amino pyrimidine compound represented by formula (I), R1, R2, L, Y, R6, W, A, m, and n being defined in the specification, and a pharmaceutically acceptable salt, a stereoisomer, a solvent compound, a hydrate, a polymorphism, a prodrug, or an isotope variant thereof. The compound can be used for treating and/or preventing protein tyrosine kinase-related diseases such as cell proliferative diseases, cancers, and immune diseases.

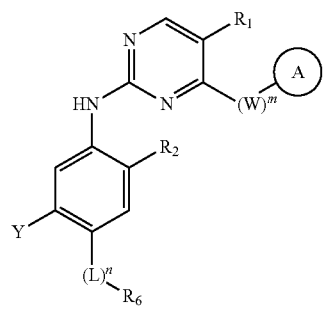

11 Claims, No Drawings

(56) References Cited

FOREIGN PATENT DOCUMENTS

| WO | WO2002079197 | * | 10/2002 | ........... C07D 405/04 |
| --- | --- | --- | --- | --- |
| WO | WO 2004/074262 A1 | | 9/2004 | |
| WO | WO 2008/124085 A2 | | 10/2008 | |
| WO | WO 2009/029998 A1 | | 3/2009 | |
| WO | WO 2009/032861 A1 | | 3/2009 | |
| WO | WO 2009/158571 A1 | | 12/2009 | |
| WO | WO 2010/138578 A1 | | 12/2010 | |
| WO | WO 2015/127872 A1 | | 11/2015 | |
| WO | WO 2015/170266 A1 | | 11/2015 | |
| WO | WO 2015/188747 A1 | | 12/2015 | |
| WO | WO 2015/195228 A1 | | 12/2015 | |
| WO | WO 2016/015453 A1 | | 2/2016 | |
| WO | WO 2016/022460 A1 | | 2/2016 | |
| WO | WO 2016/054987 A1 | | 4/2016 | |
| WO | WO 2016/070816 A1 | | 5/2016 | |
| WO | WO 2016/094821 A2 | | 6/2016 | |
| WO | WO 2016/173438 A1 | | 11/2016 | |
| WO | WO 2017/068412 A1 | | 4/2017 | |
| WO | WO 2017/120429 A1 | | 7/2017 | |
| WO | WO 2017/125530 A1 | | 7/2017 | |
| WO | WO 2018/019204 A1 | | 2/2018 | |
| WO | WO 2019/228330 A1 | | 12/2019 | |

OTHER PUBLICATIONS

Newman et. al.; DDT, vol. 8, No. 19, (2003); pp. 898-905.*
Banker, et. al., (1996), Modern Pharmaceuticals, p. 596.*
Wolff et. al., "Burger's Medicinal Chemistry and Drug Discovery," 5th Ed. Part 1, pp. 975-977 (1995).*
Huang, et. al., Bioorganic & Medicinal Chemistry Letters (2007), 17(8), 2179-2183.*
PCT/CN2017/094102, Oct. 11, 2017, International Search Report and Written Opinion.
PCT/CN2017/094102, Jan. 29, 2019, International Preliminary Report on Patentability.
Extended European Search Report for Application No. EP 17833507.1, dated Jun. 12, 2019.
EP 17833507.1, Jun. 12, 2019, Extended European Search Report.
International Search Report and Written Opinion for Application No. PCT/CN2020/073764, dated Apr. 22, 2020.
Chinese Office Action for Application No. CN201911307484.3, dated Jun. 28, 2020.

* cited by examiner

AMINO PYRIMIDINE COMPOUND FOR INHIBITING PROTEIN TYROSINE KINASE ACTIVITY

CROSS REFERENCE TO RELATED APPLICATIONS

The present application is a continuation-in-part application of PCT/CN2017/094102 filed on Jul. 24, 2017, which claims the priority of the Chinese Patent Application No. 201610594608.0 filed on Jul. 26, 2016, the entire contents of each of which are incorporated by reference herein.

FIELD OF THE PRESENT DISCLOSURE

The present disclosure belongs to the pharmaceutical field. In particular, the present disclosure relates to aminopyrimidine compounds which have inhibitory effect on protein tyrosine kinases, pharmaceutical compositions containing the same, and preparation processes and use thereof.

BACKGROUND OF THE PRESENT DISCLOSURE

Epidermal growth factor receptor (i.e., EGFR, ErbB-1 or HER1) is a member of the ErbB receptor family, and the ErbB receptor family includes four closely related receptor tyrosine kinase members: EGFR (ErbB-1), HER2/c-neu (ErbB-2), Her3 (ErbB-3) and Her4 (ErbB-4). EGFR is a cell surface receptor for extracellular protein ligands, which is a member of the epidermal growth factor family (EGF family). Mutations that affect EGFR expression or activity may result in cancer. It has been reported that EGFR is in an dysregulated state in most solid tumors such as lung cancer, breast cancer and brain tumors. It is estimated that 30% of epithelial cancers are associated with mutations, amplification or dysregulation of EGFR or its family members.

Treatments based on inhibition of EGFR by antibody medications or small molecule inhibitors (e.g., gefitinib and erlotinib) have been developed. In the case of non-small cell lung cancer (NSCLC), gefitinib and erlotinib are beneficial for 10% to 40% of patients. However, acquired resistance to gefitinib or erlotinib has become a major clinical problem after a period of treatment. Studies have confirmed that one of the main causes of drug resistance is due to the new mutation of T790M, which is the "gatekeeper" of EGFR. Researchers have then developed inhibitors against T790M, such as BIBW2992, and have shown advantages in clinical trials. However, these inhibitors targeting the T790M mutation of EGFR also possess considerable inhibitory activity against the wild-type EGFR, leading to severe toxic side effects that limit its clinical application. Therefore there is a need to further develop more effective types of selective inhibitors that target only the mutant but not the wild type of EGFR.

In the case of advanced non-small cell lung cancer with EGFR mutation, although EGFR kinase inhibitors (EGFR-TKI) such as gefitinib and erlotinib have achieved remarkable therapeutic effect. EGFR-TKI was subsequently found to be primarily or secondarily drug resistant in the treatment of non-small cell lung cancer. This raises a new challenge in the treatment of advanced non-small cell lung cancer, and it is necessary to carry out new explorations to find resolution.

The third-generation and subsequent EGFR inhibitors include compounds such as AZD9291 and CO-1686, which irreversibly inhibit EGFR, are more efficient in patients with T790M-resistant mutations, but still have an inhibitory effect on the wild-type EGFR.

Therefore, it is necessary to further develop new EGFR inhibitors that not only effectively inhibit the T790M mutation, but also have high selectivity for the T790M mutation relative to the wild type.

SUMMARY OF THE PRESENT DISCLOSURE

The present disclosure provides a novel aminopyrimidine compound and a composition comprising the same and use therof. The compound has better EGFR kinase inhibitory activity and high selectivity for the drug-resistant mutations T790M, L858R and both, and it can be used to treat, prevent, and alleviate EGFR kinase-mediated diseases.

In this regard, the technical solution adopted by the present disclosure is as follows:

In a first aspect of the invention, provided herein is a compound of formula (I):

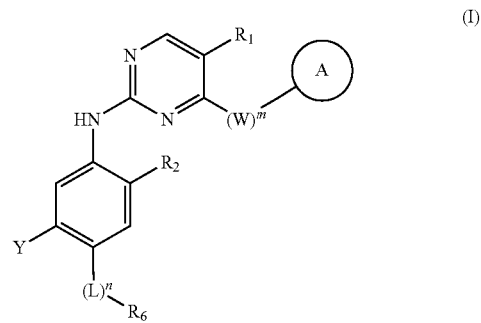

wherein, $R_1$ and $R_2$ are independently selected from H, halo, -CN, -NO$_2$, optionally substituted $C_1$-$C_6$ alkyl, optionally substituted $C_1$-$C_6$ haloalkyl, optionally substituted $C_1$-$C_6$ alkoxy, optionally substituted $C_1$-$C_6$ haloalkoxy, optionally substituted $C_1$-$C_6$ alkylthio, optionally substituted $C_1$-$C_6$ alkylamino or optionally substituted $C_1$-$C_6$ alkanoyl;

L is selected from a bond, NR$_7$, O, C(R$_7$)$_2$ or S; wherein each R$_7$ is independently selected from H, optionally substituted $C_1$-$C_6$ alkyl, such as $C_1$-$C_6$ alkyl that is substituted by $C_1$-$C_6$ alkoxy, or optionally substituted $C_1$-$C_6$ alkoxy;

Y is H, or Y is selected from the following structures:

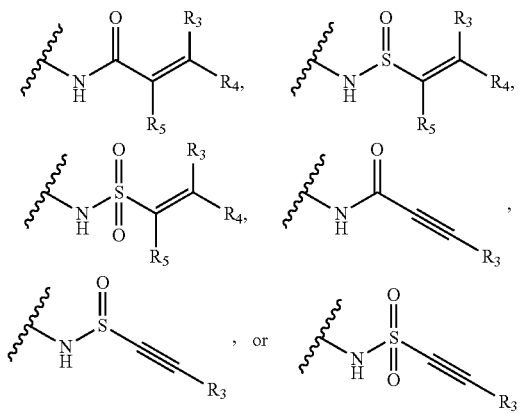

wherein $R_3$, $R_4$, and $R_5$ is independently selected from H, halo, -CN, optionally substituted $C_1$-$C_6$ alkyl or optionally substituted $C_1$-$C_6$ haloalkyl;

$R_6$ is selected from H, $C_1$-$C_6$ alkyl, $C_2$-$C_6$ alkynl or 3- to 8-membered heterocyclyl, wherein the above groups are optionally substituted by 1-3 following substituents: halo, -OH, -CN, -NO$_2$, optionally substituted $C_1$-$C_6$ alkyl, optionally substituted $C_1$-$C_6$ alkoxy, -C(O)$R_8$ or $NR_8R_9$; wherein $R_8$ and $R_9$ are each independently selected from H, optionally substituted $C_1$-$C_6$ alkyl, optionally substituted $C_1$-$C_6$ alkoxy, optionally substituted $C_1$-$C_6$ haloalkyl or optionally substituted $C_3$-$C_6$ carbocyclyl, or $R_8$ and $R_9$ together with the nitrogen atom to which they are attached form optionally substitued 4- to 6-membered heterocyclyl, which is substituted by $C_1$-$C_6$ alkyl for example:

W is selected from a bond, $C(R_{10})_2$, $NR_{10}$, O or S, wherein $R_{10}$ is selected from H, halo, -CN, -NO$_2$, optionally substituted $C_1$-$C_6$ alkyl, optionally substituted $C_1$-$C_6$ haloalkyl or optionally substituted $C_1$-$C_6$ alkoxy, as long as the chemistry permits;

m is 0, 1 or 2;

n is 0, 1 or 2;

ring A is selected from the following structures:

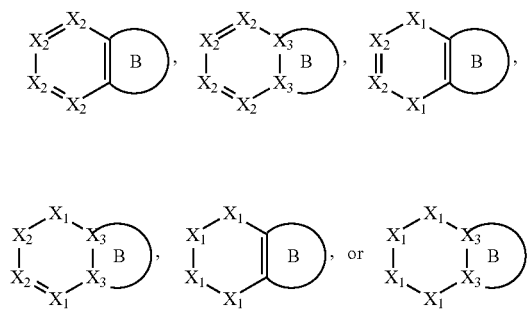

wherein each $X_1$ is independently selected from $C(R_{11})_2$, $NR_{11}$, O or S, each $X_2$ and $X_3$ is independently selected from $C(R_{11})_2$ or $NR_{11}$, wherein $X_1$ and $X_2$ could be the position of attachment to the parent core;

ring B is selected from 5-membered carbocyclyl, 5-membered heterocyclyl or 5-membered heteroaryl, which is optionally substituted by 1-3 $R_{11}$;

$R_{11}$ is independently selected from H, halo, -CN, -NO$_2$, -OH, optionally substituted $C_1$-$C_6$ alkyl, optionally substituted $C_1$-$C_6$ haloalkyl, optionally substituted $C_2$-$C_6$ alkenyl, optionally substituted $C_2$-$C_6$ alkynyl, optionally substituted $C_1$-$C_6$ alkoxy or optionally substituted $C_1$-$C_6$ haloalkoxy, as long as the chemistry permits; or, two adjacent $R_{11}$ could be taken together to form optionally substituted $C_5$-$C_8$ carbocyclyl, optionally substituted 5- to 8-membered heterocyclyl, optionally substituted $C_6$-$C_{14}$ aryl or optionally substituted 5- to 10-membered heteroaryl;

or a pharmaceutically acceptable salt, a stereoisomer, a solvate, a hydrate, a polymorph, a prodrug or an isotopic derivative thereof, Another embodiment of the above aspect is the above compound, which is a compound of formula (II):

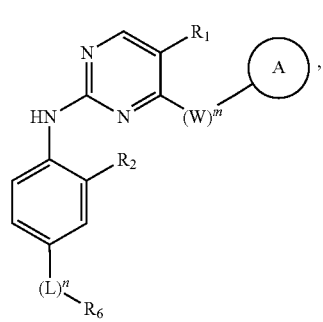

(II), wherein $R_1$, $R_2$, L, $R_6$, W, A, m and n are as defined above, or a pharmaceutically acceptable salt, a stereoisomer, a solvate, a hydrate, a polymorph, a prodrug or an isotopic derivative thereof.

Another embodiment of the above aspect is the above compound, which is a compound of formula (III):

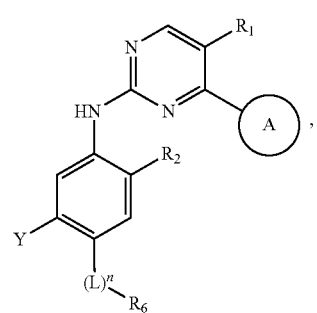

(III), wherein $R_1$, $R_2$, L, Y, $R_6$, A and n are as defined above, or a pharmaceutically acceptable salt, a stereoisomer, a solvate, a hydrate, a polymorph, a prodrug or an isotopic derivative thereof.

Another embodiment of the above aspect is the above compound, which is a compound of formula (IV):

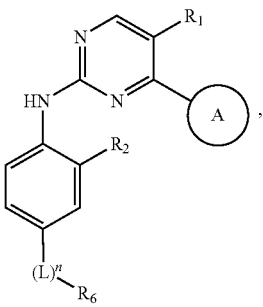

(IV), wherein $R_1$, $R_2$, L, $R_6$, A and n are as defined above, or a pharmaceutically acceptable salt, a stereoisomer, a solvate, a hydrate, a polymorph, a prodrug or an isotopic derivative thereof.

Another embodiment of the above aspect is the above compound, wherein ring A is selected from the following structures:

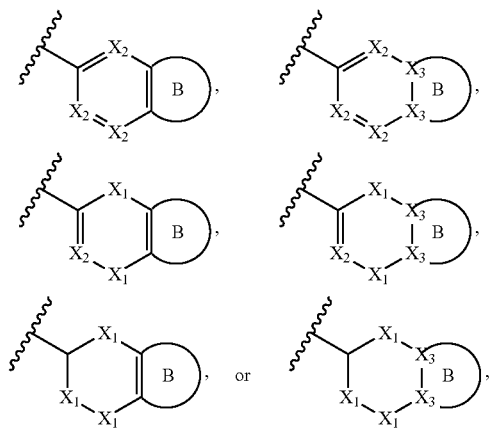

wherein ring A is optionally substituted by 1-6 $R_{11}$; preferably, ring A is selected from the following structures:

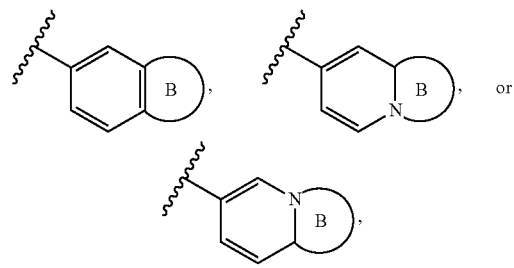

wherein ring A is optionally substituted by 1-6 $R_{11}$;
preferably, ring A is selected from the following structures:

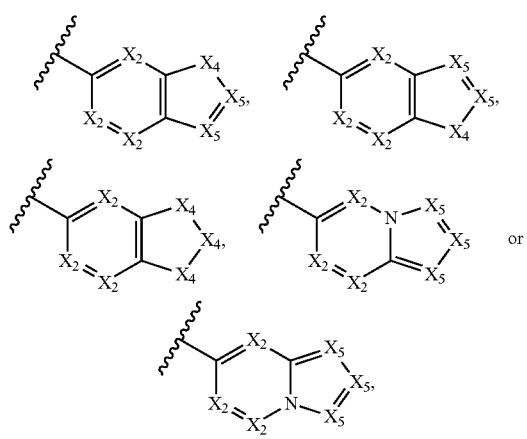

wherein ring A is optionally substituted by 1-6 $R_{11}$, wherein each $X_4$ is independently selected from $C(R_{11})_2$, $NR_{11}$, O, S, C(O), S(O) or $S(O)_2$, each $X_5$ is independently selected from $C(R_{11})_2$ or $NR_{11}$;
preferably, ring A is selected from the following structures:

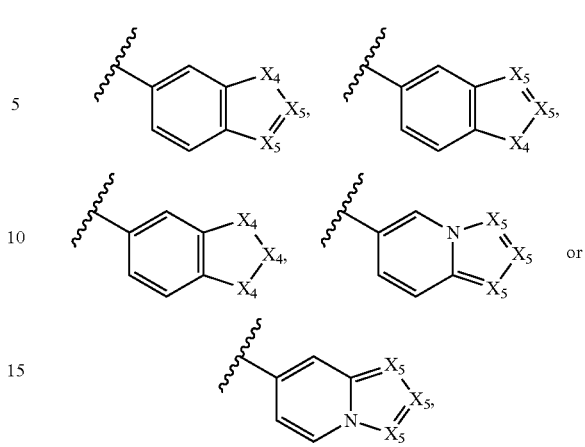

wherein ring A is optionally substituted by 1-6 $R_{11}$, wherein each $X_4$ is independently selected from $C(R_{11})_2$, $NR_{11}$, O, S, C(O), S(O) or $S(O)_2$, each $X_5$ is independently selected from $C(R_{11})_2$ or $NR_{11}$ atom;

preferably, ring A is selected from the following groups:

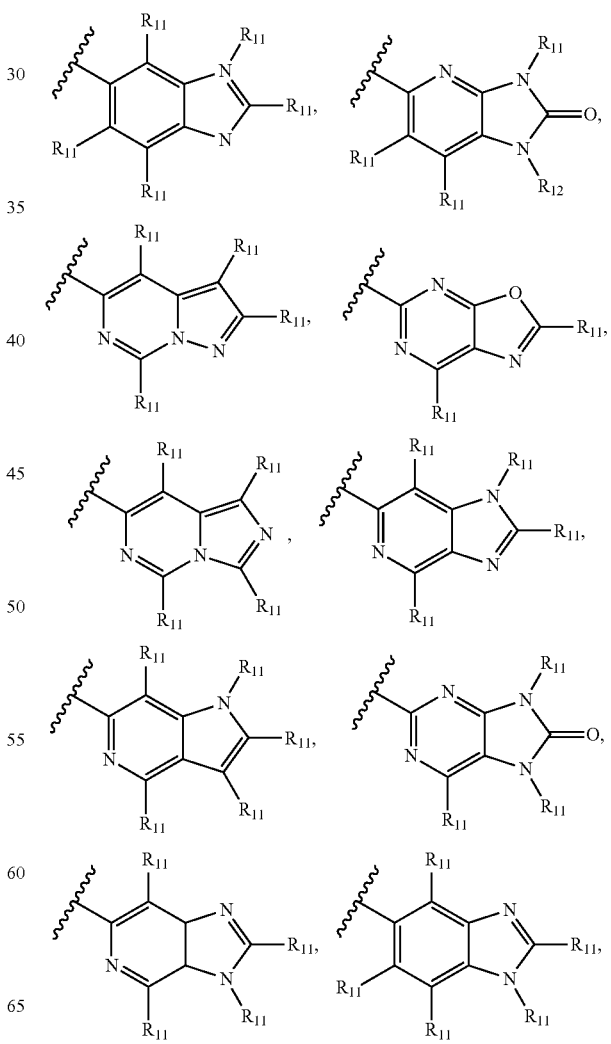

-continued
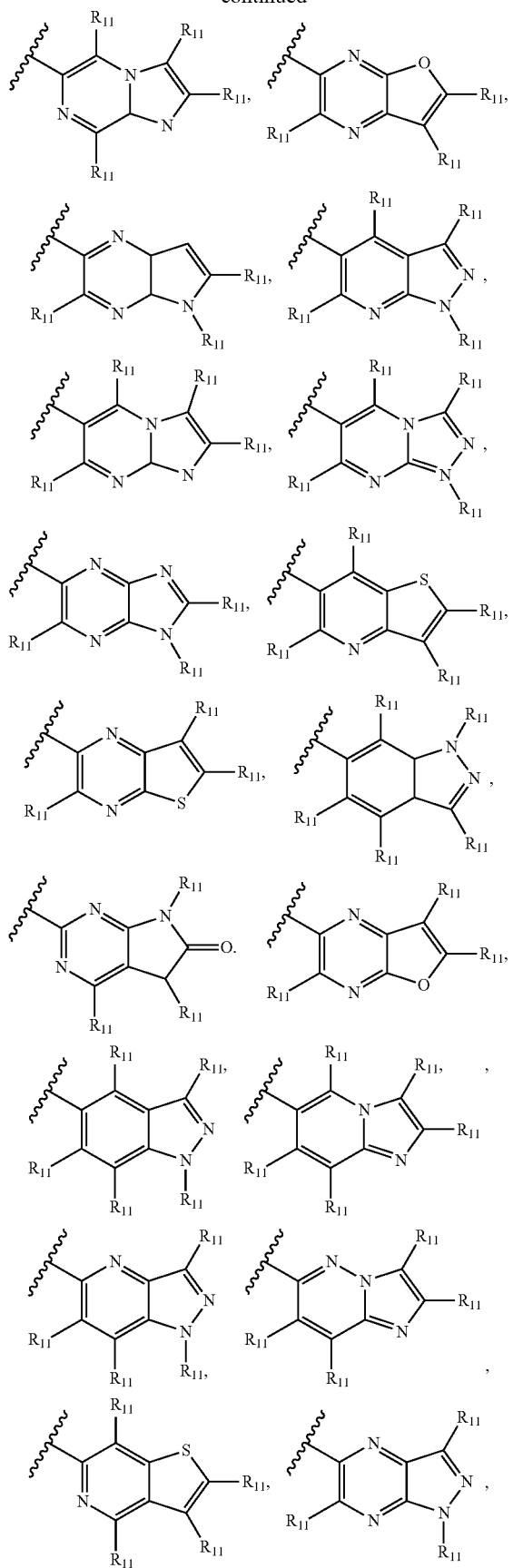
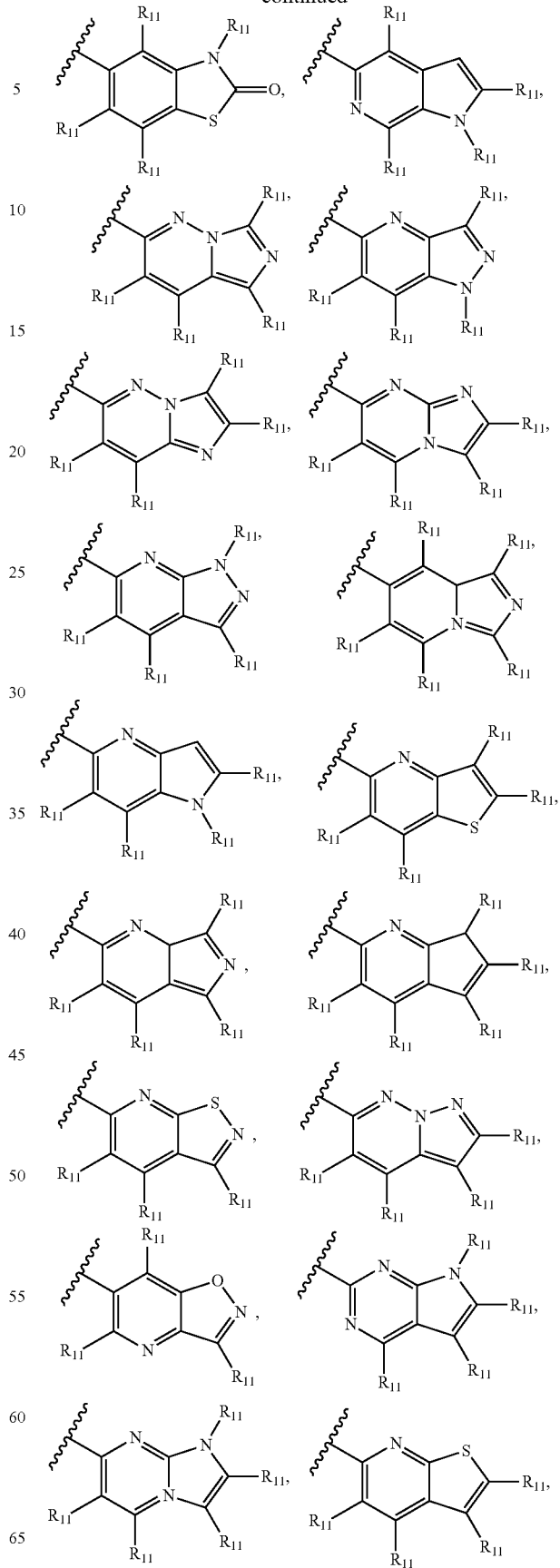

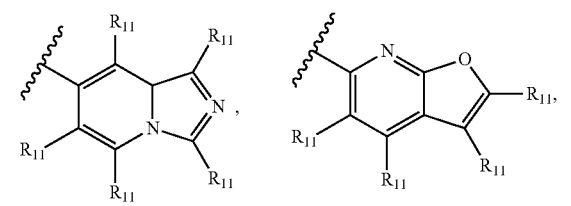
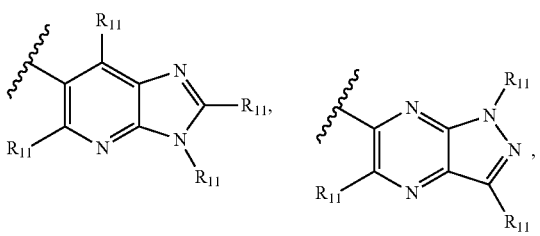
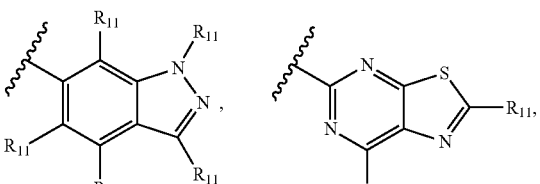
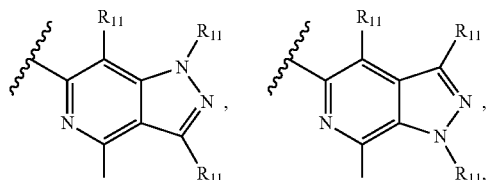
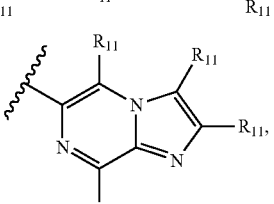
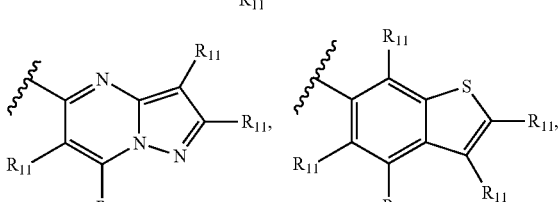
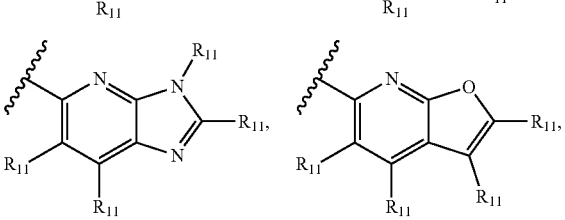
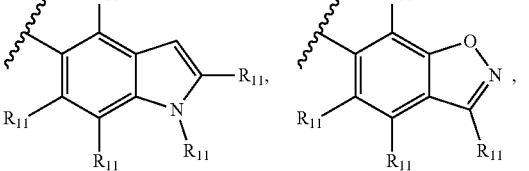
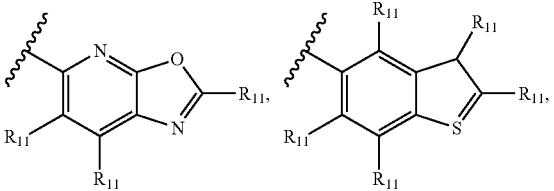

-continued
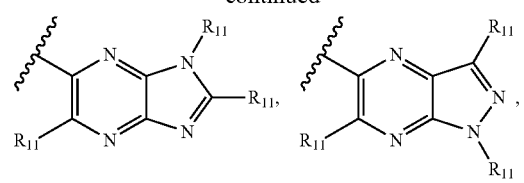
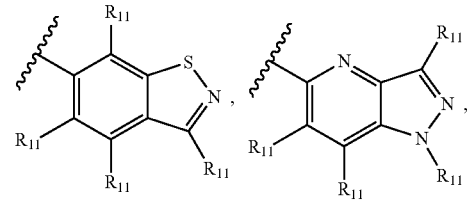
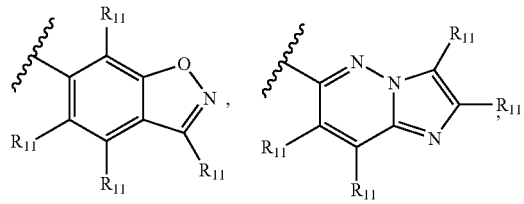
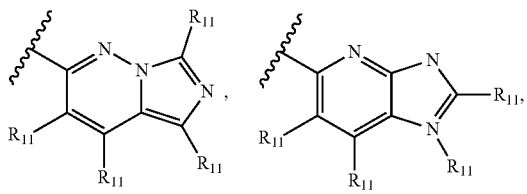
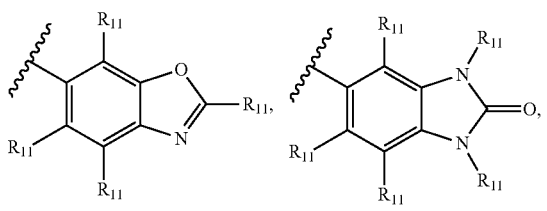
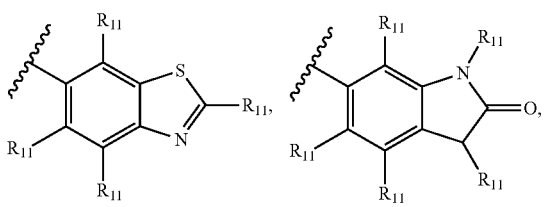
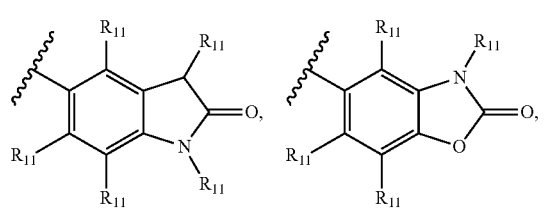
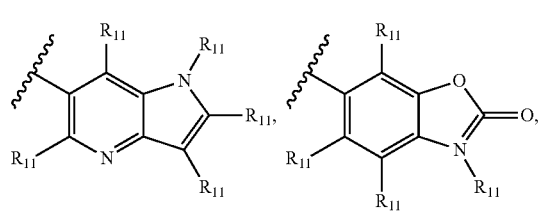
-continued
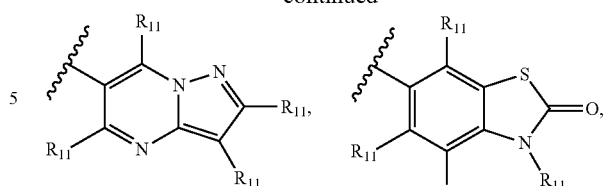
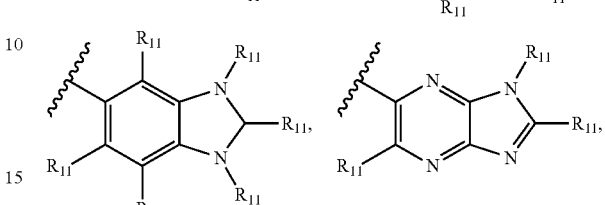
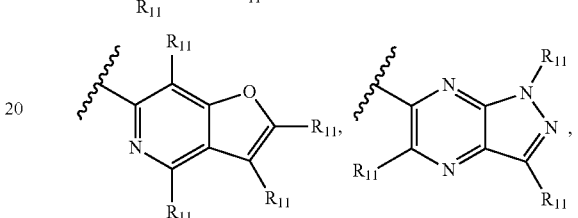
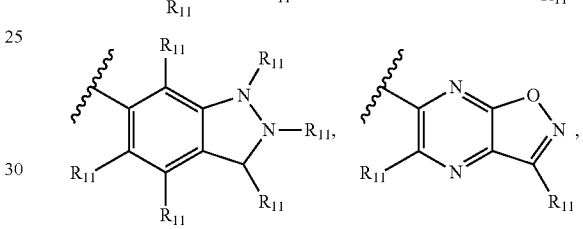
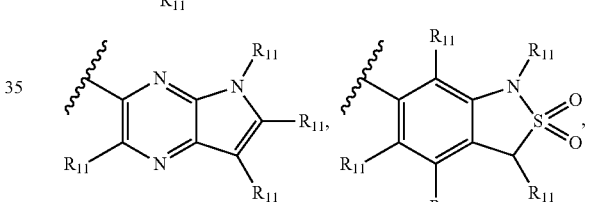
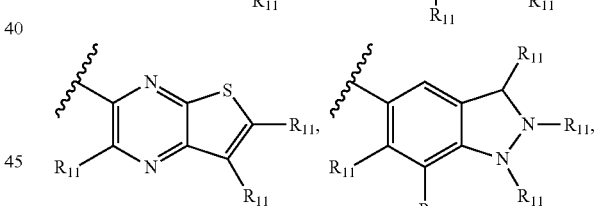
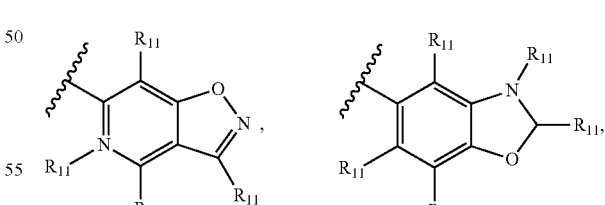
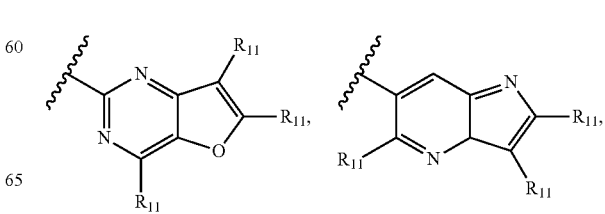

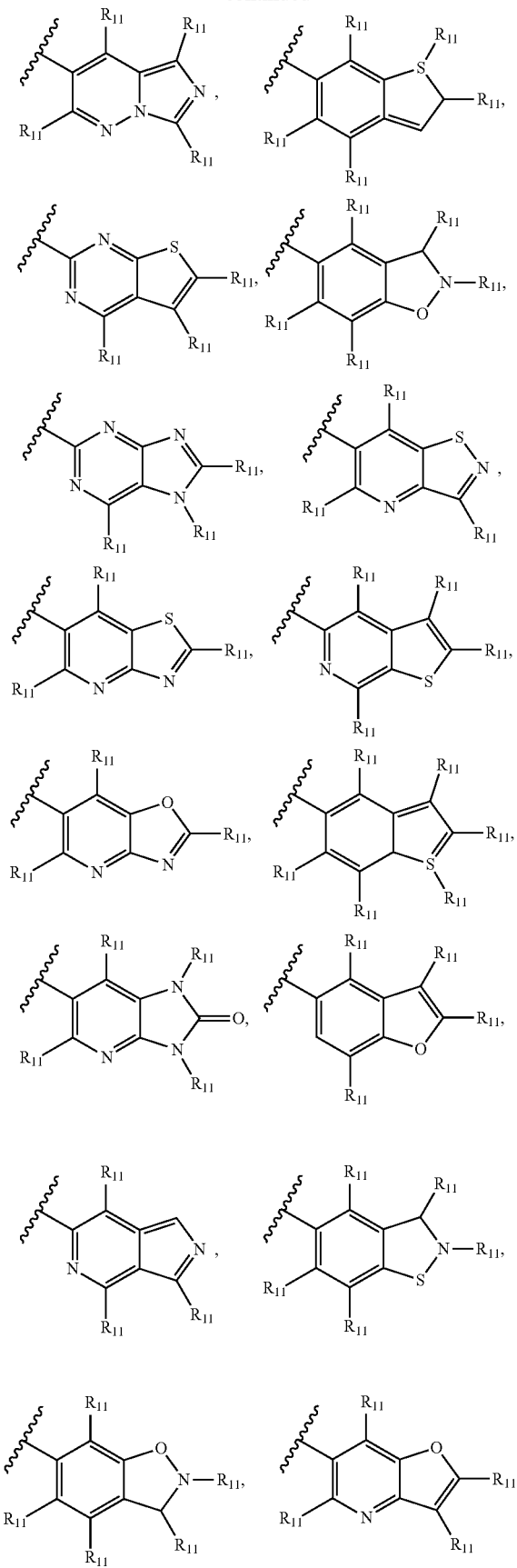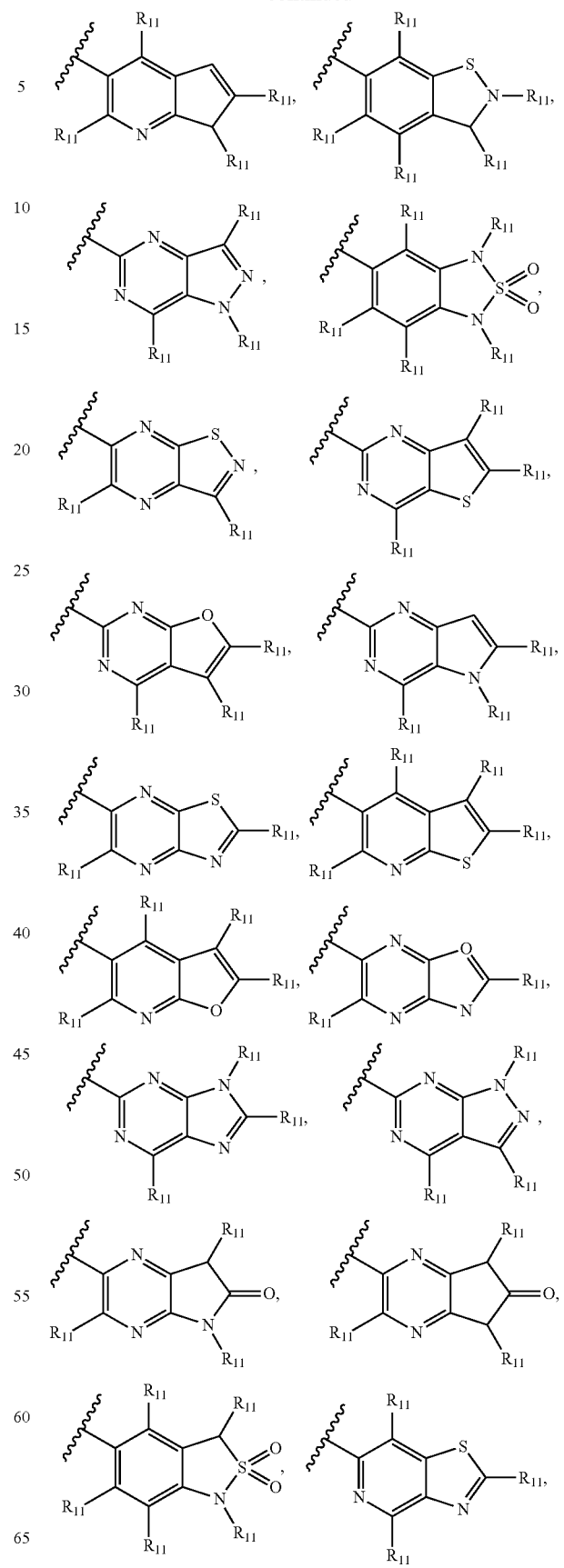

-continued

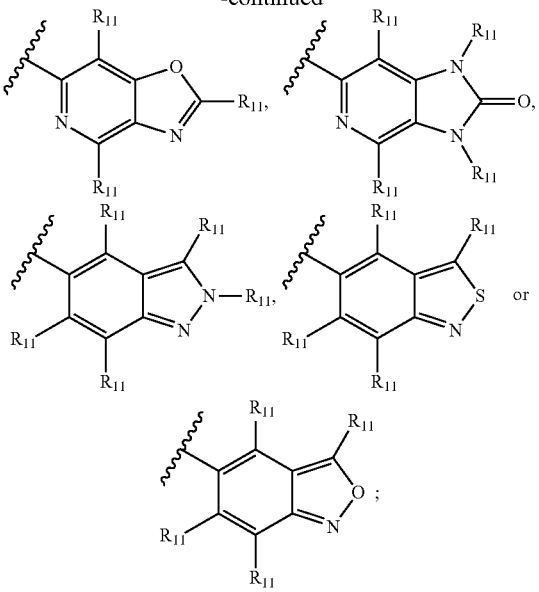

preferably, ring A is selected from the following groups:

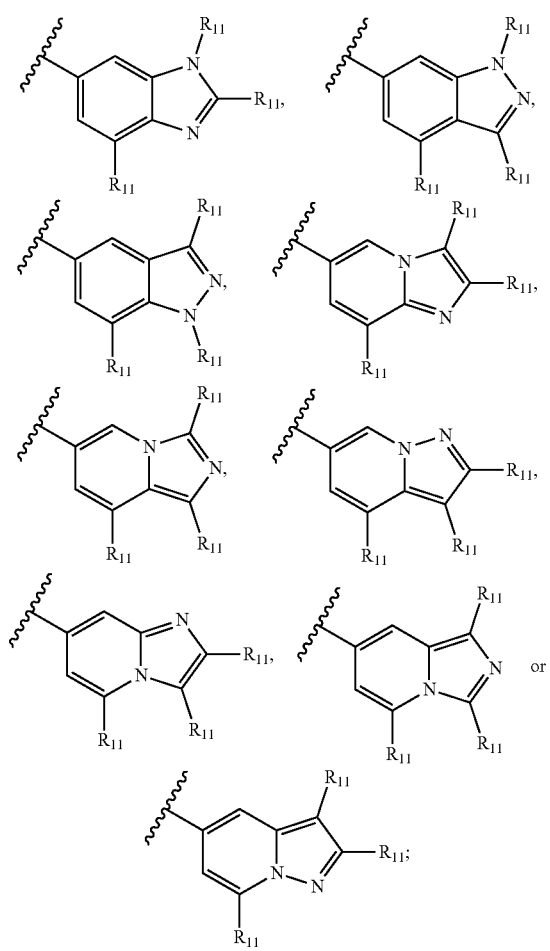

more preferably, ring A is selected from the following groups:

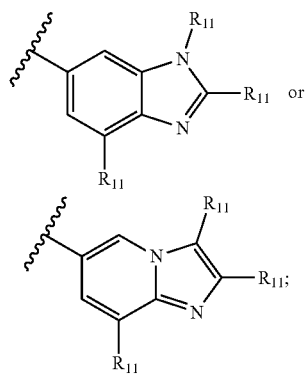

wherein, as long as the chemistry permits, $R_{11}$ is independently selected from H, halo, optionally substituted $C_1$-$C_6$ alkyl, optionally substituted $C_1$-$C_6$ haloalkyl, optionally substituted $C_{2-6}$ alkenyl, optionally substituted $C_1$-$C_6$ alkoxy or optionally substituted $C_1$-$C_6$ haloalkoxy; preferably, $R_{11}$ is independently selected from H, halo, optionally substituted $C_1$-$C_6$ alkyl or optionally substituted $C_{2-6}$ alkenyl; more preferably, $R_{11}$ is independently selected from H, -F, methyl, isopropyl or 1-propen-2-yl; or, two adjacent $R_{11}$ could be taken together to form optionally substituted $C_5$-$C_8$ carbocyclyl, optionally substituted 5- to 8-membered heterocyclyl, optionally substituted $C_6$-$C_{14}$ aryl or optionally substituted 5- to 10-membered heteroaryl;

most preferably, ring A is selected from the following groups:

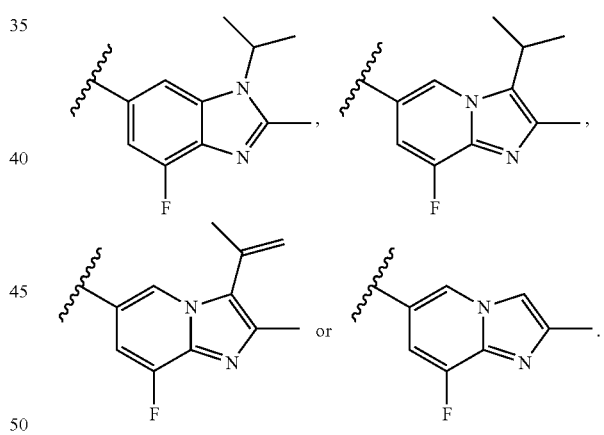

Another embodiment of the above aspect is the above compound, wherein
Y is selected from the following structures:

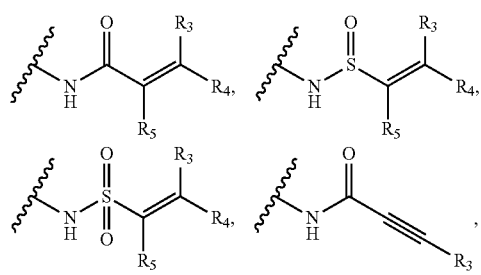

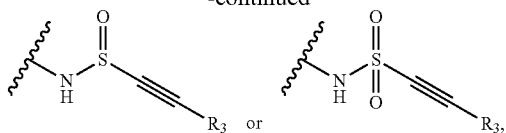

Y is selected from the following structures:

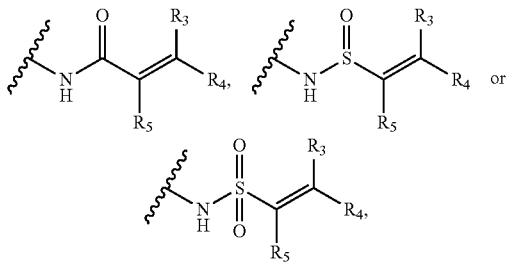

preferably, Y is selected from the following structures:

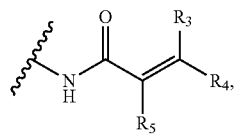

wherein $R_3$, $R_4$ and $R_5$ is independently selected from H, halo, optionally substituted $C_1$-$C_6$ alkyl or optionally substituted $C_1$-$C_6$ haloalkyl; preferably, $R_3$, $R_4$ and $R_5$ is independently selected from H or halo; more preferably, $R_3$, $R_4$ and $R_5$ are all H.

Another embodiment of the above aspect is the above compound, wherein m is 1 or 2; preferably, m is 1.

Another embodiment of the above aspect is the above compound, wherein $R_1$ is selected from H, halo, —CN, —NO$_2$, optionally substituted $C_1$-$C_6$ alkyl, optionally substituted $C_1$-$C_6$ haloalkyl, optionally substituted $C_1$-$C_6$ alkoxy, optionally substituted $C_1$-$C_6$ haloalkoxy, optionally substituted $C_1$-$C_6$ alkylthio, optionally substituted $C_1$-$C_6$ alkylamino or optionally substituted $C_1$-$C_6$ alkanoyl; preferably, $R_1$ is selected from H, halo, —CN, —NO$_2$, optionally substituted $C_1$-$C_6$ alkyl, optionally substituted $C_1$-$C_6$ haloalkyl, optionally substituted $C_1$-$C_6$ alkoxy or optionally substituted $C_1$-$C_6$ haloalkoxy; preferably, $R_1$ is selected from H or halo; more preferably, $R_1$ is selected from H or F.

Another embodiment of the above aspect is the above compound, wherein $R_2$ is selected from H, halo, optionally substituted $C_1$-$C_6$ alkyl, optionally substituted $C_1$-$C_6$ haloalkyl, optionally substituted $C_1$-$C_6$ alkoxy, optionally substituted $C_1$-$C_6$ haloalkoxy, optionally substituted $C_1$-$C_6$ alkylthio, optionally substituted $C_1$-$C_6$ alkylamino or optionally substituted $C_1$-$C_6$ alkanoyl; preferably, $R_2$ is selected from H, halo, optionally substituted $C_1$-$C_6$ alkyl, optionally substituted $C_1$-$C_6$ haloalkyl, optionally substituted $C_1$-$C_6$ alkoxy or optionally substituted $C_1$-$C_6$ haloalkoxy; preferably, $R_2$ is selected from H, halo, optionally substituted $C_1$-$C_6$ alkyl or optionally substituted $C_1$-$C_6$ alkoxy; more preferably, $R_2$ is selected from H or optionally substituted $C_1$-$C_6$ alkoxy; more preferably, $R_2$ is selected from methoxy.

Another embodiment of the above aspect is the above compound, wherein $R_6$ is selected from $C_1$-$C_6$ alkyl or 4- to 7-membered heterocyclyl; more preferably, $R_6$ is selected from $C_1$-$C_6$ alkyl or 5- to 6-membered heterocyclyl; more preferably, $R_6$ is selected from ethyl or 6-membered heterocyclyl; more preferably, $R_6$ is selected from ethyl or 6-membered heterocyclyl containing two N heteroatoms; more preferably, $R_6$ is selected from ethyl or piperazinyl;

wherein $R_6$ is optionally substituted by the following substituents: halo, —OH, —CN, —NO$_2$, optionally substituted $C_1$-$C_6$ alkyl, optionally substituted $C_1$-$C_6$ alkoxy or NR$_8$R$_9$; preferably, $R_6$ is optionally substituted by the following substituents: halo, optionally substituted $C_1$-$C_6$ alkyl, optionally substituted $C_1$-$C_6$ alkoxy or NR$_8$R$_9$; more preferably, $R_6$ is optionally substituted by the following substituents: optionally substituted $C_1$-$C_6$ alkyl or NR$_8$R$_9$;

wherein $R_8$ and $R_9$ are each independently selected from optionally substituted $C_1$-$C_6$ alkyl, optionally substituted $C_1$-$C_6$ alkoxy or optionally substituted $C_3$-$C_6$ carbocyclyl; preferably, $R_8$ and $R_9$ are each independently selected from optionally substituted $C_1$-$C_6$ alkyl; more preferably, $R_8$ and $R_9$ are both methyl;

or $R_8$ and $R_9$ together with the nitrogen atom to which they are attached form optionally substituted 4- to 6-membered heterocyclyl, which is substituted by $C_1$-$C_6$ alkyl for example.

Another embodiment of the above aspect is the above compound, wherein n is 0 or 1.

Another embodiment of the above aspect is the above compound, wherein L is selected from NR$_7$, O, C(R$_7$)$_2$ or S; preferably, L is selected from NR$_7$, O or S; more preferably, L is NR$_7$; wherein $R_7$ is selected from H, optionally substituted $C_1$-$C_6$ alkyl or optionally substituted $C_1$-$C_6$ alkoxy; preferably, $R_7$ is selected from H or optionally substituted $C_1$-$C_6$ alkyl; more preferably, $R_7$ is optionally substituted $C_1$-$C_6$ alkyl; more preferably, $R_7$ is methyl.

Another embodiment of the above aspect is the above compound, wherein the group -(L)$^n$-R$_6$ is N(Me)CH$_2$CH$_2$N(Me)$_2$ or selected from the following structures:

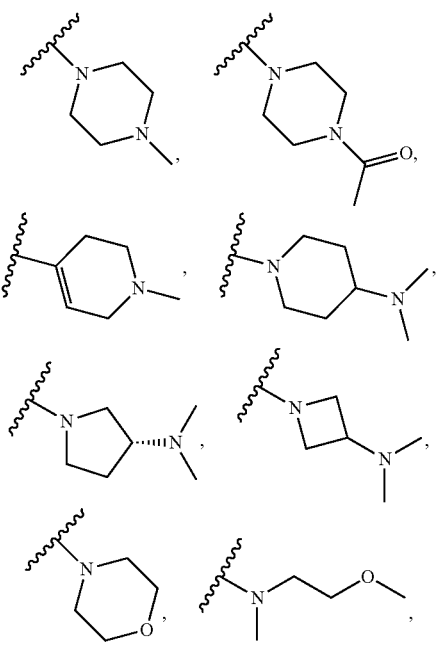

-continued

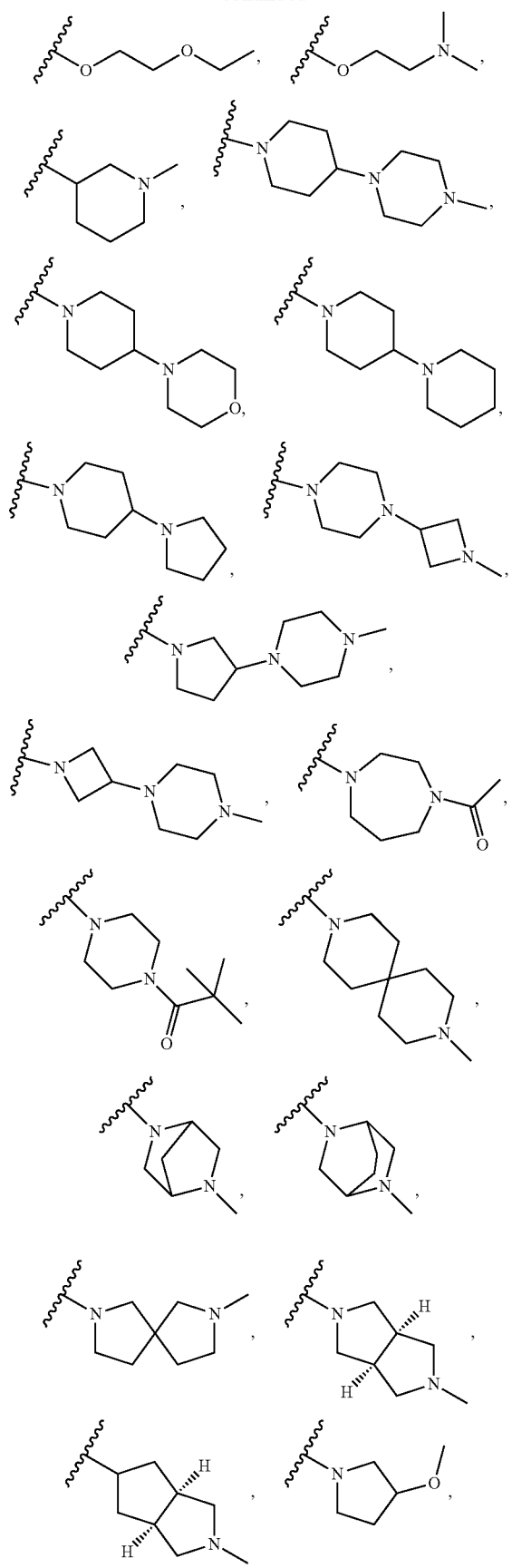

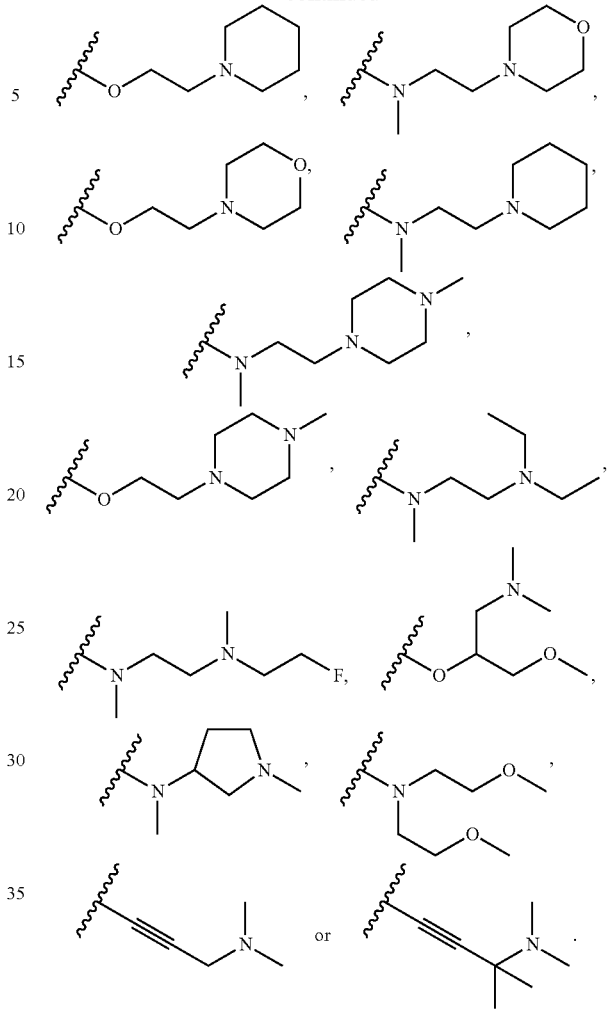

Another embodiment of the above aspect is the above compound, wherein

W is selected from $C(R_{10})_2$, $NR_{10}$, O or S; preferably, W is selected from $NR_{10}$, O or S; more preferably, W is $NR_{10}$;

as long as the chemistry permits, $R_{10}$ is selected from H, halo, —CN, —$NO_2$, optionally substituted $C_{1-6}$ alkyl, optionally substituted $C_{1-6}$ haloalkyl or optionally substituted $C_{1-6}$ alkoxyl; preferably, $R_{10}$ is selected from H, optionally substituted $C_{1-6}$ alkyl, optionally substituted $C_{1-6}$ haloalkyl or optionally substituted $C_{1-6}$ alkoxyl; more preferably, $R_{10}$ is selected from H or optionally substituted $C_{1-6}$ alkyl; more preferably, $R_{10}$ is H.

Another embodiment of the above aspect is the above compound, wherein $R_1$ is selected from H or F; $R_2$ is methoxy; -(L)$^n$-$R_6$ is selected from $N(Me)CH_2CH_2N(Me)_2$ or 4-methylpiperazin-1-yl; and L is

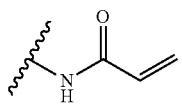 [SMILES: *NC(=O)C=C]

when it is present.

In another aspect, the disclosure provides a pharmaceutical composition comprising a compound disclosed herein and a pharmaceutically acceptable excipient. In a particular embodiment, the compound disclosed herein is provided in the pharmaceutical composition in an effective amount. In a particular embodiment, the compound disclosed herein is provided in a therapeutically effective amount. In a particular embodiment, the compound disclosed herein is provided in a prophylactically effective amount.

In another aspect, the disclosure provides a pharmaceutical composition comprising a compound disclosed herein and a pharmaceutically acceptable excipient, further comprising other therapeutic agents.

In another aspect, the disclosure provides a kit containing a compound, a pharmaceutically acceptable salt, a stereoisomer, a solvate, a hydrate, a polymorph, a prodrug or an isotopic derivative thereof, and other therapeutic agents, and pharmaceutically acceptable carriers, adjuvants or vehicles.

In another aspect, the disclosure provides a method of treating cancer caused by EGFR (including cancer caused by EGFR mutation, e.g., a cancer with a T790M mutation, a L858R mutation, and a L858R/T790M dual mutation) in a subject in need thereof, comprising: administering to the subject an effective amount of a compound disclosed herein.

In a specific embodiment, the Cancer caused by EGFR is selected from the group consisting of: non-small cell lung cancer, small cell lung cancer, lung adenocarcinoma, lung squamous cell carcinoma, pancreatic cancer, breast cancer, prostate cancer, liver cancer, skin cancer, epithelial cancer, gastrointestinal stromal tumors, leukemia, histiocytic lymphoma, nasopharyngeal carcinoma, etc. In a specific embodiment, the compound is administered orally, subcutaneously, intravenously or intramuscularly. In a specific embodiment, the compound is administered chronically.

Other objects and advantages of the present disclosure will be apparent to those skilled in the art from the specific embodiments, examples and claims.

Definitions

Chemical Definitions

Definitions of specific functional groups and chemical terms are described in more detail below.

When a range of values is listed, it is intended to encompass each value and sub-range within the range. For example "$C_1$-$C_6$ alkyl" is intended to encompass, $C_1$, $C_2$, $C_3$, $C_4$, $C_5$, $C_6$, $C_1$-$C_6$, $C_1$-$C_5$, $C_1$-$C_4$, $C_1$-$C_3$, $C_1$-$C_2$, $C_2$-$C_6$, $C_2$-$C_5$, $C_2$-$C_4$, $C_2$-$C_3$, $C_3$-$C_6$, $C_3$-$C_5$, $C_3$-$C_4$, $C_4$-$C_6$, $C_4$-$C_5$ and $C_5$-$C_6$ alkyl.

It should be understood that when described herein any of the moieties defined forth below may be substituted with a variety of substituents, and that the respective definitions are intended to include such substituted moieties within their scope as set out below. Unless otherwise stated, the term "substituted" is to be defined as set out below.

"$C_1$-$C_6$ alkyl" refers to a radical of a straight-chain or branched saturated hydrocarbon group having from 1 to 6 carbon atoms, and it is also referred to herein as "lower alkyl". In some embodiments, $C_1$-$C_4$ alkyl is particularly preferred. Examples of alkyl groups include methyl ($C_1$), ethyl ($C_2$), n-propyl ($C_3$), isopropyl ($C_3$), n-butyl ($C_4$), tert-butyl ($C_4$), sec-butyl ($C_4$), iso-butyl ($C_4$), n-pentyl ($C_5$), 3-pentanyl ($C_5$), amyl ($C_5$), neopentyl ($C_5$), 3-methyl-2-butanyl ($C_5$), tertiary amyl ($C_5$), and n-hexyl ($C_6$). Unless otherwise specified, each instance of an alkyl group is independently optionally substituted, i.e., unsubstituted (an "unsubstituted alkyl") or substituted (a "substituted alkyl") with one or more substituents; e.g., for instance from 1 to 5 substituents, 1 to 3 substituents, or 1 substituent. In certain embodiments, the alkyl group is unsubstituted $C_{1-6}$ alkyl (e.g., —$CH_3$). In certain embodiments, the alkyl group is substituted $C_{1-6}$ alkyl.

"$C_2$-$C_6$ alkenyl" refers to a radical of a straight-chain or branched hydrocarbon group having from 2 to 6 carbon atoms, one or more carbon-carbon double bonds (e.g., 1, 2, or 3 carbon-carbon double bonds). The one or more carbon-carbon double bonds can be internal (such as in 2-butenyl) or terminal (such as in 1-butenyl). In some embodiments, $C_{2-4}$ alkenyl is particularly preferred. Examples of alkenyl groups include, but are not limited to, ethenyl ($C_2$), 1-propenyl ($C_3$), 2-propenyl ($C_3$), 1-propen-2-yl ($C_3$), 1-butenyl ($C_4$), 2-butenyl ($C_4$), butadienyl ($C_4$), pentenyl ($C_5$), pentadienyl ($C_5$), hexenyl ($C_6$), and the like. Unless otherwise specified, each instance of an alkenyl group is independently optionally substituted, i.e., unsubstituted (an "unsubstituted alkenyl") or substituted (a "substituted alkenyl") with one or more substituents e.g., for instance from 1 to 5 substituents, 1 to 3 substituents, or 1 substituent. In certain embodiments, the alkenyl group is unsubstituted $C_{2-6}$ alkenyl. In certain embodiments, the alkenyl group is substituted $C_{2-6}$ alkenyl.

"$C_2$-$C_6$ alkynyl" refers to a radical of a straight-chain or branched hydrocarbon group having from 2 to 6 carbon atoms, one or more carbon-carbon triple bonds (e.g., 1, 2, or 3 carbon-carbon triple bonds), and optionally one or more carbon-carbon double bonds (e.g., 1, 2, or 3 carbon-carbon double bonds). In some embodiments, $C_{2-4}$ alkynyl is particularly preferred. In certain embodiments, alkynyl does not contain any double bonds. The one or more carbon-carbon triple bonds can be internal (such as in 2-butynyl) or terminal (such as in 1-butynyl). Examples of the alkynyl groups include, without limitation, ethynyl ($C_2$), 1-propynyl ($C_3$), 2-propynyl ($C_3$), 1-butynyl ($C_4$), 2-butynyl ($C_4$), pentynyl ($C_5$), 3-methylbut-1-ynyl ($C_5$), hexynyl ($C_6$), and the like. Unless otherwise specified, each instance of an alkynyl group is independently optionally substituted, i.e., unsubstituted (an "unsubstituted alkynyl") or substituted (a "substituted alkynyl") with one or more substituents; e.g., for instance from 1 to 5 substituents, 1 to 3 substituents, or 1 substituent. In certain embodiments, the alkynyl group is unsubstituted $C_{2-6}$ alkynyl. In certain embodiments, the alkynyl group is substituted $C_{2-6}$ alkynyl.

"$C_1$-$C_6$ alkoxy" refers to the group —OR wherein R is a substituted or unsubstituted $C_1$-$C_6$ alkyl group. In some embodiments, $C_1$-$C_4$ alkoxy group is particularly preferred. Specific alkoxy groups include, but are not limited to, methoxy, ethoxy, n-propoxy, isopropoxy, n-butoxy, tert-butoxy, sec-butoxy, n-pentyloxy, n-hexyloxy and 1,2-dimethylbutoxy.

"$C_1$-$C_6$ alkylthio" refers to the group —SR wherein R is optionally substituted $C_1$-$C_6$ alkyl. In some embodiments, $C_1$-$C_4$ alkylthio group is particularly preferred. Specifically, the $C_1$-$C_6$ alkylthio group includes, but is not limited to, methylthio, ethylthio, n-propylthio, isopropylthio, n-butylthio, tert-butylthio, sec-butylthio, n-pentylthio, n-hexylthio and 1,2-dimethylbutylthio.

"$C_1$-$C_6$ alkylamino" refers to the group —NHR or —$NR_2$, wherein R is optionally substituted $C_1$-$C_6$ alkyl. In some embodiments, $C_1$-$C_4$ alkylamino group is particularly preferred. Specifically, the $C_1$-$C_6$ alkylamino group includes, but is not limited to, methylamino, ethylamino, n-propylamino, isopropylamino, n-butylamino, t-butylamino, dimethylamino, methylethylamino and diethylamino.

"$C_1$-$C_6$ alkanoyl" refers to the group —(=O)R, wherein R is optionally substituted $C_1$-$C_6$ alkyl. In some embodiments, $C_1$-$C_4$ alkanoyl group is particularly preferred.

Exemplary $C_1$-$C_6$ alkanoyl groups include, but are not limited to, —(═O)CH$_3$, —(═O)CH$_2$CH$_3$, —(═O)CH$_2$CH$_2$CH$_3$ and —(═O)CH(CH$_3$)$_2$.

"Halo" or "halogen" means fluorine (F), chlorine (Cl), bromine (Br) and iodine (I). In some embodiments, the halo group is F, —Cl or Br. In some embodiments, the halogen group is F or Cl. In some embodiments, the halogen group is F.

Thus, "$C_1$-$C_6$ haloalkyl" and "$C_1$-$C_6$ haloalkoxy" refer to the above "$C_1$-$C_6$ alkyl" and "$C_1$-$C_6$ alkoxy", which are substituted by one or more halo groups. In some embodiments, $C_1$-$C_4$ haloalkyl group is particularly preferred, and more preferably $C_1$-$C_2$ haloalkyl group. In some embodiments, $C_1$-$C_4$ haloalkoxy group is particularly preferred, and more preferably $C_1$-$C_2$ haloalkoxy group. Exemplary haloalkyl groups include, but are not limited to, —CF$_3$, —CH$_2$F, —CHF$_2$, —CHFCH$_2$F, —CH$_2$CHF$_2$, —CF$_2$CF$_3$, —CCl$_3$, —CH$_2$Cl, —CHCl$_2$, 2,2,2-trifluoro-1,1-dimethyl-ethyl, and the like. Exemplary haloalkoxy groups include, but are not limited to: —OCH$_2$F, —OCHF$_2$, —OCF$_3$, and the like.

"$C_3$-$C_8$ carbocyclyl" refers to a radical of a non-aromatic cyclic hydrocarbon group having from 3 to 8 ring carbon atoms and zero heteroatoms. In some embodiments, $C_5$-$C_8$ carbocyclyl is preferred, which is a radical of a non-aromatic cyclic hydrocarbon group having from 5 to 8 ring carbon atoms and zero heteroatoms. In some embodiments, $C_3$-$C_6$ carbocyclyl is preferred, which is a radical of a non-aromatic cyclic hydrocarbon group having from 3 to 6 ring carbon atoms and zero heteroatoms. In some embodiments, $C_5$ carbocyclyl is preferred, which is a radical of a non-aromatic cyclic hydrocarbon group having 5 ring carbon atoms and zero heteroatoms. Carbocyclyl also includes ring systems wherein the carbocyclyl ring, as defined above, is fused with one or more aryl or heteroaryl groups wherein the point of attachment is on the carbocyclyl ring, and in such instances, the number of carbons continue to designate the number of carbons in the carbocyclic ring system. Exemplary carbocyclyl groups include, but is not limited to, cyclopropyl ($C_3$), cyclopropenyl ($C_3$), cyclobutyl ($C_4$), cyclobutenyl ($C_4$), cyclopentyl ($C_5$), cyclopentenyl ($C_5$), cyclopentadienyl ($C_5$), cyclohexyl ($C_6$), cyclohexenyl ($C_6$), cyclohexadienyl ($C_6$), as well as cycloheptyl ($C_7$), cycloheptenyl ($C_7$), cycloheptadienyl ($C_7$), cycloheptatrienyl ($C_7$), cyclooctyl ($C_8$), cyclooctenyl ($C_8$), bicyclo[2.2.1]heptanyl ($C_7$), bicyclo[2.2.2]octanyl ($C_8$), and the like. Unless otherwise specified, each instance of a carbocyclyl group is independently optionally substituted, i.e., unsubstituted (an "unsubstituted carbocyclyl") or substituted (a "substituted carbocyclyl") with one or more substituents. In certain embodiments, the carbocyclyl group is unsubstituted $C_{3-8}$ carbocyclyl. In certain embodiments, the carbocyclyl group is a substituted $C_{3-8}$ carbocyclyl.

"3- to 8-membered heterocyclyl" refers to a radical of a 3- to 8-membered non-aromatic ring system having ring carbon atoms and 1 to 3 ring heteroatoms, wherein each heteroatom is independently selected from nitrogen, oxygen, sulfur, boron, phosphorus, and silicon, wherein the carbon, nitrogen, sulfur and phosphorus atoms may be present in the oxidation state, such as C(O), S(O), S(O)$_2$, P(O), and the like. In heterocyclyl groups that contain one or more nitrogen atoms, the point of attachment can be a carbon or nitrogen atom, as valency permits. In some embodiments, 4- to 7-membered heterocyclyl is preferred, which is a radical of a 4- to 7-membered non-aromatic ring system having ring carbon atoms and 1 to 3 ring heteroatoms. In some embodiments, 5- to 8-membered heterocyclyl is preferred, which is a radical of a 5- to 8-membered non-aromatic ring system having ring carbon atoms and 1 to 3 ring heteroatoms. In some embodiments, 4- to 6-membered heterocyclyl is preferred, which is a radical of a 4- to 6-membered non-aromatic ring system having ring carbon atoms and 1 to 3 ring heteroatoms. In some embodiments, 5- to 6-membered heterocyclyl is preferred, which is a radical of a 5- to 6-membered non-aromatic ring system having ring carbon atoms and 1 to 3 ring heteroatoms. In some embodiments, 5-membered heterocyclyl is more preferred, which is a radical of a 5-membered non-aromatic ring system having ring carbon atoms and 1 to 3 ring heteroatoms. In some embodiments, the 3- to 8-membered heterocyclyl, 4- to 7-membered heterocyclyl, 5- to 8-membered heterocyclyl, 4- to 6-membered heterocyclyl, 5- to 6-membered heterocyclyl and 5-membered heterocyclyl contain 1 to 3 (more preferably 1 or 2) ring heteroatoms selected from nitrogen, oxygen and sulfur (preferably nitrogen and oxygen). Unless otherwise specified, each instance of heterocyclyl is independently optionally substituted, i.e., unsubstituted (an "unsubstituted heterocyclyl") or substituted (a "substituted heterocyclyl") with one or more substituents. In certain embodiments, the heterocyclyl group is unsubstituted 3-8 membered heterocyclyl. In certain embodiments, the heterocyclyl group is substituted 3-8 membered heterocyclyl. Heterocyclyl also includes ring systems wherein the heterocyclyl ring, as defined above, is fused with one or more carbocyclyl groups wherein the point of attachment is on the carbocyclyl ring, or ring systems wherein the heterocyclyl ring, as defined above, is fused with one or more aryl or heteroaryl groups, wherein the point of attachment is on the heterocyclyl ring; and in such instances, the number of ring members continue to designate the number of ring members in the heterocyclyl ring system. Exemplary 3-membered heterocyclyl groups containing one heteroatom include, without limitation, azirdinyl, oxiranyl, thiorenyl. Exemplary 4-membered heterocyclyl groups containing one heteroatom include, without limitation, azetidinyl, oxetanyl and thietanyl. Exemplary 5-membered heterocyclyl groups containing one heteroatom include, without limitation, tetrahydrofuranyl, dihydrofuranyl, tetrahydrothiophenyl, dihydrothiophenyl, pyrrolidinyl, dihydropyrrolyl and pyrrolyl-2,5-dione. Exemplary 5-membered heterocyclyl groups containing two heteroatoms include, without limitation, dioxolanyl, oxathiolanyl, oxathiolyl (1,2-oxathiolyl, 1,3-oxathiolyl), dithiolanyl, dihydropyrazolyl, dihydroimidazolyl, dihydrothiazolyl, dihydroisothiazolyl, dihydrooxazolyl, dihydroisoxazolyl, dihydrooxadiazolyl and oxazolidin-2-one. Exemplary 5-membered heterocyclyl groups containing three heteroatoms include, without limitation, triazolinyl, oxadiazolinyl, and thiadiazolinyl. Exemplary 6-membered heterocyclyl groups containing one heteroatom include, without limitation, piperidinyl, tetrahydropyranyl, dihydropyridinyl, tetrahydropyridinyl, and thianyl. Exemplary 6-membered heterocyclyl groups containing two heteroatoms include, without limitation, dihydropyrazinyl, piperazinyl, morpholinyl, dithianyl, dioxanyl. Exemplary 6-membered heterocyclyl groups containing two heteroatoms include, without limitation, triazinanyl. Exemplary 7-membered heterocyclyl groups containing one or two heteroatoms include, without limitation, azepanyl, diazepanyl, oxepanyl and thiepanyl. Exemplary 8-membered heterocyclyl groups containing one or two heteroatoms include, without limitation, azocanyl, oxecanyl, thiocanyl, octahydrocyclopenta[c]pyrrolyl and octahydropyrrolo[3,4-c]pyrrolyl. Exemplary 5-membered heterocyclyl groups fused to a $C_6$ aryl ring (also referred to herein as a 5,6-bicyclic heterocyclic ring) include, without limitation, indolinyl, isoindolinyl, dihydrobenzofuranyl, dihydrobenzothienyl, benzoxazolinonyl, and the like. Exemplary 6-membered heterocyclyl groups fused to an $C_6$ aryl ring (also referred to herein as a 6,6-bicyclic heterocyclic ring) include, without limitation, tetrahydroquinolinyl, tetrahydroisoquinolinyl, and the like.

"$C_6$-$C_{14}$ aryl" refers to a radical of a monocyclic or polycyclic (e.g., bicyclic or tricyclic) 4n+2 aromatic ring system (e.g., having 6, 10, or 14 π electrons shared in a cyclic array) having 6-14 ring carbon atoms and zero heteroatoms provided in the aromatic ring system. In some embodiments, an aryl group has six ring carbon atoms ("$C_6$ aryl"; e.g., phenyl). In some embodiments, an aryl group has ten ring carbon atoms ("$C_{10}$ aryl"; e.g., naphthyl such as 1-naphthyl and 2-naphthyl). In some embodiments, an aryl group has fourteen ring carbon atoms ("$C_{14}$ aryl"; e.g., anthracyl). "$C_6$-$C_{14}$ aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. Typical aryl groups include, but are not limited to, groups derived from aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, and trinaphthalene. Particularly aryl groups include phenyl, naphthyl, indenyl, and tetrahydronaphthyl. Unless otherwise specified, each instance of an aryl group is independently optionally substituted, i.e., unsubstituted (an "unsubstituted aryl") or substituted (a "substituted aryl") with one or more substituents. In certain embodiments, the aryl group is unsubstituted $C_{6-14}$ aryl. In certain embodiments, the aryl group is substituted $C_{6-14}$ aryl.

"5- to 10-membered heteroaryl" refers to a radical of a 5-10 membered monocyclic or bicyclic 4n+2 aromatic ring system (e.g., having 6 or 10 π electrons shared in a cyclic array) having ring carbon atoms and 1-4 ring heteroatoms provided in the aromatic ring system, wherein each heteroatom is independently selected from nitrogen, oxygen and sulfur. In some embodiments, 5-membered heteroaryl is preferred, which is a radical of a 5-membered monocyclic 4n+2 aromatic ring system (e.g., having 6 π electrons shared in a cyclic array) having ring carbon atoms and 1-4 ring heteroatoms, wherein each heteroatom is independently selected from nitrogen, oxygen and sulfur. In heteroaryl groups that contain one or more nitrogen atoms, the point of attachment can be a carbon or nitrogen atom, as valency permits. Heteroaryl bicyclic ring systems can include one or more heteroatoms in one or both rings. Heteroaryl includes ring systems wherein the heteroaryl ring, as defined above, is fused with one or more carbocyclyl or heterocyclyl groups wherein the point of attachment is on the heteroaryl ring, and in such instances, the number of ring members continue to designate the number of ring members in the heteroaryl ring system. Unless otherwise specified, each instance of a heteroaryl group is independently optionally substituted, i.e., unsubstituted (an "unsubstituted heteroaryl") or substituted (a "substituted heteroaryl") with one or more substituents. In certain embodiments, the heteroaryl group is unsubstituted 5- to 10-membered heteroaryl. In certain embodiments, the heteroaryl group is substituted 5- to 10-membered heteroaryl. Exemplary 5-membered heteroaryl groups containing one heteroatom include, without limitation, pyrrolyl, furanyl and thiophenyl. Exemplary 5-membered heteroaryl groups containing two heteroatoms include, without limitation, imidazolyl, pyrazolyl, oxazolyl, isoxazolyl, thiazolyl, and isothiazolyl. Exemplary 5-membered heteroaryl groups containing three heteroatoms include, without limitation, triazolyl, oxadiazolyl, and thiadiazolyl. Exemplary 5-membered heteroaryl groups containing four heteroatoms include, without limitation, tetrazolyl. Exemplary 6-membered heteroaryl groups containing one heteroatom include, without limitation, pyridinyl. Exemplary 6-membered heteroaryl groups containing two heteroatoms include, without limitation, pyridazinyl, pyrimidinyl, and pyrazinyl. Exemplary 6-membered heteroaryl groups containing three or four heteroatoms include, without limitation, triazinyl and tetrazinyl, respectively. Exemplary 7-membered heteroaryl groups containing one heteroatom include, without limitation, azepinyl, oxepinyl, and thiepinyl. Exemplary 5,6-bicyclic heteroaryl groups include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include, without limitation, naphthyridinyl, pteridinyl, quinolinyl, isoquinolinyl, cinnolinyl, quinoxalinyl, phthalazinyl, and quinazolinyl.

Alkyl, alkenyl, alkynyl, carbocyclyl, heterocyclyl, aryl, and heteroaryl groups, as defined herein, are optionally substituted groups. In general, the term "substituted", whether preceded by the term "optionally" or not, means that at least one hydrogen present on a group (e.g., a carbon or nitrogen atom) is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, any of the substituents described herein that results in the formation of a stable compound. For purposes of this invention, heteroatoms such as nitrogen may have hydrogen substituents and/or any suitable substituent as described herein which satisfy the valencies of the heteroatoms and results in the formation of a stable moiety.

Exemplary carbon atom substituents include, but are not limited to, halogen, —CN, —NO$_2$, —N$_3$, —SO$_2$H, —SO$_3$H, —OH, —OR$^{aa}$, —ON(R$^{bb}$)$_2$, —N(R$^{bb}$)$_2$, —N(R$^{bb}$)$_3$$^+$X$^-$, —N(OR$^{cc}$)R$^{bb}$, —SH, —SR$^{aa}$, —SSR$^{cc}$, —C(=O)R$^{aa}$, —CO$_2$H, —CHO, —C(OR$^{cc}$)$_2$, —CO$_2$R$^{aa}$, —OC(=O)R$^{aa}$, —OCO$_2$R$^{aa}$, —C(=O)N(R$^{bb}$)$_2$, —OC(=O)N(R$^{bb}$)$_2$, —NR$^{bb}$C(=O)R$^{aa}$, —NR$^{bb}$CO$_2$R, —NR$^{bb}$C(=O)N(R$^{bb}$)$_2$, —C(=NR$^{bb}$)R$^a$, —C(=NR$^{bb}$)OR$^{aa}$, —OC(=NR$^{bb}$)R$^{aa}$, —OC(=NR$^{bb}$)OR$^{aa}$, —C(=NR$^{bb}$)N(R$^{bb}$)$_2$, —OC(=NR$^{bb}$)N(R$^{bb}$)$_2$, —NR$^{bb}$C(=NR$^{bb}$)N(R$^{bb}$)$_2$, —C(=O)NR$^{bb}$SO$_2$R$^{aa}$, —NR$^{bb}$SO$_2$R$^{aa}$, —SO$_2$N(R$^{bb}$)$_2$, —SO$_2$R$^{aa}$, —SO$_2$OR$^{aa}$, —OSO$_2$R$^{aa}$, —S(=O)R$^{aa}$, —OS(=O)R$^{aa}$, —Si(R$^{aa}$)$_3$, —OSi(R$^{aa}$)$_3$, —C(=S)N(R$^{bb}$)$_2$, —C(=O)SR$^{aa}$, —C(=S)SR$^{aa}$, —SC(=S)SR$^{aa}$, —SC(=O)SR$^{aa}$, —OC(=O)SR$^{aa}$, —SC(=O)OR$^{aa}$, —SC(=O)R$^{aa}$, —P(=O)$_2$R$^{aa}$, —OP(=O)$_2$R$^{aa}$, —P(=O)(R$^{aa}$)$_2$, —OP(=O)(R$^{aa}$)$_2$, —OP(=O)(OR$^{cc}$)$_2$, —P(=O)$_2$N(R$^{bb}$)$_2$, —OP(=O)$_2$N(R$^{bb}$)$_2$, —P(=O)

$-(NR^{bb})_2$, $-OP(=O)(NR^{bb})_2$, $-NR^{bb}P(=O)(OR^{cc})_2$, $-NR^{bb}P(=O)(NR^{bb})_2$, $-P(R^{cc})_2$, $-P(R^{cc})_3$, $-OP(R^{cc})_2$, $-OP(R^{cc})_3$, $-B(R^{aa})_2$, $-B(OR^{cc})_2$, $-BR^{aa}(OR^{cc})$, alkyl, perhaloalkyl, alkenyl, alkynyl, carbocyclyl, heterocyclyl, aryl, and heteroaryl, wherein each alkyl, alkenyl, alkynyl, carbocyclyl, heterocyclyl, aryl, and heteroaryl is independently substituted with 0, 1, 2, 3, 4, or 5 $R^{dd}$ groups;

or two geminal hydrogens on a carbon atom are replaced with the group $=O$, $=S$, $=NN(R^{bb})_2$, $=NNR^{bb}C(=O)R^{aa}$, $=NNR^{bb}C(=O)OR^{aa}$, $=NNR^{bb}S(=O)_2R^{aa}$, $=NR^{bb}$, or $=NOR^{cc}$;

each instance of $R^{aa}$ is, independently, selected from alkyl, perhaloalkyl, alkenyl, alkynyl, carbocyclyl, heterocyclyl, aryl, and heteroaryl, or two $R^{aa}$ groups are joined to form a heterocyclyl or heteroaryl ring, wherein each alkyl, alkenyl, alkynyl, carbocyclyl, heterocyclyl, aryl, and heteroaryl is independently substituted with 0, 1, 2, 3, 4, or 5 $R^{dd}$ groups;

each instance of $R^{bb}$ is, independently, selected from hydrogen, $-OH$, $-OR^{aa}$, $-N(R^{cc})_2$, $-CN$, $-C(=O)R^{aa}$, $-C(=O)N(R^{cc})_2$, $-CO_2R^{aa}$, $-SO_2R^{aa}$, $-C(=NR^{cc})OR^{aa}$, $-C(=NR^{cc})N(R^{cc})_2$, $-SO_2N(R^{cc})_2$, $-SO_2R^{cc}$, $-SO_2OR^{cc}$, $-SOR^{aa}$, $-C(=S)N(R^{cc})_2$, $-C(=O)SR^{cc}$, $-C(=S)SR^{cc}$, $-P(=O)_2R^{aa}$, $-P(=O)(R^{aa})_2$, $-P(=O)_2N(R^{cc})_2$, $-P(=O)(NR^{cc})_2$, alkyl, perhaloalkyl, alkenyl, alkynyl, carbocyclyl, heterocyclyl, aryl, and heteroaryl, or two $R^{bb}$ groups are joined to form a heterocyclyl or heteroaryl ring, wherein each alkyl, alkenyl, alkynyl, carbocyclyl, heterocyclyl, aryl, and heteroaryl is independently substituted with 0, 1, 2, 3, 4, or 5 $R^{dd}$ groups;

each instance of $R^{cc}$ is, independently, selected from hydrogen, alkyl, perhaloalkyl, alkenyl, alkynyl, carbocyclyl, heterocyclyl, aryl, and heteroaryl, or two $R^{cc}$ groups are joined to form a heterocyclyl or heteroaryl ring, wherein each alkyl, alkenyl, alkynyl, carbocyclyl, heterocyclyl, aryl, and heteroaryl is independently substituted with 0, 1, 2, 3, 4, or 5 $R^{dd}$ groups;

each instance of $R^{dd}$ is, independently, selected from halogen, $-CN$, $-NO_2$, $-N_3$, $-SO_2H$, $-SO_3H$, $-OH$, $-OR^{ee}$, $-ON(R^{ff})_2$, $-N(R^{ff})_2$, $-N(R^{ff})_3^+X^-$, $-N(OR^{ee})R^{ff}$, $-SH$, $-SR^{ee}$, $-SSR^{ee}$, $-C(=O)R^{ee}$, $-CO_2H$, $-CO_2R^{ee}$, $-OC(=O)R^{ee}$, $-OCO_2R^{ee}$, $-C(=O)N(R^{ff})_2$, $-OC(=O)N(R^{ff})_2$, $-NR^{ff}C(=O)R^{ee}$, $-NR^{ff}CO_2R^{ee}$, $-NR^{ff}C(=O)N(R^{ff})_2$, $-C(=NR^{ff})OR^{ee}$, $-OC(=NR^{ff})R^{ee}$, $-OC(=NR^{ff})OR^{ee}$, $-C(=NR^{ff})N(R^{ff})_2$, $-OC(=NR^{ff})N(R^{ff})_2$, $-NR^{ff}C(=NR^{ff})N(R^{ff})_2$, $-NR^{ff}SO_2R^{ee}$, $-SO_2N(R^{ff})_2$, $-SO_2R^{ee}$, $-SO_2OR^{ee}$, $-OSO_2R^{ee}$, $-S(=O)R^{ee}$, $-Si(R^{ee})_3$, $-OSi(R^{ee})_3$, $-C(=S)N(R^{ff})_2$, $-C(=O)SR^{ee}$, $-C(=S)SR^{ee}$, $-SC(=S)SR^{ee}$, $-P(=O)_2R^{ee}$, $-P(=O)(R^{ee})_2$, $-OP(=O)(R^{ee})_2$, $-OP(=O)(OR^{ee})_2$, alkyl, perhaloalkyl, alkenyl, alkynyl, carbocyclyl, heterocyclyl, aryl, heteroaryl, wherein each alkyl, alkenyl, alkynyl, carbocyclyl, heterocyclyl, aryl, and heteroaryl is independently substituted with 0, 1, 2, 3, 4, or 5 $R^{gg}$ groups, or two geminal $R^{dd}$ substituents can be joined to form $=O$ or $=S$;

each instance of $R^{ee}$ is, independently, selected from alkyl, perhaloalkyl, alkenyl, alkynyl, carbocyclyl, aryl, heterocyclyl, and heteroaryl, wherein each alkyl, alkenyl, alkynyl, carbocyclyl, heterocyclyl, aryl, and heteroaryl is independently substituted with 0, 1, 2, 3, 4, or 5 $R^{gg}$ groups;

each instance of $R^{ff}$ is, independently, selected from hydrogen, alkyl, perhaloalkyl, alkenyl, alkynyl, carbocyclyl, heterocyclyl, aryl and heteroaryl, or two $R^{ff}$ groups are joined to form a heterocyclyl or heteroaryl ring, wherein each alkyl, alkenyl, alkynyl, carbocyclyl, heterocyclyl, aryl, and heteroaryl is independently substituted with 0, 1, 2, 3, 4, or 5 $R^{gg}$ groups; and each instance of $R^{gg}$ is, independently, halogen, $-CN$, $-NO_2$, $-N_3$, $-SO_2H$, $-SO_3H$, $-OH$, $-OC_{1-6}$ alkyl, $-ON(C_{1-6}$ alkyl$)_2$, $-N(C_{1-6}$ alkyl$)_2$, $-N(C_{1-6}$ alkyl$)_3^+X^-$, $-NH(C_{1-6}$ alkyl$)_2^+X^-$, $-NH_2(C_{1-6}$ alkyl$)^+X^-$, $-NH_3^+X^-$, $-N(OC_{1-6}$ alkyl$)(C_{1-6}$ alkyl$)$, $-N(OH)(C_{1-6}$ alkyl$)$, $-NH(OH)$, $-SH$, $-SC_{1-6}$ alkyl, $-SS(C_{1-6}$ alkyl$)$, $-C(=O)(C_{1-6}$ alkyl$)$, $-CO_2H$, $-CO_2(C_{1-6}$ alkyl$)$, $-OC(=O)(C_{1-6}$ alkyl$)$, $-OCO_2(C_{1-6}$ alkyl$)$, $-C(=O)NH_2$, $-C(=O)N(C_{1-6}$ alkyl$)_2$, $-OC(=O)NH(C_{1-6}$ alkyl$)$, $-NHC(=O)(C_{1-6}$ alkyl$)$, $-N(C_{1-6}$ alkyl$)C(=O)(C_{1-6}$ alkyl$)$, $-NHCO_2(C_{1-6}$ alkyl$)$, $-NHC(=O)N(C_{1-6}$ alkyl$)_2$, $-NHC(=O)NH(C_{1-6}$ alkyl$)$, $-NHC(=O)NH_2$, $-C(=NH)O(C_{1-6}$ alkyl$)$, $-OC(=NH)(C_{1-6}$ alkyl$)$, $-OC(=NH)OC_{1-6}$ alkyl, $-C(=NH)N(C_{1-6}$ alkyl$)_2$, $-C(=NH)NH(C_{1-6}$ alkyl$)$, $-C(=NH)NH_2$, $-OC(=NH)N(C_{1-6}$ alkyl$)_2$, $-OC(NH)NH(C_{1-6}$ alkyl$)$, $-OC(NH)NH_2$, $-NHC(NH)N(C_{1-6}$ alkyl$)_2$, $-NHC(=NH)NH_2$, $-NHSO_2(C_{1-6}$ alkyl$)$, $-SO_2N(C_{1-6}$ alkyl$)_2$, $-SO_2NH(C_{1-6}$ alkyl$)$, $-SO_2NH_2$, $-SO_2C_{1-6}$ alkyl, $-SO_2OC_{1-6}$ alkyl, $-OSO_2C_{1-6}$ alkyl, $-SOC_{1-6}$ alkyl, $-Si(C_{1-6}$ alkyl$)_3$, $-OSi(C_{1-6}$ alkyl$)_3$ $-C(=S)N(C_{1-6}$ alkyl$)_2$, $C(=S)NH(C_{1-6}$ alkyl$)$, $C(=S)NH_2$, $-C(=O)S(C_{1-6}$ alkyl$)$, $-C(=S)SC_{1-6}$ alkyl, $-SC(=S)SC_{1-6}$ alkyl, $-P(=O)_2(C_{1-6}$ alkyl$)$, $-P(=O)(C_{1-6}$ alkyl$)_2$, $-OP(=O)(C_{1-6}$ alkyl$)_2$, $-OP(=O)(OC_{1-6}$ alkyl$)_2$, $C_{1-6}$ alkyl, $C_{1-6}$ perhaloalkyl, $C_{2-6}$ alkenyl, $C_{2-6}$ alkynyl, $C_{3-10}$ carbocyclyl, $C_{6-10}$ aryl, 3-10 membered heterocyclyl, 5-10 membered heteroaryl; or two geminal $R^{gg}$ substituents can be joined to form $=O$ or $=S$; wherein $X^-$ is a counterion.

Exemplary nitrogen atom substituents include, but are not limited to, hydrogen, $-OH$, $-OR^{aa}$, $-N(R^{cc})_2$, $-CN$, $-C(=O)R^{aa}$, $-C(=O)N(R^{cc})_2$, $-CO_2R^{aa}$, $-SO_2R^{aa}$, $-C(=NR^{bb})R^{aa}$, $-C(=NR^{cc})OR^{aa}$, $-C(=NR^{cc})N(R^{cc})_2$, $-SO_2N(R^{cc})_2$, $-SO_2R^{cc}$, $-SO_2OR^{cc}$, $-SOR^{aa}$, $-C(=S)N(R^{cc})_2$, $-C(=O)SR^{cc}$, $-C(=S)SR^{cc}$, $-P(=O)_2R^{aa}$, $-P(=O)(R^{aa})_2$, $-P(=O)_2N(R^{cc})_2$, $-P(=O)(NR^{cc})_2$, alkyl, perhaloalkyl, alkenyl, alkynyl, carbocyclyl, heterocyclyl, aryl, and heteroaryl, or two $R^{cc}$ groups attached to a nitrogen atom are joined to form a heterocyclyl or heteroaryl ring, wherein each alkyl, alkenyl, alkynyl, carbocyclyl, heterocyclyl, aryl, and heteroaryl is independently substituted with 0, 1, 2, 3, 4, or 5 $R^{dd}$ groups, and wherein $R^{aa}$, $R^{bb}$, $R^{cc}$ and $R^{dd}$ are as defined above.

Other Definitions

The term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, Berge et al., describes pharmaceutically acceptable salts in detail in *J. Pharmaceutical Sciences* (1977) 66:1-19. Pharmaceutically acceptable salts of the compounds of the present disclosure include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Pharmaceutically acceptable salts derived from appropriate bases include alkali metal, alkaline earth metal, ammonium and N+($C_{1-4}$alkyl)$_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate, and aryl sulfonate.

A "subject" to which administration is contemplated includes, but is not limited to, humans (i.e., a male or female of any age group, e.g., a pediatric subject (e.g, infant, child, adolescent) or adult subject (e.g., young adult, middle-aged adult or senior adult)) and/or a non-human animal, e.g., a mammal such as primates (e.g., cynomolgus monkeys, rhesus monkeys), cattle, pigs, horses, sheep, goats, rodents, cats, and/or dogs. In certain embodiments, the subject is a human. In certain embodiments, the subject is a non-human animal.

Disease, disorder, and condition are used interchangeably herein.

As used herein, and unless otherwise specified, the terms "treat," "treating" and "treatment" contemplate an action that occurs while a subject is suffering from the specified disease, disorder or condition, which reduces the severity of the disease, disorder or condition, or retards or slows the progression of the disease, disorder or condition ("therapeutic treatment"), and also contemplates an action that occurs before a subject begins to suffer from the specified disease, disorder or condition ("prophylactic treatment").

In general, the "effective amount" of a compound refers to an amount sufficient to elicit the desired biological response. As will be appreciated by those of ordinary skill in this art, the effective amount of a compound disclosed herein may vary depending on such factors as the desired biological endpoint, the pharmacokinetics of the compound, the disease being treated, the mode of administration, and the age, health, and condition of the subject. An effective amount encompasses therapeutic and prophylactic treatment.

As used herein, and unless otherwise specified, a "therapeutically effective amount" of a compound is an amount sufficient to provide a therapeutic benefit in the treatment of a disease, disorder or condition, or to delay or minimize one or more symptoms associated with the disease, disorder or condition. A therapeutically effective amount of a compound means an amount of therapeutic agent, alone or in combination with other therapies, which provides a therapeutic benefit in the treatment of the disease, disorder or condition. The term "therapeutically effective amount" can encompass an amount that improves overall therapy, reduces or avoids symptoms or causes of disease or condition, or enhances the therapeutic efficacy of another therapeutic agent.

As used herein, and unless otherwise specified, a "prophylactically effective amount" of a compound is an amount sufficient to prevent a disease, disorder or condition, or one or more symptoms associated with the disease, disorder or condition, or prevent its recurrence. A prophylactically effective amount of a compound means an amount of a therapeutic agent, alone or in combination with other agents, which provides a prophylactic benefit in the prevention of the disease, disorder or condition. The term "prophylactically effective amount" can encompass an amount that improves overall prophylaxis or enhances the prophylactic efficacy of another prophylactic agent.

"Combination" and related terms mean the simultaneous or sequential administration of a therapeutic agent of the present disclosure. For example, a compound disclosed herein may be administered simultaneously or sequentially with another therapeutic agent in separate unit dosage forms, or together with another therapeutic agent in a single unit dosage form.

"Cancer caused by EGFR" refers to a cancer characterized by an unsuitable high expression of the EGFR gene or a mutation of the EGFR gene that alters the biological activity of the EGFR nucleic acid molecule or polypeptide. Cancers caused by EGFR can occur in any tissue including brain, blood, connective tissue, liver, mouth, muscle, spleen, stomach, testes, and trachea. Cancers caused by EGFR include, but are not limited to, non-small cell lung cancer, small cell lung cancer, lung adenocarcinoma, lung squamous cell carcinoma, pancreatic cancer, breast cancer, prostate cancer, liver cancer, skin cancer, epithelial cell carcinoma, gastrointestinal stromal tumor, leukemia, tissue cell lymphoma, nasopharyngeal cancer.

An "EGFR mutation" or "EGFR mutant" includes one or more deletions, substitutions or additions in the amino acid or nucleotide sequence of the EGFR protein or EGFR coding sequence. The EGFR mutation may also include one or more deletions, substitutions or additions, or fragments thereof, so long as the mutant retains or increases tyrosine kinase activity relative to the wild-type EGFR. In a particular EGFR mutation, the kinase or phosphorylation activity can be increased or decreased relative to the wild-type EGFR (e.g., at least 5%, 10%, 15%, 20%, 30%, 40%, 50%, 60%, 70%, 80%, 90% or even 100%). Exemplary EGFR mutations include, but are not limited to, the T790M mutation, the L858R mutation, and the L858R/T790M dual mutation.

DETAILED DESCRIPTION OF THE EMBODIMENTS

Compound

As used herein, "a compound disclosed herein" refers to a compound of the following formulae (I), (II), (III), (III-a), (III-b), (III-c), (IV) and (IV-a), or a pharmaceutically acceptable salt thereof. The compounds of (I), (II), (III), (III-a), (III-b), (III-c), (IV) and (IV-a) and the pharmaceutically acceptable salts thereof also include any possible stereoisomers, solvates, hydrates, polymorphs, prodrugs or isotopic derivatives.

In an embodiment, the present disclosure relates to a compound of formula (I):

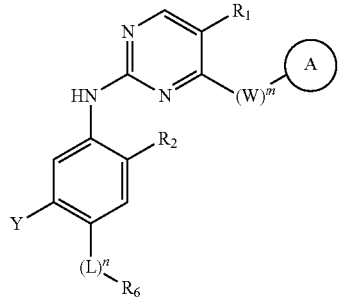

wherein, $R_1$ is selected from H, halo, —CN, —NO$_2$, optionally substituted $C_1$-$C_6$ alkyl, optionally substituted $C_1$-$C_6$ haloalkyl, optionally substituted $C_1$-$C_6$ alkoxy, optionally substituted $C_1$-$C_6$ haloalkoxy, optionally substituted $C_3$-$C_6$ carbocyclyl, optionally substituted $C_1$-$C_6$ alkylthio, optionally substituted $C_1$-$C_6$ alkylamino or optionally substituted $C_1$-$C_6$ alkanoyl;

$R_2$ is selected from H, halo, —CN, —NO$_2$, optionally substituted $C_1$-$C_6$ alkyl, optionally substituted $C_1$-$C_6$ haloalkyl, optionally substituted $C_1$-$C_6$ alkoxy, optionally substituted $C_1$-$C_6$ haloalkoxy, optionally substituted $C_1$-$C_6$ alkylthio, optionally substituted $C_1$-$C_6$ alkylamino or optionally substituted $C_1$-$C_6$ alkanoyl;

L is selected from a bond, NR$_7$, O, C(R$_7$)$_2$ or S; wherein each R$_7$ is independently selected from H, optionally substituted $C_1$-$C_6$ alkyl, such as $C_1$-$C_6$ alkyl substituted by $C_1$-$C_6$ alkoxy, or optionally substituted $C_1$-$C_6$ alkoxy;

Y is H, or Y is selected from the following structures:

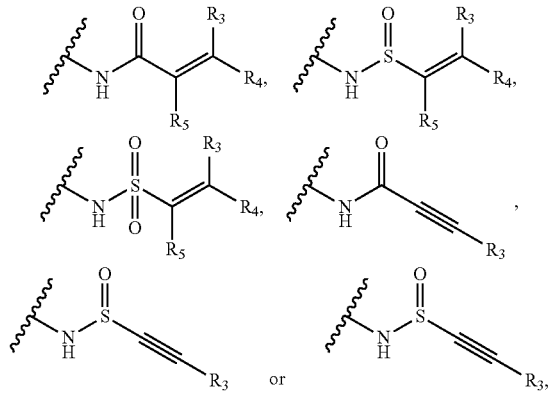

wherein R$_3$, R$_4$ and R$_5$ is independently selected from H, halo, —CN, optionally substituted $C_1$-$C_6$ alkyl or optionally substituted $C_1$-$C_6$ haloalkyl;

R$_6$ is selected from H, $C_1$-$C_6$ alkyl, $C_2$-$C_6$ alkynyl or 3- to 8-membered heterocyclyl, wherein the above groups are optionally substituted by 1-3 following substituents: halo, —OH, —CN, —NO$_2$, optionally substituted $C_1$-$C_6$ alkyl, optionally substituted $C_1$-$C_6$ alkoxy, —C(O)R$_8$ or NR$_8$R$_9$; wherein R$_8$ and R$_9$ are each independently selected from H, optionally substituted $C_1$-$C_6$ alkyl, optionally substituted $C_1$-$C_6$ alkoxy, optionally substituted $C_1$-$C_6$ haloalkyl or optionally substituted $C_3$-$C_6$ carbocyclyl, or R$_8$ and R$_9$ together with the nitrogen atom to which they are attached form optionally substituted 4- to 6-membered heterocyclyl, which is substituted by $C_1$-$C_6$ alkyl for example;

W is selected from a bond, C(R$_{10}$)$_2$, NR$_{10}$, O or S, wherein R$_{10}$ is selected from H, halo, —CN, —NO$_2$, optionally substituted $C_1$-$C_6$ alkyl, optionally substituted $C_1$-$C_6$ haloalkyl or optionally substituted $C_1$-$C_6$ alkoxy, as long as the chemistry permits;

m is 0, 1 or 2;

n is 0, 1 or 2;

ring A is selected from the following structures:

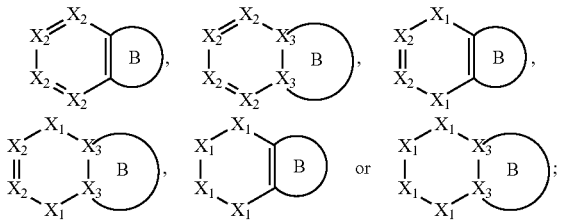

wherein each X$_1$ is independently selected from C(R$_{11}$)$_2$, NR$_{11}$, O or S, each X$_2$ and X$_3$ is independently selected from C(R$_{11}$)$_2$ or NR$_{11}$, wherein X$_1$ and X$_2$ could be the position of attachment to the parent core;

ring B is selected from 5-membered carbocyclyl, 5-membered heterocyclyl or 5-membered heteroaryl, which is optionally substituted by 1-3 R$_{11}$;

R$_{11}$ is independently selected from H, halo, —CN, —NO$_2$, —OH, optionally substituted $C_1$-$C_6$ alkyl, optionally substituted $C_1$-$C_6$ haloalkyl, optionally substituted $C_2$-$C_6$ alkenyl, optionally substituted $C_2$-$C_6$ alkynyl, optionally substituted $C_1$-$C_6$ alkoxy, optionally substituted $C_3$-$C_6$ carbocyclyl or optionally substituted $C_1$-$C_6$ haloalkoxy, as long as the chemistry permits; or, two adjacent R$_{11}$ could be taken together to form optionally substituted $C_5$-$C_8$ carbocyclyl, optionally substituted 5- to 8-membered heterocyclyl, optionally substituted $C_6$-$C_{14}$ aryl or optionally substituted 5- to 10-membered heteroaryl;

or a pharmaceutically acceptable salt, a stereoisomer, a solvate, a hydrate, a polymorph, a prodrug or an isotopic derivative thereof.

In this embodiment, preferably, R$_1$ is selected from H, halo, —CN, —NO$_2$, optionally substituted $C_1$-$C_6$ alkyl, optionally substituted $C_1$-$C_6$ haloalkyl, optionally substituted $C_1$-$C_6$ alkoxy, optionally substituted $C_1$-$C_6$ haloalkoxy, optionally substituted $C_3$-$C_6$ carbocyclyl, optionally substituted $C_1$-$C_6$ alkylthio, optionally substituted $C_1$-$C_6$ alkylamino or optionally substituted $C_1$-$C_6$ alkanoyl; preferably, R$_1$ is selected from H, halo, —CN, —NO$_2$, optionally substituted $C_1$-$C_6$ alkyl, optionally substituted $C_1$-$C_6$ haloalkyl, optionally substituted $C_1$-$C_6$ alkoxy, optionally substituted $C_1$-$C_6$ haloalkoxy, optionally substituted $C_1$-$C_6$ alkylthio, optionally substituted $C_1$-$C_6$ alkylamino or optionally substituted $C_1$-$C_6$ alkanoyl; preferably, R$_1$ is selected from H, halo, —CN, —NO$_2$, optionally substituted $C_1$-$C_6$ alkyl, optionally substituted $C_1$-$C_6$ haloalkyl, optionally substituted $C_1$-$C_6$ alkoxy, optionally substituted $C_1$-$C_6$ haloalkoxy or optionally substituted $C_3$-$C_6$ carbocyclyl; preferably, R$_1$ is selected from H, halo, —CN, —NO$_2$, optionally substituted $C_1$-$C_6$ alkyl, optionally substituted $C_1$-$C_6$ haloalkyl, optionally substituted $C_1$-$C_6$ alkoxy or optionally substituted $C_1$-$C_6$ haloalkoxy; more preferably, R$_1$ is selected from H, halo, —CN, optionally substituted $C_1$-$C_6$ alkyl, optionally substituted $C_1$-$C_6$ haloalkyl, optionally substituted $C_1$-$C_6$ alkoxy or optionally substituted $C_3$-$C_6$ carbocyclyl; more preferably, $R_1$ is selected from H or halo; more preferably, $R_1$ is selected from H, —F, —Br, —Cl, —CN, methyl, trifluoromethyl, methoxy or cyclopropyl; more preferably, $R_1$ is selected from H, —Br, —Cl, methyl or cyclopropyl; more preferably, $R_1$ is selected from H or F.

In this embodiment, preferably, $R_2$ is selected from H, halo, optionally substituted $C_1$-$C_6$ alkyl, optionally substituted $C_1$-$C_6$ haloalkyl, optionally substituted $C_1$-$C_6$ alkoxy, optionally substituted $C_1$-$C_6$ haloalkoxy, optionally substituted $C_3$-$C_6$ carbocyclyl, optionally substituted $C_1$-$C_6$ alkylthio, optionally substituted $C_1$-$C_6$ alkylamino or optionally substituted $C_1$-$C_6$ alkanoyl; preferably, $R_2$ is selected from H, halo, optionally substituted $C_1$-$C_6$ alkyl, optionally substituted $C_1$-$C_6$ haloalkyl, optionally substituted $C_1$-$C_6$ alkoxy, optionally substituted $C_1$-$C_6$ haloalkoxy, optionally substituted $C_1$-$C_6$ alkylthio, optionally substituted $C_1$-$C_6$ alkylamino or optionally substituted $C_1$-$C_6$ alkanoyl; preferably, $R_2$ is selected from H, halo, optionally substituted $C_1$-$C_6$ alkyl, optionally substituted $C_1$-$C_6$ haloalkyl, optionally substituted $C_1$-$C_6$ alkoxy or optionally substituted $C_1$-$C_6$ haloalkoxy; preferably, $R_2$ is selected from H, halo, optionally substituted $C_1$-$C_6$ alkyl, optionally substituted $C_1$-$C_6$ haloalkyl, optionally substituted $C_1$-$C_6$ alkoxy or optionally substituted $C_1$-$C_6$ haloalkoxy; preferably, $R_2$ is selected from H, halo, optionally substituted $C_1$-$C_6$ alkyl, optionally substituted $C_1$-$C_6$ alkoxy or optionally substituted $C_1$-$C_6$ haloalkoxy; preferably, $R_2$ is selected from H, halo, optionally substituted $C_1$-$C_6$ alkyl or optionally substituted $C_1$-$C_6$ alkoxy; more preferably, $R_2$ is selected from H, optionally substituted $C_1$-$C_6$ alkoxy or optionally substituted $C_1$-$C_6$ haloalkoxy; more preferably, $R_2$ is selected from H or optionally substituted $C_1$-$C_6$ alkoxy; more preferably, $R_2$ is selected from —$OCH_3$, —$OCH_2CH_3$, —$OCHF_2$, —$OCH_2CF_3$; more preferably, $R_2$ is selected from methoxy.

In this embodiment, preferably, $R_6$ is selected from $C_1$-$C_6$ alkyl, $C_2$-$C_6$ alkynyl or 3- to 8-membered heterocyclyl; preferably, $R_6$ is selected from $C_1$-$C_6$ alkyl or 4- to 7-membered heterocyclyl; more preferably, $R_6$ is selected from $C_1$-$C_6$ alkyl or 5- to 6-membered heterocyclyl; more preferably, $R_6$ is selected from ethyl or 6-membered heterocyclyl; more preferably, $R_6$ is selected from ethyl or 6-membered heterocyclyl containing one or two N heteroatom; more preferably, $R_6$ is selected from ethyl or 6-membered heterocyclyl containing two N heteroatoms; more preferably, $R_6$ is selected from ethyl, piperidyl, morpholinyl or piperazinyl; more preferably, $R_6$ is selected from ethyl or piperazinyl.

In the above embodiment of $R_6$, $R_6$ is optionally substituted by the following substituents: halo, —OH, —CN, —$NO_2$, optionally substituted $C_1$-$C_6$ alkyl, optionally substituted $C_1$-$C_6$ alkoxy or $NR_8R_9$; preferably, $R_6$ is optionally substituted by the following substituents: halo, optionally substituted $C_1$-$C_6$ alkyl, optionally substituted $C_1$-$C_6$ alkoxy or $NR_8R_9$; more preferably, $R_6$ is optionally substituted by the following substituents: optionally substituted $C_1$-$C_6$ alkyl, optionally substituted $C_1$-$C_6$ alkoxy or $NR_8R_9$; more preferably, $R_6$ is optionally substituted by the following substituents: optionally substituted $C_1$-$C_6$ alkyl or $NR_8R_9$;

wherein $R_8$ and $R_9$ are each independently selected from optionally substituted $C_1$-$C_6$ alkyl, optionally substituted $C_1$-$C_6$ alkoxy or optionally substituted $C_3$-$C_6$ carbocyclyl; preferably, $R_8$ and $R_9$ are each independently selected from optionally substituted $C_1$-$C_6$ alkyl; more preferably, $R_8$ and $R_9$ are all methyl. Or, $R_8$ and $R_9$ together with the nitrogen atom to which they are attached form optionally substituted 4- to 6-membered heterocyclyl, which is substituted by $C_1$-$C_6$ alkyl or $C_1$-$C_6$ alkoxy for example; or $R_8$ and $R_9$ together with the nitrogen atom to which they are attached form optionally substituted 4- to 6-membered heterocyclyl, which is substituted by $C_1$-$C_6$ alkyl for example; more preferably, $R_8$ and $R_9$ together with the nitrogen atom to which they are attached form 4- to 6-membered heterocyclyl containing one N heteroatom, or containing two N heteroatoms, or containing one N heteroatom and one O heteroatom, which is optionally substituted by $C_1$-$C_6$ alkyl or $C_1$-$C_6$ alkoxy; more preferably, $R_8$ and $R_9$ together with the nitrogen atom to which they are attached form 4- to 6-membered heterocyclyl containing one N heteroatom, or containing two N heteroatoms, or containing one N heteroatom and one O heteroatom, which is optionally substituted by $C_1$-$C_6$ alkyl.

In this embodiment, preferably, L is selected from $NR_7$, O, $C(R_7)_2$ or S; preferably, L is selected from $NR_7$, O or S; more preferably, L is $NR_7$.

In the above embodiment of L, $R_7$ is selected from H, optionally substituted $C_1$-$C_6$ alkyl or optionally substituted $C_1$-$C_6$ alkoxy; preferably, $R_7$ is selected from H or optionally substituted $C_1$-$C_6$ alkyl; more preferably, $R_7$ is optionally substituted $C_1$-$C_6$ alkyl; more preferably, $R_7$ is methyl.

In this embodiment, preferably, ring A is selected from the following structures:

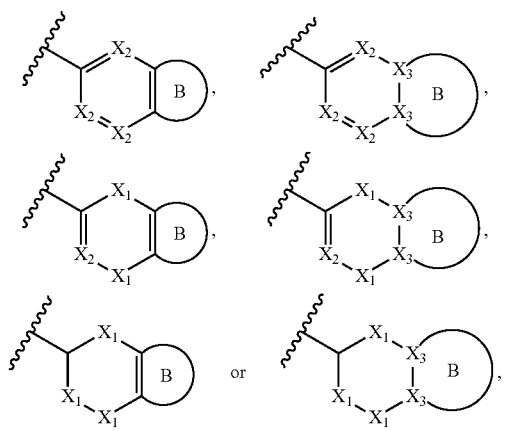

x wherein ring A is optionally substituted by 1-6 $R_{11}$;

preferably, ring A is selected from the following structures:

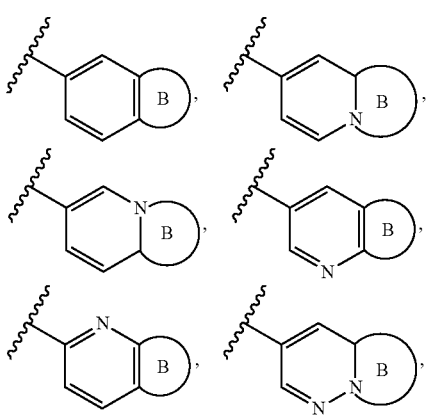

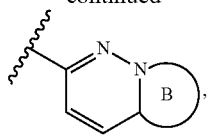

wherein ring A is optionally substituted by 1-6 $R_{11}$;
preferably, ring A is selected from the following structures:

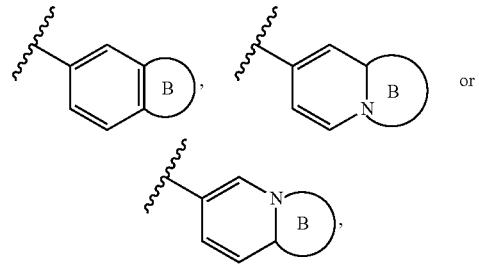

wherein ring A is optionally substituted by 1-6 $R_{11}$;
preferably, ring A is selected from the following structures:

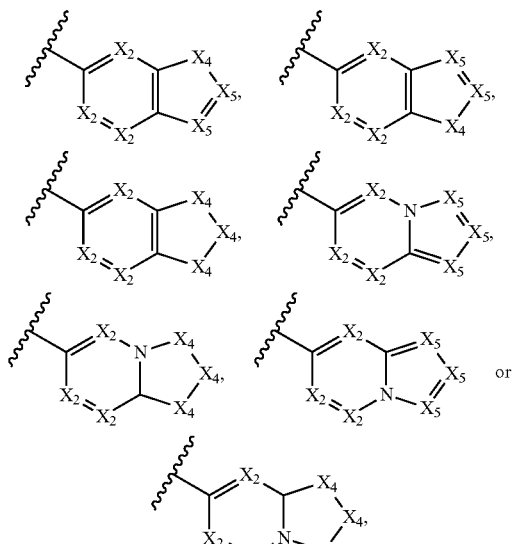

wherein ring A is optionally substituted by 1-6 $R_{11}$, wherein each $X_4$ is independently selected from $C(R_{11})_2$, $NR_{11}$, O, S, C(O), S(O) or $S(O)_2$, each $X_5$ is independently selected from $C(R_{11})_2$ or $NR_{11}$;
preferably, ring A is selected from the following structures:

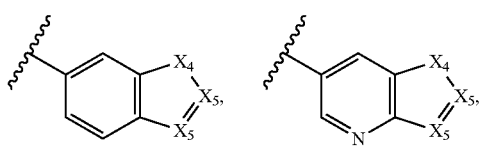

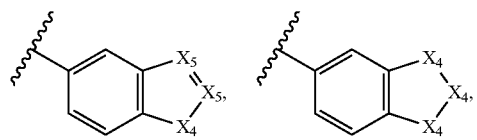

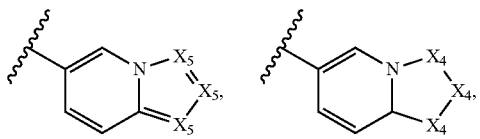

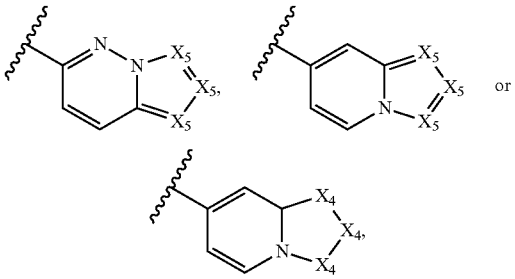

wherein ring A is optionally substituted by 1-6 $R_{11}$, wherein each $X_4$ is independently selected from $C(R_{11})_2$, $NR_{11}$, O, S, C(O), S(O) or $S(O)_2$, each $X_5$ is independently selected from $C(R_{11})_2$ or $NR_{11}$;
preferably, ring A is selected from the following structures:

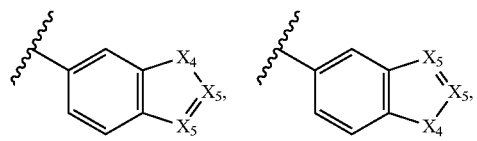

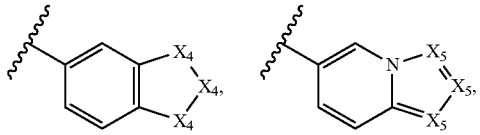

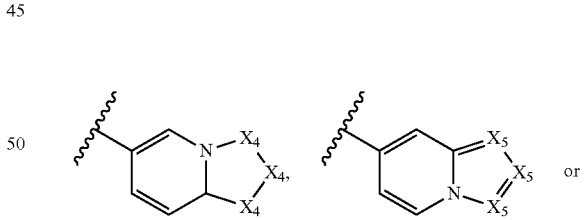

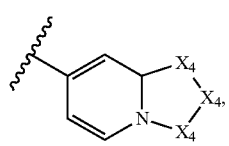

wherein ring A is optionally substituted by 1-6 $R_{11}$, wherein each $X_4$ is independently selected from $C(R_{11})_2$, $NR_{11}$, O, S, C(O), S(O) or $S(O)_2$, each $X_5$ is independently selected from $C(R_{11})_2$ or $NR_{11}$;

preferably, ring A is selected from the following groups:
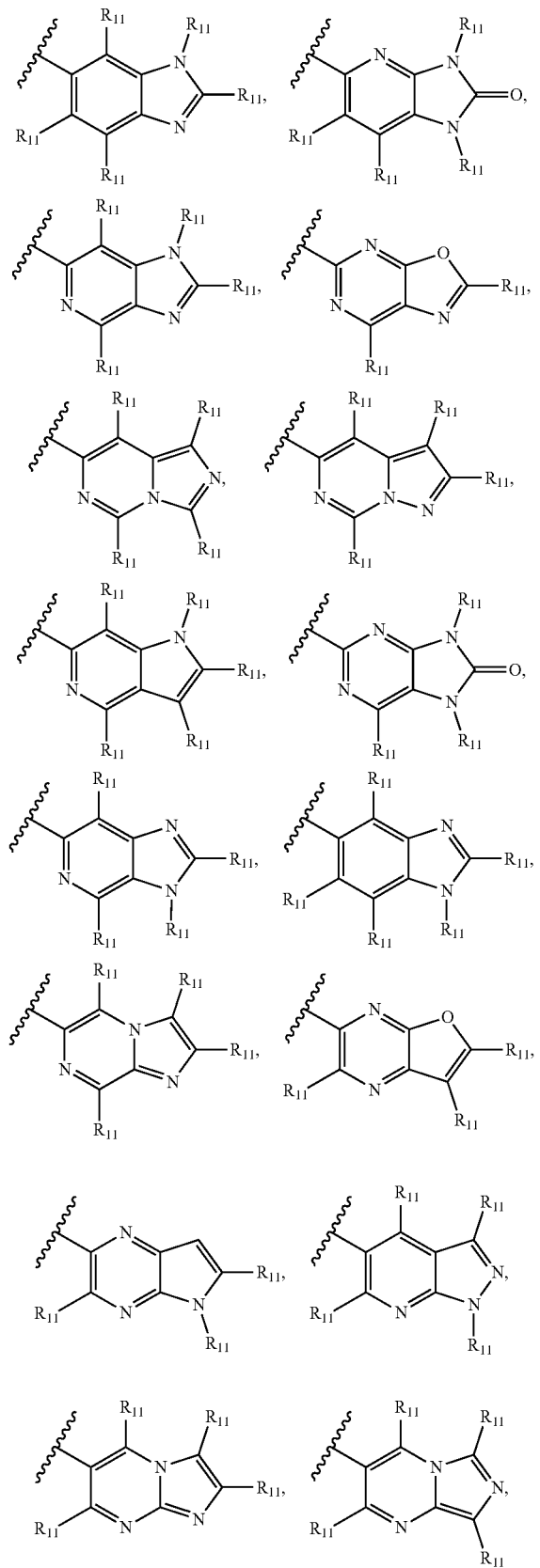
-continued
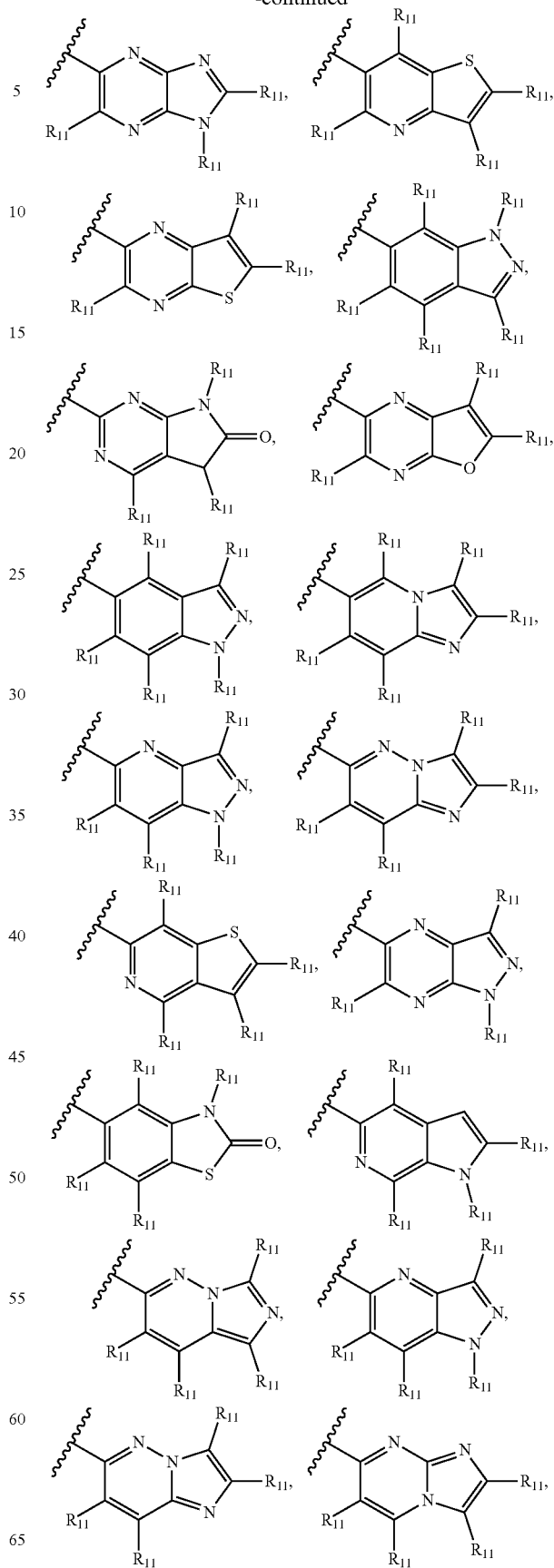

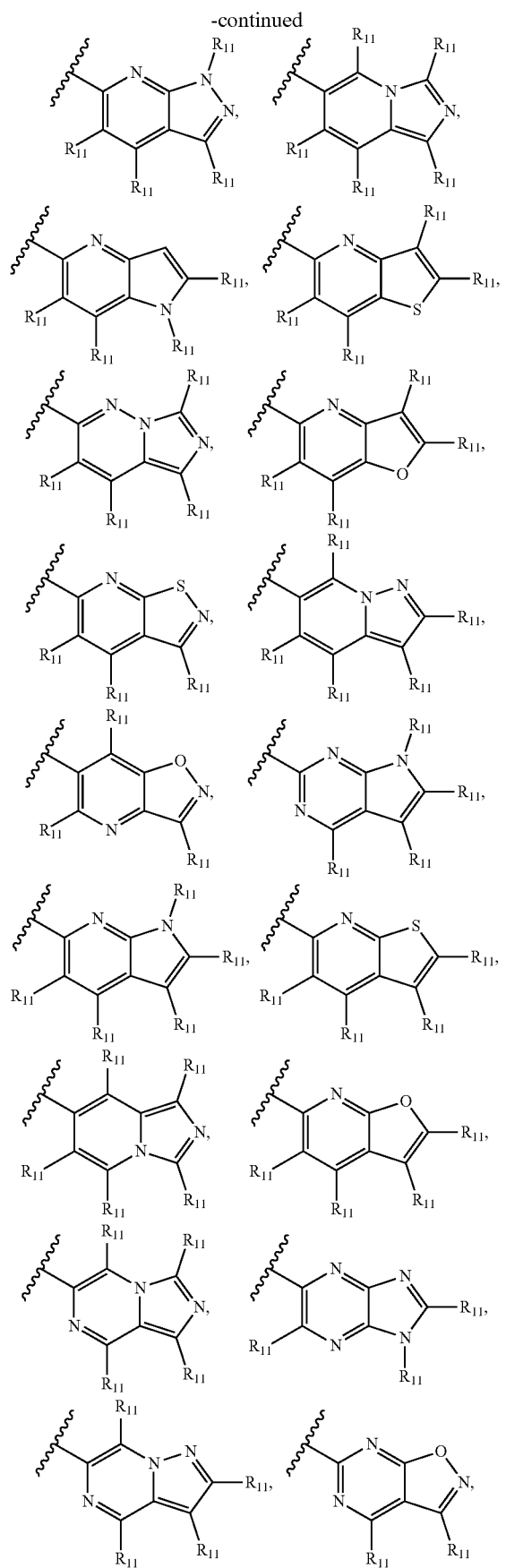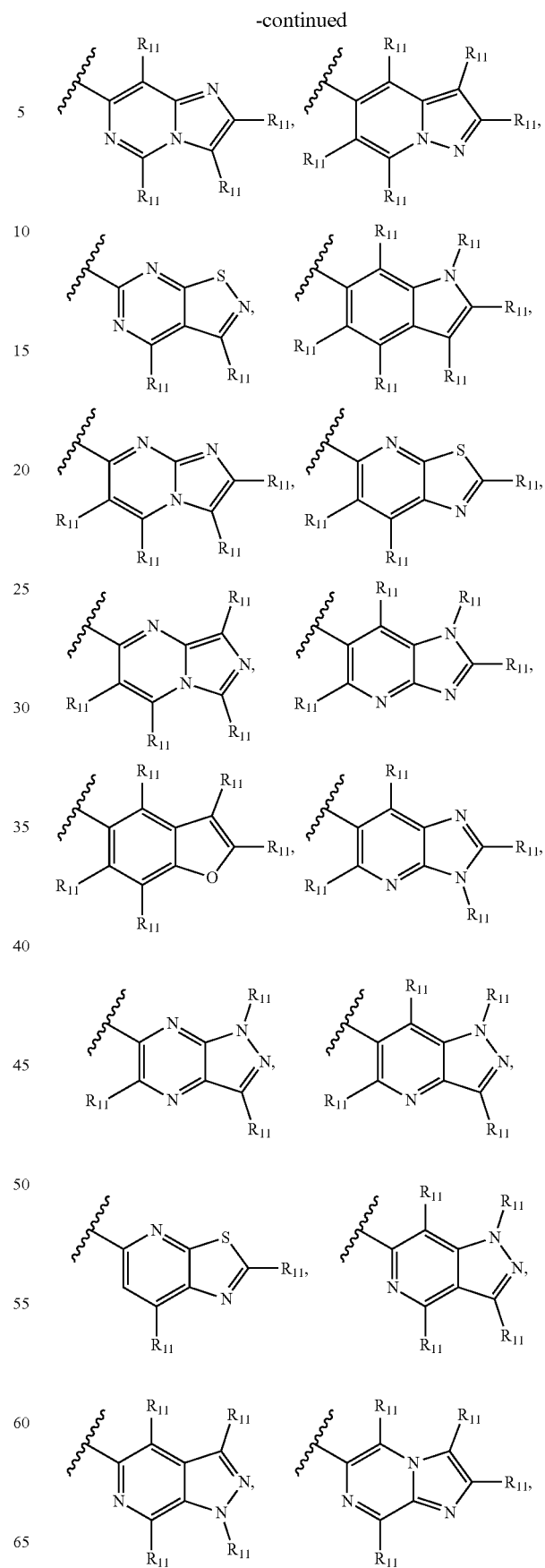

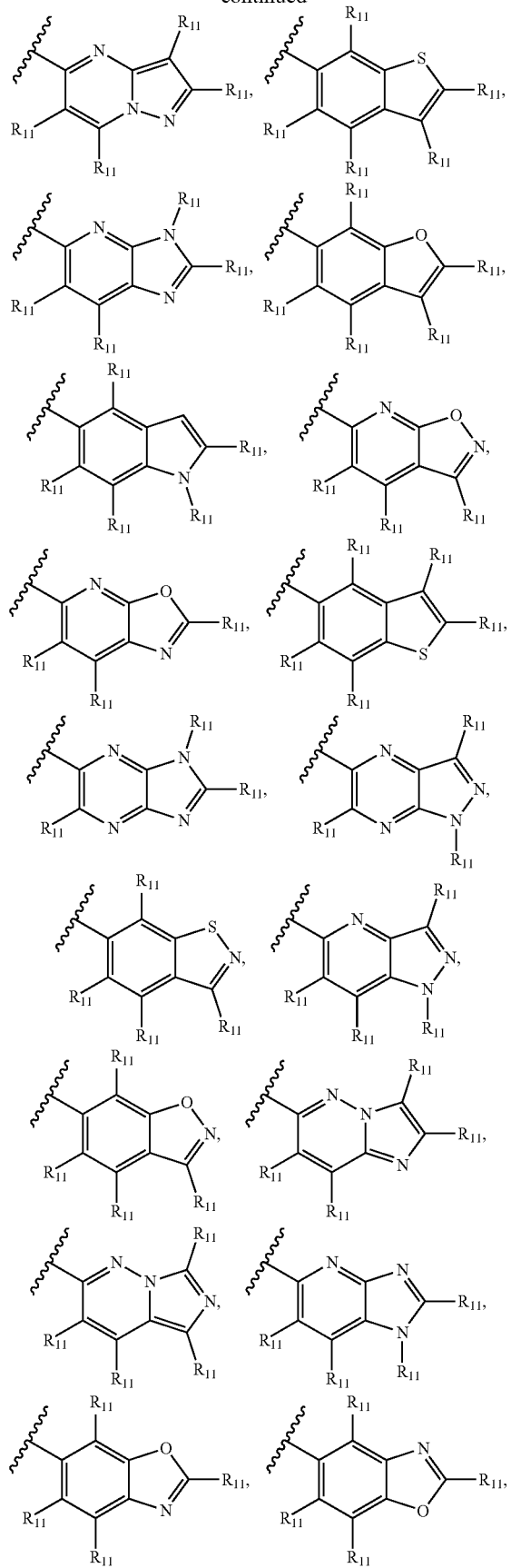
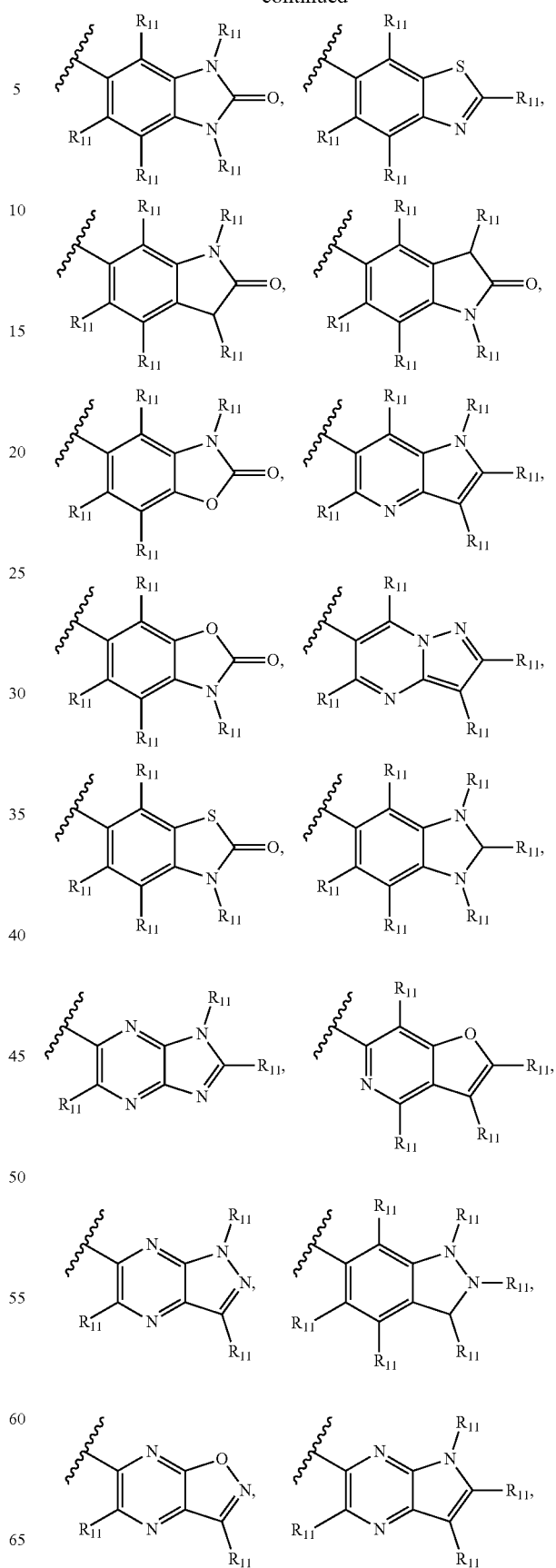

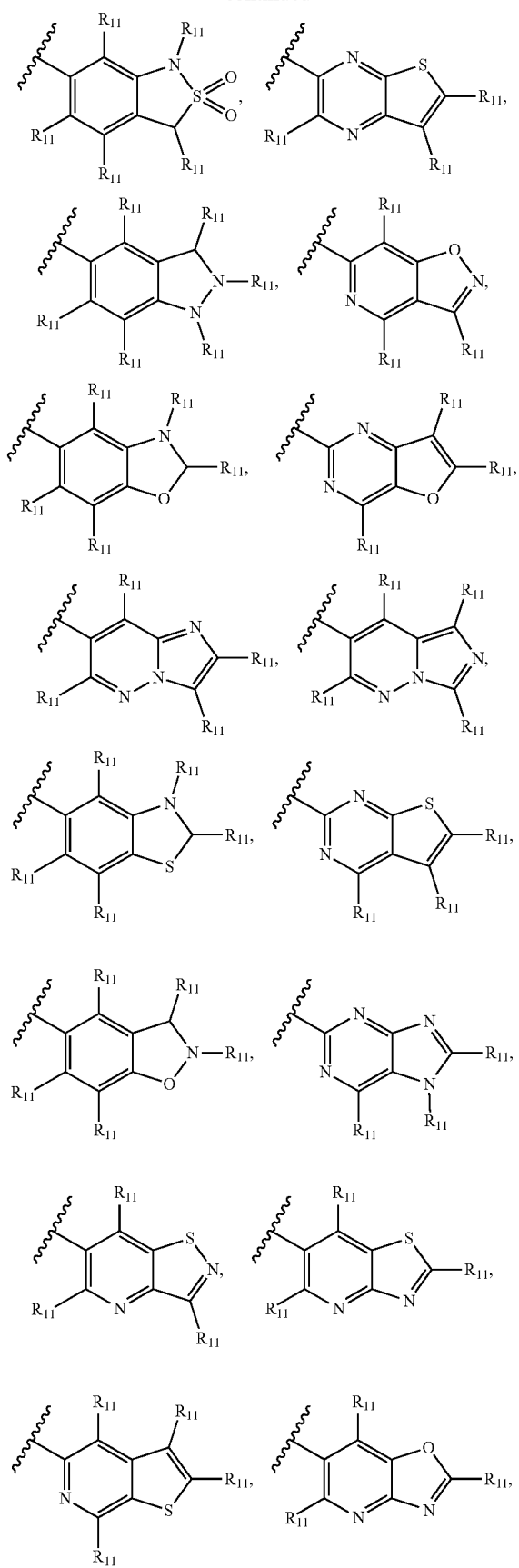
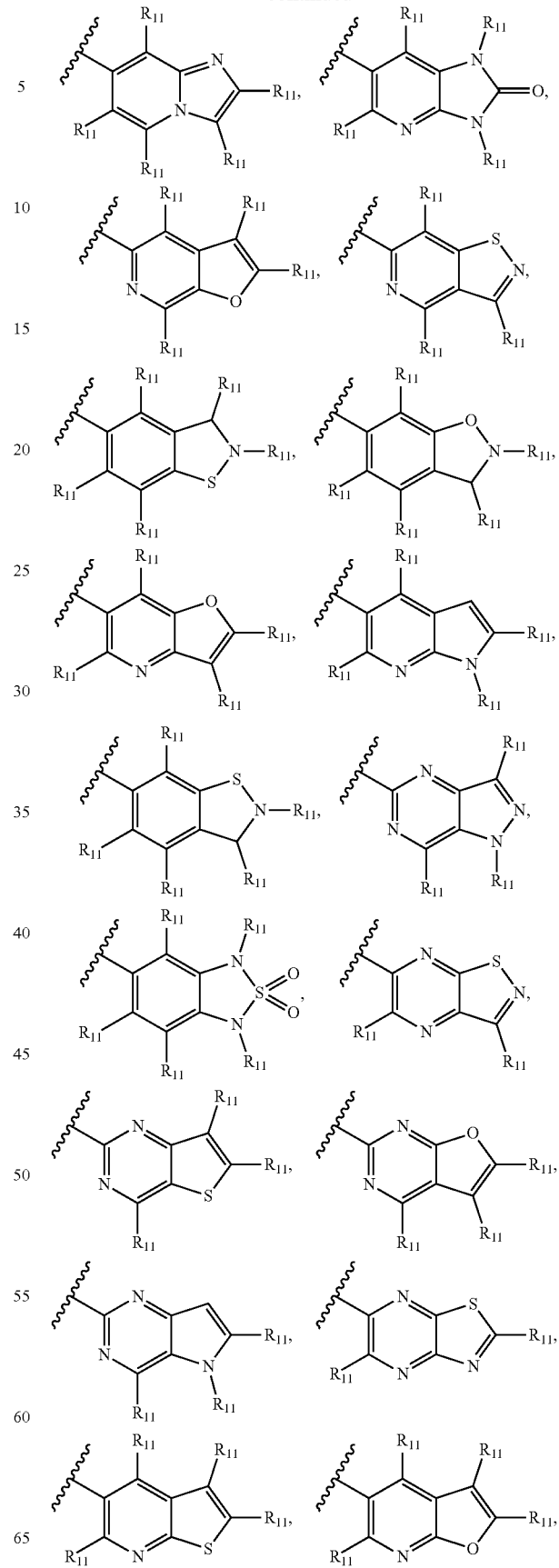

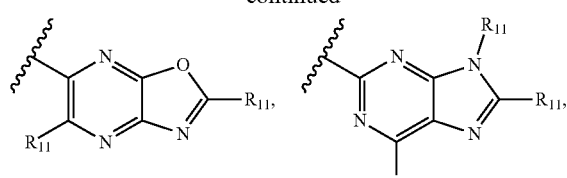
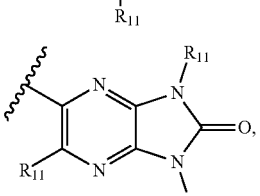
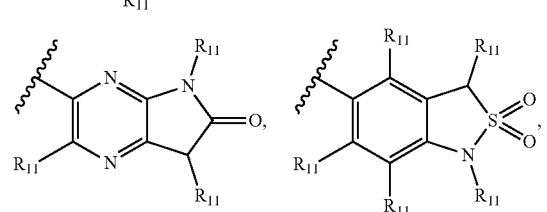
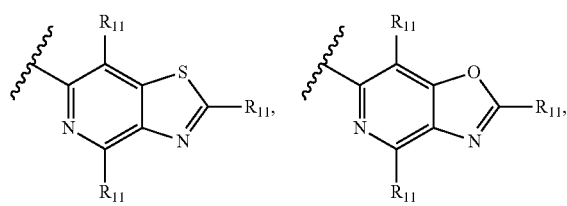
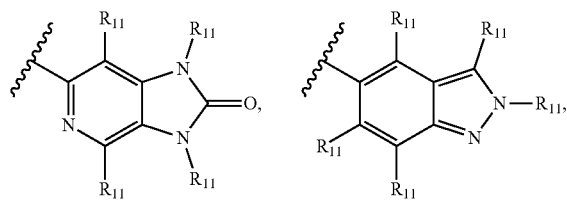
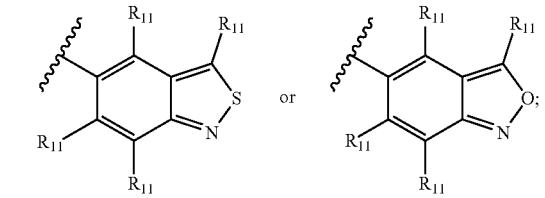
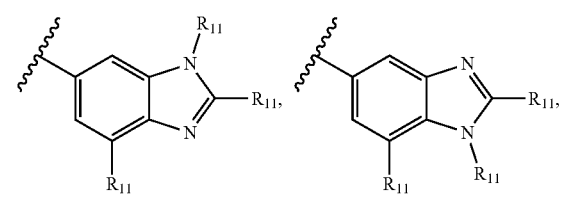
preferably, ring A is selected from the following groups:
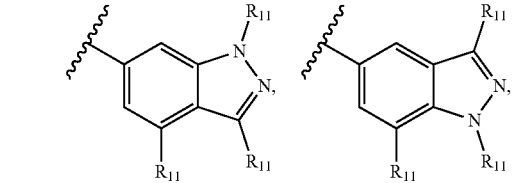
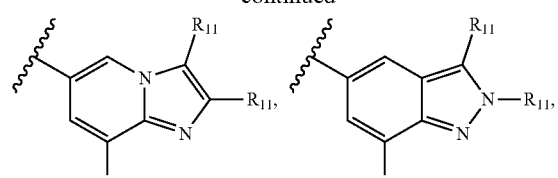
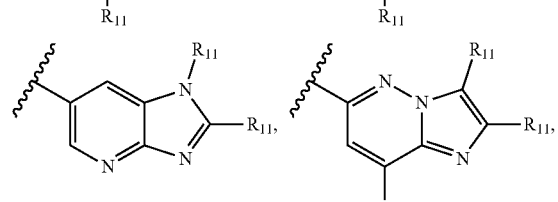
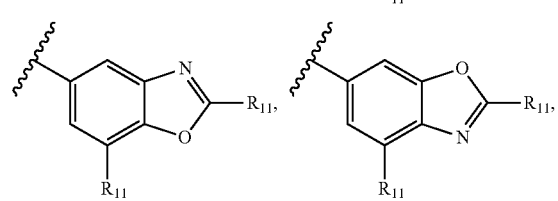
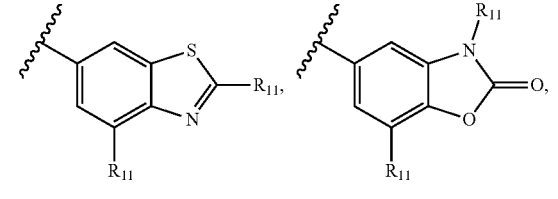
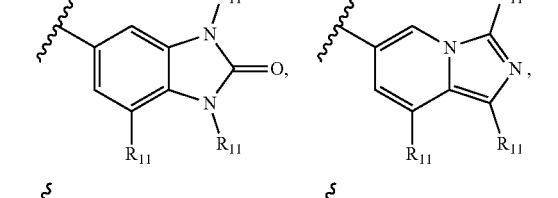
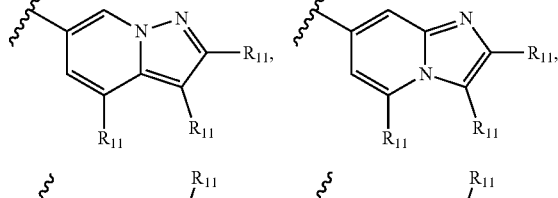
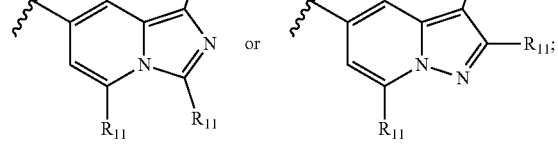
preferably, ring A is selected from the following groups:
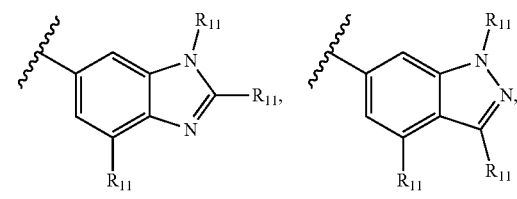

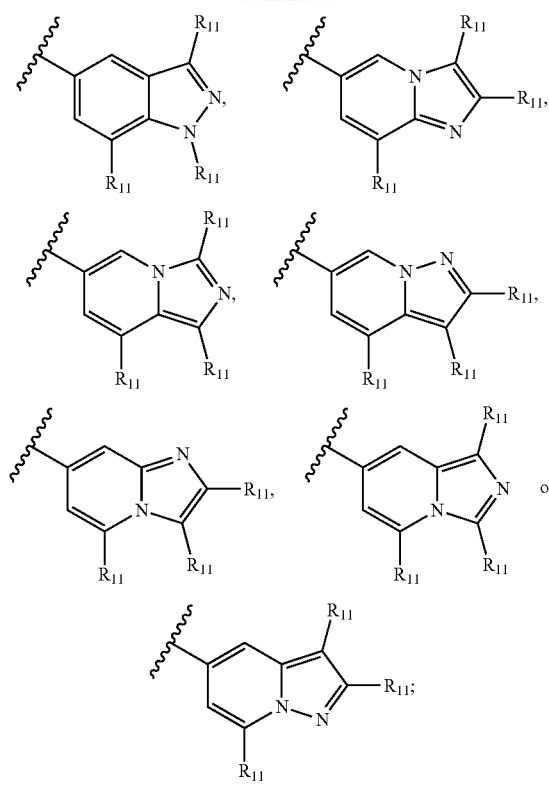
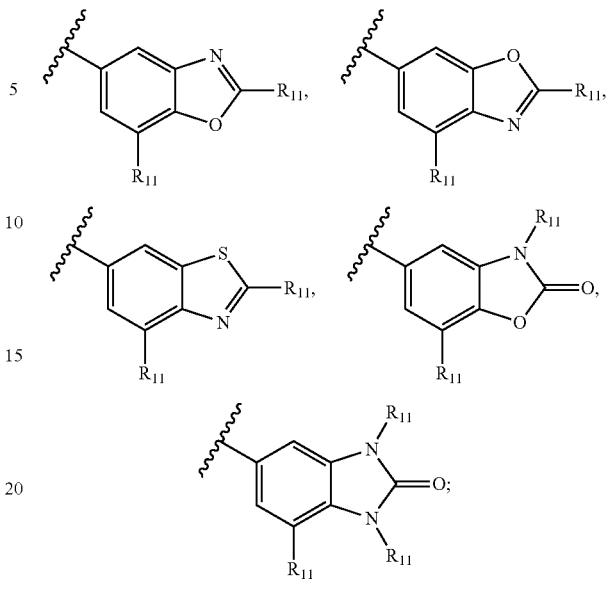

preferably, ring A is selected from the following groups:

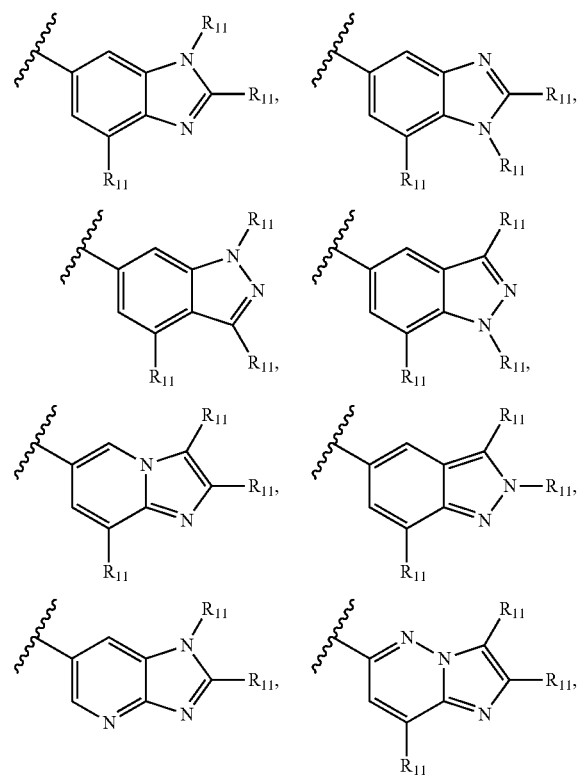

more preferably, ring A is selected from the following groups:

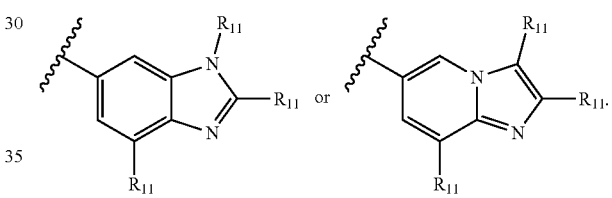

In the above embodiment of ring A, as long as the chemistry permits, $R_{11}$ is independently selected from H, halo, optionally substituted $C_1$-$C_6$ alkyl, optionally substituted $C_1$-$C_6$ haloalkyl, optionally substituted $C_{2-6}$ alkenyl, optionally substituted $C_1$-$C_6$ alkoxy, optionally substituted $C_3$-$C_6$ carbocyclyl or optionally substituted $C_1$-$C_6$ haloalkoxy; preferably, $R_{11}$ is independently selected from H, halo, optionally substituted $C_1$-$C_6$ alkyl, optionally substituted $C_1$-$C_6$ haloalkyl, optionally substituted $C_{2-6}$ alkenyl, optionally substituted $C_1$-$C_6$ alkoxy or optionally substituted $C_1$-$C_6$ haloalkoxy; preferably, $R_{11}$ is independently selected from H, halo, optionally substituted $C_1$-$C_6$ alkyl, optionally substituted $C_1$-$C_6$ haloalkyl, optionally substituted $C_2$-$C_6$ alkenyl, optionally substituted $C_1$-$C_6$ alkoxy or optionally substituted $C_3$-$C_6$ carbocyclyl; preferably, $R_{11}$ is independently selected from H, halo, optionally substituted $C_1$-$C_6$ alkyl or optionally substituted $C_{2-6}$ alkenyl; more preferably, $R_{11}$ is independently selected from H, —F, methyl, isopropyl, trifluoromethyl, 1-propen-2-yl, methoxy, tert-butoxy group, cyclopropyl; more preferably, $R_{11}$ is independently selected from H, —F, methyl, isopropyl or 1-propen-2-yl; or, two adjacent $R_{11}$ could be taken together to form optionally substituted $C_5$-$C_8$ carbocyclyl, optionally substituted 5- to 8-membered heterocyclyl, optionally substituted $C_6$-$C_{14}$ aryl or optionally substituted 5- to 10-membered heteroaryl.

Most preferably, ring A is selected from the following groups:
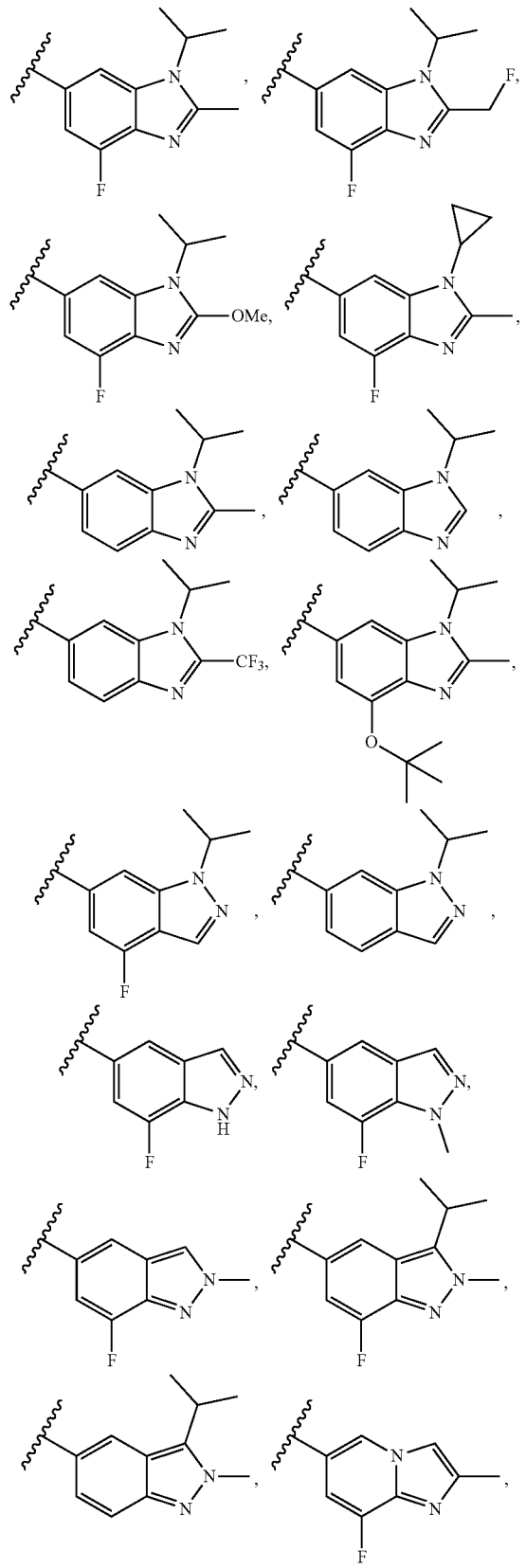
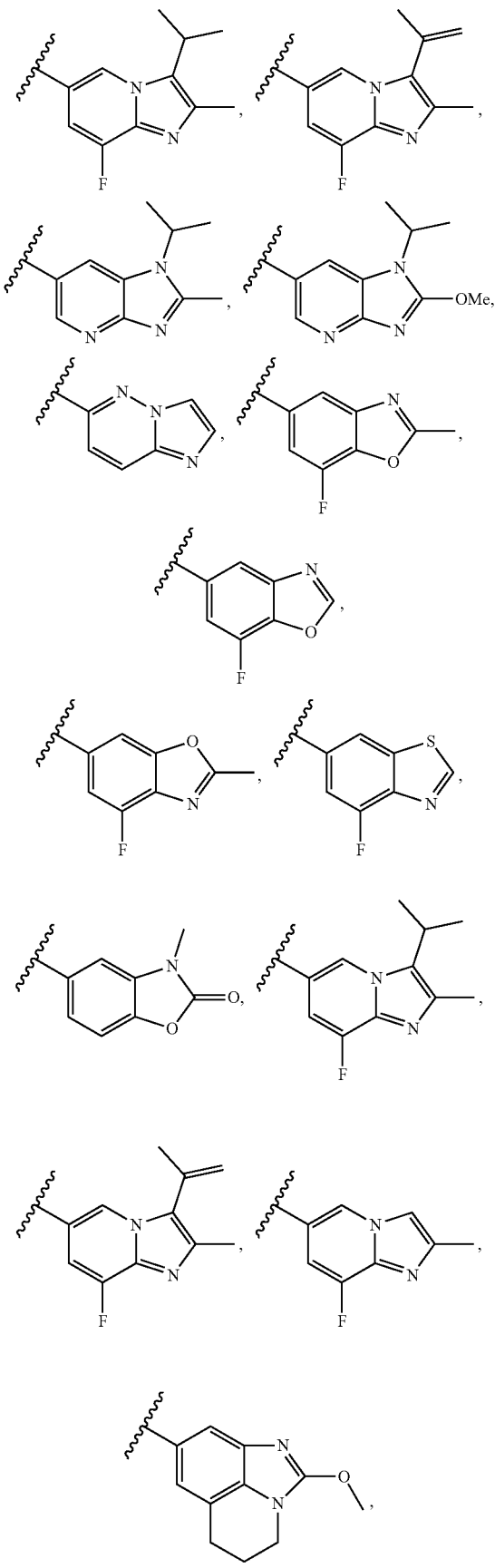

-continued

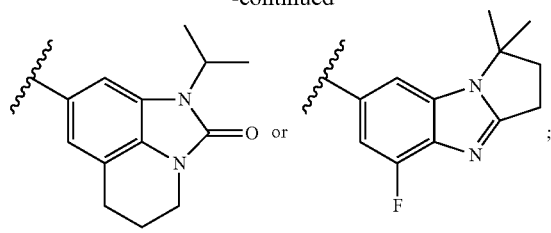

most preferably, ring A is selected from the following groups:

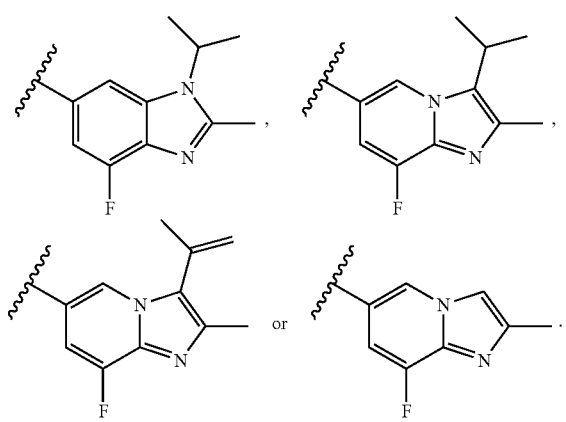

In this embodiment, preferably, Y is H; preferably, Y is selected from the following structures:

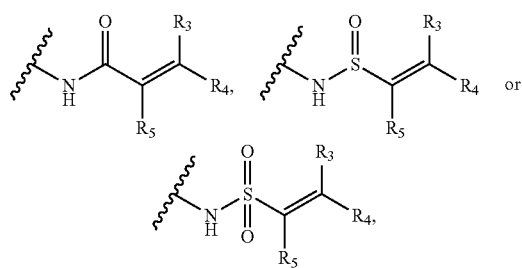

more preferably, Y is selected from the following structures:

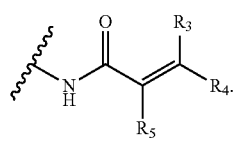

In the above embodiment of Y, $R_3$, $R_4$ and $R_5$ is independently selected from H, halo, optionally substituted $C_1$-$C_6$ alkyl or optionally substituted $C_1$-$C_6$ haloalkyl; preferably, $R_3$, $R_4$ and $R_5$ is independently selected from H or halo; more preferably, $R_3$, $R_4$ and $R_5$ are all H.

In this embodiment, preferably, W is selected from $C(R_{10})_2$, $NR_{10}$, O or S; preferably, W is selected from $NR_{10}$, O or S; more preferably, W is $NR_{10}$.

In the above embodiment of W, as long as the chemistry permits, $R_{10}$ is selected from H, halo, —CN, —NO$_2$, optionally substituted $C_{1-6}$ alkyl, optionally substituted $C_{1-6}$ haloalkyl or optionally substituted $C_{1-6}$ alkoxyl; preferably, $R_{10}$ is selected from H, optionally substituted $C_{1-6}$ alkyl, optionally substituted $C_{1-6}$ haloalkyl or optionally substituted $C_{1-6}$ alkoxyl; more preferably, $R_{10}$ is selected from H or optionally substituted $C_{1-6}$ alkyl; more preferably, $R_{10}$ is H.

In this embodiment, preferably, m is 1 or 2; preferably, m is 1; more preferably, m is 0.

In this embodiment, preferably, n is 0; preferably, n is 1.

In this embodiment, preferably,

L is selected from a bond, $NR_7$, O or S; wherein $R_7$ is selected from H or optionally substituted $C_1$-$C_6$ alkyl;

n is 0, 1 or 2;

$R_6$ is selected from H, $C_1$-$C_6$ alkyl or 3- to 8-membered heterocyclyl, wherein the above groups are optionally substituted by 1-3 following substituents: halo, —OH, —CN, —NO$_2$, optionally substituted $C_1$-$C_6$ alkyl, optionally substituted $C_1$-$C_6$ alkoxy or $NR_8R_9$, wherein $R_8$ and $R_9$ are each independently selected from H or optionally substituted $C_1$-$C_6$ alkyl; or $R_8$ and $R_9$ together with the nitrogen atom to which they are attached form optionally substituted 4- to 6-membered heterocyclyl;

In this embodiment, preferably,

L is selected from a bond or $NR_7$; wherein $R_7$ is selected from H or optionally substituted $C_1$-$C_6$ alkyl;

n is 0 or 1;

$R_6$ is selected from H, $C_1$-$C_6$ alkyl or 3- to 8-membered heterocyclyl, wherein the above groups are optionally substituted by 1-3 following substituents: halo, —OH, —CN, —NO$_2$, optionally substituted $C_1$-$C_6$ alkyl, optionally substituted $C_1$-$C_6$ alkoxy or $NR_8R_9$, wherein $R_8$ and $R_9$ are each independently selected from H or optionally substituted $C_1$-$C_6$ alkyl; or $R_8$ and $R_9$ together with the nitrogen atom to which they are attached form optionally substituted 4- to 6-membered heterocyclyl;

In this embodiment, preferably,

-(L)$^n$-$R_6$ is selected from:

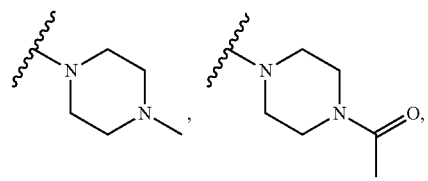

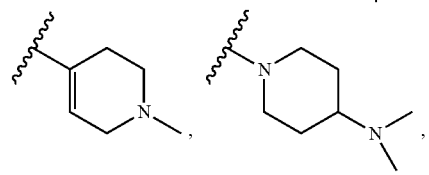

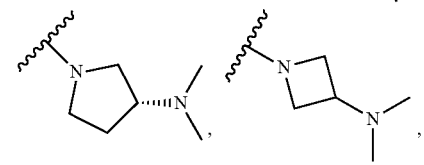

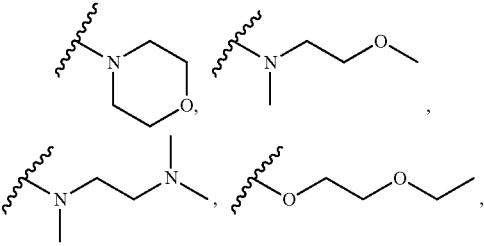

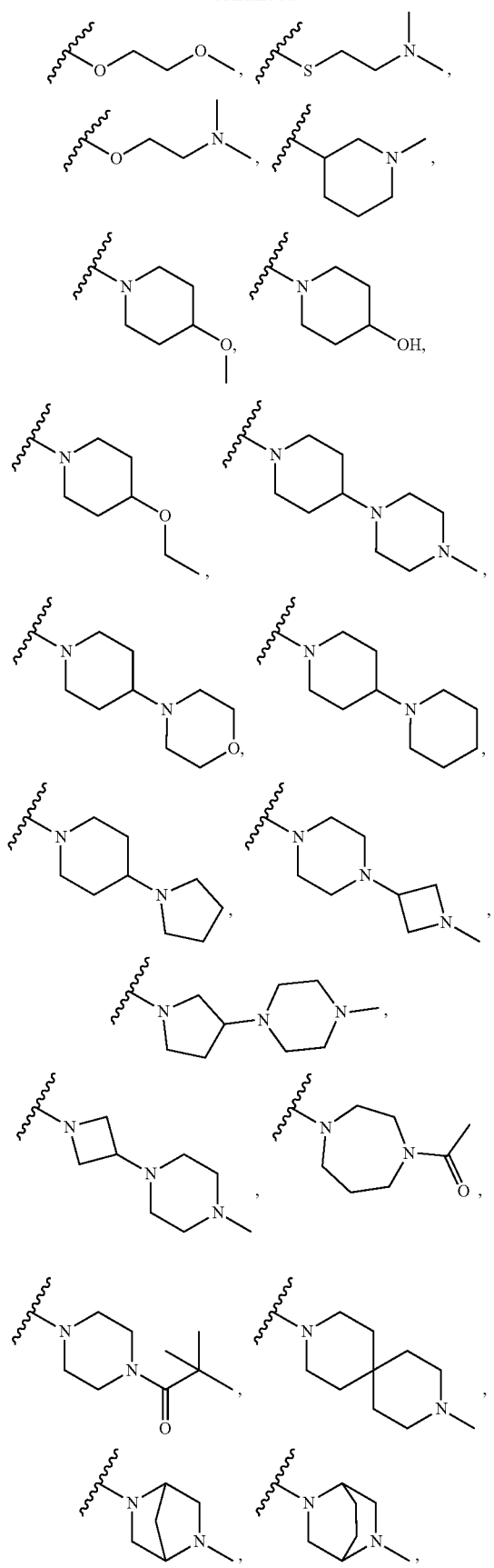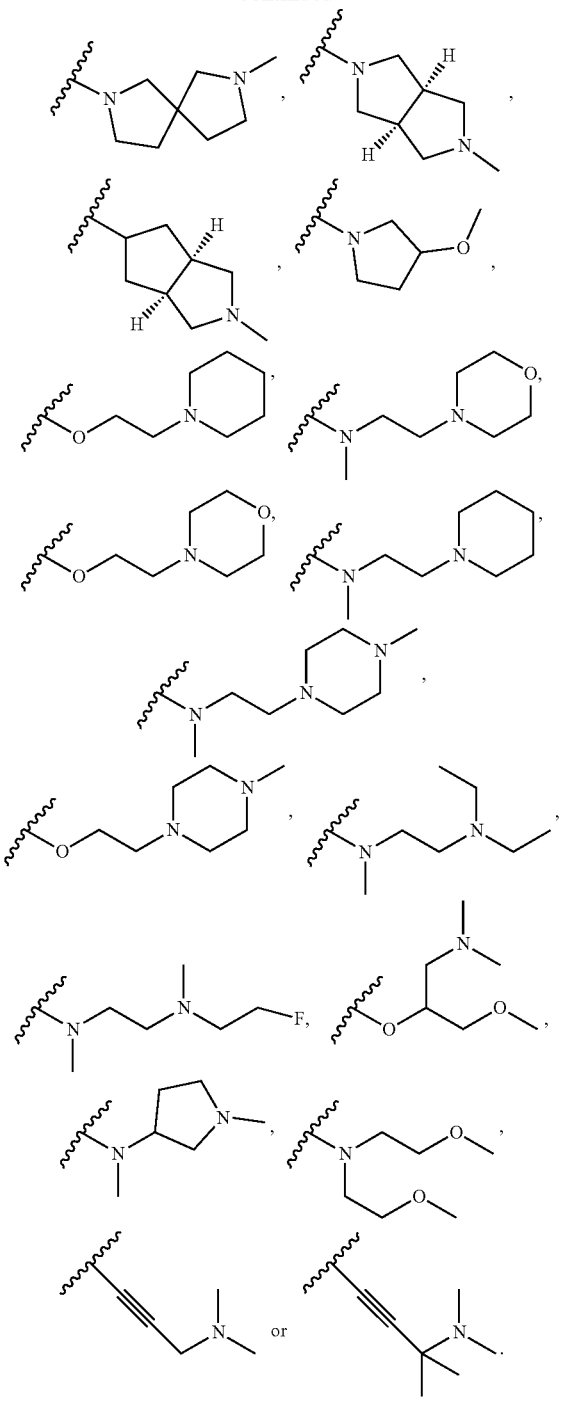
preferably, -(L)″-R₆ is selected from:
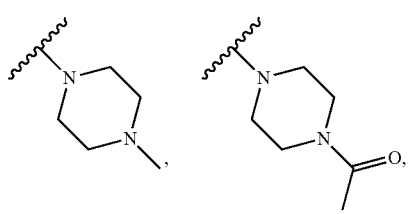

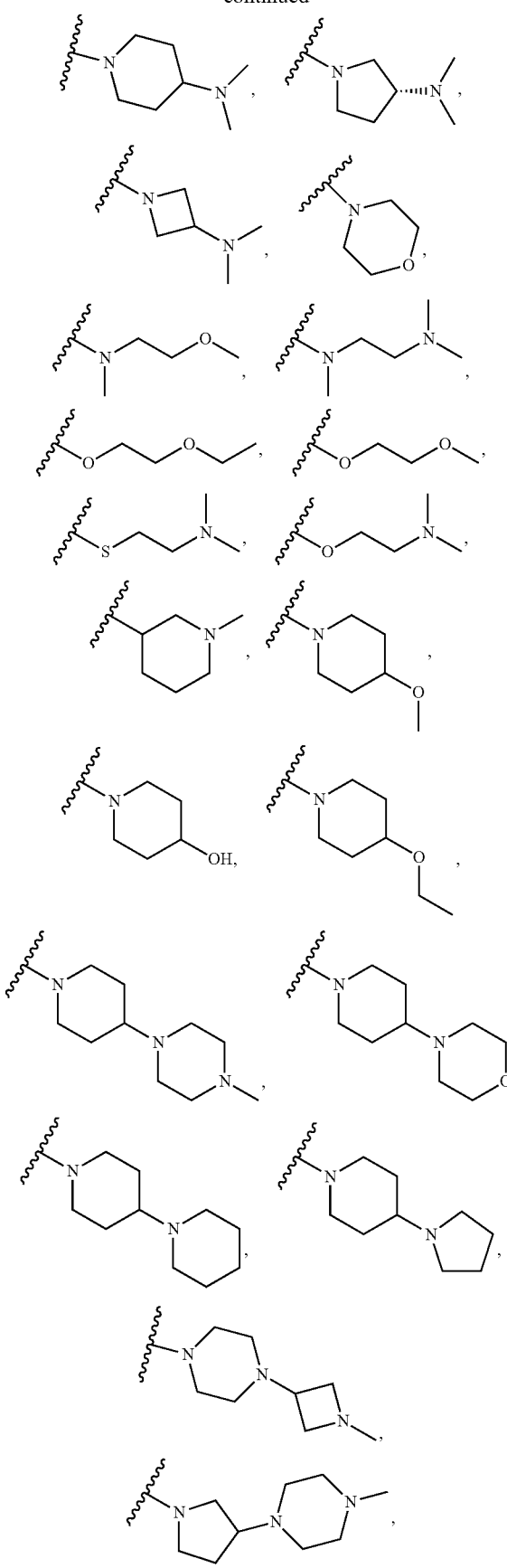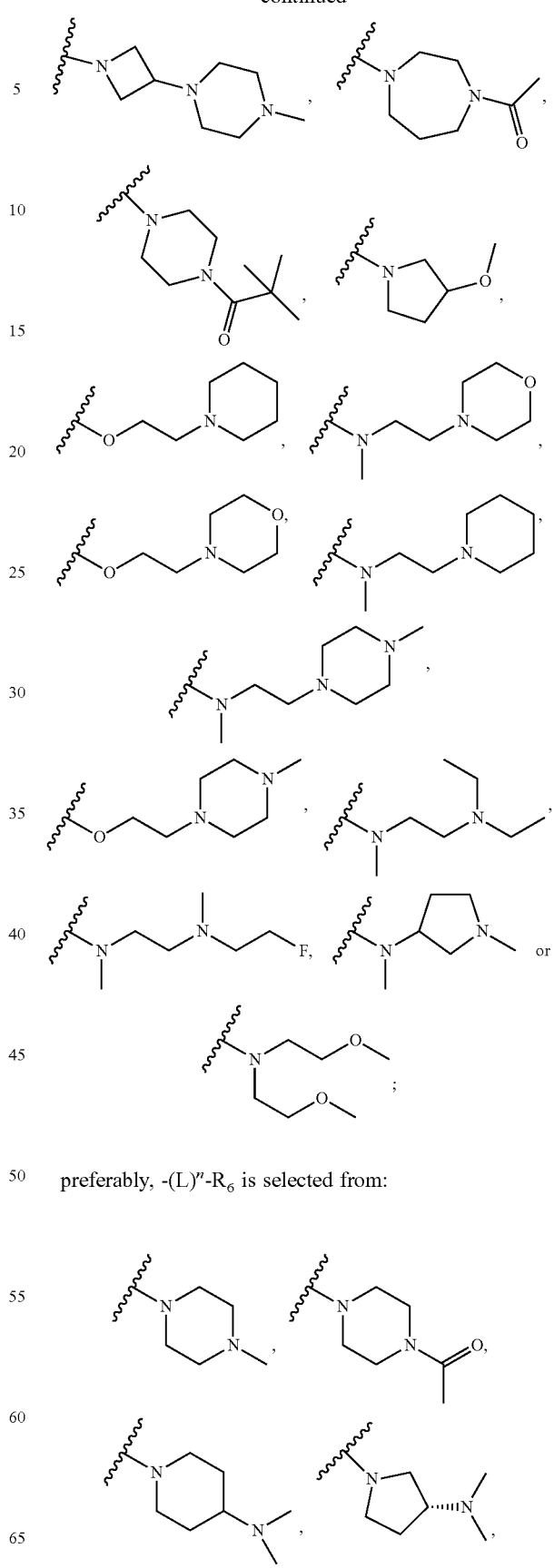
preferably, -(L)$^n$-R$_6$ is selected from:

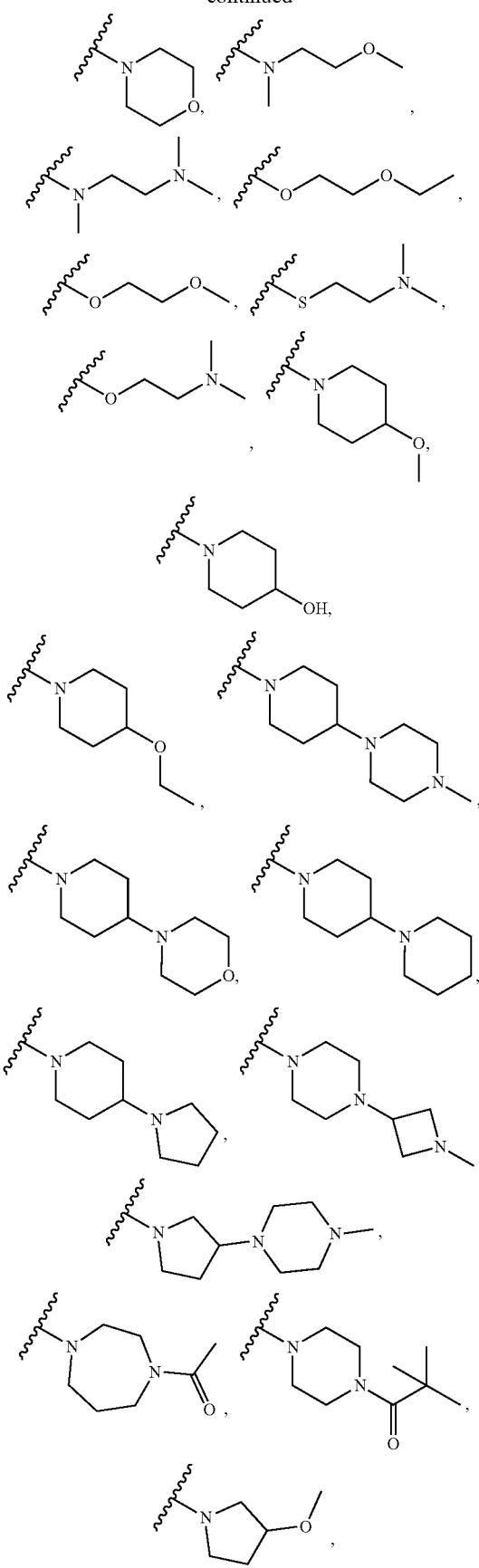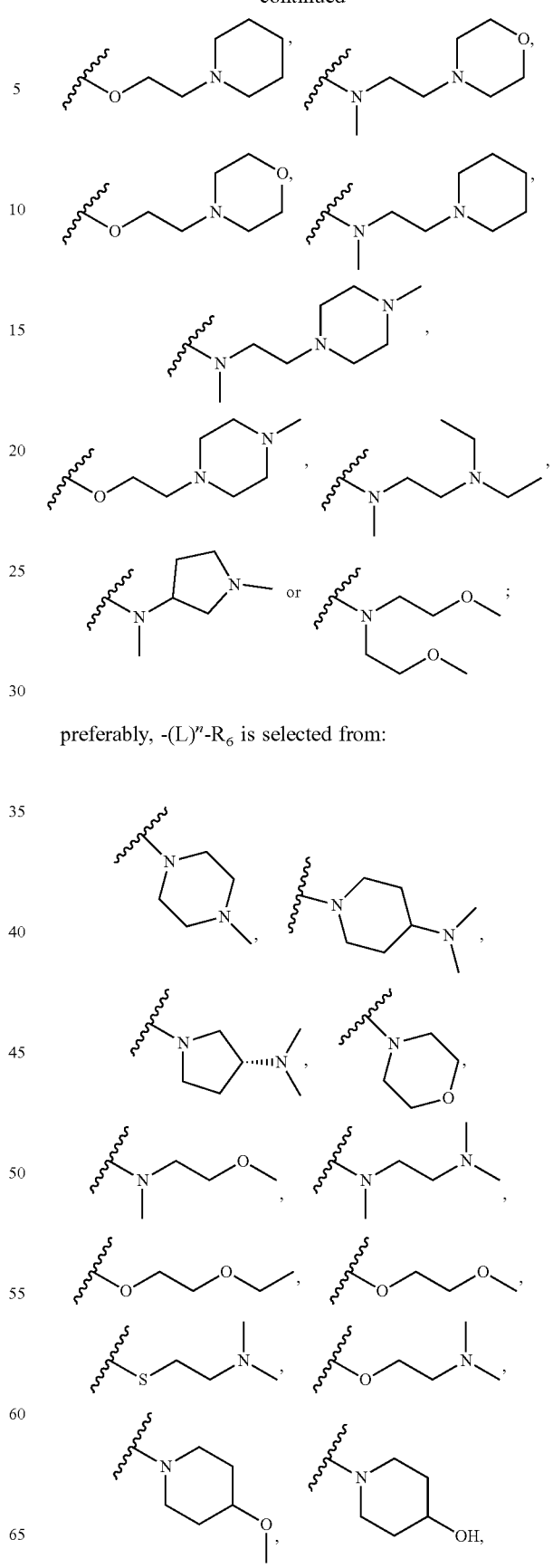
preferably, -(L)$^n$-R$_6$ is selected from:

-continued

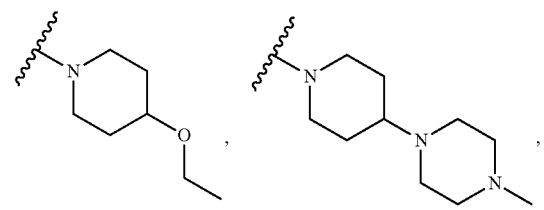

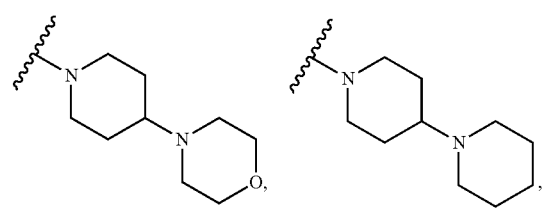

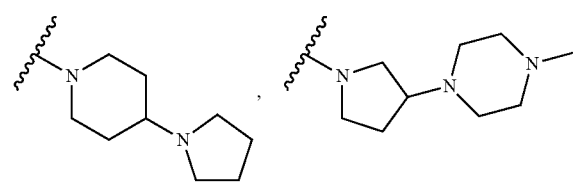

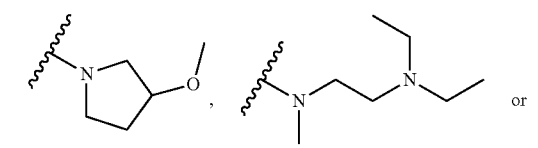

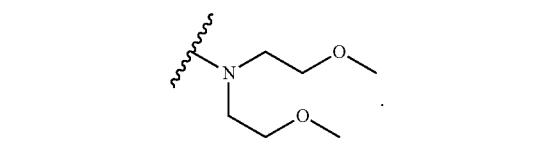

In another embodiment, the compound of formula (I) is the following compound of formula (II):

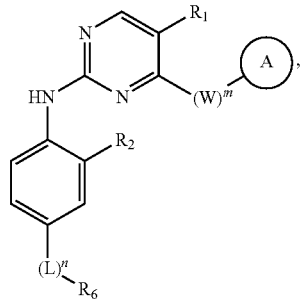
(II)

wherein $R_1$, $R_2$, L, $R_6$, W, A, m and n are as defined above.

In another embodiment, the compoud of formula (I) is the following compound of formula (III):

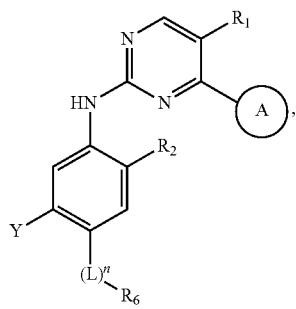
(III)

wherein
Y is selected from the following structures:

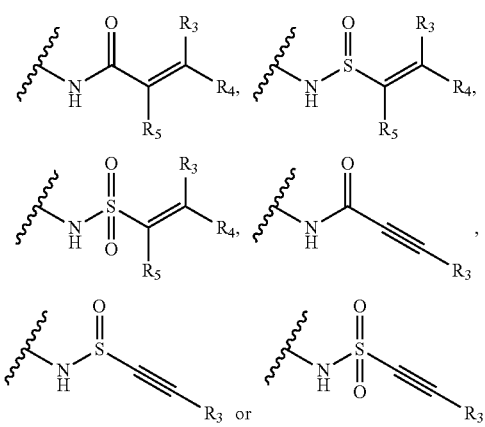

preferably, Y is selected from the following structures:

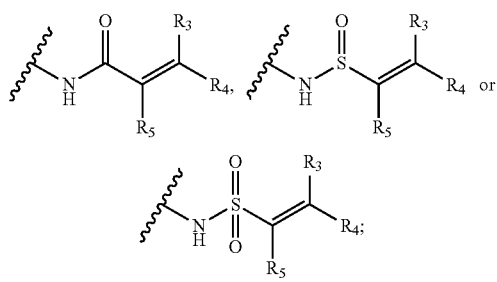

preferably, Y is the following structure:

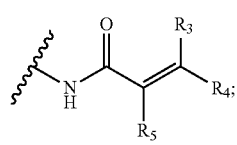

preferably, Y is the following structure:

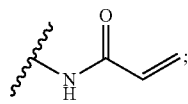 [SMILES: *NC(=O)C=C]

and R$_1$-R$_6$, L, A and n are as defined above.

In another embodiment, the compoud of formula (I) is the following compound of formula (IV):

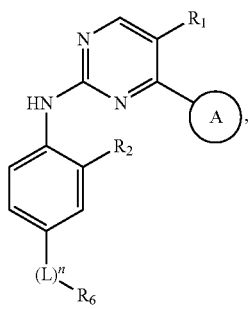

(IV)

wherein R$_1$, R$_2$, L, R$_6$, A and n are as defined above.

In another specific embodiment, the present disclosure relates to the above compound, wherein R$_1$ is selected from H, halo, —CN, optionally substituted C$_1$-C$_6$ alkyl, optionally substituted C$_1$-C$_6$ haloalkyl, optionally substituted C$_1$-C$_6$ alkoxy or optionally substituted C$_3$-C$_6$ carbocyclyl;

R$_2$ is selected from optionally substituted C$_1$-C$_6$ alkoxy or optionally substituted C$_1$-C$_6$ haloalkoxy;

-(L)$^n$-R$_6$ is selected from:

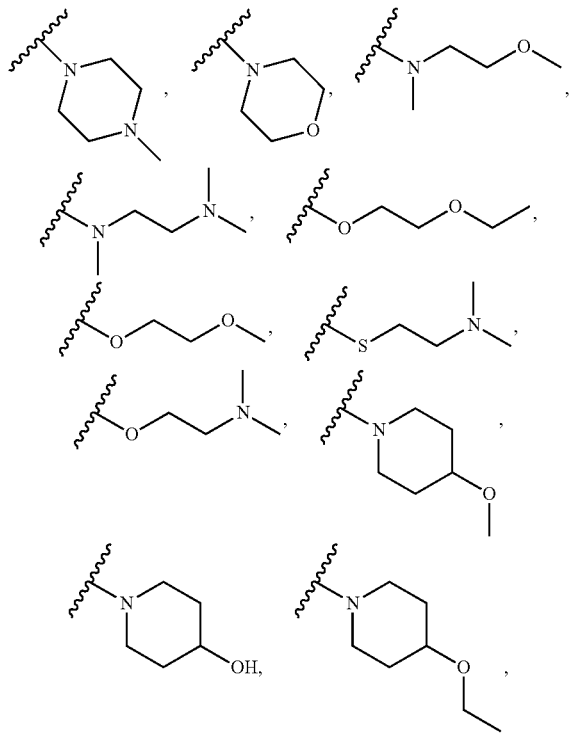

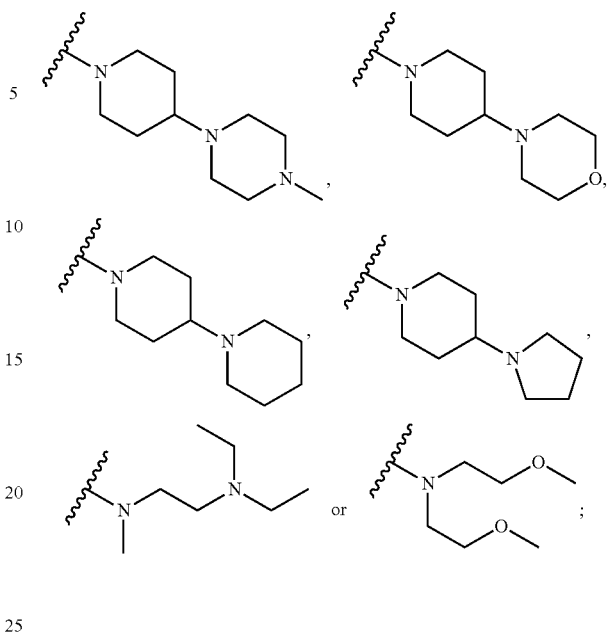

ring A is selected from:

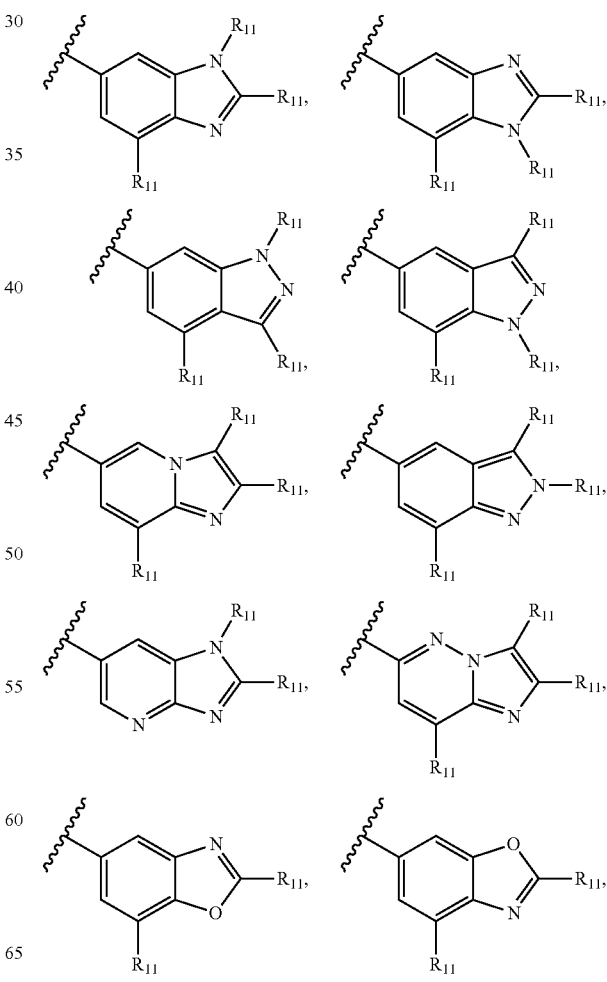

-continued

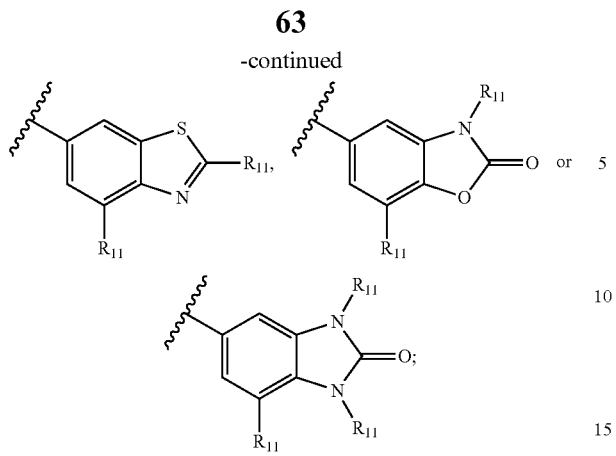

wherein, $R_{11}$ is independently selected from H, halo, optionally substituted $C_1$-$C_6$ alkyl, optionally substituted $C_2$-$C_6$ alkenyl, optionally substituted $C_1$-$C_6$ haloalkyl, optionally substituted $C_1$-$C_6$ alkoxy or optionally substituted $C_3$-$C_6$ carbocyclyl; or, two adjacent $R_{11}$ could be taken together to form optionally substituted 5- to 8-membered heterocyclyl;

or a pharmaceutically acceptable salt, a stereoisomer, a solvate, a hydrate, a polymorph, a prodrug or an isotopic derivative thereof.

In another specific embodiment, the present disclosure relates to the above compound, wherein ring A is

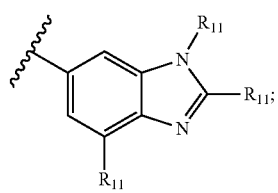

-(L)-$R_6$ is selected from:

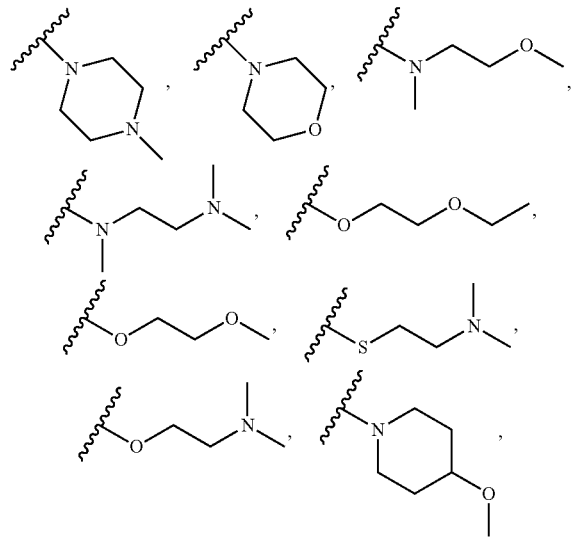

-continued

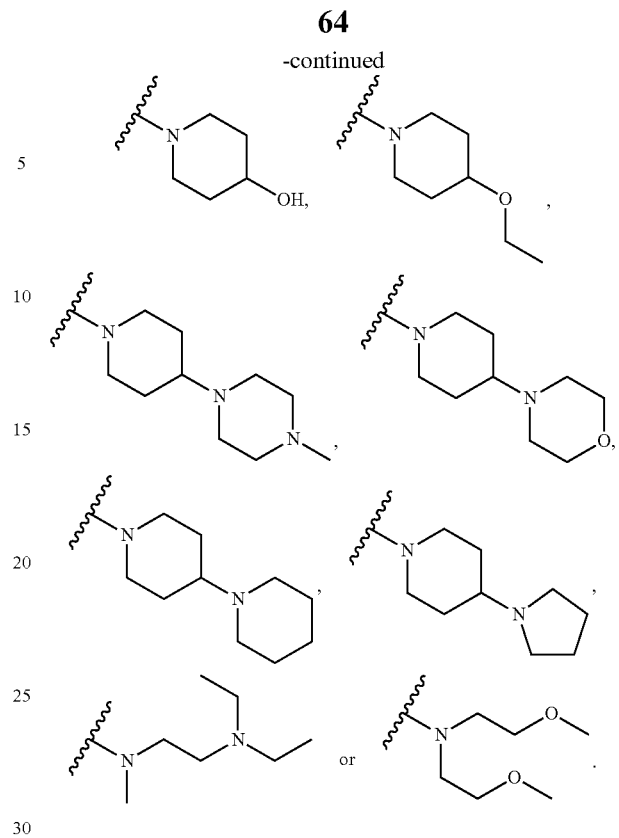

In another specific embodiment, the present disclosure relates to the above compound, wherein -(L)$^n$-$R_6$ is

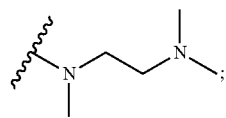 [SMILES: *N(C)CCN(C)C]

ring A is selected from:

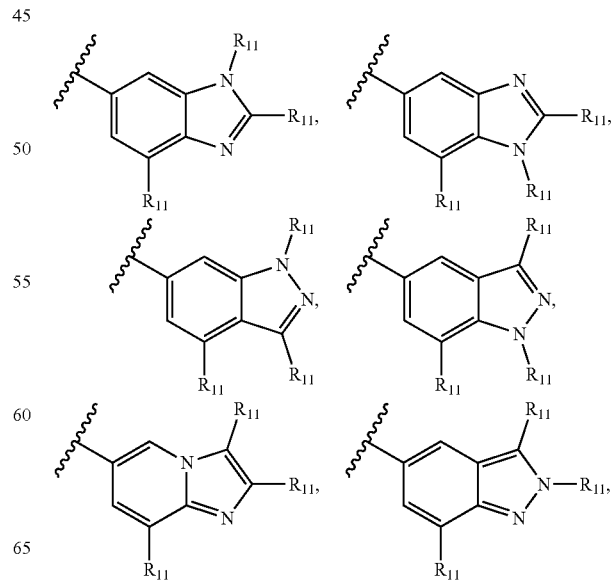

In another specific embodiment, the present disclosure relates to the compound of formula (III-a):

(III-a)

wherein, $R_1$ is selected from H, halo, —CN, optionally substituted $C_1$-$C_6$ alkyl, optionally substituted $C_1$-$C_6$ haloalkyl or optionally substituted $C_1$-$C_6$ alkoxy; preferably, $R_1$ is selected from H, halo or optionally substituted $C_1$-$C_6$ alkyl; preferably, $R_1$ is selected from H, —F, —Cl, —Br, —CN, —CH$_3$, —CF$_3$ or —OCH$_3$; preferably, $R_1$ is selected from H, —Cl, —Br or —CH$_3$;

$R_2$ is selected from optionally substituted $C_1$-$C_6$ alkoxy or optionally substituted $C_1$-$C_6$ haloalkoxy; preferably, $R_2$ is selected from —OCH$_3$, —OCH$_2$CH$_3$, —OCHF$_2$ or —OCH$_2$CF$_3$;

$R_{11}$ is selected from H, halo, optionally substituted $C_1$-$C_6$ alkyl, optionally substituted $C_2$-$C_6$ alkenyl, optionally substituted $C_1$-$C_6$ haloalkyl or optionally substituted $C_1$-$C_6$ alkoxy; preferably, $R_{11}$ is selected from H, halo or optionally substituted $C_1$-$C_6$ alkoxy; preferably, $R_{11}$ is selected from H, —F, —Cl, —Br, -Me, -iPr, 1-propen-2-yl, —CH$_2$F, CF$_3$, —OMe or —OC(CH$_3$)$_3$; preferably, $R_{11}$ is selected from H, —F, —Cl, —Br, —OMe or —OC(CH$_3$)$_3$;

$R_{12}$ is selected from H, halo, optionally substituted $C_1$-$C_6$ alkyl, optionally substituted $C_2$-$C_6$ alkenyl, optionally substituted $C_1$-$C_6$ haloalkyl or optionally substituted $C_1$-$C_6$ alkoxy; preferably, $R_{12}$ is selected from optionally substituted $C_1$-$C_6$ alkyl or optionally substituted $C_1$-$C_6$ haloalkyl; preferably, $R_{12}$ is selected from H, —F, —Cl, —Br, -Me, -iPr, 1-propen-2-yl, —CH$_2$F, CF$_3$, —OMe or —OC(CH$_3$)$_3$; preferably, $R_{12}$ is selected from -Me, -iPr or —CH$_2$F;

$R_{13}$ is selected from H, halo, optionally substituted $C_1$-$C_6$ alkyl, optionally substituted $C_2$-$C_6$ alkenyl, optionally substituted $C_1$-$C_6$ haloalkyl or optionally substituted $C_1$-$C_6$ alkoxy; preferably, $R_{13}$ is optionally substituted $C_1$-$C_6$ alkyl; preferably, $R_{13}$ is selected from H, —F, —Cl, —Br, -Me, -iPr, 1-propen-2-yl, —CH$_2$F, CF$_3$, —OMe or —OC(CH$_3$)$_3$; preferably, $R_{13}$ is selected from -Me or -iPr;

or a pharmaceutically acceptable salt, a stereoisomer, a solvate, a hydrate, a polymorph, a prodrug or an isotopic derivative thereof.

In a preferred embodiment of the above, $R_1$ is H, and $R_2$ and $R_{11}$-$R_{13}$ are as defined above.

In a preferred embodiment of the above, $R_1$ is halo (such as —F, —Cl or —Br, preferably —Cl or —Br), and $R_2$ and $R_{11}$-$R_{13}$ are as defined above.

In a preferred embodiment of the above, $R_1$ is —CN, and $R_2$ and $R_{11}$-$R_{13}$ are as defined above.

In a preferred embodiment of the above, $R_1$ is optionally substituted $C_1$-$C_6$ alkyl (such as —CH$_3$), and $R_2$ and $R_{11}$-$R_{13}$ are as defined above.

In a preferred embodiment of the above, $R_1$ is optionally substituted $C_1$-$C_6$ haloalkyl (such as —CF$_3$), and $R_2$ and $R_{11}$-$R_{13}$ are as defined above.

In a preferred embodiment of the above, $R_1$ is optionally substituted $C_1$-$C_6$ alkoxy (such as —OCH$_3$), and $R_2$ and $R_{11}$-$R_{13}$ are as defined above.

In another specific embodiment, the present disclosure relates to the compound of formula (III-a):

(III-a)

wherein,

R$_1$ is optionally substituted C$_3$-C$_6$ carbocyclyl; preferably, R$_1$ is -cyclopropyl;

and R$_2$ and R$_{11}$-R$_{13}$ are as defined above.

or a pharmaceutically acceptable salt, a stereoisomer, a solvate, a hydrate, a polymorph, a prodrug or an isotopic derivative thereof.

In a preferred embodiment of the above, R$_2$ is optionally substituted C$_1$-C$_6$ alkoxy (such as —OCH$_3$ or —OCH$_2$CH$_3$), and R$_1$ and R$_{11}$-R$_{13}$ are as defined above.

In a preferred embodiment of the above, R$_2$ is optionally substituted C$_1$-C$_6$ haloalkoxy (such as —OCHF$_2$ or —OCH$_2$CF$_3$), and R$_1$ and R$_{11}$-R$_{13}$ are as defined above.

In a preferred embodiment of the above, R$_1$ is H, and R$_1$, R$_2$, R$_{12}$ and R$_{13}$ are as defined above.

In a preferred embodiment of the above, R$_1$ is halo (such as —F, —Cl or —Br), and R$_1$, R$_2$, R$_{12}$ and R$_{13}$ are as defined above.

In a preferred embodiment of the above, R$_{11}$ is optionally substituted C$_1$-C$_6$ alkyl (such as -Me or -iPr), and R$_1$, R$_2$, R$_{12}$ and R$_{13}$ are as defined above.

In a preferred embodiment of the above, R$_{11}$ is optionally substituted C$_2$-C$_6$ alkenyl (such as 1-propen-2-yl), and R$_1$, R$_2$, R$_{12}$ and R$_{13}$ are as defined above.

In a preferred embodiment of the above, R$_{11}$ is optionally substituted C$_1$-C$_6$ haloalkyl (such as —CH$_2$F or —CF$_3$), and R$_1$, R$_2$, R$_{12}$ and R$_{13}$ are as defined above.

In a preferred embodiment of the above, R$_{11}$ is optionally substituted C$_1$-C$_6$ alkoxy (such as —OMe or —OC(CH$_3$)$_3$), and R$_1$, R$_2$, R$_{12}$ and R$_{13}$ are as defined above.

In a preferred embodiment of the above, R$_{12}$ is H, and R$_1$, R$_2$, R$_{11}$ and R$_{13}$ are as defined above.

In a preferred embodiment of the above, R$_{12}$ is halo (such as —F, —Cl or —Br), and R$_1$, R$_2$, R$_{11}$ and R$_{13}$ are as defined above.

In a preferred embodiment of the above, R$_{12}$ is optionally substituted C$_1$-C$_6$ alkyl (such as -Me or -iPr), and R$_1$, R$_2$, R$_{11}$ and R$_{13}$ are as defined above.

In a preferred embodiment of the above, R$_{12}$ is optionally substituted C$_2$-C$_6$ alkenyl (such as 1-propen-2-yl), and R$_1$, R$_2$, R$_{11}$ and R$_{13}$ are as defined above.

In a preferred embodiment of the above, R$_{12}$ is optionally substituted C$_1$-C$_6$ haloalkyl (such as —CH$_2$F or —CF$_3$, preferably —CH$_2$F), and R$_1$, R$_2$, R$_{11}$ and R$_{13}$ are as defined above.

In a preferred embodiment of the above, R$_{12}$ is optionally substituted C$_1$-C$_6$ alkoxy (such as —OMe or —OC(CH$_3$)$_3$), and R$_1$, R$_2$, R$_{11}$ and R$_{13}$ are as defined above.

In a preferred embodiment of the above, R$_{13}$ is H, and R$_1$, R$_2$, R$_{11}$ and R$_{12}$ are as defined above.

In a preferred embodiment of the above, R$_{13}$ is halo (such as —F, —Cl or —Br), and R$_1$, R$_2$, R$_{11}$ and R$_{12}$ are as defined above.

In a preferred embodiment of the above, R$_{13}$ is optionally substituted C$_1$-C$_6$ alkyl (such as -Me or -iPr), and R$_1$, R$_2$, R$_{11}$ and R$_{12}$ are as defined above.

In a preferred embodiment of the above, R$_{13}$ is optionally substituted C$_2$-C$_6$ alkenyl (such as 1-propen-2-yl), and R$_1$, R$_2$, R$_{11}$ and R$_{12}$ are as defined above.

In a preferred embodiment of the above, R$_{13}$ is optionally substituted C$_1$-C$_6$ haloalkyl (such as —CH$_2$F or —CF$_3$), and R$_1$, R$_2$, R$_{11}$ and R$_{12}$ are as defined above.

In a preferred embodiment of the above, R$_{13}$ is optionally substituted C$_1$-C$_6$ alkoxy (such as —OMe or —OC(CH$_3$)$_3$), and R$_1$, R$_2$, R$_{11}$ and R$_{12}$ are as defined above.

In another specific embodiment, the present disclosure relates to the above compound of formula (III-b):

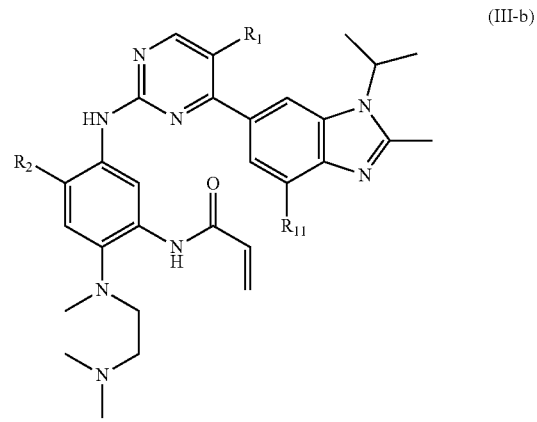

(III-b)

wherein,

R$_1$ is selected from H, halo, —CN, optionally substituted C$_1$-C$_6$ alkyl, optionally substituted C$_1$-C$_6$ haloalkyl or optionally substituted C$_1$-C$_6$ alkoxy; preferably, R$_1$ is selected from H, halo or optionally substituted C$_1$-C$_6$ alkyl; preferably, R$_1$ is selected from H, —F, —Cl, —Br, —CN, —CH$_3$, —CF$_3$ or —OCH$_3$; preferably, R$_1$ is selected from H, —Cl, —Br or —CH$_3$;

R$_2$ is selected from optionally substituted C$_1$-C$_6$ alkoxy or optionally substituted C$_1$-C$_6$ haloalkoxy; preferably, R$_2$ is selected from —OCH$_3$, —OCH$_2$CH$_3$, —OCHF$_2$ or —OCH$_2$CF$_3$;

R$_{11}$ is selected from H, halo, optionally substituted C$_1$-C$_6$ alkyl, optionally substituted C$_2$-C$_6$ alkenyl, optionally substituted C$_1$-C$_6$ haloalkyl or optionally substituted C$_1$-C$_6$ alkoxy; preferably, R$_{11}$ is selected from H, halo or optionally substituted C$_1$-C$_6$ alkoxy; preferably, R$_{11}$ is selected from H, —F, —Cl, —Br, -Me, -iPr, 1-propen-2-yl, —CH$_2$F, CF$_3$, —OMe or —OC(CH$_3$)$_3$; preferably, R$_{11}$ is selected from H, —F, —Cl, —Br, —OMe or —OC(CH$_3$)$_3$.

In another specific embodiment, the present disclosure relates to the above compound of formula (III-b):

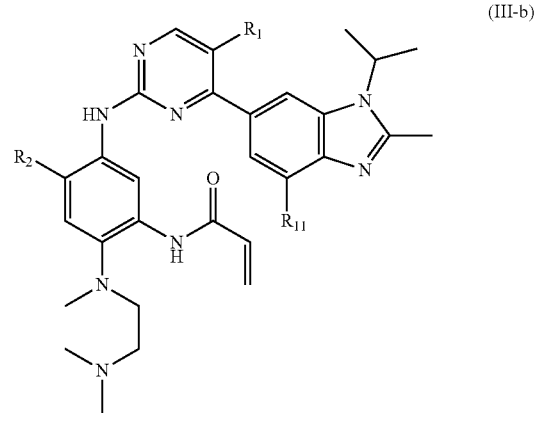

(III-b)

wherein,

R$_1$ is optionally substituted C$_3$-C$_6$ carbocyclyl; preferably, R$_1$ is -cyclopropyl;

R$_2$ and R$_{11}$ are as defined above;

or a pharmaceutically acceptable salt, a stereoisomer, a solvate, a hydrate, a polymorph, a prodrug or an isotopic derivative thereof.

In another specific embodiment, the present disclosure relates to the compound of formula (III-c):

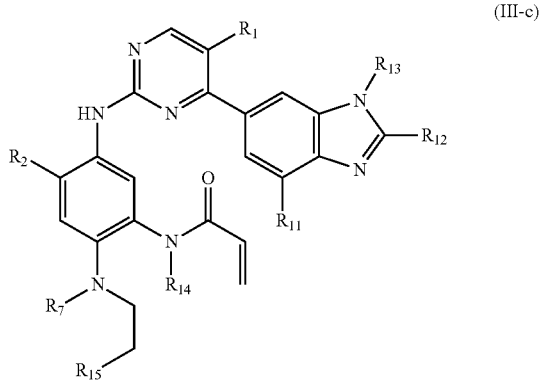

(III-c)

wherein, $R_1$ is selected from H, halo, —CN, optionally substituted $C_1$-$C_6$ alkyl, optionally substituted $C_1$-$C_6$ haloalkyl, optionally substituted $C_1$-$C_6$ alkoxy or optionally substituted $C_3$-$C_6$ carbocyclyl;

$R_2$ is selected from optionally substituted $C_1$-$C_6$ alkoxy or optionally substituted $C_1$-$C_6$ haloalkoxy;

$R_7$ is selected from H, or optionally substituted $C_1$-$C_6$ alkyl;

$R_{11}$ is selected from H, halo, optionally substituted $C_1$-$C_6$ alkyl, optionally substituted $C_2$-$C_6$ alkenyl, optionally substituted $C_1$-$C_6$ haloalkyl or optionally substituted $C_1$-$C_6$ alkoxy;

$R_{12}$ is independently selected from H, halo, —CN, —$NO_2$, —OH, optionally substituted $C_1$-$C_6$ alkyl, optionally substituted $C_1$-$C_6$ haloalkyl, optionally substituted $C_2$-$C_6$ alkenyl, optionally substituted $C_2$-$C_6$ alkynyl, optionally substituted $C_3$-$C_6$ carbocyclyl, optionally substituted $C_1$-$C_6$ alkoxy, optionally substituted $C_1$-$C_6$ alkylthio or optionally substituted $C_1$-$C_6$ haloalkoxy, as long as the chemistry permits; wherein the said optionally substituted groups are optionally further substituted by 1, 2, 3, 4, 5, 6, 7, or 8 deuteriums;

$R_{13}$ is selected from H, halo, optionally substituted $C_1$-$C_6$ alkyl, optionally substituted $C_2$-$C_6$ alkenyl, optionally substituted $C_1$-$C_6$ haloalkyl or optionally substituted $C_1$-$C_6$ alkoxy; wherein the said optionally substituted groups are optionally further substituted by 1, 2, 3, 4, 5, 6, 7, or 8 deuteriums;

or $R_{12}$ and $R_{13}$ could be taken together to form optionally substituted 5- to 8-membered heterocyclyl, or optionally substituted 5- to 10-membered heteroaryl; $R_{15}$ is selected from —OH, —CN, —$NO_2$, optionally substituted $C_1$-$C_6$ alkyl, optionally substituted $C_1$-$C_6$ alkoxy, or $NR_8R_9$; wherein $R_8$ and $R_9$ are each independently selected from H, optionally substituted $C_1$-$C_6$ alkyl, optionally substituted $C_1$-$C_6$ alkoxy, optionally substituted $C_1$-$C_6$ haloalkyl or optionally substituted $C_3$-$C_6$ carbocyclyl, or $R_8$ and $R_9$ together with the nitrogen atom to which they are attached form optionally substituted 4- to 6-membered heterocyclyl;

or a pharmaceutically acceptable salt, a stereoisomer, a solvate, a hydrate, a polymorph, a prodrug or an isotopic derivative thereof.

In another specific embodiment, the present disclosure relates to the above compound of formula (IV-a):

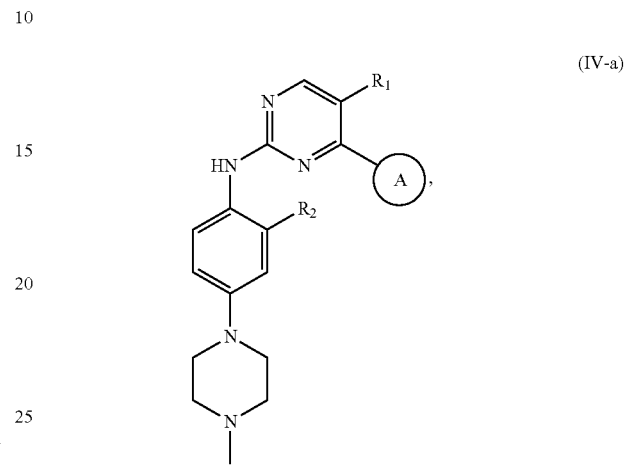

(IV-a)

wherein, $R_1$ is selected from H, halo, —CN, optionally substituted $C_1$-$C_6$ alkyl, optionally substituted $C_1$-$C_6$ haloalkyl or optionally substituted $C_1$-$C_6$ alkoxy; preferably, $R_1$ is selected from H or —F;

$R_2$ is selected from optionally substituted $C_1$-$C_6$ alkoxy or optionally substituted $C_1$-$C_6$ haloalkoxy; preferably, $R_2$ is selected from H or —$OCH_3$;

A is selected from

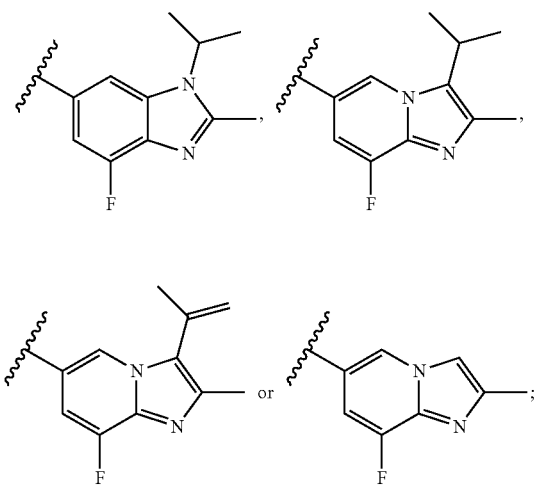

or a pharmaceutically acceptable salt, a stereoisomer, a solvate, a hydrate, a polymorph, a prodrug or an isotopic derivative thereof.

In most preferred embodiment, the compound disclosed herein is selected from the following compounds:

71
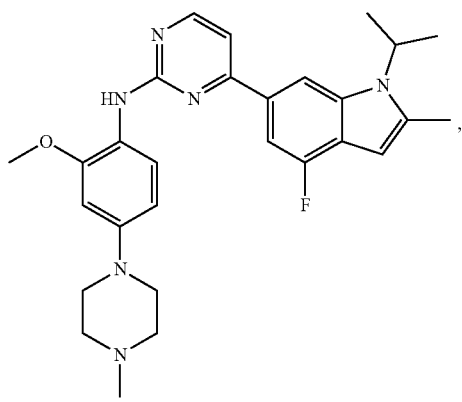
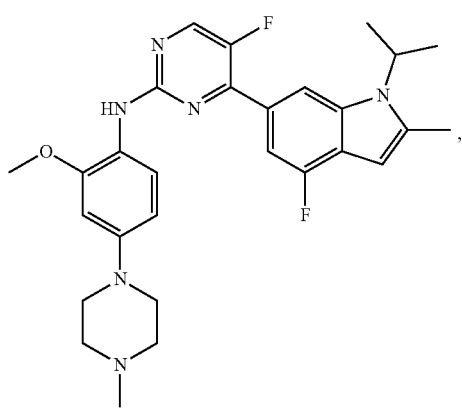
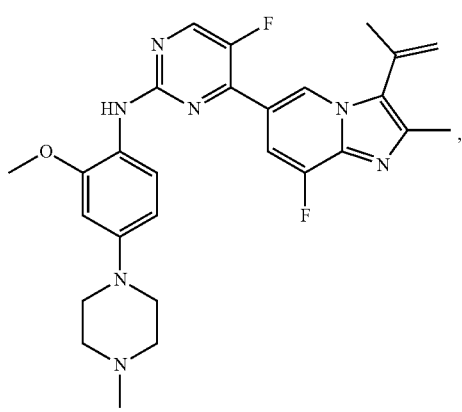
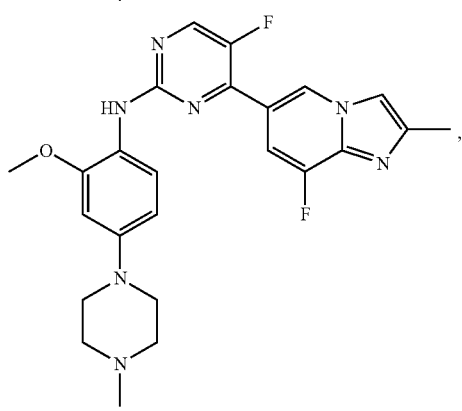
72
-continued
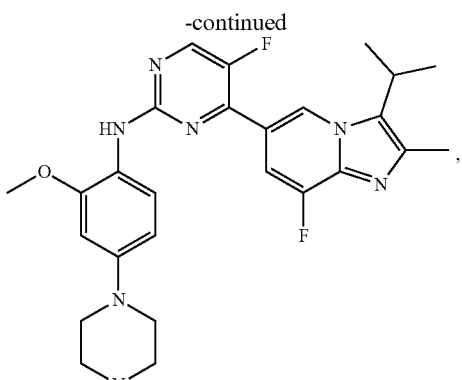
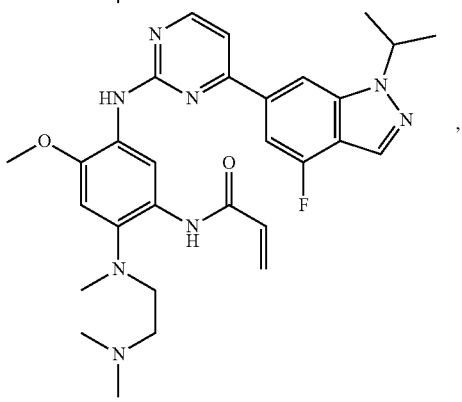
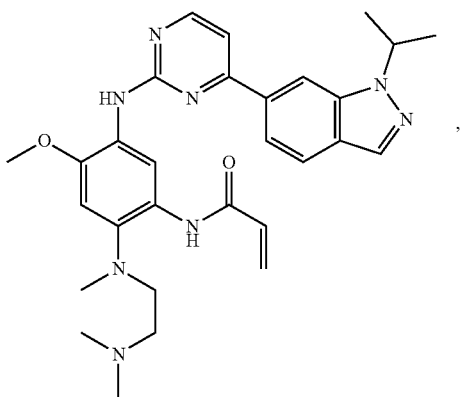
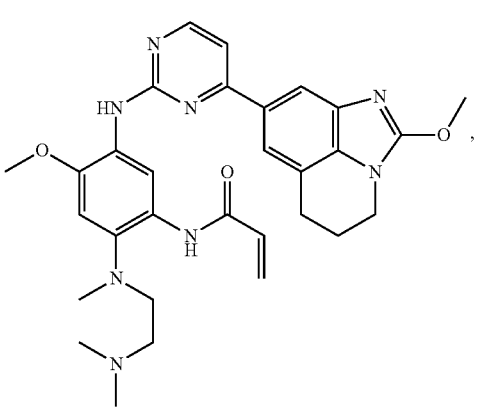

73
-continued
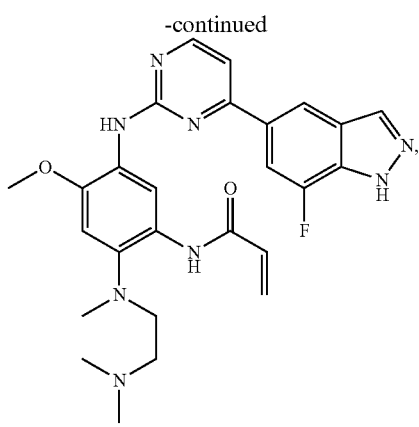
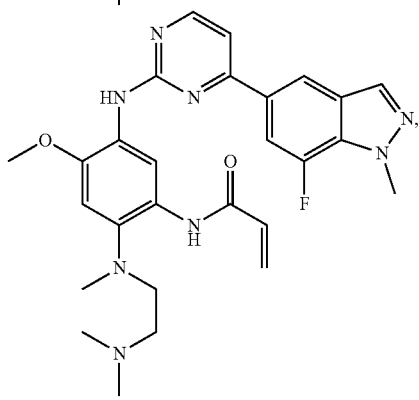
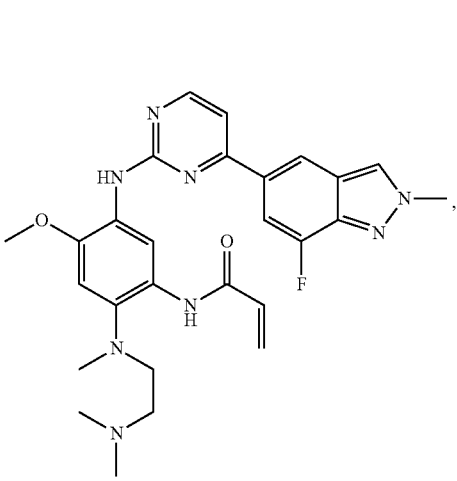
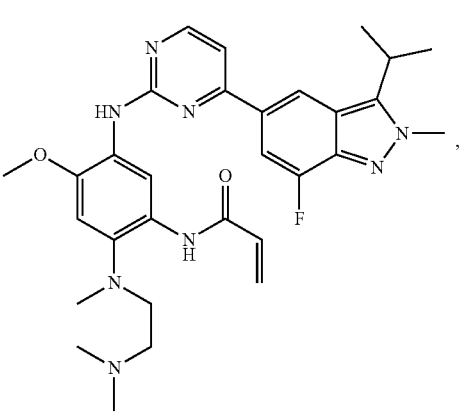
74
-continued
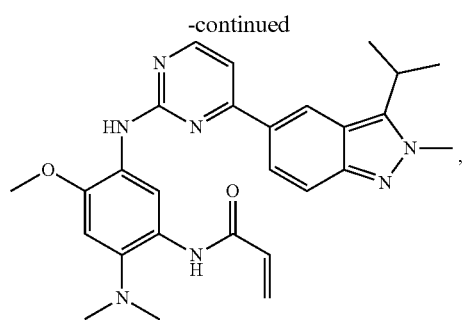
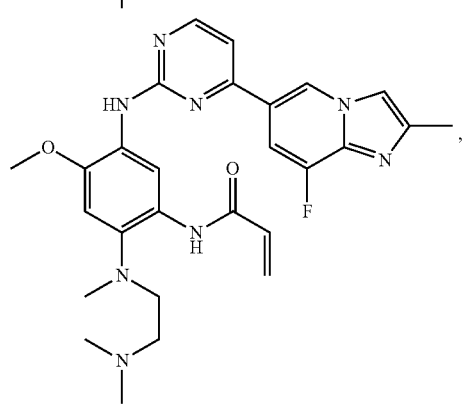
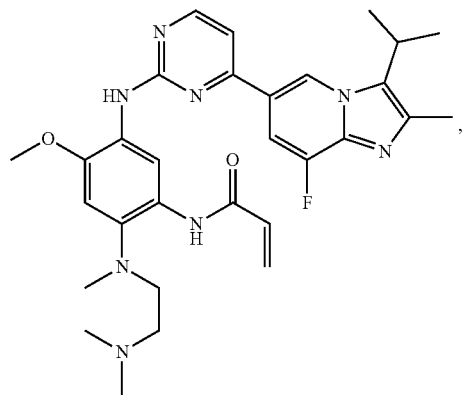
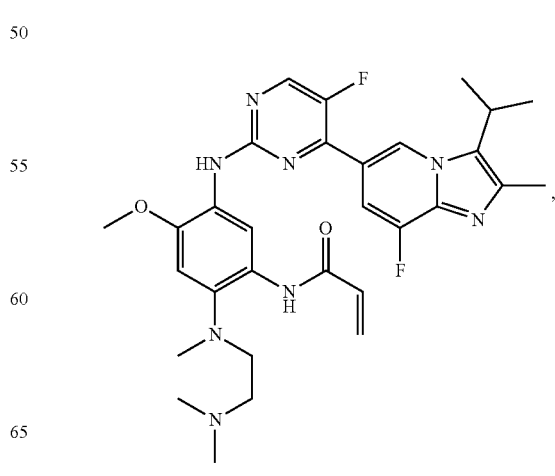

75
-continued
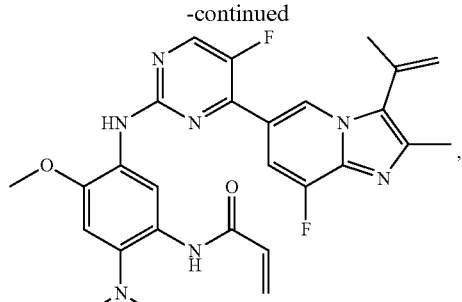
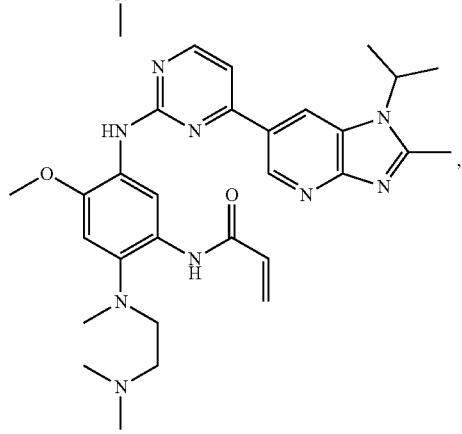
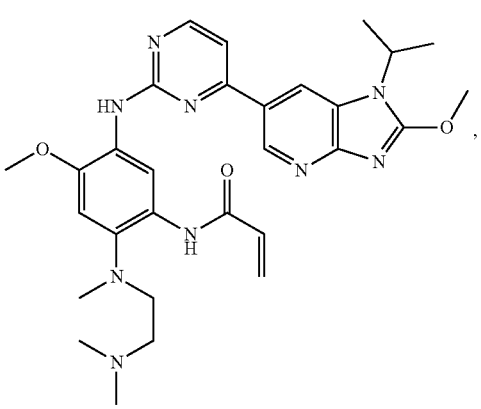
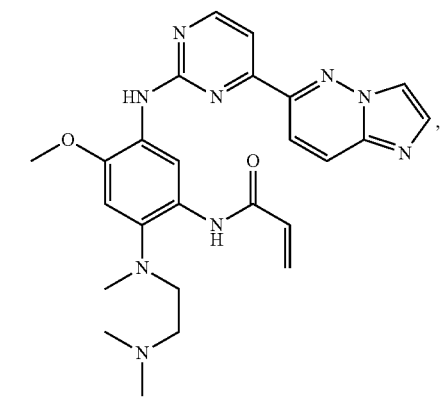
76
-continued
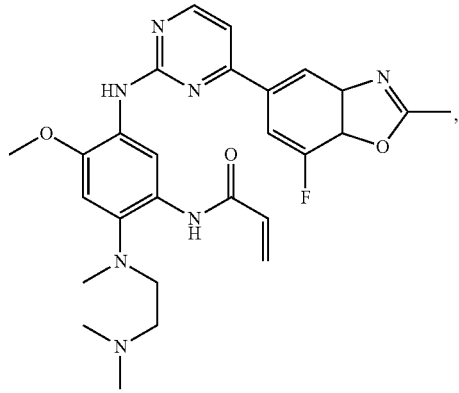
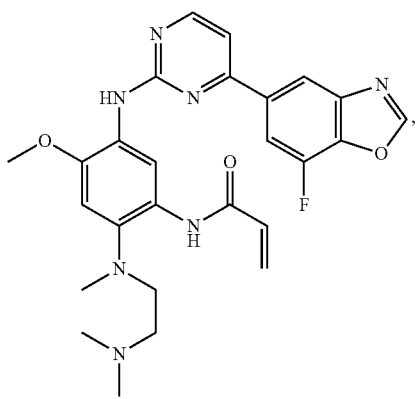
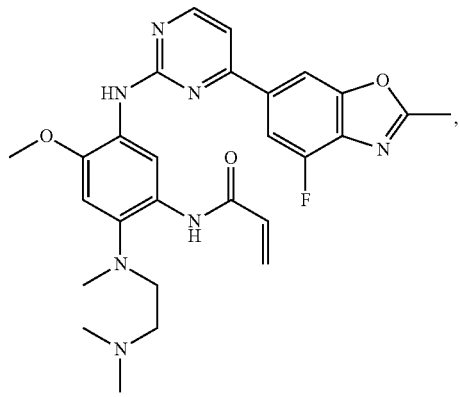
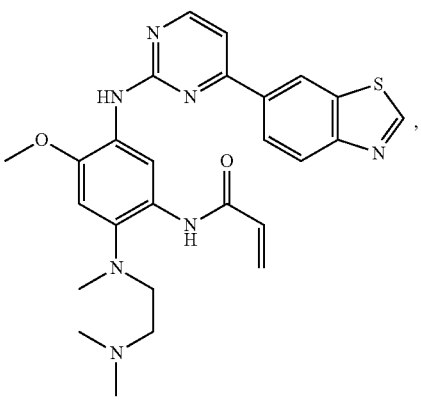

77
-continued
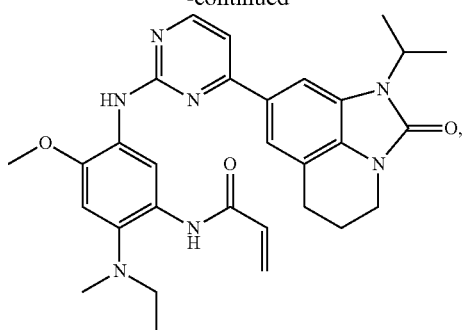
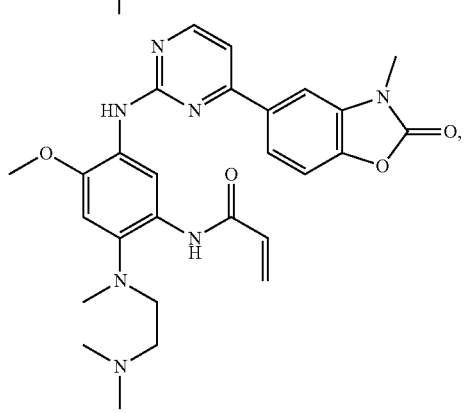
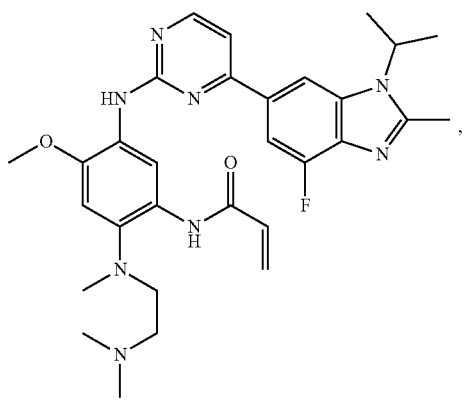
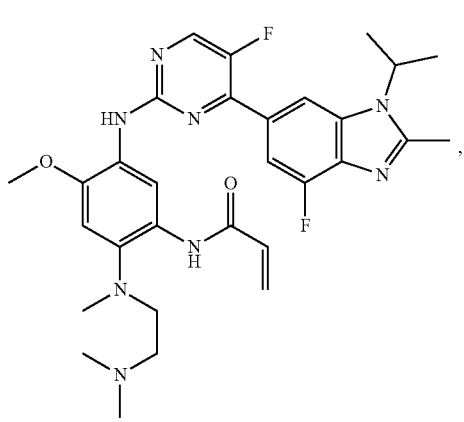
78
-continued
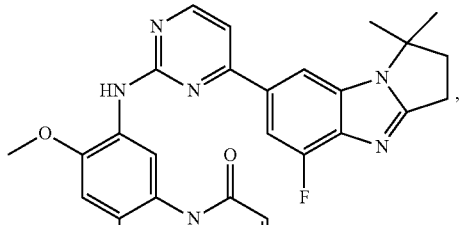
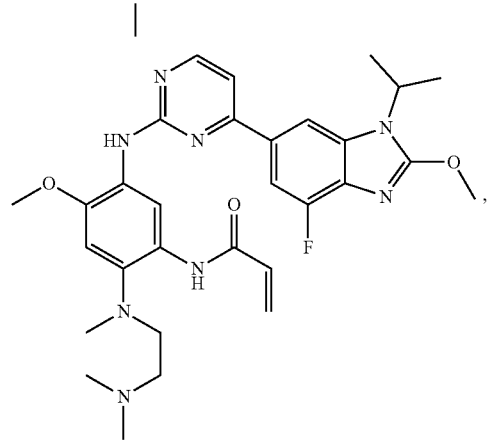
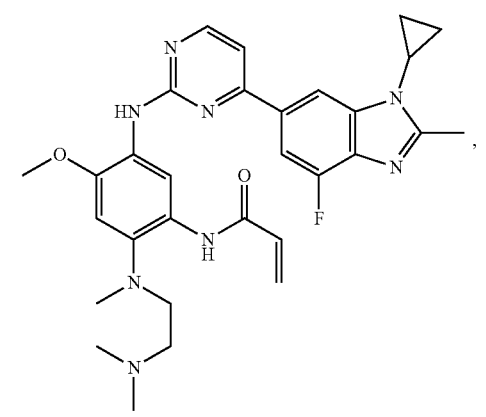
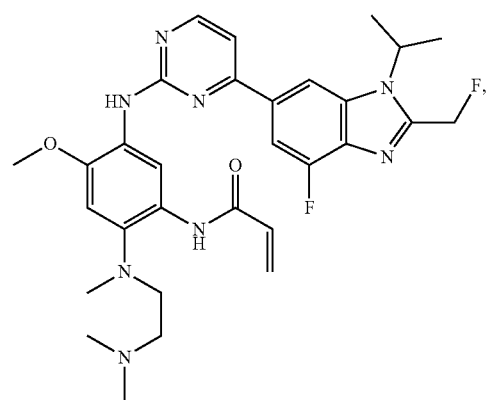

79
-continued
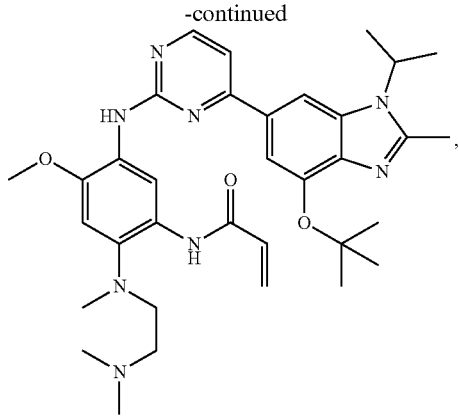
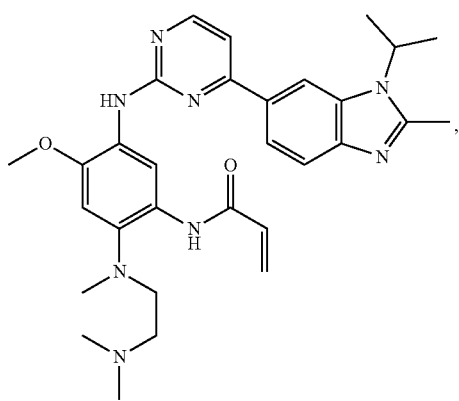
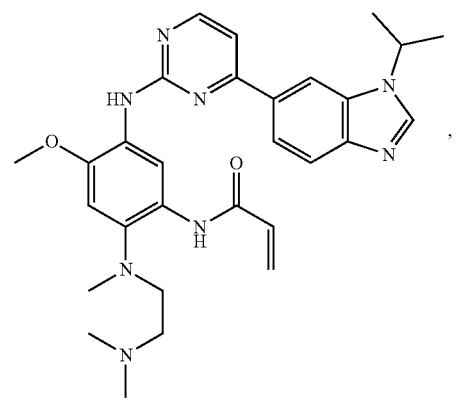
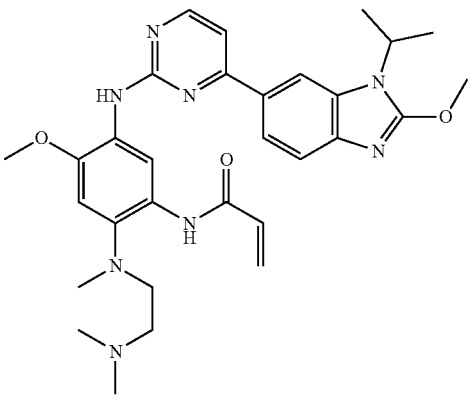
80
-continued
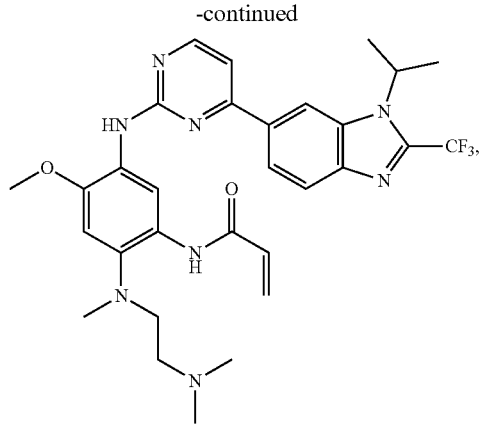
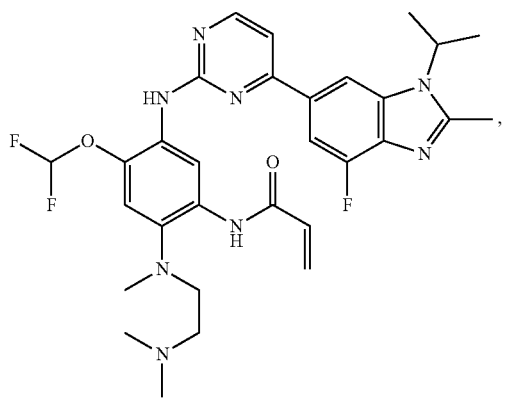
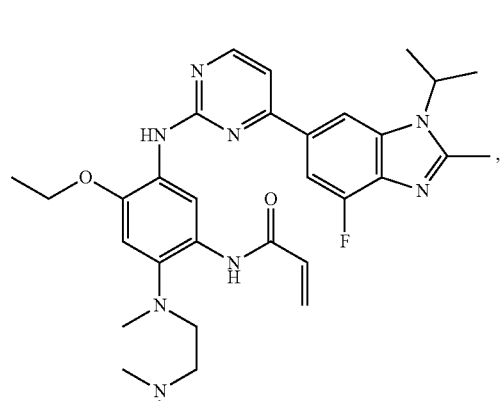
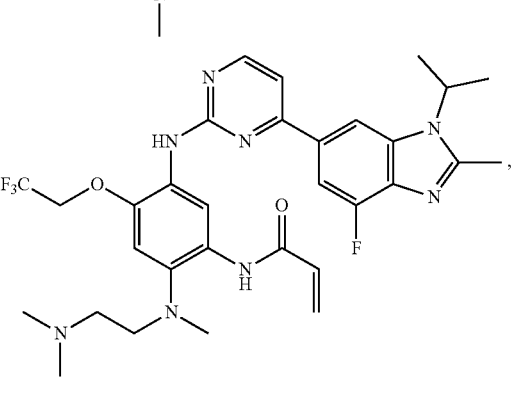

81
-continued
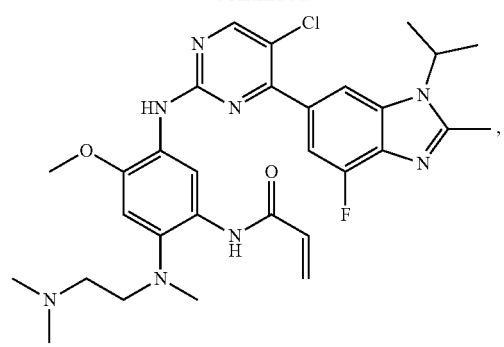
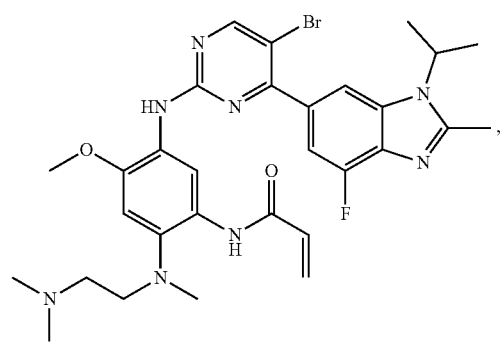
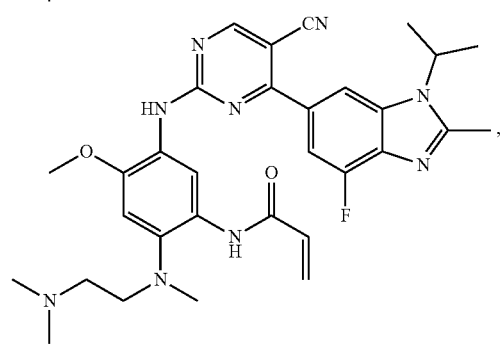
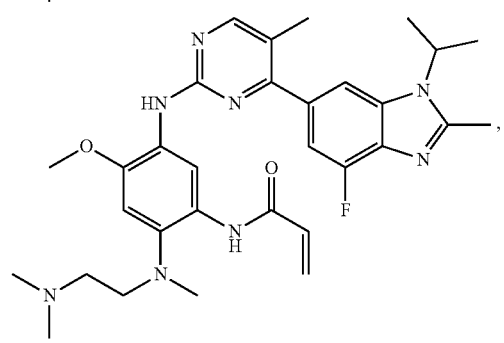
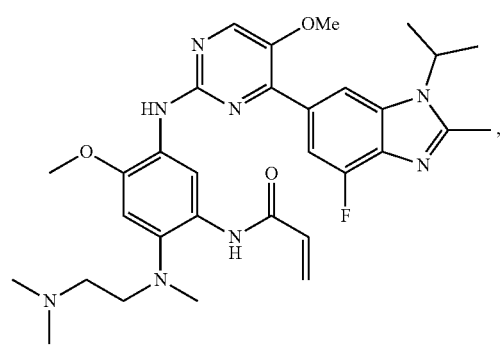
82
-continued
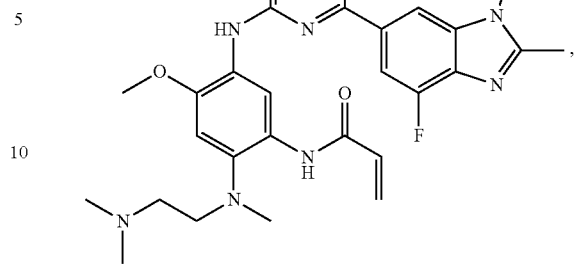
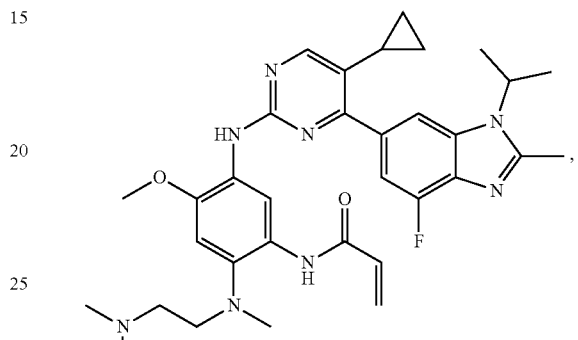
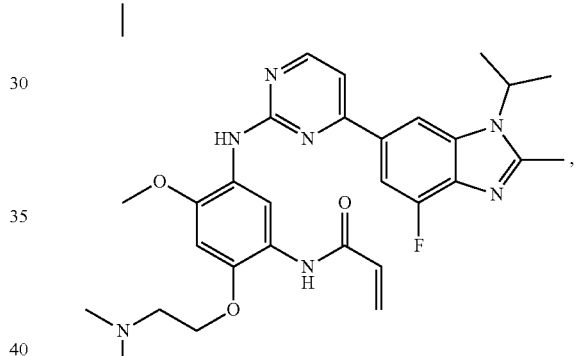
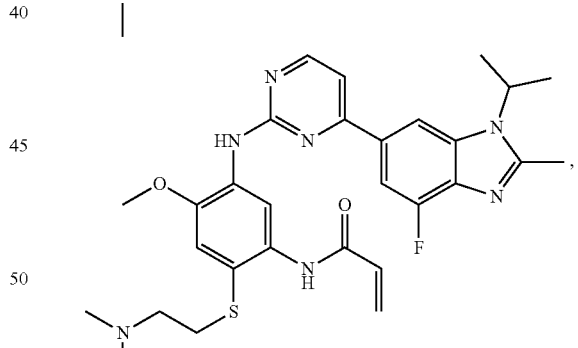
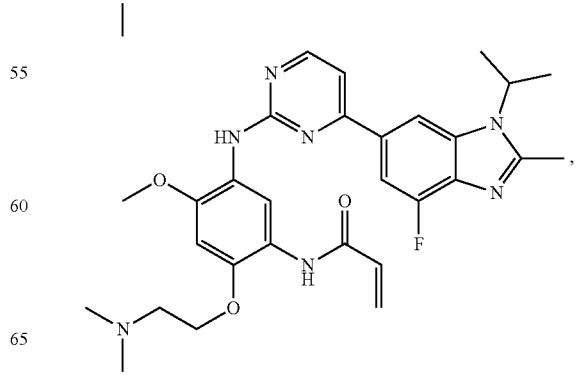

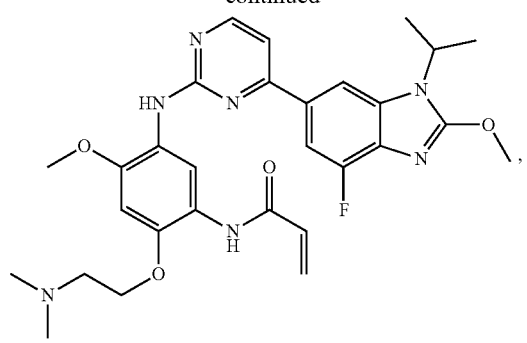
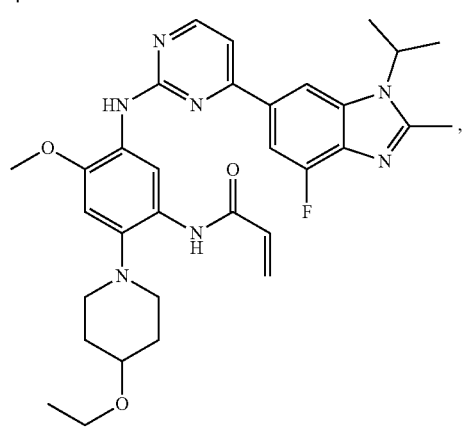
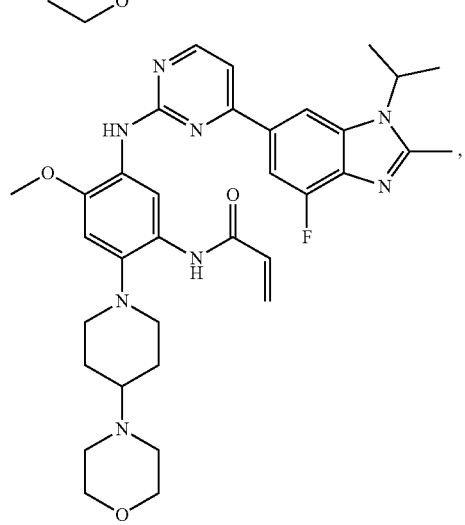
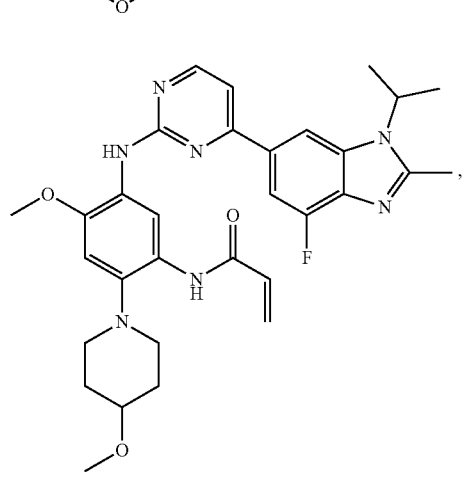
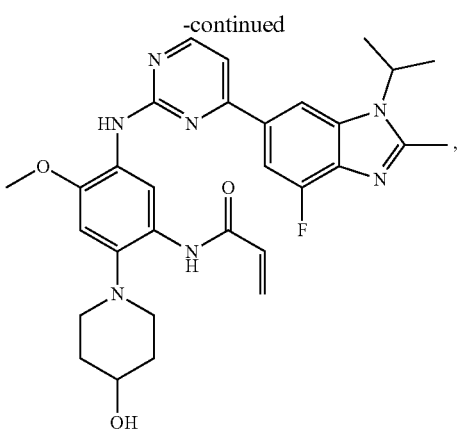
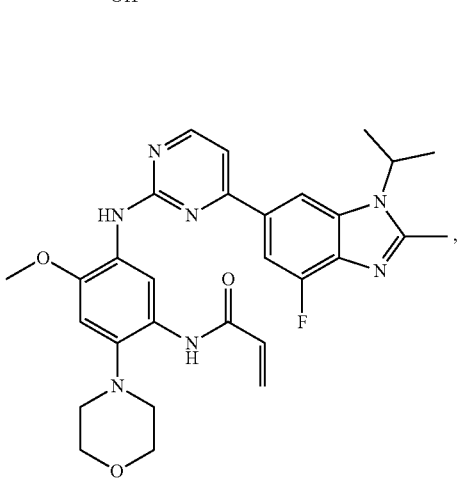
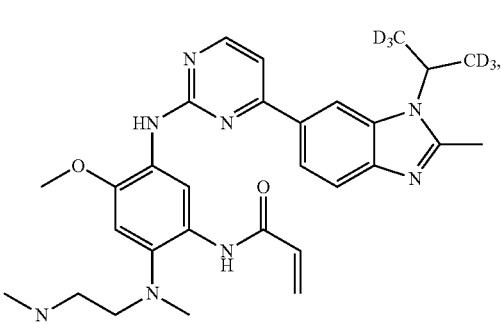
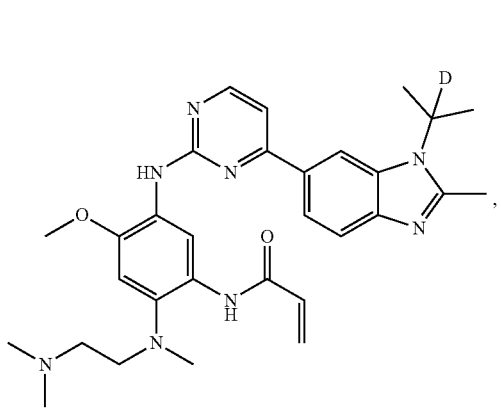

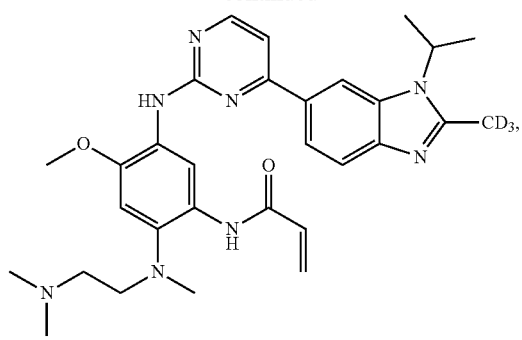
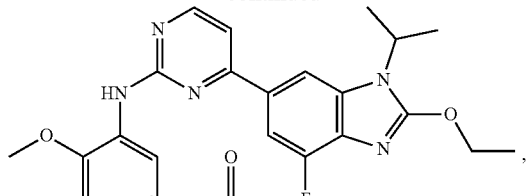
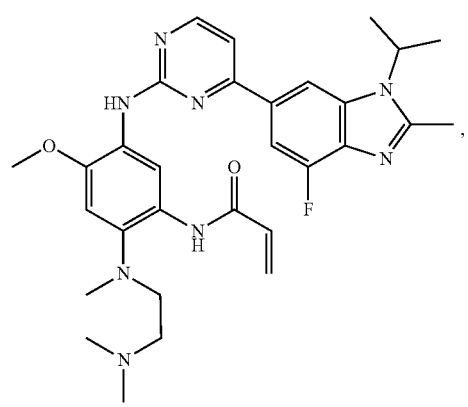
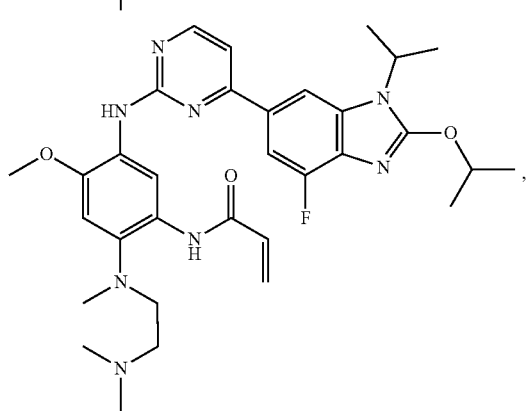
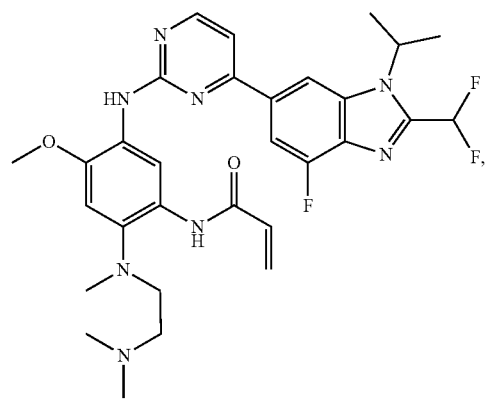
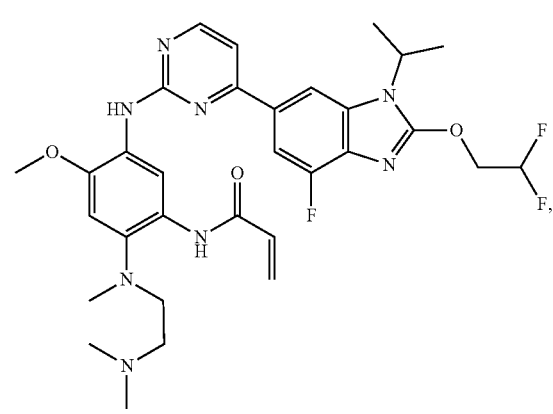
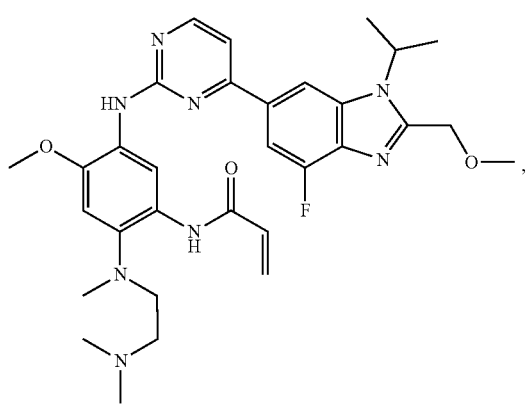
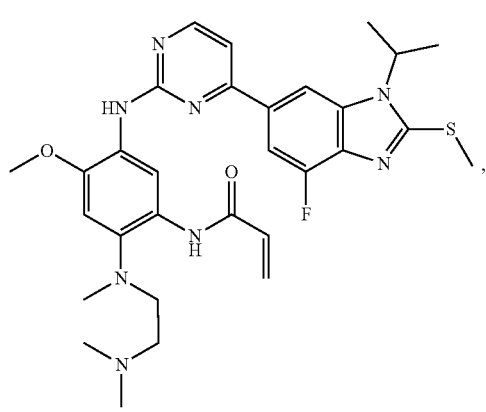

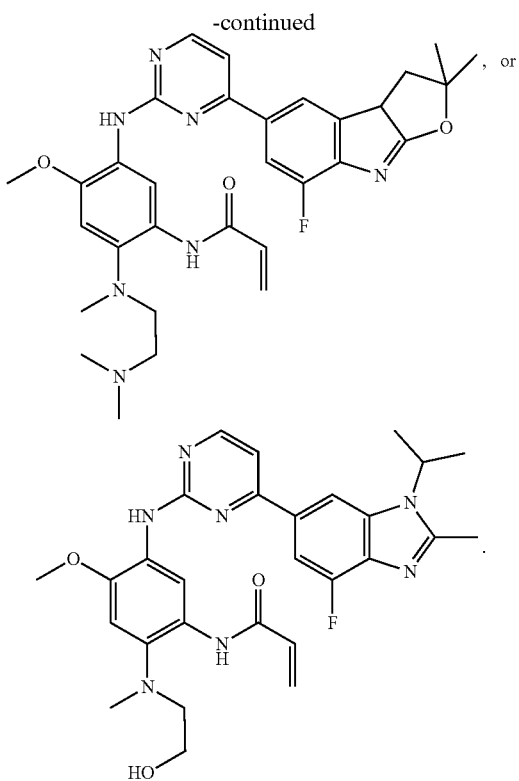

Compounds described herein can comprise one or more asymmetric centers, and thus can exist in various stereoisomeric forms, e.g., enantiomers and/or diastereomers. For example, the compounds described herein can be in the form of an individual enantiomer, diastereomer or geometric isomer (such as cis- and trans-isomer), or can be in the form of a mixture of stereoisomers, including racemic mixtures and mixtures enriched in one or more stereoisomer. Isomers can be isolated from mixtures by methods known to those skilled in the art, including chiral high pressure liquid chromatography (HPLC) and the formation and crystallization of chiral salts; or preferred isomers can be prepared by asymmetric syntheses.

Also disclosed herein are all suitable isotopical derivertives of the compounds disclosed herein. An isotope derivative of a compound disclosed herein is defined as wherein at least one atom is replaced by an atom having the same atomic number but differing in atomic mass from the atomic mass typically found in nature. Examples of isotopes that can be listed as compounds disclosed herein include hydrogen, carbon, nitrogen, oxygen, fluorine, and chlorine isotopes, such as $^2H$, $^3H$, $^{13}C$, $^{14}C$, $^{15}N$, $^{17}O$, $^{18}O$, $^{18}F$, $^{31}P$, $^{32}P$, $^{35}S$ and $^{36}Cl$, respectively. Certain isotopical derivertives of the compounds disclosed herein, such as the radioisotopes of $^3H$ and $^{14}C$, are also among them and are useful in the tissue distribution experiments of drugs and substrates. Tritium, i.e., $^3H$, and carbon-14, i.e., $^{14}C$, are easier to prepare and detect and are the first choice for isotopes. In addition, substitution with isotopes such as deuterium, i.e., $^2H$, has advantages in some therapies due to its good metabolic stability, for example, increased half-life in vivo or reduced dosage, and thus priority may be given in some cases. Isotopical derivertives of the compounds disclosed herein can be prepared by conventional procedures, for example by descriptive methods or by the preparations described in the Examples below, using appropriate isotopic derivatives of the appropriate reagents.

The compound of the present disclosure or a pharmaceutically acceptable salt thereof may be in an amorphous or crystalline form. Furthermore, the compounds of the present disclosure may exist in one or more crystalline forms. Accordingly, the invention includes within its scope all amorphous or crystalline forms of the compounds disclosed herein. The term "polymorph" refers to a crystalline form (or a salt, hydrate or solvate thereof) of a compound in a particular crystal packing arrangement. All polymorphs have the same elemental composition. Different crystalline forms typically have different X-ray diffraction patterns, infrared spectra, melting points, density, hardness, crystal shape, photoelectric properties, stability, and solubility. Recrystallization solvents, crystallization rates, storage temperatures, and other factors can result in a crystalline form that predominates. Various polymorphs of the compounds can be prepared by crystallization under different conditions.

Those skilled in the art will appreciate that many organic compounds can form complexes with solvents that react in or precipitate or crystallize from the solvent. These complexes are referred to as "solvates." When the solvent is water, the complex is referred to as a "hydrate." The invention encompasses all solvates of the compounds disclosed herein.

In addition, prodrugs are also included within the context of the present disclosure. The term "prodrug" as used herein refers to a compound which is converted in vivo to an active form thereof having a medical effect by, for example, hydrolysis in blood. Pharmaceutically acceptable prodrugs are described in T. Higuchi and V. Stella, Prodrugs as Novel Delivery Systems, A.C.S. Symposium Series, Vol. 14, Edward B. Roche, ed., Bioreversible Carriers in Drug Design, American Pharmaceutical Association and Pergamon Press, 1987, and D. Fleisher, S. Ramon and H. Barbra "Improved oral drug delivery: solubility limitations overcome by the use of prodrugs", Advanced Drug Delivery Reviews (1996) 19(2) 115-130, each is incorporated herein by reference.

A prodrug is any covalently bonded carrier which, when administered to a patient, releases the compound of formula (I) in vivo. Prodrugs are typically prepared by modifying functional groups in such a way that the modifications can be cleaved by routine manipulation or in vivo to yield the parent compound. Prodrugs include, for example, compounds disclosed herein wherein a hydroxy, amine or sulfhydryl group is bonded to any group which, when administered to a patient, can be cleaved to form a hydroxy, amine or sulfhydryl group. Thus, representative examples of prodrugs include, but are not limited to, acetate, formate and benzoate derivatives of alcohol, mercapto and amine functional groups of the compounds of formula (I). Further, in the case of a carboxylic acid (—COOH), an ester such as a methyl ester, an ethyl ester or the like can be used. The ester itself may be active and/or may hydrolyze under conditions in human bodies. Suitable pharmaceutically acceptable hydrolysable in vivo ester groups include those groups which readily decompose in the human body to release the parent acid or a salt thereof.

Pharmaceutical Compositions, Formulations and Kits

In another aspect, the invention provides a pharmaceutical composition comprising a compound of the present disclosure (also referred to as the "active ingredient") and a pharmaceutically acceptable excipient. In certain embodiments, the pharmaceutical composition comprises an effective amount of the active ingredient. In certain embodiments, the pharmaceutical composition comprises a therapeutically effective amount of the active ingredient. In certain embodiments, the pharmaceutical composition comprises a prophylactically effective amount of the active ingredient.

A pharmaceutically acceptable excipient for use in the present disclosure refers to a non-toxic carrier, adjuvant or vehicle which does not destroy the pharmacological activity of the compound formulated together. Pharmaceutically acceptable carriers, adjuvants, or vehicles that can be used in the compositions of the present disclosure include, but are not limited to, ion exchangers, alumina, aluminum stearate, lecithin, serum proteins (e.g., human serum albumin), buffer substances (such as phosphate), glycine, sorbic acid, potassium sorbate, a mixture of partial glycerides of saturated plant fatty acids, water, salt or electrolyte (such as protamine sulfate), disodium hydrogen phosphate, potassium hydrogen phosphate, sodium chloride, zinc salt, silica gel, magnesium trisilicate, polyvinyl pyrrolidone, cellulose-based materials, polyethylene glycol, sodium carboxymethyl cellulose, polyacrylate, wax, polyethylene-polyoxypropylene block polymers, polyethylene glycol and lanolin.

The present disclosure also includes kits (e.g., pharmaceutical packs). Kits provided may include a compound disclosed herein, other therapeutic agents, and a first and a second containers (eg, vials, ampoules, bottles, syringes, and/or dispersible packages or other materials) containing the compound disclosed herein or other therapeutic agents. In some embodiments, kits provided can also optionally include a third container containing a pharmaceutically acceptable excipient for diluting or suspending the compound disclosed herein and/or other therapeutic agent. In some embodiments, the compound disclosed herein provided in the first container and the other therapeutic agents provided in the second container is combined to form a unit dosage form.

The following formulation examples illustrate representative pharmaceutical compositions that may be prepared in accordance with this invention. The present disclosure, however, is not limited to the following pharmaceutical compositions.

Exemplary Formulation 1—Tablets: A compound of the present disclosure may be admixed as a dry powder with a dry gelatin binder in an approximate 1:2 weight ratio. A minor amount of magnesium stearate is added as a lubricant. The mixture is formed into 0.3-30 mg tablets (0.1-10 mg of active compound per tablet) in a tablet press.

Exemplary Formulation 2—Tablets: A compound of the present disclosure may be admixed as a dry powder with a dry gelatin binder in an approximate 1:2 weight ratio. A minor amount of magnesium stearate is added as a lubricant. The mixture is formed into 30-90 mg tablets (10-30 mg of active compound per tablet) in a tablet press.

Exemplary Formulation 3—Tablets: A compound of the present disclosure may be admixed as a dry powder with a dry gelatin binder in an approximate 1:2 weight ratio. A minor amount of magnesium stearate is added as a lubricant. The mixture is formed into 90-150 mg tablets (30-50 mg of active compound per tablet) in a tablet press.

Exemplary Formulation 4—Tablets: A compound of the present disclosure may be admixed as a dry powder with a dry gelatin binder in an approximate 1:2 weight ratio. A minor amount of magnesium stearate is added as a lubricant. The mixture is formed into 150-240 mg tablets (50-80 mg of active compound per tablet) in a tablet press.

Exemplary Formulation 5—Tablets: A compound of the present disclosure may be admixed as a dry powder with a dry gelatin binder in an approximate 1:2 weight ratio. A minor amount of magnesium stearate is added as a lubricant. The mixture is formed into 240-270 mg tablets (80-90 mg of active compound per tablet) in a tablet press.

Exemplary Formulation 6—Tablets: A compound of the present disclosure may be admixed as a dry powder with a dry gelatin binder in an approximate 1:2 weight ratio. A minor amount of magnesium stearate is added as a lubricant. The mixture is formed into 270-450 mg tablets (90-150 mg of active compound per tablet) in a tablet press.

Exemplary Formulation 7—Tablets: A compound of the present disclosure may be admixed as a dry powder with a dry gelatin binder in an approximate 1:2 weight ratio. A minor amount of magnesium stearate is added as a lubricant. The mixture is formed into 450-900 mg tablets (150-300 mg of active compound) in a tablet press.

Exemplary Formulation 8—Capsules: A compound of the present disclosure may be admixed as a dry powder with a starch diluent in an approximate 1:1 weight ratio. The mixture is filled into 250 mg capsules (125 mg of active compound per capsule).

Exemplary Formulation 9—Liquid: A compound of the present disclosure (125 mg) may be admixed with sucrose (1.75 g) and xanthan gum (4 mg) and the resultant mixture may be blended, passed through a No. 10 mesh U.S. sieve, and then mixed with a previously made solution of microcrystalline cellulose and sodium carboxymethyl cellulose (11:89, 50 mg) in water. Sodium benzoate (10 mg), flavor, and color are diluted with water and added with stirring. Sufficient water may then be added to produce a total volume of 5 mL.

Exemplary Formulation 10—Injection: A compound of the present disclosure may be dissolved or suspended in a buffered sterile saline injectable aqueous medium to a concentration of approximately 5 mg/mL.

Administration

The pharmaceutical composition provided by the present disclosure can be administered by a variety of routes including, but not limited to, oral administration, parenteral administration, inhalation administration, topical administration, rectal administration, nasal administration, oral administration, vaginal administration, administration by implant or other means of administration. For example, parenteral administration as used herein includes subcutaneous administration, intradermal administration, intravenous administration, intramuscular administration, intra-articular administration, intraarterial administration, intrasynovial administration, intrasternal administration, intracerebroventricular administration, intralesional administration, and intracranial injection or infusion techniques.

Generally, the compounds provided herein are administered in an effective amount. The amount of the compound actually administered will typically be determined by a physician, in the light of the relevant circumstances, including the condition to be treated, the chosen route of administration, the actual compound administered, the age, weight, and response of the individual patient, the severity of the patient's symptoms, and the like.

When used to prevent the disorder disclosed herein, the compounds provided herein will be administered to a subject at risk for developing the condition, typically on the advice and under the supervision of a physician, at the dosage levels described above. Subjects at risk for developing a particular condition generally include those that have a family history of the condition, or those who have been identified by genetic testing or screening to be particularly susceptible to developing the condition.

The pharmaceutical compositions provided herein can also be administered chronically ("chronic administration"). Chronic administration refers to administration of a compound or pharmaceutical composition thereof over an extended period of time, e.g., for example, over 3 months, 6 months, 1 year, 2 years, 3 years, 5 years, etc, or may be continued indefinitely, for example, for the rest of the subject's life. In certain embodiments, the chronic administration is intended to provide a constant level of the compound in the blood, e.g., within the therapeutic window over the extended period of time.

The pharmaceutical compostions of the present disclosure may be further delivered using a variety of dosing methods. For example, in certain embodiments, the pharmaceutical composition may be given as a bolus, e.g., in order to raise the concentration of the compound in the blood to an effective level. The placement of the bolus dose depends on the systemic levels of the active ingredient desired throughout the body, e.g., an intramuscular or subcutaneous bolus dose allows a slow release of the active ingredient, while a bolus delivered directly to the veins (e.g., through an IV drip) allows a much faster delivery which quickly raises the concentration of the active ingredient in the blood to an effective level. In other embodiments, the pharmaceutical composition may be administered as a continuous infusion, e.g., by IV drip, to provide maintenance of a steady-state concentration of the active ingredient in the subject's body. Furthermore, in still yet other embodiments, the pharmaceutical composition may be administered as first as a bolus dose, followed by continuous infusion.

The compositions for oral administration can take the form of bulk liquid solutions or suspensions, or bulk powders. More commonly, however, the compositions are presented in unit dosage forms to facilitate accurate dosing. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. Typical unit dosage forms include prefilled, premeasured ampules or syringes of the liquid compositions or pills, tablets, capsules or the like in the case of solid compositions. In such compositions, the compound is usually a minor component (from about 0.1 to about 50% by weight or preferably from about 1 to about 40% by weight) with the remainder being various vehicles or excipients and processing aids helpful for forming the desired dosing form.

With oral dosing, one to five and especially two to four and typically three oral doses per day are representative regimens. Using these dosing patterns, each dose provides from about 0.01 to about 20 mg/kg of the compound provided herein, with preferred doses each providing from about 0.1 to about 10 mg/kg, and especially about 1 to about 5 mg/kg.

Transdermal doses are generally selected to provide similar or lower blood levels than are achieved using injection doses, generally in an amount ranging from about 0.01 to about 20% by weight, preferably from about 0.1 to about 20% by weight, preferably from about 0.1 to about 10% by weight, and more preferably from about 0.5 to about 15% by weight.

Injection dose levels range from about 0.1 mg/kg/hour to at least 10 mg/kg/hour, all for from about 1 to about 120 hours and especially 24 to 96 hours. A preloading bolus of from about 0.1 mg/kg to about 10 mg/kg or more may also be administered to achieve adequate steady state levels. The maximum total dose is not expected to exceed about 2 g/day for a 40 to 80 kg human patient.

Liquid forms suitable for oral administration may include a suitable aqueous or nonaqueous vehicle with buffers, suspending and dispensing agents, colorants, flavors and the like. Solid forms may include, for example, any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate; a glidant such as colloidal silicon dioxide; a sweetening agent such as sucrose or saccharin; or a flavoring agent such as peppermint, methyl salicylate, or orange flavoring.

Injectable compositions are typically based upon injectable sterile saline or phosphate-buffered saline or other injectable excipients known in the art. As before, the active compound in such compositions is typically a minor component, often being from about 0.05 to 10% by weight with the remainder being the injectable excipient and the like.

Transdermal compositions are typically formulated as a topical ointment or cream containing the active ingredient(s). When formulated as a ointment, the active ingredients will typically be combined with either a paraffinic or a water-miscible ointment base. Alternatively, the active ingredients may be formulated in a cream with, for example an oil-in-water cream base. Such transdermal formulations are well-known in the art and generally include additional ingredients to enhance the dermal penetration of stability of the active ingredients or Formulation. All such known transdermal formulations and ingredients are included within the scope provided herein.

The compounds provided herein can also be administered by a transdermal device. Accordingly, transdermal administration can be accomplished using a patch either of the reservoir or porous membrane type, or of a solid matrix variety.

The above-described components for orally administrable, injectable or topically administrable compositions are merely representative. Other materials as well as processing techniques and the like are set forth in Part 8 of *Remington's Pharmaceutical Sciences,* 17th edition, 1985, Mack Publishing Company, Easton, Pa., which is incorporated herein by reference.

The compounds of the present disclosure can also be administered in sustained release forms or from sustained release drug delivery systems. A description of representative sustained release materials can be found in Remington's Pharmaceutical Sciences.

The present disclosure also relates to the pharmaceutically acceptable formulations of a compound of the present disclosure. In one embodiment, the formulation comprises water. In another embodiment, the formulation comprises a cyclodextrin derivative. The most common cyclodextrins are α-, β- and γ-cyclodextrins consisting of 6, 7 and 8 α-1,4-linked glucose units, respectively, optionally comprising one or more substituents on the linked sugar moieties, which include, but are not limited to, methylated, hydroxyalkylated, acylated, and sulfoalkylether substitution. In certain embodiments, the cyclodextrin is a sulfoalkyl ether β-cyclodextrin, e.g., for example, sulfobutyl ether β-cyclodextrin, also known as Captisol. See, e.g., U.S. Pat. No. 5,376,645. In certain embodiments, the formulation comprises hexapropyl-β-cyclodextrin (e.g., 10-50% in water).

Combination

Compounds of the present disclosure, or a pharmaceutically acceptable composition thereof, are administered in combination with other therapeutic agents to treat diseases. Examples of known therapeutic agents include, but are not limited to, Adriamycin, dexamethasone, vincristine, cyclophosphamide, fluorouracil, topotecan, taxol, interferons, platinum derivatives, taxane (e.g., paclitaxel), *vinca* alkaloids (e.g., vinblastine), anthracyclines (e.g., doxorubicin), epipodophyllotoxins (e.g., etoposide), cisplatin, an mTOR inhibitor (e.g., a rapamycin), methotrexate, actinomycin D, dolastatin 10, colchicine, emetine, trimetrexate, metoprine, cyclosporine, daunorubicin, teniposide, amphotericin, alkylating agents (e.g., chlorambucil), 5-fluorouracil, campthothecin, cisplatin, metronidazole, and Gleevec™, among others. In other embodiments, a compound of the present disclosure is administered in combination with a biologic agent, such as Avastin or VECTIBIX.

In certain embodiments, compounds of the present disclosure, or a pharmaceutically acceptable composition thereof, are administered in combination with an antiproliferative or chemotherapeutic agent selected from any one or more of abarelix, aldesleukin, alemtuzumab, alitretinoin, allopurinol, altretamine, amifostine, anastrozole, arsenic trioxide, asparaginase, azacitidine, BCG Live, bevacuzimab, fluorouracil, bexarotene, bleomycin, bortezomib, busulfan, calusterone, capecitabine, camptothecin, carboplatin, carmustine, celecoxib, cetuximab, chlorambucil, cladribine, clofarabine, cyclophosphamide, cytarabine, dactinomycin, darbepoetin alfa, daunorubicin, denileukin, dexrazoxane, docetaxel, doxorubicin, doxorubicin hydrochloride, dromostanolone propionate, epirubicin, epoetin alfa, erlotinib, estramustine, etoposide phosphate, etoposide, exemestane, filgrastim, floxuridine fludarabine, fulvestrant, gefitinib, gemcitabine, gemtuzumab, goserelin acetate, histrelin acetate, hydroxyurea, ibritumomab, idarubicin, ifosfamide, imatinib mesylate, interferon alfa-2a, interferon alfa-2b, irinotecan, lenalidomide, letrozole, leucovorin, leuprolide acetate, levamisole, lomustine, megestrol acetate, melphalan, mercaptopurine, 6-MP, mesna, methotrexate, methoxsalen, mitomycin C, mitotane, mitoxantrone, nandrolone, nelarabine, nofetumomab, oprelvekin, oxaliplatin, paclitaxel, palifermin, pamidronate, pegademase, pegaspargase, pegfilgrastim, pemetrexed disodium, pentostatin, pipobroman, plicamycin, porfimer sodium, procarbazine, quinacrine, rasburicase, rituximab, sargramostim, sorafenib, streptozocin, sunitinib maleate, talc, tamoxifen, temozolomide, teniposide, VM-26, testolactone, thioguanine, 6-TG, thiotepa, topotecan, toremifene, tositumomab, trastuzumab, tretinoin, ATRA, uracil mustard, valrubicin, vinblastine, vincristine, vinorelbine, zoledronate, or zoledronic acid.

Other examples of agents the compounds of this disclosure may also be combined with include, without limitation: treatments for Alzheimer's Disease such as donepezil hydrochloride and rivastigmine; treatments for Parkinson's Disease such as L-DOPA/carbidopa, entacapone, ropinrole, pramipexole, bromocriptine, pergolide, trihexephendyl, and amantadine; agents for treating Multiple Sclerosis (MS) such as beta interferon, glatiramer acetate, and mitoxantrone; treatments for asthma such as albuterol and montelukast; agents for treating schizophrenia such as zyprexa, risperdal, seroquel, and haloperidol; anti-inflammatory agents such as corticosteroids, TNF blockers, IL-1RA, azathioprine, cyclophosphamide, and sulfasalazine; immunomodulatory and immunosuppressive agents such as cyclosporin, tacrolimus, rapamycin, mycophenolate mofetil, interferons, corticosteroids, cyclophophamide, azathioprine, and sulfasalazine; neurotrophic factors such as acetylcholinesterase inhibitors, MAO inhibitors, interferons, anticonvulsants, ion channel blockers, riluzole, and anti-Parkinsonian agents; agents for treating cardiovascular disease such as beta-blockers, ACE inhibitors, diuretics, nitrates, calcium channel blockers, and statins; agents for treating liver disease such as corticosteroids, cholestyramine, interferons, and anti-viral agents; agents for treating blood disorders such as corticosteroids, antileukemic agents, and growth factors; and agents for treating immunodeficiency disorders such as gamma globulin.

Those other active agents can be administered separately from the compositions containing the compounds of the present disclosure as part of a multiple dosing regimen. Alternatively, those active agents may be part of a single dosage form, mixed with a compound disclosed herein in a single composition. If administered as part of a multiple dosing regimen, the two active agents can be provided simultaneously, sequentially, or at intervals from one another (usually within 5 hours of each other).

Treatment

The disclosure provides a method for inhibiting a protein tyrosine kinase (such as EGFR kinase) or treating a disease (such as cancer, cell proliferative disease, inflammation, infection, immune disease, organ transplantation, viral disease, cardiovascular disease or metabolic disease, comprising the steps of administering a compound disclosed herein, or a pharmaceutically acceptable salt, stereoisomer, solvate, hydrate, crystal form, prodrug or isotope derivative thereof, to a subject in need of the treatment, or a pharmaceutical composition disclosed herein.

The compounds disclosed herein are useful in the treatment of cancer caused by EGFR. In particular, the compounds are useful for treating cancer caused by EGFR that expresses an EGFR mutant and for treating cancer caused by EGFR that is refractory to RTKI therapy (e.g., erlotinib or gefitinib).

The compounds disclosed herein are inhibitors of at least one mutant of EGFR and are therefore suitable for treatment of one or more cancers that is related to the activity of one or more EGFR mutants (e.g., deletion mutations, activating mutations, resistance mutations, or combinations thereof, specific examples include T790M mutations, L858R mutation and the L858R/T790M dual mutation. Accordingly, in a particular embodiment, the disclosure provides a method of treating a mutant EGFR mediated disorder comprising administering a compound disclosed herein, or a pharmaceutically acceptable salt thereof, a stereoisomer thereof, a solvate, a hydrate, a crystal form, a prodrug or an isotope derivative, to a patient in need thereof, or administering the pharmaceutical composition of the present disclosure.

Cancers treatable by the compounds disclosed herein include, but are not limited to, hyperproliferative diseases such as non-small cell lung cancer (NSCLS), small cell lung cancer, lung adenocarcinoma, lung squamous cell carcinoma, pancreatic cancer, breast cancer, prostate cancer, liver cancer, skin cancer, epithelial cell carcinoma, gastrointestinal stromal tumors, leukemia, histiocytic lymphoma, and nasopharyngeal carcinoma. In addition, the compounds disclosed herein are also useful for prevention of cancer recurrence in patients in need of such treatment.

An effective amount of a compound disclosed herein will generally be administered in a single or multiple doses at an average daily dose of from 0.01 mg to 50 mg of compound per kilogram of patient body weight, preferably from 0.1 mg to 25 mg of compound per kilogram of patient body weight. In general, the compounds disclosed herein may be administered to a patient in need of such treatment in a daily dosage range of from about 1 mg to about 3500 mg per patient, preferably from 10 mg to 1000 mg. For example, the daily dose per patient can be 10, 20, 30, 40, 50, 60, 70, 80, 90, 100, 150, 200, 250, 300, 350, 400, 500, 600, 700, 800, 900 or 1000 mg. It can be administered one or more times daily, weekly (or several days apart) or on an intermittent schedule. For example, the compound can be administered one or more times per day on a weekly basis (e.g., every Monday), continually or for several weeks, such as 4-10 weeks. Alternatively, the administration may be continued for several days (e.g., 2-10 days), followed by a few days (e.g., 1-30 days) without administration of the compound, and the cycle may be repeated indefinitely or repeated for a given number of times, such as 4-10. Cycles. For example, the compounds disclosed herein may be administered daily for 5 days, then intermittently for 9 days, then administered daily for 5 days, then intermittent for 9 days, and so on, and the cycle is repeated indefinitely or repeated 4-10 times.

When EGFR-TKI (e.g., erlotinib or gefitinib) is used in combination with a compound disclosed herein, the individual components of the combination therapy can be administered at their dosage level and regimen for monotherapy. For example, erlotinib has been orally administered at a dose of 150 mg per day for the treatment of non-small cell lung cancer, and has been orally administered at a dose of 100 mg per day for pancreatic cancer. In another example, gefitinib has been orally administered at a dose of 250 mg per day for the treatment of non-small cell lung cancer.

Preferably, when EGFR-TKI (e.g., erlotinib or gefitinib) is used in combination with a compound disclosed herein, the dosage level of one or both components is reduced compared to when used alone.

EXAMPLES

The following examples are provided to provide those skilled in the art with a complete disclosure and description of how to carry out, prepare, and evaluate the methods and compounds claimed herein, which are only for illustrative purpose and not constitute any limitation of the scope of the invention.

Synthetic Method

The compounds of the present disclosure can be prepared according to conventional methods in the art and using suitable reagents, starting materials, and purification methods known to those skilled in the art.

The preparation of the compounds of the formula I of the present disclosure is more specifically described below, but these specific methods do not constitute any limitation to the present disclosure. The compounds of the present disclosure may also be conveniently prepared by combining various synthetic methods described in the specification or known in the art, and such combinations are readily available to those skilled in the art to which the present disclosure pertains.

Usually, in the preparation, each reaction is usually carried out in an inert solvent at room temperature to reflux temperature (e.g., 0° C. to 100° C., preferably 0° C. to 80° C.). The reaction time is usually from 0.1 to 60 hours, preferably from 0.5 to 24 hours.

Synthesis of Intermediate Compounds

Synthesis of Intermediate Compound 4-fluoro-1-isopropyl-2-methyl-6-(4,4,5,5-tetramethyl-1,3,2-dioxaborolan-2-yl)-1H-benzo[d]imidazole

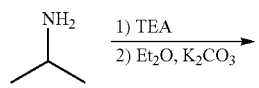

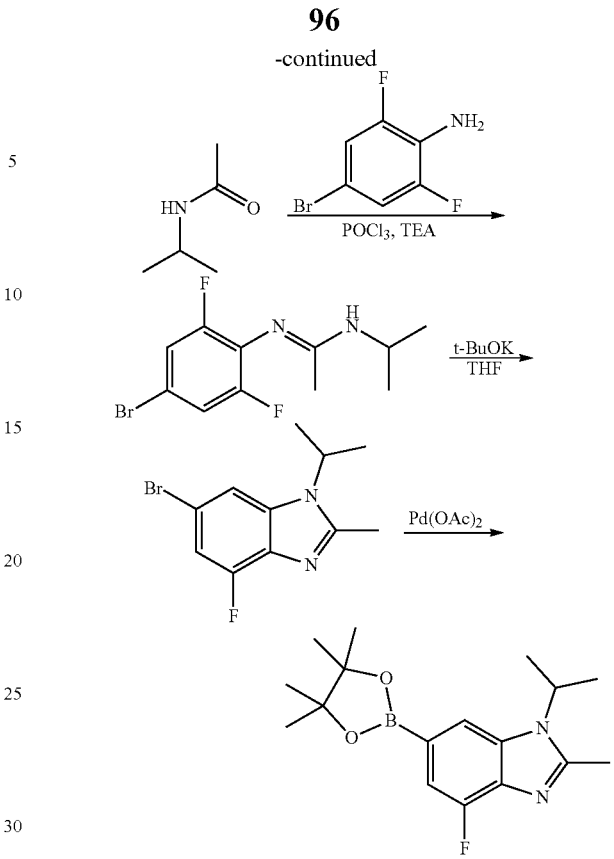

Step 1 Synthesis of Compound N-isopropylacetamide

In an ice bath, acetic anhydride (16.15 mL) was slowly added into the solution of triethylamine (TEA, 23.58 mL) and isopropylamine (10 g) in dichloromethane (100 mL), and after the addition was completed, the reaction was stirred overnight at rt. The dichloromethane was removed under reduced pressure. Diethyl ether was added, followed by a large amount of potassium carbonate, and the mixture was stirred overnight. The solid was filtered, and the filtrate was concentrated under reduced pressure to give 16.0 g a colorless clear oil, yield: 100%. LC-MS(APCI): m/z=102.1 (M+1); $^1$H NMR (500 MHz, CDCl$_3$) (δ/ppm) 4.14-3.99 (m, 1H), 1.94 (s, 3H), 1.13 (d, J=6.6 Hz, 6H).

Step 2 Synthesis of Compound (E)-N'-(4-bromo-2,6-difluorophenyl)-N-isopropylacetimidamide At room temperature, phosphorus oxychloride (6.5 mL) was added to a solution of 4-bromo-2,6-difluoroaniline (9.00 g, 43.27 mmol), N-isopropylacetamide (8.74 g, 86.54 mmol), and triethylamine (10 mL) in toluene (130 mL), and the reaction was stirred under reflux for 3 hours. After cooling to room temperature, the solvent of the reaction was removed under reduced pressure. The crude product was dissolved in 150 mL of dichloromethane and washed with saturated sodium bicarbonate solution for 3-4 times, dried over anhydrous sodium sulfate, the filtrate was concentrated under reduced pressure, and the filtrate was separated on column chromatography (eluant:petroleum ether/ethyl acetate (v/v)=5:1), to afford 12.0 g of a pale yellow solid. Yield: 95.6%. LC-MS(APCI): m/z=291.1 (M+1).

Step 3 Synthesis of Compound 6-bromo-4-fluoro-1-isopropyl-2-methyl-1H-benzo[d]imidazole Under nitrogen protection, potassium tert-butoxide (3.65 g, 32.6 mmol) was added into (E)-N'-(4-bromo-2,6-difluorophenyl)-N-isopropylacetimidamide (4.50 g, 15.5 mmol) in anhydrous tetrahydrofuran, the reaction was carried out at 70° C. for 2 hours. After cooling to room temperature, and filtered on Celite, the filter cake was washed with dichloromethane, the filtrate was washed with brine, dried over anhydrous sodium sulfate, the filtrate was concentrated under reduced pressure, and the filtrate was separated on column chromatography (eluant:petroleum ether/ethyl acetate (v/v)=5:1), to afford 4.0 g of a pale yellow solid. Yield: 95.6%. LC-MS(APCI): m/z=271.1 (M+1).

Step 4 Synthesis of Compound 4-fluoro-1-isopropyl-2-methyl-6-(4,4,5,5-tetramethyl-1,3,2-dioxaborolan-2-yl)-1H-benzo[d]imidazole Under nitrogen protection, palladium acetate (28 mg) and tricyclohexylphosphine (54.3 mg) was added into the solution of 6-bromo-4-fluoro-1-isopropyl-2-methyl-H-benzo[d]imidazole (300 mg, 1.10 mmol), bis(pinacolato)diboron (422 mg, 1.70 mmol) and potassium acetate (326 mg, 3.3 mmol) in anhydrous dimethyl sulfoxide (DMSO, 5 mL), and the reaction was carried out at 100° C. under nitrogen protection for 2 hours. After cooling to room temperature, the reaction was filtered on Celite, the filter cake was washed with ethyl acetate, the filtrate was washed with brine, dried over anhydrous sodium sulfate, the filtrate was concentrated under reduced pressure, and the filtrate was separated on column chromatography (eluant:petroleum ether/ethyl acetate (v/v)=3:1), to affard 260 mg of a pale yellow solid. Yield: 74.3%. LC-MS(APCI): m/z=319.3 (M+1).

Synthesis of Intermediate Compound N-(5-amino-2-((2-(dimethylamino)ethyl)(methyl)amino)-4-methoxyphenyl)acrylamide

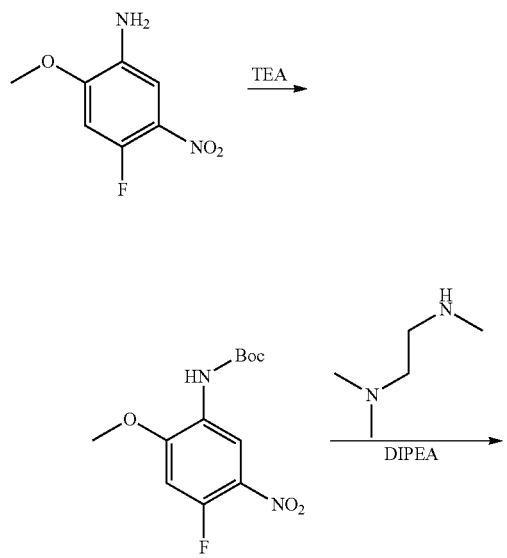

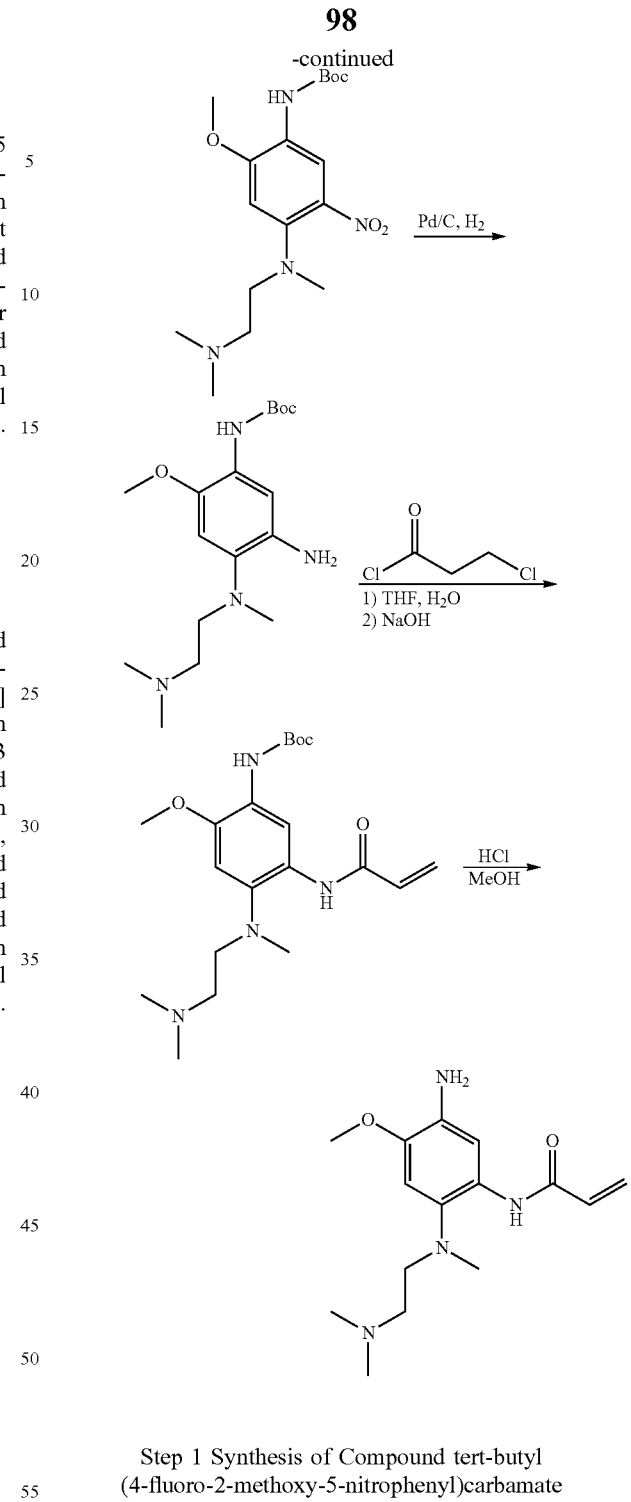

Step 1 Synthesis of Compound tert-butyl (4-fluoro-2-methoxy-5-nitrophenyl)carbamate In an ice bath, Boc anhydride (7.05 g, 32.20 mmol) was slowly added into the mixed solution of 4-fluoro-2-methoxy-5-nitroaniline (4.0 g, 21.50 mmol) and triethylamine (TEA, 3.60 g, 35.64 mmol) in dichloromethane (65 mL), and after the addition was complete, the reaction mixture was reacted at 40° C. overnight. After cooling to room temperature, the reaction was diluted with water (100 mL), extracted with dichloromethane (100 mL×3), and the organic phase was combined, washed with brine (100 mL), dried over anhydrous sodium sulfate, the solvent was removed, and the filtrate was separated on column chromatography (eluant:petroleum ether/ethyl acetate (v/v)=2:1), to afford 3.6 g of a yellow solid, yield: 58.8%. LC-MS(APCI): m/z=287.2 (M+1).

Step 2 Synthesis of Compound tert-butyl (4-((2-(dimethylamino)ethyl)(methyl)amino)-2-methoxy-5-nitrophenyl)carbamate $N^1,N^1,N^2$-trimethylethane-1,2-diamine (2.14 g, 20.40 mmol) was added into the mixed solution of tert-butyl (4-fluoro-2-methoxy-5-nitrophenyl)carbamate (4.0 g, 21.50 mmol) and N,N-diisopropylethylamine (DIPEA, 4.92 mL, 27.20 mmol) in N,N-dimethylformamide (28 mL), the reaction solution was reacted at 90° C. for 5 hours. After cooling to room temperature, it was diluted with water (100 mL), extracted with ethyl acetate (100 mL×3), and the organic phase was combined, washed with brine (100 mL×3), dried over anhydrous sodium sulfate, and the solvent was removed to afford 5.0 g of a brown oil, which was used in the next reaction without purification. LC-MS(APCI): m/z=369.3 (M+1).

Step 3 Synthesis of Compound tert-butyl (5-amino-4-((2-(dimethylamino)ethyl)(methyl)amino)-2-methoxyphenyl)carbamate Pd/C (500 mg) was added into the solution of tert-butyl (4-((2-(dimethylamino)ethyl)(methyl)amino)-2-methoxy-5-nitrophenyl)carbamate (5.00 g, 13.6 mmol) in methanol (65 mL), the reaction was stirred under a balloon of hydrogen gas overnight. Filtered on Celite, the filtrate was concentrated under reduced pressure, and the filtrate was separated on column chromatography (eluant:dichloromethane/methanol (v/v)=20:1), to afford 4.0 g of a brown-yellow oil, yield over two steps: 86.8%. LC-MS(APCI): m/z=339.3 (M+1).

Step 4 Synthesis of Compound tert-butyl (5-acrylamido-4-((2-(dimethylamino)ethyl)(methyl)amino)-2-methoxyphenyl)carbamate At room temperature, 3-chloropropanoyl chloride (1.80 g, 14.20 mmol) was added into the mixed solution of tert-butyl (5-amino-4-((2-(dimethylamino)ethyl)(methyl)amino)-2-methoxyphenyl)carbamate (4.00 g, 11.80 mmol) in tetrahydrofuran (95 mL) and water (9.5 mL), and was reacted for 1 hour at room temperature. Sodium hydroxide (2.40 g) was added into the reaction, and reacted at 65° C. overnight. After cooling to room temperature, the reaction mixture was concentrated under reduced pressure. The residue was diluted with water (100 mL), extracted with dichloromethane (100 mL×3), and the organic phase was combined, washed with brine (100 mL), dried over anhydrous sodium sulfate, the solvent was removed, and the filtrate was separated on column chromatography (eluant:dichloromethane/methanol (v/v)=20:1), to afford 3.20 g of a brown-yellow solid, yield: 69.2%. LC-MS(APCI): m/z=393.3 (M+1).

Step 5 Synthesis of Compound N-(5-amino-2-((2-(dimethylamino)ethyl)(methyl)amino)-4-methoxyphenyl)acrylamide At room temperature, HCl in methanol (4 M, 5 mL) was added into tert-butyl ((5-acrylamido-4-((2-(dimethylamino) ethyl)(methyl)amino)-2-methoxyphenyl)carbamate (392 mg, 1.00 mmol) in methanol (2 mL), the reaction was reacted overnight, methanol was removed under reduced pressure, saturated sodium bicarbonate (30 mL) was added, extracted with dichloromethane (30 mL×3), and the organic phase was combined, washed with brine (30 mL), dried over anhydrous sodium sulfate and concentrated under reduced pressure to afford 292 mg of a yellow solid, yield: 95%. LC-MS(APCI): m/z=293.3 (M+1).

Synthesis of Intermediate Compound 2-methoxy-4-(4-methylpiperazin-1-yl)aniline

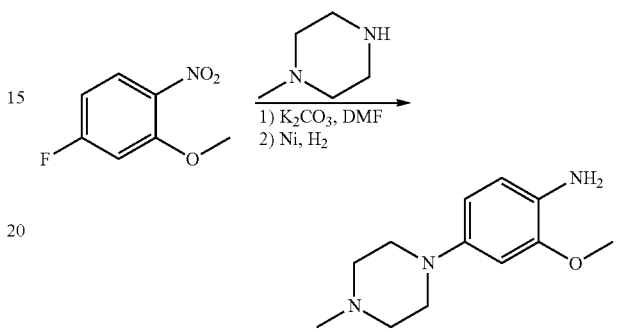

A reaction mixture of 5-fluoro-2-nitroanisole (1.5 g, 8.7 mmol), 1-methylpiperazine (1.0 g, 10.5 mmol) and potassium carbonate (2.4 g, 17.4 mmol) in N,N-dimethylformamide (DMF, 5 mL) was heated to 80° C. for 18 hours, and after cooling to room temperature, 50 mL water was poured into the reaction, and filtered to give the precipitate, which was used directly in the next step. Under a hydrogen atmosphere, the precipitate was dissolved in 30 mL methanol, Raney nickel (200 mg) was added, and the mixture was reacted under the hydrogen atmosphere at room temperature for 5 hours. After filtration, the filtrate was collected and purified by column chromatography to give the product 2-methoxy-4-(4-methylpiperazin-1-yl)aniline 1.6 g, yield 85%. LC-MS(APCI): m/z=221.3 (M+1).

Synthesis of Intermediate Compound 6-(2-chloro-5-fluoropyrimidin-4-yl)-4-fluoro-1-isopropyl-2-methyl-1H-benzo[d]imidazole

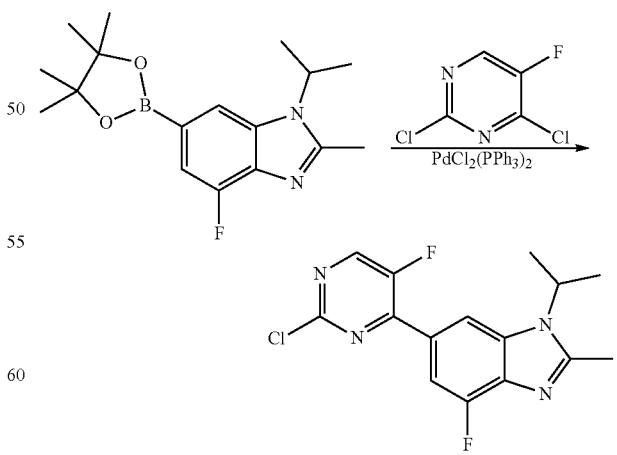

Under a nitrogen atmosphere, 2,4-dichloro-5-fluoropyrimidine (517 mg, 3.1 mmol), sodium carbonate (583 mg, 5.5 mmol) was dissolved in a mixed solution of 1 mL water and 5 mL ethylene glycol dimethyl ether, PdCl$_2$(PPh$_3$)$_2$ (4.7 mg, 66 μmol) was added, heated to 80° C., and then a solution of 4-fluoro-1-isopropyl-2-methyl-6-(4,4,5,5-tetramethyl-1,3,2-dioxaborolan-2-yl-1H-benzo[d]imidazole (700 mg, 2.2 mmol) in ethylene glycol dimethyl ether (40 mL) was added, stirred at this temperature for 4 hours, and then 30 mL water was added, stirring was continued for 25 minutes, filtered and dired the filter cake at 80° C. and then washed with isopropyl alcohol, the product 6-(2-chloro-5-fluoropyrimidin-4-yl)-4-fluoro-1-isopropyl-2-methyl-1H-benzo[d]imidazole 425 mg was obtained after drying, yield: 60%. LC-MS(APCI): m/z=322.7 (M+1).

Synthesis of Intermediate Compound 4-fluoro-1-isopropyl-2-methoxy-6-(4,4,5,5-tetramethyl-1,3,2-dioxaborolan-2-yl)-1H-benzo[d]imidazole

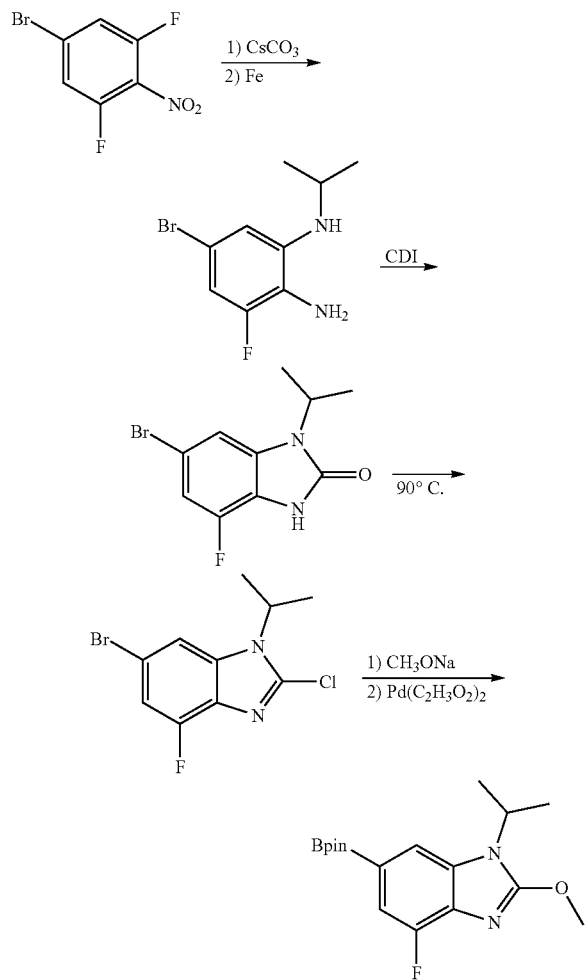

Step 1 Synthesis of Compound 5-bromo-3-fluoro-N$^1$-isopropylbenzene-1,2-diamine The compound 4-bromo-2,6-difluoro-2nitroaniline (4.08 g, 17.1 mmol) was dissolved in 30 mL anhydrous tetrahydrofuran, cooled in an ice bath, and then cesium carbonate (5.59 g, 17.1 mmol) was added and stirred uniformly. Isopropylamine (1.01 g, 17.1 mmol) was slowly added dropwise, after the addition was complete, the reaction was allowed to warm up and reacted overnight. The insoluble solid was removed by suction filtration, and the combined filtrate was evaporated to give a white solid product, which was used in the next step directly. The product of the above step was dissolved by adding ethanol-water (4/1, v/v, 30 mL), reduced iron powder (5.74 g) and ammonium chloride (1.80 g) was added, and the mixture was heated under reflux at 90° C. for 2.5 hours. After cooling to room temperature, the insoluble solid was removed by suction filtration, and most of the ethanol was evaporated under reduced pressure. 20 mL of saturated aqueous solution of sodium bicarbonate was added, 20 mL of EA was used for extraction. The organic phase was dried over anhydrous sodium sulfate, 3.93 g of a crude product was obtained after evaporating to dryness.

Step 2 Synthesis of Compound 6-bromo-4-fluoro-1-isopropyl-1,3-dihydro-2H-benzo[d]imidazole-2-one To 1.0 g of the crude compound 5-bromo-3-fluoro-N$^1$-isopropylbenzene-1,2-diamine was added 4 mL anhydrous DMF at room temperature and stirred to dissolve, and then CDI (N,N'-carbonyldiimidazole, 0.66 g, 4.05 mmol) was added and reacted at room temperature overnight. The reaction was poured into 20 mL water, extracted with EA (5 mL*3), and the organic phase was combined, dried over anhydrous sodium sulfate, and evaporated to dryness to afford a crude product, which was used in the next step without purification.

Step 3 Synthesis of Compound 6-bromo-2-chloro-4-fluoro-1-isopropyl-1H-benzo[d]imidazole Under nitrogen protection, to the compound 6-bromo-4-fluoro-1-isopropyl-1,3-dihydro-2H-benzo[d]imidazole-2-one was added 5 mL of phosphorus oxychloride, 5 mL of toluene, and heated under reflux at 90° C. for 72 hours, the reaction mixture was cooled, and then poured into ice bath-cooled saturated sodium bicarbonate-EA (20 mL-10 mL) and stirred for 10 minutes until layers were separated. The organic phase was dried and purified on column chromatography (PE/EA, v/v, 20/1) to afford 0.57 g product.

Step 4 Synthesis of Intermediate Compound 4-fluoro-1-isopropyl-2-methoxy-6-(4,4,5,5-tetramethyl-1,3,2-dioxaborolan-2-yl)-1H-benzo[d]imidazole The compound 6-bromo-2-chloro-4-fluoro-1-isopropyl-1H-benzo[d]imidazole (0.57 g, 1.96 mmol) was dissolved in 5 mL anhydrous DMF, sodium methoxide (0.65 g, 11.75 mmol) was added in one portion and the reaction was stirred at room temperature overnight. The completion of the reaction was monitored and showed by LC-MS, and the reaction was quenched by adding 0.5 mL saturated aqueous ammonium chloride dropwise, 50 mL water was added, and extracted with EA (10 mL*2). The organic phase was combined, dried over anhydrous sodium sulfate, and evaporated to dryness to afford a white solid product, which was used in the next step without purification. Under nitrogen protection, the above white solid, Bis(pinacolato)diboron (597 mg, 2.35 mmol), tricyclohexylphosphine (56 mg, 0.2 mmol), and potassium acetate (577 mg, 5.88 mmol) was added into anhydrous DMSO (5 mL). The mixture was stirred uniformly and purged with nitrogen for 5 times. Then, palladium acetate (22 mg, 0.1 mmol) was added and purged with nitrogen for 3 times, and the reaction was stirred and heated in an oil bath at 90° C. for 1.5 hours. The reaction solution was cooled to room temperature, 50 mL of water was added, and extracted with PE-EA (v/v, 1/1, O1 mL*2). The organic phase was combined, evaporated and purified on column chromatography (PE/EA, v/v, 4/1) to afford the compound 51, 0.49 g in total.

Synthesis of Intermediate Compound 4-fluoro-1-cyclopropyl-2-methyl-6-(4,4,5,5-tetramethyl-1,3,2-dioxaborolan-2-yl)-1H-benzo[d]imidazole and Intermediate Compound 6-(2-chloropyrimidin-4-yl)-1-cyclopropyl-4-fluoro-2-methyl-1H-benzo[d]imidazole

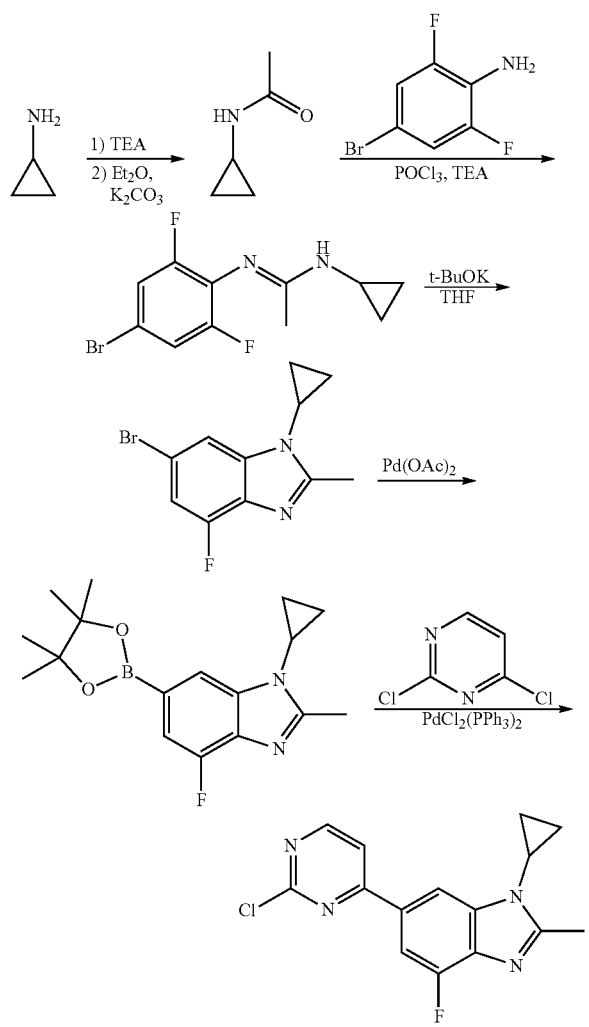

Step 1 Synthesis of Compound N-cyclopropylacetamide

In an ice bath, acetic anhydride (16 mL) was slowly added into the solution of triethylamine (23 mL) and isopropylamine (9 g) in dichloromethane (100 mL). After the addition was completed, the reaction was stirred overnight at rt. The dichloromethane was removed under reduced pressure. Diethyl ether was added, followed by a large amount of potassium carbonate, and the mixture was stirred overnight. The solid was filtered, and the filtrate was concentrated under reduced pressure to give 17 g a colorless clear oil, yield: 100%. LC-MS(APCI): m/z=100.1 (M+1).

Step 2 Synthesis of Compound (E)-N'-(4-bromo-2,6-difluorophenyl)-N-cyclopropylacetimidamide At room temperature, phosphorus oxychloride (6.70 mL) was added into the solution of 4-bromo-2,6-difluoroaniline (10.0 g, 48.00 mmol) and N-isocyclopropylacetamide (9.50 g, 96.00 mmol), triethylamine (10 mL) in toluene (150 mL), and the reaction mixture was stirred under reflux for 3 hours. After cooling to room temperature, the reaction solvent was removed under reduced pressure. The crude was dissolved into 150 mL dichloromethane, washed with saturated sodium bicarbonate for 3-4 times, and dried over anhydrous sodium sulfate. The filtrate was concentrated under reduced pressure, and the filtrate was separated on column chromatography (eluant:petroleum ether/ethyl acetate (v/v)=5:1), to afford 12 g of a white solid. Yield: 86.5%. LC-MS(APCI): m/z=289.1 (M+1).

Step 3 Synthesis of Compound (6-bromo-4-fluoro-1-cyclopropyl-2-methyl)-1 Hbenzo[d]imidazole Under nitrogen protection, potassium tert-butoxide (7.00 g, 62.5 mmol) was added into (E)-N'-(4-bromo-2,6-difluorophenyl)-N-cyclopropylacetimidamide (12 g, 41.7 mmol) in anhydrous tetrahydrofuran (100 mL), and the reaction was reacted at 80° C. for 2 hours. After cooling to room temperature, it was filtered on Celite, and the filter cake was washed with dichloromethane. The filtrate was washed with brine, dried over anhydrous sodium sulfate. The filtrate was concentrated under reduced pressure, and the filtrate was separated on column chromatography (eluant:petroleum ether/ethyl acetate (v/v)=3:1), to afford 10.0 g of a pale yellow solid. Yield: 81.1%. LC-MS(APCI): m/z=269.1 (M+1).

Step 4 Synthesis of Intermediate Compound 4-fluoro-1-cyclopropyl-2-methyl-6-(4,4,5,5-tetramethyl-1,3,2-dioxaborolan-2-yl)-1H-benzo[d]imidazole Under nitrogen protection, palladium acetate (800 mg) and tricyclohexylphosphine (1.60 g) was added into the solution of 6-bromo-4-fluoro-1-cyclopropyl-2-methyl-1Hbenzo[d]imidazole (10 g, 37.17 mmol), bis(pinacolato)diboron (14 g, 55.76 mmol) and potassium acetate (10.9 g, 111.51 mmol) in anhydrous dimethyl sulfoxide (DMSO, 100 mL). The reaction was reacted under nitrogen protection at 100° C. for 2 hours. After cooling to room temperature, it was filtered on Celite, and the filter cake was washed with ethyl acetate. The filtrate was washed with brine, and dried over anhydrous sodium sulfate. The filtrate was concentrated under reduced pressure, and the filtrate was separated on column chromatography (eluant:petroleum ether/ethyl acetate (v/v)=3:1), to afford 8.60 g of a white solid. Yield: 73.2%. LC-MS(APCI): m/z=317.3 (M+1).

Step 5 Synthesis of Intermediate Compound 6-(2-chloropyrimidin-4-yl)-1-cyclopropyl-4-fluoro-2-methyl-1H-benzo[d]imidazole Under nitrogen protection, acetonitrile (9 mL) and water (3 mL) was added into the mixture of 4-fluoro-1-cyclopropyl-2-methyl-6-(4,4,5,5-tetramethyl-1,3,2-dioxaborolan-2- yl)-1H-benzo[d]imidazole (1.00 g, 3.16 mmol) and 2,4-dichloropyrimidine (566 mg, 3.82 mmol), sodium carbonate (839 mg, 7.91 mmol), bis(triphenylphosphine)palladium(II) chloride (111 mg, 0.16 mmol), and the reaction was stirred under nitrogen protection at 80° C. for 2 hours. After cooling to room temperature, it was filtered on Celite, the filter cake was washed with dichloromethane, and the filtrate was washed with brine, and dried over anhydrous sodium sulfate. The filtrate was concentrated under reduced pressure, and the filtrate was separated on column chromatography (eluant:petroleum ether/ethyl acetate (v/v)=3:1) to afford 900 mg of a white solid. Yield was 94.3%. LC-MS(APCI): m/z=303.1 (M+1).

Synthesis of Intermediate Compound 6-(2-chloro-pyrimidin-4-yl)-4-fluoro-2-(fluoromethyl)-1-isopropyl-1H-benzo[d]imidazole

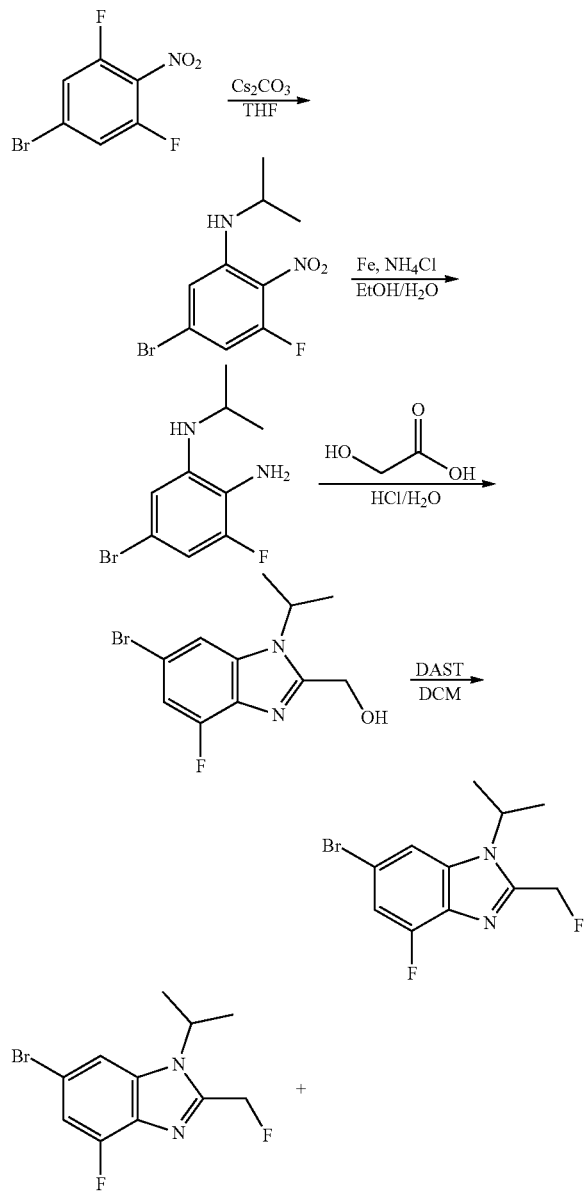

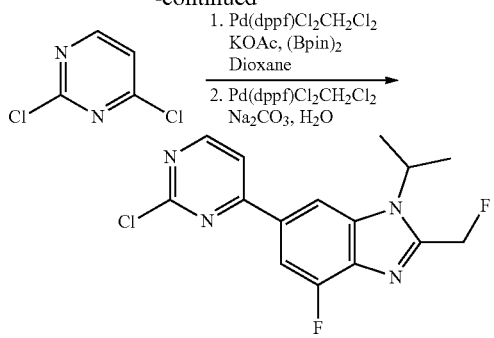

Step 1 Synthesis of Compound 5-bromo-3-fluoro-N-isopropyl-2-nitroaniline

In an ice bath, cesium carbonate (5.86 g, 18.00 mmol) and isopropylamine (1.06 g, 18.00 mmol) were sequentially added into the solution of 5-bromo-1,3-difluoro-2-nitrobenzene (4.28 g, 18.00 mmol) in anhydrous tetrahydrofuran (50 mL), and the reaction mixture was warmed to room temperature naturally. After the mixture was stirred overnight, it was filtered on Celite, and the filtrate was concentrated under reduced pressure to give a crude product, which was used in the next step without purification. Yield was 100%.

Step 2 Synthesis of Compound 5-bromo-3-fluoro-N-isopropylaminebenzene-1,2-diamine The above crude product was dissolved into a mixed solvent of ethanol and water (30 mL, v/v=3/1), reduced iron powder (6.05 g, 108 mmol) and ammonium chloride (2.91 g, 54 mmol) was added, and the reaction mixture was heated to reflux for 2.5 hrs. After cooling to room temperature, it was filtered on Celite, the filtrate was concentrated under reduced pressure, and the filtrate was separated on column chromatography (eluant:petroleum ether/ethyl acetate (v/v)=50:1), to afford 4.296 g of a brown liquid. Yield was 96.6%. LC-MS(APCI): m/z=247.1 (M+1).

Step 3 Synthesis of Compound (6-bromo-4-fluoro-1-isopropyl-1H-benzo[d]imidazole-2-yl) methanol 6 N diluted hydrochloric acid (15 mL) and water (23 mL) was added into the mixture of 5-bromo-3-fluoro-N-isopropylaminebenzene-1,2-diamine (4.00 g, 16.26 mmol) and glycolic acid (6.18 g, 81.30 mmol), and the reaction was refluxed for 2 hrs. After cooling to room temperature, its pH was adjusted with concentrated aqueous ammonia to basic, extracted with dichloromethane (100 mL×3). The organic phase was combined, washed with brine (100 mL) and dried over anhydrous sodium sulfate. The solvent was removed, and the filtrate was separated on column chromatography (eluant:petroleum ether/ethyl acetate (v/v)=1:1), to afford 3.7 g of a pale yellow solid, yield was 79.8%. LC-MS (APCI): m/z=287.2 (M+1); $^1$H NMR (400 MHz, CDCl3): δ 7.45 (d, J=1.5 Hz, 1H), 7.07 (dd, J=9.6, 1.5 Hz, 1H), 5.47 (br, 1H), 4.97-4.85 (m, 3H), 1.63 (d, J=7.0 Hz, 6H).

Step 4 Synthesis of Compound 6-bromo-4-fluoro-2-(fluoromethyl)-1-isopropyl-1H-benzo[d]imidazole In an ice bath, DAST fluorinating reagent (0.64 mL, 4.80 mmol) was slowly added into the solution of (6-bromo-4- fluoro-1-isopropyl-1H-benzo[d]imidazole-2-yl) methanol (1.14 g, 4.00 mmol) in anhydrous dichloromethane (30 mL), and the reaction mixture was reacted in an ice bath for 30 min. The reaction was quenched with saturated solution of sodium bicarbonate, extracted with dichloromethane (30 mL×3). The organic phase was combined, washed with brine (50 mL) and dried over anhydrous sodium sulfate. The solvent was removed, and the filtrate was separated on column chromatography (eluant:petroleum ether/ethyl acetate (v/v)=3:1), to afford 860 mg of a pale yellow solid, yield was 75.4%. LC-MS(APCI): m/z=289.2 (M+1); $^1$H NMR (400 MHz, CDCl3): δ 7.52 (s, 1H), 7.15 (dd, J=9.5, 1.4 Hz, 1H), 5.70 (s, 1H), 5.58 (s, 1H), 4.84 (dt, J=13.6, 6.8 Hz, 1H), 1.67 (d, J=6.9 Hz, 6H).

Step 5 Synthesis of Intermediate Compound 6-(2-chloropyrimidin-4-yl)-4-fluoro-2-(fluoromethyl)-1-isopropyl-1H-benzo[d]imidazole Under nitrogen protection, pd(dppf)Cl$_2$.DCM (81 mg, 0.1 mmol) was added into the mixture of 6-bromo-4-fluoro-2-(fluoromethyl)-1-isopropyl-1H-benzo[d]imidazole (340 mg, 1.18 mmol), bis(pinacolato)diboron (360 mg, 1.42 mmol) and potassium acetate (230 mg, 2.36 mmol) in anhydrous dioxane (16 mL), and the reaction was reacted under nitrogen protection at 100° C. overnight.

After cooling to room temperature, under nitrogen protection, the reaction mixture was added 2,4-dichloropyrimidine (213 mg, 1.42 mmol), sodium carbonate (250 mmol, 2.36 mmol), pd(dppf)Cl$_2$.DCM (81 mg, 0.1 mmol) and water (4 mL), and the reaction was reacted under nitrogen protection to 80° C. for 2.5 hrs. After cooling to room temperature, it was filtered on Celite, the filtrate was concentrated under reduced pressure, and the filtrate was separated on column chromatography (eluant:petroleum ether/ ethyl acetate (v/v)=1:1), to afford 290 mg of a yellow solid. Yield was 76.1%. LC-MS(APCI): m/z=323.2 (M+1).

Synthesis of Intermediate Compound 6-(2-chloropyrimidin-4-yl)-1-isopropyl-2-methyl-1H-imidazo[4,5-b]pyridine

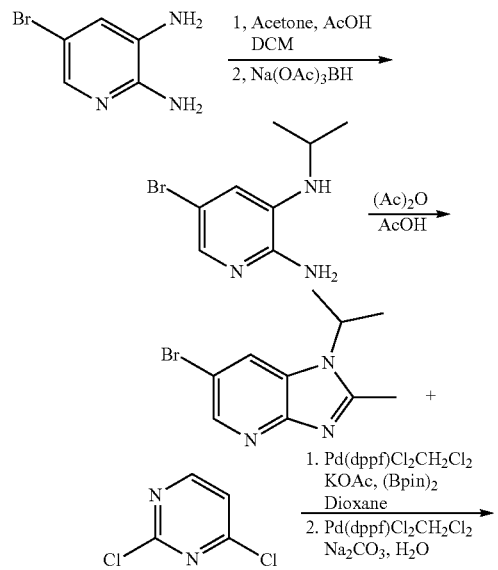

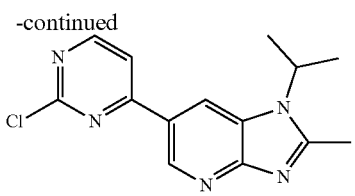

Step 1 Synthesis of 5-bromo-N$^3$-isopropylpyridine-2,3-diamine

At room temperature, glacial acetic acid (0.86 mL, 15.00 mmol) was added into the solution of 5-bromopyridine-2,3-diamine (2.82 g, 15.00 mmol) and acetone (870 mg, 15.00 mmol) in anhydrous dichloromethane (30 mL), and the reaction was stirred at room temperature for 5 hrs. After cooling in an ice bath, sodium triacetoxyborohydride (4.77 g, 22.50 mmol) was added portionwise, and the reaction mixture was warmed naturally, and reacted at room temperature overnight. The pH was adjusted to 8 with saturated sodium bicarbonate, extracted with dichloromethane (50 mL×3). The organic phase was washed with brine separately, dried over anhydrous sodium sulfate, concentrated under reduced pressure, and the filtrate was separated on column chromatography (eluant:dichloromethane /methanol (v/v)=35:1), to afford 1.5 solid. Yield was 47.8%. LC-MS (APCI): m/z=230 (M+1). $^1$H NMR (400 MHz, DMSO-d6): δ 7.25 (d, J=2.1 Hz, 1H), 6.61 (d, J=2.0 Hz, 1H), 5.74 (Br, 2H), 4.80 (d, J=7.3 Hz, 1H), 3.60-3.44 (m, 1H), 1.14 (d, J=6.3 Hz, 6H).

Step 2 Synthesis of 6-bromo-1-isopropyl-2-methyl-1H-imidazo[4,5-b]pyridine

Acetic anhydride (2 mL) was added into the solution of 5-bromo-N$^3$-isopropylpyridine-2,3-diamine (1.50 g, 7.16 mmol) in acetic acid (15 mL), and the reaction was reacted under reflux at 125° C. for 2 hrs. Then, the reaction was cooled to room temperature. The reaction solvent was removed under reduced pressure, the pH of the residue was adjusted to 8 with saturated sodium bicaronate, extracted with dichloromethane (50 mL×3). The organic phase was washed with brine separately, dried over anhydrous sodium sulfate, concentrated under reduced pressure, and the filtrate was separated on column chromatography (eluant:dichloromethane/methanol (v/v)=25:1), to afford 1.4 solid. Yield was 47.8%. LC-MS(APCI): m/z=254.0 (M+1). $^1$H NMR (400 MHz, DMSO-d6): δ 8.39 (dd, J=5.7, 2.1 Hz, 2H), 4.76 (hept, J=6.9 Hz, 1H), 2.62 (s, 3H), 1.54 (d, J=6.9 Hz, 6H).

Step 3 Synthesis of Intermediate Compound 6-(2-chloropyrimidin-4-yl)-1-isopropyl-2-methyl-1H-imidazo[4,5-b]pyridine The synthetic step is the same as the synthetic step 5 of intermediate compound 6-(2-chloropyrimidin-4-yl)-4-fluoro-2-(fluoromethyl)-1-isopropyl-1H-benzo[d]imidazole, and afforded product 6-(2-chloropyrimidin-4-yl)-1-isopropyl-2-methyl-H-imidazo[4,5-b]pyridine (510 mg of a white solid). Yield was 91.1%. LC-MS(APCI): m/z=287.8 (M+1); $^1$H NMR (400 MHz, DMSO-d6): δ 9.16 (d, J=2.0 Hz, 1H), 8.83 (d, J=5.3 Hz, 1H), 8.72 (d, J=2.1 Hz, 1H), 8.36 (d, J=5.3 Hz, 1H), 4.87 (dt, J=13.8, 6.9 Hz, 1H), 2.68 (s, 3H), 1.62 (d, J=6.9 Hz, 6H).

Synthesis of Intermediate Compound 6-(2-chloro-pyrimidin-4-yl)-1-isopropyl-2-methoxy-1H-imidazo[4,5-b]pyridine

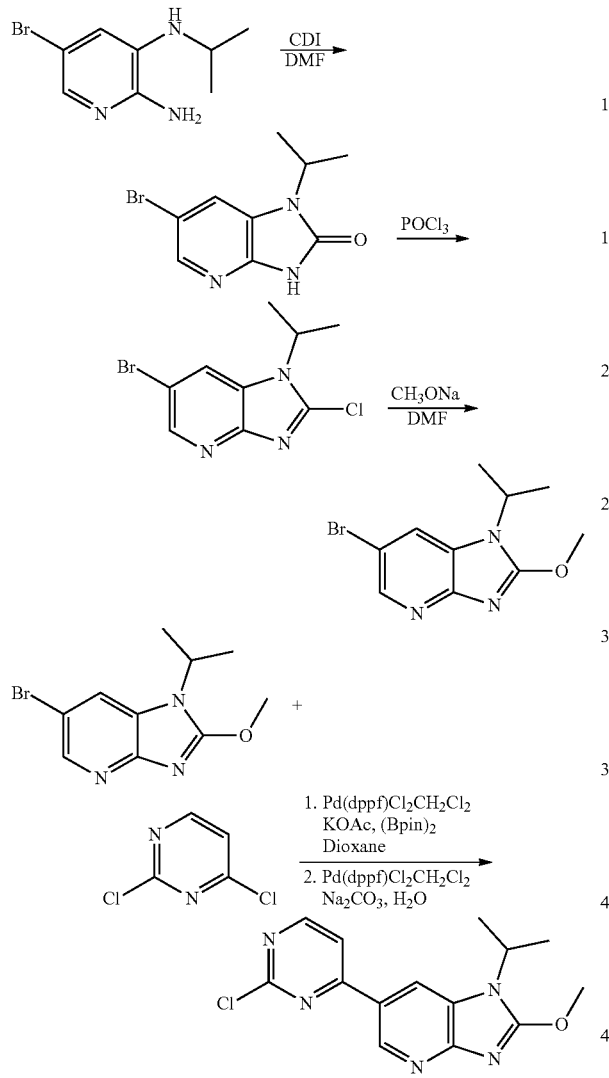

Step 1 Synthesis of 6-bromo-1-isopropyl-1,3-dihydro-2H-imidazo[4,5-b]pyridine-2-one At room temperature, CDI (4.5 g, 627.83 mmol) was added into 5-bromo-N³-isopropylpyridine-2,3-diamine (1.6 g, 6.96 mmol) in anhydrous acetonitrile (50 mL), and the reaction was reacted at room temperature overnight. The reaction was quenched by adding water, extracted with ethyl acetate (50 mL×3), and the combined organic layer was washed with brine, dried over anhydrous sodium sulfate, concentrated under reduced pressure, and the filtrate was separated on column chromatography (eluant: dichloromethane/methanol (v/v)=25:1), to afford 1.00 g of a white solid, yield was 83.0%. LC-MS(APCI): m/z=256.0 (M+1).

Step 2 Synthesis of 6-bromo-2-chloro-1-isopropyl-1H-imidazo[4,5-b]pyridine

At room temperature, 6-bromo-1-isopropyl-1,3-dihydro-2H-imidazo[4,5-b]pyridine-2-one (1.00 g, 3.92 mmol) was dissolved in phosphorus oxychloride (20 mL), and the reaction was refluxed overnight. After cooling to room temperature, the reaction solvent was removed under reduced pressure, the pH of the residue was adjusted to neutral with saturated sodium bicarbonate, extracted with dichloromethane (50 mL×3). The organic phase was washed with brine separately, dried over anhydrous sodium sulfate, concentrated under reduced pressure, and the filtrate was separated on column chromatography (eluant:petroleum ether/ethyl acetate (v/v)=1:1), to afford 950 mg of a white solid. Yield was 88.5%. LC-MS(APCI): m/z=274.0 (M+1).

Step 3 Synthesis of 6-bromo-2-methoxy-1-isopropyl-1H-imidazo[4,5-b]pyridine

In an ice bath, sodium methoxide (245 mg, 4.50 mmol) was added into 6-bromo-2-chloro-1-isopropyl-1H-imidazo[4,5-b]pyridine (500 mg, 1.80 mmol) in anhydrous DMF (10 mL), warmed up naturally, and the reaction was stirred overnight. The reaction was quenched by adding water, extracted with ethyl acetate (50 mL×3). The organic layer was combined and washed with brine, dried over anhydrous sodium sulfate, concentrated under reduced pressure, and the filtrate was separated on column chromatography (eluant:petroleum ether/ethyl acetate (v/v)=1:1), to afford 450 mg of a white solid, yield was 93.0%. LC-MS(APCI): m/z=270.0 (M+1).

Step 4 Synthesis of Intermediate Compound 6-(2-chloropyrimidin-4-yl)-1-isopropyl-2-methoxy-1H-imidazo[4,5-b]pyridine The synthetic step is the same as the synthetic step 5 of intermediate compound 6-(2-chloropyrimidin-4-yl)-4-fluoro-2-(fluoromethyl)-1-isopropyl-1H-benzo[d]imidazole, and afforded 185 mg of a white solid. Yield was 75.9%. LC-MS(APCI): m/z=304.1 (M+1).

Synthesis of Intermediate Compound 1-isopropyl-2-methoxy-6-(4,4,5,5-tetramethyl-1,3,2-dioxaborolan-2-yl)-1H-benzo[d]imidazole and 6-(2-chloropyrimidin-4-yl)-1-isopropyl-2-methoxy-1H-benzo[d]imidazole

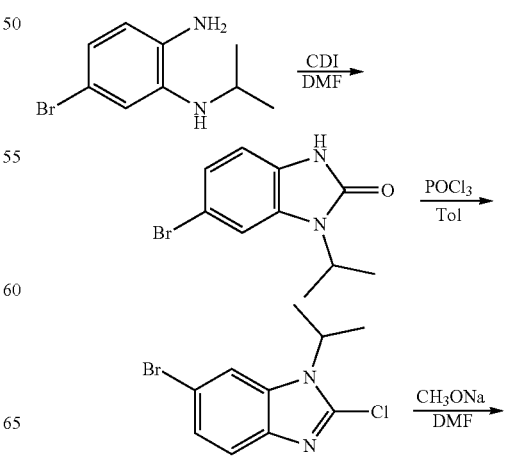

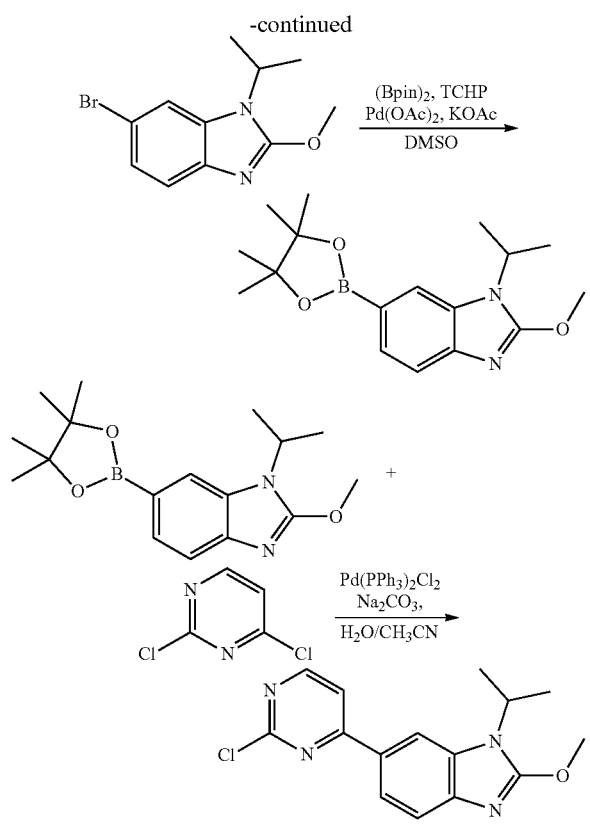

Step 1 Synthesis of 6-bromo-1-isopropyl-1,3-dihydro-2H-benzo[d]imidazole-2-one At room temperature, CDI (650 mg, 4.00 mmol) was added into 5-bromo-$N^1$-isopropylbenzene-1,2-diamine (912 mg, 4.00 mmol) in anhydrous DMF (10 mL), and the reaction was reacted at room temperature overnight. The reaction was quenched by adding water, extracted with ethyl acetate (50 mL×3), and the organic layer was combined, washed with brine, and dried over anhydrous sodium sulfate, concentrated under reduced pressure, and the filtrate was separated on column chromatography (eluant:dichloromethane /methanol (v/v)=25:1), to afford 850 mg a brown-yellow solid, yield was 83.0%. LC-MS(APCI): m/z=256.4 (M+1).

Step 2 Synthesis of 6-bromo-2-chloro-1-isopropyl-1H-benzo[d]imidazole

At room temperature, 6-bromo-1-isopropyl-1,3-dihydro-2H-benzo[d]imidazole-2-one (850 mg, 3.34 mmol) was dissolved in phosphorus oxychloride (10 mL), and the reaction was refluxed for 3 days. After cooling to room temperature, the reaction solvent was removed under reduced pressure, the pH of the residue was adjusted to neutral with saturated sodium bicarbonate, extracted with dichloromethane (50 mL×3). The organic phase was washed with brine separately, dried over anhydrous sodium sulfate, concentrated under reduced pressure, and the filtrate was separated on column chromatography (eluant:petroleum ether/ethyl acetate (v/v)=5:1), to afford 850 mg of a solid. Yield was 90.4%. LC-MS(APCI): m/z=272.9 (M+1).

Step 3 Synthesis of 6-bromo-2-methoxy-1-isopropyl-1H-benzo[d]imidazole

In an ice bath, sodium methoxide (420 mg, 7.80 mmol) was added into 6-bromo-2-chloro-1-isopropyl-1H-benzo[d]imidazole (850 mg, 3.12 mmol) in anhydrous DMF (10 mL), the reaction was warmed naturally, and the reaction mixture was stirred overnight. The reaction was quenched by adding water, extracted with ethyl acetate (50 mL×3), the organic layer was combined, washed with brine, dried over anhydrous sodium sulfate, concentrated under reduced pressure, and the filtrate was separated on column chromatography (eluant:petroleum ether/ethyl acetate (v/v)=5:1), to afford 570 mg of a brown-yellow solid, yield was 71.0%. LC-MS (APCI): m/z=269.0 (M+1).

Step 4 Synthesis of Intermediate Compound 1-isopropyl-2-methoxy-6-(4,4,5,5-tetramethyl-1,3,2-dioxaborolan-2-yl)-1H-benzo[d]imidazole Under nitrogen protection, TCHP (52 mg, 0.18 mmol) and Pd(Oac)$_2$ (20 mg, 0.09 mmol) was added into the mixture of 6-bromo-2-methoxy-1-isopropyl-1H-benzo[d]imidazole (520 mg, 1.87 mmol), bis(pinacolato)diboron (570 mg, 2.24 mmol) and potassium acetate (550 mg, 5.61 mmol) in anhydrous DMSO (13 mL). Under nitrogen protection, the reaction was reacted at 100° C. for 2 hrs. After cooling to room temperature, the reaction was quenched by adding water, extracted with ethyl acetate (50 mL×3), the organic layer was combined, washed with brine, dried over anhydrous sodium sulfate, concentrated under reduced pressure, and the filtrate was separated on column chromatography (eluant:petroleum ether/ethyl acetate (v/v)=4:1), to afford 562 mg of a brown-yellow solid, yield was 95.2%. LC-MS (APCI): m/z=317.1 (M+1).

Step 5 Synthesis of Intermediate Compound 6-(2-chloropyrimidin-4-yl)-1-isopropyl-2-methoxy-1H-benzo[d]imidazole Under nitrogen protection, Pd(PPh$_3$)$_2$Cl$_2$ (35 mg, 0.05 mmol) was added into 1-isopropyl-2-methoxy-6-(4,4,5,5-tetramethyl-1,3,2-dioxaborolan-2-yl)-1H-benzo[d]imidazole (562 mg, 1.78 mmol), 2,4-dichloropyrimidine (320 mg, 2.13 mmol) and sodium carbonate (480 mg, 4.45 mmol) in the mixture of acetonitrile (12 mL) and water (4 mL). Under nitrogen protection, the reaction was reacted at 80° C. for 2.5 hrs. After cooling to room temperature, filtered on Celite, the filtrate was concentrated under reduced pressure, and the filtrate was separated on column chromatography (eluant: petroleum ether/ethyl acetate (v/v)=1:1), to afford 582 mg of a white solid. Yield was 100%. LC-MS(APCI): m/z=303.0 (M+1).

Synthesis of Intermediate Compound 5-(2-chloropyrimidin-4-yl)-3-methylbenzo[d]oxazole-2(3H)-one

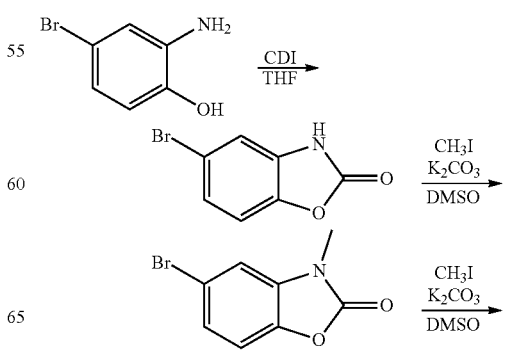

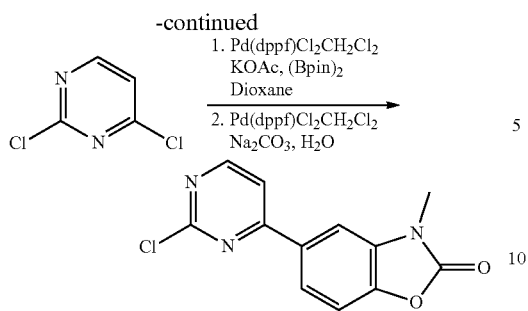

Step 1 Synthesis of 5-bromobenzo[d]oxazole-2(3H)-one

At room temperature, CDI (1.95 g, 12.00 mmol) was added into 2-amino-4-bromophenol (1.88 g, 10.00 mmol) in anhydrous THF (50 mL), and the reaction was refluxed at 85° C. for 2 hrs. After cooling to room temperature, the reaction was quenched with 2 N diluted hydrochloric acid, extracted with ethyl acetate (50 mL×3), the combined organic layer was washed with saturated solution of sodium bicarbonate and brine, dried over anhydrous sodium sulfate, and concentrated under reduced pressure to afford 2.15 g of a brown-yellow solid, yield was 100%. LC-MS(APCI): m/z=212 (M−1).

Step 2 Synthesis of 5-bromo-3-methylbenzo[d]oxazole-2(3H)-one

At room temperature, methyl iodide (795 mg, 4.80 mmol) was added dropwise to 5-bromobenzo[d]oxazole-2(3H)-one (1.00 g, 4.67 mmol) and potassium carbonate (1.29 g, 9.34 mmol) in anhydrous DMSO (20 mL), and the reaction was reacted at room temperature overnight. The reaction was quenched by adding water, extracted with ethyl acetate (50 mL×3), the combined organic layer was washed with water and brine, dried over anhydrous sodium sulfate, concentrated under reduced pressure, and the filtrate was separated on column chromatography to afford 910 mg of a brown-yellow solid, yield was 85.5%. LC-MS(APCI): m/z=228.0 (M−1).

Step 3 Synthesis of Intermediate Compound 5-(2-chloropyrimidin-4-yl)-3-methylbenzo[d]oxazole-2(3H)-one The synthetic step was the same as the synthetic step 5 of intermediate compound 6-(2-chloropyrimidin-4-yl)-4-fluoro-2-(fluoromethyl)-1-isopropyl-1H-benzo[d]imidazole, and afforded product 5-(2-chloropyrimidin-4-yl)-3-methylbenzo[d]oxazole-2(3H)-one (340 mg, white solid). Yield was 75.9%. LC-MS(APCI): m/z=262.0 (M+1); $^1$H NMR (400 MHz, DMSO-$d_6$): δ 8.84 (d, J=5.3 Hz, 1H), 8.20 (d, J=5.4 Hz, 1H), 8.08-8.02 (m, 2H), 7.52 (d, J=8.2 Hz, 1H), 3.44 (s, 3H).

Synthesis of Intermediate Compound 6-(2-chloropyrimidin-4-yl)-4-fluoro-1-isopropyl-1H-indazole

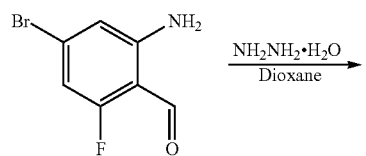

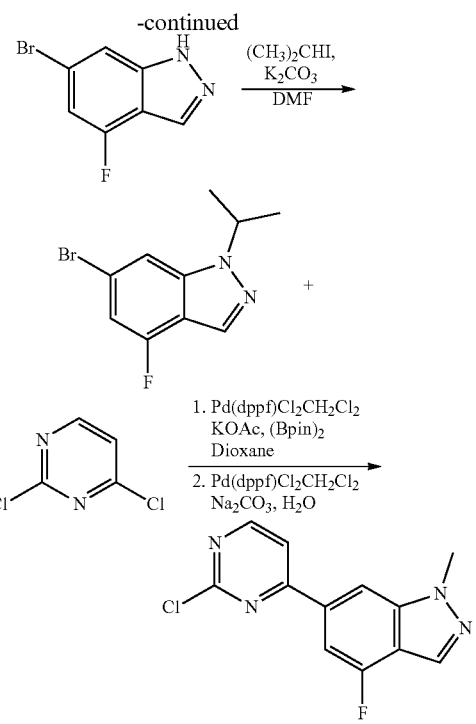

Step 1 Synthesis of 6-bromo-4-fluoro-1H-indazole

At room temperature, hydrazine hydrate (10 mL) was added into the solution of 4-bromo-2,6-difluorobenzaldehyde (5.00 g, 22.60 mmol) in 1,4-dioxane (10 mL), and the reaction was reacted at 95° C. for 1.5 hrs. After cooling to room temperature, it was added into the mixture of ice and water, extracted with ethyl acetate (50 mL×3), the organic layer was combined, dried over anhydrous sodium sulfate, and concentrated with pressure to afford 3.5 g of a yellow solid, yield was 71.0%. LC-MS(APCI): m/z=215.1 (M+1).

Step 2 Synthesis of 6-bromo-4-fluoro-1-isopropyl-1H-indazole

At room temperature, 2-iodopropane (1.58 g, 9.30 mmol) was added dropwise to 6-bromo-4-fluoro-1H-indazole (1.60 g, 7.44 mmol) and potassium carbonate (1.50 g, 11.16 mmol) in anhydrous DMSO (8 mL), and the reaction was reacted at room temperature overnight. The reaction was quenched by adding water, extracted with ethyl acetate (50 mL×3), the combined organic layer was washed with water and brine, dried over anhydrous sodium sulfate, concentrated under reduced pressure, and the filtrate was separated on column chromatography (eluant:petroleum ether/ethyl acetate (v/v)=9:1) to afford 960 mg of a pale yellow solid, yield was 50.2%. LC-MS(APCI): m/z=257.0 (M−1).

Step 3 Synthesis of Intermediate Compound 6-(2-chloropyrimidin-4-yl)-4-fluoro-1-isopropyl-1H-indazole The synthetic steps is the same as the synthetic step 5 of intermediate compound 6-(2-chloropyrimidin-4-yl)-4-fluoro-2-(fluoromethyl)-1-isopropyl-1H-benzo[d]imidazole, and afforded product 6-(2-chloropyrimidin-4-yl)-4-fluoro-1-isopropyl-1H-indazole (447 mg, white solid). Yield was 76.8%. LC-MS(APCI): m/z=291.0 (M+1); ¹H NMR (400 MHz, CDCl₃): δ 8.69 (d, J=5.2 Hz, 1H), 8.13 (s, 2H), 7.68 (d, J=5.3 Hz, 1H), 7.41 (d, J=10.8 Hz, 1H), 4.99 (dt, J=13.2, 6.6 Hz, 1H), 1.64 (d, J=6.7 Hz, 6H).

Synthesis of Intermediate Compound 6-(2-chloro-pyrimidin-4-yl)-1-isopropyl-1H-indazole

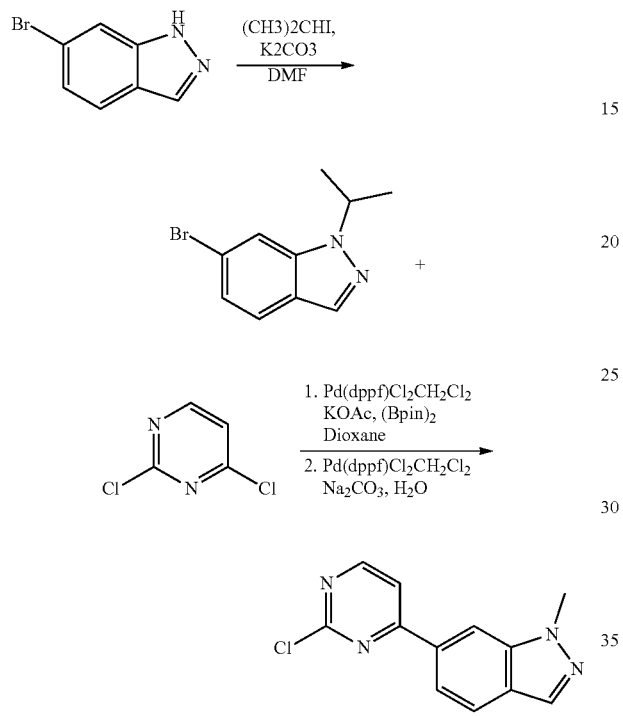

Step 1 Synthesis of 6-bromo-1-isopropyl-1H-indazole

At room temperature, 2-iodopropane (2.00 g, 12.18 mmol) was added dropwise to 6-bromo-1H-indazole (2.00 g, 10.15 mmol) and potassium carbonate (1.96 g, 14.21 mmol) in anhydrous DMSO (20 mL), and the reaction was reacted at room temperature overnight. The reaction was quenched by adding water, extracted with ethyl acetate (50 mL×3), the combined organic layer was washed with water and brine, dried over anhydrous sodium sulfate, concentrated under reduced pressure, and the filtrate was separated on column chromatography (eluant:petroleum ether/ethyl acetate (v/v) =5:1) to afford 1.17 g of a pale yellow oil, yield was 48.03%. LC-MS(APCI): m/z=240.9 (M−1).

Step 2 Synthesis of Intermediate Compound 6-(2-chloropyrimidin-4-yl)-1-isopropyl-1H-indazole The synthetic step is the same as the synthetic step 5 of intermediate compound 6-(2-chloropyrimidin-4-yl)-4-fluoro-2-(fluoromethyl)-1-isopropyl-1H-benzo[d]imidazole, and afforded product 6-(2-chloropyrimidin-4-yl)-1-isopropyl-1H-indazole (290 mg, white solid). Yield was 63.9%. LC-MS(APCI): m/z=273.0 (M+1).

Synthesis of Intermediate Compound 6-(2-chloro-pyrimidin-4-yl)-8-fluoro-2-methyl-3-(prop-1-en-2-yl)imidazo[1,2-a]pyridine

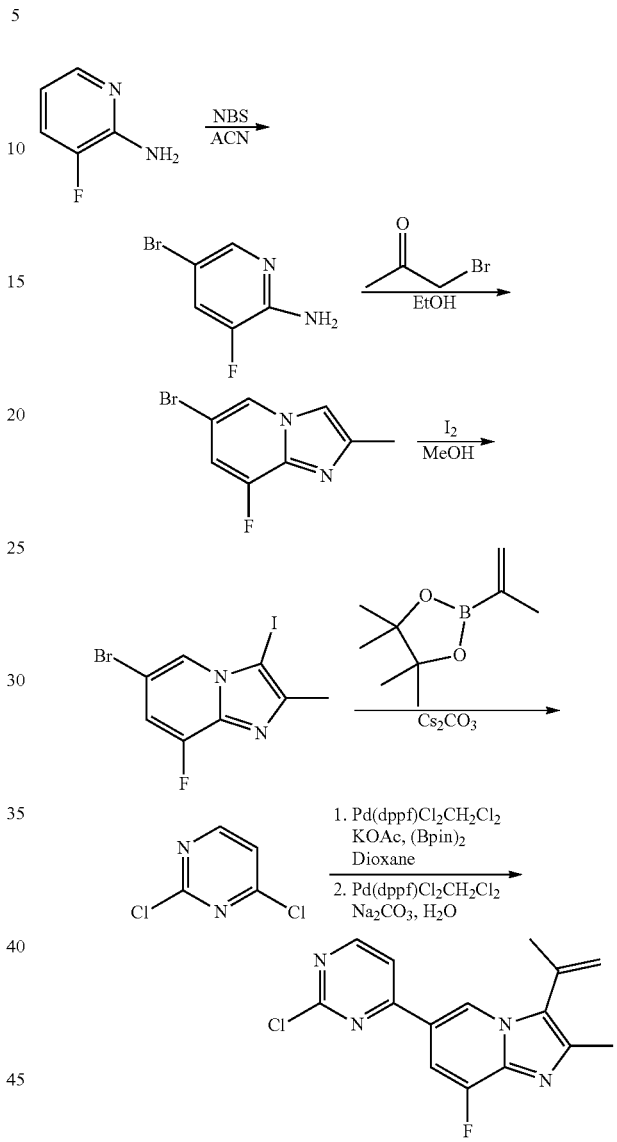

Step 1 Synthesis of Compound 5-bromo-3-fluoropyridine-2-amine

Under nitrogen protection, N-bromosuccinimide (NBS, 5.47 g, 30.57 mmol) was added portionwise into 3-fluoro-pyridine-2-amine (3.36 g, 29.97 mmol) in acetonitrile (150 mL), and the reaction was reacted under nitrogen protection at room temperature for 2 hours. Acetonitrile was removed by concentrating under reduced pressure, quenched by adding saturated solution of sodium thiosulfate, extracted with ethyl acetate (100 mL×3). The organic phase was combined and washed with brine, dried over anhydrous sodium sulfate, concentrated under reduced pressure, and the filtrate was separated on column chromatography (eluant:petroleum ether/ethyl acetate (v/v)=5:1), to afford 5.0 g of a white solid, yield was 87.3%. LC-MS(APCI): m/z=191.1 (M+1).

Step 2 Synthesis of Compound 6-bromo-8-fluoro-2-methylimidazo[1,2-a]pyridine 1-bromoprop-2-one (10.00 g, 73.3 mmol) was added into 5-bromo-3-fluoropyridine-2-amine (7.00 g, 36.6 mmol) in ethanol (70 mL), and the reaction was refluxed under nitrogen protection overnight. Solid was slowly precipitated after cooling to room temperature, filtered, washed with cold ethanol, dried in vacuo to afford 3.5 g of a white solid, yield: 41.8%. LC-MS(APCI): m/z=229.1 (M+1); $^1$H NMR (400 MHz, DMSO-$d_6$): δ 9.12 (s, 1H), 8.16-8.09 (m, 2H), 2.48 (s, 3H).

Step 3 Synthesis of Compound 6-bromo-8-fluoro-3-iodo-2-methylimidazo[1,2-a]pyridine Elemental iodine (4.60 g, 18.3 mmol) was added into 6-bromo-8-fluoro-2-methylimidazo[1,2-a]pyridine (3.50 g, 15.30 mmol) and sodium acetate (2.01 g, 24.5 mmol) in methanol (20 mL), and the reaction was reacted under nitrogen protection at room temperature for 3 hours. Methanol was removed by concentrating under reduced pressure, the reaction was quenched by adding saturated solution of sodium thiosulfate, extracted with ethyl acetate (100 mL×3). The organic phase was combined, washed with brine, dried over anhydrous sodium sulfate, concentrated under reduced pressure, and the filtrate was separated on column chromatography (eluant:petroleum ether/ethyl acetate (v/v)=3:1), to afford 2.8 g of a white solid, yield was 51.7%. LC-MS (APCI): m/z=355.1 (M+1).

Step 4 Synthesis of Compound 6-bromo-8fluoro-2methyl-3-(prop-1-en-2-yl)imidazo[1,2-a]pyridine Under nitrogen protection, Pd(dppf)Cl$_2$■CH$_2$Cl$_2$ (250 mg, 0.31 mmol) was added into 6-bromo-8-fluoro-3-iodo-2-methylimidazo[1,2-a]pyridine (1.17 g, 3.32 mmol), pinacolyl 2-propenylboronate (557 mg, 3.31 mmol) and cesium carbonate (2.16 g, 6.64 mmol) in the mixed solvent of 1,4-dioxane (20 mL) and water (5 mL), and the reaction was reacted under nitrogen protection at 80° C. for 1 hour. After cooling to room temperature, it was filtered on Celite, the filter cake was washed with dichloromethane, the filtrate was concentrated under reduced pressure, and the filtrate was separated on column chromatography (eluant:petroleum ether/ethyl acetate (v/v)=10:1), to afford 600 mg of a white solid. Yield was 67.4.9%. LC-MS(APCI): m/z=269.1 (M+1).

Step 5 Synthesis of Intermediate Compound 6-(2-chloropyrimidin-4-yl)-8-fluoro-2-methyl-3-(prop-1-en-2-yl)imidazo[1,2-a]pyridine The synthetic step is the same as the synthetic step 5 of intermediate compound 6-(2-chloropyrimidin-4-yl)-4-fluoro-2-(fluoromethyl)-1-isopropyl-1H-benzo[d]imidazole, and afforded product 6-(2-chloropyrimidin-4-yl)-8-fluoro-2-methyl-3-(prop-1-en-2-yl)imidazo[1,2-a]pyridine (800 mg, white solid). Yield was 100%. LC-MS(APCI): m/z=303.0 (M+1).

Synthesis of Intermediate Compound 6-(2-chloropyrimidin-4-yl)-8-fluoro-2-methyl-imidazo[1,2-a]pyridine

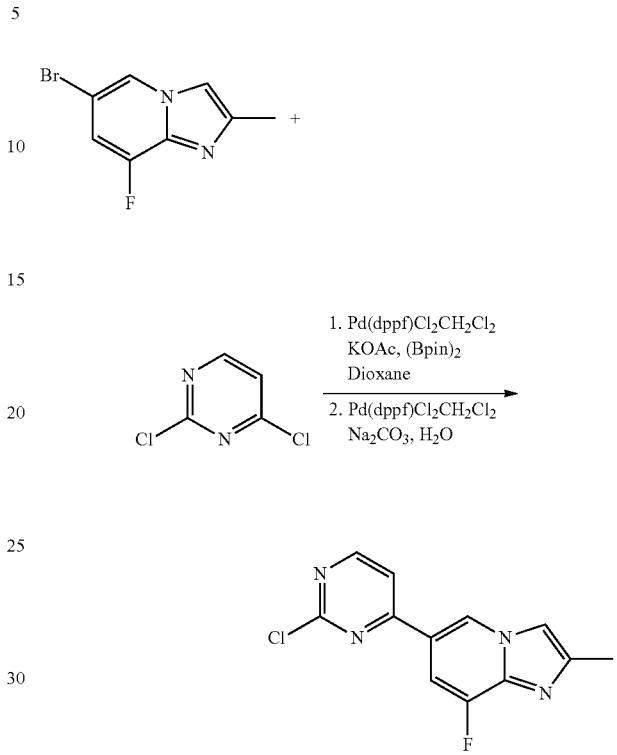

The synthetic step is the same as the synthetic step 5 of intermediate compound 6-(2-chloropyrimidin-4-yl)-4-fluoro-2-(fluoromethyl)-1-isopropyl-1H-benzo[d]imidazole, and afforded product 6-(2-chloropyrimidin-4-yl)-8-fluoro-2-methyl-imidazo[1,2-a]pyridine (630 mg, white solid). Yield was 80.00%. LC-MS(APCI): m/z=263.0 (M+1).

Synthesis of Intermediate Compound 4-tert-butoxy-1-isopropyl-2-methyl-6-(4,4,5,5-tetramethyl-1,3,2-dioxaborolan-2-yl)-1H-benzo[d]imidazole and 6-(2-chloropyrimidin-4-yl)-4-tert-butoxy-1-isopropyl-2-methyl-1H-benzo[d]imidazole

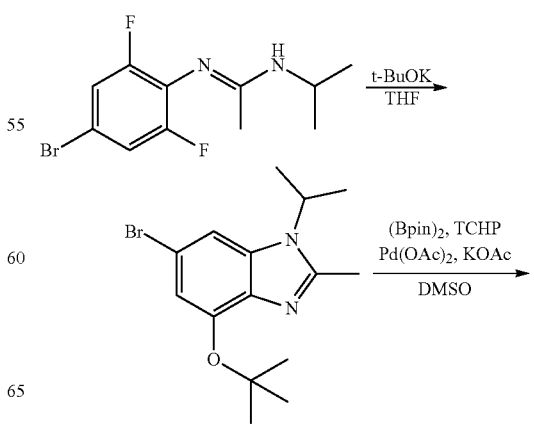

-continued

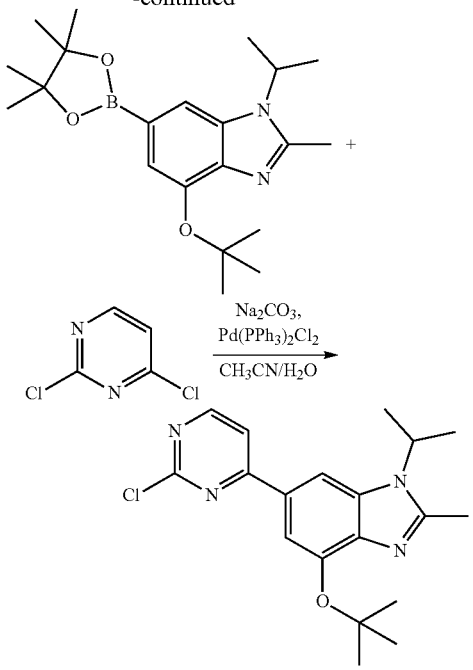

Step 1 Synthesis of Compound 6-bromo-4-(tert-butoxy)-1-isopropyl-2-methyl-1H-benzo[d]imidazole Under nitrogen protection, potassium tert-butoxide (3.65 g, 32.6 mmol) was added into (E)-N'-(4-bromo-2,6-difluorophenyl)-N-isopropylacetimidamide (4.50 g, 15.5 mmol) in anhydrous tetrahydrofuran, and the reaction was reacted at 70° C. for 2 hrs. After cooling to room temperature, it was filtered on Celite, the filter cake was washed with dichloromethane, the filtrate was washed with brine, dried over anhydrous sodium sulfate, the filtrate was concentrated under reduced pressure, and the filtrate was separated on column chromatography (eluent: petroleum ether/ethyl acetate (v/v)=5:1), to afford 4.0 g of a pale yellow solid, as a mixture. Yield: 95.6%. LC-MS(APCI): m/z=271.1 (M+1) & 324.1 (M+1).

Step 2 Synthesis of Intermediate Compound 4-tert-butoxy-1-isopropyl-2-methyl-6-(4,4,5,5-tetramethyl-1,3,2-dioxaborolan-2-yl)-1H-benz o[d]imidazole Under nitrogen protection, palladium acetate (466 mg) and tricyclohexylphosphine (900 mg) was added into the above mixture (5.00 mg), bis(pinacolato)diboron (7.00 g) and potassium acetate (5.40 g) in anhydrous DMSO (50 mL), and the reaction was reacted under nitrogen protection at 100° C. for 2 hrs. After cooling to room temperature, it was filtered on Celite, the filter cake was washed with ethyl acetate, the filtrate was washed with brine, dried over anhydrous sodium sulfate, the filtrate was concentrated under reduced pressure, and the filtrate was separated on column chromatography (eluent: petroleum ether/ethyl acetate (v/v)=3:1), and afforded product 4-tert-butoxy-1-isopropyl-2-methyl-6-(4,4,5,5-tetramethyl-1,3,2-dioxaborolan-2-yl-1H-benz o[d]imidazole (1.3 g). LC-MS(APCI): m/z=373.3 (M+1).

Step 3 Synthesis of Intermediate Compound 6-(2-chloropyrimidin-4-yl)-4-tert-butoxy-1-isopropyl-2-methyl-1H-benzo[d]imidazole Under nitrogen protection, acetonitrile (9 mL) and water (3 mL) was added into the mixture of 4-tert-butyl-1-isopropyl-2-methyl-6-(4,4,5,5-tetramethyl-1,3,2-dioxaborolan-2-yl)-1H-benzo[d]imidazole (600 mg, 1.60 mmol) and 2,4-dichloropyrimidine (290 mg, 1.90 mmol), sodium carbonate (430 mg, 4.00 mmol), bis(triphenylphosphine)palladium(II) chloride (56 mg, 0.08 mmol), and the reaction was stirred under nitrogen protection at 80° C. for 2 hrs. After cooling to room temperature, it was filtered on Celite, the filter cake was washed with dichloromethane, washed with brine, dried over anhydrous sodium sulfate, the filtrate was concentrated under reduced pressure, and the filtrate was separated on column chromatography (eluant:petroleum ether/ethyl acetate (v/v)=2:1), and afforded product 6-(2-chloropyrimidin-4-yl)-4-tert-butoxy-1-isopropyl-2-methyl-1H-benzo[d] imidazole (700 mg, yellow solid). Yield: 100%. LC-MS (APCI): m/z: 359.1 (M+1).

Synthesis of Intermediate Compound 5-(2-chloropyrimidin-4-yl)-7-fluoro-2-methylbenzo[d]oxazole

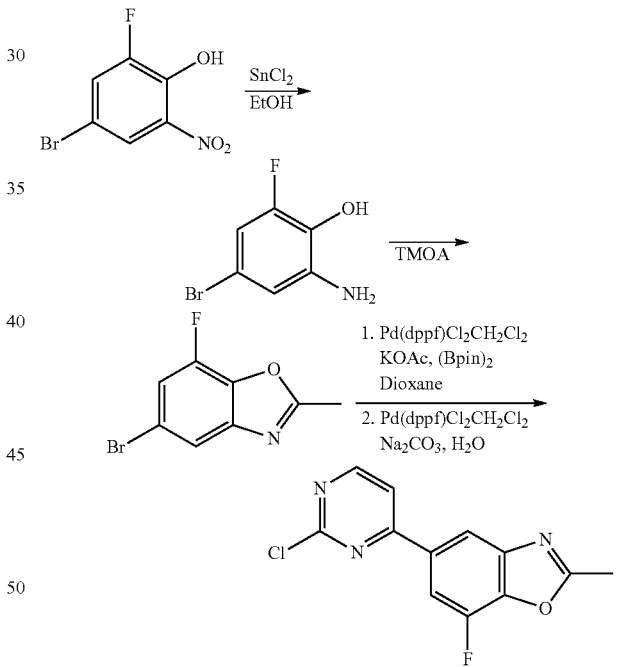

Step 1: Synthesis of Compound 2-amino-4-bromo-6-fluorophenol

At room temperature, SnCl$_2$.2H$_2$O (14.3 g, 63.50 mmol) was added into 4-bromo-2-fluoro-6-nitrophenol (3.00 g, 12.7 mmol) in ethanol (100 mL), and the reaction was refluxed for 2 hrs. After cooling to room temperature, it was added into ice-water, and the stirring was continued for 0.5 hrs. Ethanol was removed under reduce pressure, extracted with ethyl acetate (100 mL×3), the combined organic layer was washed with water and brine, dried over anhydrous sodium sulfate, and concentrated under reduced pressure to afford 2.0 g of a pale yellow solid, yield was 76.4%, LC-MS(APCI): m/z=206.1 (M+1).

Step 2: Synthesis of Compound 5-bromo-7-fluoro-2-methylbenzo[d]oxazole 2-amino-4-bromo-6-fluorophenol (700 mg, 3.41 mmol) was added into triethyl orthoacetate (20 mL), and the reaction was refluxed at 150° C. for 2 hrs. After cooling to room temperature, the reaction was quenched by adding saturated solution of sodium bicarbonate, extracted with ethyl acetate (50 mL×3), the combined organic layer was washed with water and brine, dried over anhydrous sodium sulfate, concentrated under reduced pressure, and the concentrate was separated by column chromatography (eluant: petroleum ether/ethyl acetate (v/v)=1:1), to afford 600 mg of a pale yellow solid, yield was 76.5%, LC-MS(APCI): m/z=229.9 (M+1).

Step 3 Synthesis of Intermediate Compound 5-(2-chloropyrimidin-4-yl)-7-fluoro-2-methylbenzo[d]oxazole The synthetic step is the same as the synthetic step 5 of intermediate compound 6-(2-chloropyrimidin-4-yl)-4-fluoro-2-(fluoromethyl)-1-isopropyl-1H-benzo[d]imidazole, and afforded product 5-(2-chloropyrimidin-4-yl)-7-fluoro-2-methylbenzo[d]oxazole (700 mg, white solid). Yield was 98.20%. LC-MS(APCI): m/z=264.1 (M+1).

Synthesis of Intermediate Compound 6-(2-chloropyrimidin-4-yl)-4-fluoro-2-methylbenzo[d]oxazole

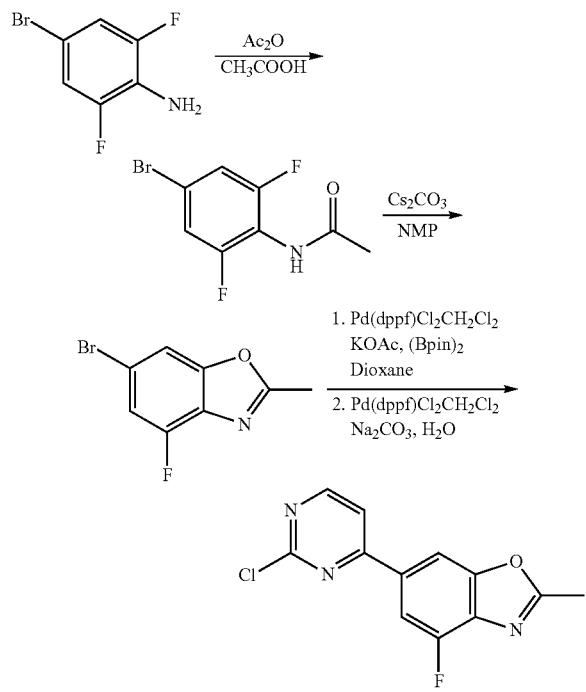

Step 1: Synthesis of Compound N-(4-bromo-2,6-difluorophenyl)acetamide

At room temperature, acetic anhydride (9 mL) was added dropwise to 4-bromo-2,6-difluoroaniline (3.00 g, 14.42 mmol) in glacial acetic acid (30 mL), and the reaction was reacted at room temperature for 2 hrs. It was added into ice-water, the solid was filtered, the filter cake was dissolved in dichloromethane, washed with saturated solution of sodium bicarbonate and brine, dried over anhydrous sodium sulfate, concentrated under reduced pressure to afford 3.058 g of a pale yellow solid, yield was 85.28%, LC-MS(APCI): m/z=249.1 (M+1). $^1$H NMR (400 MHz, DMSO-d6): δ 9.74 (s, 1H), 7.54 (d, J=7.2 Hz, 2H), 2.06 (s, 3H).

Step 2: Synthesis of Compound 6-bromo-4-fluoro-2-methylbenzo[d]oxazole

Cesium carbonate (8.00 g) was added into N-(4-bromo-2,6-difluorophenyl)acetamide (3.00 g) in anhydrous NMP (19 mL), and the reaction was refluxed at 150° C. for 2 hrs. After cooling to room temperature, the reaction was quenched by adding water, extracted with ethyl acetate (50 mL×3), the combined organic layer was washed with water and brine, dried over anhydrous sodium sulfate, concentrated under reduced pressure, and the concentrate was separated by column chromatography (eluant:petroleum ether/ethyl acetate (v/v)=9:1), to afford 760 mg of a pale yellow solid, yield was 27.6%, LC-MS(APCI): m/z=230.0 (M+1).

Step 3 Synthesis of Intermediate Compound 6-(2-chloropyrimidin-4-yl)-4-fluoro-2-methylbenzo[d]oxazole The synthetic step is the same as the synthetic step 5 of intermediate compound 6-(2-chloropyrimidin-4-yl)-4-fluoro-2-(fluoromethyl)-1-isopropyl-1H-benzo[d]imidazole, and afforded 6-(2-chloropyrimidin-4-yl)-4-fluoro-2-methylbenzo[d]oxazole (700 mg of a white solid). Yield was 98.20%. LC-MS(APCI): m/z=264.0 (M+1).

Synthesis of Intermediate Compound 5-(2-chloropyrimidin-4-yl)-7-fluoro-benzo[d]oxazole

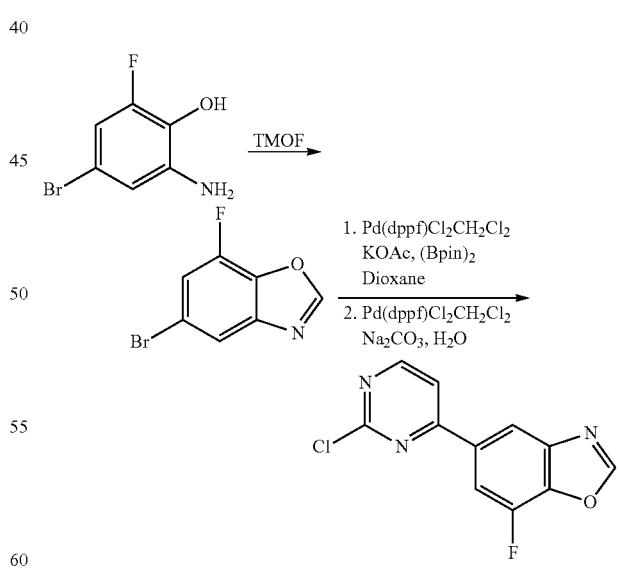

Step 1 Synthesis of Compound 5-bromo-7-fluorobenzo[d]oxazole 2-amino-4-bromo-6-fluorophenol (1.20 g, 5.80 mmol) was added into triethyl orthoacetate (20 mL), and the reaction was refluxed at 150° C. for 2 hrs. After cooling to room temperature, the reaction was quenched by adding saturated solution of sodium bicarbonate, extracted with ethyl acetate (50 mL×3), the combined organic layer was washed with water and brine, dried over anhydrous sodium sulfate, concentrated under reduced pressure, and the concentrate was separated by column chromatography (eluant: petroleum ether/ethyl acetate (v/v)=3:1), to afford 800 mg of a pale yellow solid, yield was 64.2%, LC-MS(APCI): m/z=215.9 (M+1).

Step 2 Synthesis of 5-(2-chloropyrimidin-4-yl)-7-fluoro-benzo[d]oxazole

The synthetic step is the same as the synthetic step 5 of intermediate compound 6-(2-chloropyrimidin-4-yl)-4-fluoro-2-(fluoromethyl)-1-isopropyl-1H-benzo[d]imidazole, and afforded product 5-(2-chloropyrimidin-4-yl)-7-fluoro-benzo[d]oxazole (500 mg yellow-white solid). Yield was 56.2%. LC-MS(APCI): m/z=250.1 (M+1).

Synthesis of Intermediate Compound 1-isopropyl-2-methyl-6-(4,4,5,5-tetramethyl-1,3,2-dioxaborolan-2-yl)-1H-benzo[d]imidazole and 6-(2-chloropyrimidin-4-yl)-1-isopropyl-2-methyl-1H-benzo[d]imidazole

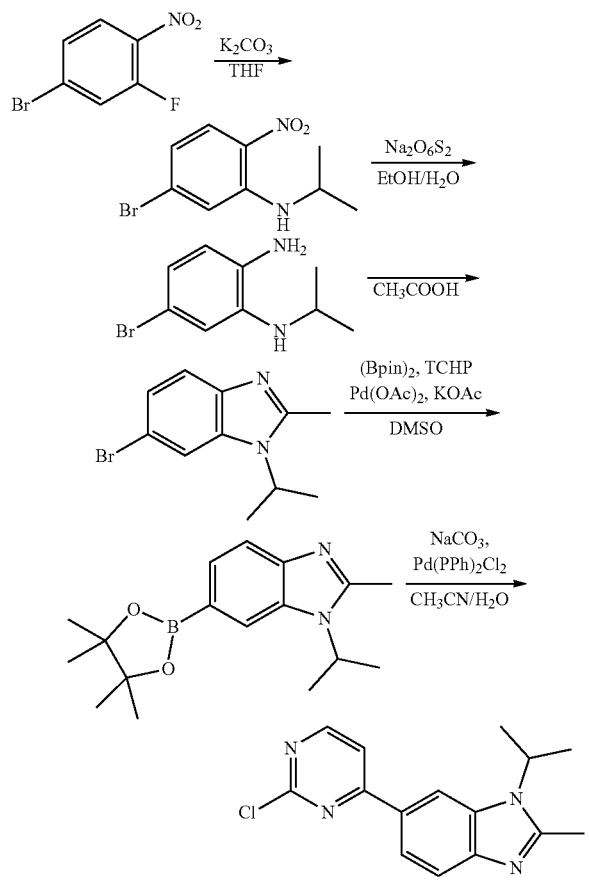

Step 1 Synthesis of 5-bromo-N-isopropyl-2-nitroaniline

In an ice bath, potassium carbonate (5.02 g, 36.36 mmol) and isopropylamine (1.55 mL, 18.18 mmol) were sequentially added into the solution of 4-bromo-2-fluoro-1-nitrobenzene (4.00 g, 18.18 mmol) in anhydrous DMF (40 mL), the reaction mixture was warmed to room temperature naturally, and the mixture was stirred overnight. The reaction was quenched by adding water, extracted with ethyl acetate (100 mL×3), the combined organic layer was washed with water and brine, dried over anhydrous sodium sulfate, and concentrated under reduced pressure to afford 4.62 g of a yellow solid, which was directly used in the next step without purification.

Step 2 Synthesis of 5-bromo-N-isopropylbenzene-1,2-diamine

The above crude was dissolved in the mixed solvent of ethanol and water (v/v=200 mL/80 mL), sodium dithionite (18.4 6 g, 89.6 mmol) was added, and the reaction was reacted at room temperature overnight. It was filtered on Celite, the filter cake was washed with ethyl acetate, ethanol was removed under reduce pressure, extracted with ethyl acetate (100 mL×3), the organic layer was combined, washed with brine, dried over anhydrous sodium sulfate, and concentrated under reduced pressure to afford 4.1 g of a brown liquid. LC-MS(APCI): m/z=229.1 (M+1).

Step 3 Synthesis of 6-bromo-1-isopropyl-2-methyl-1H-benzo[d]imidazole 5-bromo-N-isopropylbenzene-1,2-diamine (2.6 g, 11.40 mmol) was added into glacial acetic acid (40 mL), and the reaction was refluxed for 2 hrs. After cooling to room temperature, acetic acid was removed under reduce pressure, the pH of the residue was adjusted to about 7 with saturated solution of sodium bicarbonate, extracted with dichloromethane (50×3), the organic layer was combined, washed with brine, dried over anhydrous sodium sulfate, the filtrate was concentrated under reduced pressure, and the filtrate was separated on column chromatography (eluant:dichloromethane/methanol (v/v)=20:1) to afford 2.31 g a brown-yellow solid, yield was 80.10%, LC-MS(APCI): m/z=253.1 (M+1).

Step 4 Synthesis of Intermediate Compound 1-isopropyl-2-methyl-6-(4,4,5,5-tetramethyl-1,3,2-dioxaborolan-2-yl)-1H-benzo[d]imidazole Under nitrogen protection, TCHP (460 mg) and Pd(Oac)$_2$ (230 mg) were added into the mixture of 6-bromo-2-methyl-1-isopropyl-1H-benzo[d]imidazole (2.30 g, 9.10 mmol), bis(pinacolato)diboron (3.50 g, 13.6 mmol) and potassium acetate (2.70 g, 27.3 mmol) in anhydrous DMSO (25 mL), and the reaction was reacted under nitrogen protection at 100° C. for 2 hrs. After cooling to room temperature, the reaction was quenched by adding water, extracted with ethyl acetate (100 mL×3), the organic layer was combined, washed with brine, dried over anhydrous sodium sulfate, concentrated under reduced pressure, and the filtrate was separated on column chromatography (eluant:petroleum ether/ethyl acetate (v/v)=2:1), to afford 1.60 g of a brown-yellow solid, yield was 58.6%. LC-MS(APCI): m/z=301.2 (M+1).

Step 5 Synthesis of Intermediate Compound 6-(2-chloropyrimidin-4-yl)-1-isopropyl-2-methyl-1H-benzo[d]imidazole Under nitrogen protection, Pd(PPh$_3$)$_2$Cl$_2$ (58 mg, 0.08 mmol) was added into the mixture of 1-isopropyl-2-methyl- 6-(4,4,5,5-tetramethyl-1,3,2-dioxaborolan-2-yl)-1H-benzo[d]imidazole (500 mg, 1.67 mmol), 2,4-dichloropyrimidine (298 mg, 2.00 mmol) and sodium carbonate (442 mg, 4.17 mmol) in acetonitrile (9 mL) and water (3 mL), and the reaction was heated to 80° C. under nitrogen protection and reacted for 2.5 hrs. After cooling to room temperature, it was filtered on Celite, the filtrate was concentrated under reduced pressure, and the filtrate was separated on column chromatography (eluant:petroleum ether/ethyl acetate (v/v)=1:1), to afford 700 mg of a white solid. Yield was 100%. LC-MS (APCI): m/z=287.2 (M+1).

Synthesis of Intermediate Compound 1-isopropyl-6-(4,4,5,5-tetramethyl-1,3,2-dioxaborolan-2-yl)-1H-benzo[d]imidazole and 6-(2-chloropyrimidin-4-yl)-1-isopropyl-1H-benzo[d]imidazole

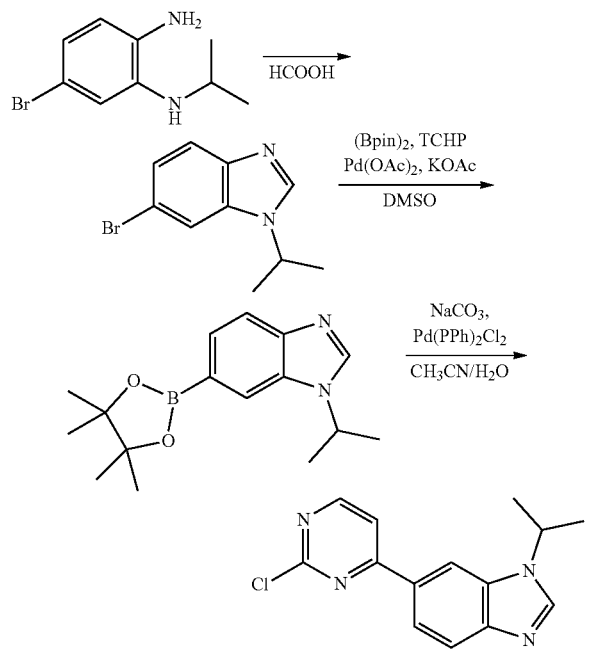

Step 1 Synthesis of 6-bromo-1-isopropyl-1H-benzo[d]imidazole 5-bromo-N-isopropylbenzene-1,2-diamine (1.50 g, 6.57 mmol) was added into formic acid (50 mL), and the reaction was refluxed for 2 hrs. After cooling to room temperature, formic acid was removed under reduce pressure, the pH of the residue was adjusted to about 7 with saturated solution of sodium bicarbonate, extracted with dichloromethane (50×3), the organic layer was combined, washed with brine, dried over anhydrous sodium sulfate, the filtrate was concentrated under reduced pressure, and the filtrate was separated on column chromatography (eluant:dichloromethane/methanol (v/v)=50:1) to afford 1.40 g of a brown-yellow solid, yield was 89.5%, LC-MS(APCI): m/z=238.2 (M+1).

Step 2 Synthesis of 1-isopropyl-6-(4,4,5,5-tetramethyl-1,3,2-dioxaborolan-2-yl)-1H-benzo[d]imidazole Under nitrogen protection, TCHP (280 mg) and Pd(OAc)$_2$ (140 mg) was added into the mixture of 6-bromo-1-isopropyl-1H-benzo[d]imidazole (1.40 g, 5.91 mmol), bis(pinacolato)diboron (2.20 g, 8.86 mmol) and potassium acetate (1.70 g, 17.72 mmol) in anhydrous DMSO (20 mL), and the reaction was reacted under nitrogen protection at 100° C. for 2 hrs. After cooling to room temperature, the reaction was quenched by adding water, extracted with ethyl acetate (100 mL×3), the organic layer was combined, washed with brine, dried over anhydrous sodium sulfate, concentrated under reduced pressure, and the filtrate was separated on column chromatography (eluant:petroleum ether/ethyl acetate (v/v)=2:1), to afford 1.60 g of a yellow oil, yield was 94.3%. LC-MS(APCI): m/z=287.2 (M+1).

Step 3 Synthesis of 6-(2-chloropyrimidin-4-yl)-1-isopropyl-H-benzo[d]imidazole Under nitrogen protection, Pd(PPh$_3$)$_2$Cl$_2$ (74 mg, 0.10 mmol) was added into the mixture of 1-isopropyl-6-(4,4,5,5-tetramethyl-1,3,2-dioxaborolan-2-yl)-1H-benzo[d]imidazole (600 mg, 2.10 mmol), 2,4-dichloropyrimidine (375 mg, 2.52 mmol) and sodium carbonate (556 mg, 5.24 mmol) in acetonitrile (9 mL) and water (3 mL), and the reaction was heated to 80° C. under nitrogen protection and reacted for 2.5 hrs. After cooling to room temperature, it was filtered on Celite, the filtrate was concentrated under reduced pressure, and the filtrate was separated on column chromatography (eluant:petroleum ether/ethyl acetate (v/v)=1:1), to afford 300 mg of a yellow solid. Yield was 52.52%. LC-MS (APCI): m/z=273.1 (M+1).

Synthesis of Intermediate Compound 6-(2-chloropyrimidin-4-yl)-1-isopropyl-2-(trifluoromethyl)-1H-benzo[d]imidazole

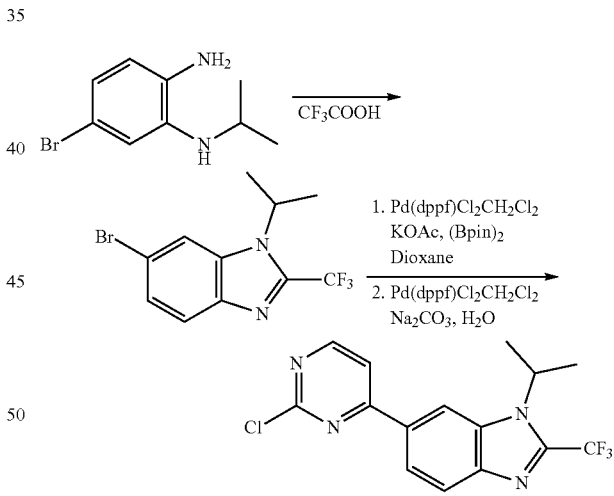

Step 1 Synthesis of 6-bromo-1-isopropyl-2-(trifluoromethyl)-1H-benzo[d]imidazole 5-bromo-N-isopropylbenzene-1,2-diamine (920 mg, 4.01 mmol) was added into trifluoroacetic acid (20 mL), and the reaction was reacted at 80° C. overnight. After cooling to room temperature, trifluoroacetic acid was removed under reduce pressure, the pH of the residue was adjusted to about 7 with saturated solution of sodium bicarbonate, extracted with dichloromethane (50×3), the organic layer was combined, washed with brine, dried over anhydrous sodium sulfate, the filtrate was concentrated under reduced pressure, and the filtrate was separated on column chromatography (eluant:dichloromethane/methanol (v/v)=20:1) to afford 900 mg of a pale yellow solid, yield was 73.3%, LC-MS(APCI): m/z=306.9 (M+1).

Step 2 Synthesis of 6-(2-chloropyrimidin-4-yl)-1-isopropyl-2-(trifluoromethyl)-1H-benzo[d]imidazole The synthetic step is the same as the synthetic step 5 of intermediate compound 6-(2-chloropyrimidin-4-yl)-4-fluoro-2-(fluoromethyl)-1-isopropyl-1H-benzo[d]imidazole, and afforded product 6-(2-chloropyrimidin-4-yl)-1-isopropyl-2-(trifluoromethyl)-1H-benzo[d]imidazole (576 mg of a white solid). Yield was 100%. LC-MS(APCI): m/z=341.0 (M+1).

Synthesis of Intermediate Compound 5-(2-chloropyrimidin-4-yl)-7-fluoro-1-(tetrahydro-2H-pyran-2-yl)-1H-indazole

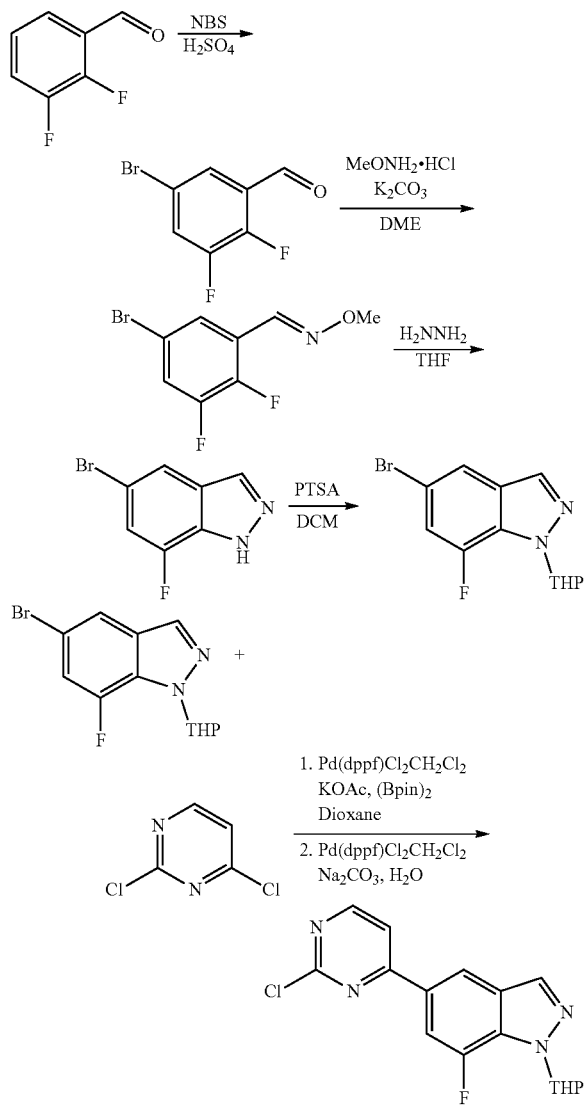

Step 1 Synthesis of 5-bromo-2,3-difluorobenzaldehyde

NBS (7.50 g, 42.00 mmol) was added into 2,3-difluorobenzaldehyde (5.00 g, 35.20 mmol) in concentrated sulfuric acid (37.7 mL), and the reaction was heated to 60° C. and the mixture was stirred overnight. After cooling to room temperature, it was added to ice-water, stirred for 10 min, extracted with petroleum ether, washed with brine, and dried over anhydrous sodium sulfate. It was concentrated under reduced pressure, and the filtrate was separated on column chromatography (100% petroleum ether) to afford 2.3 g of an oil, yield was 25.0%. LC-MS(APCI): m/z=221.1 (M+1).

Step 2 Synthesis of (E)-5-bromo-2,3-difluorobenzaldehyde-O-methyloxime

Potassium carbonate (1.73 g) was added into the solution of 5-bromo-2,3-difluorobenzaldehyde (2.3 g) and methoxyamine hydrochloride (0.96 g) in DME (26 mL), and the reaction was reacted at 45° C. overnight. After cooling to room temperature, it was filtered, washed with ethyl acetate, and the filtrate was separated on column chromatography (100% petroleum ether) to afford 2.342 g of an oil, yield was 89.1%. LC-MS(APCI): m/z=250.2 (M+1).

Step 3 Synthesis of 5-bromo-7-fluoro-1H-indazole

Hydrazine hydrate (9.5 mL) was added into the solution of (E)-5-bromo-2,3-difluorobenzaldehyde-O-methyloxime (2.34 g) in anhydrous tetrahydrofuran, and the reaction was reacted at 90° C. for 4 days. Tetrahydrofuran was removed under reduce pressure, the residue was dissolved in ethyl acetate, washed with water, and dried over anhydrous sodium sulfate. It was concentrated under reduced pressure, and the filtrate was separated on column chromatography (petroleum ether/ethyl acetate (v/v)=4:1) to afford 1.00 g of white solid, yield was 48.9%. LC-MS(APCI): m/z=215.0 (M+1). 1H NMR (500 MHz, DMSO-d6): δ 13.84 (s, 1H), 8.15 (s, 1H), 7.86 (d, J=1.3 Hz, 1H), 7.44 (d, J=10.0 Hz, 1H).

Step 4 Synthesis of 5-bromo-7-fluoro-1-(tetrahydro-2H-pyran-2-yl)-1H-indazole

At room temperature, p-toluenesulfonic acid (40 mg) was added into 5-bromo-7-fluoro-1H-indazole (1.0 g, 4.64 mmol) and 3,4-dihydro-2H-pyrane (0.78 g, 9.28 mmol) in anhydrous dichloromethane (25 mL), and the reaction mixture was reacted at room temperature overnight. the reaction was quenched by adding saturated solution of sodium bicarbonate, extracted with dichloromethane (30 mL×3), the organic layer was combined, washed with brine, and dried over anhydrous sodium sulfate. It was concentrated under reduced pressure, and the filtrate was separated on column chromatography (petroleum ether/ethyl acetate (v/v)=10:1) to afford 1.20 g of a white solid, yield was 86.8%. LC-MS(APCI): m/z=299.0 (M+1).

Step 5 Synthesis of Intermediate Compound 5-(2-chloropyrimidin-4-yl)-7-fluoro-1-(tetrahydro-2H-pyran-2-yl)-1H-indazole The synthetic step is the same as the synthetic step 5 of intermediate compound 6-(2-chloropyrimidin-4-yl)-4-fluoro-2-(fluoromethyl)-1-isopropyl-1H-benzo[d]imidazole, and afforded 600 mg of a yellow-white solid. Yield was 90.36%. LC-MS(APCI): m/z=333.0 (M+1).

Synthesis of Intermediate Compound 5-(2-chloro-pyrimidin-4-yl)-7-fluoro-1-methyl-1H-indazole

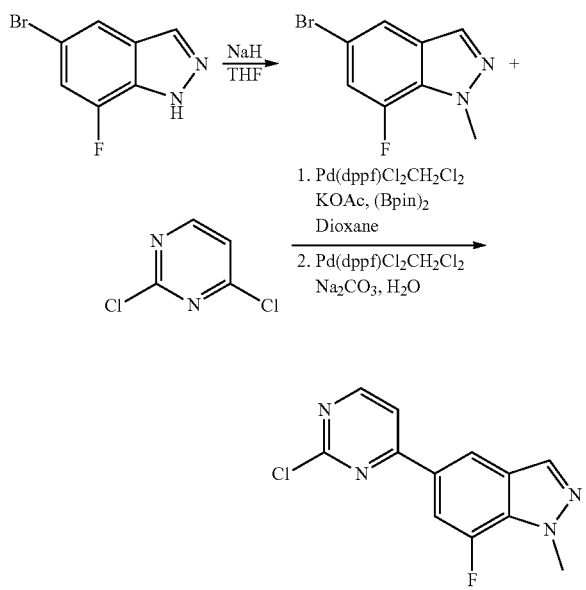

Step 1 Synthesis of 5-bromo-7-fluoro-2-methyl-2H-indazole and 5-bromo-7-fluoro-1-methyl-1H-indazole In an ice bath, sodium hydride (80 mg, 3.35 mmol) was added into the solution of 5-bromo-7-fluoro-1H-indazole (600 mg, 2.79 mmol) in anhydrous tetrahydrofuran (10 mL), and warmed to room temperature to react for 1 hr. The temperature was decreased in an ice bath, methyl iodide (0.26 mL, 4.18 mmol) was added into the reaction, and warmed to room temperature to react for 2 hrs. The reaction was quenched by adding water, extracted with ethyl acetate (50 mL×3), the organic layer was combined, washed with brine, and dried over anhydrous sodium sulfate. The filtrate was separated on column chromatography (eluant:petroleum ether/ethyl acetate (v/v)=4:1-2:1) to afford 190 mg of a white solid B(5-bromo-7-fluoro-2-methyl-2H-indazole), LC-MS(APCI): m/z=229.0 (M+1), 1H NMR (500 MHz, CDCl3): δ 7.90 (d, J=2.4 Hz, 1H), 7.63 (d, J=1.5 Hz, 1H), 7.17 (dd, J=11.0, 1.5 Hz, 1H), 4.23 (d, J=1.0 Hz, 3H).

Step 2 Synthesis of Intermediate Compound 5-(2-chloropyrimidin-4-yl)-7-fluoro-1-methyl-1H-indazole The synthetic step is the same as the synthetic step 5 of intermediate compound 6-(2-chloropyrimidin-4-yl)-4-fluoro-2-(fluoromethyl)-1-isopropyl-1H-benzo[d]imidazole, and afforded product 5-(2-chloropyrimidin-4-yl)-7-fluoro-1-methyl-1H-indazole (295 mg of a yellow-white solid). Yield was 75.6%. LC-MS(APCI): m/z=263.0 (M+1).

Synthesis of Intermediate Compound 5-(2-chloro-pyrimidin-4-yl)-7-fluoro-2-methyl-2H-indazole

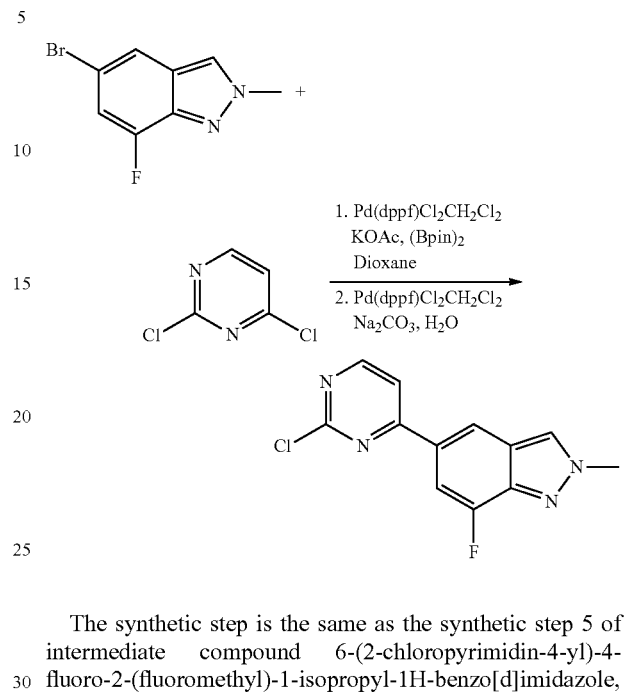

The synthetic step is the same as the synthetic step 5 of intermediate compound 6-(2-chloropyrimidin-4-yl)-4-fluoro-2-(fluoromethyl)-1-isopropyl-1H-benzo[d]imidazole, and afforded product 5-(2-chloropyrimidin-4-yl)-7-fluoro-2-methyl-2H-indazole (180 mg of a yellow-white solid). Yield was 83.5%. LC-MS(APCI): m/z=263.1 (M+1).

Synthesis of Intermediate Compound 5-(2-chloro-pyrimidin-4-yl)-7-fluoro-2-methyl-3-(prop-1-en-2-yl)-2H-indazole

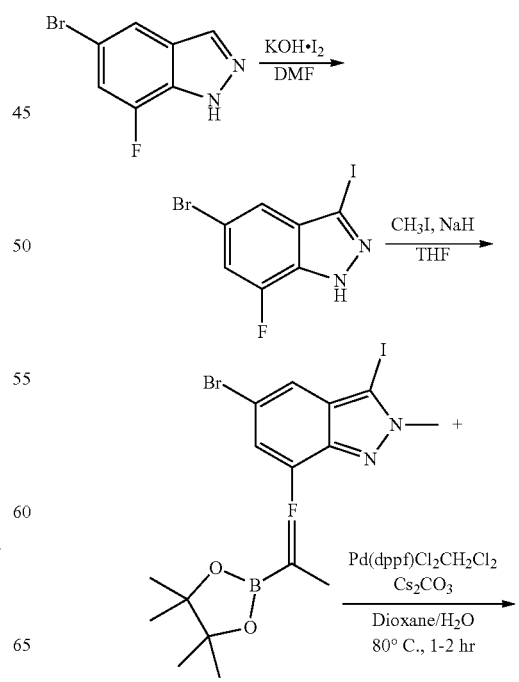

-continued

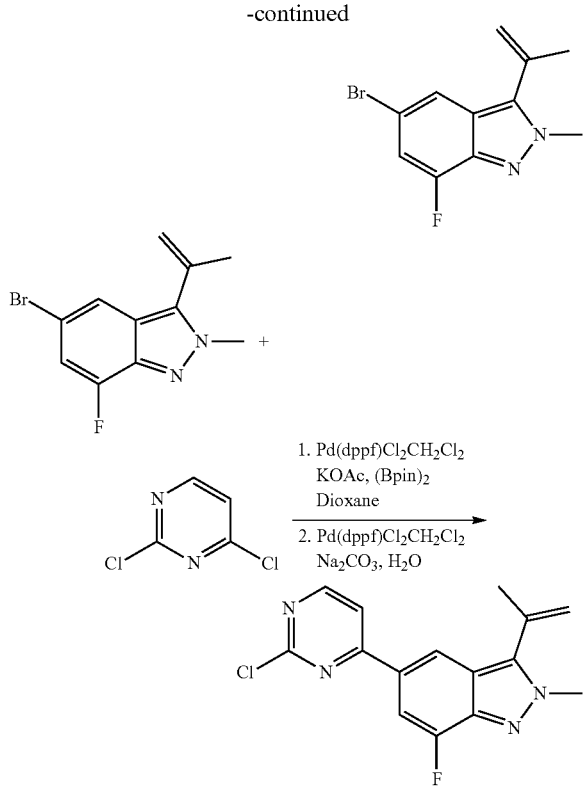

Step 3 Synthesis of 5-bromo-7-fluoro-2-methyl-3-(prop-1-en-2-yl)-2H-indazole

Under nitrogen protection, Pd(dppf)Cl$_2$·CH$_2$Cl$_2$ (150 mg) was added into 5-bromo-7-fluoro-3-iodo-2-methyl-2H-indazole (480 mg, 1.35 mmol), pinacolyl 2-propenylboronate (215 mg, 1.28 mmol) and cesium carbonate (880 mg, 2.70 mmol) in mixed solvent of dioxane (16 mL) and water (4 mL), and the reaction was reacted under nitrogen protection at 80° C. for 1 hrs. After cooling to room temperature, it was filtered on Celite, the filter cake was washed with dichloromethane, the filtrate was concentrated under reduced pressure, and the filtrate was separated on column chromatography (eluent: petroleum ether/ethyl acetate (v/v)=10:1), to afford 185 mg of a pale yellow oil. Yield: 50.6%, LC-MS (APCI): m/z=271.0 (M+1).

Step 4 Synthesis of 5-(2-chloropyrimidin-4-yl)-7-fluoro-2-methyl-3-(prop-1-en-2-yl)-2H-indazole The synthetic step is the same as the synthetic step 5 of intermediate compound 6-(2-chloropyrimidin-4-yl)-4-fluoro-2-(fluoromethyl)-1-isopropyl-1H-benzo[d]imidazole, and afforded product 5-(2-chloropyrimidin-4-yl)-7-fluoro-2-methyl-3-(prop-1-en-2-yl)-2H-indazole (190 mg of a yellow-white solid). Yield was 95.3%. LC-MS(APCI): m/z=302.9 (M+1).

Synthesis of Intermediate Compound 5-(2-chloropyrimidin-4-yl)-2-methyl-3-(prop-1-en-2-yl)-2H-indazole Step 1 Synthesis of 5-bromo-7-fluoro-3-iodo-1H-indazole At room temperature, sodium hydroxide (393 mg, 7.01 mmol) was added into the solution of 5-bromo-7-fluoro-1H-indazole (500 mg, 2.34 mmol) and elementary iodine (1.19 mg, 4.68 mmol) in anhydrous DMF (10 mL) in portions, and the reaction was stirred at room temperature for 2 hrs. The reaction was quenched by adding saturated solution of sodium thiosulfate, extracted with ethyl acetate (30 mL×3), the organic layer was combined, washed with brine, dried over anhydrous sodium sulfate, concentrated under reduced pressure, and the filtrate was separated on column chromatography (eluant:petroleum ether/ethyl acetate (v/v)=3:1), to afford 610 mg of a yellow solid. Yield was 76.9%. LC-MS (APCI): m/z=340.9 (M+1).

Step 2 Synthesis of 5-bromo-7-fluoro-3-iodo-2-methyl-2H-indazole

In an ice bath, sodium hydride (86 mg, 2.15 mmol) was added into the solution of 5-bromo-7-fluoro-3-iodo-1H-indazole (610 mg, 1.79 mmol) in anhydrous tetrahydrofuran (10 mL), the reaction was warmed to room temperature and reacted for 1 hr. The reaction was cooled again in an ice bath, methyl iodide (0.17 mL, 2.19 mmol) was added into the reaction, and the reaction was warmed to room temperature and reacted for 2 hrs. The reaction was quenched by adding water, extracted with ethyl acetate (50 mL×3), the organic layer was combined, washed with brine, and dried over anhydrous sodium sulfate. The filtrate was separated on column chromatography (eluant:petroleum ether/ethyl acetate (v/v)=10:1) to afford 190 mg of a white solid, yield was 29.9%, LC-MS(APCI): m/z=356.8 (M+1).

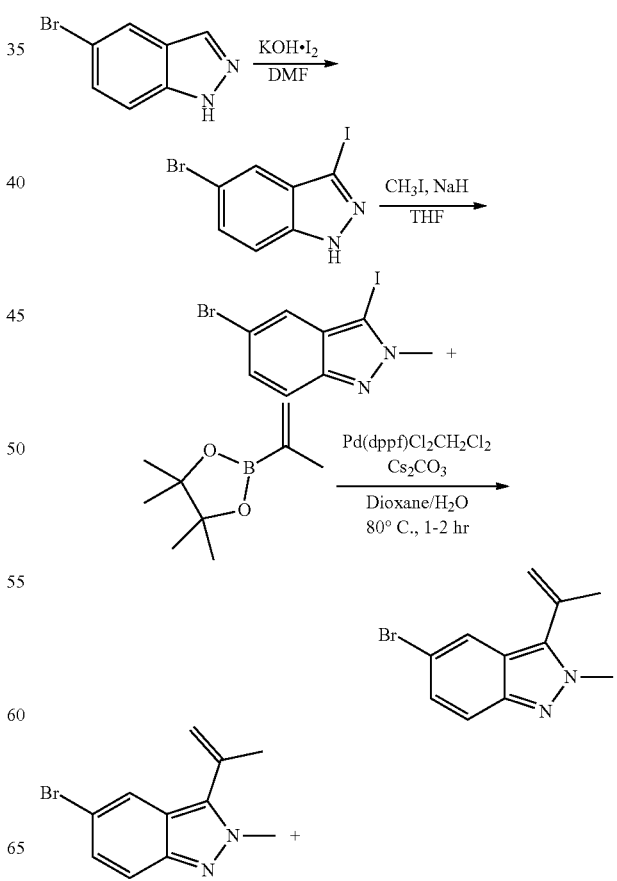

-continued

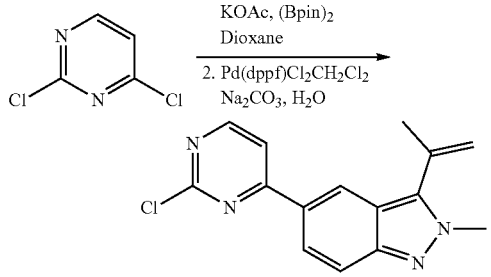

Step 1 Synthesis of 5-bromo-3-iodo-1H-indazole

At room temperature, sodium hydroxide (4.27 g, 76.13 mmol) was added into 5-bromo-1H-indazole (5.00 g, 25.38 mmol) and elementary iodine (12.9 g, 50.75 mmol) in anhydrous DMF (10 mL) in portions, and the reaction was stirred at room temperature for 2 hrs. The reaction was quenched by adding saturated solution of sodium thiosulfate, extrcted with ethyl acetate (50 mL×3), the organic layer was combined, washed with brine, dried over anhydrous sodium sulfate, and concentrated under reduced pressure to afford 8 g of a yellow solid. Yield was 90.0%. LC-MS (APCI): m/z=322.2 (M+1).

Step 2 Synthesis of 5-bromo-3-iodo-2-methyl-2H-indazole

In an ice bath, sodium hydride (500 mg, 12.00 mmol) was added into the solution of 5-bromo-3-iodo-1H-indazole (3.20 g, 10.00 mmol) in anhydrous tetrahydrofuran (30 mL), and the reaction was warmed to room temperature and reacted for 1 hr. The reaction was cooled again in an ice bath, methyl iodide (1.25 mL, 20.00 mmol) was added into the reaction, and the reaction was warmed to room temperature and reacted for 2 hrs. The reaction was quenched by adding water, extracted with ethyl acetate (50 mL×3), the organic layer was combined, washed with brine, and dried over anhydrous sodium sulfate. The filtrate was separated on column chromatography (eluent:petroleum ether/ethyl acetate (v/v)=10:1) to afford 800 mg of a white solid, yield was 23.9%, LC-MS(APCI): m/z=336.7 (M+1). $^1$H NMR (500 MHz, CDCl$_3$): δ 7.57 (s, 1H), 7.54 (d, J=9.1 Hz, 1H), 7.36 (d, J=8.1 Hz, 1H), 4.24 (s, 3H).

Step 3 preparation of 5-bromo-2-methyl-3-(prop-1-en-2-yl)-2H-indazole

Under nitrogen protection, Pd(dppf)Cl$_2$.CH$_2$Cl$_2$ (200 mg, 2.40 mmol) was added into 5-bromo-3-iodo-2-methyl-2H-indazole (800 mg, 2.40 mmol), pinacolyl 2-propenylboronate (390 mg, 2.30 mmol) and cesium carbonate (1.56 g, 4.80 mmol) in the mixed solvent of dioxane (16 mL) and water (4 mL), and the reaction was reacted under nitrogen protection at 80° C. for 1 hr. After cooling to room temperature, it was filtered on Celite, the filter cake was washed with dichloromethane, the filtrate was concentrated under reduced pressure, and the filtrate was separated on column chromatography (eluent: petroleum ether/ethyl acetate (v/v)=5:1), to afford 440 mg of a pale yellow oil. Yield: 73.3%, LC-MS(APCI): m/z=251.0 (M+1).

Step 4 Synthesis of Intermediate Compound 5-(2-chloropyrimidin-4-yl)-2-methyl-3-(prop-1-en-2-yl)-2H-indazole The synthetic step is the same as the synthetic step 5 of intermediate compound 6-(2-chloropyrimidin-4-yl)-4-fluoro-2-(fluoromethyl)-1-isopropyl-1H-benzo[d]imidazole, and afforded product 5-(2-chloropyrimidin-4-yl)-2-methyl-3-(prop-1-en-2-yl)-2H-indazole (460 mg of a yellow-white solid). Yield was 92.0%. LC-MS(APCI): m/z=285.0 (M+1).

Synthesis of Intermediate Compound 6-(2-chloropyrimidin-4-yl)imidazo[1,2-b]pyridazine

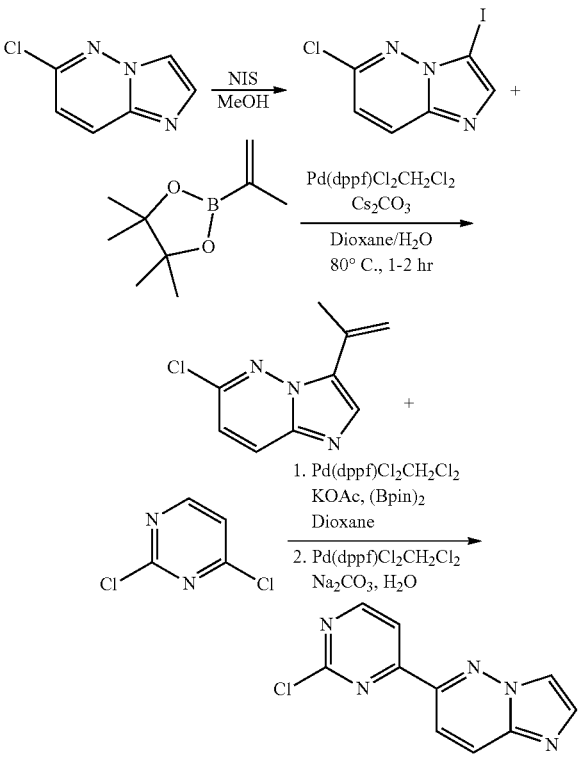

Step 1 Synthesis of 6-chloro-3-iodoimidazo[1,2-b]pyridazine

At room temperature, NIS (1.50 g, 6.50 mmol) was added into the solution of 6-chloro-3-imidazo[1,2-b]pyridazine (1.0 g, 6.50 mmol) in methanol (10 mL) in portions, and the reaction was stirred under reflux overnight. The reaction was quenched by adding saturated solution of sodium thiosulfate, extracted with dichloromethane (50 mL×3), the organic layer was combined, washed with brine, dried over anhydrous sodium sulfate, and concentrated under reduced pressure to afford 1.13 g of a yellow solid. Yield was 90.0%. LC-MS(APCI): m/z=290.1 (M+1).

Step 2 Preparation of 6-chloro-3-(prop-1-en-2-yl)imidazo[1,2-b]pyridazine

Under nitrogen protection, Pd(dppf)Cl$_2$.CH$_2$Cl$_2$ (240 mg) was added into 6-chloro-3-iodoimidazo[1,2-b]pyridazine (1.0 g, 3.57 mmol), pinacolyl 2-propenylboronate (602 mg, 3.57 mmol) and sodium carbonate (800 mg, 7.16 mmol) in the mixed solvent of dioxane (16 mL) and water (4 mL), and the reaction was reacted under nitrogen protection at 80° C. for 1 hr. After cooling to room temperature, it was filtered on Celite, the filter cake was washed with dichloromethane, the filtrate was concentrated under reduced pressure, and the filtrate was separated on column chromatography (eluent: petroleum ether/ethyl acetate (v/v)=5:1), to afford 509 mg of a pale yellow oil. Yield: 74.1%, LC-MS(APCI): m/z=194.1 (M+1).

Step 3 Synthesis of Intermediate Compound 6-(2-chloropyrimidin-4-yl)imidazo[1,2-b]pyridazine The synthetic step is the same as the synthetic step 5 of intermediate compound 6-(2-chloropyrimidin-4-yl)-4-fluoro-2-(fluoromethyl)-1-isopropyl-1H-benzo[d]imidazole, and afforded product 6-(2-chloropyrimidin-4-yl)imidazo[1,2-b]pyridazine (220 mg of a yellow-white solid). Yield was 27.6%. LC-MS(APCI): m/z=232.0 (M+1).

Synthesis of Intermediate Compound 8-(2-chloropyrimidin-4-yl)-1-isopropyl-5,6-dihydro-4H-imidazo[4,5,1-ij]quinolin-2(1H)-one

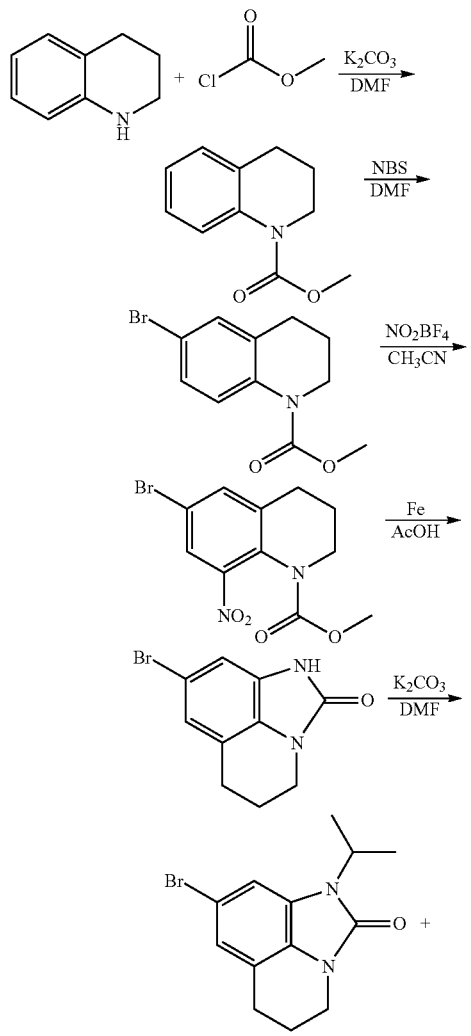

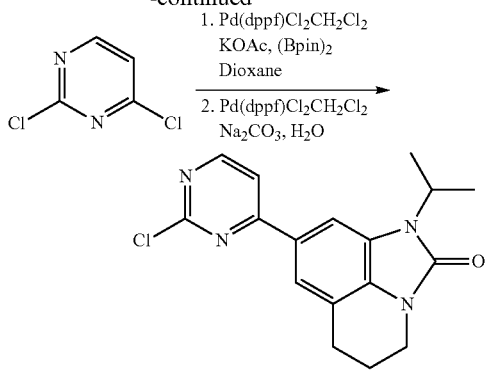

Step 1 Synthesis of methyl 3,4-dihydroquinolin-1(2H)-carboxylate

In an ice bath, methyl chloroformate (19.90 mL, 258 mmol) was slowly added into 1,2,3,4-tetrahydroquinoline (10.8 mL, 85.8 mmol) and potassium carbonate (47.6 g, 344 mmol) in anhydrous DMF (100 mL). After the addition was complete, the reaction was stirred at room temperature for 10 min, and it was warmed to 50° C. and reacted for 5 hrs. After cooling to room temperature, the reaction was quenched by adding water (200 mL), extracted with petroleum ether (100 mL×3), the organic layer was combined, washed with brine (150 mL×2), dried over anhydrous sodium sulfate, and concentrated under reduced pressure to afford 16.3 g of an oil, which was used in the next step directly. LC-MS(APCI): m/z=192.1 (M+1). $^1$H NMR (400 MHz, CDCl3): δ 7.68 (d, J=8.0 Hz, 1H), 7.20-7.14 (m, 1H), 7.10 (d, J=6.8 Hz, 1H), 7.03 (td, J=7.5, 1.0 Hz, 1H), 3.81 (s, 3H), 3.80-3.76 (m, 2H), 2.79 (t, J=6.6 Hz, 2H), 1.96 (dt, J=12.7, 6.5 Hz, 2H).

Step 2 Synthesis of methyl 6-bromo-3,4-dihydroquinolin-1(2H)-carboxylate

In an ice bath, NBS (16.7 g, 93.83 mmol) was added into the solution of methyl 3,4-dihydroquinolin-1(2H)-carboxylate (16.3 g, 85.3 mmol) in DMF (100 mL) in portions, and the reaction was stirred at rt. overnight. The reaction was quenched by adding water (200 mL), extracted with petroleum ether (100 mL×3), the organic layer was combined, washed with brine (150 mL×2), dried over anhydrous sodium sulfate, and concentrated under reduced pressure to afford 22.1 g of a solid, which was used in the next step directly. LC-MS(APCI): m/z=271.1 (M+1). $^1$H NMR (400 MHz, CDCl3): δ 7.61 (d, J=8.0 Hz, 1H), 7.31-7.25 (m, 1H), 7.23 (d, J=2.3 Hz, 1H), 3.81 (s, 3H), 3.78-3.72 (m, 2H), 2.76 (t, J=6.6 Hz, 2H), 1.94 (dt, J=12.6, 6.4 Hz, 2H).

Step 3 Synthesis of methyl 6-bromo-8-nitro-3,4-dihydroquinolin-1(2H)-carboxylate In an ice bath, a solution of methyl 6-bromo-3,4-dihydroquinolin-1(2H)-carboxylate (2.69 g, 10.00 mmol) in acetonitrile (50 mL) was slowly added into the solution of nitronium tetrafluoroborate (1.85 g, 14.00 mmol) in acetonitrile (50 mL). The reaction mixture was reacted at 0° C. for 1.5 hrs, the reaction was quenched by adding water, acetonitrile was removed under reduce pressure, water layer was extracted with ethyl acetate (50 mL×3), the organic layer was combined, washed with saturated solution of sodium bicarbonate and brine, respectively, dried over anhydrous sodium sulfate, the filtrate was concentrated under reduced pressure, and the filtrate was separated on column chromatography (eluant:petroleum ether/ethyl acetate (v/v)=5:1) to afford 890 mg of a pale yellow solid, yield was 28.4%. LC-MS(APCI): m/z=315.0 (M+1).

Step 4 Synthesis of 8-bromo-5,6-dihydro-4H-imidazo[4,5,1-ij]quinolin-2(1H)-one

Reduced iron powder (860 mg, 15.33 mmol) was added into the solution of methyl 6-bromo-8-nitro-3,4-dihydroquinolin-1(2H)-carboxylate (690 mg, 2.20 mmol) in glacial acetic acid (8 mL). The reaction mixture was reacted at 80° C. for 2.5 hrs. After cooling to room temperature, it was filtered on Celite, the filtrate was diluted by adding water, extracted with ethyl acetate (50 mL×3), the organic layer was combined, washed with brine, dried over anhydrous sodium sulfate, and the filtrate was concentrated under reduced pressure to give a crude product, which was purified by slurrying in n-hexane to afford 340 mg of a pale yellow solid, yield was 61.0%. LC-MS(APCI): m/z=253.0 (M+1), $^1$H NMR (400 MHz, DMSO-d6): δ 10.78 (s, 1H), 7.02-6.96 (m, 1H), 6.94 (d, J=1.4 Hz, 1H), 3.67 (t, J=6.0 Hz, 2H), 2.75 (t, J=6.0 Hz, 2H), 2.03-1.91 (m, 2H).

Step 5 Synthesis of 8-bromo-1-isopropyl-5,6-dihydro-4H-imidazo[4,5,1-ij]quinolin-2(1H)-one In an ice bath, sodium hydride (80 mg, 2.00 mmol) was added into the solution of 8-bromo-5,6-dihydro-4H-imidazo[4,5,1-ij]quinolin-2(1H)-one (340 mg, 1.34 mmol) in anhydrous DMF (10 mL) in portions, and the reaction was reacted at room temperature and the mixture was stirred overnight. The reaction was quenched by adding water, extracted with ethyl acetate (30 mL×3), the organic layer was combined, washed with brine, dried over anhydrous sodium sulfate, concentrated under reduced pressure, and the filtrate was separated on column chromatography (eluant:petroleum ether/ethyl acetate (v/v)=1/1) to afford 300 mg of a pale yellow solid, yield was 76.2%. LC-MS(APCI): m/z=295.0 (M+1).

Step 6 Synthesis of Intermediate Compound 8-(2-chloropyrimidin-4-yl)-1-isopropyl-5,6-dihydro-4H-imidazo[4,5,1-ij]quinolin-2(1H)-one The synthetic step is the same as the synthetic step 5 of intermediate compound 6-(2-chloropyrimidin-4-yl)-4-fluoro-2-(fluoromethyl)-1-isopropyl-1H-benzo[d]imidazole, and afforded product 8-(2-chloropyrimidin-4-yl)-1-isopropyl-5,6-dihydro-4H-imidazo[4,5,1-ij]quinolin-2(1H)-one (300 mg of a white solid). Yield was 67.3%. LC-MS(APCI): m/z=329.0 (M+1); $^1$H NMR (400 MHz, CDCl3): δ 8.67 (d, J=5.3 Hz, 1H), 7.86 (s, 1H), 7.74 (s, 1H), 7.71 (d, J=5.4 Hz, 1H), 4.86 (dt, J=14.0, 7.0 Hz, 1H), 4.00 (t, J=6.0 Hz, 2H), 3.04 (t, J=6.0 Hz, 2H), 2.32-2.22 (m, 2H), 1.71 (d, J=7.0 Hz, 6H).

Synthesis of Intermediate Compound 8-(2-chloropyrimidin-4-yl)-2-methoxy-5,6-dihydro-4H-imidazo[4,5,1-ij]quinoline

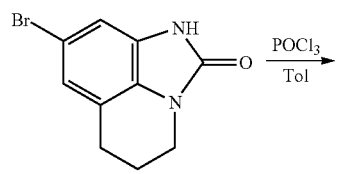

Step 1 Synthesis of 8-bromo-2-chloro-5,6-dihydro-4H-imidazo[4,5,1-ij]quinoline

At room temperature, 8-bromo-5,6-dihydro-4H-imidazo[4,5,1-ij]quinolin-2(1H)-one (2.60 g, 10.31 mmol) was dissolved in the mixed solution of phosphorus oxychloride (30 mL) and toluene (10 mL), and the reaction was refluxed overnight. After cooling to room temperature, the reaction solvent was removed under reduced pressure, the pH of the residue was adjusted to neutral with saturated solution of sodium bicarbonate, extracted with ethyl acetate (50 mL×3), the organic phase was washed with brine separately, dried over anhydrous sodium sulfate, concentrated under reduced pressure, and the filtrate was separated on column chromatography (eluant:petroleum ether/ethyl acetate (v/v)=3:1), to afford 1.46 g of a white solid. Yield was 52.4%. LC-MS (APCI): m/z=270.9 (M+1).

Step 2 Synthesis of 8-bromo-2-methoxy-5,6-dihydro-4H-imidazo[4,5,1-ij]quinoline

In an ice bath, sodium methoxide (730 mg, 13.5 mmol) was added into 8-bromo-2-chloro-5,6-dihydro-4H-imidazo[4,5,1-ij]quinoline (750 mg, 2.77 mmol) in anhydrous DMF (15 mL), the reaction was warmed naturally, and the reaction mixture was stirred overnight. The reaction was quenched by adding water, extracted with ethyl acetate (50 mL×3), the organic layer was combined, washed with brine, dried over anhydrous sodium sulfate, concentrated under reduced pressure, and the filtrate was separated on column chromatography (eluant:petroleum ether/ethyl acetate (v/v)=5:1), to afford 560 mg of a pale yellow solid, yield was 76.0%. LC-MS(APCI): m/z=267.0 (M+1).

Step 3 Synthesis of Intermediate Compound 8-(2-chloropyrimidin-4-yl)-2-methoxy-5,6-dihydro-4H-imidazo[4,5,1-ij]quinoline The synthetic step is the same as the synthetic step 5 of intermediate compound 6-(2-chloropyrimidin-4-yl)-4- fluoro-2-(fluoromethyl)-1-isopropyl-1H-benzo[d]imidazole, and afforded product 8-(2-chloropyrimidin-4-yl)-2-methoxy-5,6-dihydro-4H-imidazo[4,5,1-ij]quinoline (300 mg of a yellow solid). Yield was 66.4%. LC-MS(APCI): m/z=301.0 (M+1).

Synthesis of Intermediate Compound 6-(2-chloropyrimidin-4-yl)benzo[d]thiophene

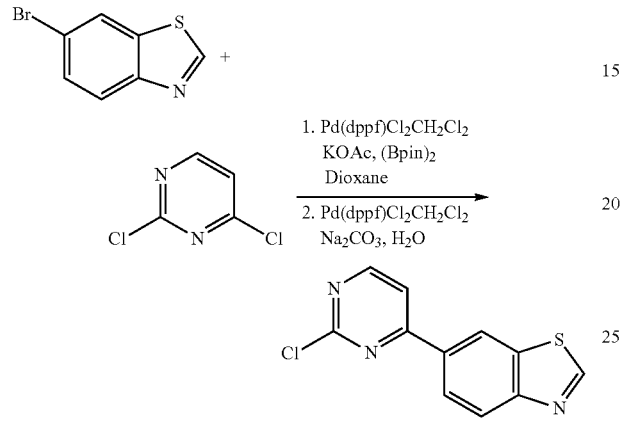

The synthetic step is the same as the synthetic step 5 of intermediate compound 6-(2-chloropyrimidin-4-yl)-4-fluoro-2-(fluoromethyl)-1-isopropyl-1H-benzo[d]imidazole, and afforded product 6-(2-chloropyrimidin-4-yl)benzo[d]thiophene (120 mg of a yellow solid). Yield was 66.4%. LC-MS (APCI): m/z=248.0 (M+1).

Synthesis of Intermediate Compound N-(5-amino-2-((2-(dimethylamino)ethyl)(methyl)amino)-4-methoxyphenyl)acrylamide

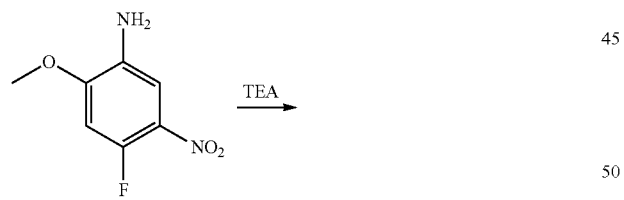

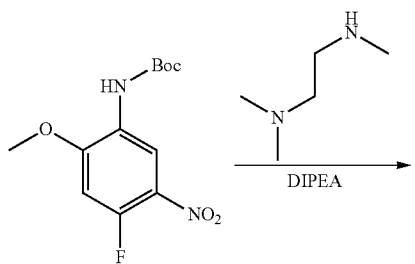

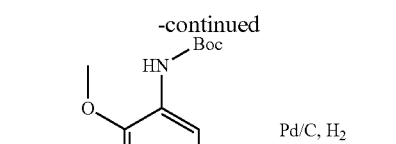

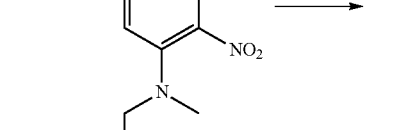

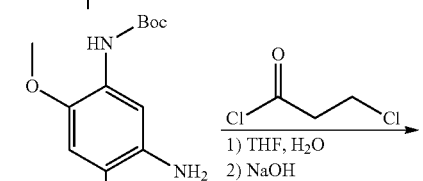

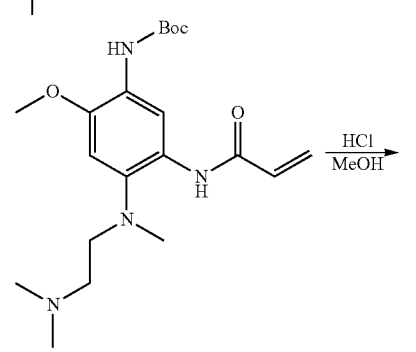

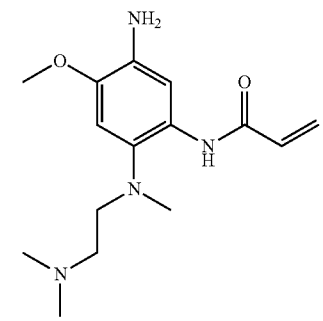 [SMILES: C=CC(=O)Nc1cc(N)c(OC)cc1N(C)CCN(C)C]

Step 1 Synthesis of Compound tert-butyl (4-fluoro-2-methoxy-5-nitrophenyl)carbamate In an ice bath, Boc anhydride (7.05 g, 32.20 mmol) was slowly added into the mixture of 4-fluoro-2-methoxy-5-nitroaniline (4.0 g, 21.50 mmol) and triethylamine (TEA, 3.60 g, 35.64 mmol) in dichloromethane (65 mL). After the addition was complete, the reaction was reacted at 40° C. overnight. After cooling to room temperature, it was diluted by adding water (100 mL), extracted with dichloromethane (100 mL×3), the organic phase was combined, washed with brine (100 mL), dried over anhydrous sodium sulfate, the solvent was removed, and the filtrate was separated on column chromatography (eluant:petroleum ether/ethyl acetate (v/v)=2:1), to afford 3.6 g of a yellow solid, yield: 58.8%. LC-MS(APCI): m/z=287.2 (M+1).

Step 2 Synthesis of Compound tert-butyl (4-((2-(dimethylamino)ethyl)(methyl)amino)-2-methoxy-5-nitrophenyl)carbamate $N^1,N^1,N^2$-trimethylethane-1,2-diamine (2.14 g, 20.40 mmol) was added into the mixture of tert-butyl (4-fluoro-2-methoxy-5-nitrobenzene)carbamate (4.0 g, 21.50 mmol) and N,N-diisopropylethylamine (DIPEA, 4.92 mL, 27.20 mmol) in N,N-dimethylformamide (28 mL), and the reaction was reacted at 90° C. for 5 hours. After cooling to room temperature, it was diluted by adding water (100 mL), extracted with ethyl acetate (100 mL×3), the organic phase was combined, washed with brine (100 mL×3), dried over anhydrous sodium sulfate, and the solvent was removed to afford 5.0 g of a brown oil, which was used in the next reaction without purification. LC-MS(APCI): m/z=369.3 (M+1).

Step 3 Synthesis of Compound tert-butyl (5-amino-4-((2-(dimethylamino)ethyl)(methyl)amino)-2-methoxyphenyl)carbamate Pd/C (500 mg) was added into the solution of tert-butyl (4-((2-(dimethylamino)ethyl)(methyl)amino)-2-methoxy-5-nitrophenyl)carbamate (5.00 g, 13.6 mmol) in methanol (65 mL), and the reaction was stirred under a balloon of hydrogen gas overnight. The reaction was filtered on Celite, the filtrate was concentrated under reduced pressure, and the filtrate was separated on column chromatography (eluant: dichloromethane /methanol (v/v)=20:1), to afford 4.0 g of a brown-yellow oil, yield over two steps: 86.8%. LC-MS (APCI): m/z=339.3 (M+1).

Step 4 Synthesis of Compound tert-butyl (5-acrylamido-4-((2-(dimethylamino)ethyl)(methyl)amino)-2-methoxyphenyl)carbamate At room temperature, 3-chloropropanoyl chloride (1.80 g, 14.20 mmol) was added into tert-butyl (5-amino-4-((2-(dimethylamino)ethyl)(methyl)amino)-2-methoxyphenyl)carbamate (4.00 g, 11.80 mmol) in the mixed solution of tetrahydrofuran (95 mL) and water (9.5 mL), and reacted at room temperature for 1 hour. Sodium hydroxide (2.40 g) was added into the reaction, and the reaction was reacted at 65° C. overnight. After cooling to room temperature, the reaction mixture was concentrated under reduced pressure. The residue was diluted by adding water (100 mL), extracted with dichloromethane (100 mL×3), the organic phase was combined, washed with brine (100 mL), dried over anhydrous sodium sulfate, the solvent was removed, and the filtrate was separated on column chromatography (eluant: dichloromethane /methanol (v/v)=20:1), to afford 3.20 g of a brown-yellow solid, yield: 69.2%. LC-MS(APCI): m/z=393.3 (M+1).

Step 5 Synthesis of Intermediate Compound N-(5-amino-2-((2-(dimethylamino)ethyl)(methyl)amino)-4-methoxyphenyl)acrylamide At room temperature, HCl in methanol (4 M, 5 mL) was added into tert-butyl ((5-acrylamido-4-((2-(dimethylamino)ethyl)(methyl)amino)-2-methoxyphenyl)carbamate (392 mg, 1.00 mmol) in methanol (2 mL), and the reaction was stirred overnight. Methanol was removed under reduce pressure, saturated sodium bicarbonate (30 mL) was added, extracted with dichloromethane (30 mL×3), the organic phase was combined, washed with brine (30 mL), dried over anhydrous sodium sulfate and concentrated under reduced pressure to afford 292 mg of a yellow solid, yield: 95%. LC-MS(APCI): m/z=293.3 (M+1).

Synthesis of Intermediate Compound 5-(difluoromethoxy)-$N^1$-(2-(dimethylamino)ethyl)-$N^1$-methyl-2-nitrobenzene-1,4-diamine

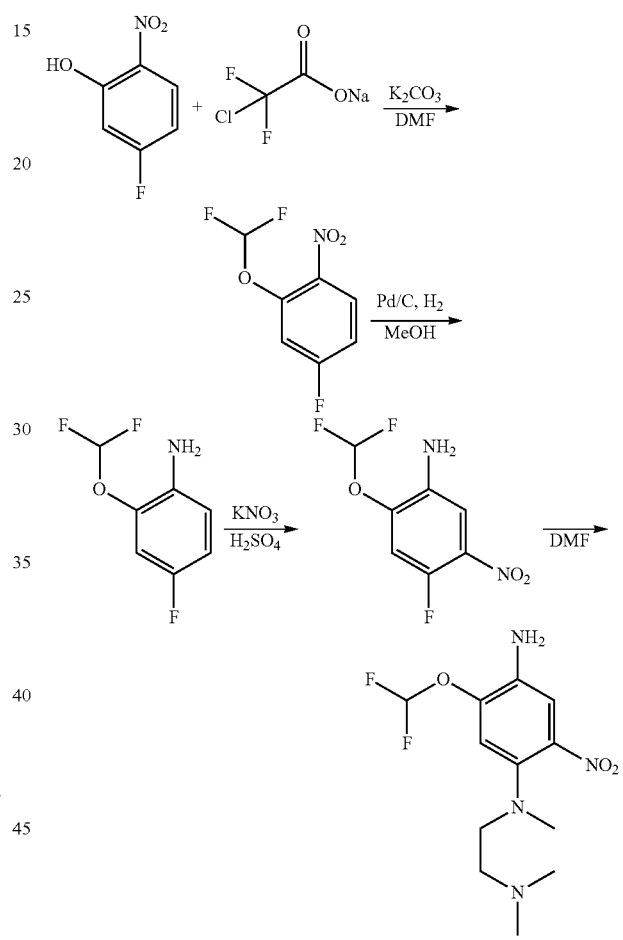

Step 1 Synthesis of 2-(difluoromethoxy)-4-fluoro-1-nitrobenzene

At room temperature, potassium carbonate (6.60 g, 47.7 mmol) was added into the solution of 5-fluoro-2-nitrophenol (5.0 g, 31.8 mmol) and sodium difluorochloroacetate (7.30 g, 47.7 mmol) in DMF (100 mL), and the reaction was reacted at 90° C. for 5 hrs. DMF was removed under reduce pressure, then diluted with adding water (200 mL), extracted with dichloromethane (200 mL×3), the organic layer was combined, washed with brine, dried over anhydrous sodium sulfate, concentrated under reduced pressure, and the filtrate was separated on column chromatography (eluant:petroleum ether/ethyl acetate (v/v)=30:1), to afford 4.17 g of a yellow oil. Yield was 63.3%.

Step 2 Synthesis of 2-(difluoromethoxy)-4-fluoroaniline

10% Pd/C (400 mg) was added into the solution of 2-(difluoromethoxy)-4-fluoro-1-nitrobenzene (4.17 g, 20.1 mmol) in methanol (40 mL), and then reacted under hydrogen gas (balloon) at room temperature overnight, filtered on Celite, the filtrate was concentrated under reduced pressure, and the filtrate was separated on column chromatography (eluant:petroleum ether/ethyl acetate (v/v)=50:1), to afford 2.982 g of a pale yellow oil, yield was 83.7%. LC-MS (APCI): m/z=178.1M+1).

Step 3 Synthesis of 2-(difluoromethoxy)-4-fluoro-5-nitroaniline

At 0° C., 2-(difluoromethoxy)-4-fluoroaniline (1.5 g) was dissolved in 3 ml concentrated sulfuric acid, potassium nitrate (1.1 g) was added in portions, and the reaction was stirred at room temperature. After LC-MS detection shows the reaction was complete, the system was slowly poured into 100 ml saturated NaHCO$_3$ in ice-water, solid precipitated out, filtered, the filtrate was extracted with 60 ml dichloromethane 3 time, the filter cake was dissolved in dichloromethane, the extraction was filtered again, dried over anhydrous sodium sulfate, the filtrate was concentrated under reduced pressure, and the filtrate was separated on column chromatography (eluant:petroleum ether/ethyl acetate (v/v)=30:1), to afford 1.3 g of a brown oil, yield was 69.1%. LC-MS(APCI): m/z=223.1M+1).

Step 4 Synthesis of Intermediate Compound 5-(difluoromethoxy)-N$^1$-(2-(dimethylamino)ethyl)-N$^1$-methyl-2-nitrobenzene-1,4-diamine At room temperature, potassium carbonate (2.0 g, 14.4 mmol) was added into 2-(difluoromethoxy)-4-fluoro-5-nitroaniline (1.6 g, 7.2 mmol) and N,N,N'-trimethylethylenediamine (1.1 g, 10.8 mmol) in acetonitrile (20 mL). The reaction was reacted at 80° C. for 3 hrs. After cooling to room temperature, it was filtered on Celite, the filtrate was concentrated under reduced pressure, and the filtrate was separated on column chromatography (eluant:dichloromethane/methanol (v/v)=10:1), to afford 2.0 g of a red-brown oily solid, yield was 45.5%. LC-MS(APCI): m/z=305.2M+1).

Synthesis of Intermediate Compound N$^1$-(2-(dimethylamino)ethyl)-5-ethoxy-N$^1$-methyl-2-nitrobenzene-1,4-diamine

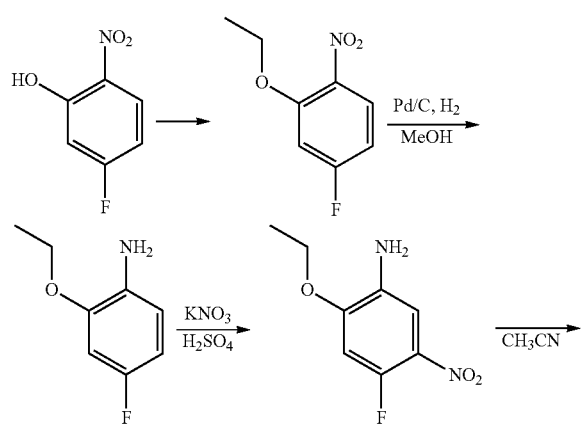

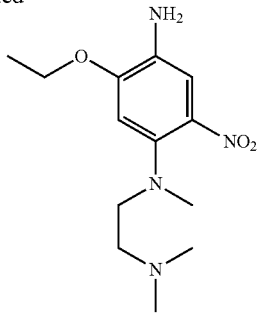

Step 1 Synthesis of 2-ethoxy-4-fluoro-1-nitrobenzene 5-fluoro-2-nitrophenol (5.0 g, 31.8 mmol), potassium carbonate (13.17 g, 95.4 mmol) were suspended in 150 mL DMF, ethyl iodide (5.00 mL, 63.6 mmol) was added dropwise, and the reaction was heated to 37° C. with stirring. After TLC detected the reaction was complete, the system was poured in ice-water, extracted with ethyl acetate (200 mL×3), the organic layer was combined, washed with brine, dried over anhydrous sodium sulfate, concentrated under reduced pressure, and the filtrate was separated on column chromatography (eluant:petroleum ether/ethyl acetate (v/v)=20:1), to afford 4.8 g of a yellow oil. Yield was 83.1%.

Step 2 Synthesis of 2-ethoxy-4-fluoroaniline

10% Pd/C (400 mg) was added into the solution of 2-ethoxy-4-fluoro-1-nitrobenzene (4.8 g, 26.0 mmol) in methanol (40 mL), and reacted under hydrogen gas (balloon) at room temperature overnight, filtered on Celite, the filtrate was concentrated under reduced pressure, and the filtrate was separated on column chromatography (eluant: petroleum ether/ethyl acetate (v/v)=50:1), and afforded product 3.8 g of a pale yellow oil, LC-MS(APCI): m/z=156.1 (M+1). $^1$H NMR (400 MHz, CDCl3) δ 6.63 (dd, J=8.5, 5.8 Hz, 1H), 6.56 (dd, J=10.4, 2.7 Hz, 1H), 6.50 (td, J=8.5, 2.7 Hz, 1H), 4.04 (q, J=7.0 Hz, 2H), 3.42 (br, 2H), 1.45 (t, J=7.0 Hz, 3H).

Step 3 Synthesis of 2-ethoxy-4-fluoro-5-nitroaniline

At 0° C., 2-ethoxy-4-fluoroaniline (2.0 g. 12.90 mmol) was dissolved in 10 ml concentrated sulfuric acid, potassium nitrate (1.56 g, 15.5 mmol) was added in the system in portions, and warmed to room temperature naturally with stirring. After LC-MS detected the reaction was complete, the reaction was worked up, the system was slowly poured in 100 ml ice-water, concentrated aqueous ammonia was added dropwise to adjust the pH value to 7-8, extracted several times by adding ethyl acetate, the organic phase was dried over anhydrous sodium sulfate, and concentrated under reduced pressure to afford 512 mg of a brown solid, yield was 20.0%. LC-MS(APCI): m/z=201.0M+1).

Step 4 Synthesis of Intermediate Compound N$^1$-(2-(dimethylamino)ethyl)-5-ethoxy-N$^1$-methyl-2-nitrobenzene-1,4-diamine At room temperature, potassium carbonate (983 mg, 7.12 mmol) was added into 2-(ethoxy)-4-fluoro-5-nitroaniline (512 mg, 3.56 mmol) and N,N,N'-trimethylethylenediamine (545 mg, 5.34 mmol) in acetonitrile (10 mL). The reaction was reacted at 80° C. for 3 hrs. After cooling to room temperature, it was filtered on Celite, the filtrate was concentrated under reduced pressure, and the filtrate was separated on column chromatography (eluant:dichloromethane/methanol (v/v)=10:1), to afford 635 mg of a red-brown oil, yield was 63.3%, LC-MS(APCI): m/z=283.2 (M+1).

Synthesis of Intermediate Compound N-(2-(dimethylamino)ethyl)-$N^1$-methyl-2-nitro-5-(2,2,2-trifluoroethoxy)benzene-1,4-diamine

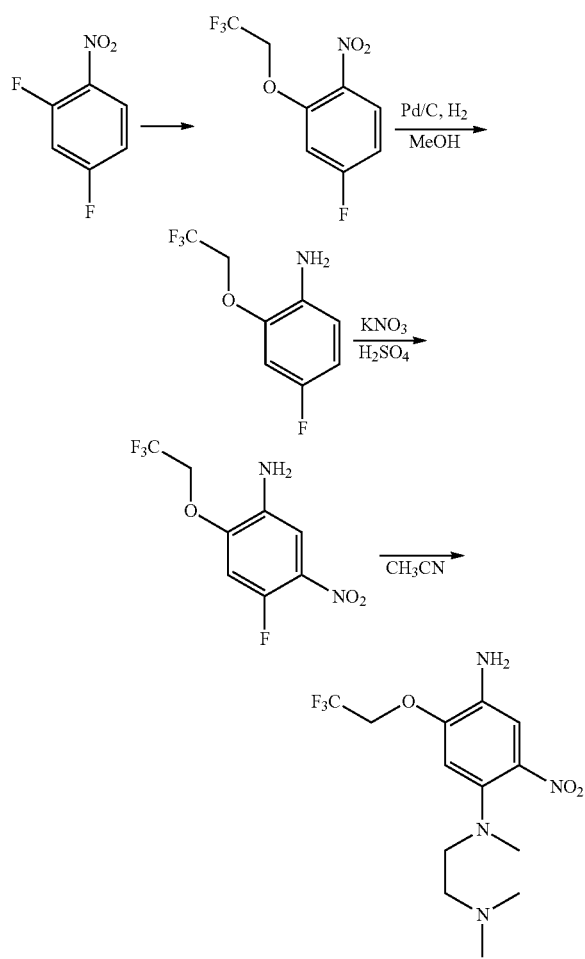

Step 1 Synthesis of 4-fluoro-1-nitro-2-(2,2,2-trifluoroethoxy)benzene 2,4-difluoro-1-nitrobenzene (10 g, 62.9 mmol), cesium carbonate (20.5 g, 62.9 mmol) were suspended in 100 mL THF, trifluoro ethanol (6.29 g, 62.9 mmol) was added dropwise, and the reaction was reacted at room temperature overnight. After TLC detected the reaction was complete, the system was poured in ice-water, extracted with ethyl acetate (200 mL×3), the organic layer was combined, washed with brine, dried over anhydrous sodium sulfate, concentrated under reduced pressure, and the filtrate was separated on column chromatography (eluant:petroleum ether/ethyl acetate (v/v)=20:1), to afford 15 g of a yellow solid. Yield was 99.8%.

Step 2 Synthesis of 4-fluoro-2-(2,2,2-trifluoroethoxy)aniline 4-fluoro-1-nitro-2-(2,2,2-trifluoroethoxy)benzene (15 g, 62.76 mmol) was dissolved in the mixed solvent of ethanol and water (50 mL, v/v=4/1), reduced iron powder (21 g, 0.38 mol) and ammonium chloride (10 g, 0.19 mol) were added, and the reaction was heated at reflux for 2.5 hrs. After cooling to room temperature, it was filtered on Celite, the filtrate was concentrated under reduced pressure, and the filtrate was separated on column chromatography (eluant: petroleum ether/ethyl acetate (v/v)=20:1), and afforded product 11.8 g of a yellow oil. Yield was 85.9%. LC-MS (APCI): m/z=210.1 (M+1).

Step 3 Synthesis of 4-fluoro-5-nitro-2-(2,2,2-trifluoroethoxy)aniline

At 0° C., 4-fluoro-2-(2,2,2-trifluoroethoxy)aniline (3.00 g. 14.35 mmol) was dissolved in 10 ml concentrated sulfuric acid, potassium nitrate (1.70 g, 17.22 mmol) was added in the system in portions, and warmed to 5° C. naturally with stirring. After LC-MS detected the reaction was complete, the reaction was worked up, and the system was slowly poured in 100 ml ice-water, extracted several time by adding ethyl acetate, the organic phase was dried over anhydrous sodium sulfate, and concentrated under reduced pressure to afford 3.2 g of a brown solid. LC-MS(APCI): m/z=255.0M+1).

Step 4 Synthesis of Intermediate Compound N-(2-(dimethylamino)ethyl)-$N^1$-methyl-2-nitro-5-(2,2,2-trifluoroethoxy)benzene-1,4-diamine At room temperature, potassium carbonate (3.5 g, 25.2 mmol) was added into 4-fluoro-5-nitro-2-(2,2,2-trifluoroethoxy)aniline (3.2 g, 12.6 mmol) and N,N,N'-trimethylethylenediamine (1.90 g, 18.9 mmol) in acetonitrile (20 mL). The reaction was reacted at 80° C. for 3 hrs. After cooling to room temperature, it was filtered on Celite, the filtrate was concentrated under reduced pressure, and the filtrate was separated on column chromatography (eluant:dichloromethane/methanol (v/v)=10:1), to afford 3.2 g of a red-brown oil, yield was 75.6%, LC-MS(APCI): m/z=337.1M+1).

Synthesis of Intermediate Compound $N^2$-(2-(dimethylamino)ethyl)-6-methoxy-$N^2$-methyl-3-nitrobenzene-2,5-diamine

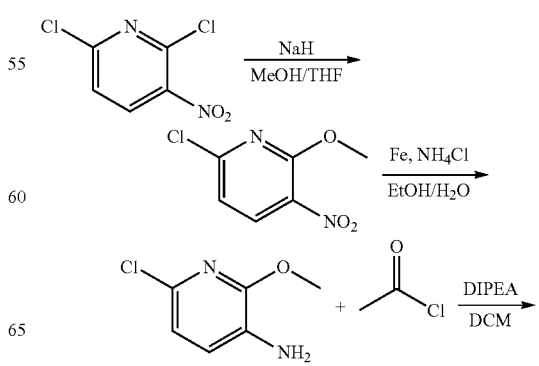

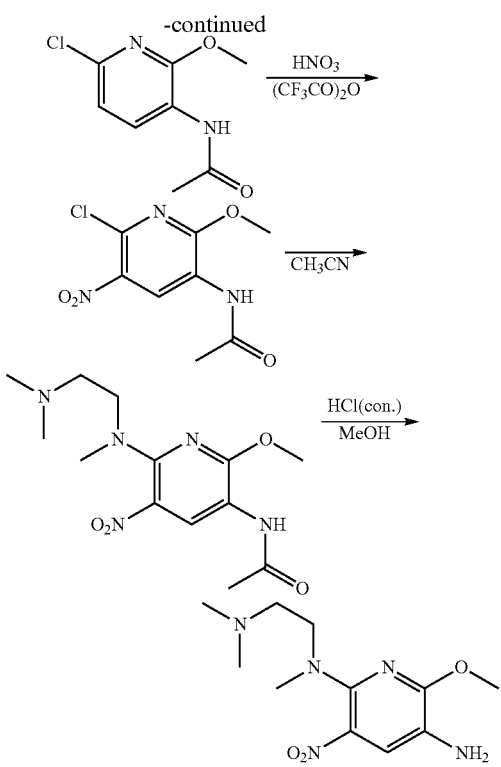

Step 1 Synthesis of
6-chloro-2-methoxy-3-nitropyridine

In an ice bath, sodium hydride (1.0 g, 25 mmol, 60%) was added into 2,6-dichloro-3-nitropyridine (4.80 g, 25 mmol) and anhydrous methanol (800 mg) in anhydrous tetrahydrofuran (60 mL) in portions, and the reaction was slowly warmed to room temperature and reacted overnight. After TLC detected the reaction was complete, tetrahydrofuran was removed by concentrating under reduced pressure, the system was poured in ice-water, extracted with ethyl acetate (100 mL×3), the organic layer was combined, washed with brine, dried over anhydrous sodium sulfate, concentrated under reduced pressure, and the filtrate was separated on column chromatography (eluant:petroleum ether/ethyl acetate (v/v)=30:1), to afford 3 g of a yellow solid. Yield was 64%.

Step 2 Synthesis of
6-chloro-2-methoxypyridine-3-amine 6-chloro-2-methoxy-3-nitropyridine (1.00 g, 5.32 mmol) was dissolved in the mixed solvent of ethanol and water (40 mL, v/v=4/1), reduced iron powder (1.89 g, 31.92 mol) and ammonium chloride (846 mg, 15.96 mol) were added, the reaction mixture was heated to reflux for 1.5 hrs. After cooling to room temperature, it was filtered on Celite, the filtrate was concentrated under reduced pressure, and the filtrate was separated on column chromatography (eluant: petroleum ether/ethyl acetate (v/v)=10:1), to afford 0.8 g of a yellow solid. Yield was 94.6%. LC-MS(APCI): m/z=159.0 (M+1).

Step 3 synthesis of
N-(6-chloro-2-methoxypyridine-3-yl)acetamide

In an ice bath, acetyl chloride (397 mg, 5.06 mmol) in anhydrous dichloromethane (10 mL) was added dropwise to 6-chloro-2-methoxypyridine-3-amine (800 mg, 5.06 mmol) and DIPEA (981 mg, 7.59 mmol) in anhydrous dichloromethane (30 mL), and the reaction was stirred for 1.5 hrs. The reaction mixture was washed with 50 ml water, 50 mL 1N diluted hydrochloric acid and 80 ml brine sequentially, dried over anhydrous sodium sulfate, filtered, evaporated to dry under reduced pressure, to afford 1.0 g of a pale yellow solid. Yield was 98.8%, LC-MS(APCI): m/z=201.1 (M+1).

Step 4: synthesis of N-(6-chloro-2-methoxy-5-nitro-pyridine-3-yl)acetamide

To a 100 ml one-neck flask were added N-(6-chloro-2-methoxypyridine-3-yl)acetamide (1.10 g, 5.50 mmol) and 10 ml trifluoroacetic anhydride, which was cooled to −10° C. in an ice salt bath, fuming nitric acid (0.1 ml) was added dropwise while the temperature was controlled to below −5° C. After the addition was complete, the reaction was continued in the ice salt bath for 2 hours. The reaction mixture was slowly added to crushed ice, solid was precipitated, and filtered. The obtained crude product was oven dried at 60° C., purified by slurrying with ethyl acetate, to afford 1.0 g of a yellow solid. Yield was 73.9%, LC-MS(APCI): m/z=246.1 (M+1). $^1$H NMR (400 MHz, DMSO-d6): δ 9.92 (s, 1H), 9.18 (s, 1H), 4.07 (s, 3H), 2.17 (s, 3H).

Step 5 Synthesis of N-(6-((2-(dimethylamino)ethyl)(methyl)thyl)amino)-2-methoxy-5-nitropyridine-3-yl)acetamide A solution of N-(6-chloro-2-methoxy-5-nitropyridine-3-yl)acetamide (1.00 g, 4.10 mmol) and N,N,N'-trimethylethylenediamine (630 mg, 6.20 mmol) in acetonitrile (30 mL) was reacted at 80° C. for 3 hrs. After cooling to room temperature, it was filtered on Celite, the filtrate was concentrated under reduced pressure, and the filtrate was separated on column chromatography (eluant:dichloromethane/methanol (v/v)=10:1), to afford 1.2 g of a red-brown oil, yield was 93.8%, LC-MS(APCI): m/z=312.2 (M+1).

Step 6 Synthesis of Intermediate Compound $N^2$-(2-(dimethylamino)ethyl)-6-methoxy-$N^2$-methyl-3-nitrobenzene-2,5-diamine Concentrated hydrochloric acid (0.6 mL) was added into N-(6-((2-(dimethylamino)ethyl)(methyl)amino)-2-methoxy-5-nitropyridine-3-yl)acetamide (1.2 g, 3.85 mmol) in methanol (30 mL), and reacted at 60° C. overnight. The reaction mixture was evaporated to dry under reduced pressure, 200 ml dichloromethane and 160 ml saturated solution of sodium bicarbonate were added, stirred until bubble disappeared and separated the organic layer, dried over anhydrous sodium sulfate, filtered, and concentrated under reduced pressure. The filtrate was separated on column chromatography (eluant:dichloromethane /methanol (v/v)=10:1), to afford 320 mg of a red-brown oil, yield was 30.8%, LC-MS(APCI): 270.1 (M+1).

149

Synthesis of Example Compounds

Example 1 Preparation of N-(2-((2-(dimethylamino)ethyl)(methyl)amino)-5-((5-chloro-4-(4-fluoro-1-isopropyl-2-m ethyl-1H-benzo[d]imidazole-6-yl)pyrimidin-2-yl)amino)-4-methoxyphenyl)acrylamide

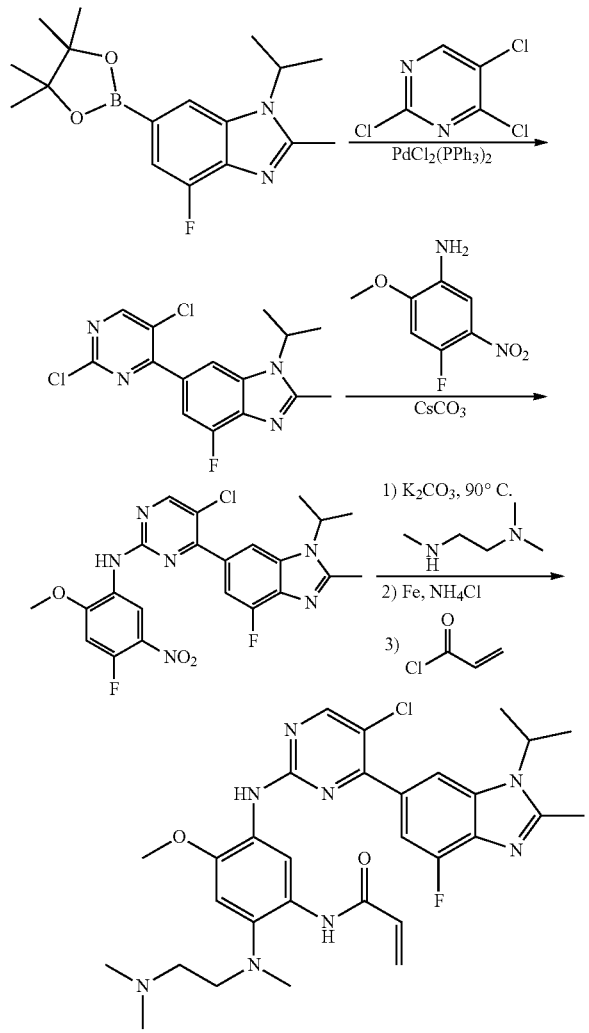

Step 1 Synthesis of Compound 6-(2,5-dichloropyrimidin-4-yl)-4-fluoro-1-isopropyl-2-methyl-1H-benzo[d]imidazole The compound 2,4,5-trichloropyrimidine (206 mg, 1.12 mmol), compound 4-fluoro-1-isopropyl-2-methyl-6-(4,4,5,5-tetramethyl-1,3,2-dioxaborolan-2-yl)-1H-benzo[d]imidazole (357 mg, 1.12 mmol), Pd(PPh$_3$)$_2$Cl$_2$ (43 mg, 0.06 mmol) were added into an one-neck reaction flask, flushed with nitrogen gas for three times, and under nitrogen protection were added DMF (5 mL) and aqueous sodium carbonate solution (2M, 2 mL), and the reaction was stirred at 60° C. for 2 hours. The heating was removed, and after cooled to room temperature, the reaction was poured in 50 mL water, extracted with ethyl acetate (5 mL*2), the organic phase was combined, the solvent was evaporated to dry under reduced pressure, and purified using preparative TLC (PE/EA, V/V, 1.5/1), to afford a white solid, 118 mg in total, yield was 31%.

150

Step 2 Synthesis of Compound 5-chloro-4-(4-fluoro-1-isopropyl-2-methyl-1H-benzo[d]imidazole-6-yl)-N-(4-fluoro-2-meth oxy-5-nitrophenyl)pyrimidin-2-amine Under nitrogen protection, the compound 6-(2,5-dichloropyrimidin-4-yl)-4-fluoro-1-isopropyl-2-methyl-1H-benzo[d]imidazole (118 mg, 0.35 mmol), 4-fluoro-2-methoxy-5-nitroaniline (78 mg, 0.42 mmol), Xant-phos (20 mg, 0.035 mmol), Pd$_2$(dba)$_3$ (16 mg, 0.017 mmol) and cesium carbonate (283 mg, 0.87 mmol) was added into one-neck reaction flask, then anhydrous dioxane (2 mL) was added, flushed with nitrogen gas for three times, and the reaction was stirred at 90° C. overnight. The solvent was evaporated to dry under reduced pressure, and purified with preparative TLC (PE/EA, V/V, 1/1) to afford a grey solid, 30 mg in total.

Step 3 Synthesis of Compound N-(2-((2-(dimethylamino)ethyl)(methyl)amino)-5-((5-chloro-4-(4-fluoro-1-isopropyl-2-meth yl-1H-benzo[d]imidazole-6-yl)pyrimidin-2-yl)amino)-4-methoxyphenyl)acrylamide The compound 5-chloro-4-(4-fluoro-1-isopropyl-2-methyl-1H-benzo[d]imidazole-6-yl)-N-(4-fluoro-2-meth oxy-5-nitrophenyl)pyrimidin-2-amine (30 mg, 0.061 mmol) was evenly dispersed in acetonitrile (5 mL), trimethylethylenediamine (13 mg, 0.123 mmol), potassium carbonate (17 mg, 0.123 mmol) were added, heated to 90° C. and refluxed for 1.5 hours. After cooling to room temperature, the reaction mixture was filtered to remove the insoluble solid, the filtrate was evaporated to dry to afford a red oil. The red oil was dissolved in ethanol-water (4 mL+1 mL), reduced iron powder (42 mg) and ammonium chloride (13 mg) were added, the reaction was heated at 90° C. under reflux for 5 hours. The reaction was cooled to room temperature, filtered to remove insoluble solid, the filtrate was evaporated to dry, and the obtained oil was dissolved in 10 mL dichloromethane (DCM), 2 mL saturated solution of sodium bicarbonate was added, and cooled in an ice bath. 1M acryloyl chloride (0.12 mL) was added dropwise into the above two-phase system, and reacted in an ice bath for 30 minutes. The layers were separated, the organic phase was evaporated to dry, and purified with preparative TLC (DCM/MeOH, V/V, 30/1), to afford a grey-green solid, 10 mg in total. LC-MS(APCI): m/z=596.3 (M+1).

Example 2 Preparation of N-(2-((2-(dimethylamino)ethyl)(methyl)amino)-5-((5-methyl-4-(4-fluoro-1-isopropyl-2-methyl-1H-benzo[d]imidazole-6-yl)pyrimidin-2-yl)amino)-4-methoxyphenyl)acrylamide

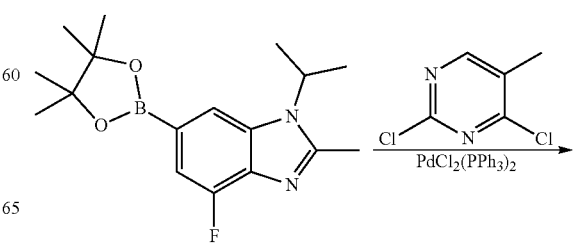

-continued

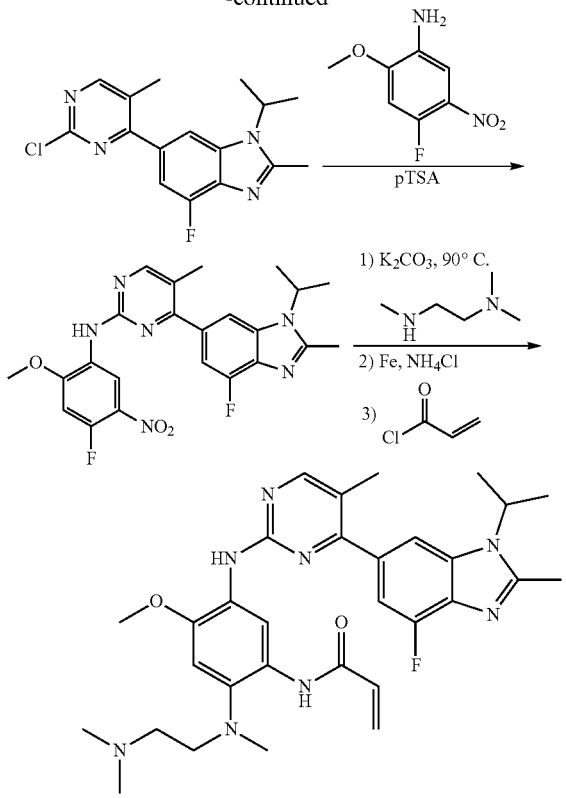

Step 1 Synthesis of Compound 6-(2-chloro-5-methylpyrimidin-4-yl)-4-fluoro-1-isopropyl-2-methyl-1H-benzo[d]imidazole The compound 2,4-dichloro-5-methylpyrimidine (200 mg, 1.23 mmol), compound 4-fluoro-1-isopropyl-2-methyl-6-(4,4,5,5-tetramethyl-1,3,2-dioxaborolan-2-yl)-1H-benzo[d]imidazole (391 mg, 1.23 mmol), Pd(PPh$_3$)$_2$Cl$_2$ (52 mg, 0.074 mmol) were added into one-neck reaction flask, flushed with nitrogen gas for three times, and under nitrogen protection were added DMF (5 mL) and aqueous solution of sodium carbonate (2 M, 2.5 mL), and the reaction was stirred at 80° C. for 3.5 hours. The heating was removed. After cooling to room temperature, the reaction mixture was poured in 50 mL water, extracted with ethyl acetate (5 mL*2), the organic phase was combined, the solvent was evaporated to dry under reduced pressure, and purified with preparative TLC (PE/EA, V/V, 2/1), to afford a white solid, 210 mg in total, yield was 53.6%.

Step 2 Synthesis of Compound 4-(4-fluoro-1-isopropyl-2-methyl-1H-benzo[d]imidazole-6-yl)-N-(4-fluoro-2-methoxy-5-nitrophenyl)-5-methylpyrimidin-2-amine Under nitrogen protection, the compound 6-(2-chloro-5-methylpyrimidin-4-yl)-4-fluoro-1-isopropyl-2-methyl-1H-benzo[d]imidazole (210 mg, 0.66 mmol), 4-fluoro-2-methoxy-5-nitroaniline (147 mg, 0.79 mmol), pTSA (454 mg, 2.64 mmol) were added into one-neck reaction flask, then anhydrous dioxane (2 mL) was added, flushed with nitrogen gas for three times, the reaction was stirred at 100° C. for 24 hours. The solvent was evaporated to dry under reduced pressure, and purified with preparative TLC (PE/EA, V/V, 1/1), to afford a grey solid, 162 mg in total.

Step 3 Synthesis of Compound N-(2-(((2-(dimethylamino)ethyl)(methyl)amino)-5-((5-methyl-4-(4-fluoro-1-isopropyl-2-methyl-1H-benzo[d]imidazole-6-yl)pyrimidin-2-yl)amino)-4-methoxyphenyl)acrylamide The compound 4-(4-fluoro-1-isopropyl-2-methyl-1H-benzo[d]imidazole-6-yl)-N-(4-fluoro-2-methoxy-5-nitrophenyl)-5-methylpyrimidin-2-amine (149 mg, 0.32 mmol) was evenly dispersed in acetonitrile (5 mL), trimethylethylenediamine (39 mg, 0.38 mmol), potassium carbonate (88 mg, 0.64 mmol) were added, the reaction was heated to 90° C. under reflux for 2 hours. After cooling the reaction to room temperature, the reaction was filtered to remove the insoluble solid, the filtrate was evaporated to dry to afford a red oil. The red oil was dissolved in ethanol-water (4 mL+1 mL), reduced iron powder (106 mg) and ammonium chloride (34 mg) were added, and the reaction was refluxed at 90° C. for 5 hours. After cooling the reaction to room temperature, the reaction was filtered to remove the insoluble solid, the filtrate was evaporated to dry, the obtained oil was dissolved in 10 mL DCM, 5 mL saturated solution of sodium bicarbonate was added, and cooled in an ice bath. 0.15M acryloyl chloride (3 mL) was added dropwise into the above two-phase system, and reacted in an ice bath for 30 minutes. The layers were separated, the organic phase was evaporated to dry, and purified with preparative TLC (DCM/MeOH, V/V, 20/1) to afford a white solid, 30 mg in total. $^1$H NMR (400 MHz, CDCl$_3$) δ 9.56 (s, 1H), 9.49 (s, 1H), 8.40 (s, 1H), 7.64-7.50 (m, 2H), 7.40-7.27 (m, 2H), 6.91 (s, 1H), 6.69 (s, 1H), 6.43 (d, J=16.8 Hz, 1H), 5.69 (d, J=10.4 Hz, 1H), 4.71 (dt, J=13.8, 6.9 Hz, 1H), 3.85 (s, 3H), 3.13 (s, 2H), 2.82 (s, 2H), 2.68 (s, 3H), 2.66 (s, 3H), 2.58 (s, 6H), 2.29 (s, 3H), 1.63 (d, J=6.9 Hz, 6H).

Example 3 Preparation of N-(2-((2-(dimethylamino)ethyl)(methyl)amino)-5-((5-methoxy-4-(4-fluoro-1-isopropyl-2-methyl-1H-benzo[d]imidazole-6-yl)pyrimidin-2-yl)amino)-4-methoxyphenyl)acrylamide

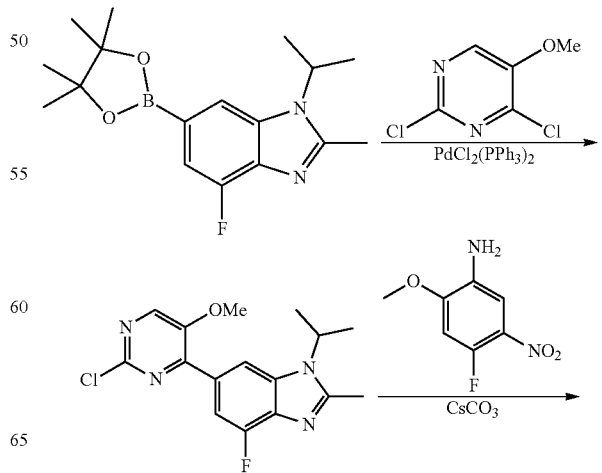

-continued

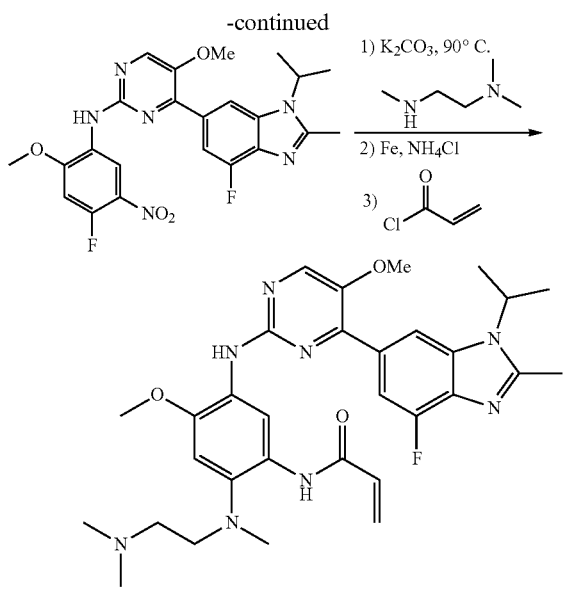

Step 1 Synthesis of Compound 6-(2-chloro-5-methoxypyrimidin-4-yl)-4-fluoro-1-isopropyl-2-methyl-1H-benzo[d]imidazole The compound 2,4-dichloro-5-methoxypyrimidine (192 mg, 1.07 mmol), compound 4-fluoro-1-isopropyl-2-methyl-6-(4,4,5,5-tetramethyl-1,3,2-dioxaborolan-2-yl)-1H-benzo[d]imidazole (310 mg, 0.97 mmol), Pd(PPh$_3$)$_2$Cl$_2$ (34 mg, 0.05 mmol) were added into one-neck reaction flask, flushed with nitrogen gas for three times, and under nitrogen protection were added DMF (5 mL) and aqueous solution of sodium carbonate (2 M, 2 mL), and the reaction was stirred at 60° C. for 3 hours. The heating was removed, and after cooling to room temperature, the reaction mixture was poured in 50 mL water, extracted with ethyl acetate (5 mL*2), the organic phase was combined, dried over anhydrous sodium sulfate, and the solvent was evaporated to dry under reduced pressure to afford 220 mg of a crude.

Step 2 Synthesis of Compound 4-(4-fluoro-1-isopropyl-2-methyl-1H-benzo[d]imidazole-6-yl)-N-(4-fluoro-2-methoxy-5-nitrophenyl)-5-methoxypyrimidin-2-amine Under nitrogen protection, the compound 6-(2-chloro-5-methoxypyrimidin-4-yl)-4-fluoro-1-isopropyl-2-methyl-1H-benzo[d]imidazole (220 mg, 0.79 mmol), 4-fluoro-2-methoxy-5-nitroaniline (145 mg, 0.79 mmol), Xant-phos (40 mg, 0.066 mmol), Pd$_2$(dba)$_3$ (26 mg, 0.031 mmol) and cesium carbonate (537 mg, 1.64 mmol) were added into one-neck reaction flask, then anhydrous dioxane (10 mL) was added, flushed with nitrogen gas for three times, and the reaction was heated at 90° C. and stirred overnight. The reaction was filtered to remove the insoluble solid, the filtrate was combined and the solvent was evaporated to dry under reduced pressure, the obtained solid was added DCM-PE (V/V, 1/4) and refluxed for 10 min. The reaction was cooled down naturally, filtered to collect solid and afforded a grey solid, 257 mg in total, yield was 67%.

Step 3 Synthesis of Compound N-(2-((2-(dimethylamino)ethyl)(methyl)amino)-5-((5-methoxy-4-(4-fluoro-1-isopropyl-2-methyl-1H-benzo[d]imidazole-6-yl)pyrimidin-2-yl)amino)-4-methoxyphenyl)acrylamide The compound 4-(4-fluoro-1-isopropyl-2-methyl-1H-benzo[d]imidazole-6-yl)-N-(4-fluoro-2-methoxy-5-nitrophenyl)-5-methoxypyrimidin-2-amine (257 mg, 0.53 mmol) was evenly dispersed in acetonitrile (5 mL), trimethylethylenediamine (65 mg, 0.64 mmol), potassium carbonate (147 mg, 1.06 mmol) were added, and the reaction was heated to reflux at 90° C. for 1.5 hours. After cooling to room temperature, the reaction was filtered to remove the insoluble solid, the filtrate was evaporated to dry to afford a red oil. The red oil was dissolved in ethanol-water (4 mL+1 mL), reduced iron powder (178 mg) and ammonium chloride (57 mg) were added, and the reaction was heated to reflux at 90° C. for 4.5 hours. After cooling the reaction to room temperature, the reaction was filtered to remove the insoluble solid, the filtrate was evaporated to dry, the obtained oil was dissolved in 10 mL DCM, 2 mL saturated solution of sodium bicarbonate was added, and cooled in an ice bath. 1M acryloyl chloride (1 mL) was added dropwise into the above two-phase system, and was reacted in an ice bath for 30 minutes. The layers were separated, the organic phase was evaporated to dry, and purified with preparative TLC (DCM/MeOH, V/V, 30/1), to afford a grey white solid, 80 mg in total. $^1$H NMR (400 MHz, CDCl$_3$) (δ/ppm) 9.50 (s, 1H), 9.40 (s, 1H), 8.32 (s, 1H), 8.16 (s, 1H), 7.85 (d, J=11.9 Hz, 1H), 7.54 (s, 1H), 6.68 (s, 1H), 6.44 (d, J=16.8 Hz, 1H), 5.82-5.63 (m, 1H), 4.70 (dt, J=13.8, 6.9 Hz, 1H), 3.88 (s, 3H), 3.87 (s, 3H), 3.21 (t, J=5.5 Hz, 2H), 2.95 (t, J=27.9 Hz, 2H), 2.69 (s, 3H), 2.67 (d, J=4.3 Hz, 3H), 2.65 (s, 3H), 2.16 (d, J=0.5 Hz, 3H), 1.65 (d, J=6.9 Hz, 6H).

Example 4 Preparation of N-(2-((2-(dimethylamino)ethyl)(methyl)amino)-5-((5-trifluoromethyl-4-(4-fluoro-1-isopropyl-2-methyl-1H-benzo[d]imidazole-6-yl)pyrimidin-2-yl)amino)-4-methoxyphenyl)acrylamide

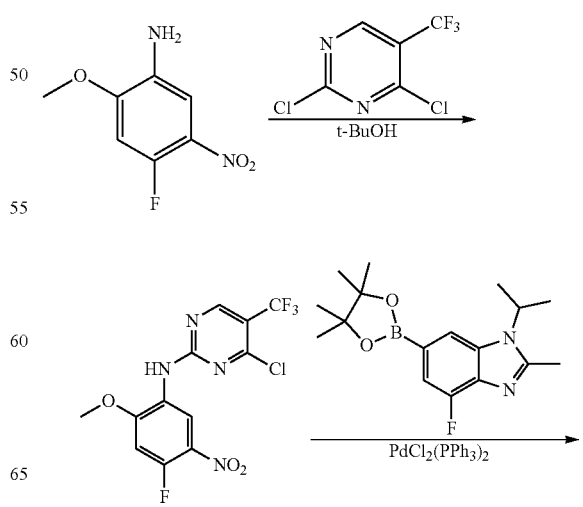

-continued

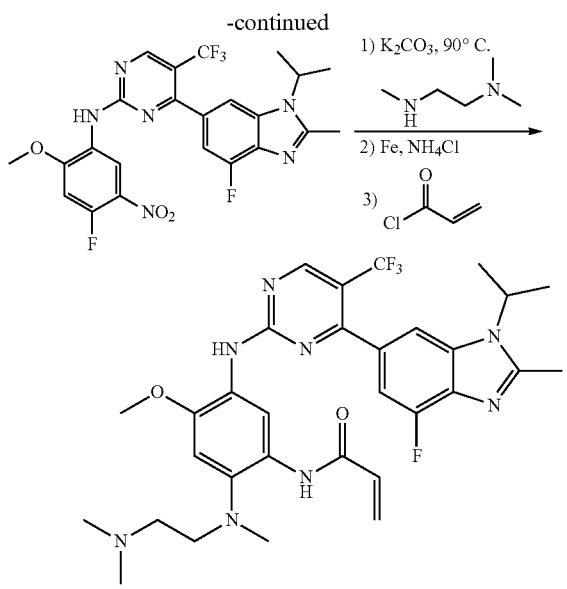

Step 1 Synthesis of Compound 4-chloro-N-(4-fluoro-2-methoxy-5-nitrophenyl)-5-(trifluoromethyl)pyrimidin-2-amine The compound 2,4-dichloro-5-trifluoromethylpyrimidine (700 mg, 3.23 mmol) was added 15 mL anhydrous tert-butyl alcohol and dissolved by stirring, 4-fluoro-2-methoxy-5-nitroaniline (600 mg, 3.23 mmol) and diisopropylethylamine (417 mg, 3.23 mmol) were added, and then heated to 60° C. overnight. After cooling the reaction to room temperature, the solid (244 mg) was collected by filtering.

Step 2 Synthesis of Compound 4-(4-fluoro-1-isopropyl-2-methyl-1H-benzo[d]imidazole-6-yl)-N-(4-fluoro-2-methoxy-5-nitrophenyl)-5-(trifluoromethyl)pyrimidin-2-amine The compound 4-chloro-N-(4-fluoro-2-methoxy-5-nitrophenyl)-5-(trifluoromethyl)pyrimidin-2-amine (244 mg, 0.66 mmol), compound 4-fluoro-1-isopropyl-2-methyl-6-(4,4,5,5-tetramethyl-1,3,2-dioxaborolan-2-yl)-1H-benzo[d]imidazole (233 mg, 0.73 mmol), Pd(PPh$_3$)$_2$Cl$_2$ (28 mg, 0.04 mmol) were added into one-neck reaction flask, flushed with nitrogen gas for three times, and under nitrogen protection were added DMF (6 mL) and aqueous solution of sodium carbonate (2 M, 1.4 mL), and the reaction was stirred at 60° C. for 2 hours. The heating was removed, and after cooling to room temperature, the reaction mixture was poured in 50 mL water, extracted with ethyl acetate (5 mL*2), the organic phase was combined, dried over anhydrous sodium sulfate, and the solvent was evaporated to dry under reduced pressure to afford a crude, refluxed with PE/EA (petroleum ether/ethyl acetate: 3 mL/3 mL) while slurrying to afford purified product of 107 mg.

Step 3 Synthesis of Compound N-(2-((2-(dimethylamino)ethyl)(methyl)amino)-5-((5-trifluoromethyl-4-(4-fluoro-1-isopropyl-2-methyl-1H-benzo[d]imidazole-6-yl)pyrimidin-2-yl)amino)-4-methoxyphenyl)acrylamide The compound 4-(4-fluoro-1-isopropyl-2-methyl-1H-benzo[d]imidazol-6-yl)-N-(4-fluoro-2-methoxy-5-nitrophenyl)-5-(trifluoromethyl)pyrimidin-2-amine (107 mg) was evenly dispersed in acetonitrile (5 mL), trimethylethylenediamine (25 mg, 0.25 mmol), potassium carbonate (57 mg, 0.41 mmol) were added, and the reaction was refluxed at 90° C. for 0.5 hours. After cooling to room temperature, the reaction was filtered to remove the insoluble solid, the filtrate was evaporated to dry to afford a red oil. The red oil was dissolved in ethanol-water (4 mL+1 mL), reduced iron powder (50 mg) and ammonium chloride (17 mg) were added, and the reaction was refluxed at 90° C. for 3 hours. After cooling the reaction to room temperature, the reaction was filtered to remove the insoluble solid, the filtrate was evaporated to dry, and the obtained oil was dissolved in 10 mL DCM, 2 mL saturated solution of sodium bicarbonate was added, and cooled in an ice bath. IM acryloyl chloride (0.4 mL) was added dropwise into the above two-phase system, and reacted in an ice bath for 30 minutes. The layers were separated, the organic phase was evaporated to dry, and purified with preparative TLC (DCM/MeOH, V/V, 30/1), to afford a grey-white solid (40 mg). $^1$H NMR (400 MHz, CDCl$_3$) (δ/ppm) 9.62 (s, 1H), 9.50 (s, 1H), 8.63 (s, 1H), 8.42 (d, J=1.2 Hz, 1H), 8.21 (d, J=11.8 Hz, 1H), 7.60 (s, 1H), 6.91 (s, 1H), 6.77 (s, 1H), 6.48 (dd, J=16.9, 1.6 Hz, 1H), 6.40-5.72 (m, 1H), 5.71 (dd, J=10.2, 1.6 Hz, 1H), 4.72 (dt, J=14.0, 7.0 Hz, 1H), 3.89 (s, 3H), 3.19 (s, 2H), 2.89 (s, 2H), 2.73 (s, 3H), 2.65 (s, 3H), 2.63 (s, 6H), 1.65 (d, J=7.0 Hz, 6H).

Example 5 Preparation of N-(2-((2-(dimethylamino)ethyl)(methyl)amino)-5-((4-(5-fluoro-1,1-dimethyl-2,3-dihydro-1H-benzo[d]imidazole[1,2-a]pyrrol-6-yl)pyrimidin-2-yl)amino)-4-methoxyphenyl)acrylamide

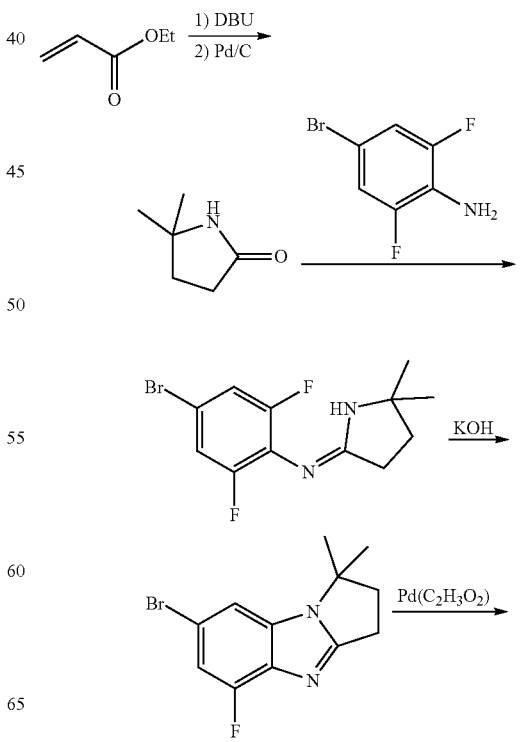

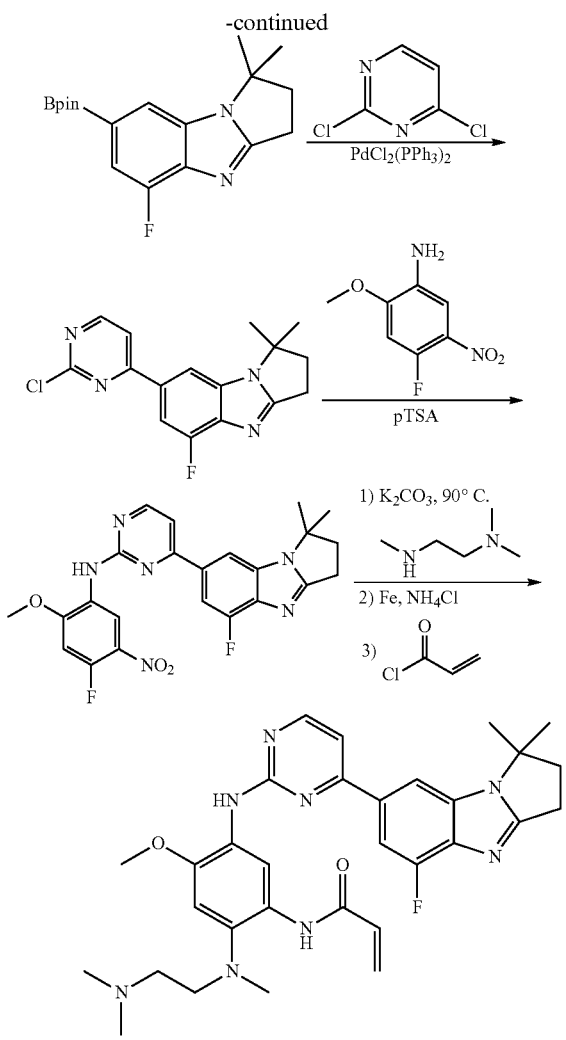

Step 1 Synthesis of Compound 5,5-dimethylpyrrolidin-2-one

Ethyl acrylate (1.24 g, 12.4 mmol), 2-nitropropane (1.10 g, 12.4 mmol) and DBU (1,8-diazabicycloundec-7-ene, 189 mg, 1.24 mmol) were dissolved in 25 mL anhydrous tetrahydrofuran, and the reaction was heated to reflux overnight. After cooling the reaction to room temperature, 4N hydrochloric acid (20 mL), EA (20 mL) were added, the layers were separated, and the organic phase dried over anhydrous sodium sulfate. It was filtered by sucking, and the filtrate was evaporated to dry under reduced pressure to afford a yellow-green oil. The above oil was dissolved in 30 mL anhydrous tetrahydrofuran, 5% Pd/C (234 mg) was added, hydrogen gas (4 atm) was introduced and reacted at room temperature for 72 h. The Pd/C was removed by sucking filtration, and the filtrate was evaporated to dry under reduced pressure to afford a crude (1.4 g).

Step 2 Synthesis of Compound (Z)—N-(4-bromo-2,6-difluorophenyl)-5,5-dimethylpyrrolidin-2-imine The compound 5,5-dimethylpyrrolidin-2-one was dissolved in 30 mL toluene, 4-bromo-2,6-difluoroaniline (2.8 g, 12.4 mmol), triethylamine (1.3 g, 12.4 mmol) and phosphorus oxychloride (1.9 g, 12.4 mmol) were added, and the reaction was heated to reflux at 110° C. for 5 hours. The reaction was cooled in an ice bath, 10 mL EA, 20 mL saturated solution of sodium bicarbonate were added, stirred for 10 minutes, and the layers were separated. The organic phase was evaporated to dry and purified on column chromatography (PE/EA, v/v, 2/1), to afford compound 53 (2.27 g).

Step 3 Synthesis of Compound 7-bromo-5-fluoro-1,1-dimethyl-2,3-dihydro-1H-benzo[d]pyrrolo[1,2-a]imidazole The compound (Z)—N-(4-bromo-2,6-difluorophenyl)-5,5-dimethylpyrrolidin-2-imine was dissolved in 20 mL dimethyl sulfoxide, potassium hydroxide (0.84 g, 14.98 mmol) was added in one portion, and the reaction was heated to 100° C. under nitrogen protection and stirred overnight. The reaction was cooled to room temperature, poured in 200 mL water, extracted with EA (10 mL*2), the organic phase was evaporated to dry and purified on column chromatography (PE/EA, v/v, 3/1), to afford 689 mg product. $^1$H NMR (400 MHz, CDCl$_3$) δ 7.33 (s, 1H), 7.09 (d, J=9.8 Hz, 1H), 3.13-3.03 (m, 2H), 2.54 (t, J=7.6 Hz, 2H), 1.63 (s, 6H).

Step 4 Synthesis of Compound 5-fluoro-1,1-dimethyl-7-(4,4,5,5-tetramethyl-1,3,2-dioxaborolan-2-yl)-2,3-dihydro-1H-benzo[d]pyrrolo[1,2-a]imidazole Under nitrogen protection the compound 7-bromo-5-fluoro-1,1-dimethyl-2,3-dihydro-1H-benzo[d]pyrrolo[1,2-a]imidazole (698 mg, 2.43 mmol), Bis(pinacolato)diboron (680 mg, 2.68 mmol), tricyclohexylphosphine (115 mg, 0.41 mmol) and potassium acetate (715 mg, 7.29 mmol) were added into 5 mL anhydrous dimethyl sulfoxide, stirred evenly, flushed with nitrogen gas for three times, palladium acetate (60 mg, 0.27 mmol) was added, flushed with nitrogen gas for three times, and the reaction was stirred at 90° C. for 45 minutes. After cooling the reaction to room temperature, it was poured in 50 mL water, extracted with EA-PE (v/v, 1/1, 10 mL*2), the organic phase was combined was evaporated to dry to afford a crude which was used in the next step directly.

Step 5 Synthesis of Compound 7-(2-chloropyrimidin-4-yl)-5-fluoro-1,1-dimethyl-2,3-dihydro-1H-benzo[d]pyrrolo[1,2-a]imidazole Under nitrogen protection, the compound 5-fluoro-1,1-dimethyl-7-(4,4,5,5-tetramethyl-1,3,2-dioxaborolan-2-yl)-2,3-dihydro-1H-benz o[d]pyrrolo[1,2-a]imidazole, 2,4-dichloropyrimidine (362 mg, 2.43 mmol), 2M aqueous solution of sodium carbonate (4.8 mL) were added into 8 mL DMF, flushed with nitrogen gas for three times, Pd(PPh$_3$)$_2$Cl$_2$ (84 mg, 0.12 mmol) was added, flushed with nitrogen gas for three times, and the reaction was heated and stirred at 60° C. for 1 hour. After cooling the reaction system to room temperature, it was poured in 50 mL water, and extracted with EA (10 mL*2). The organic phase was combined, washed with water and brine, and then dried over anhydrous sodium sulfate. It was filtered by sucking, the collected filtrate was evaporated to dry under reduced pressure to afford a crude (793 mg), which was used in the next step directly.

Step 6 Synthesis of Compound 4-(5-fluoro-1,1-dimethyl-2,3-dihydro-1H-benzo[d]pyrrolo[1,2-d]imidazol-7-yl)-N-(4-fluoro-2-methoxy-5-nitrophenyl)pyrimidin-2-amine The compound 7-(2-chloropyrimidin-4-yl)-5-fluoro-1,1-dimethyl-2,3-dihydro-1H-benzo[d]pyrrolo[1,2-a]imidazole was dissolved in anhydrous 10 mL dioxane, 4-fluoro-2-methoxy-5-nitroaniline (466 mg, 2.5 mmol), pTSA (p-toluenesulfonamide, 1.72 g, 10 mmol) were added, the reaction was heated to 100° C. and stirred overnight. Dioxane was evaporated to dry, 20 mL DCM, and 20 mL saturated solution of sodium bicarbonate were added, stirred for 10 minutes, filtered by sucking, and the layers were separated. The organic phase was evaporated to dry and purified on column chromatography (DCM/MeOH, v/v, 80/1), concentrated to obtain a solid, which was purified by refluxing with PE-EA (v/v, 1/1, 20 mL) and slurrying for 1 hour, to afford a pure product (414 mg).

Step 7 Synthesis of Compound N-(2-((2-(dimethylamino)ethyl)(methyl)amino)-5-((4-(5-fluoro-1,1-dimethyl-2,3-dihydro-1H-benzo[d]imidazole[1,2-a]pyrrol-6-yl)pyrimidin-2-yl)amino)-4-methoxyphenyl)acrylamide The compound 4-(5-fluoro-1,1-dimethyl-2,3-dihydro-1H-benzo[d]pyrrolo[1,2-d]imidazol-7-yl)-N-(4-fluoro-2-methoxy-5-nitrophenyl)pyrimidin-2-amine was evenly dispersed in acetonitrile (10 mL), trimethylethylenediamine (109 mg, 1.06 mmol), potassium carbonate (246 mg, 1.78 mmol) were added, and the reaction was heated to reflux at 90° C. for 2 hours. After cooling to room temperature, the reaction was filtered to remove the insoluble solid, the filtrate was evaporated to dry to afford a red oil. The red oil was dissolved in ethanol-water (8 mL+2 mL), reduced iron powder (199 mg) and ammonium chloride (95 mg) were added, and the reaction was heated to reflux at 100° C. for 4.5 hours. After cooling the reaction to room temperature, the reaction was filtered to remove the insoluble solid, the filtrate was evaporated to dry, the obtained oil was dissolved in 10 mL DCM, 10 mL saturated solution of sodium bicarbonate was added, and cooled in an ice bath. IM acryloyl chloride (1.7 mL) was added dropwise into the above two-phase system, and reacted in an ice bath for 30 minutes. The layers were separated, the organic phase was evaporated to dry, and purified with preparative TLC (DCM/MeOH, V/V, 20/1), to afford a grey-white solid (90 mg). $^1$H NMR (400 MHz, CDCl$_3$) (δ/ppm) 9.49 (s, 1H), 9.39 (s, 1H), 8.51 (d, J=5.3 Hz, 1H), 7.95 (d, J=1.3 Hz, 1H), 7.82-7.71 (m, 1H), 7.62 (d, J=8.0 Hz, 1H), 7.15 (d, J=5.3 Hz, 1H), 6.69 (s, 1H), 6.45 (dd, J=16.8, 1.9 Hz, 1H), 5.72 (dd, J=10.2, 1.9 Hz, 1H), 3.89 (s, 3H), 3.29 (t, J=5.4 Hz, 2H), 3.11 (t, J=7.6 Hz, 4H), 2.78 (s, 6H), 2.72 (s, 3H), 2.63-2.48 (m, 2H), 1.69 (s, 6H).

Example 6 Preparation of N-(2-((2-(dimethylamino)ethyl)(methyl)amino)-5-((4-(4-fluoro-1-isopropyl-2-methoxy-1H-benzo[d]imidazole-6-yl)pyrimidin-2-yl)amino)-4-methoxyphenyl)acrylamide

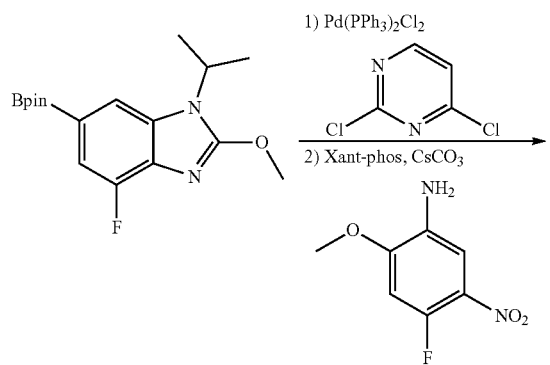

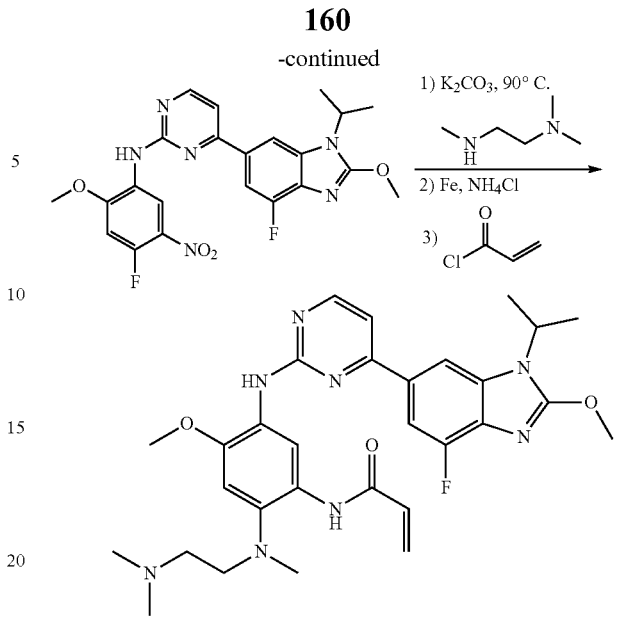

Step 1 Synthesis of Compound 4-(4-fluoro-1-isopropyl-2-methoxy-1H-benzo[d]imidazole-6-yl)-N-(4-fluoro-2-methoxy-5-nitrophenyl)pyrimidin-2-amine Under nitrogen protection, intermediate compound 4-fluoro-1-isopropyl-2-methoxy-6-(4,4,5,5-tetramethyl-1,3,2-dioxaborolan-2-yl-1H-benzo[d]imidazole, 2,4-dichloropyrimidine (478 mg, 1.43 mmol), 2M aqueous solution of sodium carbonate (2.8 mL) were added into 5 mL DMF, flushed with nitrogen gas for three times, Pd(PPh$_3$)$_2$Cl$_2$ (50 mg, 0.072 mmol) was added, flushed with nitrogen gas for three times, and then the reaction was heated to 60° C. and stirred for 35 minutes. The reaction system was cooled to room temperature, poured in 50 mL water, and extracted with EA (10 mL*2). The organic phase was combined, washed with water and brine, and then dried over anhydrous sodium sulfate. It was filtered by sucking, the filtrate was collected and evaporated to dry under reduced pressure, to afford a grey solid as a crude product, which was used in the next step directly. Under nitrogen protection, the above grey solid was dissolved in 15 mL anhydrous dioxane, 4-fluoro-2-methoxy-5-nitroaniline (266 mg, 1.43 mmol), Xant-phos (42 mg, 0.072 mmol), cesium carbonate (1.16 g, 3.58 mmol) were added, replaced with nitrogen gas for 3 times, Pd$_2$(dba)$_3$ (66 mg, 0.072 mmol) was added, replaced with nitrogen gas for 3 times, the reaction was stirred at 90° C. overnight. The reaction was filtered to remove the insoluble solid, dioxane was evaporated to dry and purified by column chromatography (DCM) to afford a pure product (293 mg).

Step 2 Synthesis of Compound N-(2-((2-(dimethylamino)ethyl)(methyl)amino)-5-((4-(4-fluoro-1-isopropyl-2-methoxy-1H-benzo[d]imidazole-6-yl)pyrimidin-2-yl)amino)-4-methoxyphenyl)acrylamide The compound 4-(4-fluoro-1-isopropyl-2-methoxy-1H-benzo[d]imidazole-6-yl)-N-(4-fluoro-2-methoxy-5-nitrophenyl)pyrimidin-2-amine (157 mg, 0.334 mmol) was evenly dispersed in acetonitrile (10 mL), trimethylethylenediamine (51 mg), potassium carbonate (69 mg) were added, and the reaction was heated to reflux at 90° C. for 2.5 hours. After cooling to room temperature, the reaction was filtered to remove the insoluble solid, the filtrate was evaporated to dry to afford a red oil. The red oil was dissolved in ethanol-water (8 mL+2 mL), reduced iron powder (112 mg) and ammonium chloride (37 mg) were added, and the reaction was heated to reflux at 100° C. overnight. After cooling the reaction to room temperature, the reaction was filtered to remove the insoluble solid, the filtrate was evaporated to dry, the obtained oil was dissolved in 5 mL DCM, 5 mL saturated solution of sodium bicarbonate was added, and cooled in an ice bath. IM acryloyl chloride (0.7 mL) was added dropwise into the above two-phase system, and reacted in an ice bath for 30 minutes. The layers were separated, the organic phase was evaporated to dry, and purified with preparative TLC (DCM/MeOH, V/V, 30/1), to afford 80 mg of a product. $^1$H NMR (400 MHz, CDCl$_3$) (δ/ppm) 9.59 (s, 1H), 8.49 (d, J=5.3 Hz, 1H), 7.90 (d, J=1.2 Hz, 1H), 7.83-7.55 (m, 2H), 7.11 (t, J=8.4 Hz, 1H), 6.73 (s, 1H), 6.45 (dd, J=16.9, 1.8 Hz, 1H), 5.71 (d, J=11.8 Hz, 1H), 4.74 (dt, J=13.7, 6.8 Hz, 1H), 4.25 (d, J=3.1 Hz, 3H), 3.91 (s, 3H), 3.25-3.08 (m, 2H), 2.72 (s, 3H), 2.59 (s, 6H), 1.56 (dd, J=6.9, 2.6 Hz, 6H).

Example 7 Preparation of N-(2-((2-(dimethylamino) ethoxy)-5-((4-(4-fluoro-1-isopropyl-2-methoxy-1H-benzo[d]imidazole-6-yl)pyrimidin-2-yl)amino)-4-methoxyphenyl)acrylamide

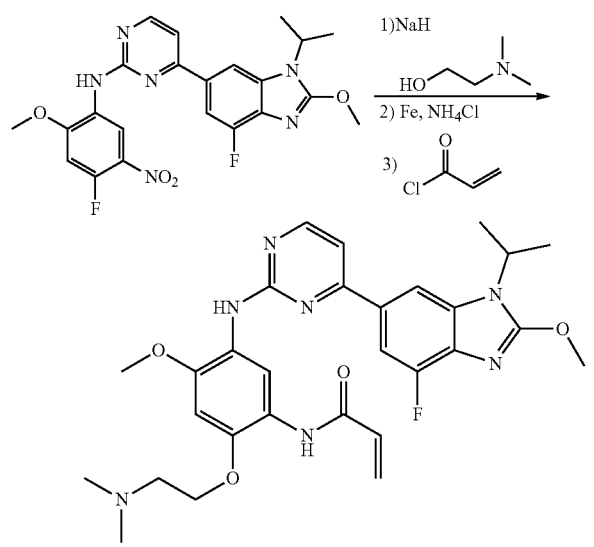

2-dimethylaminoethanol (130 mg, 1.456 mmol) was dissolved in anhydrous dioxane (2.5 mL), sodium hydride (58 mg, 1.456 mmol), 4-(4-fluoro-1-isopropyl-2-methoxy-1H-benzo[d]imidazole-6-yl)-N-(4-fluoro-2-methoxy-5-nitrophenyl)pyrimidin-2-amine (137 mg, 0.291 mmol) were added, and stirred at room temperature for 75 minutes. the reaction was quenched by adding 0.5 mL saturated solution of ammonium chloride dropwise, 50 mL water was added, extracted with EA (10 mL*2), the organic phase was combined and dried over anhydrous sodium sulfate, which was evaporated to dry to afford a red oil. The red oil was dissolved in ethanol-water (10 mL+2.5 mL), reduced iron powder (81 mg) and ammonium chloride (32 mg) were added, and the reaction was heated to reflux at 80° C. overnight. After cooling the reaction to room temperature, the reaction was filtered to remove the insoluble solid, the filtrate was evaporated to dry, the obtained oil was dissolved in 5 mL DCM, 5 mL saturated solution of sodium bicarbonate was added, and cooled in an ice bath. 1M acryloyl chloride (0.45 mL) was added dropwise into the above two-phase system, and reacted in an ice bath for 30 minutes. The layers were separated, the organic phase was evaporated to dry, and purified with preparative TLC (DCM/MeOH, V/V, 30/1), and afforded 50 mg of a product. $^1$H NMR (400 MHz, CDCl$_3$) (δ/ppm) 9.83-9.34 (m, 2H), 8.46 (t, J=7.3 Hz, 1H), 8.00-7.38 (m, 3H), 7.18-7.00 (m, 1H), 6.62 (d, J=3.7 Hz, 1H), 6.51-6.20 (m, 2H), 5.69 (dd, J=10.0, 1.7 Hz, 1H), 4.72 (tt, J=16.1, 7.9 Hz, 1H), 4.25 (s, 3H), 4.21-4.06 (m, 2H), 3.87 (s, 3H), 2.67 (m, 2H), 2.40 (s, 6H), 1.54 (d, 6H).

Example 8 Preparation of N-(2-((2-(dimethylamino) ethyl)(methyl)amino)-5-((5-bromo-4-(4-fluoro-1-isopropyl-2-methyl-1H-benzo[d]imidazole-6-yl) pyrimidin-2-yl)amino)-4-methoxyphenyl)acrylamide

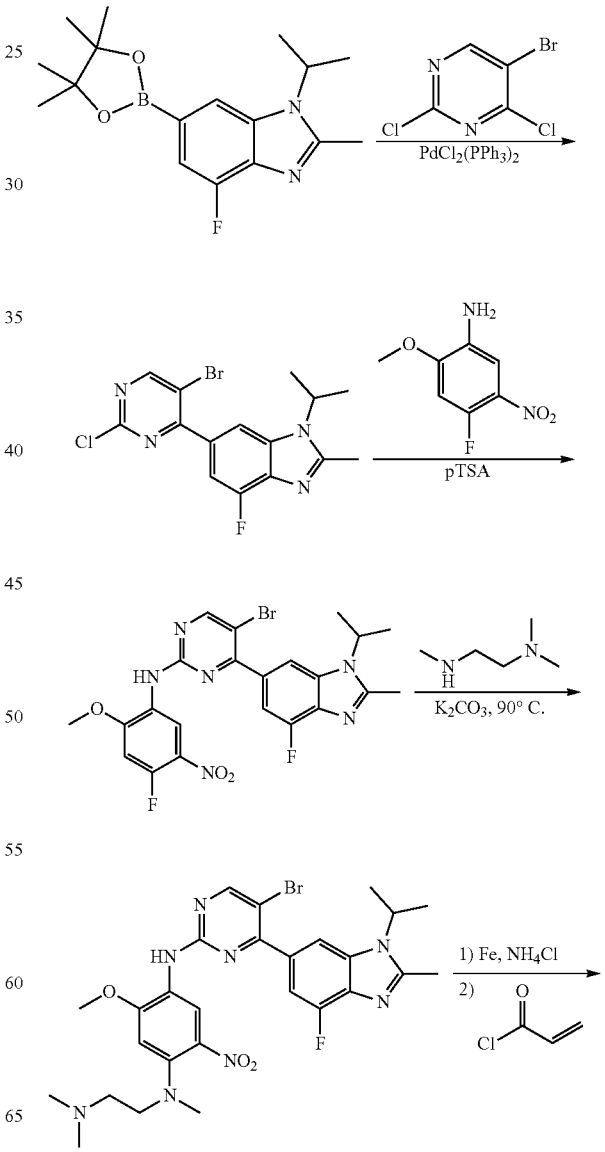

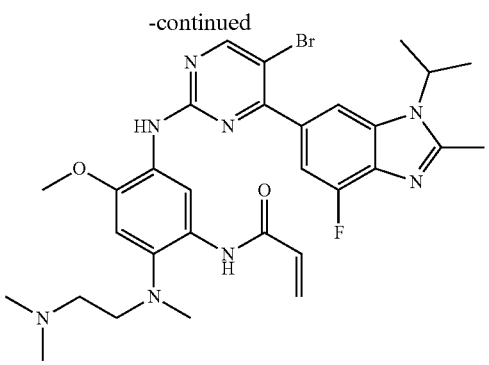

Step 1 Synthesis of Compound 6-(5-bromo-2-chloropyrimidin-4-yl)-4-fluoro-1-isopropyl-2-methyl-1H-benzo[d]imidazole The compound 5-bromo-2,4-dichloropyrimidine (200 mg, 0.88 mmol), compound 4-fluoro-1-isopropyl-2-methyl-6-(4,4,5,5-tetramethyl-1,3,2-dioxaborolan-2-yl)-1H-benzo[d]imidazole (279 mg, 0.88 mmol), Pd(PPh$_3$)$_2$Cl$_2$ (37 mg, 0.053 mmol) were placed in a two-neck flask, flushed with nitrogen gas for three times, and under nitrogen protection DMF (5 mL) and 2M Na$_2$CO$_3$ (1.8 mL, 3.51 mmol) were added, and the reaction was stirred at 60° C. for 3 hours. The heating was removed, and after cooling to room temperature, the reaction mixture was poured in 50 mL water, extracted with ethyl acetate (5 mL*2), the organic phase was combined, dried over anhydrous sodium sulfate, and the solvent was evaporated to dry under reduced pressure to afford a crude product (185 mg).

Step 2 Synthesis of Compound 5-bromo-4-(4-fluoro-1-isopropyl-2-methyl-1H-benzo[d]imidazole-6-yl)-N-(4-fluoro-2-meth oxy-5-nitrophenyl)pyrimidin-2-amine Under nitrogen protection, the compound 6-(5-bromo-2-chloropyrimidin-4-yl)-4-fluoro-1-isopropyl-2-methyl-1H-benzo[d]imidazole (185 mg), 4-fluoro-2-methoxy-5-nitroaniline (408 mg, 0.58 mmol), pTSA (332 mg, 1.93 mmol) were added into one-neck reaction flask, then anhydrous dioxane (2 mL) was added, flushed with nitrogen gas for three times, and the reaction was heated to 100° C. and stirred for 24 hours. The solvent was evaporated to dry under reduced pressure, and purified with preparative TLC (PE/EA, V/V, 1/1), to afford a grey solid (166 mg).

Step 3 Synthesis of Compound N$^1$-(5-bromo-4-(4-fluoro-1-isopropyl-2-methyl-1H-benzo[d]imidazole-6-yl)pyrimidin-2-yl)-N$^4$-(2-(dimethylamino)ethyl)-2-methoxy-N$^4$-methyl-5-nitrobenzene-1,4-diamine The compound 5-bromo-4-(4-fluoro-1-isopropyl-2-methyl-1H-benzo[d]imidazole-6-yl)-N-(4-fluoro-2-meth oxy-5-nitrophenyl)pyrimidin-2-amine (166 mg, 0.31 mmol) was evenly dispersed in acetonitrile (5 mL), trimethylethylenediamine (39 mg, 0.38 mmol), potassium carbonate (86 mg, 0.62 mmol) were added, and the reaction was heated to reflux at 90° C. for 2 hours, After cooling to room temperature, the reaction was filtered to remove the insoluble solid, and the filtrate was evaporated to dry to afford 153 mg of a red oil.

Step 4 Synthesis of Compound N-(2-((2-(dimethylamino)ethyl)(methyl)amino)-5-((5-bromo-4-(4-fluoro-1-isopropyl-2-meth yl-1H-benzo[d]imidazole-6-yl)pyrimidin-2-yl)amino)-4-methoxyphenyl)acrylamide The compound N$^1$-(5-bromo-4-(4-fluoro-1-isopropyl-2-methyl-1H-benzo[d]imidazole-6-yl)pyrimidin-2-yl)-N$^4$-(2-(dimethylamino)ethyl)-2-methoxy-N$^4$-methyl-5-nitrobenzene-1,4-diamine (153 mg) were dissolved in ethanol-water (4 mL+1 mL), reduced iron powder (106 mg) and ammonium chloride (34 mg) were added, and the reaction was heated to reflux at 90° C. for 5 hours. After cooling the reaction to room temperature, the reaction was filtered to remove the insoluble solid, the filtrate was evaporated to dry, the obtained oil was dissolved in 10 mL DCM, 5 mL saturated solution of sodium bicarbonate was added, and cooled in an ice bath. 0.15M acryloyl chloride (2.5 mL) was added dropwise into the above two-phase system, and reacted in an ice bath for 30 minutes. The layers were separated, the organic phase was evaporated to dry, and purified with preparative TLC (DCM/MeOH, V/V, 20/1), to afford a white solid (54 mg). $^1$H NMR (400 MHz, CDCl$_3$) (δ/ppm) 10.06 (s, 1H), 9.57 (s, 1H), 8.65 (s, 1H), 7.86 (d, J=1.4 Hz, 1H), 7.67 (s, 1H), 6.78 (s, 1H), 6.46 (dd, J=17.0, 1.7 Hz, 1H), 6.29 (dd, J=16.9, 10.2 Hz, 1H), 5.68 (dd, J=10.1, 1.7 Hz, 1H), 4.73 (dq, J=13.9, 6.9 Hz, 1H), 3.86 (s, 2H), 2.86 (t, J=5.6 Hz, 2H), 2.69 (s, 3H), 2.66 (s, 3H), 2.28 (s, 2H), 2.25 (s, 5H), 1.66 (d, J=6.9 Hz, 6H).

Example 9 Preparation of N-(2-((2-(dimethylamino)ethyl)(methyl)amino)-5-((5-cyclopropyl-4-(4-fluoro-1-isopropyl-2-methyl-1H-benzo[d]imidazole-6-yl)pyrimidin-2-yl)amino)-4-methoxyphenyl)acrylamide

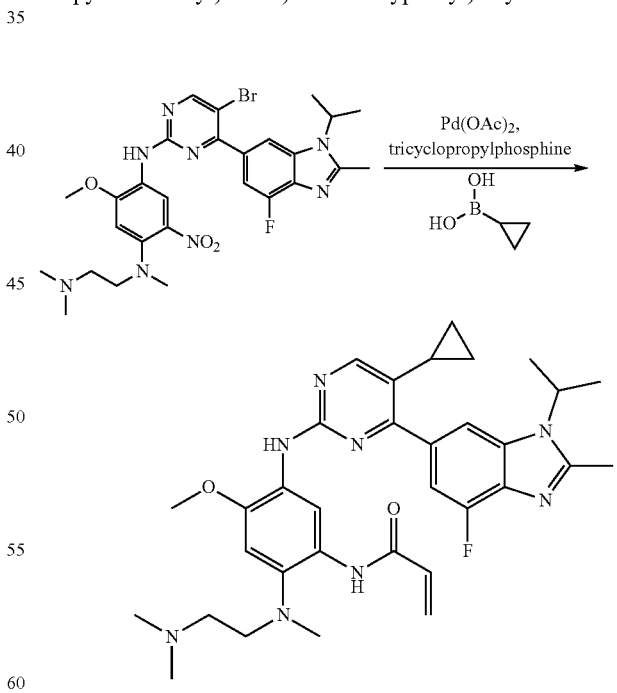

The compound N$^1$-(5-bromo-4-(4-fluoro-1-isopropyl-2-methyl-1H-benzo[d]imidazole-6-yl)pyrimidin-2-yl)-N$^4$-(2-(dimethylamino)ethyl)-2-methoxy-N$^4$-methyl-5-nitrobenzene-1,4-diamine (37 mg, 0.06 mmol), cyclopropylboronic acid (6.4 mg, 0.075 mol), tricyclopropylphosphine (6.7 mg, 0.024 mol), Pd(Oac)$_2$ (2.8 mg, 0.013 mol), K$_3$PO$_4$ (34 mg, 0.016 mol) were place in a round bottom flask, flushed with nitrogen gas for three times, under nitrogen protection was added toluene (5 mL), and stirred at 100° C. for 2 hours. After cooling to room temperature, it was filtered, the filtrate was concentrated, purified by column chromatography (DCM/MeOH, V/V, 20/1) to afford 20 mg of a pale yellow solid. It was dissolved in ethanol (10 mL) and water (3 mL), reduced iron powder (56 mg) and ammonium chloride solid (34 mg) were added, and heated to reflux for 2 hours. It was diluted with dichloromethane (20 mL), filtered, and the filtrate was concentrated to afford 18 mg of a brown oily liquid, which was dissolved in 13 mL dichloromethane, 3 mL saturated solution of sodium bicarbonate was added, and under ice-water bath 0.7 L 0.15M acryloyl chloride in dichloromethane was added dropwise, and stirred in ice-water bath for 30 minutes. The layers were separated, the water layer was extracted with dichloromethane (3 mL×3), the organic phase was combined and washed with saturated solution of sodium bicarbonate and brine sequentially, dried over anhydrous sodium sulfate, filtered and concentrated, and purified by column chromatography (DCM/MeOH, V/V, 20/1), to afford 16 mg of a white solid. 1H NMR (400 MHz, CDCl3) (δ/ppm) 8.65 (s, 1H), 8.31 (s, 1H), 7.95 (s, 1H), 7.50 (d, J=11.3 Hz, 1H), 6.93 (s, 1H), 6.58 (dd, J=16.8, 10.5 Hz, 1H), 6.41 (d, J=16.2 Hz, 1H), 5.82 (d, J=10.9 Hz, 1H), 5.34 (t, J=4.7 Hz, 1H), 3.98 (s, 3H), 3.43 (d, J=5.9 Hz, 2H), 3.24 (t, J=5.6 Hz, 2H), 2.83 (s, 6H), 2.69 (s, 3H), 2.69 (s, 3H), 2.19 (t, J=7.5 Hz, 1H), 1.67 (d, J=6.9 Hz, 6H), 0.93 (dd, J=13.1, 6.1 Hz, 3H), 0.66 (q, J=5.4 Hz, 3H).

Example 10 Preparation of N-(2-(2-methoxy-ethyl-oxy)-5-((4-(4-fluoro-1-isopropyl-2-methyl-1H-benzo [d]imidazole-6-yl)pyrimidin-2-yl)amino)-4-methoxyphenyl)acrylamide

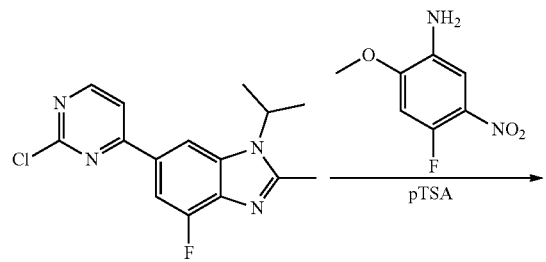

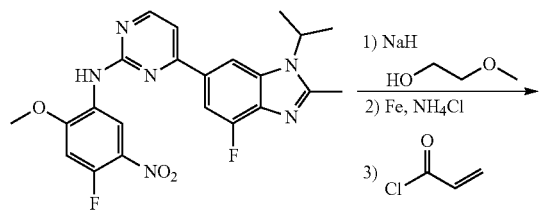

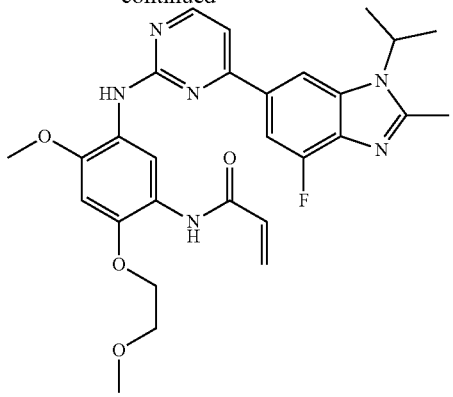

Step 1 Synthesis of Compound 4-(4-fluoro-1-isopropyl-2-methyl-1H-benzo[d]imidazole-6-yl)-N-(4-fluoro-2-methoxy-5-nitrophenyl)pyrimidin-2-amine The compound 6-(2-chloropyrimidin-4-yl)-4-fluoro-1-isopropyl-2-methyl-H-benzo[d]imidazole (740 mg) was dissolved in 10 mL anhydrous dioxane, 4-fluoro-2-methoxy-5-nitroaniline (452 mg, 2.43 mmol), pTSA (2.26 g, 13.16 mmol) were added, and the reaction was heated to 115° C. and stirred overnight. Dioxane was evaporated to dry, in an ice bath was added 20 mL EA, 20 mL 1N aqueous solution of sodium hydroxide, stirred for 10 minutes, filtered by sucking, and the layers were separated. The organic phase was evaporated to dry and purified on column chromatography (DCM/MeOH, v/v, 80/1), concentrated to afford a solid, which was purified by refluxing with PE-EA (v/v, 1/1, 20 mL) and slurrying for 1 hour to afford a pure product (200 mg).

Step 2 Synthesis of Compound N-(2-(2-methoxy-ethyl-oxy)-5-((4-(4-fluoro-1-isopropyl-2-methyl-1H-benzo[d]imidazole-6-yl)pyrimidin-2-yl)amino)-4-methoxyphenyl)acrylamide Ethylene glycol monomethyl ether (167 mg, 2.20 mmol) was dissolved in THF (4 mL), NaH (60%, 97 mg, 2.42 mmol) was added in portions, and the reaction was stirred at room temperature for 30 minutes. The solution of compound 4-(4-fluoro-1-isopropyl-2-methyl-1H-benzo[d]imidazole-6-yl)-N-(4-fluoro-2-methoxy-5-nitrophenyl)pyrimidin-2-amine (200 mg, 0.44 mmol) in anhydrous dioxane (4 mL) was slowly added, and the mixture was stirred at room temperature overnight. The reaction was concentrated, 10 mL EA and 10 mL brine were added, the layers were separated, and the water phase was extracted with ethyl acetate (10 mL×3), the organic phase was combined and washed with brine, dried over anhydrous sodium sulfate, and filtered and concentrated to afford 166 mg of a brown oily liquid, which was dissolved in ethanol (10 mL), water (2 mL), reduced iron powder (123 mg, 2.20 mmol), NH4Cl (47 mg, 0.88 mmol) were added, and heated to reflux for 2 hours. After cooling to room temperature, it was filtered, the filtrate was concentrated, dissolved in dichloromethane (10 mL), saturated sodium bicarbonate (10 mL) was added, in an ice-water bath was added dropwise 1.0M acryloyl chloride in dichloromethane (0.53 mL), and stirred for 30 minutes. The layers were separated, the water phase was extracted with dichloromethane (3 mL×3), the organic phase was combined and washed with brine, dried over anhydrous sodium sulfate, filtered and concentrated, and purified by column chromatography (DCM/MeOH, V/V, 20/1), to afford a white solid powder (51 mg). ¹H NMR (400 MHz, CDCl₃) (δ/ppm) 9.57 (s, 1H), 8.49 (d, J=5.2 Hz, 1H), 8.32 (s, 1H), 8.01 (d, J=1.3 Hz, 1H), 7.77 (d, J=11.5 Hz, 1H), 7.54 (s, 1H), 7.11 (d, J=5.3 Hz, 1H), 6.64 (s, 1H), 6.43 (dd, J=16.9, 1.5 Hz, 1H), 6.27 (dd, J=16.9, 10.2 Hz, 1H), 5.75-5.66 (m, 1H), 4.74 (p, J=7.0 Hz, 1H), 4.21-4.10 (m, 2H), 3.87 (s, 3H), 3.73-3.63 (m, 2H), 3.46 (s, 3H), 2.66 (s, 3H), 1.65 (d, J=7.0 Hz, 6H).

Example 11 Preparation of N-(2-(2-(dimethylamino)ethyl)(thio)-5-((4-(4-fluoro-1-isopropyl-2-methyl-1H-benzo[d]imidazole-6-yl)pyrimidin-2-yl)amino)-4-methoxyphenyl)acrylamide

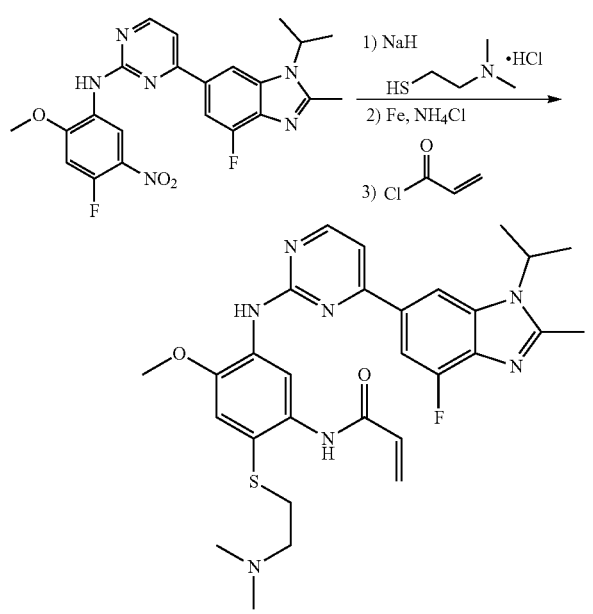

2-dimethylaminoethanethiol hydrochloride (234 mg, 1.65 mmol) was dissolved in DMF (3 mL), NaH (60%, 80 mg, 3.30 mmol) was added in portions, and stirred at room temperature for 30 minutes. A solution of the compound 4-(4-fluoro-1-isopropyl-2-methyl-1H-benzo[d]imidazole-6-yl)-N-(4-fluoro-2-methoxy-5-nitrophenyl)pyrimidin-2-amine (150 mg, 0.33 mmol) in DMF (3 mL) was slowly added, the mixture was stirred at room temperature overnight. The reaction mixture was concentrated, 10 mL EA and 10 mL brine were added, the layers were separated, the water phase was extracted with ethyl acetate (10 mL×3), the organic phase was combined and washed with brine, dried over anhydrous sodium sulfate, filtered, and concentrated to afford 173 mg of a brown oily liquid, which was extracted with ethanol (10 mL), water (2 mL), reduced iron powder (123 mg, 2.20 mmol), NH₄Cl (47 mg, 0.88 mmol) were added, and heated to reflux for 2 hours. After cooling to room temperature, the reaction was filtered, the filtrate was concentrated, extracted with dichloromethane (10 mL), saturated sodium bicarbonate (10 mL) was added, 1.0M acryloyl chloride in dichloromethane (0.53 mL) was added dropwise in ice-water bath, and stirred for 30 minutes. The layers were separated, the water phase was extracted with dichloromethane (3 mL×3), the organic phase was combined and washed with brine, dried over anhydrous sodium sulfate, filtered and concentrated, and purified by column chromatography (DCM/MeOH, V/V, 20/1), to afford 46 mg of a white solid powder. ¹H NMR (400 MHz, CDCl₃) (δ/ppm) 9.64 (s, 1H), 8.54 (d, J=5.2 Hz, 1H), 7.98 (d, J=1.3 Hz, 1H), 7.85 (d, J=18.7 Hz, 2H), 7.17 (d, J=5.3 Hz, 1H), 7.10 (s, 1H), 6.48 (dd, J=17.0, 1.5 Hz, 1H), 6.31 (dd, J=17.0, 10.2 Hz, 1H), 5.73 (d, J=10.2 Hz, 1H), 4.76 (p, J=7.0 Hz, 1H), 3.92 (s, 3H), 2.87 (t, J=6.3 Hz, 2H), 2.67 (s, 3H), 2.38 (m, 2H), 2.28 (s, 6H), 1.67 (d, J=7.0 Hz, 6H).

Example 12 Preparation of N-(2-(2-(dimethylamino)ethyl)(oxy)-5-((4-(4-fluoro-1-isopropyl-2-methyl-1H-benzo[d]imidazole-6-yl)pyrimidin-2-yl)amino)-4-methoxyphenyl)acrylamide

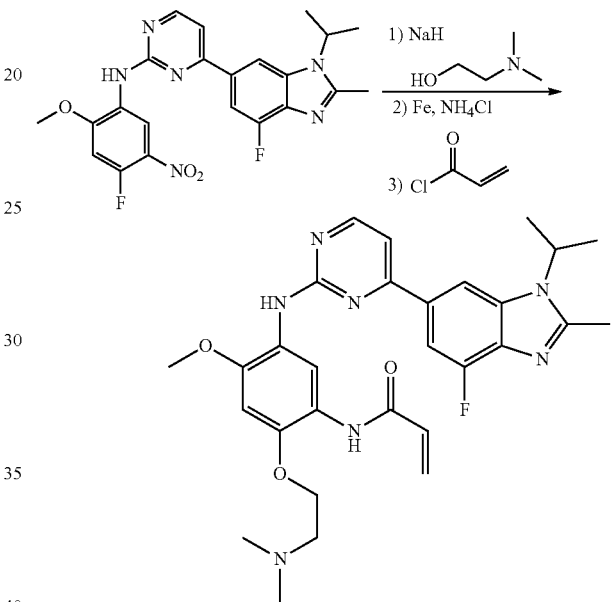

2-dimethylaminoethanol (49 mg, 0.55 mmol) was dissolved in dioxane (1 mL), NaH (60%, 24 mg, 0.61 mmol) was added in portions, and stirred at room temperature for 30 minutes. A solution of the compound 4-(4-fluoro-1-isopropyl-2-methyl-1H-benzo[d]imidazole-6-yl)-N-(4-fluoro-2-methoxy-5-nitrophenyl)pyrimidin-2-amine (50 mg, 0.11 mmol) in dioxane (1 mL) was slowly added, and the mixture was stirred at room temperature overnight. The reaction mixture was concentrated, 3 mL EA and 3 mL brine were added, the layers were separated, the water was extracted with ethyl acetate (3 mL×3), the organic phase was combined and washed with brine, dried over anhydrous sodium sulfate, filtered and concentrated to afford 43 mg of a brown oily liquid, dissolved in ethanol (3 mL), water (1 mL), reduced iron powder (41 mg, 0.73 mmol), NH₄Cl (16 mg, 0.30 mmol) were added, and heated to reflux for 2 hours. After cooling to room temperature, the reaction was filtered, the filtrate was concentrated, dissolved in dichloromethane (3 mL), saturated sodium bicarbonate (10 mL) was added, 1.0M acryloyl chloride in dichloromethane (0.18 mL) was added dropwise in ice-water bath, and stirred for 30 minutes. The layers were separated, the water phase was extracted with dichloromethane (3 mL×3), the organic phase was combined and washed with brine, dried over anhydrous sodium sulfate, filtered and concentrated, and purified by column chromatography (DCM/MeOH, V/V, 20/1), to afford a white solid powder (20 mg). $^1$H NMR (400 MHz, CDCl$_3$) (δ/ppm) 9.66 (s, 1H), 9.48 (s, 1H), 8.49 (d, J=5.3 Hz, 1H), 8.02 (d, J=1.3 Hz, 1H), 7.76 (d, J=11.5 Hz, 1H), 7.54 (s, 1H), 7.10 (d, J=5.3 Hz, 1H), 6.62 (s, 1H), 6.42 (d, J=2.4 Hz, 1H), 5.68 (d, J=11.5 Hz, 1H), 4.74 (p, J=6.8 Hz, 1H), 4.13 (t, J=5.1 Hz, 2H), 3.87 (s, 3H), 2.69 (m, 2H), 2.66 (s, 3H), 2.45-2.39 (m, 6H), 1.66 (d, J=7.0 Hz, 6H).

Example 13 Preparation of N-(2-(4-morpholinopiperidin)-1-yl)-5-((4-(4-fluoro-1-isopropyl-2-methyl-1H-benzo[d]imidazole-6-yl)pyrimidin-2-yl)amino)-4-methoxyphenyl)acrylamide

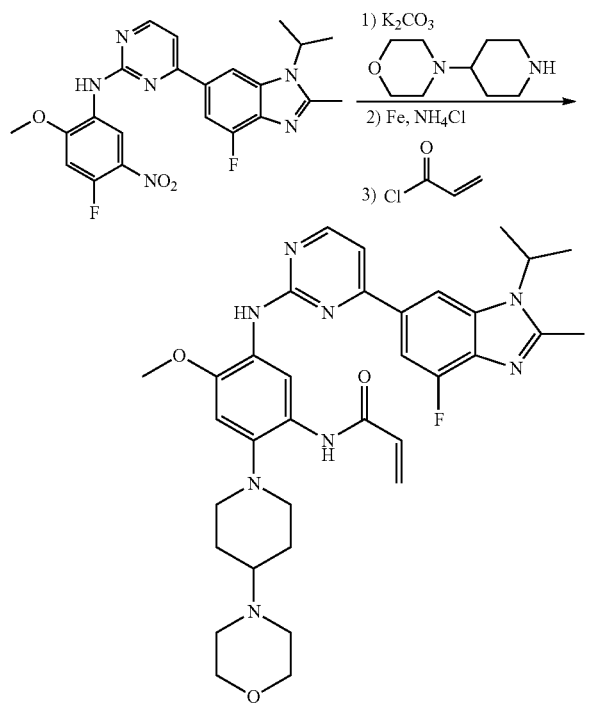

The compound 4-(4-fluoro-1-isopropyl-2-methyl-1H-benzo[d]imidazole-6-yl)-N-(4-fluoro-2-methoxy-5-nitrophenyl)pyrimidin-2-amine (150 mg, 0.33 mmol), 4-(4-piperidinyl)morpholine (67.4 mg, 0.40 mmol) was dissolved in acetonitrile (10 mL), K$_2$CO$_3$ (183 mg, 1.32 mmol) was added, and heated to reflux overnight. The reaction mixture was concentrated, 10 mL EA and 10 mL brine were added, the layers were separated, the water phase was extracted with ethyl acetate (10 mL×3), the organic phase was combined and washed with brine, dried over anhydrous sodium sulfate, filtered and concentrated to afford 180 mg of a brown oily liquid, which was dissolved in ethanol (10 mL), water (2 mL), reduced iron powder (123 mg, 2.20 mmol), NH$_4$Cl (47 mg, 0.88 mmol) were added, and heated to reflux for 2 hours. After cooling to room temperature, it was filtered, the filtrate was concentrated, dissolved in dichloromethane (10 mL), saturated sodium bicarbonate (10 mL) was added, 1.0M acryloyl chloride in dichloromethane (0.53 mL) was added dropwise in ice-water bath, and stirred in ice-water bath for 30 minutes. The layers were separated, the water phase was extracted with dichloromethane (3 mL×3), the organic phase was combined and washed with brine, dried over anhydrous sodium sulfate, filtered and concentrated, and purified by column chromatography (DCM/MeOH, V/V, 20/1), to afford a white solid powder (90 mg). $^1$H NMR (400 MHz, CDCl$_3$) (δ/ppm) 9.61 (s, 1H), 8.51 (d, J=5.0 Hz, 2H), 8.01 (d, J=1.3 Hz, 1H), 7.82 (d, J=11.5 Hz, 1H), 7.66 (s, 1H), 7.14 (d, J=5.2 Hz, 1H), 6.75 (s, 1H), 6.42 (dd, J=16.9, 1.4 Hz, 1H), 6.28 (dd, J=16.9, 10.2 Hz, 1H), 5.74 (d, J=10.1 Hz, 1H), 4.77 (p, J=7.0 Hz, 1H), 3.89 (s, 3H), 3.81 (s, 4H), 3.07 (d, J=11.6 Hz, 3H), 2.74 (d, J=11.9 Hz, 3H), 2.68 (s, 3H), 2.38 (m, 1H), 2.09 (d, J=12.1 Hz, 2H), 1.99-1.69 (m, 6H), 1.66 (d, J=7.0 Hz, 6H).

Example 14 Preparation of N-(2-(4-ethoxypiperidin)-1-yl)-5-((4-(4-fluoro-1-isopropyl-2-methyl-1H-benzo[d]imidazole-6-yl)pyrimidin-2-yl)amino)-4-methoxyphenyl)acrylamide

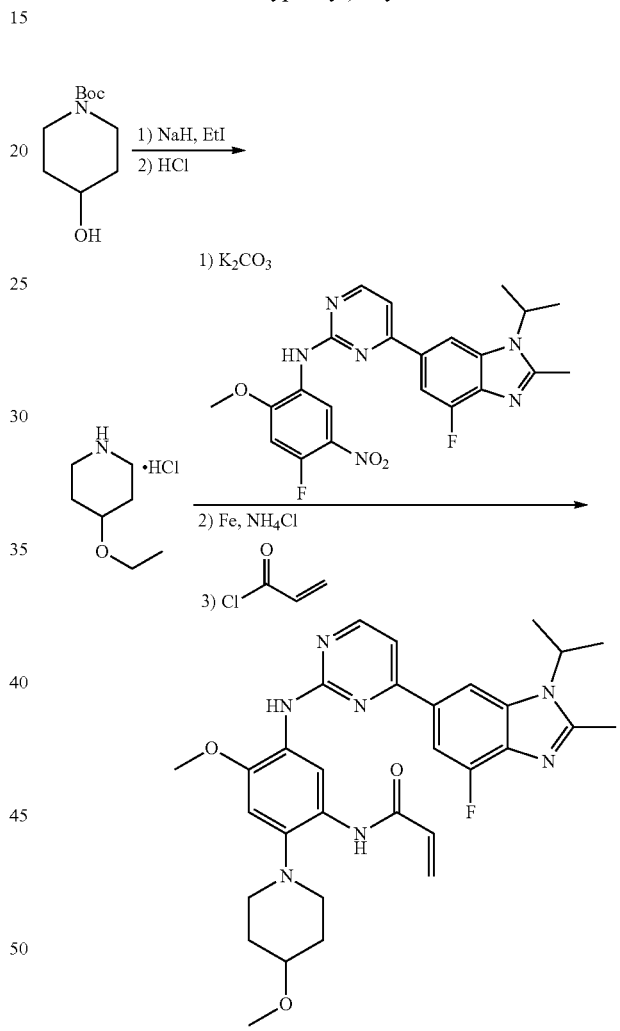

Step 1 Synthesis of Compound 4-ethoxypiperidine Hydrochloride

The compound tert-butyl 4-hydroxypiperidine-1-carboxylate (2.01 g, 10.0 mmol) was dissolved in THF (10 mL), cooled in an ice-water bath and NaH (60%, 288 mg, 12.0 mmol) was added in portions, and stirred in the ice-water bath for 30 minutes. Ethyl iodide (0.85 mL, 10.5 mmol) was added in one portion, the mixture was stirred at room temperature overnight. The reaction mixture was concentrated, 10 mL EA and 10 mL brine were added. The layers were separated, the water phase was extracted with ethyl acetate (10 mL×3), the organic phase was combined and washed with brine, dried over anhydrous sodium sulfate, filtered and concentrated to afford a colorless oily liquid (2.20 g). The oily liquid obtained above (2.20 g) was dissolved in DCM (10 mL), 4M HCl in dioxane (10 mL) was added in ice-water bath, and stirred at room temperature for 5 hours. The reaction mixture was concentrated to afford a white solid (1.33 g).

Step 2 Synthesis of Compound N-(2-(4-ethoxypiperidin)-1-yl)-5-((4-(4-fluoro-1-isopropyl-2-methyl-1H-benzo[d]imidazole-6-yl)pyrimidin-2-yl)amino)-4-methoxyphenyl)acrylamide The compound 4-(4-fluoro-1-isopropyl-2-methyl-1H-benzo[d]imidazole-6-yl)-N-(4-fluoro-2-methoxy-5-nitrophenyl)pyrimidin-2-amine (150 mg, 0.33 mmol), compound 4-ethoxypiperidine hydrochloride (82 mg, 0.49 mmol) were dissolved in acetonitrile (10 mL), K₂CO₃ (274 mg, 1.98 mmol) was added, and heated to reflux overnight. The reaction mixture was concentrated, 10 mL EA and 10 mL brine were added. The layers were separated, the water phase was extracted with ethyl acetate (10 mL×3), the organic phase was combined and washed with brine, dried over anhydrous sodium sulfate, filtered and concentrated to afford 156 mg of a brown oily liquid, which was dissolved in ethanol (10 mL), water (2 mL), reduced iron powder (123 mg, 2.20 mmol), NH₄Cl (47 mg, 0.88 mmol) were added, and heated to reflux for 2 hours. After cooling to room temperature, it was filtered, the filtrate was concentrated, dissolved in dichloromethane (10 mL), saturated sodium bicarbonate (10 mL) was added, 1.0M acryloyl chloride in dichloromethane (0.53 mL) was added dropwise in an ice-water bath, and stirred in the ice-water bath for 30 minutes. The layers were separated, the water phase was extracted with dichloromethane (3 mL×3), the organic phase was combined and washed with brine, dried over anhydrous sodium sulfate, filtered and concentrated, and purified by column chromatography (DCM/MeOH, V/V, 20/1) to afford a white solid powder (74 mg). $^1$H NMR (400 MHz, CDCl₃) (δ/ppm) 9.61 (s, 1H), 8.52 (d, J=5.2 Hz, 1H), 8.02 (d, J=1.3 Hz, 1H), 7.67 (d, J=8.3 Hz, 1H), 7.13 (d, J=5.3 Hz, 1H), 6.77 (s, 1H), 6.40 (dd, J=16.9, 1.4 Hz, 1H), 6.26 (dd, J=17.0, 10.1 Hz, 1H), 5.73 (d, J=10.1 Hz, 1H), 4.78 (p, J=7.1 Hz, 1H), 3.90 (s, 3H), 3.58 (q, J=7.0 Hz, 2H), 3.53-3.41 (m, 1H), 3.10-2.95 (m, 2H), 2.78-2.69 (m, 2H), 2.68 (s, 3H), 2.09 (d, J=19.3 Hz, 2H), 1.84-1.69 (m, 2H), 1.67 (d, J=6.9 Hz, 6H), 1.29-1.23 (m, 4H).

Example 15 Preparation of N-(2-(4-methoxypiperidin)-1-yl)-5-(4-(4-fluoro-1-isopropyl-2-methyl-1H-benzo[d]imidazole-6-yl)pyrimidin-2-yl)amino)-4-methoxyphenyl)acrylamide

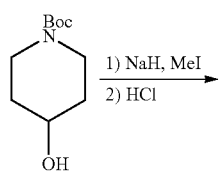

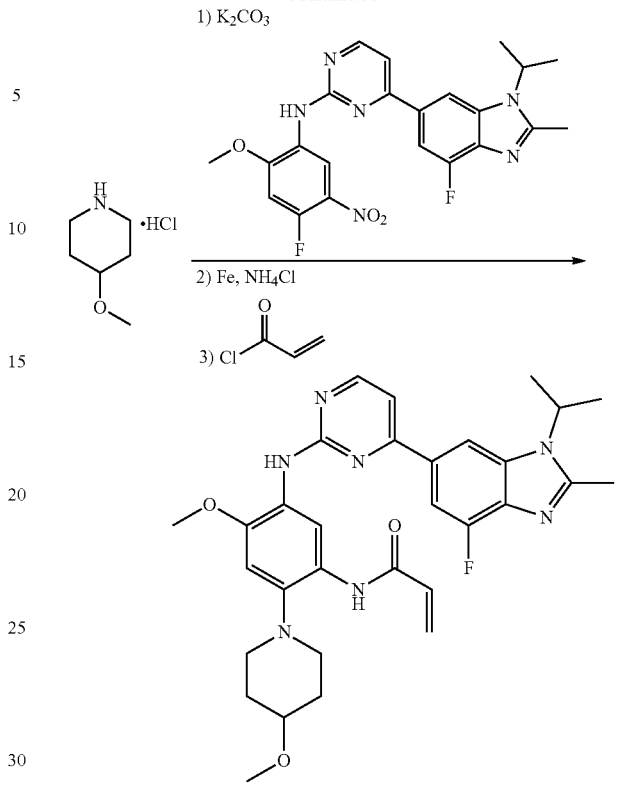

Step 1 Synthesis of Compound 4-methoxypiperidine Hydrochloride

The compound tert-butyl 4-hydroxypiperidin-1-carboxylate (2.01 g, 10.0 mmol) was dissolved in THF (10 mL), cooled in ice-water bath and NaH (60%, 288 mg, 12.0 mmol) was added in portions, and stirred in the ice-water bath for 30 minutes. Methyl iodide (0.65 mL, 10.5 mmol) was added in one portion, and the mixture was stirred at room temperature overnight. The reaction mixture was concentrated, 10 mL EA and 10 mL brine were added, the layers were separated, the water phase was extracted with ethyl acetate (10 mL×3), the organic phase was combined and washed with brine, dried over anhydrous sodium sulfate, filtered and concentrated to afford a colorless oily liquid (2.12 g). The oily liquid obtained above (2.12 g) was dissolved in DCM (10 mL), 4M HCl in dioxane (10 mL) was added in ice-water bath, and stirred at room temperature for 5 hours. The reaction mixture was concentrated to afford a white solid (1.42 g).

Step 2 Synthesis of Compound N-(2-(4-methoxypiperidin)-1-yl)-5-((4-(4-fluoro-1-isopropyl-2-methyl-1H-benzo[d]imidazole-6-yl)pyrimidin-2-yl)amino)-4-methoxyphenyl)acrylamide The compound 4-(4-fluoro-1-isopropyl-2-methyl-1H-benzo[d]imidazole-6-yl)-N-(4-fluoro-2-methoxy-5-nitrophenyl)pyrimidin-2-amine (150 mg, 0.33 mmol), compound 4-methoxypiperidine hydrochloride (78 mg, 0.49 mmol) were dissolved in acetonitrile (10 mL), K₂CO₃ (274 mg, 1.98 mmol) was added, and heated to reflux overnight. The reaction mixture was concentrated, 10 mL EA and 10 mL brine were added, the layers were separated, the water phase was extracted with ethyl acetate (10 mL×3), the organic phase was combined and washed with brine, dried over anhydrous sodium sulfate, filtered and concentrated to afford 167 mg of a brown oily liquid, which was dissolved in ethanol (10 mL), water (2 mL), reduced iron powder (123 mg, 2.20 mmol), NH$_4$Cl (47 mg, 0.88 mmol) were added, and heated to reflux for 2 hours. After cooling to room temperature, it was filtered, the filtrate was concentrated, dissolved in dichloromethane (10 mL), saturated sodium bicarbonate (10 mL) was added, 1.0M acryloyl chloride in dichloromethane (0.53 mL) was added dropwise in an ice-water bath, and stirred in the ice-water bath for 30 minutes. The layers were separated, the water phase was extracted with dichloromethane (3 mL×3), the organic phase was combined and washed with brine, dried over anhydrous sodium sulfate, filtered and concentrated, and purified by column chromatography (DCM/MeOH, V/V, 20/1), to afford a white solid powder (90 mg). $^1$H NMR (400 MHz, CDCl$_3$) (δ/ppm) 9.61 (s, 1H), 8.60 (s, 1H), 8.51 (d, J=5.2 Hz, 1H), 8.02 (d, J=1.2 Hz, 1H), 7.81 (d, J=11.5 Hz, 1H), 7.66 (s, 1H), 7.13 (d, J=5.3 Hz, 1H), 6.77 (s, 1H), 6.40 (dd, J=16.8, 1.3 Hz, 1H), 6.27 (dd, J=17.0, 10.1 Hz, 1H), 5.73 (d, J=10.1 Hz, 1H), 4.78 (p, J=7.1 Hz, 1H), 3.89 (s, 3H), 3.41 (d, J=1.0 Hz, 4H), 3.08-2.97 (m, 2H), 2.73 (t, J=10.5 Hz, 1H), 2.68 (s, 3H), 2.05 (s, 2H), 1.84-1.69 (m, 2H), 1.66 (d, J=7.0 Hz, 6H).

Example 16 Preparation of N-(2-morpholino)-5-((4-(4-fluoro-1-isopropyl-2-methyl-1H-benzo[d]imidazole-6-yl)pyrimidin-2-yl)amino)-4-methoxyphenyl)acrylamide

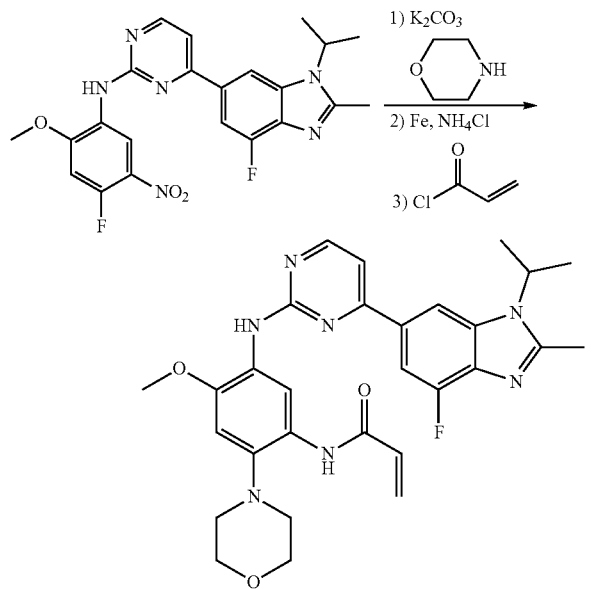

The compound 4-(4-fluoro-1-isopropyl-2-methyl-1H-benzo[d]imidazole-6-yl)-N-(4-fluoro-2-methoxy-5-nitrophenyl)pyrimidin-2-amine (150 mg, 0.33 mmol), morpholine (67 mg, 0.40 mmol) were dissolved in acetonitrile (10 mL), K$_2$CO$_3$ (183 mg, 1.32 mmol) was added, and heated to reflux overnight. The reaction mixture was concentrated, 10 mL EA and 10 mL brine were added, the layers were separated, the water phase was extracted with ethyl acetate (10 mL×3), the organic phase was combined and washed with brine, dried over anhydrous sodium sulfate, filtered and concentrated to afford 167 mg of a brown oily liquid, which was dissolved in ethanol (10 mL), water (2 mL), reduced iron powder (123 mg, 2.20 mmol), NH$_4$Cl (47 mg, 0.88 mmol) were added, and heated to reflux for 2 hours. After cooling to room temperature, it was filtered, the filtrate was concentrated, dissolved in dichloromethane (10 mL), saturated sodium bicarbonate (10 mL) was added, 1.0M acryloyl chloride in dichloromethane (0.53 mL) was added dropwise in an ice-water bath, and stirred in the ice-water bath for 30 minutes. The layers were separated, the water phase was extracted with dichloromethane (3 mL×3), the organic phase was combined and washed with brine, dried over anhydrous sodium sulfate, filtered and concentrated, and purified by column chromatography (DCM/MeOH, V/V, 20/1), to afford a white solid powder (90 mg). $^1$H NMR (400 MHz, CDCl$_3$) (δ/ppm) 9.65 (s, 1H), 8.57 (s, 1H), 8.51 (d, J=5.2 Hz, 1H), 7.99 (d, J=1.4 Hz, 1H), 7.83 (d, J=11.7 Hz, 1H), 7.68 (s, 1H), 7.14 (d, J=5.2 Hz, 1H), 6.77 (s, 1H), 6.48-6.38 (m, 1H), 6.27 (dd, J=17.0, 10.1 Hz, 1H), 5.75 (d, J=10.2 Hz, 1H), 4.76 (p, J=6.9 Hz, 1H), 3.91 (s, 3H), 3.87 (t, J=4.6 Hz, 4H), 2.88 (t, J=4.6 Hz, 4H), 2.67 (s, 3H), 1.66 (d, J=7.0 Hz, 6H).

Example 17 Preparation of N-(2-(4-hydroxypiperidine-1-yl)-5-((4-(4-fluoro-1-isopropyl-2-methyl-1H-benzo[d]imidazole-6-yl)pyrimidin-2-yl)amino)-4-methoxyphenyl)acrylamide

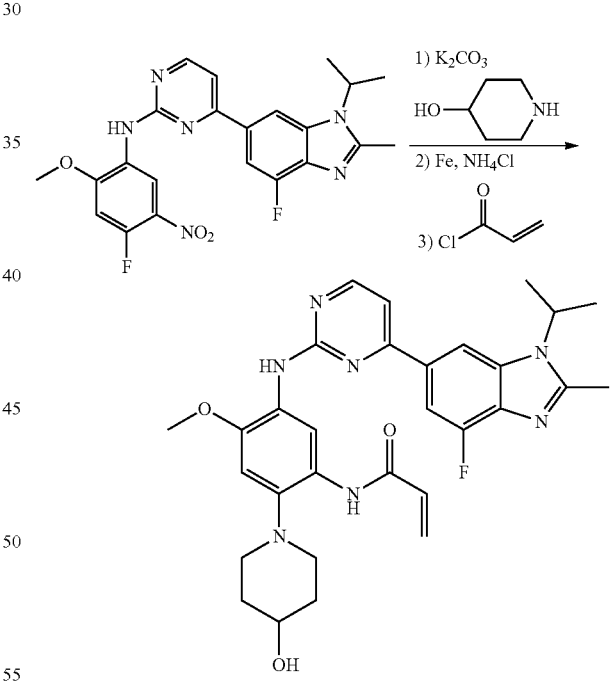

The compound 4-(4-fluoro-1-isopropyl-2-methyl-1H-benzo[d]imidazole-6-yl)-N-(4-fluoro-2-methoxy-5-nitrophenyl)pyrimidin-2-amine (150 mg, 0.330 mmol), 4-hydroxypiperidine (50 mg, 0.495 mmol) were dissolved in acetonitrile (10 mL), K$_2$CO$_3$ (183 mg, 1.32 mmol) was added, and heated to reflux overnight. The reaction mixture was concentrated, 10 mL EA and 10 mL brine were added, the layers were separated, the water phase was extracted with ethyl acetate (10 mL×3), the organic phase was combined and washed with brine, dried over anhydrous sodium sulfate, filtered and concentrated to afford 167 mg of a brown oily liquid, which was dissolved in ethanol (10 mL), water (2 mL), reduced iron powder (123 mg, 2.20 mmol), NH₄Cl (47 mg, 0.880 mmol) were added, and heated to reflux for 2 h. After cooling to room temperature, it was filtered, the filtrate was concentrated, dissolved in dichloromethane (10 mL), saturated sodium bicarbonate (10 mL) was added, 1.0M acryloyl chloride in dichloromethane (0.53 mL) was added dropwise in an ice-water bath, and stirred in the ice-water bath for 30 min. The layers were separated, the water phase was extracted with dichloromethane (3 mL×3), the organic phase was combined and washed with brine, dried over anhydrous sodium sulfate, filtered and concentrated, and purified by column chromatography (DCM/MeOH, V/V, 20/1), to afford a white solid powder (33 mg). $^1$H NMR (400 MHz, chloroform-d) δ 9.63 (s, 1H), 8.60 (s, 1H), 8.53 (d, J=5.2 Hz, 1H), 8.03 (d, J=1.3 Hz, 1H), 7.84 (d, J=11.5 Hz, 1H), 7.69 (s, 1H), 7.15 (d, J=5.3 Hz, 1H), 6.79 (s, 1H), 6.45 (d, J=1.3 Hz, 0H), 6.41 (d, J=1.4 Hz, 1H), 6.29 (dd, J=16.9, 10.1 Hz, 1H), 5.76 (d, J=10.1 Hz, 1H), 4.79 (p, J=7.0 Hz, 1H), 3.91 (s, 3H), 3.09-3.01 (m, 2H), 2.77 (ddd, J=12.1, 9.3, 2.9 Hz, 2H), 2.69 (s, 3H), 2.08 (d, J=11.6 Hz, 2H), 1.84-1.73 (m, 2H), 1.68 (d, J=7.0 Hz, 6H).

Example 18 Preparation of N-(2-((2-(dimethylamino)ethyl)(methyl)amino)-5-((5-cyano-4-(4-fluoro-1-isopropyl-2-m ethyl-1H-benzo[d]imidazole-6-yl)pyrimidin-2-yl)amino)-4-methoxyphenyl) acrylamide

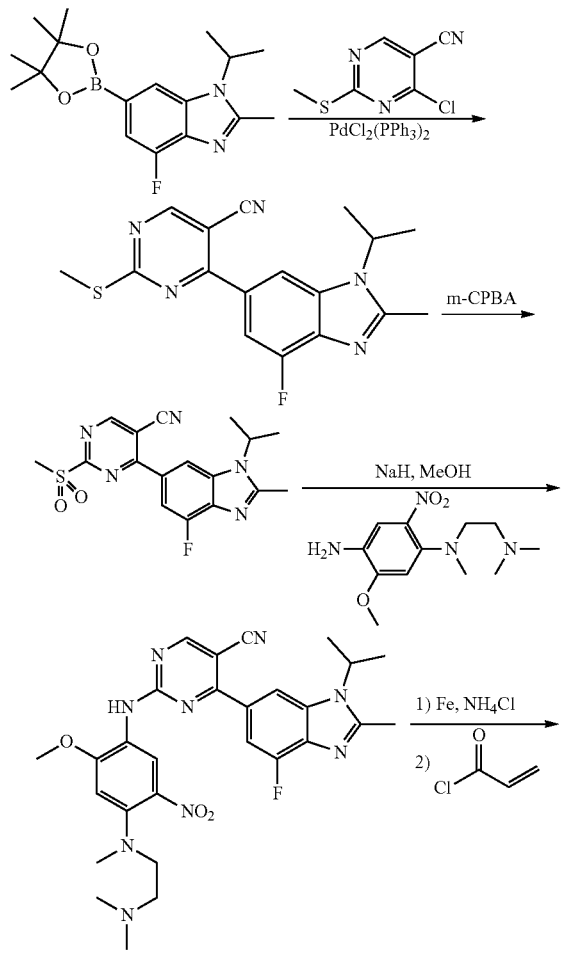

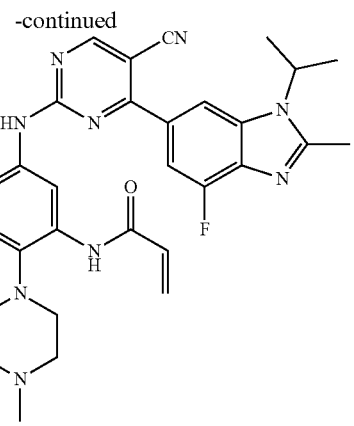

Step 1 Synthesis of Compound 4-(4-fluoro-1-isopropyl-2-methyl-1H-benzo[d]imidazole-6-yl)-2-(methylthio)pyrimidin-5-carbonitrile The compound 4-chloro-2-(methylthio)pyrimidin-5-carbonitrile (200 mg, 1.08 mmol), compound 4-fluoro-1-isopropyl-2-methyl-6-(4,4,5,5-tetramethyl-1,3,2-dioxaborolan-2-yl)-1H-benzo[d]imidazole (343 mg, 1.08 mmol), Pd(PPh₃)₂Cl₂ (45 mg, 0.06 mmol) were placed in a two-neck flask, flushed with nitrogen gas for three times, under nitrogen protection was added DMF (5 mL) and 2M Na₂CO₃ (2 mL), and the reaction was stirred at 60° C. for 2 hours. The heating was removed, and after cooling to room temperature, the reaction mixture was poured in 50 mL water, extracted with ethyl acetate (5 mL*2), the organic phase was combined, dried over anhydrous sodium sulfate, the solvent was evaporated to dry under reduced pressure, and purified with preparative TLC (P/E, V/V, 1.5/1) to afford a white solid (227 mg, 0.67 mmol).

Step 2 Synthesis of Compound 4-(4-fluoro-1-isopropyl-2-methyl-1H-benzo[d]imidazole-6-yl)-2-(methylsulfonyl)pyrimidin-5-carbonitrile The compound 4-(4-fluoro-1-isopropyl-2-methyl-1H-benzo[d]imidazole-6-yl)-2-(methylthio)pyrimidin-5-carbonitrile (461 mg, 1.35 mmol) was dissolved in 30 mL dichloromethane, cooled in ice-water bath and m-CPBA (582 mg, 3.38 mmol) was added in portions, and stirred at room temperature for 1 h. The solvent was evaporated to dry under reduced pressure, and purified by column chromatography (P/E, V/V, 1/1) to afford a pale yellow oily liquid (504 mg, 1.35 mmol).

Step 3 Synthesis of Compound 2-((4-((2-(dimethylamino)ethyl)(methyl)amino)-2-methoxy-5-nitrophenyl)amino)-4-(4-fluoro-1-isopropyl-2-methyl-1H-benzo[d]imidazole-6-yl)pyrimidin-5-carbonitrile The compound N¹-(2-(dimethylamino)ethyl)-5-methoxy-N¹-methyl-2-nitrobenzene-1,4-diamine (400 mg, 1.35 mmol) was dissolved in 10 mL DMF, 60% NaH (65 mg, 1.62 mmol) was added in portions in an ice-water bath, and stirred for 10 min. A solution of the compound 4-(4-fluoro-1-isopropyl-2-methyl-1H-benzo[d]imidazole-6-yl)-2-(methylsulfonyl)pyrimidin-5-carbonitrile (504 mg, 1.35 mmol) in THF (20 mL) was added, and stirred at room temperature for 1 h. 2 mL methanol was added, the reaction mixture was concentrated, the resulted solid was added with 15 mL water and 15 mL EA, the layers were separated, the water phase was extracted with ethyl acetate (15 mL×2), the EA layer was combined and washed with brine, dried over anhydrous sodium sulfate, filtered and concentrated, and purified by column chromatography to afford a compound (220 mg, 0.392 mmol).

Step 4 Synthesis of Compound N-(2-((2-(dimethylamino)ethyl)(methyl)amino)-5-((5-cyano-4-(4-fluoro-1-isopropyl-2-meth yl-1H-benzo[d]imidazole-6-yl)pyrimidin-2-yl)amino)-4-methoxyphenyl)acrylamide The compound 2-((4-((2-(dimethylamino)ethyl)(methyl)amino)-2-methoxy-5-nitrophenyl)amino)-4-(4-fluoro-1-isopropyl-2-methyl-1H-benzo[d]imidazole-6-yl)pyrimidin-5-carbonitrile (220 mg, 0.392 mmol) was dissolved in ethanol (10 mL), water (2 mL), reduced iron powder (109 mg, 1.96 mmol), NH$_4$Cl (42 mg, 0.783 mmol) were added, and heated to reflux for 2 h. After cooling to room temperature, it was filtered, the filtrate was concentrated, dissolved in dichloromethane (10 mL), saturated sodium bicarbonate (10 mL) was added, and 1.0M acryloyl chloride in dichloromethane (0.59 mL) was added dropwise in an ice-water bath, and stirred in the ice-water bath for 30 min. The layers were separated, the water phase was extracted with dichloromethane (3 mL×3), the organic phase was combined and washed with brine, dried over anhydrous sodium sulfate, filtered and concentrated, and purified by column chromatography (DCM/MeOH, V/V, 20/1), to afford a white solid powder (76 mg).

Example 19 Preparation of N-(2-((2-(dimethylamino)ethyl)(methyl)amino)-5-((5-fluoro-4-(4-fluoro-1-isopropyl-2-m ethyl-1H-benzo[d]imidazole-6-yl)pyrimidin-2-yl)amino)-4-methoxyphenyl)acrylamide

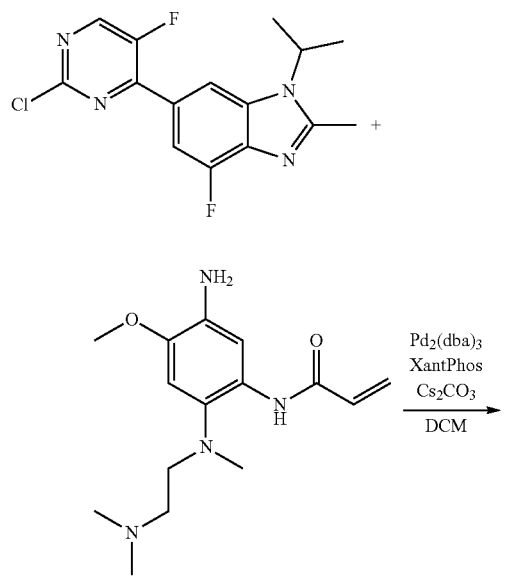

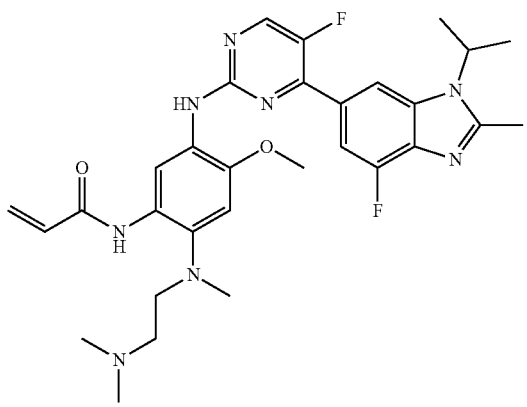

Under nitrogen protection, Pd$_2$(dba)$_3$ (60 mg) and Xantphos (80 mg) were added into 6-(2-chloro-5-fluoropyrimidin-4-yl)-4-fluoro-1-isopropyl-2-methyl-1H-benzo[d]imidazole (281 mg, 0.87 mmol), N-(5-amino-2-((2-(dimethylamino)ethyl)(methyl)amino)-4-methoxyphenyl)acrylamide (170 mg, 0.58 mmol) and potassium carbonate (200 mg, 1.46 mmol) in 2-methyl-2-butanol (10 mL), and the reaction mixture was reacted under nitrogen protection at 100° C. for 3 hrs. After cooling to room temperature, it was filtered on Celite, concentrated under reduced pressure, and the filtrate was separated on column chromatography (eluant:dichloromethane/methanol (v/v)=10:1), to afford 130 mg of a yellow solid, yield was 38.8%. LC-MS(APCI): m/z=579.3 (M+1)+, purity is 92.77% (HPLC), $^1$H NMR (400 MHz, DMSO): δ 9.85 (s, 1H), 8.71 (s, 1H), 8.58 (d, J=3.9 Hz, 1H), 8.39 (s, 1H), 8.11 (s, 1H), 7.74 (d, J=11.8 Hz, 1H), 6.99 (s, 1H), 6.25 (d, J=17.0 Hz, 1H), 5.79-5.65 (m, 1H), 4.87-4.75 (m, 1H), 3.85 (s, 3H), 3.25-3.04 (m, 2H), 2.70-2.58 (m, J=4.0 Hz, 8H), 2.50 (s, 6H), 1.56 (d, J=6.9 Hz, 6H).

Example 20 Preparation of N-(5-((4-(1-cyclopropyl-4-fluoro-2-methyl-1H-benzo[d]imidazole-6-yl)pyrimidin-2-yl)amino)-2-((2-(dimethylamino)ethyl)(methyl)amino)-4-methoxyphenyl)acrylamide

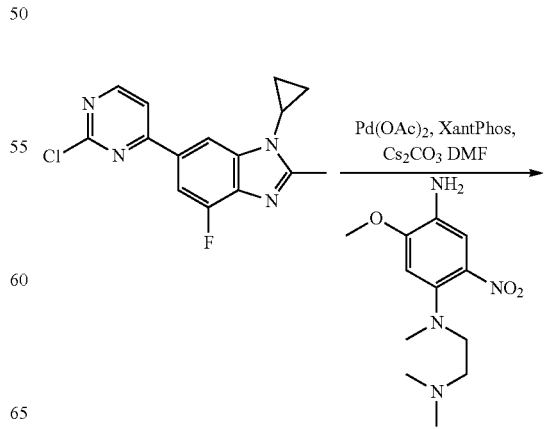

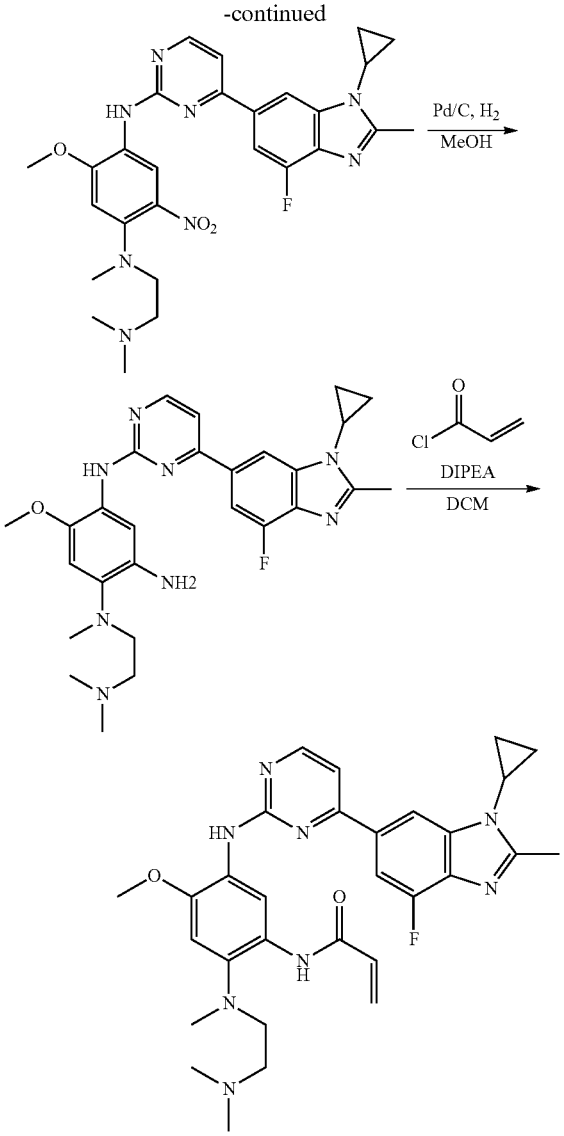

Step 1 Synthesis of Compound $N^1$-(4-(1-cyclopropyl-4-fluoro-2-methyl-1H-benzo[d]imidazole-6-yl)pyrimidin-2-yl)-$N^4$-(2-(dimethylamino)ethyl)-2-methoxy-$N^4$-methyl-5-nitrobenzene-1,4-diamine Under nitrogen protection, Pd(OAc)$_2$ (26 mg, 0.11 mmol) and Xantphos (135 mg, 0.23 mmol) were added into intermediate compound 6-(2-chloropyrimidin-4-yl)-1-cyclopropyl-4-fluoro-2-methyl-1H-benzo[d]imidazole (350 mg, 1.16 mmol), $N^1$-(2-(dimethylamino)ethyl)-5-methoxy-$N^1$-methyl-2-nitrobenzene-1,4-diamine (311 mg, 1.16 mmol) and cesium carbonate (760 mg, 2.32 mmol) in anhydrous DMF (20 mL), and the reaction mixture was reacted under nitrogen protection at 100° C. overnight. After cooling to room temperature, the reaction was quenched by adding water, extracted with ethyl acetate (50 mL×3), the organic phase was combined, washed with brine (50 mL) and dried over anhydrous sodium sulfate, the solvent was removed, and the filtrate was separated on column chromatography (eluant:dichloromethane/methanol (v/v)=10:1), to afford 360 mg of a yellow solid. LC-MS(APCI): m/z=535.2 (M+1).

Step 2 Synthesis of Compound $N^4$-(4-(1-cyclopropyl-4-fluoro-2-methyl-1H-benzo[d]imidazole-6-yl)pyrimidin-2-yl)-$N^1$-(2-(dimethylamino)ethyl)-5-methoxy-N-methylbenzene-1,2,4-triamine 10% Pd/C (50 mg) was added into compound $N^1$-(4-(1-cyclopropyl-4-fluoro-2-methyl-1H-benzo[d]imidazole-6-yl)pyrimidin-2-yl)-$N^4$-(2-(dimethylamino)ethyl)-2-methoxy-$N^4$-methyl-5-nitrobenzene-1,4-diamine (360 mg) in methanol, and reacted under hydrogen gas (balloon) at room temperature overnight, it was filtered on Celite, the filtrate was concentrated under reduced pressure, and the filtrate was separated on column chromatography (eluant:dichloromethane/methanol (v/v)=8:1), to afford 270 mg of a yellow solid. Yield over two steps: 46.7%, LC-MS(APCI): m/z=505.2 (M+1).

Step 3 Synthesis of Compound N-(5-((4-(1-cyclopropyl-4-fluoro-2-methyl-1H-benzo[d]imidazole-6-yl)pyrimidin-2-yl)amino)-2-((2-(dimethylamino)ethyl)(methyl)amino)-4-methoxyphenyl)acrylamide Under nitrogen protection, the compound $N^4$-(4-(1-cyclopropyl-4-fluoro-2-methyl-1H-benzo[d]imidazole-6-yl)pyrimidin-2-yl)-$N^1$-(2-(dimethylamino)ethyl)-5-methoxy-$N^1$-methylbenzene-1,2,4-triamine (250 mg, 0.47 mmol) was dissolved in 30 mL anhydrous dichloromethane, DIPEA (0.16 mg, 0.94 mmol) was added dropwise, the reaction system was cooled to −20° C. after the addition was complete, and at this temperature acryloyl chloride (0.76 mL, 0.47 mmol, 0.618 mmol/mL) was added slowly, and stirred for 30 minutes. Water was added, the organic phase was separated and washed with water and saturated solution of sodium bicarbonate sequentially, the organic phase was collected by concentrating under reduced pressure, and the filtrate was separated on column chromatography (eluant: dichloromethane/methanol (v/v)=10:1), to afford 120 mg of a yellow solid, yield was 45.7%. HPLC: 94.72%. LC-MS (APCI): m/z=558.2 (M+1), $^1$H NMR (500 MHz, DMSO-d6): δ 10.03 (s, 1H), 8.98 (s, 1H), 8.48 (d, J=5.2 Hz, 1H), 8.20-8.09 (m, 2H), 7.90 (d, J=12.0 Hz, 1H), 7.48 (d, J=5.2 Hz, 1H), 7.01 (s, 1H), 6.59-6.38 (m, 1H), 6.22 (dd, J=16.9, 1.0 Hz, 1H), 5.72 (d, J=11.0 Hz, 1H), 3.85 (s, 3H), 3.36-3.34 (m, 1H), 3.04-2.85 (m, 2H), 2.67 (s, 3H), 2.61 (s, 3H), 2.49-2.48 (m, 2H). 2.30 (s, 6H), 1.20-1.15 (m, J=5.9 Hz, 2H), 1.07-1.01 (m, 2H).

Example 21 Preparation of N-(2-((2-(dimethylamino)ethyl)(methyl)amino)-5-((4-(4-fluoro-2-(fluoromethyl)-1-isopropyl-1H-benzo[d]imidazole-6-yl)pyrimidin-2-yl)amino)-4-methoxyphenyl)acrylamide

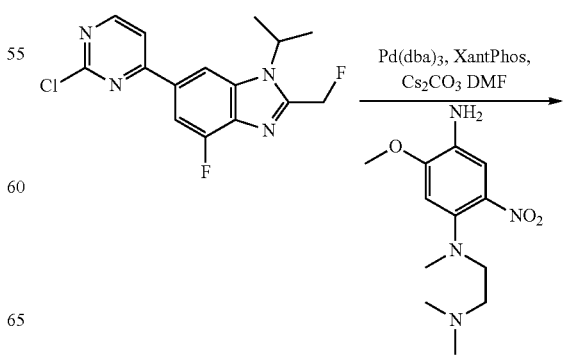

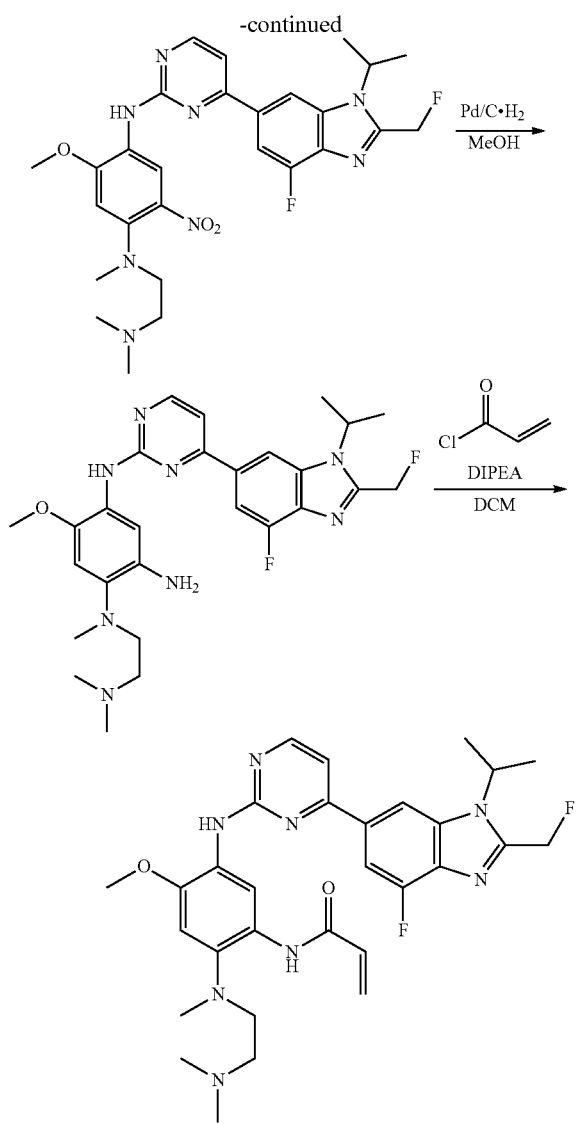

Step 2 Synthesis of Compound $N^1$-(2-(dimethylamino)ethyl)-$N^4$-(4-(4-fluoro-2-(fluoromethyl)-1-isopropyl-1H-benzo[d]imidazole-6-yl)pyrimidin-2-yl)-5-methoxy-$N^1$-methylbenzene-1,2,4-triamine The synthetic step is the same as that of Example 20 step 2, and 210 mg of a yellow solid was obtained. LC-MS (APCI): m/z=525.3 (M+1).

Step 3 Synthesis of Compound N-(2-((2-(dimethylamino)ethyl)(methyl)amino)-5-((4-(4-fluoro-2-(methyl)ethyl)-1-isopropyl-1H-benzo[d]imidazole-6-yl)pyrimidin-2-yl)amino)-4-methoxyphenyl)acrylamide The synthetic step is the same as that of Example 20 step 3, and 120 mg of a yellow solid product was obtained, yield was 50.1%. HPLC: 98.25%. LC-MS(APCI): m/z=579.3 (M+1), $^1$H NMR (400 MHz, DMSO-d6): δ 10.56 (s, 1H), 9.88 (s, 1H), 8.84 (s, 1H), 8.52 (d, J=5.2 Hz, 1H), 8.33 (s, 1H), 8.26 (s, 1H), 8.01 (d, J=12.1 Hz, 1H), 7.62 (d, J=5.3 Hz, 1H), 6.98 (s, 1H), 6.25 (dd, J=17.0, 2.0 Hz, 1H), 5.84 (s, 1H), 5.74-5.68 (m, 2H), 4.97 (dt, J=13.7, 6.7 Hz, 1H), 3.87 (s, 3H), 3.22-3.12 (m, 2H), 2.72-2.51 (m, 9H), 2.04-2.01 (m, 2H), 1.62 (d, J=6.9 Hz, 6H).

Example 22 Preparation of N-(2-((2-(dimethylamino)ethyl)(methyl)amino)-5-((4-(1-isopropyl-2-methyl-1H-imidazo[4,5-b]pyridine-6-yl)pyrimidin-2-yl)amino)-4-methoxyphenyl)acrylamide

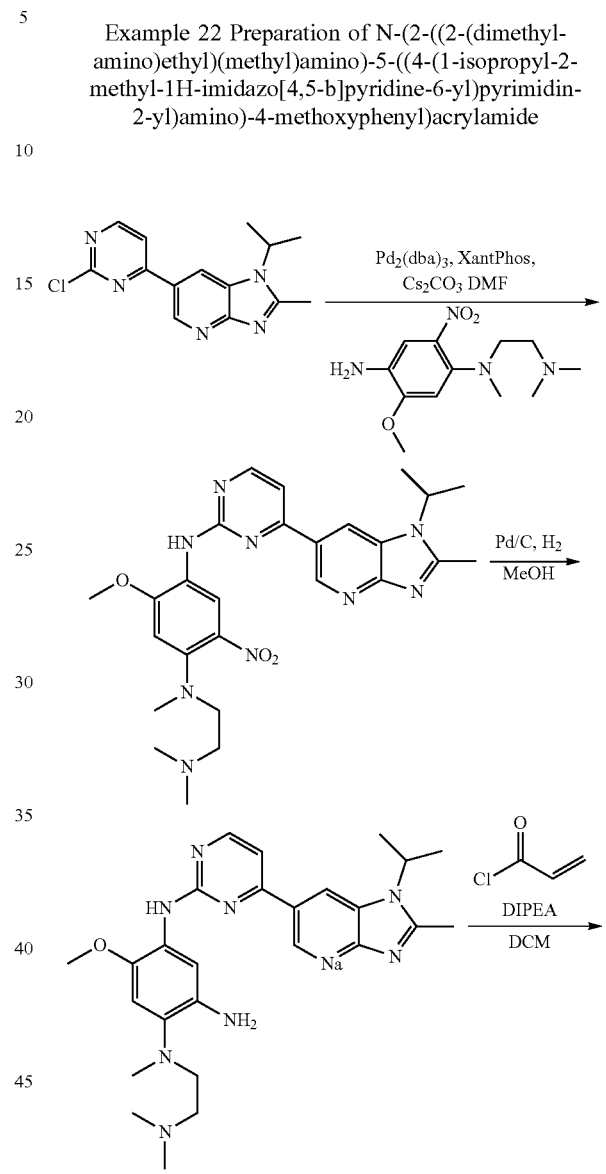

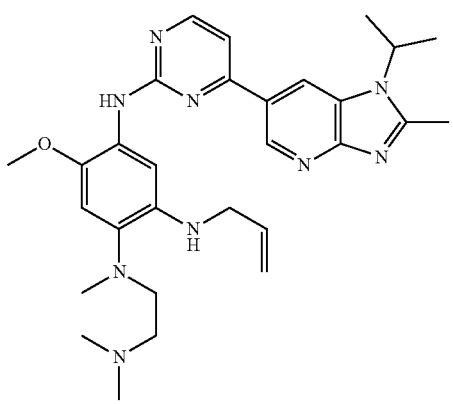

Step 1 Synthesis of Compound N$^1$-(2-(dimethyl-amino)ethyl)-N$^4$-(4-(1-isopropyl-2-methyl-1H-imidazo[4,5-b]pyridine-6-yl) pyrimidin-2-yl)-5-methoxy-N$^1$-methyl-2-nitrobenzene-1,4-diamine The synthetic step is the same as that of Example 20 step 1, and 270 mg of a brown-yellow oil was obtained. Yield was 52.1%. LC-MS(APCI): m/z=520.1 (M+1).

Step 2 Synthesis of Compound N-(2-(dimethyl-amino)ethyl)-N$^4$-(4-(1-isopropyl-2-methyl-1H-imidazo[4,5-b]pyridine-6-yl) pyrimidin-2-yl)-5-methoxy-N$^1$-methylbenzene-1,2,4-triamine The synthetic step is the same as that of Example 20 step 2, and 90 mg of a yellow solid was obtained. LC-MS(APCI): m/z=490.2 (M+1).

Step 3 Synthesis of Compound N-(2-((2-(dimethyl-amino)ethyl)(methyl)amino)-5-((4-(1-isopropyl-2-methyl-1H-imidazo[4,5-b]pyridine-6-yl)pyrimidin-2-yl)amino)-4-methoxyphenyl)acrylamide The synthetic step is the same as that of Example 20 step 3, and 15 mg of a yellow solid product was obtained. HPLC: 97.19%. LC-MS(APCI): m/z=543.5 (M+1), $^1$H NMR (500 MHz, DMSO-d6): δ 9.98 (s, 1H), 9.11 (d, J=1.8 Hz, 1H), 8.78 (s, 1H), 8.63 (d, J=1.8 Hz, 1H), 8.48 (d, J=5.2 Hz, 1H), 8.29 (s, 1H), 7.56 (d, J=5.3 Hz, 1H), 6.99 (s, 1H), 6.78-6.45 (m, 1H), 6.20 (dd, J=17.0, 1.8 Hz, 1H), 5.71 (d, J=11.7 Hz, 1H), 4.86-4.72 (m, 1H), 3.83 (s, 3H), 3.07-2.91 (m, 2H), 2.66 (s, 3H), 2.63 (s, 3H), 2.49-2.47 (m, 2H), 2.36 (s, 6H), 1.54 (d, J=6.9 Hz, 6H).

Example 23 Preparation of N$^1$-(2-(2-(dimethyl-amino)ethyl)(methyl)amino)-5-((4-(1-isopropyl-2-methoxy-1H-imidazo[4,5-b]pyridine-6-yl)pyrimidin-2-yl)amino)-4-methoxyphenyl)acrylamide

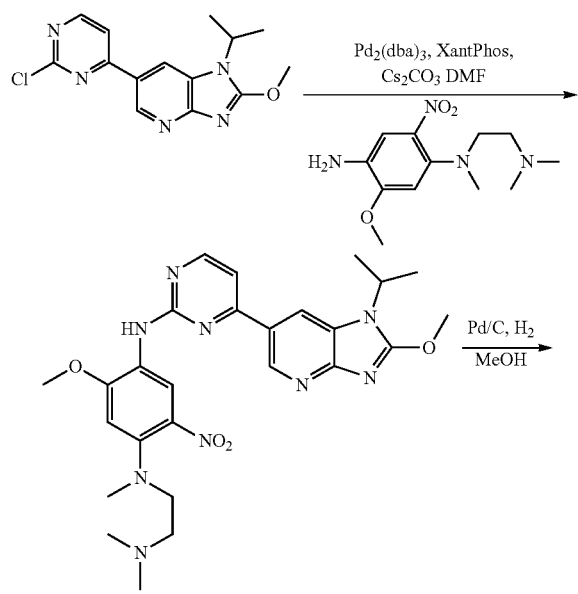

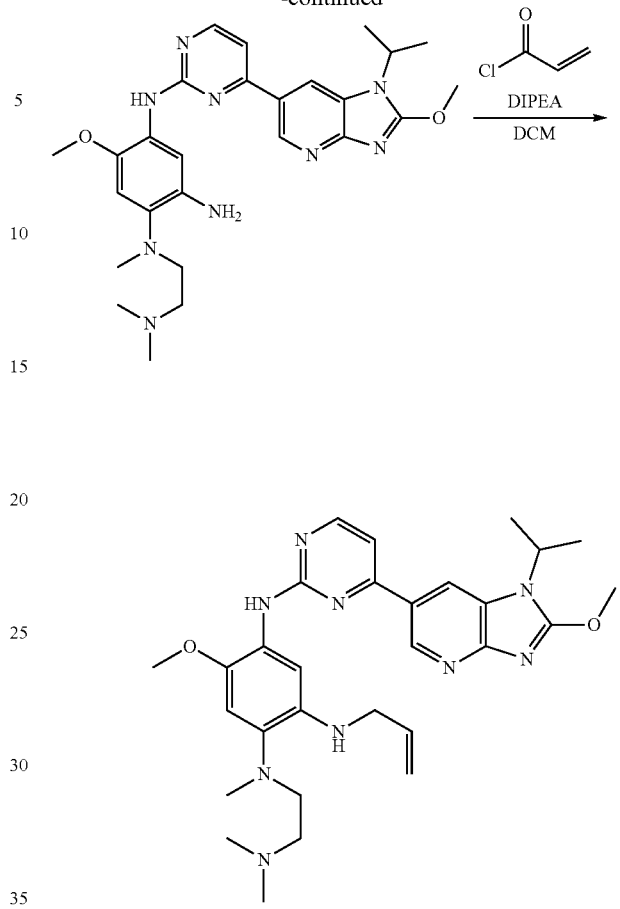

Step 1 Synthesis of Compound N-(2-(dimethyl-amino)ethyl)-N$^4$-(4-(1-isopropyl-2-methoxy-H-imidazo[4,5-b]pyridine-6-yl)pyrimidin-2-yl)-5-methoxy-N$^1$-methyl-2-nitrobenzenzene-1,4-diamine The synthetic step is the same as that of Example 20 step 1, and 100 mg of a brown-yellow oil was obtained. LC-MS (APCI): m/z=536.2 (M+1).

Step 2 Synthesis of Compound N$^1$-(2-(dimethyl-amino)ethyl)-N$^4$-(4-(1-isopropyl-2-methoxy-1H-imidazo[4,5-b]pyridine-6-yl)pyrimidin-2-yl)-5-methoxy-N$^1$-methylbenzene-1,2,4-triamine The synthetic step is the same as that of Example 20 step 2, and 35 mg of a yellow solid was obtained, LC-MS(APCI): m/z=506.3 (M+1).

Step 3 Synthesis of Compound N-(2-((2-(dimethyl-amino)ethyl)(methyl)amino)-5-((4-(1-isopropyl-2-methoxy-1H-imidazo[4,5-b]pyridine-6-yl)pyrimidin-2-yl)amino)-4-methoxyphenyl)acrylamide The synthetic step is the same as that of Example 20 step 3, and 8 mg solid was obtained, yield was 20.4%. Yield: 93.68%. LC-MS(APCI): m/z=560.2 (M+1).

Example 24 Preparation of N-(2-((2-(dimethyl-amino)ethyl)(methyl)amino)-5-((4-(1-isopropyl-2-methoxy-1H-benzo[d]imidazole-6-yl)pyrimidin-2-yl)amino)-4-methoxyphenyl)acrylamide

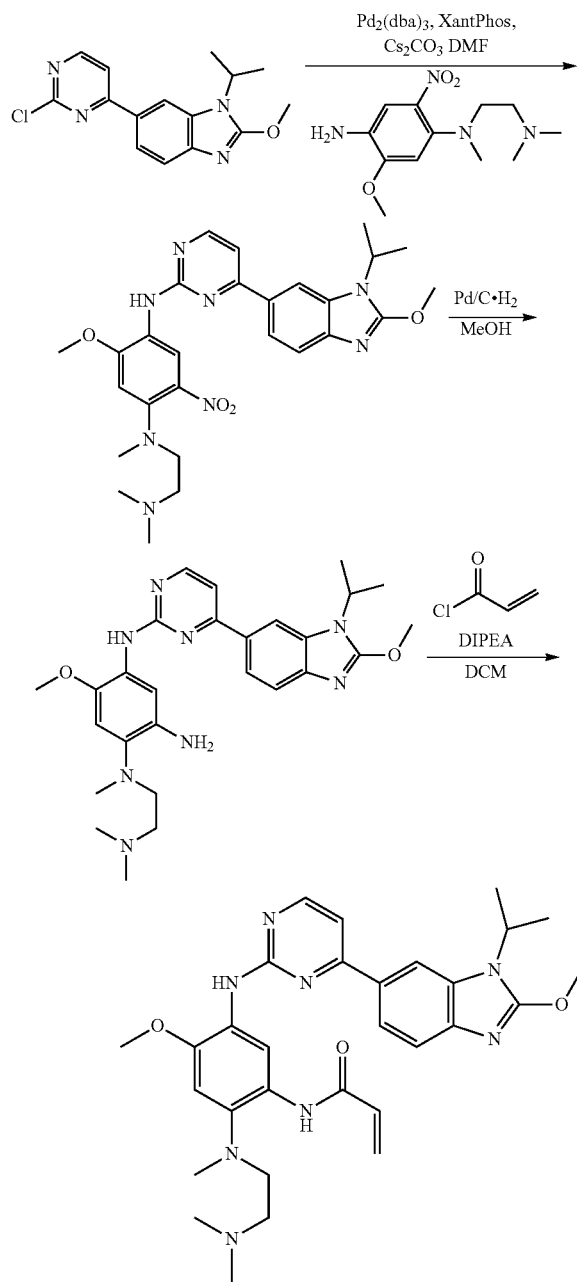

Step 1 Synthesis of Compound N¹-(2-(dimethyl-amino)ethyl)-N⁴-(4-(1-isopropyl-2-methoxy-1H-benzo[4,5-b]imidazol-6-yl) pyrimidin-2-yl)-5-methoxy-N¹-methyl-2-nitrobenzene-1,4-diamine The synthetic step is the same as that of Example 20 step 1, and a brown-yellow oil was obtained. LC-MS(APCI): m/z=535.1 (M+1).

Step 2 Synthesis of Compound N¹-(2-(dimethyl-amino)ethyl)-N⁴-(4-(1-isopropyl-2-methoxy-1H-benzo[4,5-b]imidazol-6-yl) pyrimidin-2-yl)-5-methoxy-N¹-methylbenzene-1,2,4-triamine The synthetic step is the same as that of Example 20 step 2, and 300 mg a brown-yellow solid was obtained, yield over two steps: 61.9%. LC-MS(APCI): m/z=505.1 (M+1).

Step 3 Synthesis of Compound N-(2-((2-(dimethyl-amino)ethyl)(methyl)amino)-5-((4-(1-isopropyl-2-methoxy-1H-benzo[d]imidazole-6-yl)pyrimidin-2-yl)amino)-4-methoxyphenyl)acrylamide The synthetic step is the same as that of Example 20 step 3, and 200 mg solid was obtained, yield was 59.6%. HPLC: 94.26%. LC-MS(APCI): m/z=559.1 (M+1), 1H NMR (500 MHz, DMSO-d6): δ 10.07 (s, 1H), 8.94 (s, 1H), 8.43 (d, J=5.3 Hz, 1H), 8.11 (s, 1H), 8.05 (d, J=8.5 Hz, 1H), 7.98 (s, 1H), 7.44 (d, J=5.3 Hz, 1H), 7.21 (d, J=8.3 Hz, 1H), 7.01 (s, 1H), 6.47-6.35 (m, 1H), 6.24 (dd, J=16.9, 1.9 Hz, 1H), 5.77-5.70 (m, 1H), 4.69-4.58 (m, 1H), 3.83 (s, 3H), 3.34 (s, 3H), 2.92-2.83 (m, 2H), 2.69 (s, 3H), 2.41-2.28 (m, 2H), 2.22 (s, 6H), 1.44 (d, J=6.9 Hz, 6H).

Example 25 Preparation of N-(2-((2-(dimethyl-amino)ethyl)(methyl)amino)-4-methoxy-5-((4-(3-methyl-2-oxo-2,3-di hydrobenzo[d]oxazole-5-yl)pyrimidin-2-yl)amino)phenyl)acrylamide

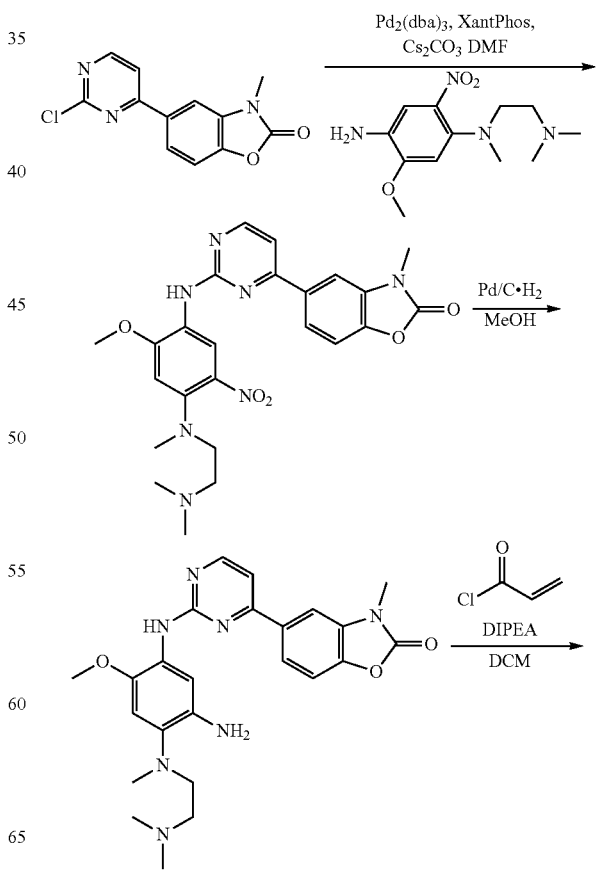

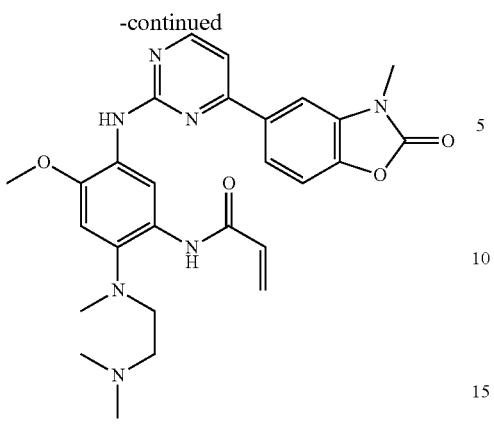

Step 1 Synthesisq of Compound 5-(2-((4-((2-(dimethylamino)ethyl)(methyl)amino)-2-methoxy-5-nitrobenzene)amino)pyrimidin-4-yl)-3-methylbenzo[d]oxazole-2(3H)-one The synthetic step is the same as that of Example 20 step 1, and the filtrate was separated on column chromatography (eluant:dichloromethane/methanol (v/v)=12:1), to afford a brown-yellow oil. LC-MS(APCI): m/z=494.0 (M+1).

Step 2 Synthesis of Compound 5-(2-((5-amino-4-((2-(dimethylamino)ethyl)(methyl)amino)-2-methoxyphenyl)amino)pyrimi din-4-yl)-3-methyl-benzo[d]oxazole-2(3H)-one The synthetic step is the same as that of Example 20 step 2, and 110 mg of a brown-yellow solid was obtained, yield over two steps: 20%. LC-MS(APCI): m/z=461.1 (M+1).

Step 3 Synthesis of Compound N-(2-((2-(dimethylamino)ethyl)(methyl)amino)-4-methoxy-5-((4-(3-methyl-2-oxo-2,3-dihydrobenzo[d]oxazole-5-yl)pyrimidin-2-yl)amino)phenyl)acrylamide The synthetic step is the same as that of Example 20 step 3, and 60 mg product was obtained, yield was 50.4%. HPLC: 97.83%. LC-MS(APCI): m/z=518.1 (M+1), $^1$H NMR (400 MHz, DMSO-d6): δ 10.06 (s, 1H), 9.11 (s, 1H), 8.52 (d, J=5.2 Hz, 1H), 8.13-8.07 (m, 3H), 7.47 (d, J=5.3 Hz, 1H), 7.42 (d, J=8.1 Hz, 1H), 7.02 (s, 1H), 6.63-6.48 (m, 1H), 6.30-6.18 (m, 1H), 5.79-5.75 (m, J=10.4 Hz, 1H), 3.88 (s, 3H), 3.39 (s, 3H), 2.98 (s, 2H), 2.68 (s, 3H), 2.59-2.51 (m, 2H), 2.34 (s, 6H).

Example 26 Preparation of N-(2-((2-(dimethylamino)ethyl)(methyl)amino)-5-((4-(4-fluoro-1-isopropyl-1H-indazole-6-yl)pyrimidin-2-yl)amino)-4-methoxyphenyl)acrylamide

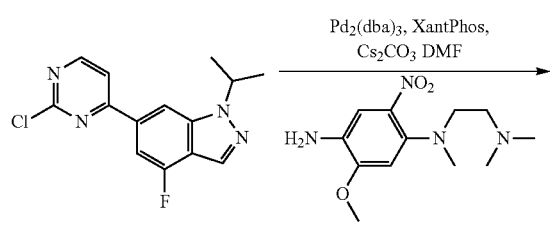

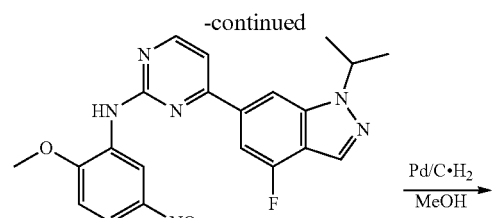

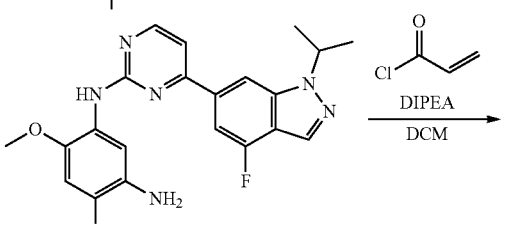

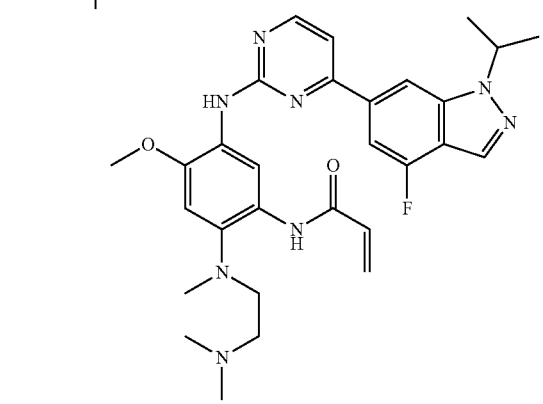

Step 1 Synthesis of Compound N$^1$-(2-(dimethylamino)ethyl)-N$^4$-(4-(4-fluoro-1-isopropyl-1H-indazole-6-yl)pyrimidin-2-yl)-5-methoxy-N$^1$-methyl-2-nitrobenzene-1,4-diamine The synthetic step is the same as that of Example 20 step 1, and the filtrate was separated on column chromatography (eluant:dichloromethane/methanol (v/v)=12:1), to afford a brown-yellow solid. LC-MS(APCI): m/z=523.1 (M+1).

Step 2 Synthesis of Compound N$^1$-(2-(dimethylamino)ethyl)-N$^4$-(4-(4-fluoro-1-isopropyl-1H-indazole-6-yl)pyrimidin-2-yl)-5-methoxy-N$^1$-methylbenzene-1,2,4-triamine The synthetic step is the same as that of Example 20 step 2, and 360 mg of an orange-yellow solid was obtained, yield over two steps: 47.4%. LC-MS(APCI): m/z=493.2 (M+1).

Step 3 Synthesis of Compound N-(2-((2-(dimethylamino)ethyl)(methyl)amino)-5-((4-(4-fluoro-1-isopropyl-1H-indazole-6-yl)pyrimidin-2-yl)amino)-4-methoxyphenyl)acrylamide The synthetic step is the same as that of Example 20 step 3, and 220 mg of a yellow solid was obtained, yield was 55.1%. HPLC: 97.27%. LC-MS(APCI): m/z=547.2 (M+1), $^1$H NMR (400 MHz, DMSO-d6): δ 10.13 (s, 1H), 9.11 (s, 1H), 8.56 (d, J=5.2 Hz, 1H), 8.42 (s, 1H), 8.24 (s, 1H), 8.20 (s, 1H), 7.84 (d, J=11.7 Hz, 1H), 7.60 (d, J=5.2 Hz, 1H), 7.03 (s, 1H), 6.50-6.38 (m, 1H), 6.27 (dd, J=16.8, 1.7 Hz, 1H), 5.76 (dd, J=10.1, 1.6 Hz, 1H), 5.17 (dt, J=13.3, 6.6 Hz, 1H), 3.86 (s, 3H), 2.95-2.86 (m, 2H), 2.70 (s, 3H), 2.41-2.31 (m, 2H), 2.24 (s, 6H), 1.49 (d, J=6.5 Hz, 6H).

Example 27 Preparation of N-(2-((2-(dimethylamino)ethyl)(methyl)amino)-5-((4-(1-isopropyl-1H-indazole-6-yl)pyrimidin-2-yl)amino)-4-methoxyphenyl)acrylamide

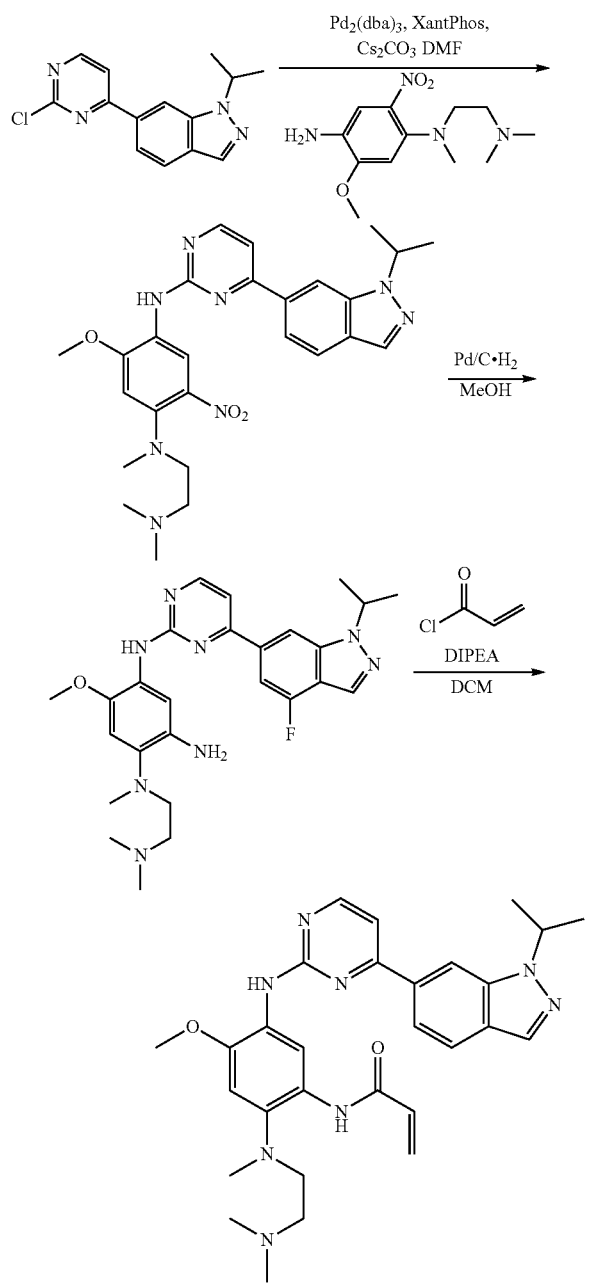

Step 1 Synthesis of Compound N$^1$-(2-(dimethylamino)ethyl)-N$^4$-(4-(1-isopropyl-1H-indazole-6-yl)pyrimidin-2-yl)-5-methoxy-N$^1$-methyl-2-nitrobenzene-1,4-diamine The synthetic step is the same as that of Example 20 step 1, and the filtrate was separated on column chromatography (eluant:dichloromethane/methanol (v/v)=12:1), to afford 360 mg of a brown-yellow solid. LC-MS(APCI): m/z=505.1 (M+1).

Step 2 Synthesis of Compound N$^1$-(2-(dimethylamino)ethyl)-N$^4$-(4-(4-fluoro-1-isopropyl-1H-indazole-6-yl)pyrimidin-2-yl)-5-methoxy-N$^1$-methylbenzene-1,2,4-triamine The synthetic step is the same as that of Example 20 step 2, and 258 mg of a yellow solid was obtained, yield over two steps: 51.3%. LC-MS(APCI): m/z=475.2 (M+1).

Step 3 Synthesis of Compound N-(2-((2-(dimethylamino)ethyl)(methyl)amino)-5-((4-(1-isopropyl-1H-indazole-6-yl)pyrimidin-2-yl)amino)-4-methoxyphenyl)acrylamide The synthetic step is the same as that of Example 20 step 3, and 135 mg of a yellow solid was obtained, yield was 46.2%. HPLC: 98.60%. LC-MS(APCI): m/z=543.2 (M+1), $^1$H NMR (400 MHz, DMSO-d6): δ 10.12 (s, 1H), 9.11 (s, 1H), 8.63-8.46 (m, 2H), 8.14 (d, J=4.6 Hz, 2H), 8.04 (d, J=8.3 Hz, 1H), 7.84 (d, J=8.5 Hz, 1H), 7.56 (d, J=5.1 Hz, 1H), 7.03 (s, 1H), 6.56-6.39 (m, 1H), 6.27 (d, J=15.9 Hz, 1H), 5.77 (d, J=10.0 Hz, 1H), 5.23-5.02 (m, 1H), 3.87 (s, 3H), 2.96-2.86 (m, 2H), 2.70 (s, 3H), 2.45-2.32 (m, 2H), 2.25 (s, 6H), 1.48 (d, J=6.5 Hz, 6H).

Example 28 Preparation of N-(2-((2-(dimethylamino)ethyl)(methyl)amino)-5-((4-(8-fluoro-3-isopropyl-2-methylimidazo[1,2-a]pyridine-6-yl)pyrimidin-2-yl)amino)-4-methoxyphenyl)acrylamide

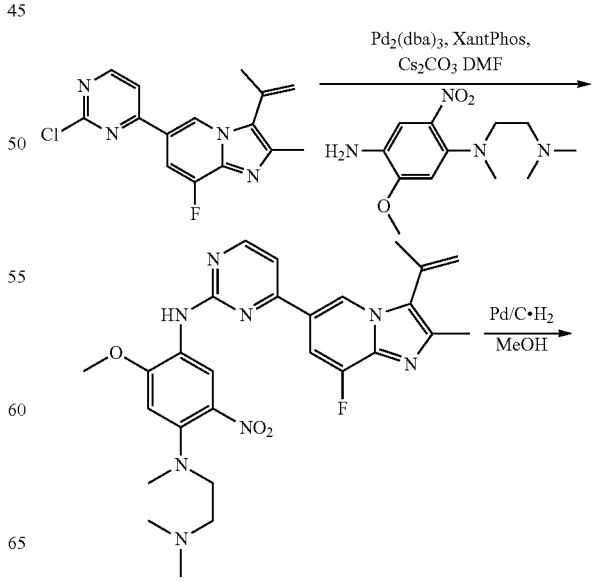

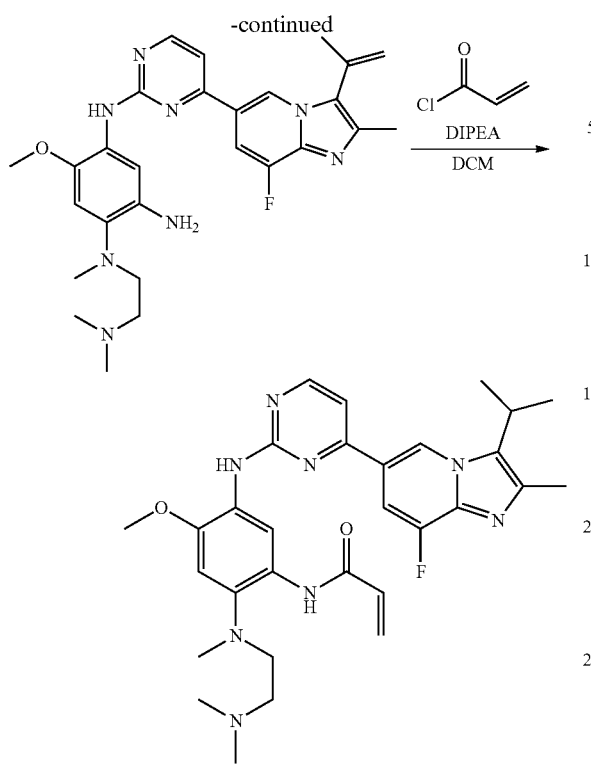

Step 1 Synthesis of Compound $N^1$-(2-(dimethyl-amino)ethyl)-$N^4$-(4-(8-fluoro-2-methyl-3-(prop-1-en-2-yl)imidazo[1,2-a]pyridine-6-yl)pyrimidin-2-yl)-5-methoxy-$N^1$-methyl-2-nitrobenzene-1,4-diamine The synthetic step is the same as that of Example 20 step 1, and the filtrate was separated on column chromatography (eluant:dichloromethane/methanol (v/v)=12:1), to afford a brown-yellow solid. LC-MS(APCI): m/z=535.2 (M+1).

Step 2 Synthesis of Compound $N^1$-(2-(dimethyl-amino)ethyl)-$N^4$-(4-(8-fluoro-2-methyl-3-(prop-1-en-2-yl)imidazo[1,2-a]pyridine-6-yl)pyrimidin-2-yl)-5-methoxy-$N^1$-methylbenzene-1,2,4-triamine The synthetic step is the same as that of Example 20 step 2, and 336 mg of an orange-yellow solid was obtained, yield over two steps: 47.3%. LC-MS(APCI): m/z=507.2 (M+1).

Step 3 Synthesis of Compound N-(2-((2-(dimethyl-amino)ethyl)(methyl)amino)-5-((4-(8-fluoro-3-iso-propyl-2-methylimidazo[1,2-a]pyridine-6-yl)pyrimi-din-2-yl)amino)-4-methoxyphenyl)acrylamide The synthetic step is the same as that of Example 20 step 3, and 120 mg of a yellow solid was obtained, yield was 55.1%. HPLC: 95.47%. LC-MS(APCI): m/z=561.2 (M+1), $^1$H NMR (400 MHz, DMSO-d6): δ 10.10 (s, 1H), 9.03 (d, J=4.0 Hz, 1H), 8.87 (s, 1H), 8.54-8.42 (m, 1H), 8.22 (s, 1H), 7.92 (d, J=12.2 Hz, 1H), 7.55 (M, 1H), 7.00 (s, 1H), 6.41 (dd, J=15.1, 11.2 Hz, 1H), 6.24 (d, J=17.1 Hz, 1H), 5.73 (d, J=9.7 Hz, 1H), 3.83 (s, 3H), 3.60-3.50 (m, 1H), 2.91-2.80 (m, 2H), 2.68 (s, 3H), 2.40 (s, 3H), 2.37-2.28 (m, 2H), 2.21 (s, 6H), 1.31 (d, J=6.4 Hz, 6H).

Example 29 Preparation of N-(2-((2-(dimethyl-amino)ethyl)(methyl)amino)-5-((4-(8-fluoro-2-meth-ylimidazo[1,2-a]pyridine-6-yl)pyrimidin-2-yl)amino)-4-methoxyphenyl)acrylamide

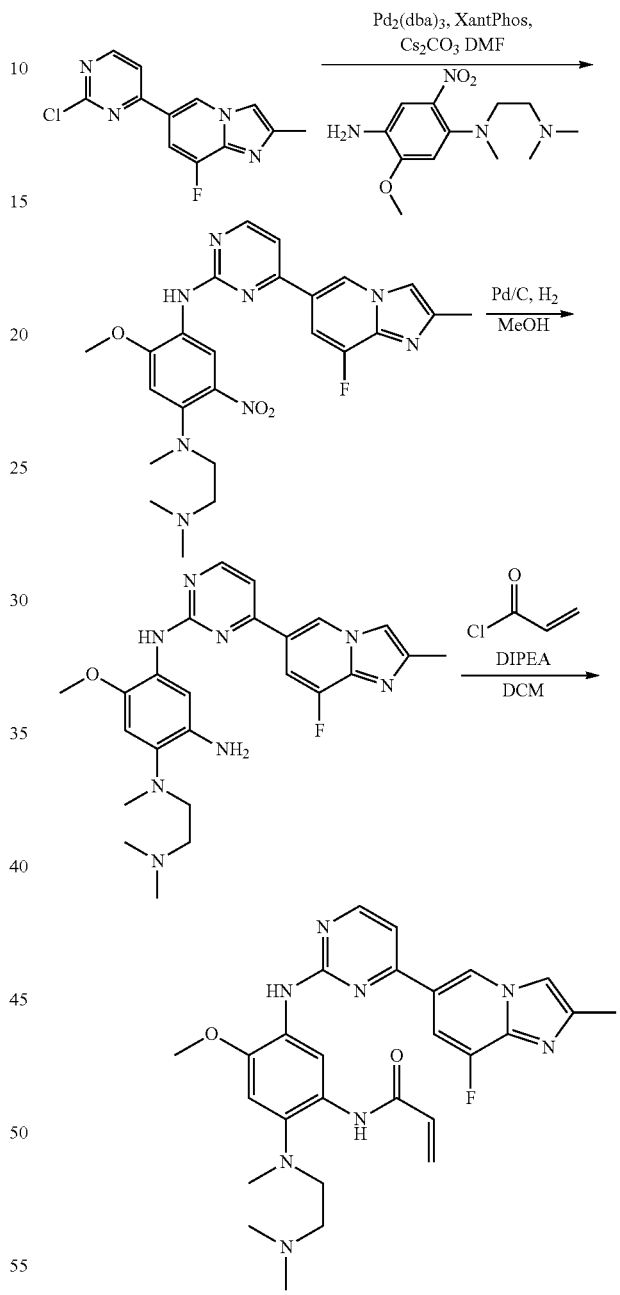

Step 1 Synthesis of Compound $N^1$-(2-(dimethyl-amino)ethyl)-$N^4$-(4-(8-fluoro-2-methyl-imidazo[1,2-a]pyridine-6-yl)pyrimidin-2-yl)-5-methoxy-$N^1$-methyl-2-nitrobenzene-1,4-diamine The synthetic step is the same as that of Example 20 step 1, and the filtrate was separated on column chromatography (eluant:dichloromethane/methanol (v/v)=12:1), to afford a brown-yellow solid. LC-MS(APCI): m/z=495.1 (M+1).

Step 2 Synthesis of Compound N¹-(2-(dimethyl-amino)ethyl)-N⁴-(4-(8-fluoro-2-methyl-imidazo[1,2-a]pyridine-6-yl)pyrimidin-2-yl)-5-methoxy-N¹-methylbenzene-1,2,4-triamine The synthetic step is the same as that of Example 20 step 2, and 160 mg of an orange-yellow solid was obtained, yield over two steps: 30.2%. LC-MS(APCI): m/z=465.2 (M+1).

Step 3 Synthesis of Compound N-(2-((2-(dimethyl-amino)ethyl)(methyl)amino)-5-((4-(8-fluoro-2-methylimidazo[1,2-a]pyridine-6-yl)pyrimidin-2-yl)amino)-4-methoxyphenyl)acrylamide The synthetic step is the same as that of Example 20 step 3, and 108 mg of a yellow solid was obtained, yield was 59.6%. HPLC: 97.92%. LC-MS(APCI): m/z=519.2 (M+1), ¹H NMR (400 MHz, DMSO-d6): 1H NMR (500 MHz, DMSO-d6): δ 10.24 (s, 1H), 9.62 (s, 1H), 9.32 (s, 1H), 8.52 (d, J=5.0 Hz, 1H), 8.00 (s, 2H), 7.89 (d, J=12.6 Hz, 1H), 7.42 (d, J=4.9 Hz, 1H), 7.04 (s, 1H), 6.49 (dd, J=15.9, 10.1 Hz, 1H), 6.33 (d, J=16.9 Hz, 1H), 5.84 (d, J=10.4 Hz, 1H), 3.89 (s, 3H), 2.94-2.85 (m, 2H), 2.70 (s, 3H), 2.37 (s, 3H), 2.35-2.28 (m, 2H), 2.23 (s, 6H).

Example 30 Preparation of N-(5-((4-(4-(tert-butoxy)-1-isopropyl-2-methyl-1H-benzo[d]imidazole-6-yl)pyrimidin-2-yl)amino)-2-((2-(dimethylamino)ethyl)(methyl)amino)-4-methoxyphenyl)acrylamide

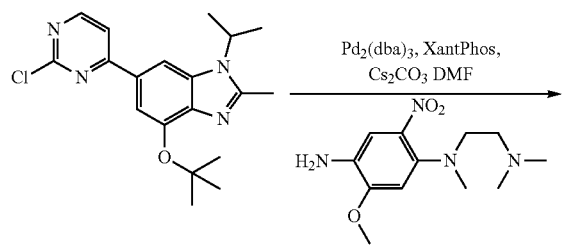

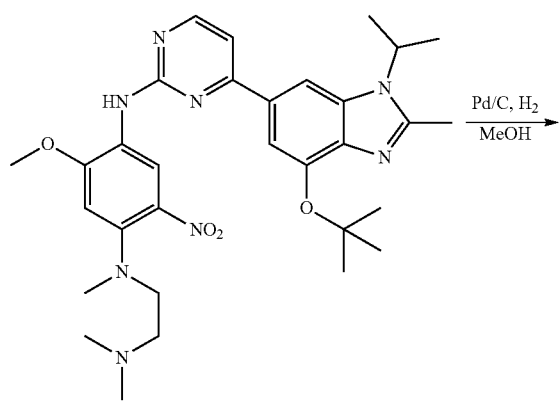

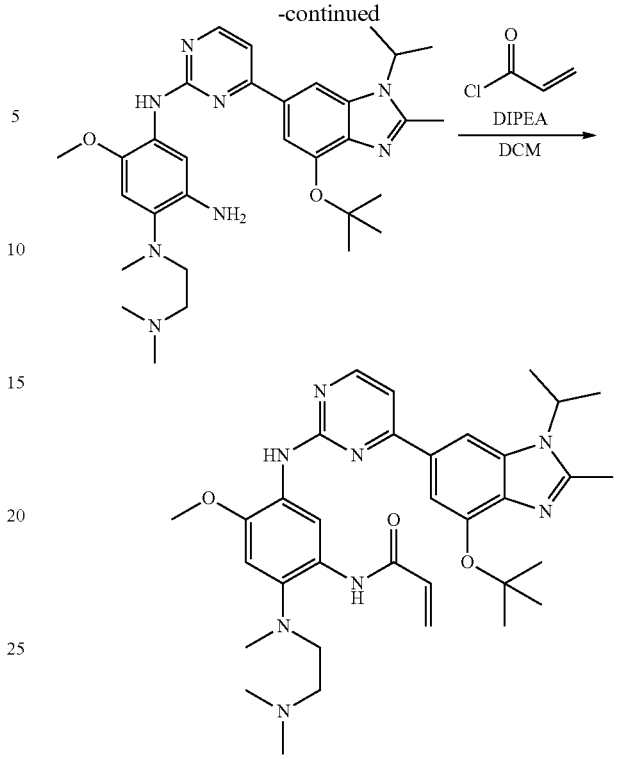

Step 1 Synthesis of Compound N¹-(4-(4-(tert-butoxy)-1-isopropyl-2-methyl-1H-benzo[d]imidazole-6-yl)pyrimidin-2-yl)-N⁴-(2-(dimethylamino)ethyl)-2-methoxy-N⁴-methyl-5-nitrobenzene-1,4-diamine The synthetic step is the same as that of Example 20 step 1, and a brown-yellow solid was obtained. LC-MS(APCI): m/z=591.2 (M+1).

Step 2 Synthesis of Compound N⁴-(4-(4-tert-butoxy)-1-isopropyl-2-methyl-1H-benzo[d]imidazole-6-yl)pyrimidin-2-yl)-N¹-(2-(dimethylamino)ethyl)-5-methoxy-N¹-methylbenzene 1,2,4-triamine The synthetic step is the same as that of Example 20 step 2, and 220 mg of a pale yellow solid was obtained, yield over two steps: 30.2%. LC-MS(APCI): m/z=561.3 (M+1).

Step 3 Synthesis of Compound N-(5-((4-(4-(tert-butoxy)-1-isopropyl-2-methyl-1H-benzo[d]imidazole-6-yl)pyrimidin-2-yl)amino)-2-((2-(dimethylamino)ethyl)(methyl)amino)-4-methoxyphenyl) acrylamide The synthetic step is the same as that of Example 20 step 3, and 54 mg of a yellow solid was obtained, yield was 23.4%. HPLC: 96.88%. LC-MS(APCI): m/z=615.4 (M+1), ¹H NMR (400 MHz, DMSO-d6): δ 9.96 (s, 1H), 8.69 (s, 1H), 8.44 (d, J=5.2 Hz, 1H), 8.20 (s, 1H), 8.06 (s, 1H), 7.50 (s, 1H), 7.43 (d, J=5.3 Hz, 1H), 7.00 (s, 1H), 6.79-6.48 (m, 1H), 6.20 (d, J=15.8 Hz, 1H), 5.72 (d, J=11.1 Hz, 1H), 4.87-4.68 (m, 1H), 3.84 (s, 3H), 3.12-2.95 (m, 2H), 2.67 (s, 3H), 2.57 (s, 3H), 2.50-2.49 (m, 2H), 2.41 (s, 6H), 1.55 (d, J=6.8 Hz, 6H), 1.37 (s, 9H).

Example 31 Preparation of N-(2-((2-(dimethyl-amino)ethyl)(methyl)amino)-5-((4-(7-fluoro-2-methylbenzo[d]oxazole-5-yl)pyrimidin-2-yl)amino)-4-methoxyphenyl)acrylamide

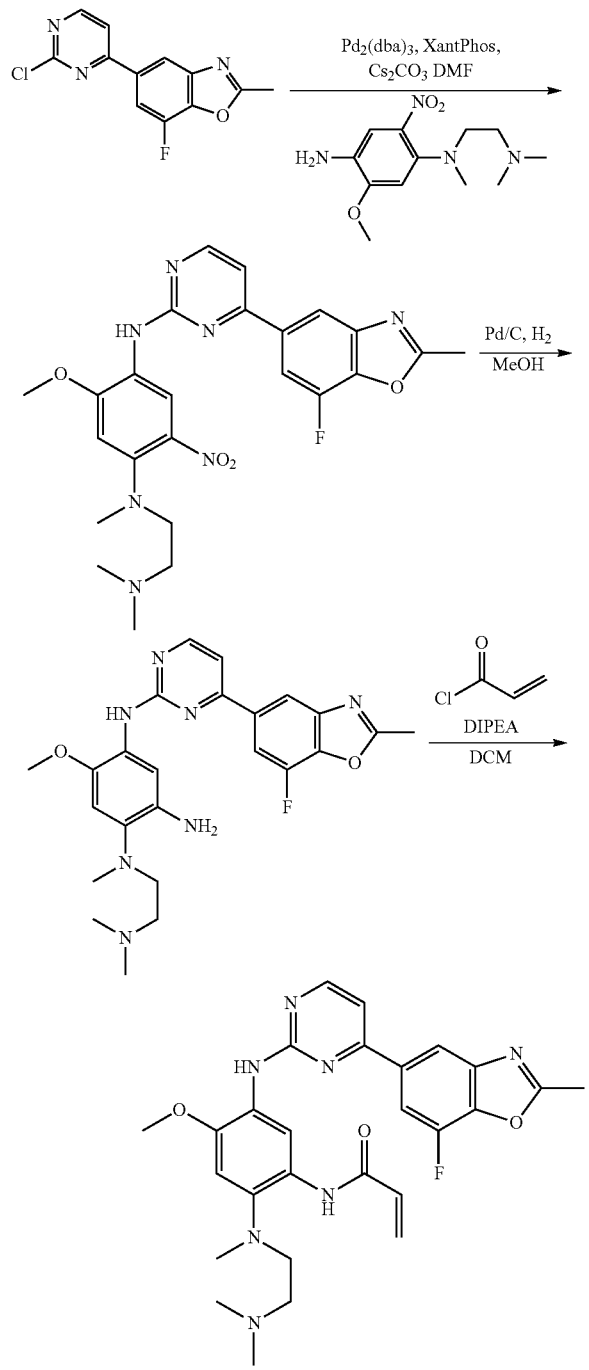

Step 1 Synthesis of Compound N$^1$-(2-(dimethylamino)ethyl)-N$^4$-(4-(7-fluoro-2-methylbenzo[d]oxazole-5-yl)pyrimidin-2-yl)-5-methoxy-N methyl-2-nitrobenzene-1,4-diamine The synthetic step is the same as that of Example 20 step 1, and the filtrate was separated on column chromatography (eluant:dichloromethane/methanol (v/v)=12:1), to afford a brown-yellow solid. LC-MS(APCI): m/z=496.2 (M+1).

Step 2 Synthesis of Compound N$^1$-(2-(dimethylamino)ethyl)-N$^4$-(4-(7-fluoro-2-methylbenzo[d]oxazole-5-yl)pyrimidin-2-yl)-5-methoxy-N$^1$-methyl-2-nitrobenzene-1,2,4-triamine The synthetic step is the same as that of Example 20 step 2, and 125 mg of an orange-yellow solid was obtained, yield over two steps: 23.5%. LC-MS(APCI): m/z 496.2 (M+1). 466.1 (M+1).

Step 3 Synthesis of Compound N-(2-((2-(dimethylamino)ethyl)(methyl)amino)-5-((4-(7-fluoro-2-methylbenzo[d]oxazole-5-yl)pyrimidin-2-yl)amino)-4-methoxyphenyl)acrylamide The synthetic step is the same as that of Example 20 step 3, and the filtrate was separated on column chromatography (eluant:dichloromethane/methanol (v/v)=12:1) to afford 55 mg of a pale yellow solid, yield was 41.0%. HPLC: 91.53%. LC-MS(APCI): m/z=520.2 (M+1), $^1$H NMR (500 MHz, DMSO-d$_6$): δ 10.05 (s, 1H), 9.12 (s, 1H), 8.51 (d, J=5.2 Hz, 1H), 8.38 (s, 1H), 8.29 (d, J=11.5 Hz, 1H), 8.15 (s, 1H), 7.54 (d, J=5.2 Hz, 1H), 7.00 (s, 1H), 6.52-6.41 (m, 1H), 6.38-6.30 (m, 1H), 5.78-5.71 (m, 1H), 3.85 (s, 3H), 2.99-2.86 (m, 2H), 2.67 (s, 3H), 2.66 (s, 3H), 2.46-2.36 (m, 2H), 2.28 (s, 6H).

Example 32 Preparation of N-(2-((2-(dimethyl-amino)ethyl)(methyl)amino)-5-((4-(4-fluoro-2-methylbenzo[d]oxazole-6-yl)pyrimidin-2-yl)amino)-4-methoxyphenyl)acrylamide

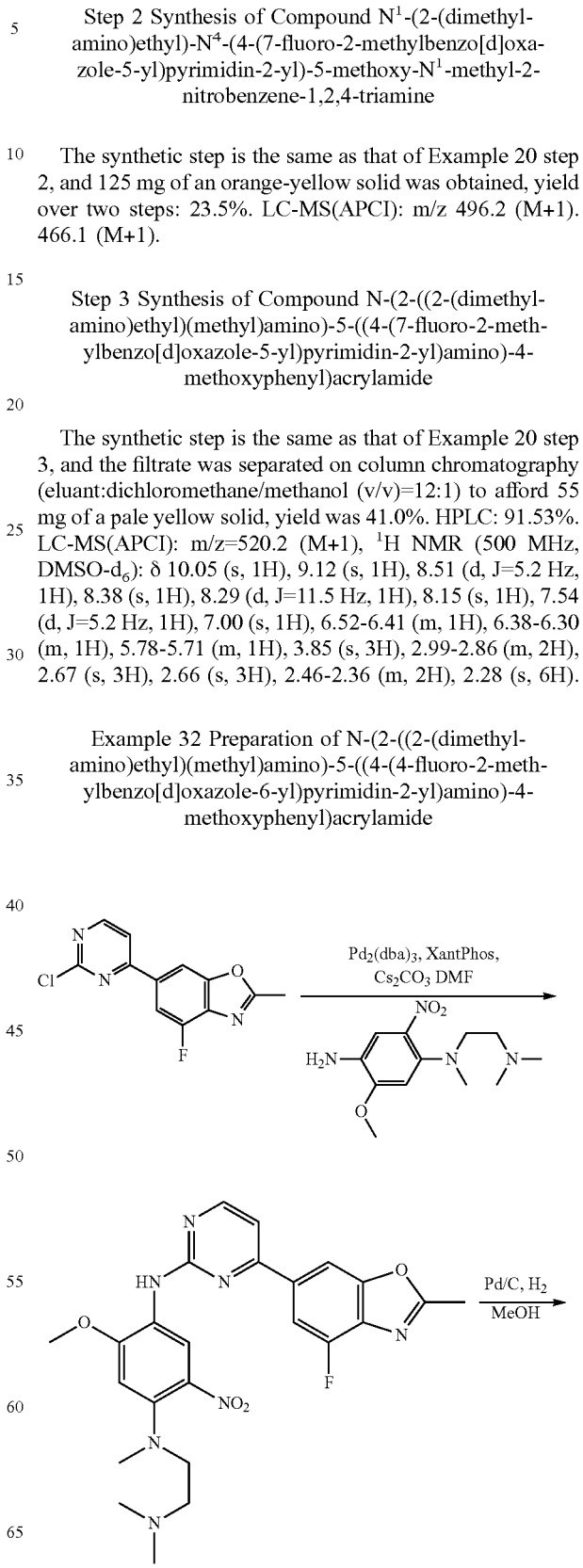

-continued

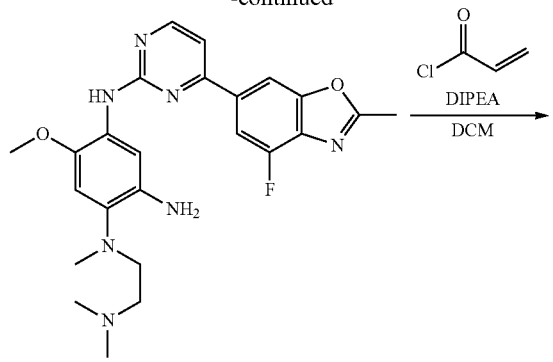

Step 1 Synthesis of Compound $N^1$-(2-(dimethylamino)ethyl)-$N^4$-(4-(4-fluoro-2-methylbenzo[d]oxazole-6-yl)pyrimidin-2-yl)-5-methoxy-N-methyl-2-nitrobenzene-1,4-diamine The synthetic step is the same as that of Example 20 step 1, and the filtrate was separated on column chromatography (eluant:dichloromethane/methanol (v/v)=12:1), to afford a brown-yellow solid. LC-MS(APCI): m/z=496.2 (M+1).

Step 2 Synthesis of Compound $N^1$-(2-(dimethylamino)ethyl)-$N^4$-(4-(4-fluoro-2-methylbenzo[d]oxazole-6-yl)pyrimidin-2-yl)-5-methoxy-$N^1$-methylbenzene-1,2,4-triamine The synthetic step is the same as that of Example 20 step 2, and 125 mg of an orange-yellow solid was obtained, yield over two steps: 23.5%. LC-MS(APCI): m/z=466.1 (M+1).

Step 6 Synthesis of Compound N-(2-((2-(dimethylamino)ethyl)(methyl)amino)-5-((4-(4-fluoro-2-methylbenzo[d]oxazole-6-yl)pyrimidin-2-yl)amino)-4-methoxyphenyl)acrylamide The synthetic step is the same as that of Example 20 step 3, and the filtrate was separated on column chromatography (eluant:dichloromethane/methanol (v/v)=12:1) to afford 10 mg of a pale yellow solid, yield was 98.43% (HPLC). LC-MS(APCI): m/z=520.2 (M+1).

Example 33 Preparation of N-(2-((2-(dimethylamino)ethyl)(methyl)amino)-5-((4-(7-fluorobenzo[d]oxazole-5-yl)pyrimidin-2-yl)amino)-4-methoxyphenyl)acrylamide

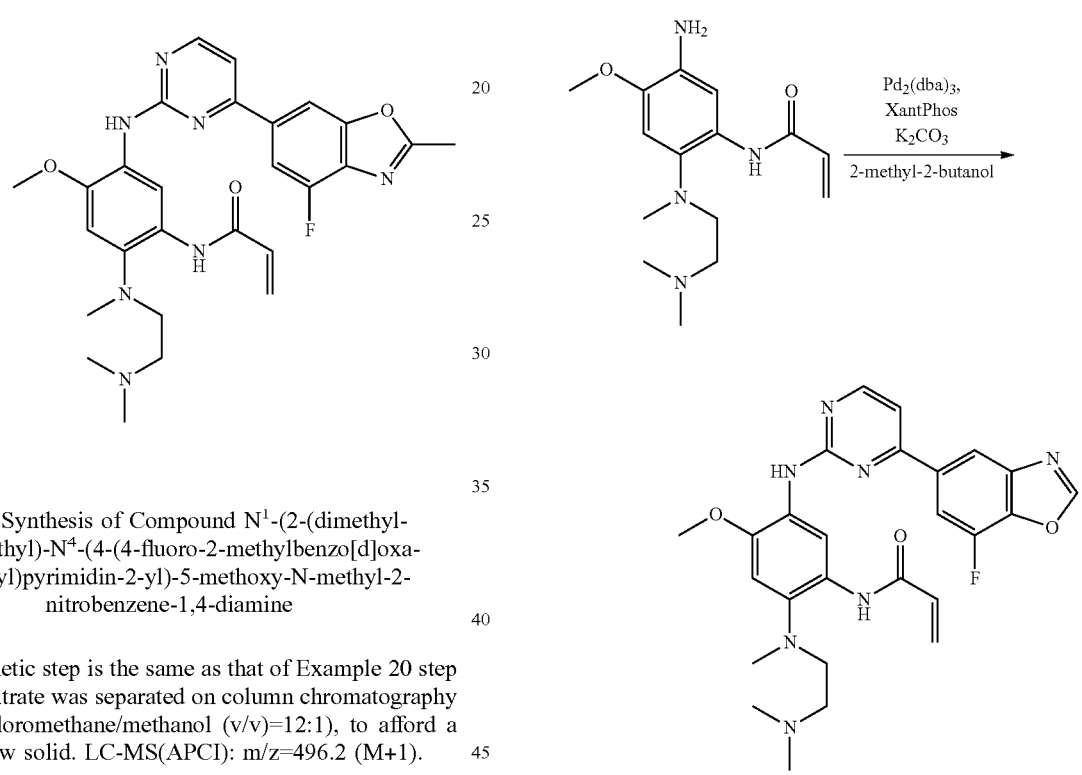

Under nitrogen protection, $Pd_2(dba)_3$ (94 mg) and Xantphos (120 mg) were added into intermediate compound 5-(2-chloropyrimidin-4-yl)-7-fluoro-benzo[d]oxazole (190 mg, 0.76 mmol), N-(5-amino-2-((2-(dimethylamino)ethyl)(methyl)amino)-4-methoxyphenyl)acrylamide (220 mg, 0.75 mmol) and potassium carbonate (270 mg, 1.90 mmol) in anhydrous 2-methyl-2-butanol (20 mL), and the reaction mixture was reacted under nitrogen protection at 100° C. for 3 hrs overnight. After cooling to room temperature, it was filtered on Celite, concentrated under reduced pressure, and the filtrate was separated on column chromatography (eluant:dichloromethane/methanol (v/v)=12:1), to afford 40 mg of a brown-yellow solid. Yield was 10.4%. HPLC: 96.01%. LC-MS(APCI): m/z=506.2 (M+1), $^1$H NMR (500 MHz, DMSO-$d_6$): δ 10.13 (s, 1H), 9.19 (s, 1H), 8.93 (s, 1H), 8.57 (s, 1H), 8.54 (d, J=5.1 Hz, 1H), 8.41 (d, J=11.6 Hz, 1H), 8.18 (s, 1H), 7.59 (d, J=5.1 Hz, 1H), 7.03 (s, 1H), 6.41 (d, J=9.2 Hz, 1H), 6.35 (d, J=16.3 Hz, 1H), 5.77 (d, J=11.2 Hz, 1H), 3.86 (s, 3H), 2.94-2.84 (m, 2H), 2.70 (s, 3H), 2.40-2.29 (m, 2H), 2.24 (s, 6H).

Example 34 Preparation of N-(2-((2-(dimethyl-amino)ethyl)(methyl)amino)-5-((5-fluoro-4-(8-fluoro-3-isopropyl-2-m ethylimidazo[1,2-a]pyridine-6-yl)pyrimidin-2-yl)amino)-4-methoxyphenyl)acrylamide

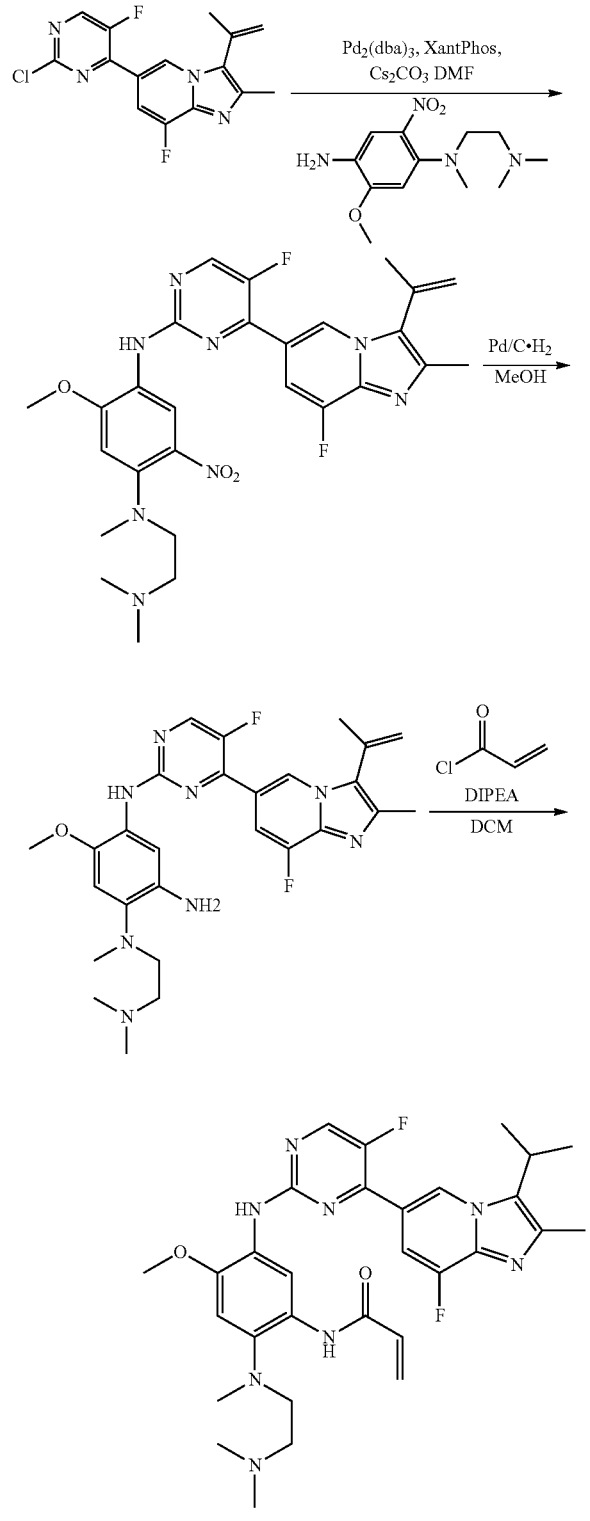

Step 1 Synthesis of Compound $N^1$-(2-(dimethyl-amino)ethyl)-$N^4$-(5-fluoro-4-(8-fluoro-2-methyl-3-(prop-1-en-2-yl)imidazo[1,2-a]pyridine-6-yl)pyrimidin-2-yl)-5-methoxy-N-methyl-2-nitrobenzene-1,4-diamine The synthetic step is the same as that of Example 20 step 1, and the filtrate was separated on column chromatography (eluant:dichloromethane/methanol (v/v)=12:1), to afford a brown-yellow solid. LC-MS(APCI): m/z=553.1 (M+1).

Step 2 Synthesis of Compound $N^1$-(2-(dimethyl-amino)ethyl)-$N^4$-(5-fluoro-4-(8-fluoro-2-methyl-3-(prop-1-en-2-yl)imidazo[1,2-a]pyridine-6-yl)pyrimidin-2-yl)-5-methoxy-N-methylbenzene-1,2,4-triamine The synthetic step is the same as that of Example 20 step 2, and 90 mg of an orange-yellow solid was obtained, yield over two steps: 47.3%. LC-MS(APCI): m/z=525.2 (M+1).

Step 3 Synthesis of Compound N-(2-((2-(dimethyl-amino)ethyl)(methyl)amino)-5-((5-fluoro-4-(8-fluoro-3-isopropyl-2-meth ylimidazo[1,2-a]pyridine-6-yl)pyrimidin-2-yl)amino)-4-methoxyphenyl)acrylamide The synthetic step is the same as that of Example 20 step 3, and 50 mg of a yellow solid was obtained, yield was 50.8%. LC-MS(APCI): m/z=579.3 (M+1), $^1$H NMR (400 MHz, DMSO-d6): δ 9.77 (s, 1H), 8.78 (s, 1H), 8.74 (s, 1H), 8.60 (d, J=3.3 Hz, 1H), 8.36 (s, 1H), 7.76 (d, J=12.2 Hz, 1H), 7.20 (s, 1H), 6.94 (s, 1H), 6.27-6.21 (m, 1H), 5.68 (d, J=11.6 Hz, 1H), 3.85 (s, 3H), 3.50-3.41 (m, 2H), 3.24-3.23 (m, 1H), 3.13-2.99 (m, 2H), 2.68 (s, 6H), 2.58 (s, 3H), 2.41 (s, 3H), 1.35 (d, J=7.1 Hz, 6H).

Example 35 Preparation of N-(2-((2-(dimethyl-amino)ethyl)(methyl)amino)-5-((4-(1-isopropyl-2-methyl-1H-benzo[d]imidazole-6-yl)pyrimidin-2-yl)amino)-4-methoxyphenyl)acrylamide

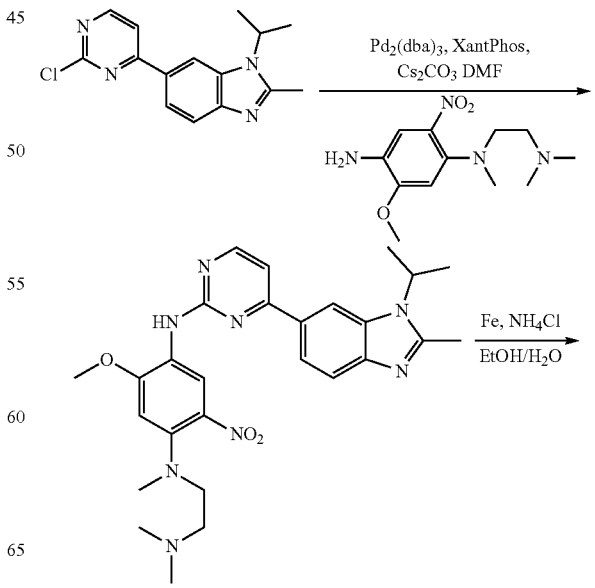

MHz, DMSO-d6): δ 10.42 (br, 1H), 9.79 (s, 1H), 8.75 (s, 1H), 8.45 (d, J=5.2 Hz, 1H), 8.34 (s, 1H), 8.12 (s, 1H), 8.05 (d, J=8.5 Hz, 1H), 7.56 (d, J=8.3 Hz, 1H), 7.49 (d, J=5.3 Hz, 1H), 6.95 (s, 1H), 6.24 (dd, J=17.0, 2.0 Hz, 1H), 5.73-5.66 (m, 1H), 4.85-4.72 (m, 1H), 3.87 (s, 3H), 3.25 (s, 2H), 2.75-2.65 (m, 5H), 2.59 (s, 3H), 2.58 (s, 3H), 2.49 (s, 3H), 1.56 (d, J=6.9 Hz, 6H).

Example 36 Preparation of N-(2-((2-(dimethyl-amino)ethyl)(methyl)amino)-5-((4-(1-isopropyl-1H-benzo[d]imidazole-6-yl)pyrimidin-2-yl)amino)-4-methoxyphenyl)acrylamide

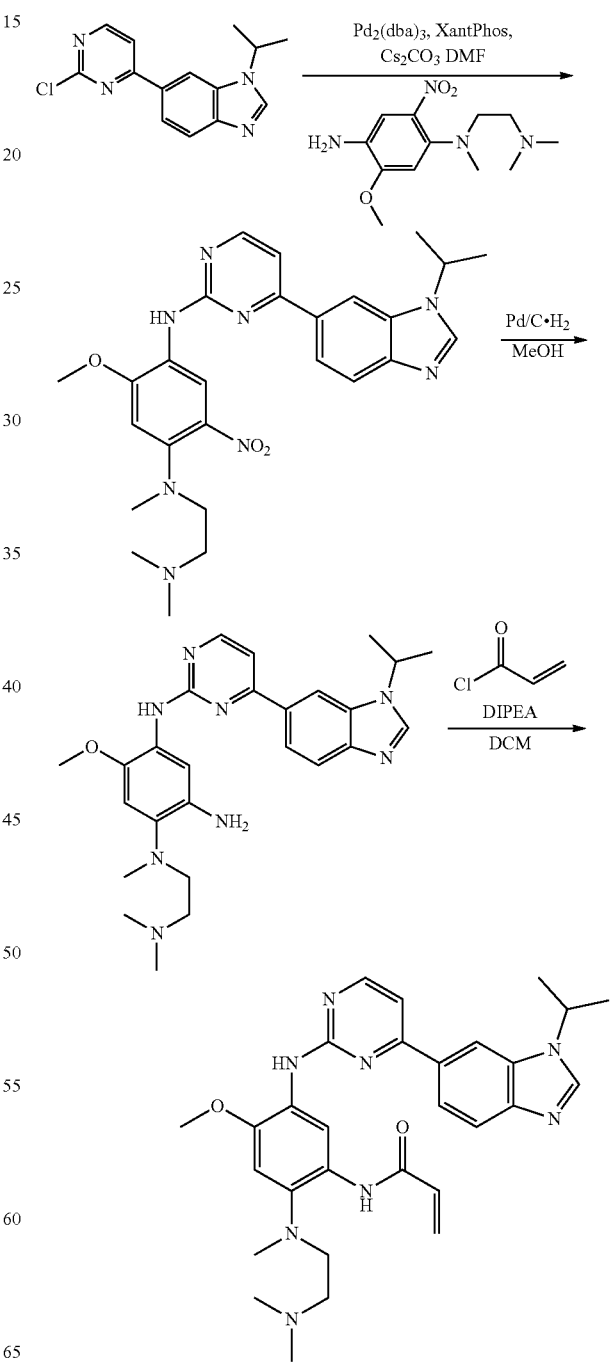

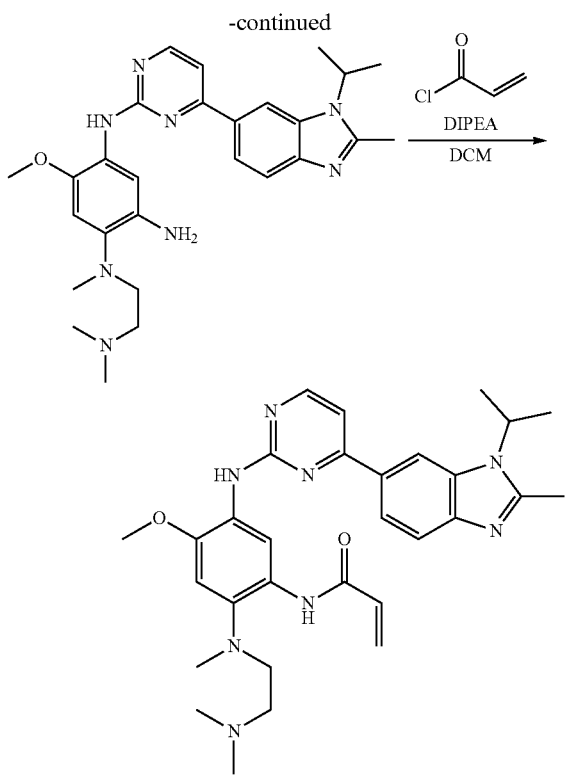

Step 1 Synthesis of Compound $N^1$-(2-(dimethyl-amino)ethyl)-$N^4$-(4-(1-isopropyl-2-methyl-1H-benzo[4,5-b]imidazol-6-yl)pyrimidin-2-yl)-5-methoxy-$N^1$-methyl-2-nitrobenzene-1,4-diamine The synthetic step is the same as that of Example 20 step 1, and a brown-yellow oil was obtained. LC-MS(APCI): m/z=519.3 (M+1).

Step 2 Synthesis of Compound $N^1$-(2-(dimethyl-amino)ethyl)-$N^4$-(4-(1-isopropyl-2-methyl-1H-benzo[4,5-b]imidazol-6-yl)pyrimidin-2-yl)-5-methoxy-$N^1$-methylbenzene-1,2,4-triamine Reduced iron powder (90 mg, 1.62 mmol) and ammonium chloride (43 mg, 0.81 mmol) were added into compound $N^1$-(2-(dimethylamino)ethyl)-$N^4$-(4-(1-isopropyl-2-methyl-1H-benzo[4,5-b]imidazol-6-yl)pyrimidin-2-yl)-5-methoxy-$N^1$-methyl-2-nitrobenzene-1,4-diamine in the mixed solvent of ethanol and water (8 mL/2 mL), and the reaction was reacted at reflux for 2 hrs, filtered on Celite, the filtrate was concentrated under reduced pressure, and the filtrate was separated on column chromatography (eluant:dichloromethane/methanol (v/v)=8:1), to afford 120 mg of a brown-yellow solid, yield over two steps: 35.2%. LC-MS(APCI): m/z=489.3 (M+1).

Step 3 Synthesis of Compound N-(2-((2-(dimethyl-amino)ethyl)(methyl)amino)-5-((4-(1-isopropyl-2-methyl-1H-benzo[d]imidazole-6-yl)pyrimidin-2-yl)amino)-4-methoxyphenyl)acrylamide The synthetic step is the same as that of Example 20 step 3, and 50 mg product was obtained, yield was 36.9%. HPLC: 95.97%. LC-MS(APCI): m/z=543.7 (M+1), $^1$H NMR (500

Step 1 Synthesis of Compound $N^1$-(2-(dimethylamino)ethyl)-$N^4$-(4-(1-isopropyl-1H-benzo[4,5-b]imidazol-6-yl)pyrimidin-2-yl)-5-methoxy-$N^1$-methyl-2-nitrobenzene-1,4-diamine The synthetic step is the same as that of Example 20 step 1, and a brown-yellow oil was obtained. LC-MS(APCI): m/z=505.2 (M+1).

Step 2 Synthesis of Compound $N^1$-(2-(dimethylamino)ethyl)-$N^4$-(4-(1-isopropyl-1H-benzo[4,5-b]imidazol-6-yl)pyrimidin-2-yl)-5-methoxy-$N^1$-methylbenzene-1,2,4-triamine The synthetic step is the same as that of Example 20 step 2, and 280 mg of a light green solid was obtained, yield over two steps: 36.8%. LC-MS(APCI): m/z=475.2 (M+1).

Step 3 Synthesis of Compound N-(2-((2-(dimethylamino)ethyl)(methyl)amino)-5-((4-(1-isopropyl-1H-benzo[d]imidazole-6-yl)pyrimidin-2-yl)amino)-4-methoxyphenyl)acrylamide The synthetic step is the same as that of Example 20 step 3, and 50 mg product was obtained, yield was 16.9%. HPLC: 96.48%. LC-MS(APCI): m/z=529.2 (M+1), $^1$H NMR (500 MHz, DMSO-d6): δ 10.12 (s, 1H), 9.11 (s, 1H), 8.48 (d, J=5.2 Hz, 1H), 8.47-8.43 (m, 2H), 8.14 (dd, J=8.5, 0.8 Hz, 1H), 8.07 (s, 1H), 7.70 (d, J=8.5 Hz, 1H), 7.50 (d, J=5.2 Hz, 1H), 7.02 (s, 1H), 6.41 (dd, J=16.9, 10.1 Hz, 1H), 6.25 (dd, J=17.0, 1.6 Hz, 1H), 5.82-5.71 (m, 1H), 4.93-4.81 (m, 1H), 3.85 (s, 3H), 2.91-2.82 (m, 2H), 2.69 (s, 3H), 2.32-2.25 (m, 2H), 2.20 (s, 6H), 1.52 (d, J=6.7 Hz, 6H).

Example 37 Preparation of N-(2-((2-(dimethylamino)ethyl)(methyl)amino)-5-((4-(1-isopropyl-2-(trifluoromethyl)-1H-benzo[d]imidazole-6-yl)pyrimidin-2-yl)amino)-4-methoxyphenyl)acrylamide

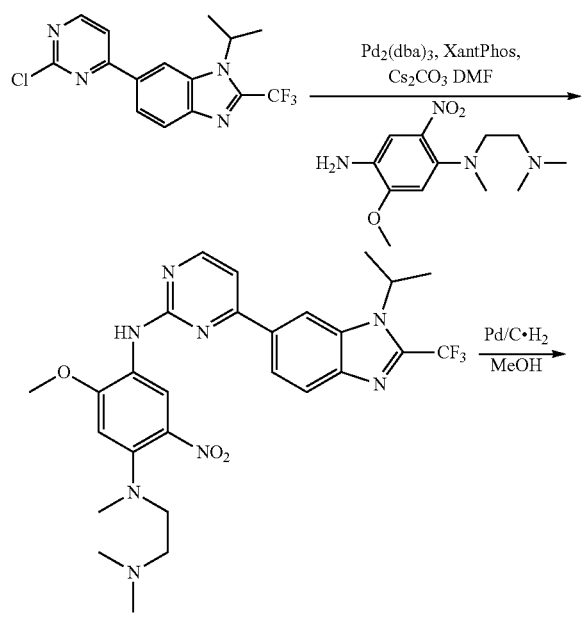

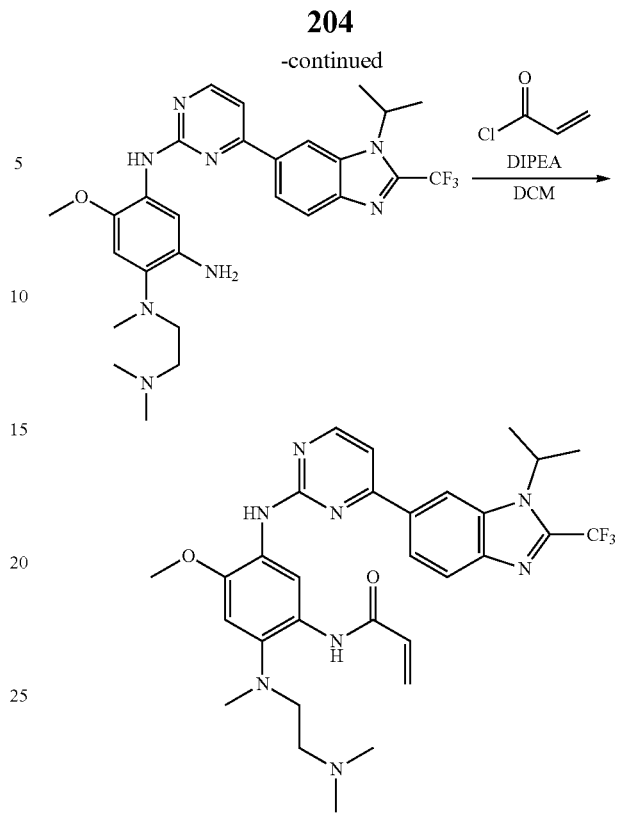

Step 1 Synthesis of Compound $N^1$-(2-(dimethylamino)ethyl)-$N^4$-(4-(1-isopropyl-2-(trifluoromethyl)-1H-benzo[4,5-b]imidazol-6-yl)pyrimidin-2-yl)-5-methoxy-$N^1$-methyl-2-nitrobenzene-1,4-diamine The synthetic step is the same as that of Example 20 step 1, and the filtrate was separated on column chromatography (eluant:dichloromethane/methanol (v/v)=12:1), to afford 250 mg of a brown-yellow solid. LC-MS(APCI): m/z=573.2 (M+1).

Step 2 Synthesis of Compound $N^1$-(2-(dimethylamino)ethyl)-$N^4$-(4-(1-isopropyl-2-(trifluoromethyl)-1H-benzo[4,5-b]imidazol-6-yl)pyrimidin-2-yl)-5-methoxy-$N^1$-methylbenzene-1,2,4-triamine The synthetic step is the same as that of Example 20 step 2, and 58 mg of a yellow-brown solid was obtained, yield over two steps: 6.34%. LC-MS(APCI): m/z=541.9 (M+1).

Step 3 Synthesis of Compound N-(2-((2-(dimethylamino)ethyl)(methyl)amino)-5-((4-(1-isopropyl-2-(trifluoromethyl)-1H-benzo[d]imidazole-6-yl)pyrimidin-2-yl)amino)-4-methoxyphenyl)acrylamide The synthetic step is the same as that of Example 20 step 3, and 40 mg crude was obtained, which was further purified on preparative TLC to afford 18 mg of a pale yellow solid, yield was 36.9%. HPLC: 96.65%. LC-MS(APCI): m/z=597.2 (M+1)+, $^1$H NMR (400 MHz, DMSO-d6): δ10.08 (s, 1H), 9.77 (s, 1H), 8.74 (s, 1H), 8.61-8.45 (m, 2H), 8.39-8.21 (m, 2H), 7.89 (d, J=8.5 Hz, 1H), 7.61 (d, J=5.2 Hz, 1H), 6.97 (s, 1H), 6.25 (d, J=17.2 Hz, 1H), 5.73 (d, J=8.4 Hz, 1H), 5.00-4.85 (m, 1H), 3.86 (s, 3H), 3.23-3.09 (m, 2H), 2.83-2.50 (m, 11H), 1.67 (d, J=6.8 Hz, 6H).

Example 38 Preparation of N-(2-((2-(dimethylamino)ethyl)(methyl)amino)-5-((4-(7-fluoro-1H-indazole-5-yl)pyrimidin-2-yl)amino)-4-methoxyphenyl)acrylamide

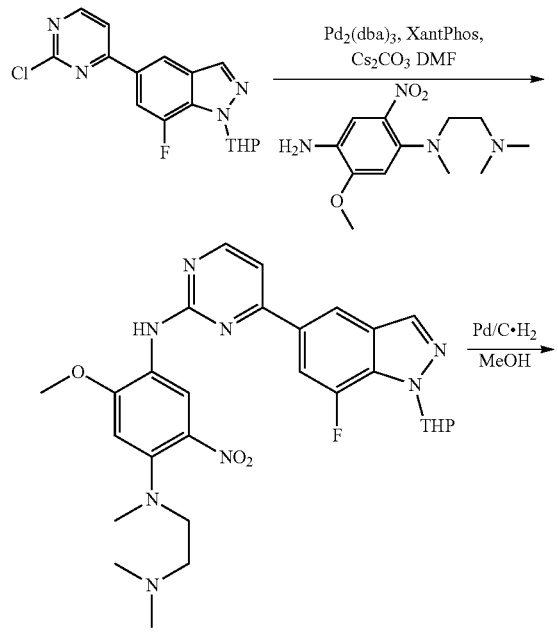

Step 1 Synthesis of Compound $N^1$-(2-(dimethylamino)ethyl)-$N^4$-(4-(7-fluoro-1-(tetrahydro-2H-pyran-2-yl)-1H-indazole-5-yl)pyrimidin-2-yl)-5-methoxy-$N^1$-methyl-2-nitrobenzene-1,4-diamine The synthetic step is the same as that of Example 20 step 1, and the filtrate was separated on column chromatography (eluant:dichloromethane/methanol (v/v)=12:1), to afford a brown-yellow solid. LC-MS(APCI): m/z=565.1 (M+1).

Step 2 Synthesis of Compound $N^1$-(2-(dimethylamino)ethyl)-$N^4$-(4-(7-fluoro-1-(tetrahydro-2H-pyran-2-yl)-1H-indazole-5-yl)pyrimidin-2-yl)-5-methoxy-$N^1$-methylbenzene-1,2,4-triamine The synthetic step is the same as that of Example 20 step 2, and 570 mg of a yellow-brown solid was obtained, yield over two steps: 71.0%. LC-MS(APCI): m/z=535.2 (M+1).

Step 3 Synthesis of Compound N-(2-((2-(dimethylamino)ethyl)(methyl)amino)-5-((4-(7-fluoro-1H-indazole-5-yl)pyrimidin-2-yl)amino)-4-methoxyphenyl)acrylamide The synthetic step is the same as that of Example 20 step 3, and 390 mg of a grey-yellow solid N-(2-(dimethylamino)ethyl)(methyl)amino)-5-((4-(7-fluoro-1-(tetrahydro-2H-pyran-2-yl)-1H-indazole-5-yl)pyrimidin-2-yl)amino)-4-methoxyphenyl)acrylamide was obtained, yield was 61.9%. LC-MS(APCI): m/z=589.2 (M+1).

Trifluoroacetic acid (5 mL) was added into the above grey-yellow solid (390 mg, 0.66 mmol) in anhydrous dichloromethane (10 mL), and the reaction was reacted at room temperature for 2 hrs. The reaction solvent was removed under reduced pressure, the pH of the residue was adjusted to basic with saturated solution of sodium bicarbonate, extracted with dichloromethane (100 mL×3), the organic layer was combined, washed with brine, dried over anhydrous sodium sulfate, the filtrate was concentrated under reduced pressure, and the filtrate was separated on column chromatography (eluant:dichloromethane/methanol (v/v)=10:1), to afford 250 mg of a grey-yellow solid, yield was 75.2%. LC-MS(APCI): m/z=505.2 (M+1), HPLC: 95.59%. $^1$H NMR (500 MHz, DMSO-$d_6$): δ 13.84 (s, 1H), 10.12 (s, 1H), 9.26 (s, 1H), 8.73 (s, 1H), 8.49 (d, J=4.7 Hz, 1H), 8.26 (s, 1H), 8.12 (d, J=12.3 Hz, 1H), 8.04 (s, 1H), 7.49 (d, J=4.4 Hz, 1H), 7.02 (s, 1H), 6.53-6.40 (m, 1H), 6.32 (d, J=17.0 Hz, 1H), 5.79 (d, J=10.3 Hz, 1H), 3.87 (s, 3H), 2.94-2.83 (m, 2H), 2.69 (s, 3H), 2.39-2.29 (m, 2H), 2.24 (s, 6H).

Example 39 Preparation of N-(2-((2-(dimethylamino)ethyl)(methyl)amino)-5-((4-(7-fluoro-1-methyl-indazole-5-yl)pyrimidin-2-yl)amino)-4-methoxyphenyl)acrylamide

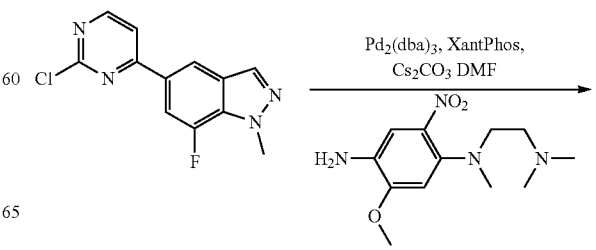

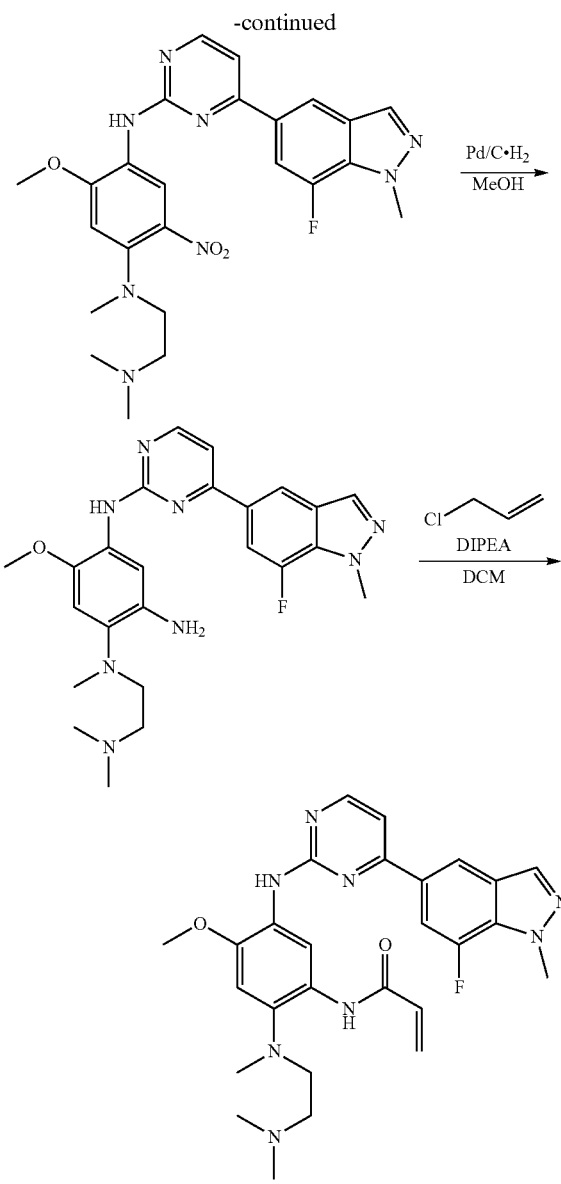

Step 1 Synthesis of Compound N¹-(2-(dimethylamino)ethyl)-N⁴-(4-(7-fluoro-1-methyl-1H-indazole-5-yl)pyrimidin-2-yl)-5-methoxy-N¹-methyl-2-nitrobenzene-1,4-diamine The synthetic step is the same as that of Example 20 step 1, and the filtrate was separated on column chromatography (eluant:dichloromethane/methanol (v/v)=11:1), to afford a brown-yellow solid. LC-MS(APCI): m/z=495.2 (M+1).

Step 2 Synthesis of Compound N¹-(2-(dimethylamino)ethyl)-N⁴-(4-(7-fluoro-1-methyl-1H-indazole-5-yl)pyrimidin-2-yl)-5-methoxy-N¹-methylbenzene-1,2,4-triamine The synthetic step is the same as that of Example 20 step 2, and 217 mg of a yellow-brown solid was obtained, yield over two steps: 43.7%. LC-MS(APCI): m/z=465.1 (M+1).

Step 3 Synthesis of Compound N-(2-((2-(dimethylamino)ethyl)(methyl)amino)-5-((4-(7-fluoro-1-methyl-1H-indazole-5-yl)pyrimidin-2-yl)amino)-4-methoxyphenyl)acrylamide The synthetic step is the same as that of Example 20 step 3, and 120 mg of a grey-yellow solid was obtained, yield was 49.3%. LC-MS(APCI): m/z=519.2 (M+1), HLPC: 93.48%. ¹H NMR (300 MHz, DMSO-d₆): δ 10.14 (s, 1H), 9.18 (s, 1H), 8.66 (s, 1H), 8.58 (d, J=2.5 Hz, 1H), 8.49 (d, J=5.2 Hz, 1H), 8.08 (s, 1H), 7.95 (d, J=13.5 Hz, 1H), 7.48 (d, J=5.3 Hz, 1H), 7.03 (s, 1H), 6.48 (dd, J=16.8, 10.1 Hz, 1H), 6.33 (dd, J=16.9, 1.9 Hz, 1H), 5.79 (dd, J=10.0, 1.9 Hz, 1H), 4.24 (s, 3H), 3.88 (s, 3H), 2.97-2.85 (m, 2H), 2.70 (s, 3H), 2.42-2.31 (m, 2H), 2.26 (s, 6H).

Example 40 Preparation of N-(2-((2-(dimethylamino)ethyl)(methyl)amino)-5-((4-(7-fluoro-2-methyl-2H-indazole-5-yl)pyrimidin-2-yl)amino)-4-methoxyphenyl)acrylamide

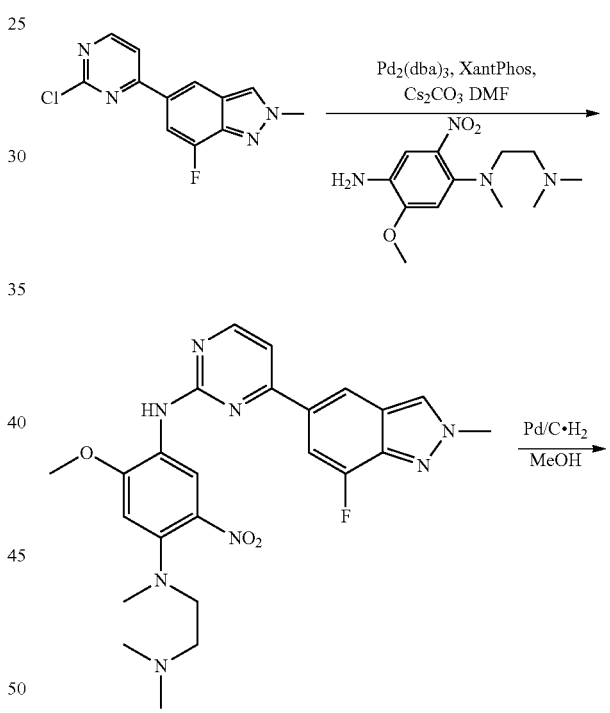

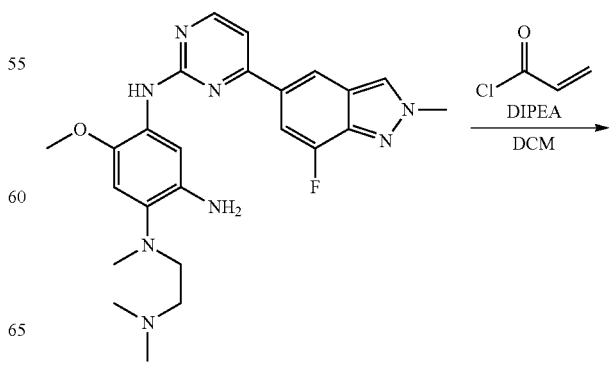

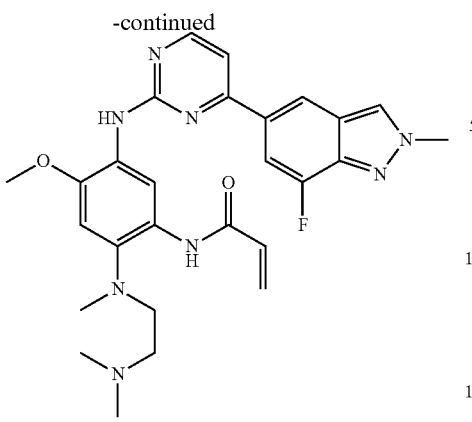

Step 1 Synthesis of Compound $N^1$-(2-(dimethyl-amino)ethyl)-$N^4$-(4-(7-fluoro-2-methyl-2H-indazole-5-yl)pyrimidin-2-yl)-5-methoxy-$N^1$-methyl-2-nitrobenzene-1,4-diamine The synthetic step is the same as that of Example 20 step 1, and the filtrate was separated on column chromatography (eluant:dichloromethane/methanol (v/v)=11:1), to afford a brown-yellow solid. LC-MS(APCI): m/z=495.2 (M+1).

Step 2 Synthesis of Compound N-(2-(dimethyl-amino)ethyl)-$N^4$-(4-(7-fluoro-2-methyl-2H-indazole-5-yl)pyrimidin-2-yl)-5-methoxy-$N^1$-methylbenzene-1,2,4-triamine The synthetic step is the same as that of Example 20 step 2, and 120 mg of a yellow-brown solid was obtained, yield over two steps: 37.5%. LC-MS(APCI): m/z=465.2 (M+1).

Step 3 Synthesis of Compound N-(2-((2-(dimethyl-amino)ethyl)(methyl)amino)-5-((4-(7-fluoro-2-methyl-2H-indazole-5-yl)pyrimidin-2-yl)amino)-4-methoxyphenyl)acrylamide The synthetic step is the same as that of Example 20 step 3, and 120 mg of a grey-yellow solid was obtained, yield was 49.3%. LC-MS(APCI): m/z=519.3 (M+1), HPLC: 97.69%, $^1$H NMR (300 MHz, DMSO-$d_6$): δ 10.11 (s, 1H), 9.23 (s, 1H), 8.73 (s, 1H), 8.51 (d, J=5.2 Hz, 1H), 8.21 (d, J=2.2 Hz, 1H), 8.14 (d, J=13.6 Hz, 1H), 8.08 (s, 1H), 7.51 (d, J=5.3 Hz, 1H), 7.04 (s, 1H), 6.55 (dd, J=16.7, 10.0 Hz, 1H), 6.34 (dd, J=16.9, 1.9 Hz, 1H), 5.81 (dd, J=10.1, 1.8 Hz, 1H), 4.21 (s, 3H), 3.89 (s, 3H), 2.99-2.91 (m, 2H), 2.70 (s, 3H), 2.49-2.41 (m, 2H), 2.31 (s, 6H).

Example 41 Preparation of N-(2-((2-(dimethyl-amino)ethyl)(methyl)amino)-5-((4-(7-fluoro-3-isopropyl-2-methyl-2H-indazole-5-yl)pyrimidin-2-yl)amino)-4-methoxyphenyl)acrylamide

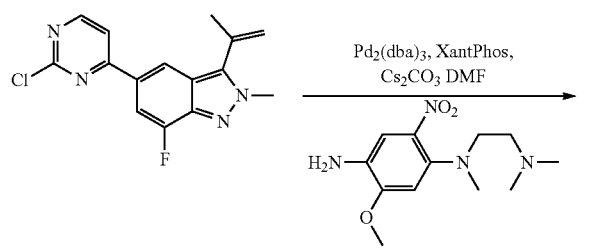

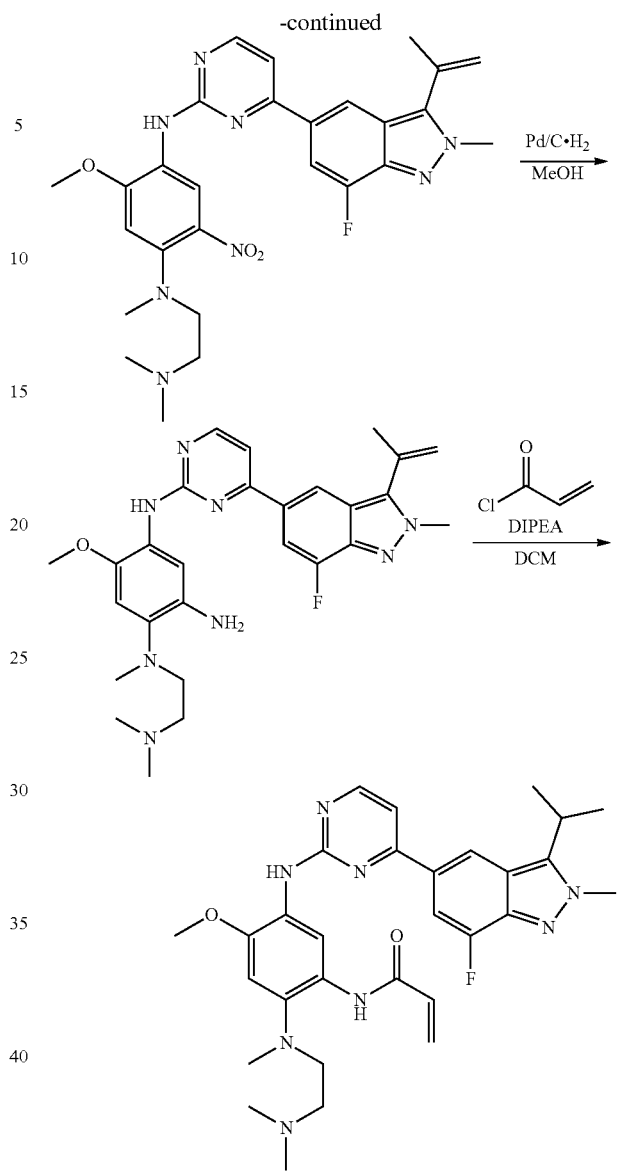

Step 1 Synthesis of Compound $N^1$-(2-(dimethyl-amino)ethyl)-$N^4$-(4-(7-fluoro-2-methyl-3-(prop-1-en-2-yl)-2H-indazole-5-yl) pyrimidin-2-yl)-5-methoxy-$N^1$-methyl-2-nitrobenzene-1,4-diamine The synthetic step is the same as that of Example 20 step 1, and the filtrate was separated on column chromatography (eluant:dichloromethane/methanol (v/v)=11:1), to afford a brown-yellow solid. LC-MS(APCI): m/z=535.2 (M+1).

Step 2 Synthesis of Compound $N^1$-(2-(dimethyl-amino)ethyl)-$N^4$-(4-(7-fluoro-3-isopropyl-2-methyl-2H-indazole-5-yl)pyrimidin-2-yl)-5-methoxy-$N^1$-methylbenzene-1,2,4-triamine The synthetic step is the same as that of Example 20 step 2, and 80 mg of a yellow-brown solid was obtained, yield over two steps: 25.1%. LC-MS(APCI): m/z=507.2 (M+1).

Step 3 Synthesis of Compound N-(2-((2-(dimethyl-amino)ethyl)(methyl)amino)-5-((4-(7-fluoro-3-iso-propyl-2-methyl-2H-indazole-5-yl)pyrimidin-2-yl)amino)-4-methoxyphenyl)acrylamide The synthetic step is the same as that of Example 20 step 3, and 15 mg of a pale yellow solid was obtained, yield was 17.0%. LC-MS(APCI): m/z=561.2 (M+1), HPLC: 98.82%.

Example 42 Preparation of N-(2-((2-(dimethyl-amino)ethyl)(methyl)amino)-5-((4-(3-isopropyl-2-methyl-2H-indazole-5-yl)pyrimidin-2-yl)amino)-4-methoxyphenyl)acrylamide

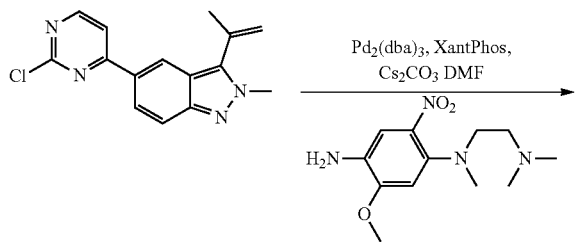

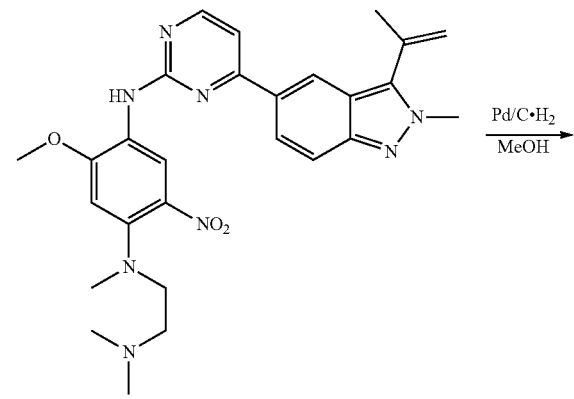

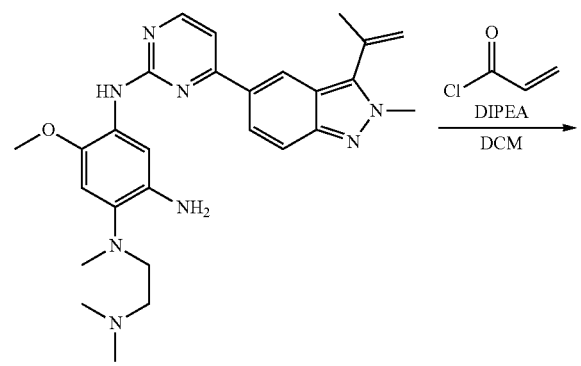

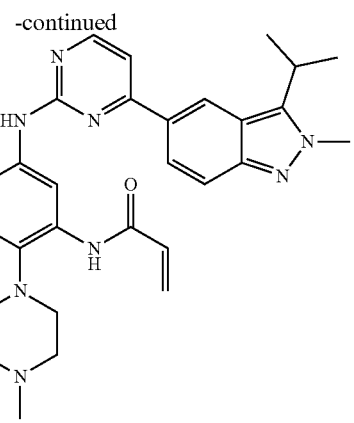

Step 1 Synthesis of Compound $N^1$-(2-(dimethyl-amino)ethyl)-$N^4$-(4-(2-methyl-3-(prop-1-en-2-yl)-2H-indazole-5-yl)pyrimidin-2-yl)-5-methoxy-N-methyl-2-nitrobenzene-1,4-diamine The synthetic step is the same as that of Example 20 step 1, and the filtrate was separated on column chromatography (eluant:dichloromethane/methanol (v/v)=11:1), to afford a brown-yellow solid. LC-MS(APCI): m/z=517.1 (M+1).

Step 2 Synthesis of Compound N-(2-(dimethyl-amino)ethyl)-$N^4$-(4-(3-isopropyl-2-methyl-2H-inda-zole-5-yl)pyrimidin-2-yl)-5-methoxy-$N^1$-methylben-zene-1,2,4-triamine The synthetic step is the same as that of Example 20 step 2, and 360 mg of a yellow-brown solid was obtained, yield over two steps: 45.4%. LC-MS(APCI): m/z=489.2 (M+1).

Step 3 Synthesis of Compound N-(2-((2-(dimethyl-amino)ethyl)(methyl)amino)-5-((4-(-3-isopropyl-2-methyl-2H-indazole-5-yl)pyrimidin-2-yl)amino)-4-methoxyphenyl)acrylamide The synthetic step is the same as that of Example 20 step 3, and 50 mg of a pale yellow solid was obtained, yield was 12.5%. LC-MS(APCI): m/z=543.7 (M+1), HPLC: 95.93%. $^1$H NMR (500 MHz, DMSO-$d_6$): δ 10.07 (s, 1H), 8.97 (s, 1H), 8.61 (s, 1H), 8.43 (d, J=5.2 Hz, 1H), 8.12 (d, J=9.1 Hz, 1H), 8.08 (s, 1H), 7.55 (d, J=9.1 Hz, 1H), 7.46 (d, J=5.2 Hz, 1H), 7.00 (s, 1H), 6.41 (dd, J=16.8, 10.1 Hz, 1H), 6.24 (d, J=16.6 Hz, 1H), 5.74 (d, J=10.2 Hz, 1H), 4.10 (s, 3H), 3.84 (s, 3H), 3.60-3.52 (m, 1H), 2.93-2.84 (m, 2H), 2.69 (s, 3H), 2.38-2.28 (m, 2H), 2.22 (s, 6H), 1.45 (d, J=7.0 Hz, 6H).

Example 43 Preparation of N-(2-((2-(dimethyl-amino)ethyl)(methyl)amino)-5-((4-(imidazo[1,2-b]pyridazine-6-yl)pyrimidin-2-yl)amino)-4-methoxy-phenyl)acrylamide

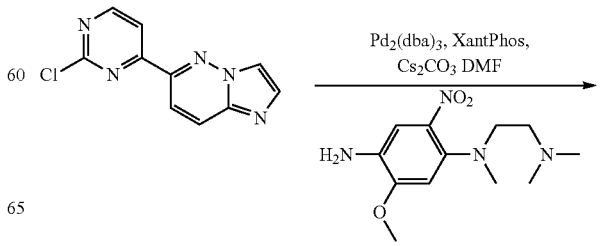

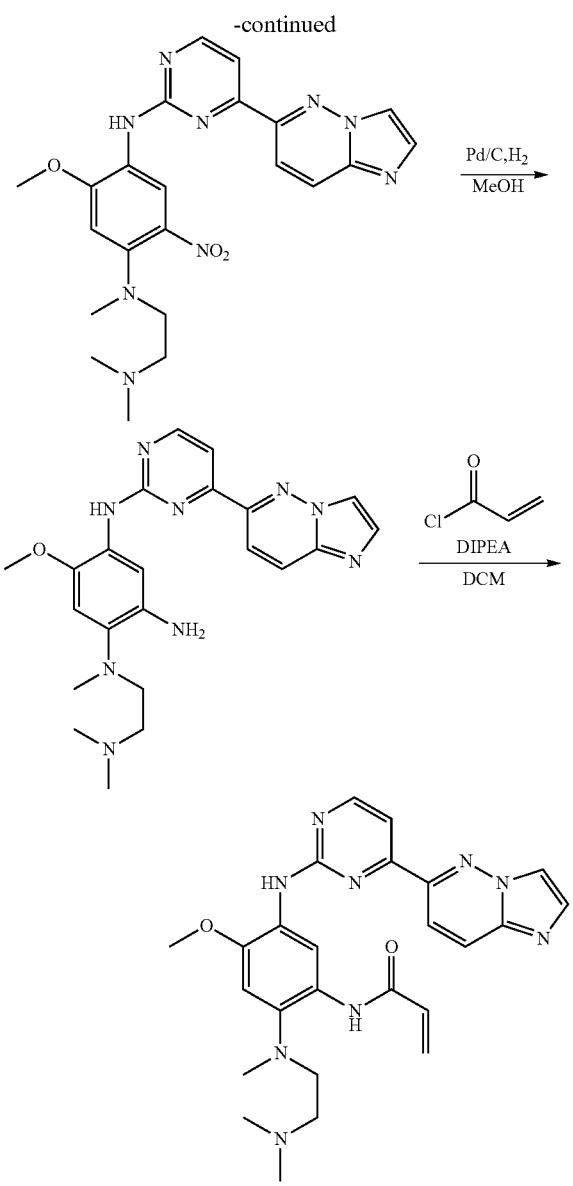

Step 1 Synthesis of Compound $N^1$-(2-(dimethyl-amino)ethyl)-$N^4$-(4-(imidazo[1,2-b]pyridazine-6-yl)pyrimidin-2-yl)-5-methoxy-$N^1$-methyl-2-nitrobenzene-1,4-diamine The synthetic step is the same as that of Example 20 step 1, and the filtrate was separated on column chromatography (eluant:dichloromethane/methanol (v/v)=11:1), to afford a brown-yellow oil. LC-MS(APCI): m/z=464.2 (M+1).

Step 2 Synthesis of Compound $N^1$-(2-(dimethyl-amino)ethyl)-$N^4$-(4-(imidazo[1,2-b]pyridazine-6-yl)pyrimidin-2-yl)-5-methoxy-$N^1$-methylbenzene-1,2,4-triamine The synthetic step is the same as that of Example 20 step 2, and 74 mg of a yellow solid was obtained, yield over two steps: 20.9%. LC-MS(APCI): m/z=434.1 (M+1).

Step 3 Synthesis of Compound N-(2-((2-(dimethyl-amino)ethyl)(methyl)amino)-5-((4-(imidazo[1,2-b]pyridazine-6-yl)pyrimidin-2-yl)amino)-4-methoxy-phenyl)acrylamide The synthetic step is the same as that of Example 20 step 3, and 57 mg of a pale yellow solid was obtained, yield was 68.9%. LC-MS(APCI): m/z=488.2 (M+1), HPLC: 97.97%. $^1$H NMR (500 MHz, DMSO-$d_6$): δ 10.09 (s, 1H), 9.08 (s, 1H), 8.63 (d, J=5.0 Hz, 1H), 8.48 (d, J=9.3 Hz, 1H), 8.42 (s, 1H), 8.33 (s, 1H), 8.18 (d, J=9.6 Hz, 1H), 7.90 (s, 1H), 7.63 (d, J=5.0 Hz, 1H), 7.02 (s, 1H), 6.54-6.41 (m, 1H), 6.35 (d, J=16.8 Hz, 1H), 5.78 (d, J=11.7 Hz, 1H), 3.86 (s, 3H), 2.99-2.84 (m, 2H), 2.69 (s, 3H), 2.48-2.48 (m, 2H), 2.26 (s, 6H).

Example 44 Preparation of N-(2-((2-(dimethyl-amino)ethyl)(methyl)amino)-5-((4-(1-isopropyl-2-oxo-1,2,5,6-tetrahydro-4H-imidazo[4,5,1-ij]quino-lin-8-yl)pyrimidin-2-yl)amino)-4-methoxyphenyl)acrylamide

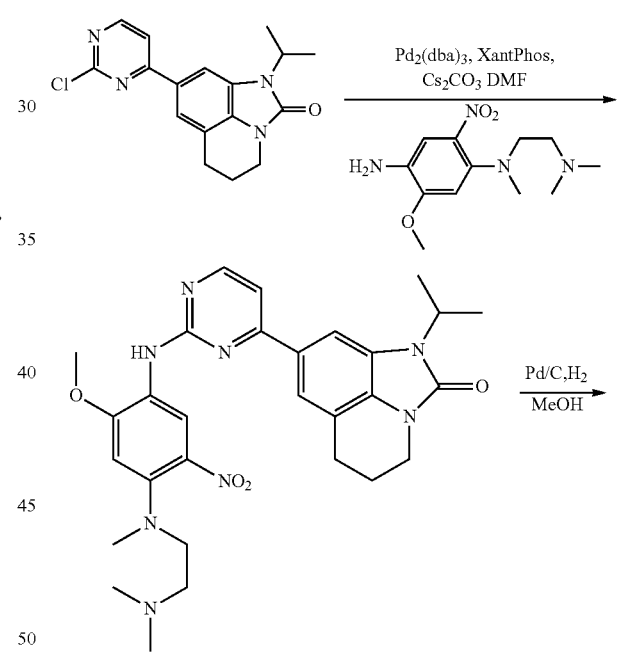

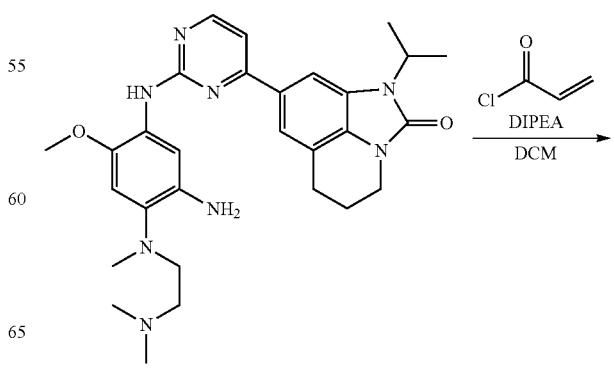

-continued

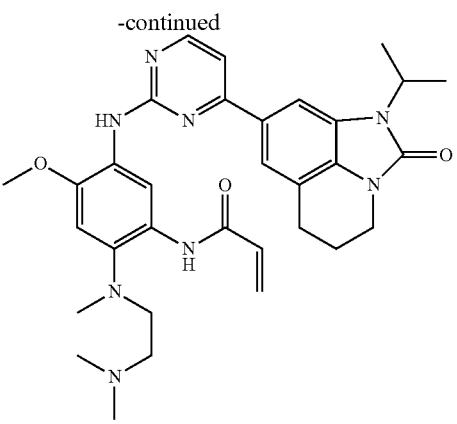

Step 1 Synthesis of Compound N$^1$-(2-(dimethylamino)ethyl)-N$^4$-(4-(1-isopropyl-2-oxo-1,2,5,6-tetrahydro-4H-imidazo[4,5,1-ij]quinolin-8-yl)pyrimidin-2-yl)-5-methoxy-N$^1$-methyl-2-nitrobenzene-1,4-diamine The synthetic step is the same as that of Example 20 step 1, and the filtrate was separated on column chromatography (eluant:dichloromethane/methanol (v/v)=11:1), to afford a brown-yellow solid. LC-MS(APCI): m/z=561.1 (M+1).

Step 2 Synthesis of Compound 8-(2-((5-amino-4-((2-(dimethylamino)ethyl)(methyl)amino)-2-methoxyphenyl)amino)pyrimidin-4-yl)-1-isopropyl-5,6-dihydro-4H-imidazo[4,5,1-ij]quinolin-2(1H)-one The synthetic step is the same as that of Example 20 step 2, and 255 mg of a yellow-brown solid was obtained, yield over two steps: 56.5%. LC-MS(APCI): m/z=530.1 (M+1).

Step 3 Synthesis of Compound N-(2-((2-(dimethylamino)ethyl)(methyl)amino)-5-((4-(1-isopropyl-2-oxo-1,2,5,6-tetrahydro-4H-imidazo[4,5,1-ij]quinolin-8-yl)pyrimidin-2-yl)amino)-4-methoxyphenyl)acrylamide The synthetic step is the same as that of Example 20 step 3, and the filtrate was separated on column chromatography (eluant:dichloromethane/methanol (v/v)=8:1) to afford 135 mg of a grey-yellow solid, yield was 48.0%. LC-MS(APCI): m/z=585.2 (M+1)$^+$, HPLC: 99.14%, $^1$H NMR (400 MHz, DMSO-d$_6$): δ 10.11 (s, 1H), 9.07 (s, 1H), 8.44 (d, J=5.3 Hz, 1H), 8.05 (s, 1H), 7.94 (s, 1H), 7.83 (s, 1H), 7.46 (d, J=5.3 Hz, 1H), 7.09-7.02 (m, 1H), 6.45 (s, 1H), 6.32-6.19 (m, 1H), 5.80-5.74 (m, 1H), 4.63 (dt, J=14.0, 6.9 Hz, 1H), 3.88 (s, 3H), 3.77 (t, J=5.4 Hz, 2H), 2.94-2.86 (m, 4H), 2.71 (s, 3H), 2.42-2.31 (m, 2H), 2.26 (s, 6H), 2.09-2.00 (m, 2H), 1.48 (d, J=6.9 Hz, 6H).

Example 45 Preparation of N-(2-((2-(dimethylamino)ethyl)(methyl)amino)-4-methoxy-5-((4-(2-methoxy-5,6-dihydro-4H-imidazo[4,5,1-ij]quinolin-8-yl)pyrimidin-2-yl)amino)phenyl)acrylamide

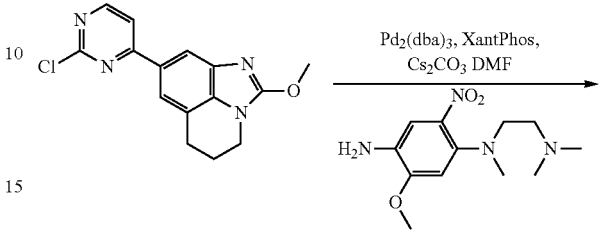

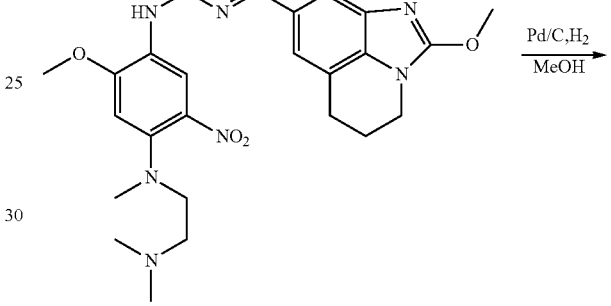

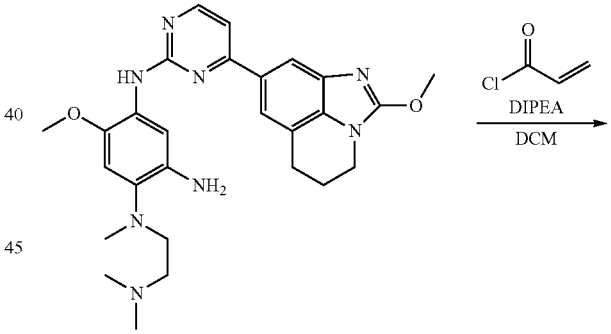

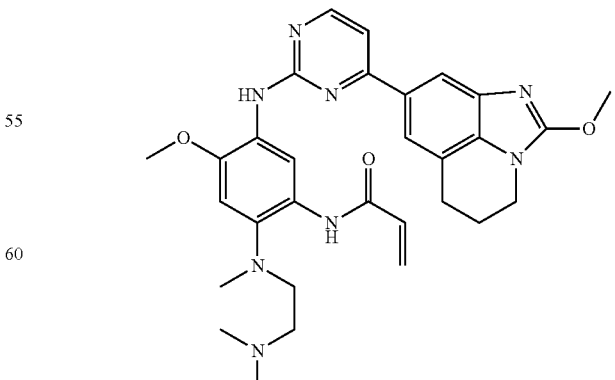

Step 1 Synthesis of Compound N¹-(2-(dimethyl-amino)ethyl)-5-methoxy-N⁴-(4-(2-methoxy-5,6-dihydro-4H-imidazo[4,5,1-ij]quinolin-8-yl)pyrimidin-2-yl)-N¹-methyl-2-nitrobenzene-1,4-diamine The synthetic step is the same as that of Example 20 step 1, and a brown-red solid was obtained. LC-MS(APCI): m/z=533.2 (M+1).

Step 2 Synthesis of Compound N-(2-(dimethyl-amino)ethyl)-5-methoxy-N⁴-(4-(2-methoxy-5,6-dihydro-4H-imidazo[4,5,1-ij]quinolin-8-yl)pyrimidin-2-yl)-N-methylbenzene-1,2,4-triamine The synthetic step is the same as that of Example 20 step 2, and 139 mg of a yellow-brown solid was obtained, yield over two steps: 27.9%. LC-MS(APCI): m/z=503.2 (M+1).

Step 3 Synthesis of Compound N-(2-((2-(dimethyl-amino)ethyl)(methyl)amino)-4-methoxy-5-((4-(2-methoxy-5,6-dihydro-4H-imidazo[4,5,1-ij]quinolin-8-yl)pyrimidin-2-yl)amino)phenyl)acrylamide The synthetic step is the same as that of Example 20 step 3, and the filtrate was separated on column chromatography (eluant:dichloromethane/methanol (v/v)=9:1) to afford 70 mg of a yellow solid, yield was 46.7%. LC-MS(APCI): m/z=557.2 (M+1)⁺, HPLC: 97.91%, ¹H NMR (400 MHz, DMSO-d₆): δ 10.06 (s, 1H), 9.13 (s, 1H), 8.41 (d, J=5.3 Hz, 1H), 7.93 (s, 1H), 7.87 (s, 1H), 7.83 (s, 1H), 7.38 (d, J=5.4 Hz, 1H), 7.00 (s, 1H), 6.48 (s, 1H), 6.21 (dd, J=16.9, 1.8 Hz, 1H), 5.74 (dd, J=10.1, 1.6 Hz, 1H), 3.86 (s, 3H), 3.74 (t, J=5.7 Hz, 2H), 3.33 (s, 3H), 2.99-2.88 (m, 2H), 2.85 (t, J=5.7 Hz, 2H), 2.66 (s, 3H), 2.48-2.47 (m, 2H), 2.28 (s, 6H), 2.07-1.98 (m, 2H).

Example 46 Preparation of N-(5-((4-(benzo[d]thi-azol-6-yl)pyrimidin-2-yl)amino)-2-((2-(dimethyl-amino)ethyl)(methyl)amino)-4-methoxyphenyl)acrylamide

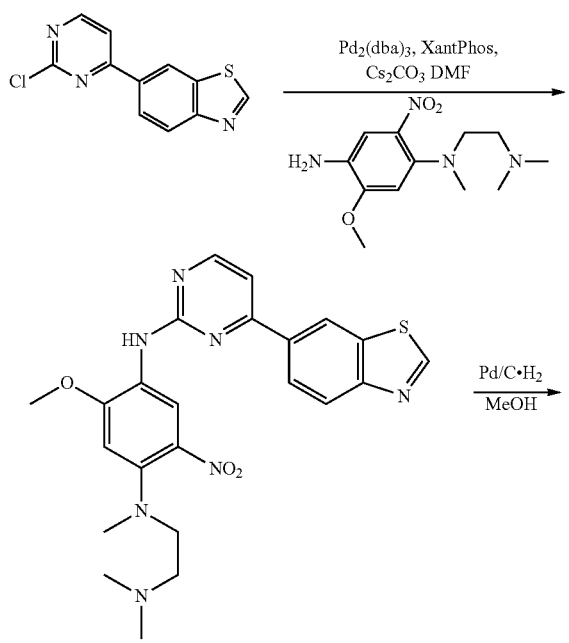

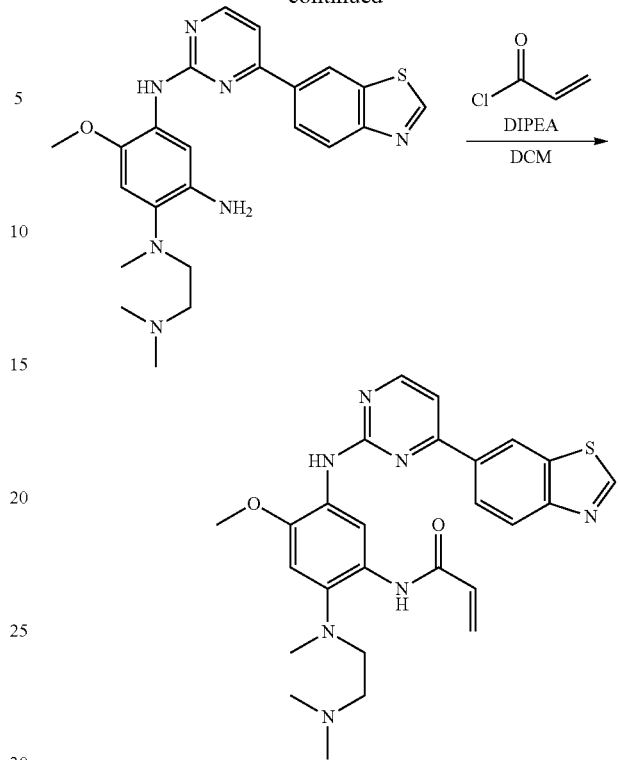

Step 1 Synthesis of Compound N¹-(4-(benzo[d]thiophene-6-yl)pyrimidin-2-yl)-N⁴-(2-(dimethyl-amino)ethyl)-2-methoxy-N⁴-methyl-5-nitrobenzene-1,4-diamine The synthetic step is the same as that of Example 20 step 1, and 486 mg of a brown-red oil was obtained. LC-MS (APCI): m/z=479.4 (M+1).

Step 2 Synthesis of Compound N⁴-(4-(benzo[d]thiophene-6-yl)pyrimidin-2-yl)-N¹-(2-(dimethyl-amino)ethyl)-5-methoxy-N¹-methylbenzene-1,2,4-triamine The synthetic step is the same as that of Example 20 step 2, and 184 mg of a yellow-brown solid was obtained, yield over two steps: 27.0%. LC-MS(APCI): m/z=450.1M+1).

Step 3 Synthesis of Compound N-(4-((4-(benzo[d]thiazol-6-yl)pyrimidin-2-yl)amino)-2-((2-(dimethyl-amino)-5-ethyl)(methyl)amino)-4-methoxyphenyl)acrylamide The synthetic step is the same as that of Example 20 step 3, and 185 mg of a yellow solid was obtained, which was purified by preparative TLC to afford 50 mg of a pale yellow solid, yield was 24.2%. LC-MS(APCI): m/z=504.1 (M+1)⁺, HPLC: 97.92%, ¹H NMR (400 MHz, DMSO-d₆): δ 10.21 (s, 1H), 9.52 (s, 1H), 9.44 (d, J=19.2 Hz, 2H), 8.57 (d, J=5.1 Hz, 1H), 8.46-8.33 (m, 1H), 8.17 (d, J=8.5 Hz, 1H), 8.05 (s, 1H), 7.58 (d, J=5.2 Hz, 1H), 7.06 (s, 1H), 6.56-6.38 (m, 2H), 5.91-5.78 (m, 1H), 3.89 (s, 3H), 2.96-2.82 (m, 2H), 2.70 (s, 3H), 2.35-2.27 (m, 2H), 2.22 (s, 6H).

Example 47 Preparation of N-(4-(difluoromethoxy)-2-((2-(dimethylaminoethyl)(methyl)amino)-5-((4-(4-fluoro-1-iso propyl-2-methyl-1H-benzo[d]imidazole6-yl)pyrimidin-2-yl)amino)phenyl)acrylamide

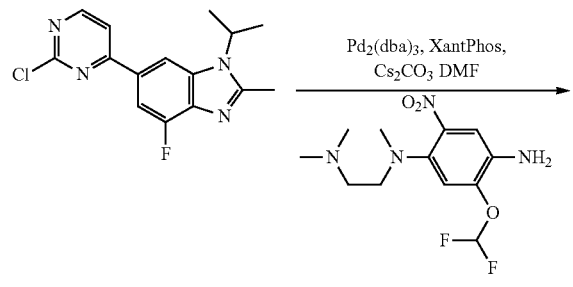

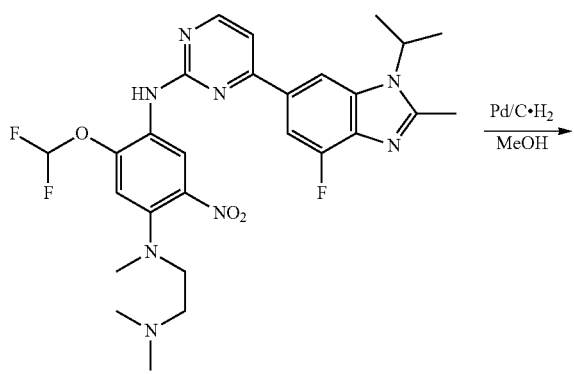

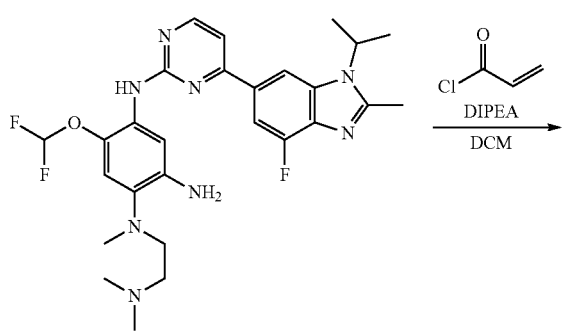

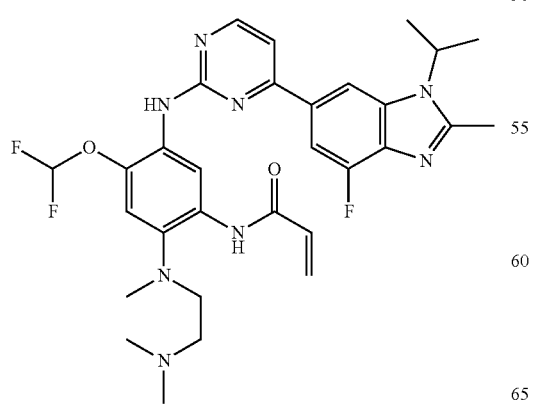

Step 1 Synthesis of Compound 2-(difluoromethoxy)-$N^4$-(2-(dimethylamino)ethyl)-$N^1$-(4-(4-fluoro-1-isopropyl-2-methyl-1H-benzo[d]imidazole-6-yl)pyrimidin-2-yl)-$N^4$-methyl-5-nitrobenzene-1,4-diamine The synthetic step is the same as that of Example 20 step 1, and 355 mg of a yellow solid was obtained. LC-MS (APCI): m/z=573.1 (M+1).

Step 2 Synthesis of Compound 5-(difluoromethoxy)-$N^1$-(2-(dimethylamino)ethyl)-$N^4$-(4-(4-fluoro-1-isopropyl-2-methyl-1H-benzo[d]imidazole-6-yl)pyrimidin-2-yl)-$N^1$-methylbenzene-1,2,4-triamine The synthetic step is the same as that of Example 20 step 2, and 235 mg of a yellow-brown solid was obtained, yield over two steps: 52.9%. LC-MS(APCI): m/z=543.2M+1).

Step 3 Synthesis of Compound N-(4-(difluoromethoxy)-2-((2-(dimethylaminoethyl)(methyl)amino)-5-((4-(4-fluoro-1-isopropyl-2-methyl-1H-benzo[d]imidazole6-yl)pyrimidin-2-yl)amino)phenyl)acrylamide The synthetic step is the same as that of Example 20 step 3, and 80 mg of a yellow solid was obtained, yield was 24.2%. LC-MS(APCI): m/z=597.1 (M+1), HPLC: 95.79%, $^1$H NMR (400 MHz, DMSO-d6): δ 9.95 (s, 1H), 8.74 (s, 2H), 8.49 (d, J=5.3 Hz, 1H), 8.21 (s, 1H), 7.83 (d, J=11.9 Hz, 1H), 7.57 (d, J=5.3 Hz, 1H), 7.16 (s, 1H), 6.31-6.27 (m, 1H), 6.26-6.22 (m, 1H), 5.88 (dd, J=10.3, 1.7 Hz, 1H), 5.79-5.76 (m, 1H), 4.88-4.73 (m, 1H), 3.15-3.07 (m, 2H), 2.69-2.52 (m, 14H), 1.58 (d, J=6.9 Hz, 6H).

Example 48 Preparation of N-(2-((2-(dimethylamino)ethyl)(methyl)amino)-4-ethoxy-5-((4-(4-fluoro-1-isopropyl-2-methyl-1H-benzo[d]imidazole-6-yl)pyrimidin-2-yl)amino)phenyl)acrylamide

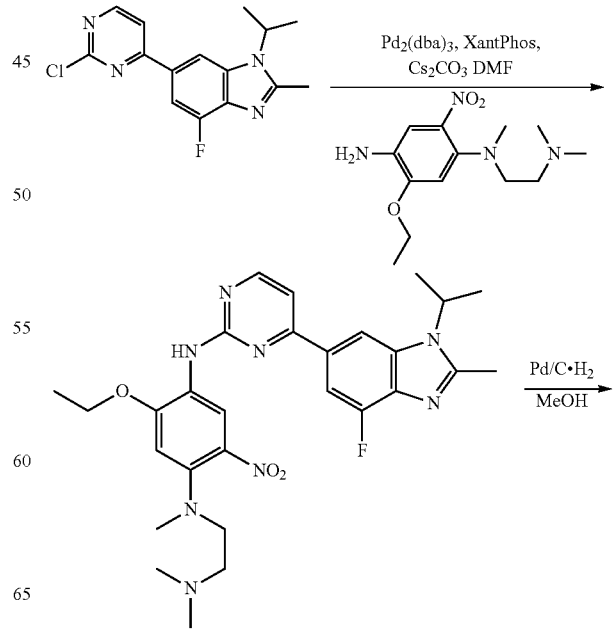

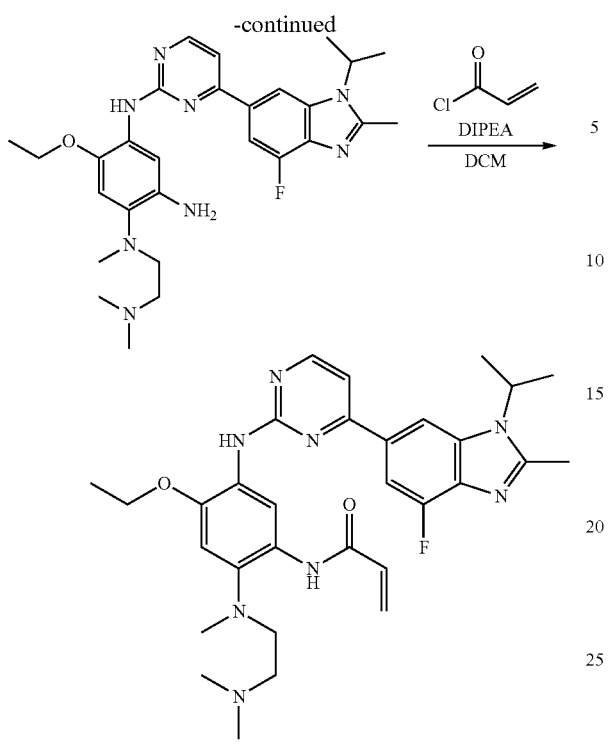

Step 1 Synthesis of Compound N$^1$-(2-(dimethyl-amino)ethyl)-5-ethoxy-N$^4$-(4-(4-fluoro-1-isopropyl-2-methyl-1H-benzo[d]imidazole-6-yl)pyrimidin-2-yl)-N-methyl-2-nitrobenzene-1,4-diamine The synthetic step is the same as that of Example 20 step 1, and 500 mg of a red solid was obtained. LC-MS(APCI): m/z=551.1 (M+1).

Step 2 Synthesis of Compound N$^1$-(2-(dimethyl-amino)ethyl)-5-ethoxy-N$^4$-(4-(4-fluoro-1-isopropyl-2-methyl-1H-benzo[d]imidazole-6-yl)pyrimidin-2-yl)-N-methylbenzene-1,2,4-triamine The synthetic step is the same as that of Example 20 step 2, and 256 mg of a pale yellow solid was obtained, yield over two steps: 46.4%. LC-MS(APCI): m/z=521.3M+1).

Step 3 Synthesis of Compound N-(2-((2-(dimethyl-amino)ethyl)(methyl)amino)-4-ethoxy-5-((4-(4-fluoro-1-isopropyl-2-meth yl-1H-benzo[d]imidazole-6-yl)pyrimidin-2-yl)amino)phenyl)acrylamide The synthetic step is the same as that of Example 20 step 3, and 150 mg of a yellow solid was obtained, yield was 24.2%. LC-MS(APCI): m/z=575.6 (M+1), HPLC: 97.22%, $^1$H NMR (400 MHz, DMSO-d6): δ 10.08 (s, 1H), 9.02 (s, 1H), 8.51 (s, 1H), 8.19 (d, J=24.3 Hz, 2H), 7.96 (d, J=11.8 Hz, 1H), 7.59 (s, 1H), 7.03 (s, 1H), 6.56-6.34 (m, 1H), 6.27 (d, J=16.8 Hz, 1H), 5.88-5.63 (m, 1H), 4.84 (s, 1H), 4.19-4.07 (m, 2H), 2.97-2.86 (m, 2H), 2.70 (s, 3H), 2.63 (s, 3H), 2.45-2.35 (m, 2H), 2.27 (s, 6H), 1.59 (d, J=4.8 Hz, 6H), 1.34 (t, J=6.0 Hz, 3H).

Example 49 Preparation of N-(2-((2-(dimethyl-amino)ethyl)(methyl)amino)-5-((4-(4-fluoro-1-isopropyl-2-methyl-1H-benzo[d]imidazole-6-yl)pyrimidin-2-yl)amino)-4-(2,2,2-trifluoroethoxy)phenyl)acrylamide

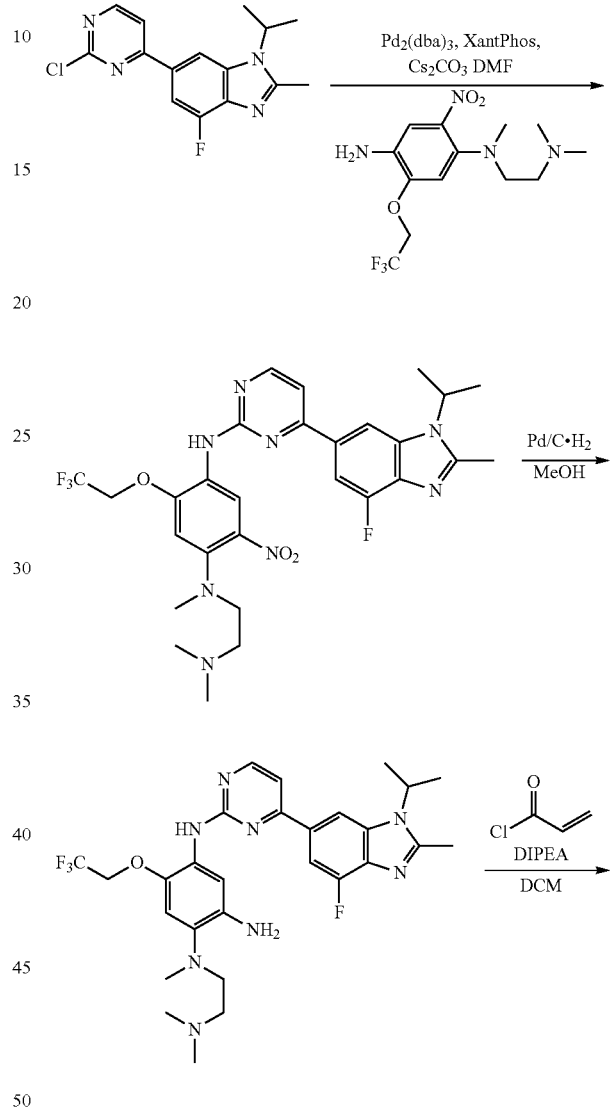

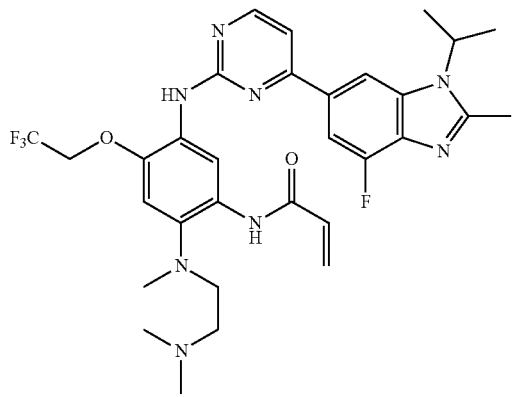

223

Step 1 Synthesis of Compound N¹-(2-(dimethyl-amino)ethyl)-N⁴-(4-(4-fluoro-1-isopropyl-2-methyl-1H-benzo[d]imidazole-6-yl)pyrimidin-2-yl)-N-methyl-2-nitro-5-(2,2,2-trifluoroethoxy)benzene-1,4-diamine The synthetic step is the same as that of Example 20 step 1, and 435 mg of a red solid was obtained. LC-MS(APCI): m/z=605.2 (M+1).

Step 2 Synthesis of Compound N¹-(2-(dimethyl-amino)ethyl)-N⁴-(4-(4-fluoro-1-isopropyl-2-methyl-1H-benzo[d]pyrimidin-6-yl)pyrimidin-2-yl)-N¹-methyl-5-(2,2,2-trifluoromethoxy)benzene-1,2,4-triamine The synthetic step is the same as that of Example 20 step 2, and 290 mg of a yellow-green solid was obtained, yield over two steps: 33.9%. LC-MS(APCI): m/z=575.6M+1).

Step 3 Synthesis of Compound N-(2-((2-(dimethyl-amino)ethyl)(methyl)amino)-5-((4-(4-fluoro-1-iso-propyl-2-methyl-1H-benzo[d]imidazole-6-yl)pyrimi-din-2-yl)amino)-4-(2,2,2-trifluoroethoxy)phenyl) acrylamide The synthetic step is the same as that of Example 20 step 3, and 140 mg of a yellow solid was obtained, yield was 43.7%. LC-MS(APCI): m/z=629.2 (M+1), HPLC: 94.62%, ¹H NMR (400 MHz, DMSO-d6): δ 9.96 (s, 1H), 8.80 (s, 1H), 8.48 (d, J=5.2 Hz, 1H), 8.31 (s, 1H), 8.20 (s, 1H), 7.87 (d, J=12.2 Hz, 1H), 7.56 (d, J=5.3 Hz, 1H), 7.18 (s, 1H), 6.34-6.19 (m, 1H), 5.87 (dd, J=10.3, 1.7 Hz, 1H), 5.82-5.67 (m, 1H), 4.86-4.75 (m, 3H), 3.10-3.02 (m, 2H), 2.66 (s, 3H), 2.61 (s, 3H), 2.50-2.40 (m, 8H), 1.57 (d, J=6.9 Hz, 6H).

Example 50 Preparation of N-(2-((2-(dimethyl-amino)ethyl)(methyl)amino)-5-((4-(1-isopropyl-2-(methyl-d₃)-1H-benzo[d]imidazole-6-yl)pyrimidin-2-yl)amino)-4-methoxyphenyl)acrylamide

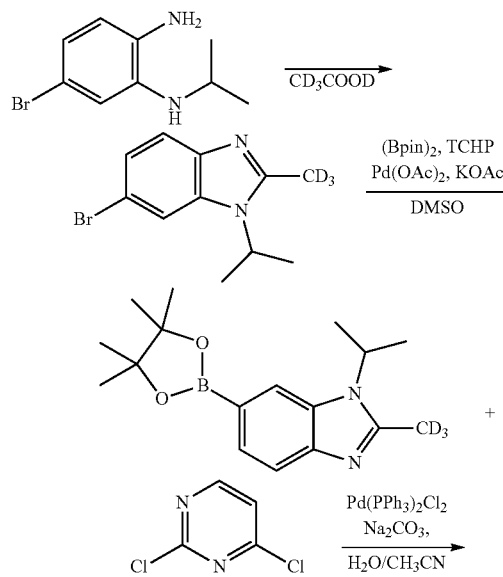

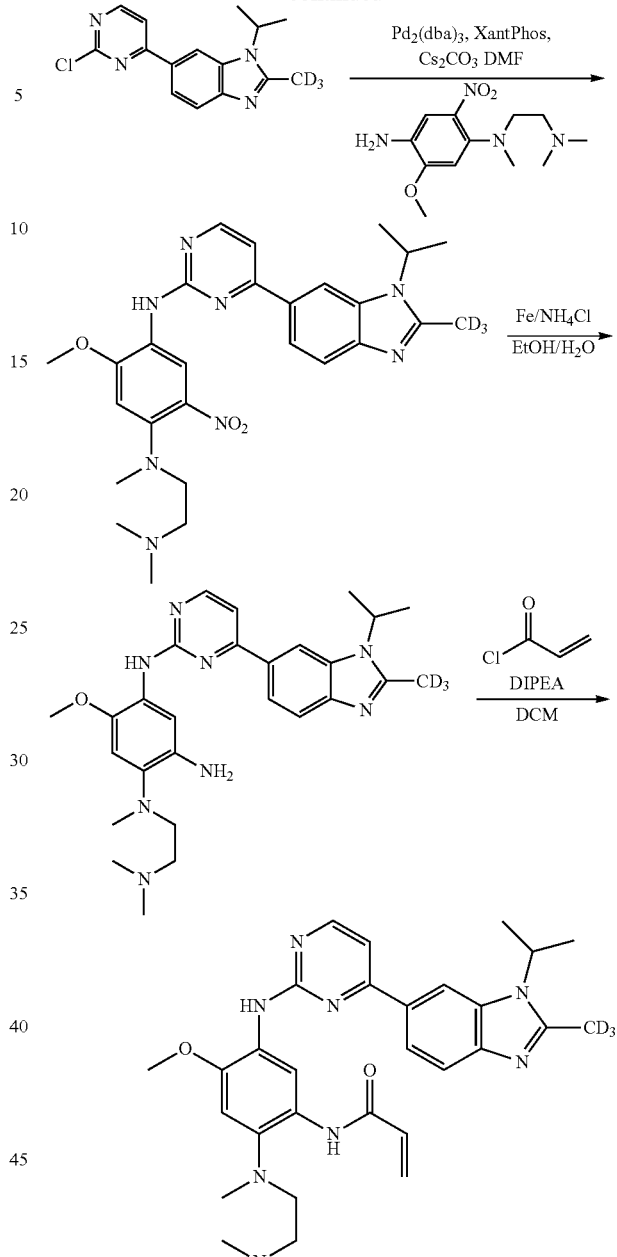

Step 1 Synthesis of Compound 6-bromo-1-isopro-pyl-2-(methyl-d₃)-1H-benzo[d]imidazole 5-bromo-N-isopropylbenzene-1,2-diamine (3.00 m, 13.10 mmol) was added into glacial acetic acid-d4 (15 mL), and the reaction was reacted under reflux for 2 hrs. After cooling to room temperature, acetic acid was removed under reduce pressure, the pH of the residue was adjusted to about 7 with saturated solution of sodium bicarbonate, extracted with dichloromethane (50 ml×3), the organic layer was combined, washed with brine, dried over anhydrous sodium sulfate, the filtrate was concentrated under reduced pressure, and the filtrate was separated on column chromatography (eluant:dichloromethane/methanol (v/v)=20:1) to afford 2.68 g of a brown-red oil, yield was 80.22%, LC-MS(APCI): m/z=256.1 (M+1).

Step 2 Synthesis of Compound 1-isopropyl-2-(methyl-d₃)-6-(4,4,5,5-tetramethyl-1,3,2-dioxaborolan-2-yl)-1H-benzo[d]imidazole Under nitrogen protection, TCHP (500 mg) and Pd(Oac)₂ (250 mg) were added into the mixture of compound 6-bromo-1-isopropyl-2-(methyl-d₃)-1H-benzo[d]imidazole (2.68 g, 10.47 mmol), bis(pinacolato)diboron (4.00 g, 15.70 mmol) and potassium acetate (3.00 g, 31.41 mmol) in anhydrous DMSO (25 mL), and under nitrogen protection, the reaction was reacted at 100° C. for 2 hrs. After cooling to room temperature, the reaction was quenched by adding water, extracted with ethyl acetate (100 mL×3), the organic layer was combined, washed with brine, dried over anhydrous sodium sulfate, concentrated under reduced pressure, and the filtrate was separated on column chromatography (eluant:petroleum ether/ethyl acetate (v/v)=2:1), to afford 2.2 g of a yellow solid, yield was 69.3%. LC-MS(APCI): m/z=304.2 (M+1).

Step 3 Synthesis of Compound 6-(2-chloropyrimidin-4-yl)-1-isopropyl-2-(methyl-d₃)-1H-benzo[d]imidazole Under nitrogen protection, Pd(PPh₃)₂Cl₂ (220 mg) was added into 1-isopropyl-2-(methyl-d₃)-6-(4,4,5,5-tetramethyl-1,3,2-dioxaborolan-2-yl)-1H-benzo[d]imidazole (2.2 g, 7.26 mmol), 2,4-dichloropyrimidine (1.30 g, 8.71 mmol) and sodium carbonate (1.90 g, 18.15 mmol) in the mixture of acetonitrile (18 mL) and water (6 mL), and under nitrogen protection the reaction was heated to 80° C. and reacted for 2.5 hrs. After cooling to room temperature, it was filtered on Celite, the filtrate was concentrated under reduced pressure, and the filtrate was separated on column chromatography (eluant:petroleum ether/ethyl acetate (v/v)=1:1), to afford 2.7 g of a white solid. Yield was 100%. LC-MS(APCI): m/z=290.2 (M+1).

Step 4 Synthesis of Compound N¹-(2-(dimethylamino)ethyl)-N⁴-(4-(1-isopropyl-2-(methyl-d₃)-1H-benzo[4,5-b]imidazol-6-yl)pyrimidin-2-yl)-5-methoxy-N¹-methyl-2-nitrobenzene-1,4-diamine The synthetic step is the same as that of Example 20 step 1, and a brown-yellow oil was obtained. LC-MS(APCI): m/z=522.3 (M+1).

Step 5 Synthesis of Compound N¹-(2-(dimethylamino)ethyl)-N⁴-(4-(1-isopropyl-2-(methyl-d₃)-1H-benzo[4,5-b]imidazol-6-yl)pyrimidin-2-yl)-5-methoxy-N-methylbenzene-1,2,4-triamine Reduced iron powder (1.30 g, 23.08 mmol) and ammonium chloride (600 mg, 11.54 mmol) were added into compound N-(2-(dimethylamino)ethyl)-N⁴-(4-(1-isopropyl-2-(methyl-d₃)-1H-benzo[4,5-b]imidazol-6-yl)pyrimidin-2-yl)-5-methoxy-N-methyl-2-nitrobenzene-1,4-diamine in the mixed solution of ethanol and water (16 mL/4 mL), and the reaction was refluxed for 2 hrs, filtered on Celite, the filtrate was concentrated under reduced pressure, and the filtrate was separated on column chromatography (eluant:dichloromethane/methanol (v/v)=8:1), to afford 1.50 g of a yellow solid, yield over three steps was 42.1%. LC-MS(APCI): m/z=492.2 (M+1).

Step 6 Synthesis of Compound N-(2-((2-(dimethylamino)ethyl)(methyl)amino)-5-((4-(1-isopropyl-2-(methyl-d₃)-1H-benzo[d]imidazole-6-yl)pyrimidin-2-yl)amino)-4-methoxyphenyl)acrylamide The synthetic step is the same as that of Example 20 step 3, and 1.13 g produt was obtained, yield was 67.7%. HPLC: 97.42%. LC-MS(APCI): m/z=546.2 (M+1), ¹H NMR (400 MHz, DMSO-d6): δ 10.07 (s, 1H), 8.95 (s, 1H), 8.39 (d, J=44.1 Hz, 2H), 8.22-7.98 (m, 2H), 7.52 (d, J=29.5 Hz, 2H), 7.00 (s, 1H), 6.34 (d, J=69.0 Hz, 2H), 5.74 (s, 1H), 4.78 (s, 1H), 3.84 (s, 3H), 2.96-2.81 (m, 2H), 2.69 (s, 3H), 2.40-2.31 (m, 2H), 2.23 (s, 6H), 1.55 (s, 6H).

Example 51 Preparation of N-(2-((2-(dimethylamino)ethyl)(methyl)amino)-4-methoxy-5-((4-(2-methyl-1-(propyl-2-yl-2-d)-1H-benzo[d]imidazole-6-yl)pyrimidin-2-yl)amino)phenyl)acrylamide

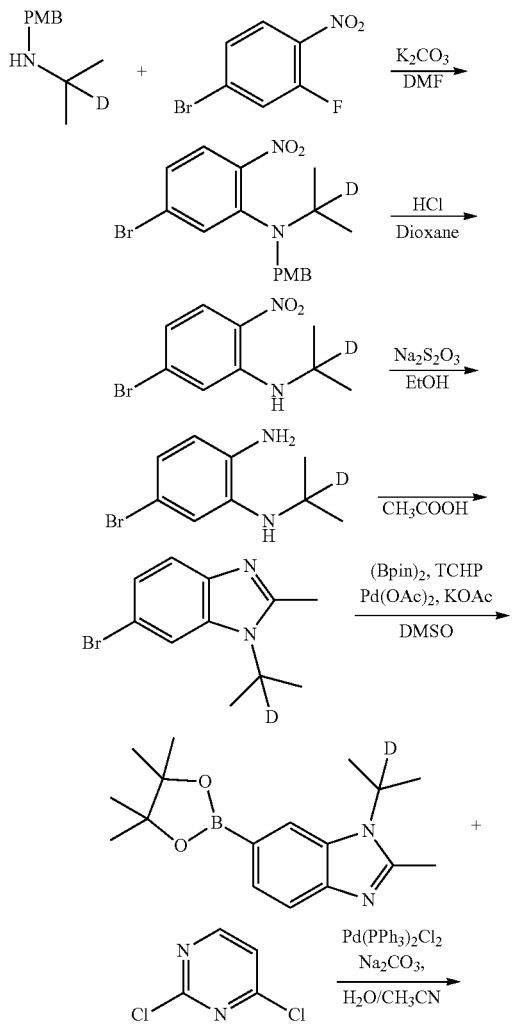

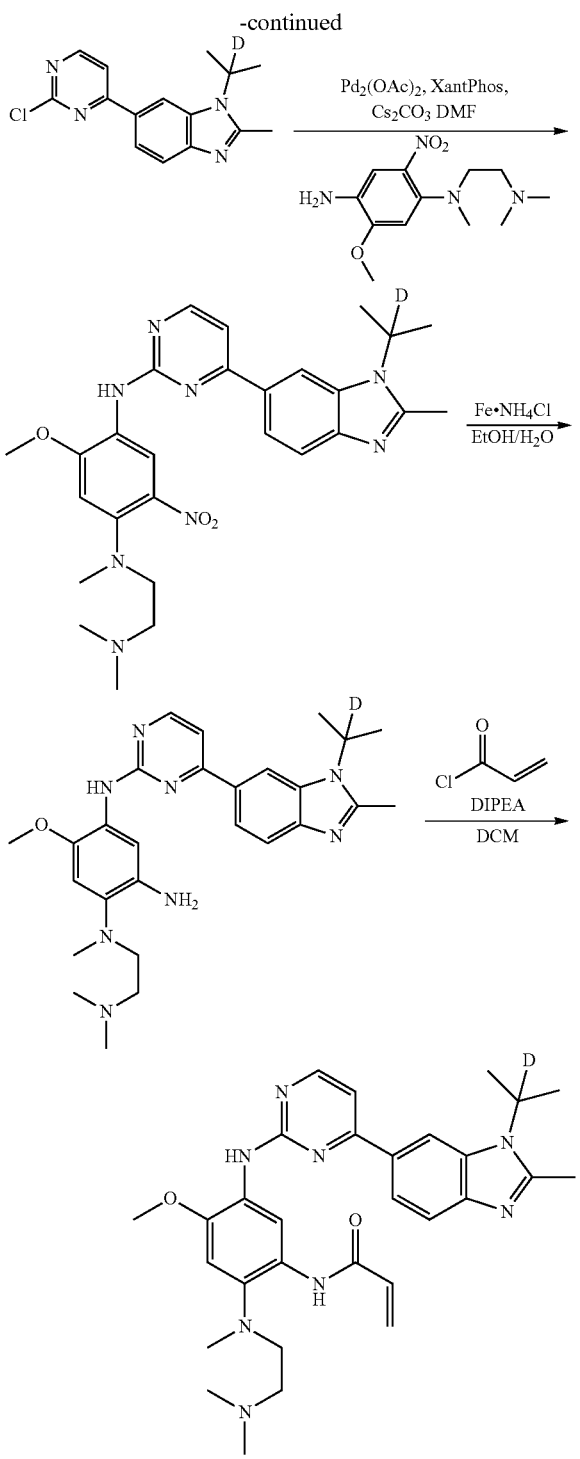

Step 1 Synthesis of Compound 5-bromo-N-(4-methoxyphenyl)-2-nitro-N-(isopropyl-2-yl-2-d)aniline At room temperature, potassium carbonate (248 mg, 1.80 mmol) and N-(4-methoxyphenyl)propan-2-d-2-amine (164 mg, 0.91 mmol) were sequentially added into the solution of 4-bromo-2-fluoro-1-nitrobenzene (200 mg, 0.90 mmol) in anhydrous DMF (3 mL), and the reaction was heated to 100° C. and reacted for 5 hrs. The reaction was quenched by adding water, extracted with ethyl acetate (20 mL×3), the combined organic layer was washed with water and brine, dried over anhydrous sodium sulfate, concentrated under reduced pressure, and the filtrate was separated on column chromatography (eluant:petroleum ether/ethyl acetate (v/v) =25:1) to afford 130 mg of a pale yellow solid, yield was 38.1%, LC-MS(APCI): m/z=380.1 (M+1).

Step 2 Synthesis of Compound 5-bromo-2-nitro-N-(propyl-2-yl-2-d)aniline

The compound 5-bromo-N-(4-methoxyphenyl)-2-nitro-N-(isopropyl-2-yl-2-d)aniline (700 mg, 1.84 mmol) was dissolved in 4N HCl in dioxane (20 mL), and the reaction was stirred under reflux for 4.5 hrs. Dioxane was removed under reduce pressure, pH was adjusted to >7 with saturated solution of sodium bicarbonate, extracted with dichloromethane (100 mL×3), the organic layer was combined, washed with brine, dried over anhydrous sodium sulfate, the filtrate was concentrated under reduced pressure, and the filtrate was separated on column chromatography (eluant: petroleum ether/ethyl acetate (v/v)=99:1) to afford 450 mg of a pale yellow liquid, yield was 94.4%. LC-MS(APCI): m/z=260.1 (M+1).

Step 3 Synthesis of Compound 5-bromo-$N^1$-(propyl-2-yl-2-d)phenyl-1,2-diamine

The compound 5-bromo-2-nitro-N-(propyl-2-yl-2-d)aniline (450 mg, 1.73 mmol) was dissolved in the mixed solvent of ethanol and water (v/v=20 mL/8 mL), sodium dithionite (900 mg) was added, and the reaction was reacted at room temperature overnight, filtered on Celite, the filter cake was washed with ethyl acetate, removed under reduce pressure ethanol, extracted with ethyl acetate (100 mL×3), the organic layer was combined, washed with brine, dried over anhydrous sodium sulfate, concentrated under reduced pressure, and the filtrate was separated on column chromatography (eluant:petroleum ether/ethyl acetate (v/v)=20:1) to afford 328 mg of a brown solid, yield was 82.8%. LC-MS(APCI): m/z=230.1 (M+1).

Step 4 Synthesis of Compound 6-bromo-2-methyl-1-(propyl-2-yl-2-d)-1H-benzo[d]imidazole The compound 5-bromo-$N^1$-(propyl-2-yl-2-d)phenyl-1,2-diamine (885 g, 3.85 mmol) was added into glacial acetic acid (15 mL), and the reaction was reacted under reflux for 2 hrs. After cooling to room temperature, acetic acid was removed under reduce pressure, the pH of the residue was adjusted to about 7 with saturated solution of sodium bicarbonate, extracted with dichloromethane (50 mL×3), the organic layer was combined, washed with brine, dried over anhydrous sodium sulfate, the filtrate was concentrated under reduced pressure, and the filtrate was separated on column chromatography (eluant:dichloromethane /methanol (v/v)=20:1) to afford 844 mg of a brown-red oil, yield was 86.7%, LC-MS(APCI): m/z=254.1 (M+1).

Step 5 Synthesis of Compound 2-methyl-1-(propyl-2-yl-2-d)-6-(4,4,5,5-tetramethyl-1,3,2-dioxaborolan-2-yl)-1H-benzo[d]imidazole Under nitrogen protection, TCHP (140 mg) and Pd(Oac)2 (100 mg) were added into the mixture of 6-bromo-2-methyl-1-propyl-2-yl-2-d)-1H-benzo[d]imidazole (840 mg), bis(pinacolato)diboron (1.27 g) and potassium acetate (987 mg) in anhydrous DMSO (10 mL), and under nitrogen protection, the reaction was reacted at 100° C. for 2 hrs. After cooling to room temperature, the reaction was quenched by adding water, extracted with ethyl acetate (50 mL×3), the organic layer was combined, washed with brine, dried over anhydrous sodium sulfate, concentrated under reduced pressure, and the filtrate was separated on column chromatography (eluant:petroleum ether/ethyl acetate (v/v)=2:1), to afford 566 mg of a yellow solid, yield was 56.5%. LC-MS(APCI): m/z=302.2 (M+1).

Step 6 Synthesis of Compound 6-(2-chloropyrimidin-4-yl)-2-methyl-1-(propyl-2-yl-2-d)-1H-benzo[d]imidazole Under nitrogen protection, Pd(PPh$_3$)$_2$Cl$_2$ (100 mg) was added into the mixture of 2-methyl-1-(propyl-2-yl-2-d)-6-(4,4,5,5-tetramethyl-1,3,2-dioxaborolan-2-yl)-1H-benzo[d]imidazole (566 mg, 1.88 mmol), 2,4-dichloropyrimidine (336 mg, 2.26 mmol) and sodium carbonate (498 mg, 4.70 mmol) in acetonitrile (9 mL) and water (3 mL), and under nitrogen protection the reaction was heated to 80° C. and reacted for 2.5 hrs. After cooling to room temperature, it was filtered on Celite, the filtrate was concentrated under reduced pressure, and the filtrate was separated on column chromatography (eluant:petroleum ether/ethyl acetate (v/v)=1:1), to afford 500 mg of a white solid. Yield was 92.7%. LC-MS (APCI): m/z=288.2 (M+1).

Step 7 Synthesis of Compound N$^1$-(2-(dimethylamino)ethyl)-5-methoxy-N$^1$-methyl-N$^4$-(4-(2-methyl-1-(propyl-2-yl-2-d)-1H-benzo[d]imidazole-6-yl)pyrimidin-2-yl)-2-nitrobenzene-1,4-diamine Under nitrogen protection, Pd(OAc)$_2$ (120 mg) and Xantphos (200 mg) were added into 6-(2-chloropyrimidin-4-yl)-2-methyl-1-(propyl-2-yl-2-d)-1H-benzo[d]imidazole (500 mg, 1.74 mmol), N$^1$-(2-(dimethylamino)ethyl)-5-methoxy-N$^1$-methyl-2-nitrobenzene-1,4-diamine (467 mg, 1.74 mmol) and cesium carbonate (1.40 g, 4.36 mmol) in anhydrous DMF (15 mL), and the reaction mixture was reacted under nitrogen protection at 100° C. overnight, and after cooling to room temperature, it was filtered on Celite, the filtrate was concentrated under reduced pressure, and the filtrate was separated on column chromatography (eluant: dichloromethane /methanol (v/v)=10:1), to afford a brown oil. LC-MS(APCI): m/z=520.3 (M+1).

Step 8 Synthesis of Compound N$^1$-(2-(dimethylamino)ethyl)-5-methoxy-N$^1$-methyl-N$^4$-(4-(2-methyl-1-(propyl-2-yl-2-d)-1H-benzo[d]imidazole-6-yl)pyrimidin-2-yl)benzene-1,2,4-triamine Reduced iron powder (6 eq) and ammonium chloride (3 eq) were added into N$^1$-(2-(dimethylamino)ethyl)-5-methoxy-N$^1$-methyl-N$^4$-(4-(2-methyl-1-(propyl-2-yl-2-d)-1H-benzo[d]imidazole-6-yl)pyrimidin-2-yl)-2-nitrobenzene-1,4-diamine in the mixed solvent of ethanol and water (16 mL/4 mL), and the reaction was reacted under reflux for 2 hrs, filtered on Celite, the filtrate was concentrated under reduced pressure, and the filtrate was separated on column chromatography (eluant:dichloromethane/methanol (v/v) =8:1), to afford 300 mg of a red solid, yield over three steps was 35.3%. LC-MS(APCI): m/z=490.2 (M+1).

Step 9 Synthesis of Compound N-(2-((2-(dimethylamino)ethyl)(methyl)amino)-4-methoxy-5-((4-(2-methyl-1-(propyl-2-yl-2-d)-1H-benzo[d]imidazole-6-yl)pyrimidin-2-yl)amino)phenyl)acrylamide The synthetic step is the same as that of Example 20 step 3, and 110 mg product was obtained, yield was 33.2%. HPLC: 95.14%. LC-MS(APCI): m/z=544.2 (M+1), $^1$H NMR (500 MHz, DMSO-d$_6$): δ 10.56 (br, 1H), 9.82 (s, 1H), 8.76 (s, 1H), 8.45 (d, J=5.3 Hz, 1H), 8.33 (s, 1H), 8.12 (s, 1H), 8.04 (d, J=8.5 Hz, 1H), 7.55 (d, J=8.5 Hz, 1H), 7.49 (d, J=5.3 Hz, 1H), 6.94 (s, 1H), 6.23 (d, J=16.9 Hz, 1H), 5.69 (d, J=10.2 Hz, 1H), 3.86 (s, 3H), 3.28-3.21 (m, 5H), 2.68 (s, 6H), 2.59-2.56 (m, 5H), 1.55 (s, 6H).

Example 52 Preparation of N-(2-((2-(dimethylamino)ethyl)(methyl)amino)-4-methoxy-5-((4-(2-methyl-1-(propyl-2-yl-1,1,1,3,3,3-d$_6$)-1H-benzo[d]imidazole-6-yl)pyrimidin-2-yl)amino)phenyl)acrylamide

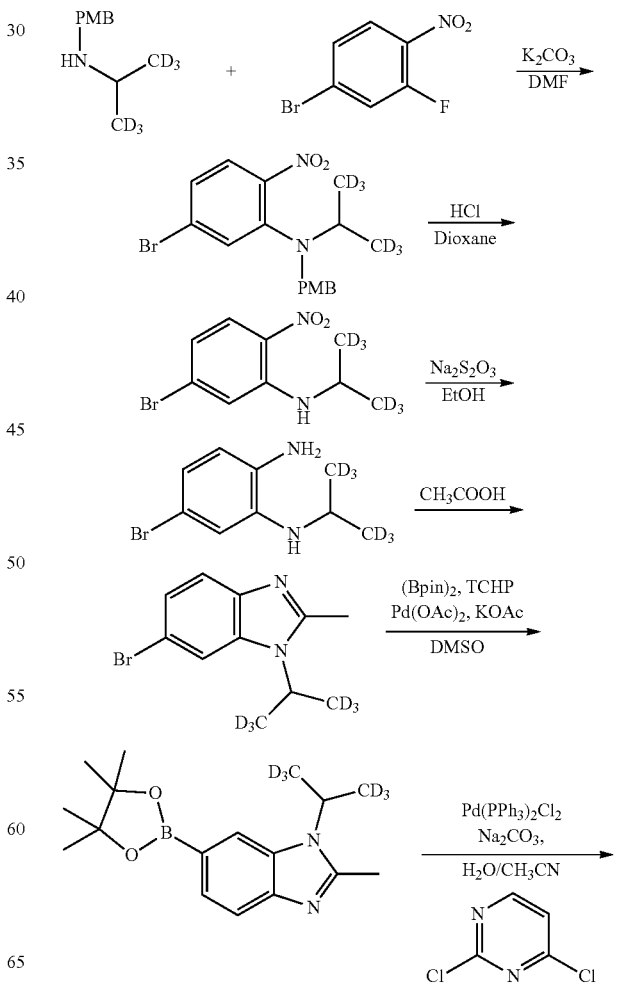

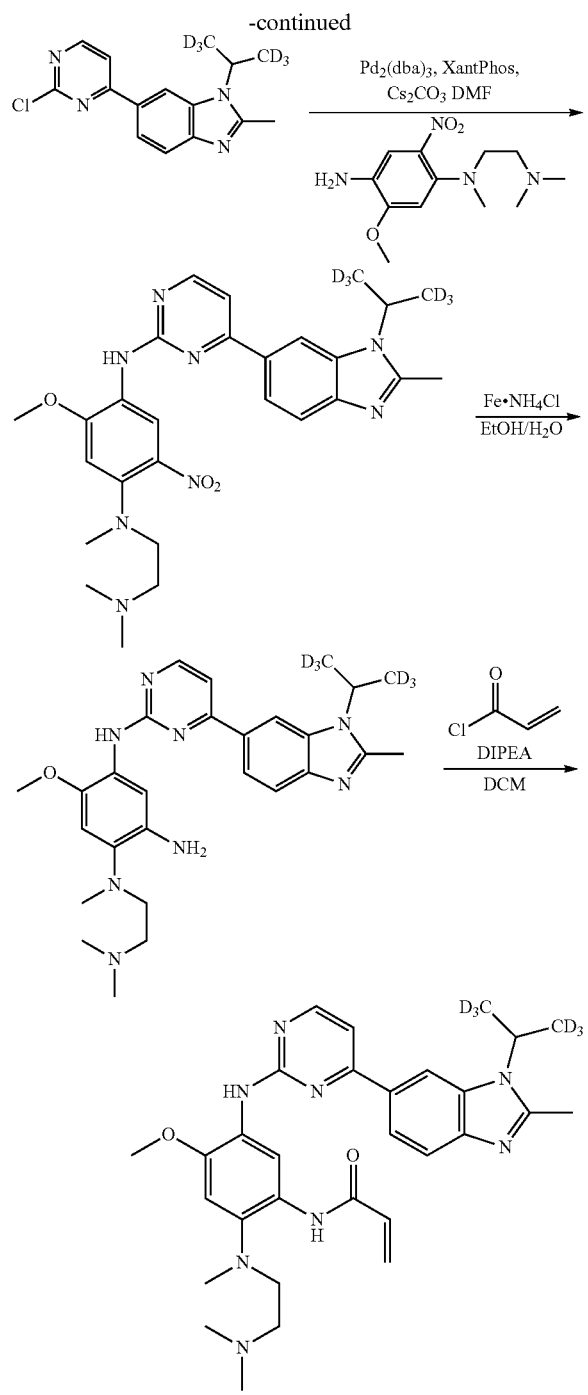

Step 1 Synthesis of 5-bromo-N-(4-methoxyphenyl)-2-nitro-N-(isopropyl-2-yl-1,1,1,3,3,3-$d_6$)aniline At room temperature, potassium carbonate (4.10 g, 30.0 mmol) and N-(4-methoxyphenyl)propane-1,1,1,3,3,3-$d_6$-2-amine (1.85 g, 10.00 mmol) were sequentially added into 4-bromo-2-fluoro-1-nitrobenzene (2.18 g, 10.0 mmol) in anhydrous DMF (10 mL), and the reaction was heated to 100° C. and reacted for 5 hrs. The reaction was quenched by adding water, extracted with ethyl acetate (100 mL×3), the combined organic layer was washed with water and brine, dried over anhydrous sodium sulfate, the filtrate was concentrated under reduced pressure, and the filtrate was separated on column chromatography (eluant:petroleum ether/ethyl acetate (v/v)=25:1) to afford 3.00 g of a pale yellow liquid, yield was 80%, LC-MS(APCI): m/z=385.1 (M+1).

Step 2 Synthesis of 5-bromo-2-nitro-N-(propyl-2-yl-1,1,1,3,3,3-$d_6$)aniline 5-bromo-N-(4-methoxyphenyl)-2-nitro-N-(isopropyl-2-yl-1,1,1,3,3,3-$d_6$)aniline (3.00 g, 7.79 mmol) was dissolved in 4N HCl in dioxane (20 mL), and the reaction was stirred under reflux for 4.5 hrs. Dioxane was removed under reduce pressure, the pH was adjusted to >7 with saturated solution of sodium bicarbonate, extracted with dichloromethane (100 mL×3), the organic layer was combined, washed with brine, dried over anhydrous sodium sulfate, the filtrate was concentrated under reduced pressure, and the filtrate was separated on column chromatography (eluant:petroleum ether/ethyl acetate (v/v)=99:1) to afford 1.54 g of a pale yellow liquid, yield was 75%. LC-MS(APCI): m/z=265.1 (M+1).

Step 3 Synthesis of 5-bromo-$N^1$-(propyl-2-yl-1,1,1,3,3,3-$d_6$)phenyl-1,2-diamine 5-bromo-2-nitro-N-(propyl-2-yl-1,1,3,3,3-$d_6$)aniline (1.54 g, 5.84 mmol) was dissolved in the mixed solvent of ethanol and water (v/v=120 mL/50 mL), sodium dithionite (5.93 g, 28.8 mmol) was added, and the reaction was reacted at room temperature overnight, filtered on Celite, the filter cake was washed with ethyl acetate, ethanol was removed under reduce pressure, extracted with ethyl acetate (100 mL×3), the organic layer was combined, washed with brine, dried over anhydrous sodium sulfate, concentrated under reduced pressure, and the filtrate was separated on column chromatography (eluant:petroleum ether/ethyl acetate (v/v) =20:1) to afford 1.00 g of a pale yellow liquid, yield was 73.2%. LC-MS(APCI): m/z=235.1 (M+1).

Step 4 Synthesis of 6-bromo-2-methyl-1-(propyl-2-yl-1,1,1,3,3,3-$d_6$)-1H-benzo[d]imidazole 5-bromo-$N^1$-(propyl-2-yl-1,1,1,3,3,3-$d_6$)phenyl-1,2-diamine (1.00 g, 4.27 mmol) was added into glacial acetic acid (10 mL), and the reaction was reacted under reflux for 2 hrs. After cooling to room temperature, acetic acid was removed under reduce pressure, the pH of the residue was adjusted to about 7 with saturated solution of sodium bicarbonate, extracted with dichloromethane (50 mL×3), the organic layer was combined, washed with brine, dried over anhydrous sodium sulfate, the filtrate was concentrated under reduced pressure, and the filtrate was separated on column chromatography (eluant:dichloromethane /methanol (v/v) =20:1) to afford 580 mg of a brown-red oil, yield was 80.22%, LC-MS(APCI): m/z=259.1 (M+1).

Step 5 Synthesis of 2-methyl-1-(propyl-2-yl-1,1,1,3,3,3-$d_6$)-6-(4,4,5,5-tetramethyl-1,3,2-dioxaborolan-2-yl)-1H-benzo[d]imidazole Under nitrogen protection, TCHP (40 mg, 0.12 mmol) and Pd(Oac)$_2$ (15 mg, 0.06 mmol) were added into the mixture of 6-bromo-2-methyl-1-(propyl-2-yl-1,1,1,3,3,3-$d_6$)-1H-benzo[d]imidazole (300 mg, 1.24 mmol), bis(pinacolato) diboron (380 mg, 1.50 mmol) and potassium acetate (370 mg, 3.72 mmol) in anhydrous DMSO (10 mL), and under nitrogen protection, the reaction was reacted at 100° C. for 2 hrs. After cooling to room temperature, the reaction was quenched by adding water, extracted with ethyl acetate (50 mL×3), the organic layer was combined, washed with brine, dried over anhydrous sodium sulfate, concentrated under reduced pressure, and the filtrate was separated on column chromatography (eluant:petroleum ether/ethyl acetate (v/v)=2:1), to afford 266 mg of a yellow solid, yield was 69.8%. LC-MS(APCI): m/z=307.2 (M+1).

Step 6 Synthesis of 6-(2-chloropyrimidin-4-yl)-2-methyl-1-(propyl-2-yl-1,1,1,3,3,3-$d_6$)-1H-benzo[d]imidazole Under nitrogen protection, Pd(PPh$_3$)$_2$Cl$_2$ (80 mg) was added into the mixture of 2-methyl-1-(propyl-2-yl-1,1,1,3,3,3-$d_6$)-6-(4,4,5,5-tetramethyl-1,3,2-dioxaborolan-2-yl)-1H-benzo[d]imidazole (560 mg, 1.80 mmol), 2,4-dichloropyrimidine (320 mg, 0.17 mmol) and sodium carbonate (4.00 mg, 3.60 mmol) in acetonitrile (12 mL) and water (4 mL), and under nitrogen protection the reaction was heated to 80° C. for 2.5 hrs. After cooling to room temperature, it was filtered on Celite, the filtrate was concentrated under reduced pressure, and the filtrate was separated on column chromatography (eluant:petroleum ether/ethyl acetate (v/v)=1:1), to afford 560 mg of a white solid. Yield was 100%. LC-MS(APCI): m/z=293.2 (M+1).

Step 7 Synthesis of Compound N-(2-(dimethylamino)ethyl)-5-methoxy-$N^1$-methyl-$N^4$-(4-(2-methyl-1-(propyl-2-yl-1,1,1,3,3,3-$d_6$)-1H-benzo[d]imidazole-6-yl)pyrimidin-2-yl)-2-nitrobenzene-1,4-diamine The synthetic step is the same as that of Example 20 step 1, and 400 mg of a brown oil was obtained. LC-MS(APCI): m/z=525.3 (M+1).

Step 8 synthesis of N-(2-(dimethylamino)ethyl)-5-methoxy-$N^1$-methyl-$N^4$-(4-(2-methyl-1-(propyl-2-yl-1,1,1,3,3,3-$d_6$)-1H-benzo[d]imidazole-6-yl)pyrimidin-2-yl)benzene-1,2,4-triamine Reduced iron powder (6eq) and ammonium chloride (3eq) were added into $N^1$-(2-(dimethylamino)ethyl)-5-methoxy-$N^1$-methyl-$N^4$-(4-(2-methyl-1-(propyl-2-yl-1,1,1,3,3,3-$d_6$)-1H-benzo[d]imidazole-6-yl)pyrimidin-2-yl)-2-nitrobenzene-1,4-diamine in the mixed solvent of ethanol and water (16 mL/4 mL), and the reaction was reacted under reflux for 2 hrs, filtered on Celite, the filtrate was concentrated under reduced pressure, and the filtrate was separated on column chromatography (eluant:dichloromethane/methanol (v/v)=8:1), to afford 370 mg of a red solid, yield over three steps was 41.5%. LC-MS(APCI): m/z=495.2 (M+1).

Step 9 Synthesis of Compound N-(2-((2-(dimethylamino)ethyl)(methyl)amino)-4-methoxy-5-((4-(2-methyl-1-(propyl-2-yl-1,1,1,3,3,3-$d_6$)-1H-benzo[d]imidazole-6-yl)pyrimidin-2-yl)amino)phenyl)acrylamide The synthetic step is the same as that of Example 20 step 3, and 200 mg product was obtained, yield was 48.7%. HPLC: 95.55%. LC-MS(APCI): m/z=549.2 (M+1), $^1$H NMR (400 MHz, DMSO-$d_6$): δ 10.01 (s, 1H), 8.90 (s, 1H), 8.46 (d, J=5.3 Hz, 1H), 8.34 (s, 1H), 8.14 (s, 1H), 8.09 (dd, J=8.5, 1.4 Hz, 1H), 7.58 (d, J=8.5 Hz, 1H), 7.50 (d, J=5.3 Hz, 1H), 7.01 (s, 1H), 6.74-6.44 (m, 1H), 6.26 (dd, J=16.9, 1.9 Hz, 1H), 5.80-5.70 (m, 1H), 4.84-4.72 (m, 1H), 3.87 (s, 3H), 3.09-2.91 (m, 2H), 2.68 (s, 3H), 2.59 (s, 3H), 2.50-2.27 (m, 8H).

Example 53 Preparation of N-(2-((2-(dimethylamino)ethyl)(methyl)amino)-5-((4-(4-fluoro-1-isopropyl-2-methyl-1H-benzo[d]imidazole-6-yl)pyrimidin-2-yl)amino)-4-methoxyphenyl)acrylamide (compound 5)

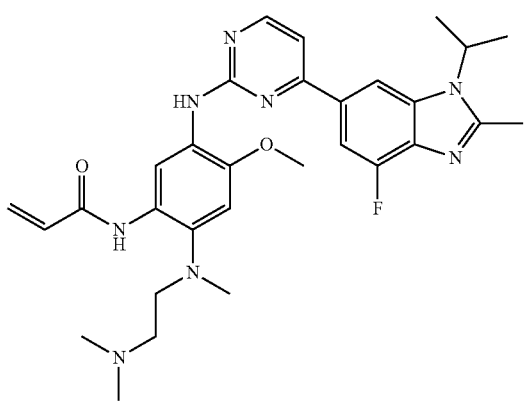

The specific synthetic steps are as follows:

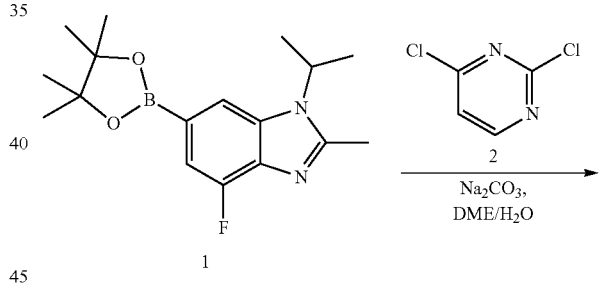

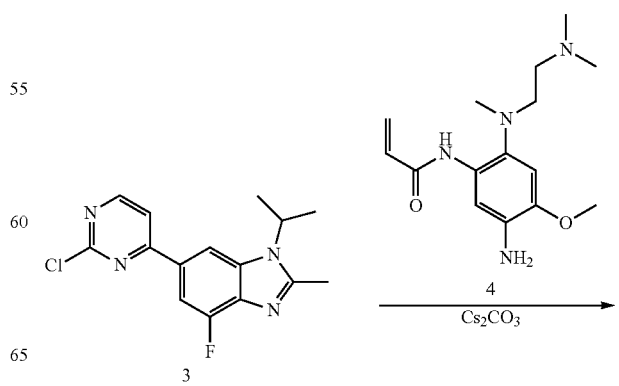

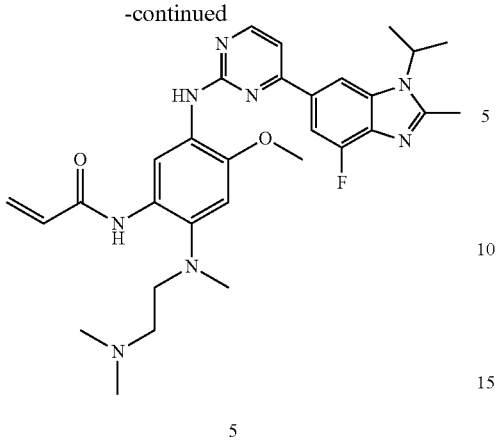

5

Step 1 Synthesis of Compound 3

Under nitrogen protection, ethylene glycol dimethyl ether (2 mL) and water (1 mL) were added into the mixture of 4-fluoro-1-isopropyl-2-methyl-6-(4,4,5,5-tetramethyl-1,3,2-dioxaborolan-2-yl)-1H-benzo[d]imidazole (compound 1, 260 mg, 0.82 mmol) and 2,4-dichloropyrimidine (compound 2, 122.2 mg, 0.82 mmol), sodium carbonate (217 mg, 2.05 mmol), bis(triphenylphosphine)palladium(II) chloride (50 mg, 0.07 mmol), and the reaction was stirred and reacted under nitrogen protection at 80° C. for 1 hour. After cooling to room temperature, it was filtered on Celite, the filter cake was washed with dichloromethane, the filtrate was washed with brine, dried over anhydrous sodium sulfate, and the filtrate was concentrated under reduced pressure to afford 330 mg of a pale yellow solid, which was used in the next step directly. Yield was 100%. LC-MS(APCI): m/z=305.1 (M+1).

Step 2 Synthesis of Compound 5

Under nitrogen protection, anhydrous dioxane (4 mL) was added into the mixture of 6-(2-chloropyrimidin-4-yl)-4-fluoro-1-isopropyl-2-methyl-1H-benzo[d]imidazole (compound 3, 330 mg, 0.82 mmol) and N-(5-amino-2-((2-(dimethylamino)ethyl)(methyl)amino)-4-methoxyphenyl) acrylamide (compound 4, 290 mg, 1.00 mmol), cesium carbonate (667 mg, 2.1 mmol), Pd$_2$(dba)$_3$ (38 mg) and 4,5-bis(diphenylphosphino)-9,9-dimethylxanthene (Xant-Phos, 49 mg), and the reaction was stirred and reacted under nitrogen protection at 110° C. overnight. After cooling to room temperature, it was filtered on Celite, the filter cake was washed with dichloromethane, the filtrate was concentrated under reduced pressure, and the filtrate was separated on column chromatography (eluant:dichloromethane/methanol (v/v)=10:1), to afford a crude, which was purified by preparative TLC (DCM/MeOH v/v=15/1) to afford 25 mg of a yellow solid. Yield was 5.44%. LC-MS(APCI): m/z=561.4 (M+1); $^1$H NMR (300 MHz, DMSO-d$_6$) (δ/ppm) 9.91 (br, 1H), 8.84 (s, 1H), 8.48 (d, J=5.3 Hz, 1H), 8.32-8.13 (m, 2H), 7.89 (d, J=12.5 Hz, 1H), 7.56 (d, J=5.3 Hz, 1H), 6.99 (s, 1H), 6.25 (d, J=17.3 Hz, 1H), 5.77-5.70 (m, 2H), 4.90-4.74 (m, 1H), 3.85 (s, 3H), 2.69-2.62 (m, 4H), 2.60 (s, 3H), 2.51-2.48 (m, 9H), 1.57 (d, J=6.9 Hz, 6H).

Example 54 Preparation of 4-(4-fluoro-1-isopropyl-2-methyl-1H-benzo[d]imidazole-6-yl)-N-(2-methoxy-4-(4-methylpiperazin-1-yl)phenyl)pyrimidin-2-amine (compound 7)

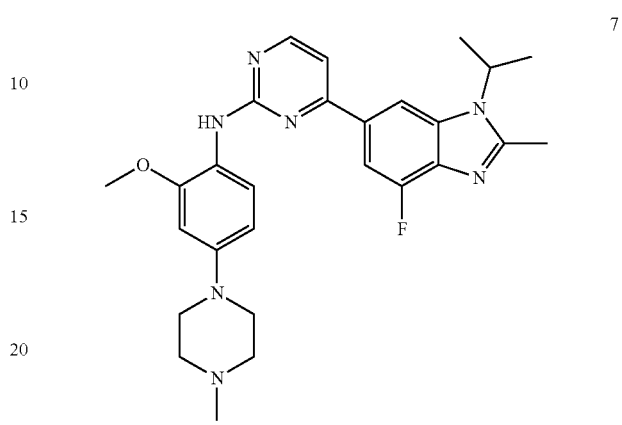

The specific synthetic steps are as follows:

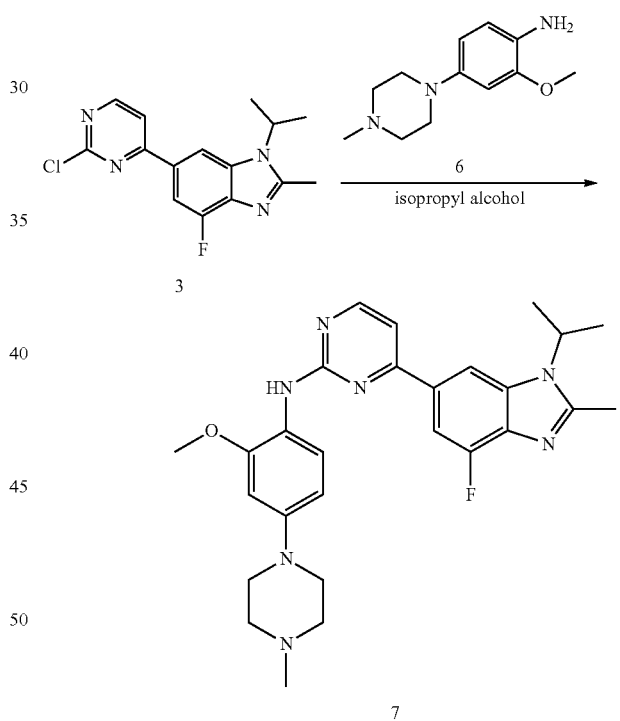

Step 1 Synthesis of Compound 7

P-toluenesulfonic acid (150 mg, 0.84 mmol) was added to the solution of 6-(2-chloropyrimidin-4-yl)-4-fluoro-1-isopropyl-2-methyl-1H-benzo[d]imidazole (compound 3, 130 mg, 0.42 mmol) and 2-methoxy-4-(4-methylpiperazin-1-yl) aniline (compound 6, 111 mg, 0.50 mmol) in isopropyl alcohol (3 mL), and reacted under microwave at 180° C. for 1 hour. The reaction mixture was concentrated under reduced pressure, the residue was adjusted to basic with saturated sodium bicarbonate, extracted with dichloromethane (30 mL×3), the organic phase was combined, washed with brine (30 mL) and dried over anhydrous sodium sulfate, the solvent was removed, and the filtrate was separated on column chromatography (eluant:dichloromethane/methanol (v/v)=13:1), to afford 40 mg of a pale yellow solid, yield was 19.4%. LC-MS(APCI): m/z=490.3 (M+1); $^1$H NMR (500 MHz, DMSO-$d_6$) (δ/ppm) 8.42 (d, J=5.2 Hz, 1H), 8.26 (s, 1H), 8.06 (s, 1H), 7.82 (d, J=8.7 Hz, 1H), 7.74 (d, J=12.1 Hz, 1H), 7.44 (d, J=5.2 Hz, 1H), 6.67 (d, J=2.2 Hz, 1H), 6.51 (dd, J=8.7, 2.3 Hz, 1H), 4.90-4.71 (m, 1H), 3.81 (s, 3H), 3.21-3.14 (m, 4H), 2.67-2.53 (m, 7H), 2.32 (s, 3H), 1.59 (d, J=6.9 Hz, 6H).

Example 55 Preparation of 5-fluoro-4-(4-fluoro-1-isopropyl-2-methyl-1H-benzo[d]imidazole-6-yl)-N-(2-methoxy-4-(4-methylpiperazin-1-yl)phenyl)pyrimidin-2-amine (compound 9)

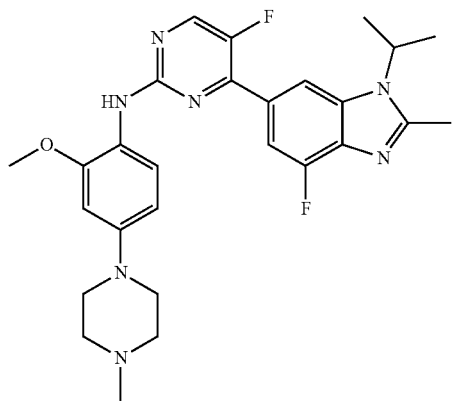

9

The specific synthetic steps are as follows:

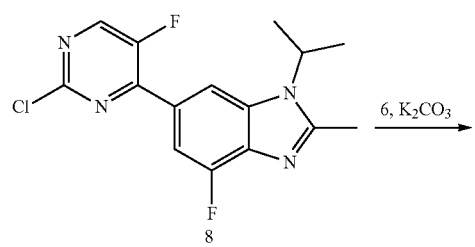

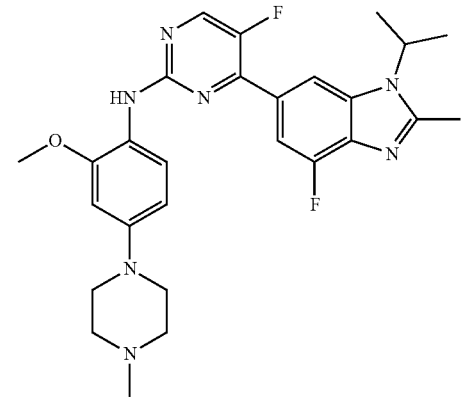

9

Under nitrogen protection, tert-pentanol (5 mL) was added into the mixture of 6-(2-chloro-5-fluoropyrimidin-4-yl)-4-fluoro-1-isopropyl-2-methyl-1H-benzo[d]imidazole (compound 8, 200 mg, 0.62 mmol) and 2-methoxy-4-(4-methylpiperazin-1-yl)aniline (compound 6, 165 mg, 0.75 mmol), potassium carbonate (214 mg, 1.55 mmol), Pd$_2$(dba)$_3$ (37 mg) and Xant-Phos (46 mg), and the reaction was stirred and reacted under nitrogen protection at 100° C. for 3 hours. After cooling to room temperature, it was filtered on Celite, the filter cake was washed with dichloromethane, the filtrate was concentrated under reduced pressure, and the filtrate was separated on column chromatography (eluant: dichloromethane /methanol (v/v)=13:1), to afford 47 mg of a yellow solid. Yield was 14.9%. LC-MS(APCI): m/z=508.3 (M+1); $^1$H NMR (500 MHz, DMSO-$d_6$) (δ/ppm) 8.49 (d, J=3.7 Hz, 1H), 8.21 (s, 1H), 8.14 (s, 1H), 7.65 (d, J=8.6 Hz, 1H), 7.59 (d, J=12.2 Hz, 1H), 6.65 (d, J=1.1 Hz, 1H), 6.48 (dd, J=8.6, 1.8 Hz, 1H), 4.79 (M, 1H), 3.79 (s, 3H), 3.16 (M, 4H), 2.61 (s, 3H), 2.56 (M, 4H), 2.29 (s, 3H), 1.56 (d, J=6.8 Hz, 6H).

Example 56 Preparation of N-(2-((2-(dimethylamino)ethyl)(methyl)amino)-5-((5-fluoro-4-(8-fluoro-2-methyl-3-(prop-1-en-2-yl)imidazo[1,2-a]pyridine-6-yl)pyrimidin-2-yl)amino)-4-methoxyphenyl)acrylamide (compound 18)

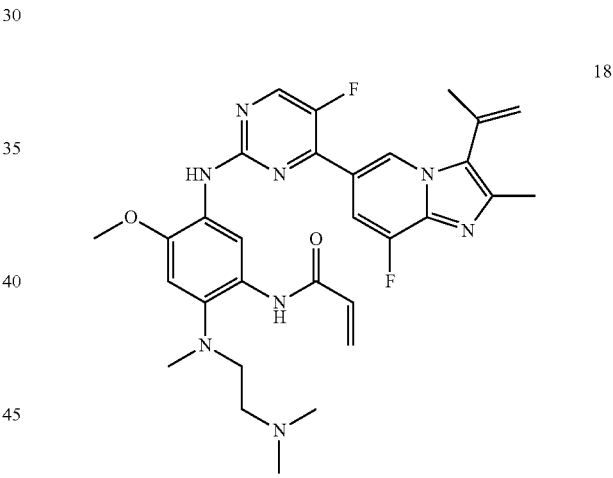

18

The specific synthetic steps are as follows:

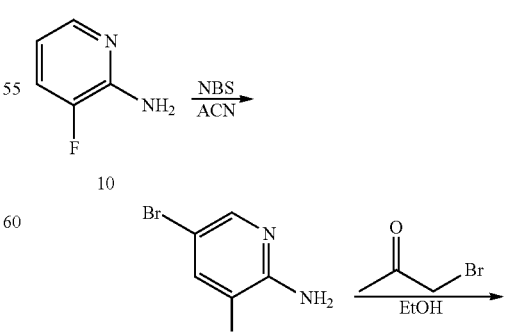

10

11

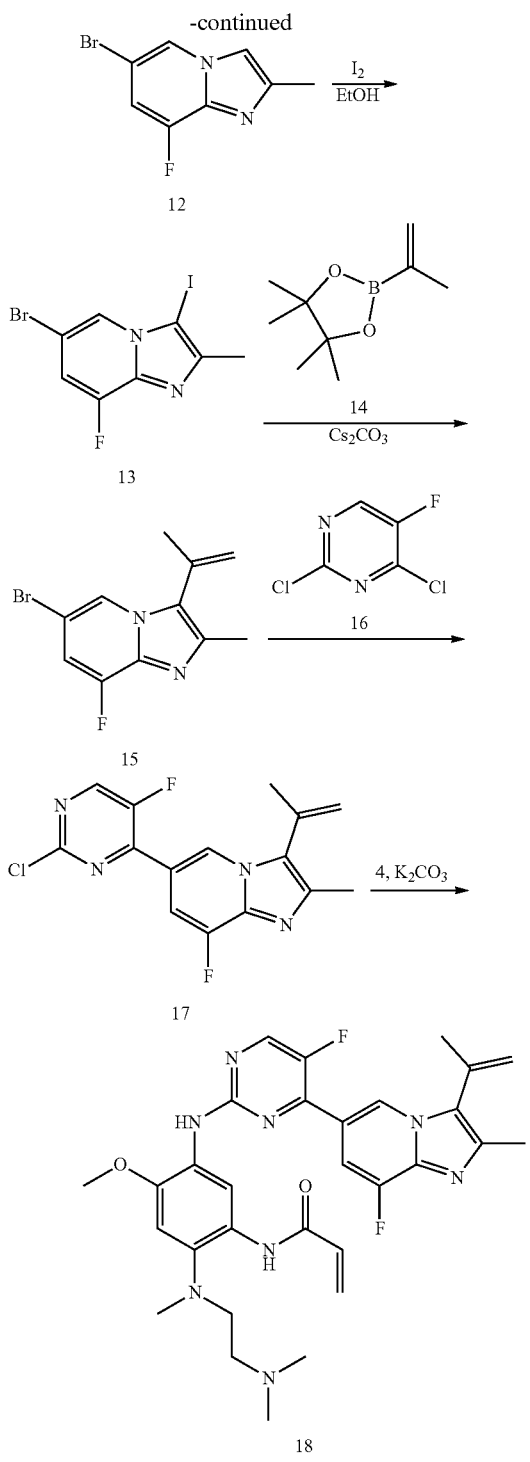

(100 mL×3). The organic phase was combined and the filtrate was washed with brine, dried over anhydrous sodium sulfate, concentrated under reduced pressure, and the filtrate was separated on column chromatography (eluant:petroleum ether/ethyl acetate (v/v)=5:1), to afford 5.0 g of a white solid, yield was 87.3%. LC-MS(APCI): m/z=191.1 (M+1).

Step 2 Synthesis of Compound 12

1-bromoprop-2-one (10.00 g, 73.3 mmol) was added into 5-bromo-3-fluoropyridine-2-amine (compound 11, 7.00 g, 36.6 mmol) in ethanol (70 mL), and the reaction was reacted under reflux under nitrogen protection overnight. After cooling to room temperature, solid was precipitated slowly, which was filtered, washed with cold ethanol, dried in vacuo to afford 3.5 g of a white solid, yield: 41.8%. LC-MS(APCI): m/z=229.1 (M+1); $^1$H NMR (400 MHz, DMSO-$d_6$) (δ/ppm) 9.12 (s, 1H), 8.16-8.09 (m, 2H), 2.48 (s, 3H).

Step 3 Synthesis of Compound 13

Elementary iodine (4.60 g, 18.3 mmol) was added into 6-bromo-8-fluoro-2-methylimidazo[1,2-a]pyridine (compound 12, 3.50 g, 15.30 mmol) and sodium acetate (2.01 g, 24.5 mmol) in methanol (20 mL), and the reaction was reacted under nitrogen protection at room temperature for 3 hours. Methanol was removed by concentrating under reduced pressure, the reaction was quenched by adding saturated solution of sodium thiosulfate, extracted with ethyl acetate (100 mL×3). The organic phase was combined and the filtrate was washed with brine, dried over anhydrous sodium sulfate, concentrated under reduced pressure, and the filtrate was separated on column chromatography (eluant:petroleum ether/ethyl acetate (v/v)=3:1), to afford 2.8 g of a white solid, yield was 51.7%. LC-MS(APCI): m/z=355.1 (M+1).

Step 4 Synthesis of Compound 15

Under nitrogen protection, Pd(dppf)Cl$_2$■CH$_2$Cl$_2$ (250 mg, 0.31 mmol) was added into 6-bromo-8-fluoro-3-iodo-2-methylimidazo[1,2-a]pyridine (compound 13, 1.17 g, 3.32 mmol), pinacolyl 2-propenylboronate (compound 14, 557 mg, 3.31 mmol) and cesium carbonate (2.16 g, 6.64 mmol) in the mixed solvent of 1,4-dioxane (20 mL) and water (5 mL), and the reaction was reacted under nitrogen protection at 80° C. for 1 hour. After cooling to room temperature, it was filtered on Celite, the filter cake was washed with dichloromethane, the filtrate was concentrated under reduced pressure, and the filtrate was separated on column chromatography (eluant:petroleum ether/ethyl acetate (v/v)=10:1), to afford 600 mg of a white solid. Yield was 67.4.9%. LC-MS(APCI): m/z=269.1 (M+1).

Step 5 Synthesis of Compound 17

Under nitrogen protection, Pd(dppf)Cl$_2$■CH$_2$Cl$_2$ (200 mg, 0.25 mmol) was added into 6-bromo-8-fluoro-2-methyl-3-(prop-1-en-2-yl)imidazo[1,2-a]pyridine (compound 15, 660 mg, 2.46 mmol), bis(pinacolato)diboron (750 mg, 3.00 mmol) and potassium acetate (490 mg, 4.92 mmol) in anhydrous 1,4-dioxane (16 mL), and the reaction was reacted under nitrogen protection at 80° C. for 2 hours. After cooling to room temperature, under nitrogen protection, 2,4-dichloro-5-fluoropyrimidine (compound 16, 410 mg, 2.46 mmol), sodium carbonate (520 mg, 4.92 mmol) and water (4 mL) were added into the reaction, and the reaction Step 1 Synthesis of Compound 11

Under nitrogen protection, N-bromosuccinimide (NBS, 5.47 g, 30.57 mmol) was added into 3-fluoropyridine-2-amine (compound 10, 3.36 g, 29.97 mmol) in acetonitrile (150 mL) in portions, and the reaction was reacted under nitrogen protection at room temperature for 2 hours. Acetonitrile was removed by concentrating under reduced pressure, the reaction was quenched by adding saturated solution of sodium thiosulfate, extracted with ethyl acetate was reacted under nitrogen protection at 80° C. for 2 hours. After cooling to room temperature, it was filtered on Celite, the filter cake was washed with dichloromethane, the filtrate was concentrated under reduced pressure, and the filtrate was separated on column chromatography (eluant:petroleum ether/ethyl acetate (v/v)=3:1), to afford 600 mg of a white solid, yield was 76.2%. LC-MS(APCI): m/z=321.1 (M+1).

Step 6 Synthesis of Compound 18

Under nitrogen protection, tert-pentanol (10 mL) was added into the mixture of 6-(2-chloro-5-fluoropyrimidin-4-yl)-8-fluoro-2-methyl-3-(prop-1-en-2-yl)imidazo[1,2-a]pyridine (compound 17, 125 mg, 0.38 mmol) and N-(5-amino-2-((2-(dimethylamino)ethyl)(methyl)amino)-4-methoxy-phenyl)acrylamide (compound 4, 125 mg, 0.43 mmol), potassium carbonate (135 mg, 0.98 mmol), Pd$_2$(dba)$_3$ (30 mg) and Xant-Phos (40 mg), and the reaction was stirred and reaction under nitrogen protection at 100° C. for 3 hours. After cooling to room temperature, it was filtered on Celite, the filter cake was washed with dichloromethane, the filtrate was concentrated under reduced pressure, and the filtrate was separated on column chromatography (eluant:dichloromethane/methanol (v/v)=10:1), to afford a crude solid, which was purified by preparative TLC (DCM/MeOH v/v=10/1) to afford 26 mg of a pale yellow solid, yield was 11.9%. LC-MS(APCI): m/z=577.6 (M+1); $^1$H NMR (400 MHz, CDCl$_3$) (δ/ppm) 9.60 (s, 1H), 8.77 (s, 1H), 8.41 (d, J=3.7 Hz, 1H), 8.12 (d, J=11.8 Hz, 1H), 7.72 (s, 1H), 6.75 (s, 1H), 6.53 (d, J=15.5 Hz, 1H), 5.75 (d, J=9.5 Hz, 1H), 5.64 (s, 1H), 5.30 (s, 1H), 3.93 (s, 3H), 3.33-3.18 (m, 2H), 3.14-2.90 (m, 2H), 2.86-2.63 (m, 9H), 2.51 (s, 3H), 2.19 (s, 3H).

Example 57 Preparation of 5-fluoro-4-(8-fluoro-2-methyl-3-(prop-1-en-2-yl)imidazo[1,2-a]pyridine-6-yl)-N-(2-methoxy-4-(4-methylpiperazin-1-yl)phenyl)pyrimidin-2-amine (compound 19)

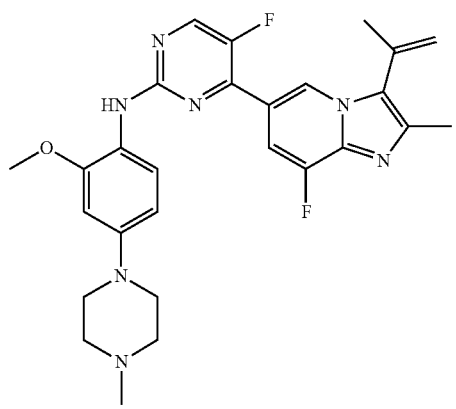

The specific synthetic steps are as follows:

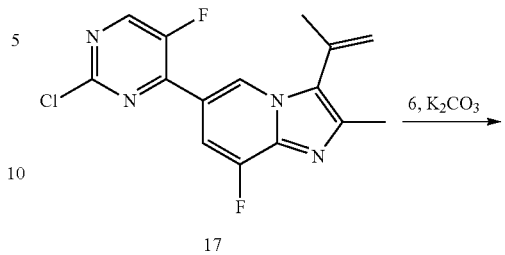

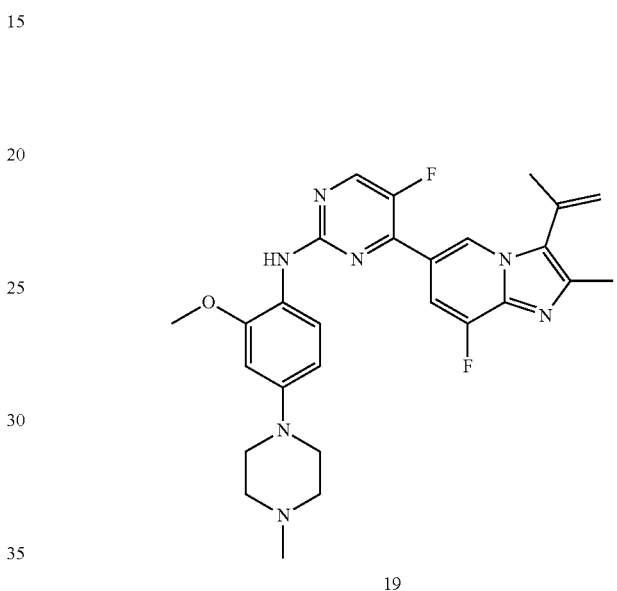

Under nitrogen protection, tert-pentanol (10 mL) was added into the mixture of 6-(2-chloro-5-fluoropyrimidin-4-yl)-8-fluoro-2-methyl-3-(prop-1-en-2-yl)imidazo[1,2-a]pyridine (compound 17, 260 mg, 0.81 mmol) and 2-methoxy-4-(4-methylpiperazin-1-yl)aniline (compound 6, 150 mg, 0.67 mmol), potassium carbonate (234 mg, 1.70 mmol), Pd$_2$(dba)$_3$ (70 mg) and Xant-Phos (80 mg), and the reaction was stirred and reacted under nitrogen protection at 100° C. for 3 hours. After cooling to room temperature, it was filtered on Celite, the filter cake was washed with dichloromethane, the filtrate was concentrated under reduced pressure, and the filtrate was separated on column chromatography (eluant:dichloromethane /methanol (v/v)=13:1), to afford 115 mg of a dark-yellow solid, yield was 14.9%. LC-MS(APCI): m/z=506.6 (M+1); $^1$H NMR (500 MHz, DMSO-d$_6$) (δ/ppm) 8.72 (d, J=1.2 Hz, 1H), 8.50 (d, J=3.8 Hz, 1H), 8.32 (s, 1H), 7.61 (d, J=12.4 Hz, 1H), 7.55 (d, J=8.7 Hz, 1H), 6.64 (d, J=2.5 Hz, 1H), 6.48 (dd, J=8.7, 2.5 Hz, 1H), 5.68-5.64 (m, 1H), 5.32-5.29 (m, 1H), 3.78 (s, 3H), 3.19-3.14 (m, 4H), 2.61-2.54 (m, 4H), 2.38 (s, 3H), 2.30 (s, 3H), 2.13 (s, 3H).

Example 58 Preparation of 5-fluoro-4-(8-fluoro-2-methylimidazo[1,2-a]pyridine-6-yl)-N-(2-methoxy-4-(4-methylpiperazin-1-yl)phenyl)pyrimidin-2-amine (Compound 20)

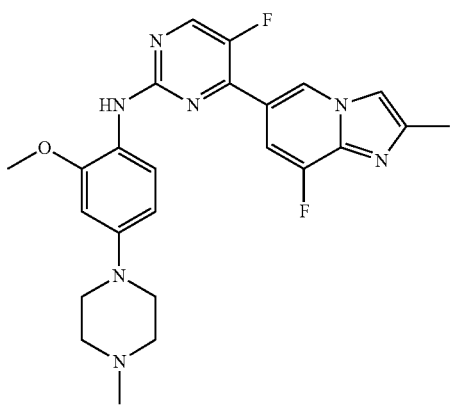

The specific synthetic steps are as follows:

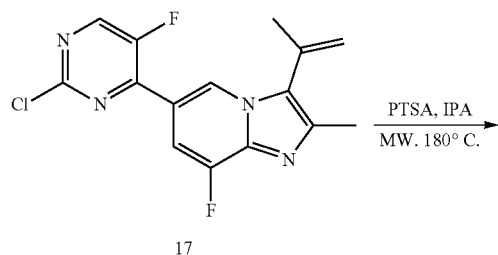

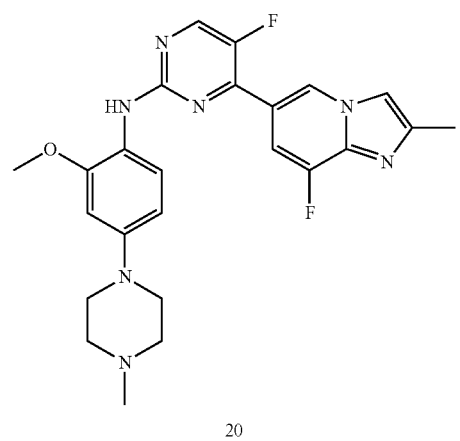

P-toluene sulfonic acid (269 mg, 1.56 mmol) was added to 6-(2-chloro-5-fluoropyrimidin-4-yl)-8-fluoro-2-methyl-3-(prop-1-en-2-yl)imidazo[1,2-a]pyridine (compound 17, 250 mg, 0.78 mmol) and 2-methoxy-4-(4-methylpiperazin-1-yl)aniline (compound 6, 172 mg, 0.78 mmol) in isopropyl alcohol (10 mL), and reacted under a microwave at 180° C. for 1.5 hours. The reaction mixture was concentrated under reduced pressure, the residue was adjusted to basic with saturated sodium bicarbonate, extracted with dichloromethane (30 mL×3), the organic phase was combined, washed with brine (30 mL) and dried over anhydrous sodium sulfate, the solvent was removed, and the filtrate was separated on column chromatography (eluant:dichloromethane/methanol (v/v)=13:1), to afford 50 mg of a pale yellow solid as a crude, which was purified with preparative TLC (DCM/MeOH v/v=12/1) to afford 32 mg of a pale yellow solid, yield was 8.8%. LC-MS(APCI): m/z=466.5 (M+1); $^1$H NMR (400 MHz, CDCl$_3$) (δ/ppm) 8.77 (s, 1H), 8.32 (d, J=3.6 Hz, 1H), 8.18 (d, J=8.7 Hz, 1H), 7.75 (d, J=12.1 Hz, 1H), 7.52 (s, 1H), 7.50-7.45 (m, 1H), 6.63-6.58 (m, 1H), 6.58-6.55 (m, 1H), 3.90 (s, 3H), 3.24-3.17 (m, 4H), 2.66-2.59 (m, 4H), 2.50 (s, 3H), 2.37 (s, 3H).

Example 59 Preparation of 5-fluoro-4-(8-fluoro-3-isopropyl-2-methylimidazo[1,2-a]pyridine-6-yl)-N-(2-methoxy-4-(4-methylpiperazin-1-yl)phenyl)pyrimidin-2-amine (Compound 21)

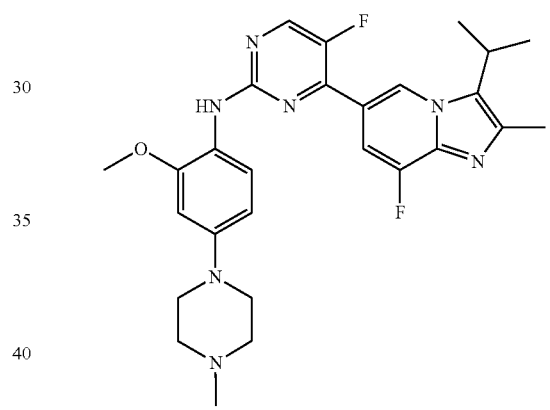

The specific synthetic steps are as follows:

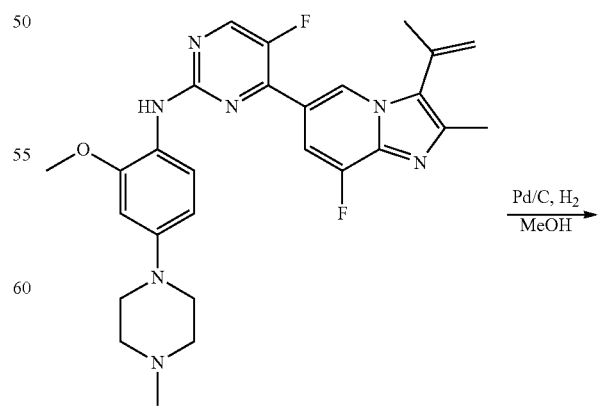

245

-continued

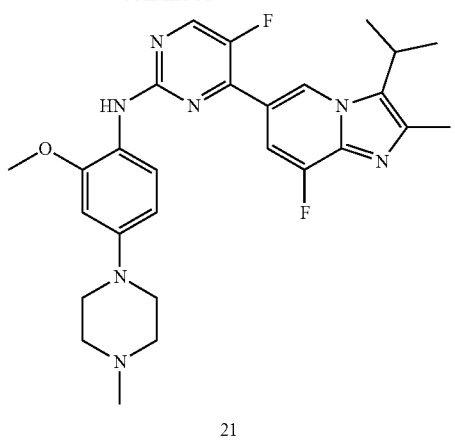

21

At room temperature, Pd/C (20 mg) was added into 5-fluoro-4-(8-fluoro-2-methyl-3-(prop-1-en-2-yl)imidazo[1,2-a]pyridine-6-yl)-N-(2-methoxy-4-(4-methylpiperazin-1-yl)phenyl)pyrimidin-2-amine (compound 19, 80 mg, 0.16 mmol) in methanol (5 mL), and the reaction was stirred and reacted under a balloon of hydrogen gas for 48 hours. It was filtered on Celite, the filter cake was washed with dichloromethane, the filtrate was concentrated under reduced pressure, and the filtrate was separated on column chromatography to afford 40 mg of a pale yellow solid, yield was 50%. LC-MS(APCI): m/z=508.1 (M+1); $^1$H NMR (500 MHz, DMSO-d$_6$) (δ/ppm) 8.76 (s, 1H), 8.54 (d, J=3.7 Hz, 1H), 8.35 (s, 1H), 7.63-7.54 (m, 2H), 6.67 (d, J=2.2 Hz, 1H), 6.51 (dd, J=8.8, 2.3 Hz, 1H), 3.80 (s, 3H), 3.51-3.43 (m, 1H), 3.22-3.12 (m, 4H), 2.63-2.53 (m, 4H), 2.43 (s, 3H), 2.31 (s, 3H), 1.38 (d, J=7.1 Hz, 6H).

Example 60 Preparation of N-(5-((4-(2-(difluoromethyl)-4-fluoro-1-isopropyl-1H-benzo[d]imidazol-6-yl)pyrimidin-2-yl)amino)-2-((2-(dimethylamino)ethyl)(methyl)amino)-4-methoxyphenyl)acrylamide

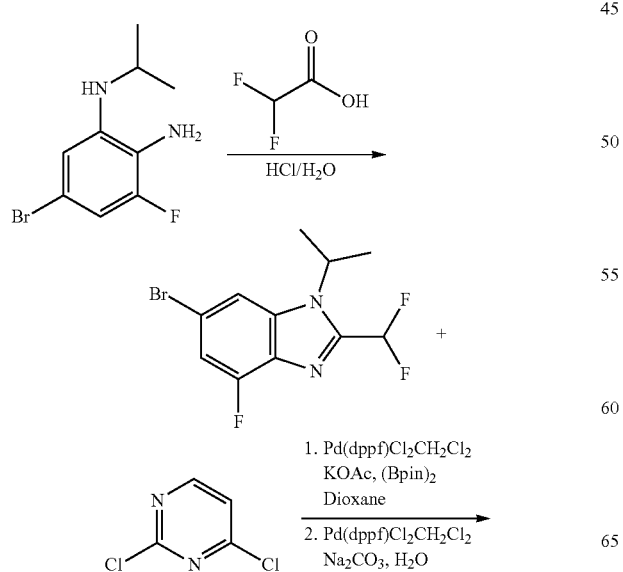

246

-continued

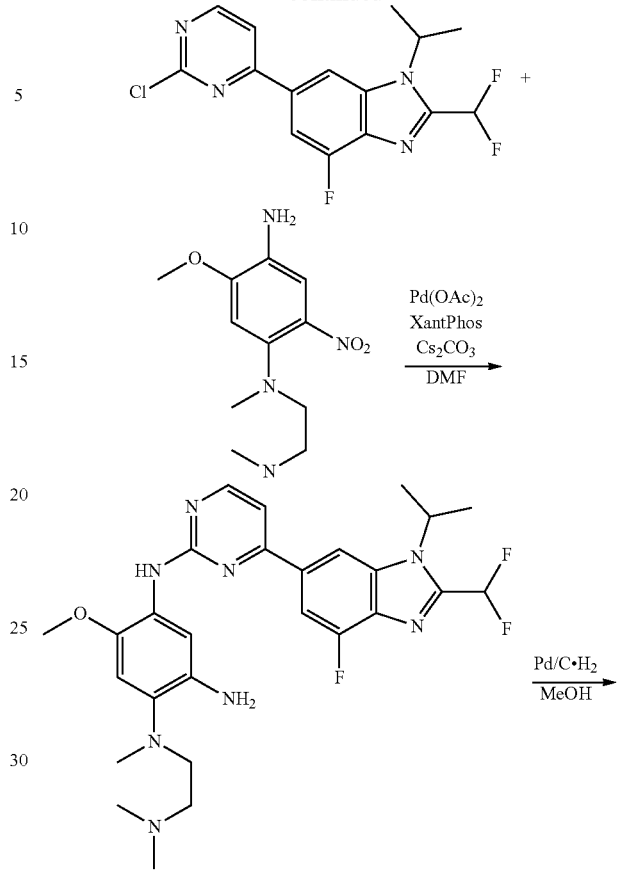

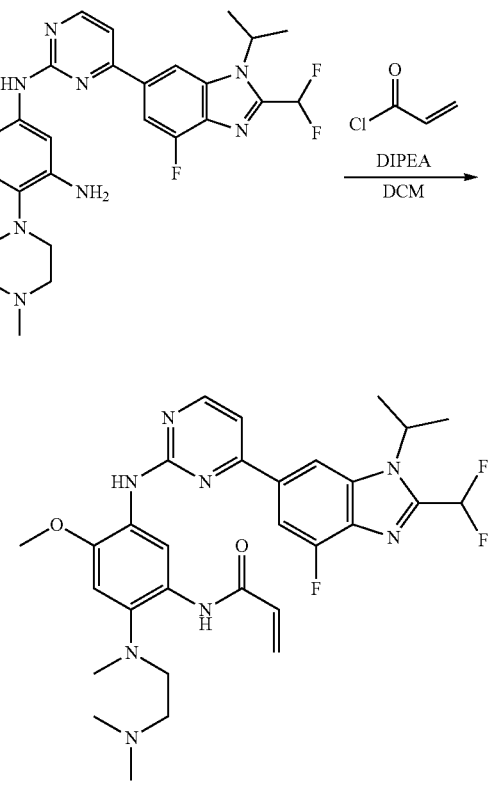

Step 2 Synthesis of Compound 6-(2-chloropyrimidin-4-yl)-2-(difluoromethyl)-4-fluoro-1-isopropyl-1H-benzo[d]imidazole Under nitrogen protection, bis(pinacolato)diboron (197 mg, 0.78 mmol), potassium acetate (127 mg, 1.29 mmol), and pd(dppf)Cl$_2$.DCM (53 mg) were sequentially added into the solution of 6-bromo-2-(difluoromethyl)-4-fluoro-1-isopropyl-1H-benzo[d]imidazole (200 mg, 0.65 mmol) in anhydrous 1,4-dioxane (10 mL), and stirred under nitrogen protection at 100° C. overnight.

After cooling to room temperature, under nitrogen protection, the above reaction mixture was added 2,4-dichloropyrimidine (116 mg, 0.78 mmol), sodium carbonate (137 mg, 1.29 mmol), pd(dppf)Cl$_2$.DCM (53 mg) and water (2.5 mL), and reacted under nitrogen protection at 80° C. for 2 hours. After cooling to room temperature, it was filtered on Celite, the filter cake was washed with ethyl acetate, and then the combined filtrate was poured into water (50 mL), extracted with ethyl acetate (50 mL×3). The organic layer was combined, washed with water and brine, and concentrated under reduced pressure to afford a crude product. The crude product was purified by column chromatography to give 222 mg of a white solid, yield was 99.5%. LC-MS (APCI): m/z=341.0 (M+1).

Step 3 Synthesis of Compound $N^1$-(4-(2-(difluoromethyl)-4-fluoro-1-isopropyl-1H-benzo[d]imidazol-6-yl)pyrimidin-2-yl)-$N^4$-(2-(dimethylamino)ethyl)-2-methoxy-$N^4$-methyl-5-nitrobenzene-1,4-diamine Under nitrogen protection, $N^1$-(2-(dimethylamino)ethyl)-5-methoxy-$N^1$-methyl-2-nitrobenzene-1,4-diamine (208 mg, 0.78 mmol), cesium carbonate (527 mg, 1.62 mmol), Pd(OAc)$_2$ (15 mg, 0.06 mmol) and XantPhos (75 mg, 0.12 mmol) were sequentially added into the solution of the 6-(2-chloropyrimidin-4-yl)-2-(difluoromethyl)-4-fluoro-1-isopropyl-1H-benzo[d]imidazole (222 mg, 0.65 mmol) in DMF (10 mL), and reacted under nitrogen protection at 100° C. overnight. After cooling to room temperature, it was filtered on Celite, the filter cake was washed with dichloromethane (50 mL×3), then the combined filtrate was poured into water (50 mL), extracted with dichloromethane (50 mL×3). The organic layer was combined, washed with water and brine, and concentrated under reduced pressure to afford a crude product. The crude product was separated on column chromatography (eluant:dichloromethane /methanol (v/v)=10:1) to give 200 mg of a red solid. LC-MS(APCI): m/z=573.0 (M+1).

Step 4 Synthesis of Compound $N^4$-(4-(2-(difluoromethyl)-4-fluoro-1-isopropyl-1H-benzo[d]imidazol-6-yl)pyrimidin-2-yl)-$N^1$-(2-(dimethylamino)ethyl)-5-methoxy-N-methylbenzene-1,2,4-triamine Pd/C (30 mg) was added into the solution of $N^1$-(4-(2-(difluoromethyl)-4-fluoro-1-isopropyl-1H-benzo[d]imidazol-6-yl)pyrimidin-2-yl)-$N^4$-(2-(dimethylamino)ethyl)-2-methoxy-$N^4$-methyl-5-nitrobenzene-1,4-diamine (200 mg, 0.35 mmol) in methanol (20 mL), and reacted under a balloon of hydrogen gas overnight. The reaction mixture was filtered on Celite, the filtrate was concentrated under reduced pressure, and separated on column chromatography (eluant:dichloromethane/methanol (v/v)=10:1), to afford 137 mg of a yellow solid, yield over two steps: 38.9%. LC-MS(APCI): m/z=543.1 (M+1).

Step 5 Synthesis of Compound N-(5-((4-(2-(difluoromethyl)-4-fluoro-1-isopropyl-1H-benzo[d]imidazol-6-yl)pyrimidin-2-yl)amino)-2-((2-(dimethylamino)ethyl)(methyl)amino)-4-methoxyphenyl)acrylamide DIPEA (65 mg, 0.50 mmol) was added into the solution of the $N^4$-(4-(2-(difluoromethyl)-4-fluoro-1-isopropyl-1H-benzo[d]imidazol-6-yl)pyrimidin-2-yl)-$N^1$-(2-(dimethylamino)ethyl)-5-methoxy-$N^1$-methylbenzene-1,2,4-triamine (135 mg, 0.25 mmol) in 10 mL dichloromethane. The reaction system was cooled to −20° C. after the addition was complete, and at this temperature acryloyl chloride (23 mg, 0.25 mmol) was added dropwise, and stirred at −20° C. for 1 hr. The reaction was quenched by adding water (20 mL), and extracted with dichloromethane (10 mL×3). The organic layer was washed with water and brine, dried over anhydrous sodium sulfate, filtered and concentrated to afford a yellow oil, and the yellow oil was purified by column chromatography to give 50 mg of a yellow solid. LC-MS (APCI): m/z=597.1 (M+1), HPLC: 98.71%. $^1$H NMR (400 MHz, DMSO-d$_6$) δ 10.07 (s, 1H), 8.95 (s, 1H), 8.53 (d, J=5.2 Hz, 1H), 8.35 (d, J=0.7 Hz, 1H), 8.28 (s, 1H), 8.09 (d, J=12.1 Hz, 1H), 7.64 (d, J=5.2 Hz, 1H), 7.49 (t, J=52.0 Hz, 1H), 7.02 (s, 1H), 6.48-6.36 (m, 1H), 6.26-6.20 (m, 1H), 5.73 (dd, J=10.1, 1.8 Hz, 1H), 5.02 (dt, J=13.6, 6.8 Hz, 1H), 3.84 (s, 3H), 2.92-2.83 (m, 2H), 2.70 (s, 3H), 2.40-2.31 (m, 2H), 2.24 (s, 6H), 1.63 (d, J=6.9 Hz, 6H).

Example 61 Preparation of N-(2-((2-(dimethylamino)ethyl)(methyl)amino)-5-((4-(4-fluoro-2-isopropoxy-1-isopropyl-1H-benzo[d]imidazol-6-yl)pyrimidin-2-yl)amino)-4-methoxyphenyl)acrylamide

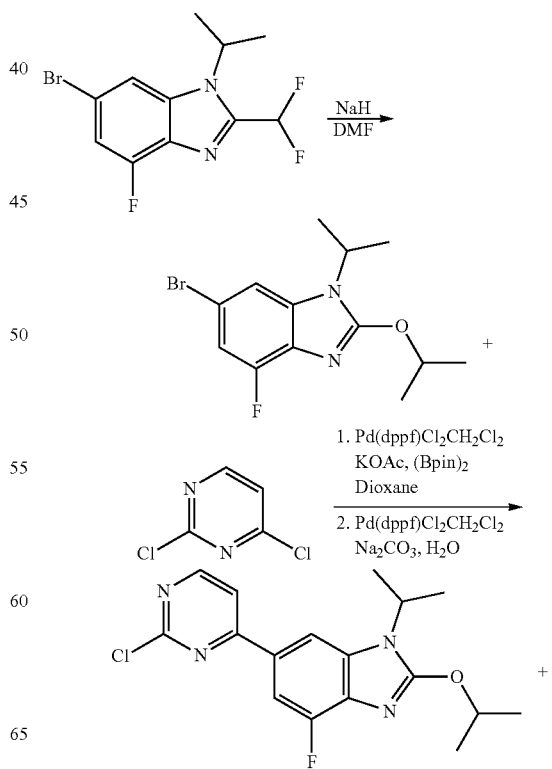

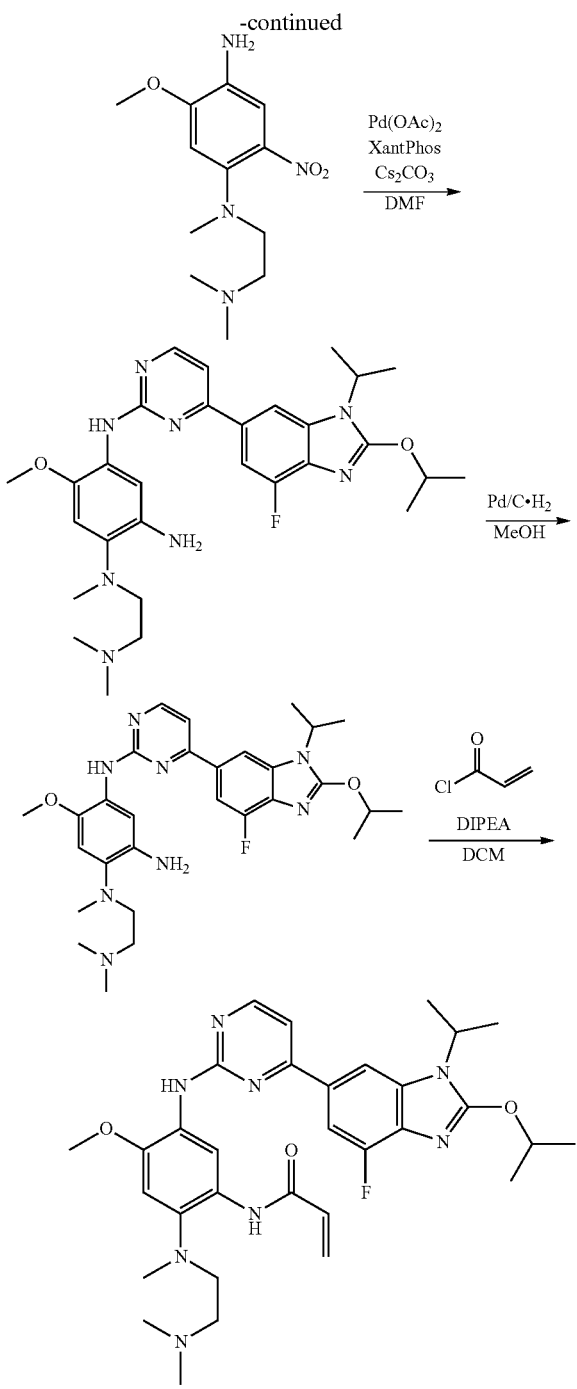

Step 1 Synthesis of Compound 6-bromo-4-fluoro-2-isopropoxy-1-isopropyl-1H-benzo[d]imidazole NaH (60%, 27 mg, 0.68 mmol) was added into the solution of the propan-2-ol (25 mg, 0.41 mmol) in 5 mL DMF at 0° C., and stirred for 30 minutes at 0° C. Then 6-bromo-2-chloro-4-fluoro-1-isopropyl-1H-benzo[d]imidazole (100 mg, 0.34 mmol) was added, and stirred at room temperature for 2 hours. The reaction was quenched by adding water (20 mL), and extracted with ethyl acetate (2×30 mL), the organic layer was washed with water and brine, concentrated under reduced pressure, and purified by column chromatography to afford 100 mg of a colourless oil. LC-MS(APCI): m/z=314.2 (M+1).

Step 2 synthesis of 6-(2-chloropyrimidin-4-yl)-4-fluoro-2-isopropoxy-1-isopropyl-1H-benzo[d]imidazole Under nitrogen protection, bis(pinacolato)diboron (194 mg, 0.76 mmol), potassium acetate (127 mg, 1.29 mmol), and pd(dppf)Cl$_2$.DCM (53 mg) were sequentially added into the solution of the 6-bromo-4-fluoro-2-isopropoxy-1-isopropyl-H-benzo[d]imidazole (200 mg, 0.63 mmol) in anhydrous 1,4-Dioxane (10 mL), and stirred under nitrogen protection at 100° C. overnight.

After cooling to room temperature, under nitrogen protection, the above reaction mixture was added 2,4-dichloropyrimidine (114 mg, 0.76 mmol), sodium carbonate (134 mg, 1.26 mmol), pd(dppf)Cl$_2$.DCM (52 mg) and water (2.5 mL), and reacted under nitrogen protection at 80° C. for 2 hours. After cooling to room temperature, it was filtered on Celite, the filter cake was washed with ethyl acetate, and then the combined filtrate was poured into water (50 mL), extracted with ethyl acetate (50 mL×3). The organic layer was combined, washed with water and brine, and concentrated under reduced pressure to afford a crude product. The crude product was purified by column chromatography to give 220 mg of a white solid. LC-MS(APCI): m/z=349.0 (M+1).

Step 3 Synthesis of N$^1$-(2-(dimethylamino)ethyl)-N$^4$-(4-(4-fluoro-2-isopropoxy-1-isopropyl-1H-benzo[d]imidazol-6-yl)pyrimidin-2-yl)-5-methoxy-N$^1$-methyl-2-nitrobenzene-1,4-diamine Under nitrogen protection, N$^1$-(2-(dimethylamino)ethyl)-5-methoxy-N$^1$-methyl-2-nitrobenzene-1,4-diamine (169 mg, 0.63 mmol), Caesium carbonate (514 mg, 1.58 mmol), Pd(OAc)$_2$ (15 mg, 0.06 mmol) and XantPhos (75 mg, 0.12 mmol) were sequentially added into the solution of the 6-(2-chloropyrimidin-4-yl)-4-fluoro-2-isopropoxy-1-isopropyl-1H-benzo[d]imidazole (220 mg, 0.63 mmol) in DMF (10 mL), and reacted under nitrogen protection at 100° C. overnight. After cooling to room temperature, it was filtered on Celite, the filter cake was washed with dichloromethane (50 mL×3), and then the combined filtrate was poured into water (50 mL), extracted with dichloromethane (50 mL×3). The organic layer was combined, washed with water and brine, and concentrated under reduced pressure to afford a crude product. The crude product was separated on column chromatography (eluant:dichloromethane/methanol (v/v) =10:1) to afford 190 mg of a red solid. LC-MS(APCI): m/z=581.0 (M+1).

Step 4 synthesis of N$^1$-(2-(dimethylamino)ethyl)-N$^4$-(4-(4-fluoro-2-isopropoxy-1-isopropyl-1H-benzo[d]imidazol-6-yl)pyrimidin-2-yl)-5-methoxy-N$^1$-methylbenzene-1,2,4-triamine Pd/C (20 mg) was added into the solution of N$^1$-(2-(dimethylamino)ethyl)-N$^4$-(4-(4-fluoro-2-isopropoxy-1-isopropyl-1H-benzo[d]imidazol-6-yl)pyrimidin-2-yl)-5-methoxy-N$^1$-methyl-2-nitrobenzene-1,4-diamine (190 mg) in methanol (20 mL), and reacted under a balloon of hydrogen gas overnight. The reaction mixture was filtered on Celite, the filtrate was concentrated under reduced pressure, and separated on column chromatography (eluant:

dichloromethane/methanol (v/v)=10:1), to afford 157 mg of a red-yellow solid, yield over two steps: 45.3%. LC-MS (APCI): m/z=551.1 (M+1).

Step 5 Synthesis of N-(2-((2-(dimethylamino)ethyl)(methyl)amino)-5-((4-(4-fluoro-2-isopropoxy-1-isopropyl-1H-benzo[d]imidazol-6-yl)pyrimidin-2-yl)amino)-4-methoxyphenyl)acrylamide DIPEA (73 mg, 0.56 mmol) was added into the solution of the $N^1$-(2-(dimethylamino)ethyl)-$N^4$-(4-(4-fluoro-2-isopropoxy-1-isopropyl-1H-benzo[d]imidazol-6-yl)pyrimidin-2-yl)-5-methoxy-N-methylbenzene-1,2,4-triamine (155 mg, 0.28 mmol) in dichloromethane (20 mL). The reaction system was cooled to −20° C. after the addition was complete, and at this temperature acryloyl chloride (25 mg, 0.28 mmol) was added dropwise, and stirred at −20° C. for 1 hour. The reaction was quenched by adding water (20 mL), and extracted with dichloromethane (20 mL×3). The organic layer was washed with water and brine, dried over anhydrous sodium sulfate, filtered and concentrated to afford a yellow oil, and the yellow oil was separated on column chromatography to give 37 mg of a yellow solid. LC-MS (APCI): m/z=605.1 (M+1), HPLC: 91.52%, $^1$H NMR (300 MHz, DMSO-$d_6$) δ 10.11 (s, 1H), 9.02 (s, 1H), 8.48 (d, J=5.2 Hz, 1H), 8.12 (d, J=10.6 Hz, 2H), 7.92 (d, J=12.3 Hz, 1H), 7.53 (d, J=5.2 Hz, 1H), 7.03 (s, 1H), 6.44 (dd, J=16.8, 9.7 Hz, 1H), 6.26 (d, J=17.3 Hz, 1H), 5.81-5.66 (m, 1H), 5.39-5.23 (m, 1H), 4.86-4.68 (m, 1H), 3.86 (s, 3H), 2.98-2.85 (m, 2H), 2.71 (s, 3H), 2.42-2.32 (m, 2H), 2.26 (s, 6H), 1.49 (d, J=6.7 Hz, 6H), 1.44 (d, J=6.1 Hz, 6H).

Example 62 Preparation of N-(2-((2-(dimethylamino)ethyl)(methyl)amino)-5-((4-(2-ethoxy-4-fluoro-1-isopropyl-1H-benzo[d]imidazol-6-yl)pyrimidin-2-yl)amino)-4-methoxyphenyl)acrylamide

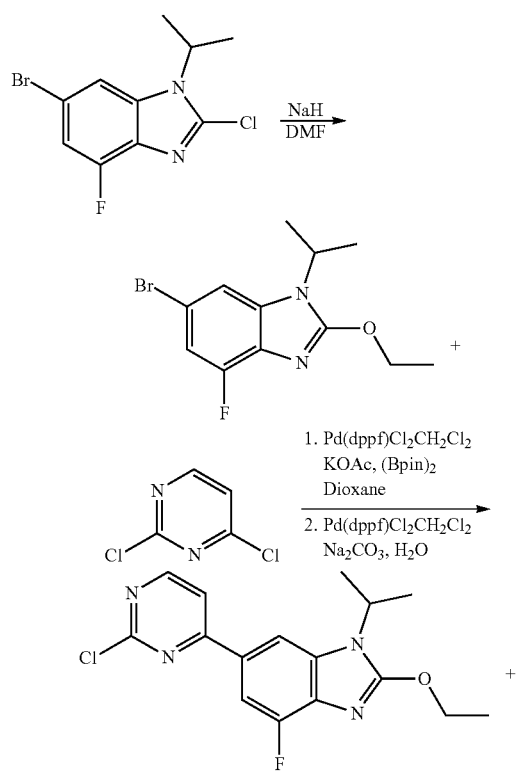

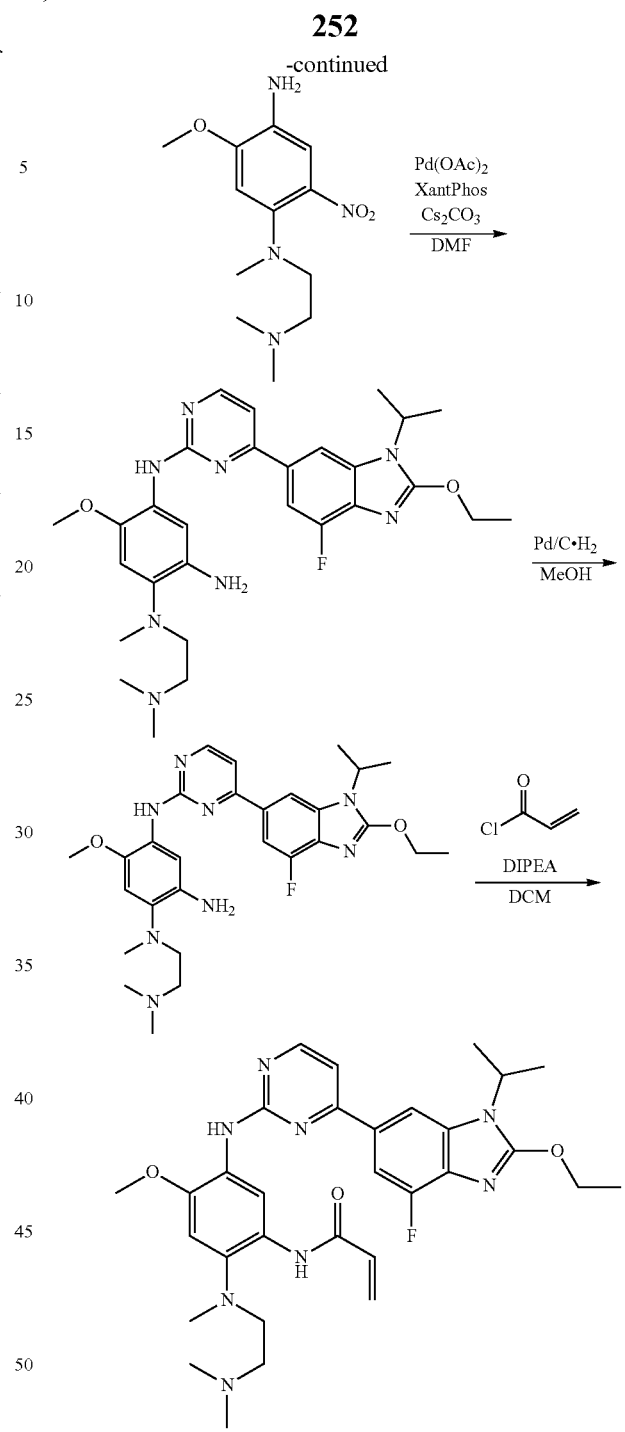

Step 1 Synthesis of Compound 6-bromo-2-ethoxy-4-fluoro-1-isopropyl-1H-benzo[d]imidazole NaH (60%, 72 mg, 1.81 mmol) was added into the solution of ethanol (83 mg, 1.81 mmol) in 10 mL DMF at 0° C., and stirred for 30 minutes at 0° C. Then 6-bromo-2-chloro-4-fluoro-1-isopropyl-1H-benzo[d]imidazole (440 mg, 1.51 mmol) was added, and stirred at room temperature for 2 hours. The reaction was quenched by adding water (20 mL), and extracted with ethyl acetate (30 mL×2). The organic layer was washed water and brine, concentrated under reduced pressure, and purified by column chromatography to afford 387 mg of a white solid. LC-MS(APCI): m/z=300.2 (M+1).

Step 2 Synthesis of 6-(2-chloropyrimidin-4-yl)-2-ethoxy-4-fluoro-1-isopropyl-1H-benzo[d]imidazole Under nitrogen protection, bis(pinacolato)diboron (152 mg, 0.60 mmol), potassium acetate (98 mg, 1.0 mmol), and Pd(dppf)Cl$_2$.DCM (41 mg) were sequentially added into the solution of the 6-bromo-2-ethoxy-4-fluoro-1-isopropyl-1H-benzo[d]imidazole (150 mg, 0.50 mmol) in anhydrous 1,4-Dioxane (10 mL), and stirred under nitrogen protection at 100° C. overnight.

After cooling to room temperature, under nitrogen protection, the above reaction mixture was added 2,4-dichloropyrimidine (89 mg, 0.60 mmol), sodium carbonate (106 mg, 1.00 mmol) and Pd(dppf)Cl$_2$.DCM (41 mg) and water (2.5 mL), and reacted under nitrogen protection at 80° C. for 2 hours. After cooling to room temperature, it was filtered on Celite, the filter cake was washed with ethyl acetate, and then the combined filtrate was poured into H$_2$O (50 mL), extracted with ethyl acetate (50 mL×3). The organic layer was combined, washed with water and brine, and concentrated under reduced pressure to give a crude product, and the crude product was purified by column chromatography to afford 140 mg of a white solid. LC-MS(APCI): m/z=335.0 (M+1).

Step 3 Synthesis of N$^1$-(2-(dimethylamino)ethyl)-N$^4$-(4-(2-ethoxy-4-fluoro-1-isopropyl-1H-benzo[d]imidazol-6-yl)pyrimidin-2-yl)-5-methoxy-N$^1$-methyl-2-nitrobenzene-1,4-diamine N$^1$-(2-(dimethylamino)ethyl)-5-methoxy-N$^1$-methyl-2-nitrobenzene-1,4-diamine (112 mg, 0.42 mmol), caesium carbonate (341 mg, 1.05 mmol), Pd(OAc)$_2$ (9.5 mg, 0.04 mmol) and XantPhos (46 mg, 0.08 mmol) were sequentially added into the solution of the 6-(2-chloropyrimidin-4-yl)-2-ethoxy-4-fluoro-1-isopropyl-1H-benzo[d]imidazole (140 mg, 0.42 mmol) in DMF (10 mL), and reacted under nitrogen protection at 100° C. overnight. After cooling to room temperature, it was filtered on Celite, the filter cake was washed with dichloromethane (50 mL×3), and then the combined filtrate was poured into water (50 mL), extracted with dichloromethane (50 mL×3). The organic layer was combined, washed with water and brine, concentrated under reduced pressure to give a crude product. The crude product was purified by column chromatography to afford 115 mg of a red solid (115 mg). LC-MS(APCI): m/z=566.30 (M+1).

Step 4 Synthesis of N$^1$-(2-(dimethylamino)ethyl)-N$^4$-(4-(4-fluoro-2-ethoxy-1-isopropyl-1H-benzo[d]imidazol-6-yl)pyrimidin-2-yl)-5-methoxy-N$^1$-methylbenzene-1,2,4-triamine Pd/C (20 mg) was added into the solution of N$^1$-(2-(dimethylamino)ethyl)-N$^4$-(4-(2-ethoxy-4-fluoro-1-isopropyl-1H-benzo[d]imidazol-6-yl)pyrimidin-2-yl)-5-methoxy-N$^1$-methyl-2-nitrobenzene-1,4-diamine (115 mg) in methanol (20 mL), and reacted under a balloon of hydrogen gas overnight. The reaction mixture was filtered on Celite, the filtrate was concentrated under reduced pressure, and separated on column chromatography (eluant:dichloromethane/methanol (v/v)=10:1), to afford 62 mg of a red-yellow solid, yield over two steps: 27.6%. LC-MS(APCI): m/z=536.3 (M+1).

Step 5 Synthesis of N-(2-((2-(dimethylamino)ethyl)(methyl)amino)-5-((4-(2-ethoxy-4-fluoro-1-isopropyl-1H-benzo[d]imidazol-6-yl)pyrimidin-2-yl)amino)-4-methoxyphenyl)acrylamide DIPEA (31 mg, 0.24 mmol) was added into the solution of the N$^1$-(2-(dimethylamino)ethyl)-N$^4$-(4-(4-fluoro-2-ethoxy-1-isopropyl-1H-benzo[d]imidazol-6-yl)pyrimidin-2-yl)-5-methoxy-N$^1$-methylbenzene-1,2,4-triamine (62 mg, 0.0.12 mmol) in dichloromethane (20 mL). The reaction system was cooled to −20° C. after the addition was complete, and at this temperature acryloyl chloride (0.12 mmol) was added dropwise, and stirred at −20° C. for 1 hour. The reaction was quenched by adding water (20 mL), and extracted with dichloromethane (20 mL×3). The organic layer was washed with water and brine, dried over anhydrous sodium sulfate, filtered and concentrated to afford yellow oil, and the yellow oil was separated on column chromatography to give 15 mg of a yellow solid. LC-MS (APCI): m/z=591.3 (M+1), HPLC: 96.17%.

Example 63 Preparation of N-(2-((2-(dimethylamino)ethyl)(methyl)amino)-5-((4-(4-fluoro-1-isopropyl-2-(methylthio)-1H-benzo[d]imidazol-6-yl)pyrimidin-2-yl)amino)-4-methoxyphenyl)acrylamide

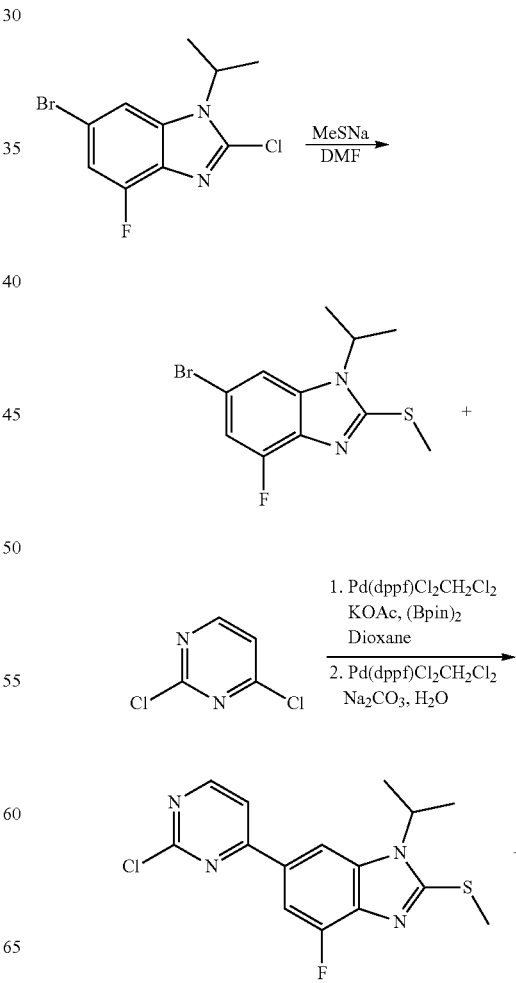

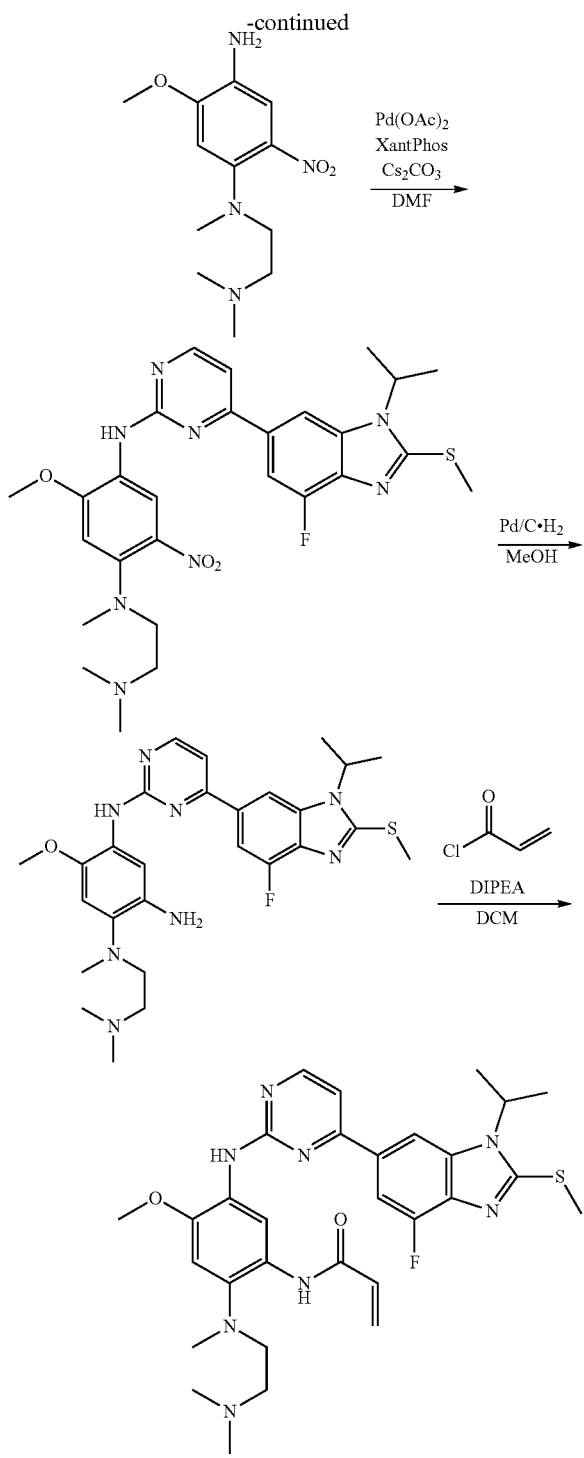

Step 1 Synthesis of Compound 6-bromo-4-fluoro-1-isopropyl-2-(methylthio)-1H-benzo[d]imidazole CH$_3$SNa (48 mg, 0.68 mmol) was added into the solution of the 6-bromo-2-chloro-4-fluoro-1-isopropyl-1H-benzo[d]imidazole (100 mg, 0.34 mmol) in DMF (5 mL) at 0° C., and stirred at room temperature overnight. The reaction was quenched by adding water (20 mL), and extracted with ethyl acetate (30 mL×2). The organic layer was washed with water and brine, and concentrated under reduced pressure to afford a crude product, and the crude product was purified by column chromatography to give 100 mg of a white oil. LC-MS(APCI): m/z=303.0 (M+1).

Step 2 Synthesis of 6-(2-chloropyrimidin-4-yl)-4-fluoro-1-isopropyl-2-(methylthio)-1H-benzo[d]imidazole Under nitrogen protection, bis(pinacolato)diboron (400 mg, 1.58 mmol), potassium acetate (258 mg, 2.64 mmol), and Pd(dppf)Cl$_2$.DCM (108 mg) were sequentially added into the solution of the 6-bromo-4-fluoro-1-isopropyl-2-(methylthio)-1H-benzo[d]imidazole (400 mg, 1.32 mmol) in anhydrous 1,4-Dioxane (10 mL), and stirred under nitrogen protection at 100° C. overnight.

After cooling to room temperature, under nitrogen protection, the above reaction mixture was added 2,4-dichloropyrimidine (235 mg, 1.58 mmol), sodium carbonate (280 mg, 2.64 mmol) and Pd(dppf)Cl$_2$.DCM (108 mg) and water (2.5 mL), and reacted under nitrogen protection to 80° C. for 2 hours. After cooling to room temperature, it was filtered on Celite, the filter cake was washed with ethyl acetate, and then the combined filtrate was poured into water (50 mL), extracted with ethyl acetate (50 mL×3). The organic layer was combined, washed with water and brine, concentrated under reduced pressure to afford a crude product. The crude product was purified by column chromatography to afford 415 mg of a yellow solid. LC-MS(APCI): m/z=337.0 (M+1).

Step 3 Synthesis of $N^1$-(2-(dimethylamino)ethyl)-$N^4$-(4-(4-fluoro-1-isopropyl-2-(methylthio)-1H-benzo[d]imidazol-6-yl)pyrimidin-2-yl)-5-methoxy-$N^1$-methyl-2-nitrobenzene-1,4-diamine Under nitrogen protection, $N^1$-(2-(dimethylamino)ethyl)-5-methoxy-$N^1$-methyl-2-nitrobenzene-1,4-diamine (278 mg, 1.04 mmol), caesium carbonate (845 mg, 2.59 mmol), Pd(OAc)$_2$ (23 mg, 0.10 mmol) and XantPhos (116 mg, 0.20 mmol) was added into to the solution of the 6-(2-chloropyrimidin-4-yl)-4-fluoro-1-isopropyl-2-(methylthio)-1H-benzo[d]imidazole (350 mg, 1.04 mmol) in DMF (15 mL), and reacted under nitrogen protection at 100° C. overnight. After cooling to room temperature, it was filtered on Celite, the filter cake was washed with dichloromethane, and then the combined filtrate was poured into water (50 mL), and extracted with dichloromethane (50 mL×3). The organic layer was combined, washed with water and brine, and concentrated under reduced pressure to afford a crude product. The crude produce was purified by column chromatography to afford 120 mg of a red solid. LC-MS(APCI): m/z=569.30 (M+1).

Step 4 Synthesis of $N^1$-(2-(dimethylamino)ethyl)-$N^4$-(4-(2-methylthio-4-fluoro-1-isopropyl-1H-benzo[d]imidazo 1-6-yl)pyrimidin-2-yl)-5-methoxy-$N^1$-methylbenzene-1,2,4-triamine Pd/C (20 mg) was added into the solution of $N^1$-(2-(dimethylamino)ethyl)-$N^4$-(4-(4-fluoro-1-isopropyl-2-(methylthio)-1H-benzo[d]imidazol-6-yl)pyrimidin-2-yl)-5-methoxy-$N^1$-methyl-2-nitrobenzene-1,4-diamine (120 mg) in methanol (20 mL), and reacted under a balloon of hydrogen gas overnight. The reaction mixture was filtered on Celite, the filtrate was concentrated under reduced pressure, and separated on column chromatography (eluant:

dichloromethane/methanol (v/v)=10:1) to afford 70 mg of a red-yellow solid, yield over two steps: 27.6%. LC-MS (APCI): m/z=539.3 (M+1).

Step 5 Synthesis of N-(2-((2-(dimethylamino)ethyl) (methyl)amino)-5-((4-(4-fluoro-1-isopropyl-2-(methylthio)-1H-benzo[d]imidazol-6-yl)pyrimidin-2-yl) amino)-4-methoxyphenyl)acrylamide DIPEA (34 mg, 0.26 mmol) was added into the solution of the $N^1$-(2-(dimethylamino)ethyl)-$N^4$-(4-(2-methylthio-4-fluoro-1-isopropyl-1H-benzo[d]imidazo 1-6-yl)pyrimidin-2-yl)-5-methoxy-$N^1$-methylbenzene-1,2,4-triamine (70 mg, 0.13 mmol) in dichloromethane (20 mL). The reaction system was cooled to −20° C. after the addition was complete, and at this temperature acryloyl chloride (12 mg, 0.13 mmol) was added dropwise, and stirred at −20° C. for 1 hour. The reaction was quenched by adding water (20 mL), and extracted with dichloromethane (20 mL×3). The organic layer was washed with water and brine, dried over anhydrous sodium sulfate, filtered and concentrated to afford a yellow oil, and the yellow oil was separated on column chromatography to give 20 mg of a yellow solid. LC-MS (APCI): m/z=593.0 (M+1), HPLC: 94.06%.

Example 64 Preparation of N-(5-((4-(2-(2,2-difluoroethoxy)-4-fluoro-1-isopropyl-1H-benzo[d]imidazol-6-yl)pyrimidin-2-yl)amino)-2-((2-(dimethylamino)ethyl)(methyl)amino)-4-methoxyphenyl) acrylamide

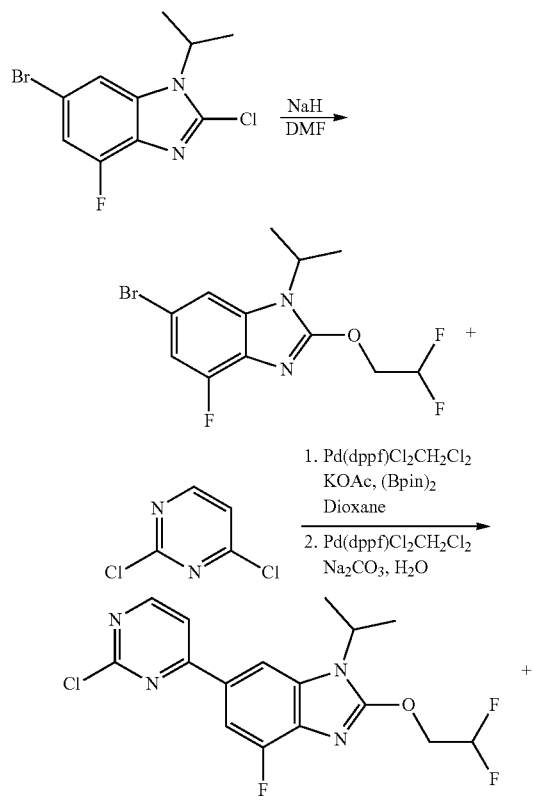

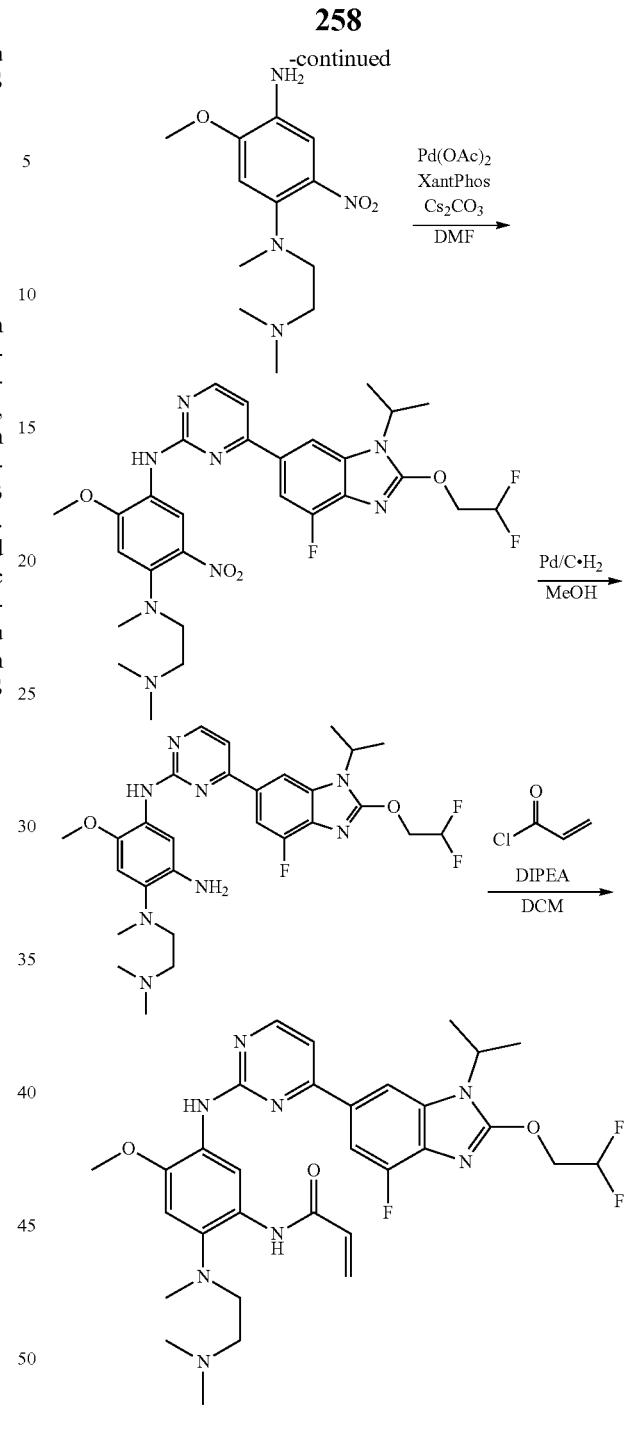

Step 1 Synthesis of Compound 6-bromo-2-(2,2-difluoroethoxy)-4-fluoro-1-isopropyl-1H-benzo[d] imidazole NaH (60%, 72 mg, 1.81 mmol) was added into the solution of the 2,2-difluoroethanol (203 mg, 2.5 mmol) in DMF (10 mL) at 0° C., and stirred for 30 minutes at 0° C. Then 6-bromo-2-chloro-4-fluoro-1-isopropyl-1H-benzo[d] imidazole (600 mg, 2.06 mmol) was added, and stirred at room temperature for 2 hours. The reaction was quenched by adding water (20 mL), and extracted with ethyl acetate (30 mL×2). The organic layer was washed with water and brine, concentrated under reduced pressure, and purified by column chromatography to afford 588 mg of a white solid. LC-MS(APCI): m/z=337.2 (M+1). $^1$H NMR (400 MHz, CDCl$_3$) δ7.25 (d, J=1.5 Hz, 1H), 7.08 (dd, J=9.8, 1.6 Hz, 1H), 6.20 (tt, J=54.8, 3.9 Hz, 1H), 4.78 (td, J=13.4, 3.9 Hz, 2H), 4.61 (dt, J=13.9, 6.9 Hz, 1H), 1.57 (s, 3H), 1.55 (s, 3H).

Step 2 Synthesis of 6-(2-chloropyrimidin-4-yl)-2-(2, 2-difluoroethoxy)-4-fluoro-1-isopropyl-1H-benzo[d] imidazole Under nitrogen protection, bis(pinacolato)diboron (363 mg, 1.43 mmol), potassium acetate (233 mg, 2.38 mmol), Pd(dppf)Cl$_2$.DCM (98 mg) were sequentially added into the solution of the 6-bromo-2-(2,2-difluoroethoxy)-4-fluoro-1-isopropyl-1H-benzo[d]imidazole (400 mg, 1.19 mmol) in anhydrous 1,4-Dioxane (10 mL), and stirred under nitrogen protection at 100° C. overnight.

After cooling to room temperature, under nitrogen protection, the above reaction mixture was added 2,4-dichloropyrimidine (213 mg, 1.43 mmol), sodium carbonate (253 mg, 2.38 mmol), Pd(dppf)Cl$_2$.DCM (98 mg) and water (2.5 mL), and stirred at 80° C. for 2 hours. After cooling to room temperature, it was filtered on Celite, the filter cake was washed with ethyl acetate, and then the combined filtrate was poured into water (50 mL), and extracted with ethyl acetate (50 mL×3). The organic layer was combined, washed with water and brine, and concentrated under reduced pressure to afford a crude product. The crude product was purified by column chromatography to afford 600 mg of a white solid. LC-MS(APCI): m/z=371.0 (M+1). $^1$H NMR (400 MHz, CDCl$_3$) δ 8.63 (d, J=5.3 Hz, 1H), 8.01 (d, J=1.4 Hz, 1H), 7.62 (d, J=5.3 Hz, 1H), 7.59 (dd, J=11.3, 1.4 Hz, 1H), 6.23 (tt, J=54.8, 3.9 Hz, 1H), 4.84 (td, J=13.4, 3.9 Hz, 2H), 4.76 (dt, J=13.9, 6.9 Hz, 1H), 1.63 (d, J=6.9 Hz, 6H).

Step 3 Synthesis of N$^1$-(4-(2-(2,2-difluoroethoxy)-4-fluoro-1-isopropyl-1H-benzo[d]imidazol-6-yl)pyrimidin-2-yl)-N$^4$-(2-(dimethylamino)ethyl)-2-methoxy-N$^4$-methyl-5-nitrobenzene-1,4-diamine Under nitrogen protection, N$^1$-(2-(dimethylamino)ethyl)-5-methoxy-N$^1$-methyl-2-nitrobenzene-1,4-diamine (362 mg, 1.35 mmol), caesium carbonate (1.10 g, 3.38 mmol), Pd(OAc)$_2$ (30 mg, 0.14 mmol) and XantPhos (156 mg, 0.28 mmol) were sequentially added into the solution of the 6-(2-chloropyrimidin-4-yl)-2-(2,2-difluoroethoxy)-4-fluoro-1-isopropyl-1H-benzo[d]imidazole (600 mg, 0.62 mmol) in DMF (10 mL) and stirred at 100° C. overnight. After cooling to room temperature, it was filtered on Celite, the filter cake was washed with dichloromethane, and then the combined filtrate was poured into water (50 mL), extracted with dichloromethane (50 mL×3). The organic layer was combined, washed with water and brine, and concentrated under reduced pressure to afford a crude product. The crude produce was separated on column chromatography to afford 442 mg of a red solid. LC-MS(APCI): m/z=603.30 (M+1).

Step 4 Synthesis of N$^4$-(4-(2-(2,2-difluoroethoxy)-4-fluoro-1-isopropyl-1H-benzo[d]imidazol-6-yl)pyrimidin-2-yl)-N$^1$-(2-(dimethylamino)ethyl)-5-methoxy-N$^1$-methylbenzene-1,2,4-triamine Pd/C (20 mg) was added into the solution of N$^1$-(4-(2-(2,2-difluoroethoxy)-4-fluoro-1-isopropyl-1H-benzo[d]imidazol-6-yl)pyrimidin-2-yl)-N$^4$-(2-(dimethylamino)ethyl)-2-methoxy-N$^4$-methyl-5-nitrobenzene-1,4-diamine (442 mg) in methanol (30 mL), and reacted under a balloon of hydrogen gas overnight. The reaction mixture was filtered on Celite, the filtrate was concentrated under reduced pressure, and separated on column chromatography (eluant: dichloromethane/methanol (v/v)=10:1), to afford 290 mg of a red-yellow solid, yield over two steps: 37.6%. LC-MS (APCI): m/z=573.2 (M+1).

Step 5 Synthesis of N-(5-((4-(2-(2,2-difluoroethoxy)-4-fluoro-1-isopropyl-1H-benzo[d]imidazol-6-yl)pyrimidin-2-yl)amino)-2-((2-(dimethylamino)ethyl)(methyl)amino)-4-methoxyphenyl)acrylamide DIPEA (132 mg, 1.02 mmol) was added into the solution of the N$^4$-(4-(2-(2,2-difluoroethoxy)-4-fluoro-1-isopropyl-1H-benzo[d]imidazol-6-yl)pyrimidin-2-yl)-N$^1$-(2-(dimethylamino)ethyl)-5-methoxy-N$^1$-methylbenzene-1,2,4-triamine (290 mg, 0.51 mmol) in dichloromethane (30 mL). The reaction system was cooled to −20° C. after the addition was complete, and and at this temperature acryloyl chloride (0.51 mmol) was added dropwise, and stirred at −20° C. for 1 hr. The reaction was quenched by adding water (20 mL), and extracted with dichloromethane (20 mL×3). The organic layer was washed with water and brine, dried over anhydrous sodium sulfate, filtered and concentrated to afford a yellow oil, and the yellow oil was separated on column chromatography to give 120 mg of a yellow solid. LC-MS (APCI): m/z=627.2 (M+1), HPLC: 96.70%, $^1$H NMR (300 MHz, DMSO-d$_6$) δ 10.07 (s, 1H), 9.01 (s, 1H), 8.50 (s, 1H), 8.17 (s, 2H), 8.05-7.82 (m, 1H), 7.56 (s, 1H), 7.02 (s, 1H), 6.75-6.16 (m, J=103.8, 34.6 Hz, 3H), 5.77 (s, 1H), 5.01-4.74 (m, 3H), 3.87 (s, 3H), 3.04-2.88 (m, 2H), 2.69 (s, 3H), 2.57-2.51 (m, 2H), 2.33 (s, 6H), 1.52 (s, 6H).

Example 65 Preparation of N-(2-((2-(dimethylamino)ethyl)(methyl)amino)-5-((4-(4-fluoro-1-isopropyl-2-(methoxy methyl)-1H-benzo[d]imidazol-6-yl)pyrimidin-2-yl)amino)-4-methoxyphenyl) acrylamide

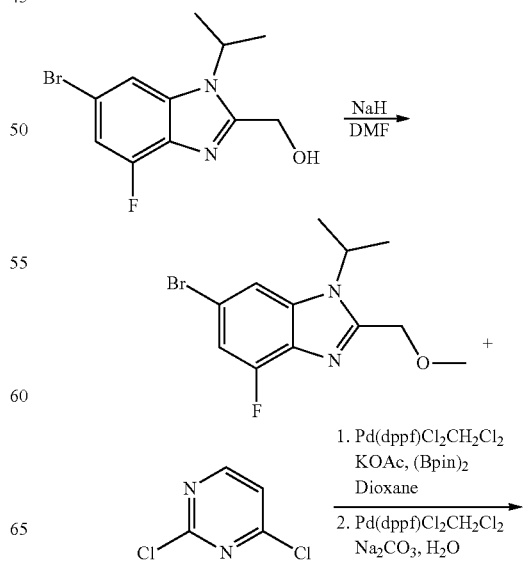

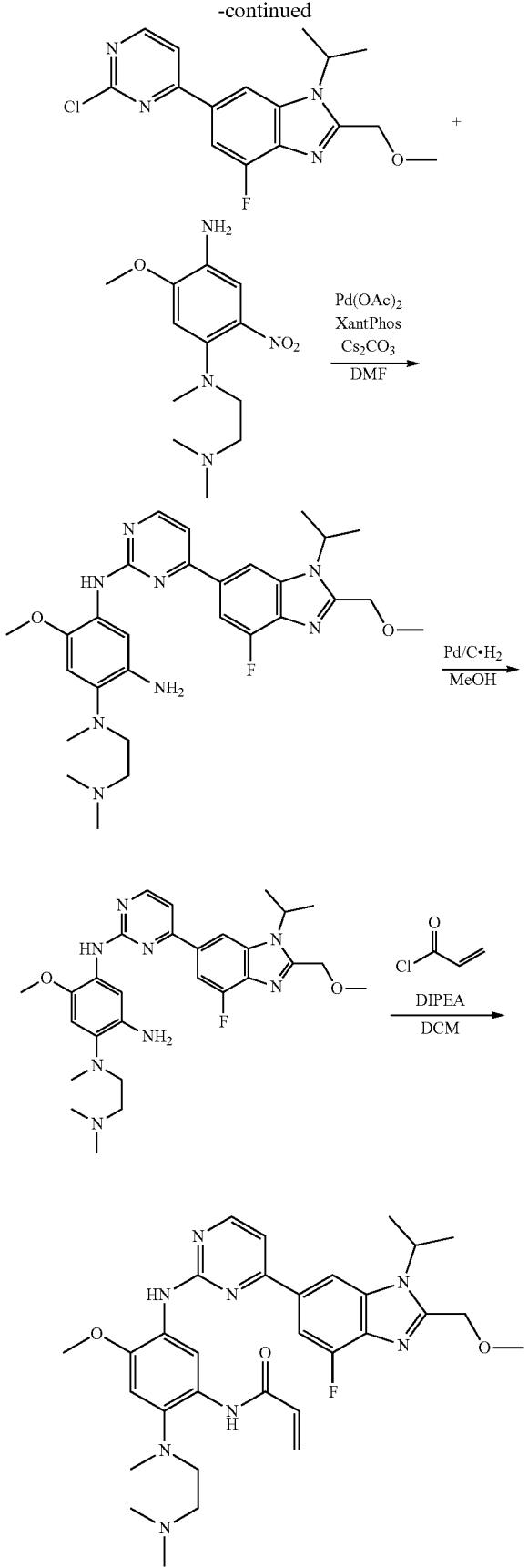

Step 1 Synthesis of Compound 6-bromo-4-fluoro-1-isopropyl-2-(methoxymethyl)-1H-benzo[d]imidazole NaH (60%, 16 mg, 0.42 mmol) was added into the solution of the (6-bromo-4-fluoro-1-isopropyl-1H-benzo[d]imidazol-2-yl)methanol (100 mg, 0.35 mmol) in DMF (10 mL) at 0° C., and stirred for 30 minutes at 0° C. Then the $CH_3I$ (59 mg, 0.42 mmol) was added, and stirred at room temperature for 1 hour. The reaction was quenched by adding water (20 mL), and extracted with ethyl acetate (30 mL×2). The organic layer was washed with water and brine, and concentrated under reduced pressure, and purified by column chromatography to afford 68 mg of a white solid. LC-MS(APCI): m/z=300.1 (M+1). $^1$H NMR (400 MHz, $CDCl_3$) δ 7.50 (d, J=1.3 Hz, 1H), 7.12 (dd, J=9.6, 1.4 Hz, 1H), 4.91 (dt, J=13.9, 7.0 Hz, 1H), 4.74 (s, 2H), 3.38 (s, 3H), 1.63 (d, J=7.0 Hz, 6H).

Step 2 Synthesis of 6-(2-chloropyrimidin-4-yl)-4-fluoro-1-isopropyl-2-(methoxymethyl)-1H-benzo[d]imidazole Under nitrogen protection, bis(pinacolato)diboron (203 mg, 0.80 mmol), potassium acetate (130 mg, 1.32 mmol), and $Pd(dppf)Cl_2$.DCM (54 mg) were sequentially added into the solution of the 6-bromo-4-fluoro-1-isopropyl-2-(methoxymethyl)-1H-benzo[d]imidazole (200 mg, 0.66 mmol) in anhydrous 1,4-Dioxane (10 mL) and stirred at 100° C. overnight.

After cooling to room temperature, under nitrogen protection, the above reaction mixture was added 2,4-dichloropyrimidine (119 mg, 0.80 mmol), sodium carbonate (140 mg, 1.32 mmol) and $Pd(dppf)Cl_2$.DCM (54 mg) and water (2.5 mL), and stirred at 80° C. for 2 hours. After cooling to room temperature, it was filtered on Celite, the filter cake was washed with ethyl acetate, and then the combined filtrate was poured into water (50 mL), and extracted with ethyl acetate (50 mL×3). The organic layer was combined, washed with water and brine, concentrated under reduced pressure to afford a crude product. The crude product was purified by column chromatography to afford 148 mg of a white-yellow solid. LC-MS(APCI): m/z=335.1 (m+1).

Step 3 Synthesis of $N^1$-(2-(dimethylamino)ethyl)-$N^4$-(4-(4-fluoro-1-isopropyl-2-(methoxymethyl)-1H-benzo[d]imidazol-6-yl)pyrimidin-2-yl)-5-methoxy-$N^1$-methyl-2-nitrobenzene-1,4-diamine Under nitrogen protection, $N^1$-(2-(dimethylamino)ethyl)-5-methoxy-$N^1$-methyl-2-nitrobenzene-1,4-diamine (120 mg, 0.44 mmol), caesium carbonate (359 mg, 1.10 mmol), $Pd(OAc)_2$ (9 mg, 0.04 mmol) and XantPhos (47 mg, 0.08 mmol) were added into the solution of the 6-(2-chloropyrimidin-4-yl)-4-fluoro-1-isopropyl-2-(methoxymethyl)-1H-benzo[d]imidazole (148 mg, 0.44 mmol) in DMF (10 mL), and reacted under nitrogen protection at 100° C. overnight. After cooling to room temperature, it was filtered on Celite, the filter cake was washed with dichloromethane, and then the combined filtrate was poured into water (50 mL), and extracted with dichloromethane (50 mL×3). The organic layer was combined, washed with water and brine, concentrated under reduced pressure to afford a crude product. The crude product was separated on column chromatography to afford 150 mg of a red solid. LC-MS(APCI): m/z=567.3 (M+1).

Step 4 Synthesis of N¹-(2-(dimethylamino)ethyl)-N⁴-(4-(4-fluoro-1-isopropyl-2-(methoxymethyl)-1H-benzo[d]imidazol-6-yl)pyrimidin-2-yl)-5-methoxy-N¹-methylbenzene-1,2,4-triamine Pd/C (20 mg) was added into the solution of N¹-(2-(dimethylamino)ethyl)-N⁴-(4-(4-fluoro-1-isopropyl-2-(methoxymethyl)-1H-benzo[d]imidazol-6-yl)pyrimidin-2-yl)-5-methoxy-N¹-methyl-2-nitrobenzene-1,4-diamine (150 mg) in methanol (30 mL), and reacted under a balloon of hydrogen gas overnight. The reaction mixture was filtered on Celite, the filtrate was concentrated under reduced pressure, and separated on column chromatography (eluant: dichloromethane/methanol (v/v)=10:1), to afford 98 mg of a red-yellow solid, yield over two steps: 41.6%. LC-MS (APCI): m/z=537.2 (M+1).

Step 5 Synthesis of N-(2-((2-(dimethylamino)ethyl)(methyl)amino)-5-((4-(4-fluoro-1-isopropyl-2-(methoxymethyl)-1H-benzo[d]imidazol-6-yl)pyrimidin-2-yl)amino)-4-methoxyphenyl)acrylamide DIPEA (46 mg, 0.36 mmol) was added into the solution of the N¹-(2-(dimethylamino)ethyl)-N⁴-(4-(4-fluoro-1-isopropyl-2-(methoxymethyl)-1H-benzo[d]imidazol-6-yl)pyrimidin-2-yl)-5-methoxy-N¹-methylbenzene-1,2,4-triamine (98 mg, 0.18 mmol) in dichloromethane (15 mL). The reaction system was cooled to −20° C. after the addition was complete, and at this temperature acryloyl chloride (0.18 mmol) was added dropwise, and stirred at −20° C. for 1 hour. The reaction was quenched by adding water (20 mL), extracted with dichloromethane (20 mL×3). The organic layer was washed with water and brine, dried over anhydrous sodium sulfate, filtered and concentrated to afford yellow oil, and the yellow oil was separated on column chromatography to give 50 mg of a yellow solid. LC-MS (APCI): m/z=591.2 (M+1), HPLC: 97.88%, ¹H NMR (300 MHz, DMSO-d₆) δ 10.64 (s, 1H), 9.81 (s, 1H), 8.77 (s, 1H), 8.51 (d, J=5.2 Hz, 1H), 8.27 (d, J=5.4 Hz, 2H), 7.95 (d, J=12.2 Hz, 1H), 7.60 (d, J=5.3 Hz, 1H), 6.96 (s, 1H), 6.24 (dd, J=16.9, 2.0 Hz, 1H), 5.69 (dd, J=10.2, 1.9 Hz, 1H), 4.92 (dt, J=13.7, 6.8 Hz, 1H), 4.74 (s, 2H), 3.88 (s, 3H), 3.71-3.44 (m, 2H), 3.32 (s, 3H), 3.20-3.03 (m, 2H), 2.71 (s, 6H), 2.59 (s, 3H), 1.60 (d, J=6.9 Hz, 6H).

Example 66 Preparation of N-(2-((2-(dimethylamino)ethyl)(methyl)amino)-5-((4-(8-fluoro-2,2-dimethyl-2,3-dihydro benzo[4,5]imidazo[2,1-b]oxazol-6-yl)pyrimidin-2-yl)amino)-4-methoxyphenyl)acrylamide

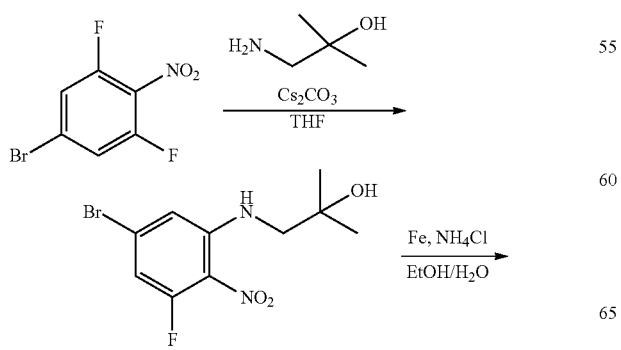

-continued

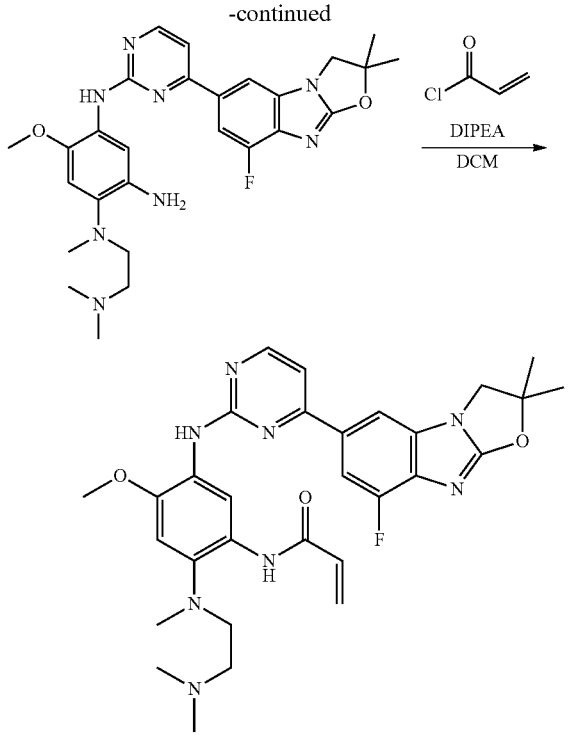

Step 1 Synthesis of Compound 1-((5-bromo-3-fluoro-2-nitrophenyl)amino)-2-methylpropan-2-ol In an ice bath, cesium carbonate (3.26 g, 10.00 mmol) and 1-amino-2-methylpropan-2-ol (891 mg, 10.00 mmol) were sequentially added into the solution of 5-bromo-1,3-difluoro-2-nitrobenzene (2.38 g, 10.00 mmol) in anhydrous tetrahydrofuran (30 mL), and the reaction mixture was warmed to room temperature naturally. After the reaction mixture was stirred overnight, it was filtered on Celite, and the filtrate was concentrated under reduced pressure to give a crude product. The crude produce was purified by silica gel chromatography to afford 2.70 g of an orange solid. LC-MS (APCI): m/z=304.9 (M−1).

Step 2 Synthesis of Compound 1-((2-amino-5-bromo-3-fluorophenyl)amino)-2-methylpropan-2-ol The reduced iron powder (3.00 g, 52.90 mmol) and ammonium chloride (1.4 g, 26.5 mmol) were added into the solution of the 1-(5-bromo-3-fluoro-2-nitrophenylamino)-2-methylpropan-2-ol (2.70 g, 8.80 mmol) in ethanol and water (25 mL, v:v=4:1), the reaction mixture was heated to 90° C. for 2 hours. After cooling to room temperature, it was filtered on Celite, the filtrate was concentrated under reduced pressure to afford a yellow oil, and the yellow oil was purified by column chromatography to afford 2.40 g of a white solid. LC-MS(APCI): m/z=277.0 (M+1).

Step 3 Synthesis of Compound 1-(6-bromo-4-fluoro-1H-benzo[d]imidazol-1-yl)-2-methylpropan-2-ol Under nitrogen protection, Trimethyl Orthoformate (1.40 g, 13.04 mmol) and p-Toluenesulfonic acid monohydrate (165 mg, 0.87 mmol) were added into the solution of the 1-(2-amino-5-bromo-3-fluorophenylamino)-2-methylpropan-2-ol (2.40 g, 8.70 mmol) in toluene (50 mL), and stirred at 50° C. for 1 hour. The reaction mixture was concentrated directly under reduced pressure to give a yellow oil. The yellow oil was purified by column chromatography to give 1.95 g of a white solid. LC-MS(APCI): m/z=287.1 (M+1).

Step 4 Synthesis of Compound 6-bromo-8-fluoro-2,2-dimethyl-2,3-dihydrobenzo[4,5]imidazo[2,1-b]oxazole Under nitrogen protection, CuCl (8.60 mg, 0.09 mmol) and (t-BuO)₂ (511 mg, 3.50 mmol) were added into the solution of the 1-(6-bromo-4-fluoro-H-benzo[d]imidazol-1-yl)-2-methylpropan-2-ol (500 mg, 1.75 mmol) in toluene (10 mL), and stirred at 80° C. overnight. After cooling to room temperature, the reaction was quenched by adding the 20 mL saturated solution of Na₂SO₃, and extracted with ethyl acetate (30 mL×3). The organic layer was washed water and brine, dried over anhydrous sodium sulfate, filtered and concentrated to afford a yellow oil, and the yellow oil was purified by column chromatography to give 234 mg of a white solid. LC-MS(APCI): m/z=285.0 (M+1).

Step 5 Synthesis of 6-(2-chloropyrimidin-4-yl)-8-fluoro-2,2-dimethyl-2,3-dihydrobenzo[4,5]imidazo[2,1-b]oxazole Under nitrogen protection, bis(pinacolato)diboron (537 mg, 2.11 mmol), potassium acetate (345 mg, 3.52 mmol), Pd(dppf)Cl₂.DCM (54 mg) were sequentially added into the solution of the 6-bromo-8-fluoro-2,2-dimethyl-2,3-dihydrobenzo[4,5]imidazo[2,1-b]oxazole (500 mg, 1.76 mmol) in anhydrous 1,4-Dioxane (20 mL), and stirred at 100° C. overnight.

After cooling to room temperature, under nitrogen protection, 2,4-dichloropyrimidine (315 mg, 2.11 mmol), sodium carbonate (373 mg, 3.52 mmol) and Pd(dppf)Cl₂.DCM (54 mg) and water (2.5 mL) were sequentially added into the above reaction mixture, and stirred at 80° C. for 2 hours. After cooling to room temperature, it was filtered on Celite, the filter cake was washed with ethyl acetate, and then the combined filtrate was poured into water (50 mL), extracted with ethyl acetate (50 mL×3). The organic layer was combined, washed with water and brine, and concentrated under reduced pressure to afford a crude product. The crude product was purified by column chromatography to afford 400 mg of a yellow solid. Yield was 71.5%, LC-MS(APCI): m/z=318.9 (M+1).

Step 6 Synthesis of N¹-(2-(dimethylamino)ethyl)-N⁴-(4-(8-fluoro-2,2-dimethyl-2,3-dihydrobenzo[4,5]imidazo[2,1-b]oxazol-6-yl)pyrimidin-2-yl)-5-methoxy-N¹-methyl-2-nitrobenzene-1,4-diamine Under nitrogen protection, N¹-(2-(dimethylamino)ethyl)-5-methoxy-N¹-methyl-2-nitrobenzene-1,4-diamine (306 mg, 1.14 mmol), caesium carbonate (932 mg, 2.86 mmol), Pd(OAc)₂ (26 mg, 0.11 mmol) and XantPhos (132 mg, 0.22 mmol) were added into the solution of the 6-(2-chloropyrimidin-4-yl)-8-fluoro-2,2-dimethyl-2,3-dihydrobenzo[4,5]imidazo[2,1-b]oxazole (400 mg, 1.26 mmol) in DMF (10 mL), and stirred at 100° C. overnight. After cooling to room temperature, it was filtered on Celite, the filter cake was washed with dichloromethane, then the combined filtrate was poured into water (50 mL), extracted with dichloromethane (50 mL×3). The organic layer was combined, washed with water and brine, concentrated under reduced pressure to afford a crude product. The crude product was separated on column chromatography to afford 335 mg of a red solid. LC-MS(APCI): m/z=551.0 (M+1).

Step 7 synthesis of N-(2-(dimethylamino)ethyl)-$N^4$-(4-(8-fluoro-2,2-dimethyl-2,3-dihydrobenzo[4,5]imidazo[2,1-b]oxazol-6-yl)pyrimidin-2-yl)-5-methoxy-$N^1$-methylbenzene-1,2,4-triamine Pd/C (20 mg) was added into the solution of $N^1$-(2-(dimethylamino)ethyl)-$N^4$-(4-(8-fluoro-2,2-dimethyl-2,3-dihydrobenzo[4,5]imidazo[2,1-b]oxazol-6-yl)pyrimidin-2-yl)-5-methoxy-$N^1$-methyl-2-nitrobenzene-1,4-diamine (335 mg) in methanol (30 mL), and reacted under a balloon of hydrogen gas overnight. The reaction mixture was filtered on Celite, the filtrate was concentrated under reduced pressure, and separated on column chromatography (eluant: dichloromethane/methanol (v/v)=10:1), to afford 265 mg of a red-yellow solid, yield over two steps: 44.7%. LC-MS (APCI): m/z=521.1 (M+1).

Step 8 synthesis of N-(2-((2-(dimethylamino)ethyl)(methyl)amino)-5-((4-(8-fluoro-2,2-dimethyl-2,3-dihydrobenzo[4,5]imidazo[2,1-b]oxazol-6-yl)pyrimidin-2-yl)amino)-4-methoxyphenyl)acrylamide DIPEA (165 mg, 1.27 mmol) was added into the solution of the $N^1$-(2-(dimethylamino)ethyl)-$N^4$-(4-(8-fluoro-2,2-dimethyl-2,3-dihydrobenzo[4,5]imidazo[2,1-b]oxazol-6-yl)pyrimidin-2-yl)-5-methoxy-$N^1$-methylbenzene-1,2,4-triamine (265 mg, 0.51 mmol) in dichloromethane (30 mL). The reaction system was cooled to −20° C. after the addition was complete, and at this temperature acryloyl chloride (0.51 mmol) was added dropwise, and stirred at −20° C. for 1 hour. The reaction was quenched by adding water (20 mL), extracted with dichloromethane (20 mL×3). The organic layer was washed with water and brine, dried over anhydrous sodium sulfate, filtered and concentrated to afford yellow oil, and the yellow oil was separated on column chromatography (eluant:dichloromethane/methanol (v/v)=12:1) to give 47 mg of a yellow solid. LC-MS(APCI): m/z=575.2 (M+1), HPLC: 96.87%, $^1$H NMR (300 MHz, DMSO-$d_6$) δ 10.14 (s, 1H), 9.16 (s, 1H), 8.48 (s, 1H), 8.22 (s, 1H), 8.03 (s, 1H), 7.89 (d, J=14.0 Hz, 1H), 7.51-7.34 (m, 1H), 7.14-6.98 (m, 1H), 6.55-6.36 (m, 1H), 6.25 (d, J=16.4 Hz, 1H), 5.77 (d, J=10.0 Hz, 1H), 4.19 (s, 2H), 3.87 (s, 3H), 2.98-2.82 (m, 2H), 2.70 (s, 3H), 2.44-2.10 (m, 8H), 1.66 (s, 6H).

Example 67 Preparation of N-(5-((4-(4-fluoro-1-isopropyl-2-methyl-1H-benzo[d]imidazol-6-yl)pyrimidin-2-yl)amino)-2-((2-hydroxyethyl)(methyl)amino)-4-methoxyphenyl)acrylamide

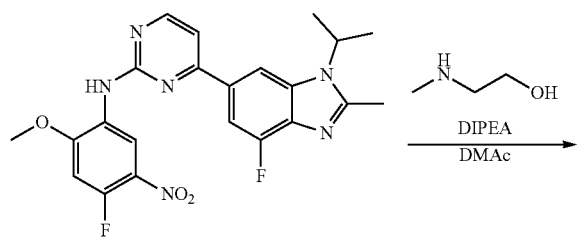

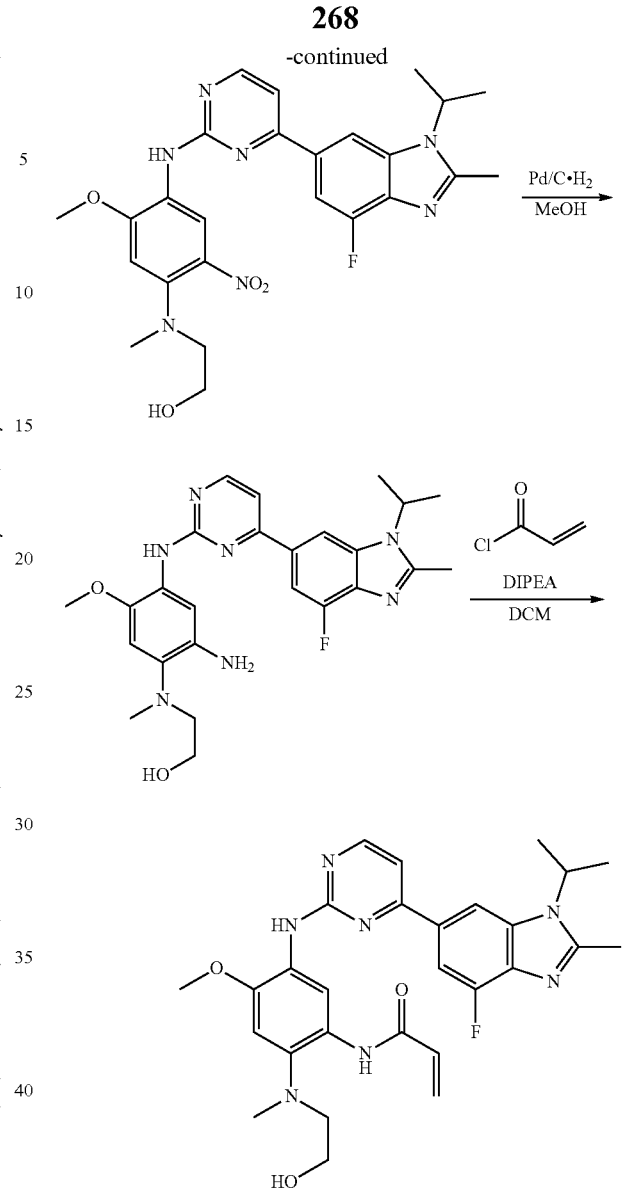

Step 1 Synthesis of Compound 2-((4-((4-(4-fluoro-1-isopropyl-2-methyl-1H-benzo[d]imidazol-6-yl)pyrimidin-2-yl)amino)-5-methoxy-2-nitrophenyl)(methyl)amino)ethan-1-ol 4-(4-fluoro-1-isopropyl-2-methyl-1H-benzo[d]imidazol-6-yl)-N-(4-fluoro-2-methoxy-5-nitrophenyl)pyrimidin-2-amine (2.17 g, 4.77 mmol), N-methyl-2-hydroxyethylamine (360 mg, 4.77 mmol) and DIPEA (930 mg, 7.60 mmol), dimethylacetamide (10 mL) were added into 50 mL sealed tube, and reacted under sealed condition at 140° C. for 8 hours. After cooling to room temperature, the reaction was quenched by adding water (20 mL), and filtered. The filter cake was washed with methanol (2 mL), and then the residue was diluted with water (30 mL) and extracted with dichloromethane (30 mL×3). The combined organic phases were washed with brine (270 mL), dried over anhydrous sodium sulfate, filtered and concentrated under reduced pressure to afford 2.1 g of a red solid. LC-MS(APCI): m/z=510.2 (M+1).

Step 2 Synthesis of 2-((2-amino-4-((4-(4-fluoro-1-isopropyl-2-methyl-1H-benzo[d]imidazol-6-yl)pyrimidin-2-yl)amino)-5-methoxyphenyl)(methyl)amino)ethan-1-ol Pd/C (20 mg) was added into the solution of 2-((4-((4-(4-fluoro-1-isopropyl-2-methyl-1H-benzo[d]imidazol-6-yl)pyrimidin-2-yl)amino)-5-methoxy-2-nitrophenyl)(methyl)amino)ethan-1-ol (200 mg) in methanol (30 mL), and reacted under a balloon of hydrogen gas overnight. The reaction mixture was filtered on Celite, the filtrate was concentrated under reduced pressure, and separated on column chromatography (eluant:dichloromethane/methanol (v/v)=10:1), to afford 120 mg of a red-yellow solid. LC-MS (APCI): m/z=479.6 (M+1).

Step 3 Synthesis of N-(5-((4-(4-fluoro-1-isopropyl-2-methyl-1H-benzo[d]imidazol-6-yl)pyrimidin-2-yl)amino)-2-((2-hydroxyethyl)(methyl)amino)-4-methoxyphenyl)acrylamide DIPEA (0.50 mmol) was added into the solution of the 2-((2-amino-4-((4-(4-fluoro-1-isopropyl-2-methyl-1H-benzo[d]imidazol-6-yl)pyrimidin-2-yl)amino)-5-methoxyphenyl)(methyl)amino)ethan-1-ol (120 mg, 0.25 mmol) in dichloromethane (20 mL). The reaction system was cooled to −20° C. after the addition was complete, and at this temperature acryloyl chloride (0.25 mmol) was added dropwise, and stirred at −20° C. for 1 hr. The reaction was quenched by adding water (20 mL), extracted with dichloromethane (20 mL×3), the organic layer was washed with water and brine, dried over anhydrous sodium sulfate, filtered and concentrated to afford yellow oil, and the yellow oil was separated on column chromatography to give 25 mg of a yellow solid. LC-MS(APCI): m/z=534.3 (M+1), HPLC: 94.09%, $^1$H NMR (500 MHz, DMSO-$d_6$) δ 9.63 (s, 1H), 8.97 (s, 1H), 8.46 (d, J=5.2 Hz, 1H), 8.20 (d, J=11.7 Hz, 2H), 7.89 (d, J=12.2 Hz, 1H), 7.52 (d, J=5.3 Hz, 1H), 6.94 (s, 1H), 6.51 (dd, J=16.9, 10.2 Hz, 1H), 6.22 (dd, J=17.0, 1.7 Hz, 1H), 5.70 (dd, J=10.2, 1.6 Hz, 1H), 5.34 (t, J=4.7 Hz, 1H), 4.80 (dt, J=13.9, 7.0 Hz, 1H), 3.83 (s, 3H), 3.59 (dd, J=9.7, 4.8 Hz, 2H), 2.85 (t, J=4.9 Hz, 2H), 2.71 (s, 3H), 2.60 (s, 3H), 1.55 (d, J=6.9 Hz, 6H).

Example 68 Preparation of N-(2-((2-(dimethylamino)ethyl)(methyl)amino)-5-((4-(4-fluoro-1-isopropyl-2-methyl-1H-benzo[d]imidazol-6-yl)pyrimidin-2-yl)amino)-4-methoxyphenyl)-N-methylacrylamide

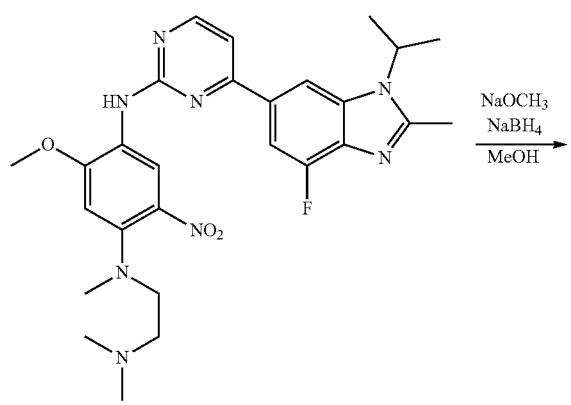

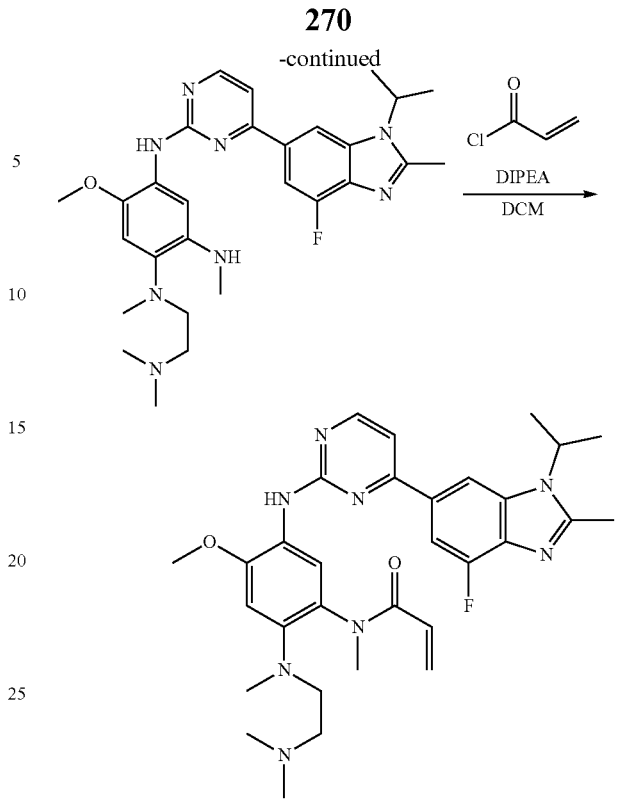

Step 1 Synthesis of $N^1$-(2-(dimethylamino)ethyl)-$N^4$-(4-(4-fluoro-1-isopropyl-2-methyl-1H-benzo[d]imidazol-6-yl)pyrimidin-2-yl)-5-methoxy-$N^1$,$N^2$-dimethylbenzene-1,2,4-triamine A mixture of the $N^1$-(2-(dimethylamino)ethyl)-$N^4$-(4-(4-fluoro-1-isopropyl-2-methyl-1H-benzo[d]imidazol-6-yl)pyrimidin-2-yl)-5-methoxy-N-methylbenzene-1,2,4-triamine (506 mg, 1.00 mmol) and paraformaldehyde (150 mg, 5.00 mmol) were dissolved into methanol (50 ml) and NaOMe (270 mg, 5.00 mmol) was added, and the mixture was refluxed for 2 h. After cooling to 0° C., NaBH$_4$ (190 mg, 5.00 mmol) was added, and the mixture was stirred under reflux for 1 hour. The mixture was poured into ice water, extracted with DCM, and the organic layer was combined, dried over anhydrous sodium sulfate, and the solvent was evaporated to afford a crude product, which was purified by column chromatography (eluant:dichloromethane/methanol (v/v)=10:1) to give 180 mg of the title compound, LC-MS (APCI): m/z=521.2 (M+1), HPLC: 94.14%.

Step 2 Synthesis of N-(2-((2-(dimethylamino)ethyl)(methyl)amino)-5-((4-(4-fluoro-1-isopropyl-2-methyl-1H-benzo[d]imidazol-6-yl)pyrimidin-2-yl)amino)-4-methoxyphenyl)-N-methylacrylamide DIPEA (90 mg, 0.69 mmol) was added into the solution of the $N^1$-(2-(dimethylamino)ethyl)-$N^4$-(4-(4-fluoro-1-isopropyl-2-methyl-1H-benzo[d]imidazol-6-yl)pyrimidin-2-yl)-5-methoxy-$N^1$,$N^2$-dimethylbenzene-1,2,4-triamine (180 mg, 0.35 mmol) in dichloromethane (20 mL). The reaction system was cooled to −20° C. after the addition was complete, acryloyl chloride (0.35 mmol) was added dropwise, and stirred at −20° C. for 1 hour. The reaction was quenched by adding water (20 mL), and extracted with dichloromethane (20 mL×3). The organic layer was washed with water and brine, dried over anhydrous sodium sulfate, filtered and concentrated to afford yellow oil, and the yellow oil was separated on column chromatography (eluant:dichloromethane/methanol (v/v)=10:1) to give 50 mg of a yellow solid. LC-MS(APCI): m/z=575.2 (M+1), HPLC: 98.88%, $^1$H NMR (300 MHz, DMSO-$d_6$) δ 8.50 (d, J=5.3 Hz, 1H), 8.21 (d, J=6.0 Hz, 2H), 7.92 (s, 1H), 7.76 (d, J=12.2 Hz, 1H), 7.59 (d, J=5.3 Hz, 1H), 6.88 (s, 1H), 6.26-6.08 (m, 2H), 5.52 (dd, J=8.0, 4.6 Hz, 1H), 4.83 (dt, J=13.8, 6.9 Hz, 1H), 3.92 (s, 3H), 3.22 (s, 3H), 3.08 (dd, J=13.2, 6.6 Hz, 2H), 2.70 (s, 3H), 2.62 (s, 3H), 2.58 (d, J=7.6 Hz, 2H), 2.30 (s, 6H), 1.59 (d, J=6.8 Hz, 6H).

Biological Activity Test (1) Kinase Inhibition Assay

Reagents and Materials:

WT EGFR (Carna, Cat. No. 08-115), EGFR [L858R] (Carna, Cat. No. 08-502), EGFR [L858R/T790M] (Carna, Cat. No. 08-510), ATP (Sigma, Cat. No. A7699-1G), DMSO (Sigma, Cat. No. D2650), 96-well plate (Corning, Cat. No. 3365), 384-well plate (Greiner, Cat. No. 784076), HTRF Kinase TK Kit (Cisbio, Cat. No. 62TK0PEJ), Erlotinib (Selleckchem, Cat. No. S7787), EGFR [d746-750] (Life Technologies, Cat. No. PV6178), 5× Kinase Buffer A (Life Technologies, Cat. No. PV3186), Kinase Tracer 199 (Life Technologies, Cat. No. PV5830), LanthaScreen® Eu-anti-GST antibody (Life Technologies, Cat. No. PV5594).

Specific Experimental Protocol:

Compound preparation: the test compound was dissolved in DMSO to make a 20 mM stock solution. Then, it was diluted in DMSO with a 3-fold series gradient dilution for 10 times. The dilutions were diluted 10 fold with buffer when dosing.

WT EGFR and EGFR [L858R/T790M] kinase assay: WT EGFR or EGFR [L858R/T790M] kinase was mixed with different concentrations of pre-diluted compounds for 10 minutes in 5× Kinase Buffer A in duplicate. The corresponding substrate and ATP were added and reacted at room temperature for 20 minutes (in which a negative and a positive control were set: the negative control is blank and the positive control is erlotinib). After the reaction, the detection reagent (the reagent in the HTRF Kinase TK kit) was added, and after incubation at room temperature for 30 minutes, the enzyme activity in the presence of the compounds of the present disclosure at each concentration was measured by an Evnvision microplate reader, and the inhibition of the enzyme by the compound at each concentrations were calculated. The inhibitions of the enzyme activity by the compounds at different concentrations were then fitted using Graphpad 5.0 software according to the four-parameter equation, and the $IC_{50}$ values were calculated, wherein A represents $IC_{50} \leq 1$ nM, B represents $IC_{50}$ of 1-50 nM, C represents $IC_{50}$ of 50-100 nM, and D represents IC50>100 nM.

The compounds of the present disclosure were tested in the above kinase inhibition assay, and the compounds of the present disclosure were found to have potent activity against EGFR [L858R/T790M] and superior selectivity over WT EGFR. The results for the representative example compounds are summarized in Table 1 below.

TABLE 1

| Example No. | WT EGFR $IC_{50}$(nM) | EGFR(L858R/T790M) $IC_{50}$(nM) |
|---|---|---|
| AZD9291 | B | A |
| 1 | B | A |
| 2 | B | A |
| 3 | B | B |
| 4 | B | A |

TABLE 1-continued

| Example No. | WT EGFR $IC_{50}$(nM) | EGFR(L858R/T790M) $IC_{50}$(nM) |
|---|---|---|
| 5 | B | A |
| 6 | B | A |
| 7 | B | A |
| 8 | B | B |
| 9 | D | B |
| 10 | D | C |
| 11 | B | A |
| 12 | A | A |
| 13 | B | B |
| 14 | D | B |
| 15 | D | B |
| 16 | D | B |
| 17 | D | B |
| 18 | B | A |
| 19 | B | A |
| 20 | B | A |
| 21 | B | A |
| 22 | B | B |
| 23 | B | B |
| 24 | B | B |
| 25 | B | B |
| 26 | B | A |
| 27 | B | A |
| 28 | B | B |
| 29 | B | B |
| 30 | A | A |
| 31 | B | A |
| 32 | B | B |
| 33 | B | A |
| 34 | B | A |
| 35 | B | A |
| 36 | B | A |
| 37 | B | B |
| 38 | B | A |
| 39 | B | A |
| 40 | B | A |
| 41 | A | A |
| 42 | A | A |
| 43 | C | B |
| 44 | B | A |
| 45 | B | A |
| 46 | B | A |
| 47 | B | A |
| 48 | B | A |
| 49 | A | A |
| 50 | B | B |
| 51 | B | B |
| 52 | B | A |
| 53 | B | A |
| 54 | B | A |
| 55 | B | B |
| 56 | B | B |
| 57 | D | B |
| 58 | D | D |
| 59 | D | C |
| 60 | B | A |
| 61 | B | B |
| 62 | B | A |
| 63 | B | A |
| 64 | B | A |
| 65 | B | A |
| 66 | B | B |
| 68 | B | A |

(2) Cytotoxicity Test

The in vitro anti-proliferative activity of the compounds of the present disclosure against three types of tumor cells that cultured in vitro was tested by MTS method. The experimental results show that the compounds of the present disclosure have inhibitory effect on the in vitro proliferation of cancer cells that cultured in vitro; wherein the inhibition of in vitro proliferation of lung cancer cells is stronger than that of skin cancer cells.

Cell Line:

Skin cancer cell line A431 (purchased from the American Type Culture Collection (ATCC)); lung cancer cells NCI-H1975 (purchased from the American Type Culture Collection (ATCC)) and HCC827 (purchased from the American Type Culture Collection (ATCC)). All of the cells were cultured in RPMI1640 medium containing 10% fetal bovine serum, 100 U/ml penicillin, and 100 μg/ml streptomycin.

Reagents and Materials:

RPMI-1640 (GIBCO, Cat. No. A10491-01); fetal bovine serum (GIBCO, Cat. No. 10099141); 0.25% trypsin-EDTA (GIBCO, Cat. No. 25200); penicillin-streptomycin, liquid (GIBCO, Cat. No. 15140-122); DMSO (Sigma, Cat. No. D2650); MTS Test Kit (Promega, Cat. No. G3581), 96-well plate (Corning, Cat. No. 3365).

Specific Experimental Protocol:

Compound preparation: the test compound was dissolved in DMSO to make a 20 mM stock solution and stored at −20° C. Before use, it was diluted in DMSO with a 3-fold series gradient dilution for 10 times. The dilutions were diluted 4 fold with cell culture medium RPMI-1640.

MTS cell viability assay: cells in logarithmic growth phase was digested with 0.25% trypsin-EDTA, and 150 μl of the cells was inoculated in 96-well plates at an optimized density. After 24 hours, the compound diluted 4 fold by adding the medium, 50 l/well (generally 10 Concentrations were selected: 100, 33.3, 11.1, 3.70, 1.23, 0.412, 0.137, 0.0457, 0.0152, 0.00508 μM). A well added with the same volume of 0.5% DMSO was used as a control. After the cells were cultured for further 72 hours, the cell viability was detected with MTS.

Specific procedure: cells were adhered, the medium was discarded, and a mixture containing 20 μL MTS and 100 μL medium was added to each well. The OD490 was detected after being placed in the incubator for 1-4 hours, and the OD650 value was used as a reference. A dose-effect curve was prepared using GraphPad Prism software and IC50 was calculated, where A represents $IC_{50} \leq 10$ nM, B represents $IC_{50}$ of 10-100 nM, C represents $IC_{50}$ of 100-400 nM, D represents $IC_{50}$ of 400-1000 nM, and E represents $IC_{50} \geq 1000$ nM.

The compounds of the present disclosure were tested in the above cytotoxicity assay, and the compounds of the present disclosure were found to have potent activity against lung cancer cells NCI-H1975 and HCC827 and superior selectivity over skin cancer cells A431. The results of the in vitro inhibition of the proliferation of cancer cells by representative examples are summarized in Table 2 below.

TABLE 2

| Example No. | A431 (WT) $IC_{50}$(nM) | HCC827 (Del19) $IC_{50}$(nM) | H1975 (L858R/T790M) $IC_{50}$(nM) | Selectivity A431 (WT)/H1975 |
|---|---|---|---|---|
| AZD9291 | C | B | A | 20~50 |
| 1 | E | B | B | >100 |
| 2 | E | B | B | >100 |
| 6 | E | B | B | 0~20 |
| 7 | E | B | B | 20~50 |
| 8 | E | B | A | >100 |
| 9 | E | D | B | >100 |
| 10 | E | D | E | / |
| 11 | D | B | B | 0~20 |
| 12 | C | A | B | 0~20 |
| 13 | E | B | B | 0~20 |
| 14 | E | D | E | / |
| 15 | E | C | E | 0~20 |
| 16 | E | C | E | / |
| 17 | E | C | B | >100 |
| 20 | C | B | A | 20~50 |
| 21 | C | A | A | >100 |
| 22 | C | B | B | 0~20 |
| 23 | D | B | B | 20~50 |
| 24 | D | B | B | 0~20 |
| 25 | E | C | C | 0~20 |
| 26 | D | B | B | 20~50 |
| 27 | D | B | B | 0~20 |
| 28 | D | B | A | 50~100 |
| 29 | D | C | B | 0~20 |
| 30 | E | A | B | >100 |
| 31 | E | B | B | >100 |
| 32 | E | B | B | 20~50 |
| 33 | E | B | B | 20~50 |
| 34 | E | B | B | 20~50 |
| 35 | D | B | A | 50~100 |
| 38 | E | B | B | 50~100 |
| 39 | C | B | B | 20~50 |
| 40 | D | B | B | 20~50 |
| 41 | C | A | B | 20~50 |
| 42 | C | A | B | 20~50 |
| 43 | E | C | C | 0~20 |
| 44 | D | A | A | 50~100 |
| 45 | D | B | B | 20~50 |
| 46 | C | B | B | 0~20 |
| 47 | D | A | A | 50~100 |
| 48 | D | A | A | >100 |
| 49 | B | A | A | 50~100 |
| 50 | C | B | B | 0~20 |
| 51 | C | B | B | 20~50 |
| 52 | C | A | A | 20~50 |
| 53 | D | A | A | 50~100 |
| 54 | D | C | D | 0~20 |
| 55 | D | D | D | 0~20 |
| 56 | E | B | B | 20~50 |
| 57 | E | E | E | 0~20 |
| 58 | E | E | E | / |
| 59 | E | E | E | 0~20 |
| 60 | D | B | A | >100 |
| 61 | C | B | A | 20~50 |
| 62 | E | B | A | >100 |
| 63 | E | B | B | >100 |
| 64 | C | B | A | 50~100 |
| 65 | C | A | A | >100 |
| 66 | D | B | A | >100 |
| 68 | E | A | B | 50~100 |

It is to be understood that the examples are merely illustrative of the invention and are not intended to limit the scope of the invention, and the experimental methods in which the specific conditions are not indicated, are carried out generally in accordance with conventional conditions, or in accordance with the conditions suggested by the manufacturer. Parts and percentages are parts by weight and percentage by weight unless otherwise stated.

The above is a further detailed description of the present disclosure in connection with the specific preferred embodiments, and the specific embodiments of the present disclosure are not limited to the description. It will be apparent to those skilled in the art that the present disclosure may be practiced by making various simple deduction and replacement, without departing from the spirit and scope of the invention.

The invention claimed is:
1. A compound of formula (III):

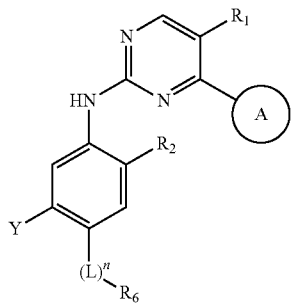

(III)

wherein,
R$_1$ is selected from H, halo, —CN, optionally substituted C$_1$-C$_6$ alkyl, optionally substituted C$_1$-C$_6$ haloalkyl, or optionally substituted C$_3$-C$_6$ carbocyclyl;
R$_2$ is selected from optionally substituted C$_1$-C$_6$ alkoxy, or optionally substituted C$_1$-C$_6$ haloalkoxy;
-(L)$^n$-R$_6$ is:

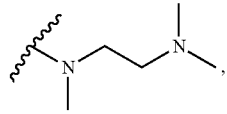 [SMILES: *N(C)CCN(C)C]

Y is the following structure:

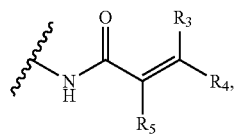

wherein R$_3$, R$_4$ and R$_5$ are independently selected from H, halo, —CN, optionally substituted C$_1$-C$_6$ alkyl or optionally substituted C$_1$-C$_6$ haloalkyl;
ring A is selected from the following structures:

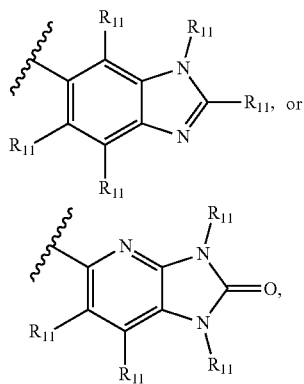

R$_{11}$ is independently selected from H, halo, —CN, C$_1$-C$_6$ alkyl, or optionally substituted C$_3$-C$_6$ carbocyclyl, as long as the chemistry permits; or, two adjacent R$_{11}$ could be taken together to form optionally substituted C$_5$-C$_8$ carbocyclyl, or optionally substituted 5- to 8-membered heterocyclyl;
or a pharmaceutically acceptable salt, a stereoisomer, a solvate, a hydrate, or an isotopically labeled compound thereof.

2. The compound according to claim 1, wherein
R$_{11}$ is independently selected from H, halo, or C$_1$-C$_6$ alkyl, or, two adjacent R$_{11}$ could be taken together to form optionally substituted 5- to 8-membered heterocyclyl;
or a pharmaceutically acceptable salt, a stereoisomer, a solvate, a hydrate, or an isotopically labeled compound thereof.

3. The compound of formula (III-a):

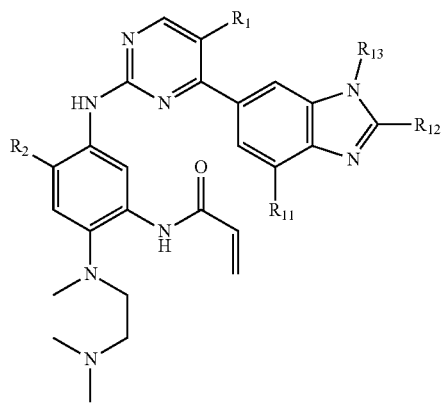

(III-a)

wherein,
R$_1$ is selected from H, halo, —CN, optionally substituted C$_1$-C$_6$ alkyl, optionally substituted C$_1$-C$_6$ haloalkyl, or optionally substituted C$_3$-C$_6$ carbocyclyl;
R$_2$ is selected from optionally substituted C$_1$-C$_6$ alkoxy or optionally substituted C$_1$-C$_6$ haloalkoxy;
R$_{11}$ is selected from H, halo, optionally substituted C$_1$-C$_6$ alkyl, optionally substituted C$_1$-C$_6$ haloalkyl or optionally substituted C$_1$-C$_6$ alkoxy;
R$_{12}$ is selected from H, or C$_1$-C$_6$ alkyl;
R$_{13}$ is optionally substituted C$_1$-C$_6$ alkyl;
or a pharmaceutically acceptable salt, a stereoisomer, a solvate, a hydrate, or an isotopically labeled compound thereof.

4. The compound of formula (III-c):

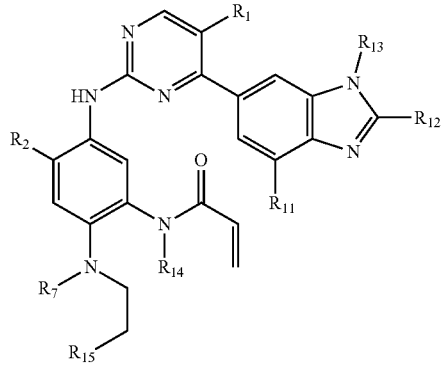

(III-c)

wherein,
- $R_1$ is selected from H, halo, —CN, optionally substituted $C_1$-$C_6$ alkyl, optionally substituted $C_1$-$C_6$ haloalkyl, optionally substituted $C_1$-$C_6$ alkoxy or optionally substituted $C_3$-$C_6$ carbocyclyl;
- $R_2$ is selected from optionally substituted $C_1$-$C_6$ alkoxy or optionally substituted $C_1$-$C_6$ haloalkoxy;
- $R_7$ is selected from H, or optionally substituted $C_1$-$C_6$ alkyl;
- $R_{11}$ is selected from H, halo, optionally substituted $C_1$-$C_6$ alkyl, optionally substituted $C_2$-$C_6$ alkenyl, optionally substituted $C_1$-$C_6$ haloalkyl or optionally substituted $C_1$-$C_6$ alkoxy;
- $R_{12}$ is independently selected from H, halo, —CN, —NO$_2$, —OH, optionally substituted $C_1$-$C_6$ alkyl, optionally substituted $C_1$-$C_6$ haloalkyl, optionally substituted $C_2$-$C_6$ alkenyl, optionally substituted $C_2$-$C_6$ alkynyl, optionally substituted $C_3$-$C_6$ carbocyclyl, optionally substituted $C_1$-$C_6$ alkoxy, optionally substituted $C_1$-$C_6$ alkylthio or optionally substituted $C_1$-$C_6$ haloalkoxy, as long as the chemistry permits; wherein the said optionally substituted groups are optionally further substituted by 1, 2, 3, 4, 5, 6, 7, or 8 deuteriums;
- $R_{13}$ is selected from H, halo, optionally substituted $C_1$-$C_6$ alkyl, optionally substituted $C_2$-$C_6$ alkenyl, optionally substituted $C_1$-$C_6$ haloalkyl or optionally substituted $C_1$-$C_6$ alkoxy; wherein the said optionally substituted groups are optionally further substituted by 1, 2, 3, 4, 5, 6, 7, or 8 deuteriums;
- or $R_{12}$ and $R_{13}$ could be taken together to form optionally substituted 5- to 8-membered heterocyclyl, or optionally substituted 5- to 10-membered heteroaryl;
- $R_{14}$ is selected from H, optionally substituted $C_1$-$C_6$ alkyl, or optionally substituted $C_1$-$C_6$ haloalkyl;
- $R_{15}$ is selected from —OH, —CN, —NO$_2$, optionally substituted $C_1$-$C_6$ alkyl, optionally substituted $C_1$-$C_6$ alkoxy, or NR$_8$R$_9$; wherein R$_8$ and R$_9$ are each independently selected from H, optionally substituted $C_1$-$C_6$ alkyl, optionally substituted $C_1$-$C_6$ alkoxy, optionally substituted $C_1$-$C_6$ haloalkyl or optionally substituted $C_3$-$C_6$ carbocyclyl, or R$_8$ and R$_9$ together with the nitrogen atom to which they are attached form optionally substituted 4- to 6-membered heterocyclyl;
- or a pharmaceutically acceptable salt, a stereoisomer, a solvate, a hydrate, or an isotopically labeled compound thereof.

5. The Compound according to claim 1, which is selected from:

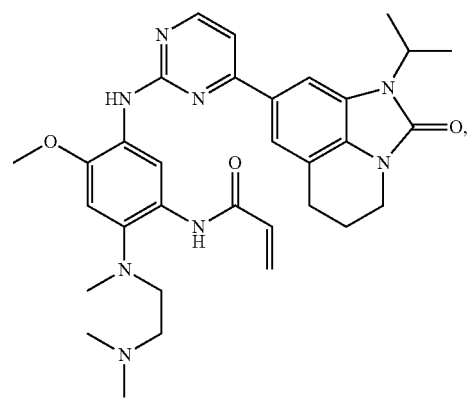

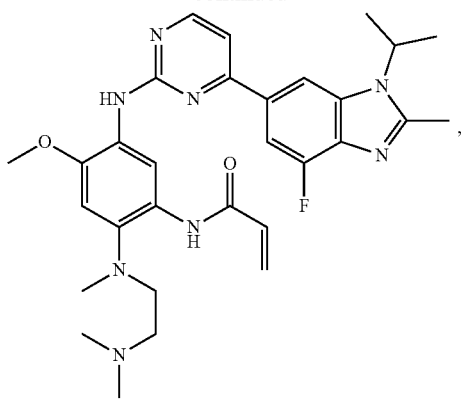

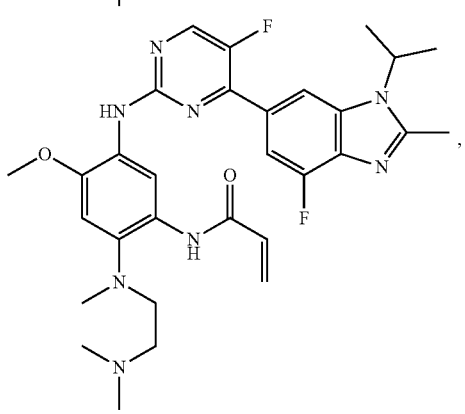

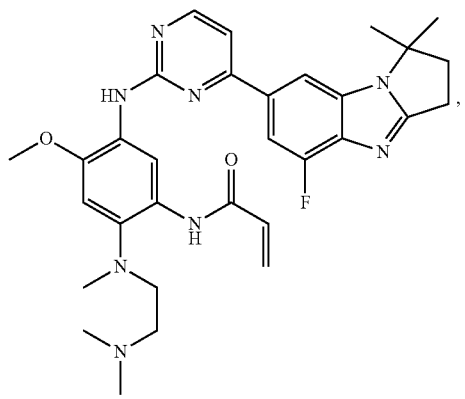

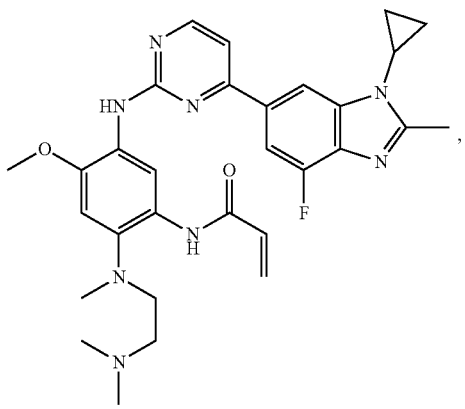

279
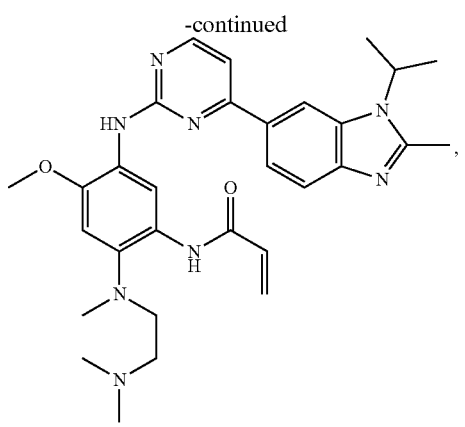
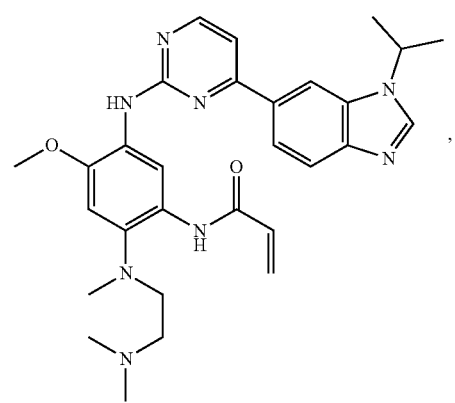
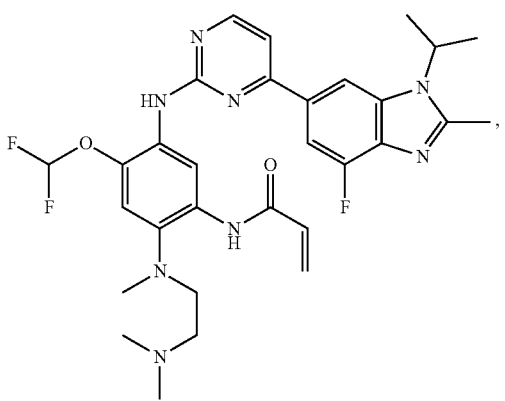
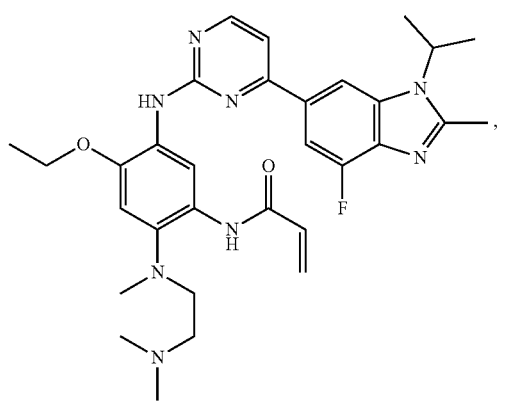
280
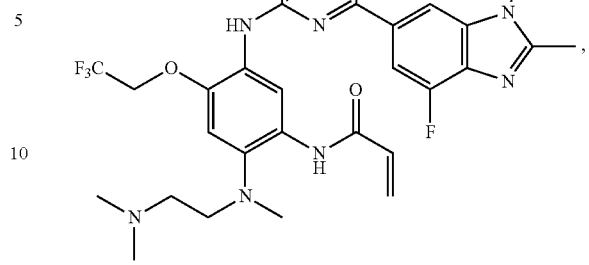
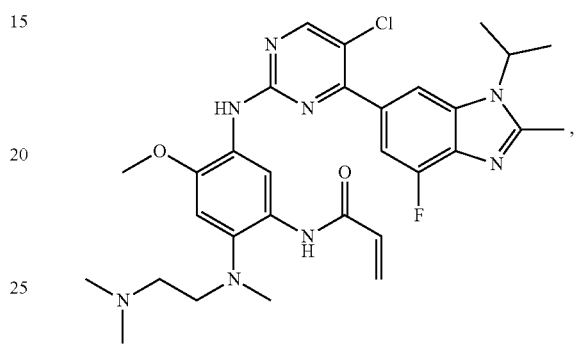
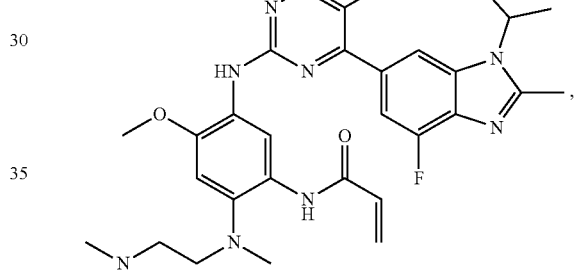
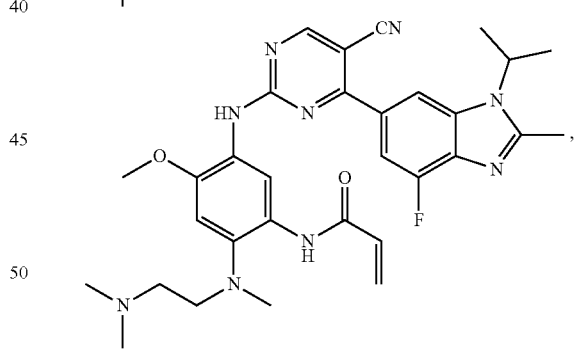
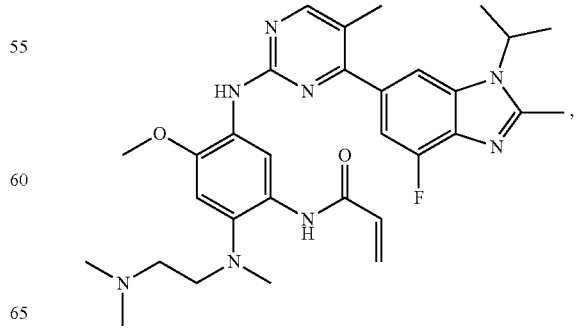

-continued

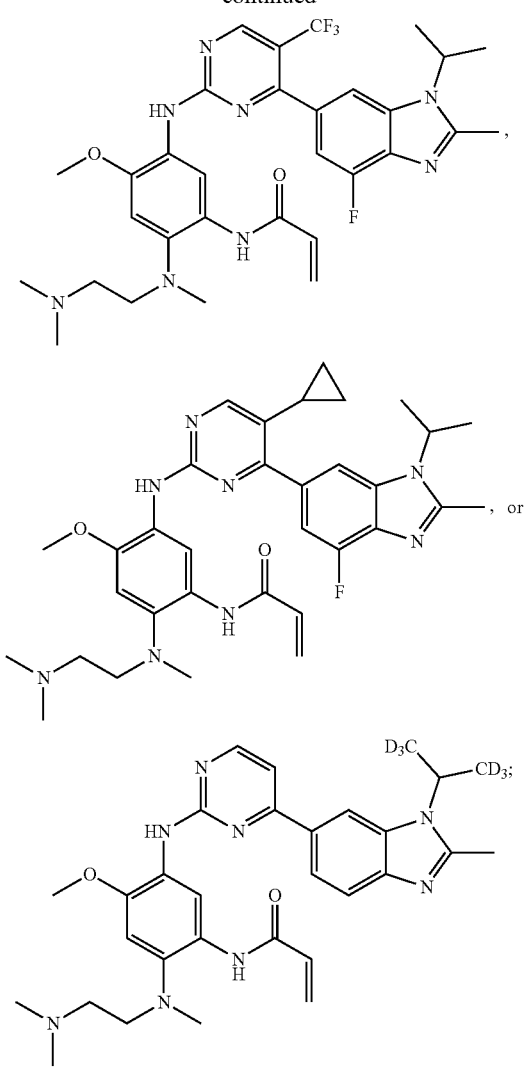

or a pharmaceutically acceptable salt thereof.

6. The compound according to claim 5 having the following structure:

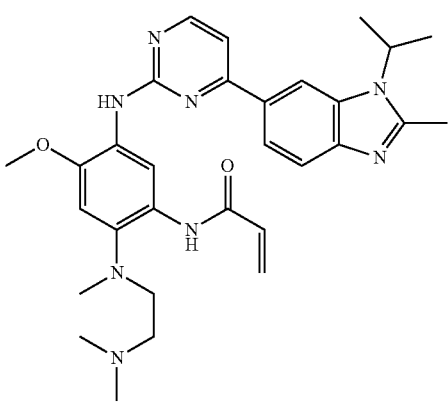

or a pharmaceutically acceptable salt thereof.

7. The compound according to claim 5 having the following structure:

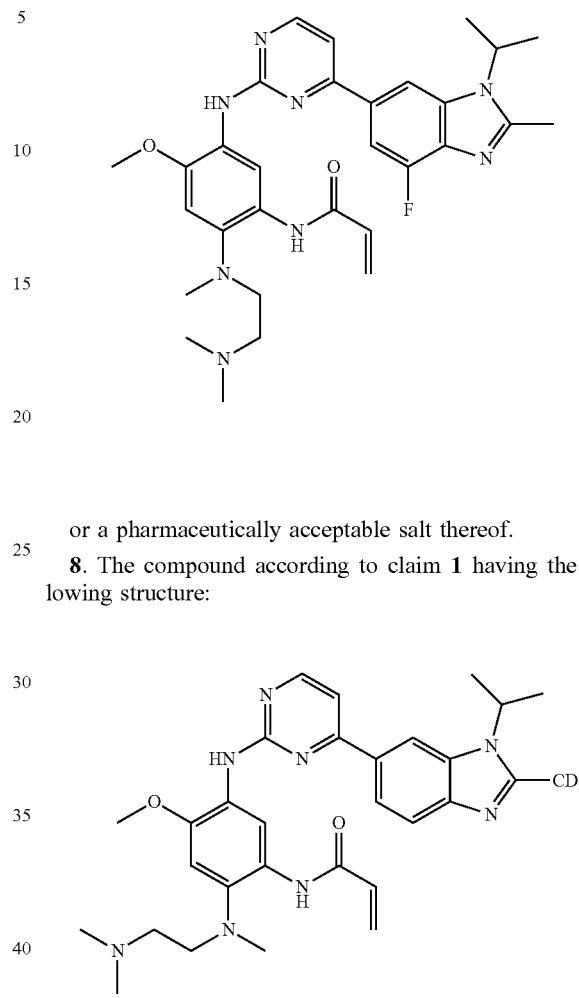

or a pharmaceutically acceptable salt thereof.

8. The compound according to claim 1 having the following structure:

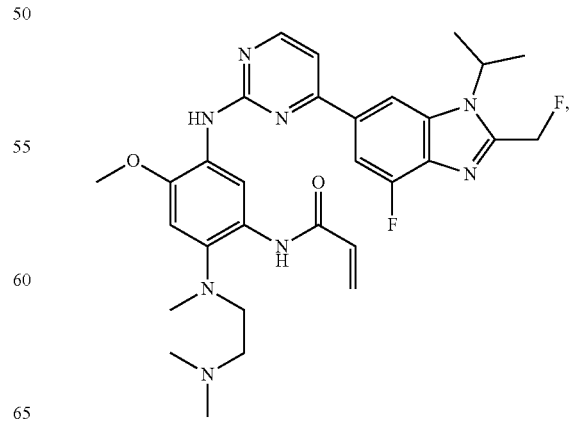

or a pharmaceutically acceptable salt thereof.

9. The Compound according to claim 4, which is selected from:

283
-continued
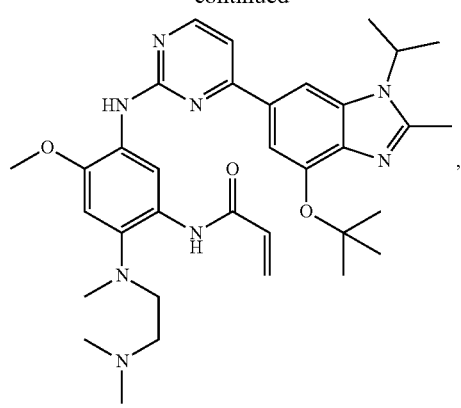
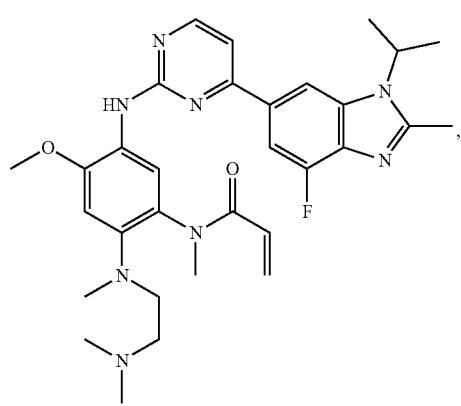
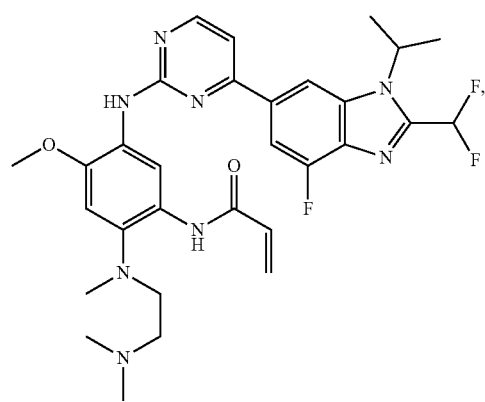
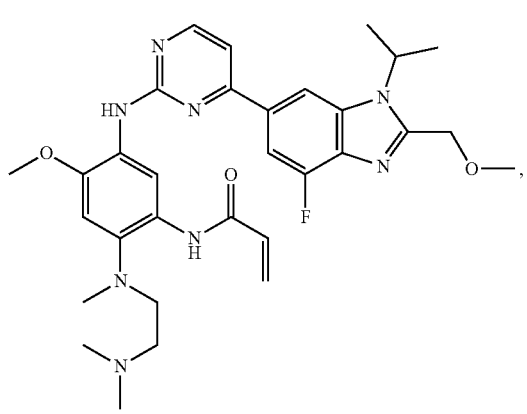
284
-continued
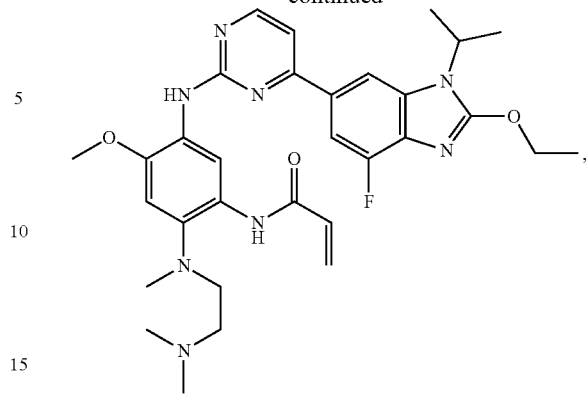
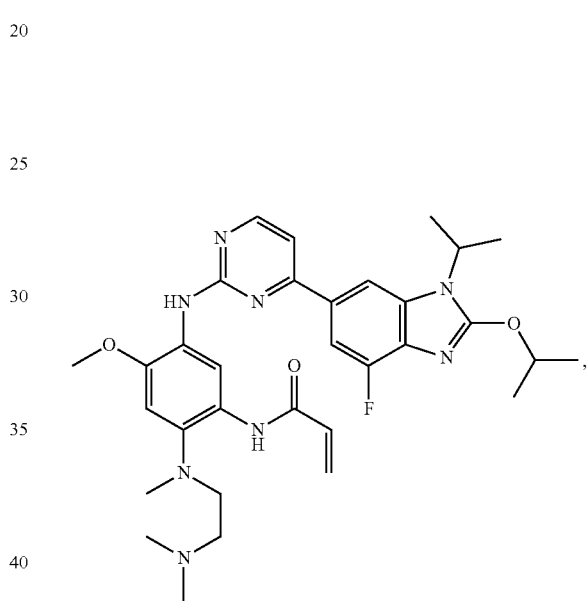
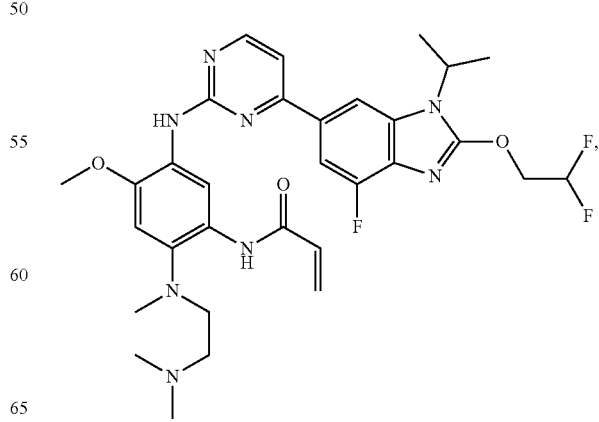

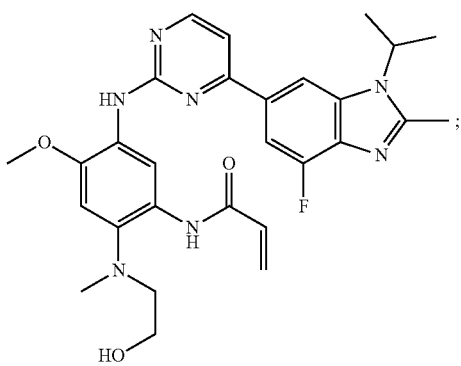
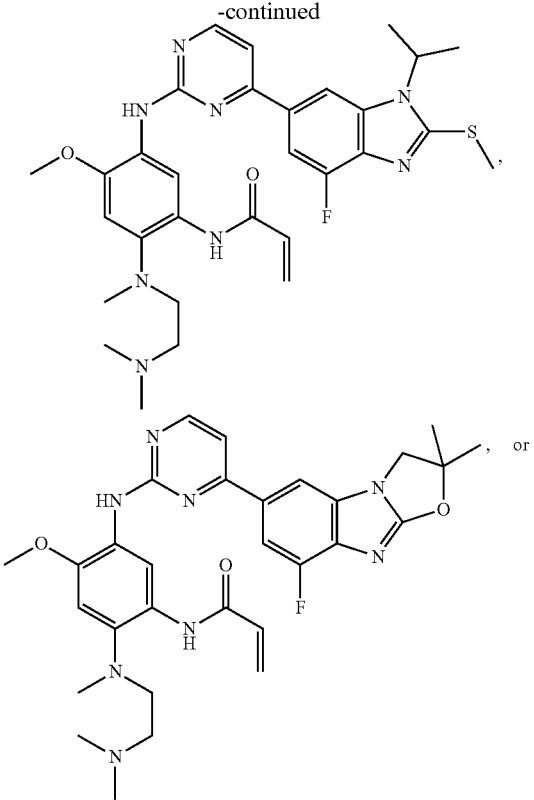

or a pharmaceutically acceptable salt thereof.

10. A pharmaceutical composition, comprising
a compound according to claim 1, or a pharmaceutically acceptable salt, a stereoisomer, a solvate, a hydrate, or an isotopically labeled compound thereof, and
a pharmaceutically acceptable excipient.

11. A pharmaceutical composition, comprising
a compound according to claim 4, or a pharmaceutically acceptable salt, a stereoisomer, a solvate, a hydrate, or an isotopically labeled compound thereof, and
a pharmaceutically acceptable excipient.

* * * * *